US008637032B2

(12) United States Patent
Long et al.

(10) Patent No.: US 8,637,032 B2
(45) Date of Patent: Jan. 28, 2014

(54) ANTAGONIST ANTI-CD40 MONOCLONAL ANTIBODIES AND METHODS FOR THEIR USE

(75) Inventors: Li Long, Hercules, CA (US); Mohammad Luqman, Danville, CA (US); Asha Yabannavar, Lafayette, CA (US); Isabel Zaror, El Cerrito, CA (US); Sang Hoon Lee, Palo Alto, CA (US); Deborah Hurst, Piedmont, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 13/612,070

(22) Filed: Sep. 12, 2012

(65) Prior Publication Data

US 2013/0011405 A1    Jan. 10, 2013

Related U.S. Application Data

(60) Division of application No. 11/932,472, filed on Oct. 31, 2007, now Pat. No. 8,277,810, which is a continuation-in-part of application No. 10/577,390, filed as application No. PCT/US2004/037152 on Nov. 4, 2004, now abandoned, said application No. 11/932,472 is a continuation-in-part of application No. 10/578,387, filed as application No. PCT/US2004/037281 on Nov. 4, 2004, now abandoned, said application No. 11/932,472 is a continuation-in-part of application No. 10/577,642, filed as application No. PCT/US2004/036954 on Nov. 4, 2004, now abandoned, said application No. 11/932,472 is a continuation-in-part of application No. 10/578,400, filed as application No. PCT/US2004/036955 on Nov. 4, 2004, now abandoned, said application No. 10/578,401, filed as application No. PCT/US2004/037159 on Nov. 4, 2004, now abandoned, said application No. 11/932,472 is a continuation-in-part of application No. 10/578,590, filed as application No. PCT/US2004/036958 on Nov. 4, 2004, now abandoned, said application No. 11/932,472 is a continuation-in-part of application No. 10/576,943, filed as application No. PCT/US2004/036957 on Nov. 4, 2004, now abandoned.

(60) Provisional application No. 60/517,337, filed on Nov. 4, 2003, provisional application No. 60/525,579, filed on Nov. 26, 2003, provisional application No. 60/565,710, filed on Apr. 27, 2004, provisional application No. 60/565,709, filed on Apr. 26, 2004, provisional application No. 60/611,794, filed on Sep. 21, 2004, provisional application No. 60/565,634, filed on Apr. 27, 2004, provisional application No. 60/613,885, filed on Sep. 28, 2004.

(51) Int. Cl.
*A61K 39/395* (2006.01)
*C07K 16/28* (2006.01)

(52) U.S. Cl.
USPC ............... 424/153.1; 424/130.1; 424/133.1; 424/141.1; 424/143.1; 424/144.1; 424/152.1; 424/173.1; 530/387.1; 530/387.3; 530/388.1; 530/388.2; 530/388.22; 530/388.7; 530/388.73

(58) Field of Classification Search
None
See application file for complete search history.

(56) References Cited

U.S. PATENT DOCUMENTS

| | | | |
|---|---|---|---|
| 5,397,703 | A | 3/1995 | de Boer et al. |
| 5,677,165 | A | 10/1997 | de Boer et al. |
| 5,801,227 | A | 9/1998 | Fanslow, III et al. |
| 5,874,082 | A | 2/1999 | de Boer |
| 6,004,552 | A | 12/1999 | de Boer et al. |
| 6,056,959 | A | 5/2000 | de Boer et al. |
| 6,315,998 | B1 | 11/2001 | de Boer et al. |
| 6,899,879 | B2 | 5/2005 | de Boer et al. |
| 6,923,956 | B1 | 8/2005 | Tschope et al. |
| 7,063,845 | B2 | 6/2006 | Mikayama et al. |
| 7,193,064 | B2 | 3/2007 | Mikayama et al. |
| 7,537,763 | B2 | 5/2009 | Mikayama et al. |
| 7,790,166 | B2 | 9/2010 | de Boer et al. |
| 8,277,810 | B2 | 10/2012 | Long et al. |
| 2003/0211100 | A1 | 11/2003 | Bedian et al. |
| 2005/0053598 | A1 | 3/2005 | Burke et al. |
| 2007/0098717 | A1 | 5/2007 | Long et al. |
| 2007/0098718 | A1 | 5/2007 | Long et al. |
| 2007/0110754 | A1 | 5/2007 | Long et al. |
| 2007/0148163 | A1 | 6/2007 | Takahashi et al. |
| 2007/0218060 | A1 | 9/2007 | Long et al. |

(Continued)

FOREIGN PATENT DOCUMENTS

| | | |
|---|---|---|
| EP | 1 391 464 A1 | 2/2004 |
| EP | 2 223 017 | 2/2005 |

(Continued)

OTHER PUBLICATIONS

Balint, R., et al., "Antibody Engineering by Parsimonious Mutagenesis," *Gene*, 1993, pp. 109-118, vol. 137, No. 27.

(Continued)

*Primary Examiner* — Phillip Gambel
(74) *Attorney, Agent, or Firm* — Alston & Bird LLP

(57) ABSTRACT

Compositions and methods of therapy for treating diseases mediated by stimulation of CD40 signaling on CD40-expressing cells are provided. The methods comprise administering a therapeutically effective amount of an antagonist anti-CD40 antibody or antigen-binding fragment thereof to a patient in need thereof. The antagonist anti-CD40 antibody or antigen-binding fragment thereof is free of significant agonist activity, but exhibits antagonist activity when the antibody binds a CD40 antigen on a human CD40-expressing cell. Antagonist activity of the anti-CD40 antibody or antigen-binding fragment thereof beneficially inhibits proliferation and/or differentiation of human CD40-expressing cells, such as B cells.

69 Claims, 30 Drawing Sheets

(56) References Cited

U.S. PATENT DOCUMENTS

| | | |
|---|---|---|
| 2008/0057070 A1 | 3/2008 | Long et al. |
| 2008/0254026 A1 | 10/2008 | Long et al. |

FOREIGN PATENT DOCUMENTS

| | | |
|---|---|---|
| EP | 1 707 627 A1 | 4/2006 |
| EP | 1 914 243 A2 | 4/2008 |
| WO | WO 94/01547 A3 | 1/1994 |
| WO | WO 95/17202 A1 | 6/1995 |
| WO | WO 96/18413 A1 | 6/1996 |
| WO | WO 97/04801 | 2/1997 |
| WO | WO 97/31025 A1 | 8/1997 |
| WO | WO 99/42075 A2 | 8/1999 |
| WO | WO 01/34649 A3 | 5/2001 |
| WO | WO 01/83755 A3 | 11/2001 |
| WO | WO 02/04021 A1 | 1/2002 |
| WO | WO 02/22212 A2 | 3/2002 |
| WO | WO 02/28480 A2 | 4/2002 |
| WO | WO 02/28481 A2 | 4/2002 |
| WO | WO 02/28904 A3 | 4/2002 |
| WO | WO 02/28905 A2 | 4/2002 |
| WO | WO 02/060485 A2 | 8/2002 |
| WO | WO 02/078766 A2 | 10/2002 |
| WO | WO 02/088186 A1 | 11/2002 |
| WO | WO 03/029296 A1 | 4/2003 |
| WO | WO 03/040170 A2 | 5/2003 |
| WO | WO 03/045978 A3 | 6/2003 |
| WO | WO 2005/044294 A2 | 5/2005 |
| WO | WO 2005/044304 A2 | 5/2005 |
| WO | WO 2005/044305 A2 | 5/2005 |
| WO | WO 2005/044306 A2 | 5/2005 |
| WO | WO 2005/044307 A2 | 5/2005 |
| WO | WO 2005/044854 A2 | 5/2005 |
| WO | WO 2005/044855 A2 | 5/2005 |
| WO | WO 2007/124299 A2 | 11/2007 |

OTHER PUBLICATIONS

Benoit et al., "Increased inhibition of proliferation of human B cell lymphomas following ligation of CD40, and either CD19, CD20, CD95 or surface immunoglobulin," *Immunopharmacology*, 1996, vol. 35, pp. 129-139.

Boon, L., et al., "Prevention of Experimental Autoimmune Encephalomyelitis in the Common Marmoset (*Callithrix jacchus*) Using a Chimeric Antagonist Monoclonal Antibody Against Human CD40 is Associated with Altered B Cell Responses," *Journal of Immunology*, 2001, pp. 2942-2949, vol. 167, No. 5.

Ellmark, P., et al., "Modulation of the CD40-CD40 Ligand Interaction Using Human Anti-CD40 Single-Chain Antibody Fragments Obtained from the n-CoDeR Phage Display Library," *Immunology*, 2002, pp. 456-463, vol. 106, No. 4.

Funakoshi, S., et al., "Differential In Vitro and In Vivo Antitumor Effects Mediated by Anti-CD40 and Anti-CD20 Monoclonal Antibodies Against Human B-Cell Lymphomas," *Journal of Immunology*, 1996, vol. 19, No. 2, pp. 93-101.

Gisselbrecht, C., et al., "Interleukin-2 Treatment in Lymphoma: A Phase II Multicenter Study," *Blood*, 1994, pp. 2081-2085, vol. 83, No. 8.

Hager A-C Malmborg, et al., "Affinity and Epitope Profiling of Mouse Anti-CD40 Monoclonal Antibodies," *Scandinavian Journal of Immunology*, 2003, pp. 517-524, vol. 57, No. 6.

Little, M., et al., "Of Mice and Men: Hybridoma and Recombinant Antibodies," *Review Immunology Today*, 2000, pp. 364-370, vol. 21.

Maloney, D.G., et al., "IDEC-C2B8: Results of a Phase I Multiple-Dose Trial in Patients with Relapsed Non-Hodgkin's Lymphoma," *Journal of Clinical Oncology*, 1997, vol. 15, No. 10, pp. 3266-3274.

Rosenberg, S.A., et al., "A Progress Report on the Treatment of 157 Patients with Advanced Cancer Using Lymphokine-Activated Killer Cells and Interleukin-2 or High-Dose Interleukin-2 Alone," *The New England Journal of Medicine*, 1987, pp. 889-897, vol. 316, No. 15.

Singh et al., The Role of Polar Interactions in the Molecular Recognition of CD40L with its Receptor CD40, *Protein Science*, 1998, pp. 1124-1135, vol. 7.

Tai, Y., et al., "Mechanisms by which SGN-40, a Humanized Anti-CD40 Antibody, Induces Cytotoxicity in Human Multiple Myeloma Cells: Clinical Implications," *Cancer Research*, 2004, pp. 2846-2852, vol. 64, No. 8.

Weng Wen-Kai, et al., "Human anti-CD40 Antagonistic Antibodies Inhibit the Proliferation of Human B Cell Non-Hodgkin's Lymphoma," *Blood*, 2001, p. 466a, vol. 98, No. 11, Part 1, Abstract #1947.

|  | Daudi | | Namalwa | |
|---|---|---|---|---|
| Exp. | CD40 | CD20 | CD40 | CD20 |
| E090403 | 14403.0 | 93676.5 | 3296.4 | 6200.1 |
| E091003 | 13214.9 | 108438.5 | 3081.5 | 4788.2 |
| E091103 | 13702.6 | 100509.1 | 3165.7 | 3988.3 |
| E091203 | 13278.9 | 128158.3 | 3164.9 | 4618.0 |
| Average | 13,649.9 | 107,695.6 | 3,177.1 | 4,898.7 |
| Stdev | 546.7 | 14915.9 | 88.8 | 933.4 |

CHIR 12.12 light chain:

leader:

MALPAQLLGLLMLWVSGSSG variable:

DIVMTQSPLSLTVTPGEPASISCRSSQSLLYSNGYNYLDWYLQKPGQSPQVLISLGSNRASG
VPDRFSGSGSGTDFTLKISRVEAEDVGVYYCMQARQTPFTFGPGTKVDIR constant:

RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

FIGURE 9B

CHIR-12.12 heavy chain:

leader:

MEFGLSWVFLVAILRGVQC variable:

QVQLVESGGGVVQPGRSLRLSCAASGFTFSSYGMHWVRQAPGKGLEWVAVISYEESNRYHAD
SVKGRFTISRDNSKITLYLQMNSLRTEDTAVYYCARDGGIAAPGPDYWGQGTLVTVSS constant:

ASTKGPSVFPLAPASKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK alternative constant region:

ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIGURE 10A

DNA sequence of light chain of CHIR-12.12:

5'atggcgctccctgctcagctcctggggctgctaatgctctgggtctctggatccagtggggatattgtgatgactcagtctccactctc
cctgaccgtcacccctggagagccggcctccatctcctgcaggtccagtcagagcctcctgtatagtaatggatacaactatttggattg
gtacctgcagaagccagggcagtctccacaggtcctgatctctttggttctaatcgggcctccggggtccctgacaggttcagtggca
gtggatcaggcacagattttacactgaaaatcagcagagtggaggctgaggatgttggggtttattactgcatgcaagctcgacaaact
ccattcacttcggccctgggaccaaagtggatatcagacgaactgtggctgcaccatctgtcttcatcttcccgccatctgatgagcagt
tgaaatctggaactgcctctgttgtgtgcctgctgaataacttctatcccagagaggccaaagtacagtggaaggtggataacgccctcc
aatcgggtaactcccaggagagtgtcacagagcaggacagcaaggacagcacctacagcctcagcagcaccctgacgctgagcaa
agcagactacgagaaacacaaagtctacgcctgcgaagtcacccatcagggcctgagctcgcccgtcacaaagagcttcaacaggg
gagagtgttag3'

FIGURE 10B

DNA sequence of heavy chain of CHIR-12.12 (including introns):

5'atggagtttgggctgagctgggttttccttgttgctattttaagaggtgtccagtgtcaggtgcagttggtggagtctgggggaggcgt
ggtccagcctgggaggtccctgagactctcctgtgcagcctctggattcaccttcagtagctatggcatgcactgggtccgccaggctc
caggcaaggggctggagtgggtggcagttatatcatatgaggaaagtaatagataccatgcagactccgtgaagggccgattcacca
tctccagagacaattccaagatcacgctgtatctgcaaatgaacagcctgagaactgaggacacggctgtgtattactgtgcgagagat
gggggtatagcagcacctgggcctgactactggggccagggaaccctggtcaccgtctcctcagcaagtaccaagggcccatccgt
cttccccctggcgccctgctagcaagagcacctctgggggcacagcggccctgggctgcctggtcaaggactacttccccgaaccgg
tgacggtgtcgtggaactcaggcgccctgaccagcggcgtgcacacctteeggctgtcctacagtcctcaggactctactccctcag
cagcgtggtgaccgtgccctccagcagcttgggcacccagacctacatctgcaacgtgaatcacaagcccagcaacaccaaggtgg
acaagagagttggtgagaggccagcacagggagggagggtgtctgctggaagccaggctcagcgctcctgcctggacgcatcccg
gctatgcagtcccagtccagggcagcaaggcaggccccgtctgcctcttcacccggaggcctctgcccgcccactcatgctcagg
gagagggtcttctgctttcccaggctctgggcaggcacaggctaggtgcccctaacccaggccctgcacacaaggggcaggt
gctgggctcagacctgccaagagccatatccgggaggaccctgccctgacctaagccaccccaaaggccaaactctccactccc
tcagctcggacacctttctcctcccagattccagtaactcccaatcttctctctgcagagcccaaatcttgtgacaaaactcacacatgc
ccaccgtgcccaggtaagccagcccaggcctcgccctccagctcaaggcgggacaggtgccctagagtagcctgcatccagggac
aggccccagccgggtgctgacacgtccacctccatctcttcctcagcacctgaactcctggggggaccgtcagtcttcctcttccccc
caaaacccaaggacaccctcatgatctcccggacccctgaggtcacatgcgtggtggtggacgtgagccacgaagaccctgaggtca
agttcaactggtacgtggacggcgtggaggtgcataatgccaagacaaagccgcgggaggagcagtacaacagcacgtaccgtgt
ggtcagcgtcctcaccgtcctgcaccaggactggctgaatggcaaggagtacaagtgcaaggtctccaacaaagccctcccagccc
ccatcgagaaaaccatctccaaagccaaaggtgggacccgtggggtgcgagggccacatggacagaggccggctcggcccacc
tctgccctgagagtgaccgctgtaccaacctctgtccctacagggcagccccgagaaccacaggtgtacaccctgcccccatcccgg
gaggagatgaccaagaaccaggtcagcctgacctgcctggtcaaaggcttctatcccagcgacatcgccgtggagtgggagagcaa
tgggcagccggagaacaactacaagaccacgcctcccgtgctggactccgacggctccttcttcctctatagcaagctcaccgtggac
aagagcaggtggcagcaggggaacgtcttctcatgctccgtgatgcatgaggctctgcacaaccactacacgcagaagagcctctcc
ctgtctccgggtaaatga3'

FIGURE 11A

CHIR-5.9 light chain:

leader:

MALLAQLLGLLMLWVPGSSG variable:

AIVMTQPPLSSPVTLGQPASISCRSSQSLVHSDGNTYLNWLQQRPGQPPRLLIYKFFRRLSG
VPDRFSGSGAGTDFTLKISRVEAEDVGVYYCMQVTQFPHTFGQGTRLEIK constant:

RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

FIGURE 11B

CHIR-5.9 heavy chain:

leader:

MGSTAILALLLAVLQGVCA variable:

EVQLVQSGAEVKKPGESLKISCKGSGYSFTSYWIGWVRQMPGKGLEWMGIIYPGDSDTRYSP
SFQGQVTISADKSISTAYLQWSSLKASDTAMYYCARGTAAGRDYYYYGMDVWGQGTTVTVS
S constant:

ASTKGPSVFPLAPASKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK alternative constant region:

ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSV
MHEALHNHYTQKSLSLSPGK

FIGURE 12A

Coding sequence for short isoform of human CD40:

```
  1 atggttcgtc tgcctctgca gtgcgtcctc tggggctgct tgctgaccgc tgtccatcca
 61 gaaccaccca ctgcatgcag agaaaaacag tacctaataa acagtcagtg ctgttctttg
121 tgccagccag gacagaaact ggtgagtgac tgcacagagt tcactgaaac ggaatgcctt
181 ccttgcggtg aaagcgaatt cctagacacc tggaacagag agacacactg ccaccagcac
241 aaatactgcg accccaacct agggcttcgg gtccagcaga gggcaccctc agaaacagac
301 accatctgca cctgtgaaga aggctggcac tgtacgagtg aggctgtgaa gagctgtgtc
361 ctgcaccgct catgctcgcc cggctttggg gtcaagcaga ttgctacagg ggtttctgat
421 accatctgcg agccctgccc agtcggcttc ttctccaatg tgtcatctgc tttcgaaaaa
481 tgtcacccct ggacaaggtc cccaggatcg gctgagagcc ctggtggtga tccccatcat
541 cttcgggatc ctgtttgcca tcctcttggt gctggtcttt atcaaaaagg tggccaagaa
601 gccaaccaat aa
```

FIGURE 12B

Encoded short isoform of human CD40:

```
  1 mvrlplqcvl wgclltavhp epptacrekq ylinsqccsl cqpgqklvsd cteftetecl
 61 pcgesefldt wnrethchqh kycdpnlglr vqqkgtsetd tictceegwh ctseacescv
121 lhrscspgfg vkqiatgvsd ticepcpvgf fsnvssafek chpwtrspgs aespggdphh
181 lrdpvchplg aglyqkggqe anq
```

FIGURE 12C

Coding sequence for long isoform of human CD40:

```
  1 atggttcgtc tgcctctgca gtgcgtcctc tggggctgct tgctgaccgc tgtccatcca
 61 gaaccaccca ctgcatgcag agaaaaacag tacctaataa acagtcagtg ctgttctttg
121 tgccagccag gacagaaact ggtgagtgac tcacagagt tcactgaaac ggaatgcctt
181 ccttgcggtg aaagcgaatt cctagacacc tggaacagag agacacactg ccaccagcac
241 aaatactgcg acccaaacct agggcttcgg gtccagcaga agggcacctc agaaacagac
301 accatctgca cctgtgaaga aggctggac tgtacgagtg aggcctgtga gagctgtgtc
361 ctgcaccgct catgctcgcc cggctttggg gtcaagcaga ttgctacagg ggtttctgat
421 accatctgcg agcctgccc agtcggcttc ttctccaatg tgtcatctgc ttcgaaaaa
481 tgtcaccctt ggacaagctg tgagaccaaa gacctggttg tgcaacaggc aggcacaaac
541 aagactgatg ttgtctgtgg tccccaggat cggctgagag ccctggtggt gatccccatc
601 atcttcggga tcctgtttgc catcctcttg gtgctggtct tatcaaaaa ggtggccaag
661 aagccaacca ataaggcccc caccccaag caggaacccc aggagatcaa tttcccgac
721 gatcttcctg gctccaacac tgctgctcca gtgcaggaga ctttacatgg atgccaaccg
781 gtcacccagg aggatggcaa agagagtcgc atctcagtgc aggagagaca gtga
```

FIGURE 12D

Encoded long isoform of human CD40:

```
  1 mvrlplqcvl wgclltavhp epptacrekq ylinsqccsl cqpgqklvsd cteftetecl
 61 pcgesefldt wnrethchqh kycdpnlglr vqqkgtsetd ticceegwh ctseacescv
121 lhrscspgfg vkqiatgvsd ticepcpvgf fsnvssafek chpwtscetk dlvvqqagtn
181 ktdvvcgpqd rlralvvipi ifgilfaill vlvfikkvak kptnkaphpk qepqeinfpd
241 dlpgsntaap vqetlhgcqp vqedgkesr isvqerq
```

FIGURE 18A
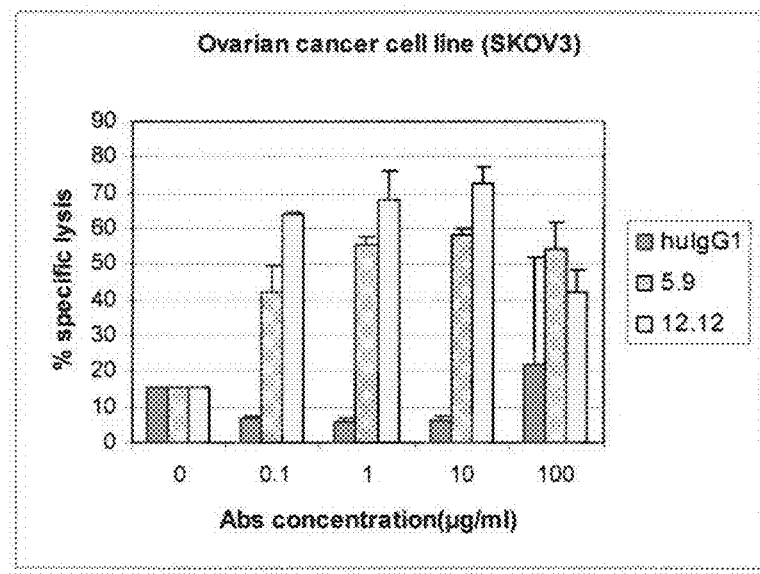
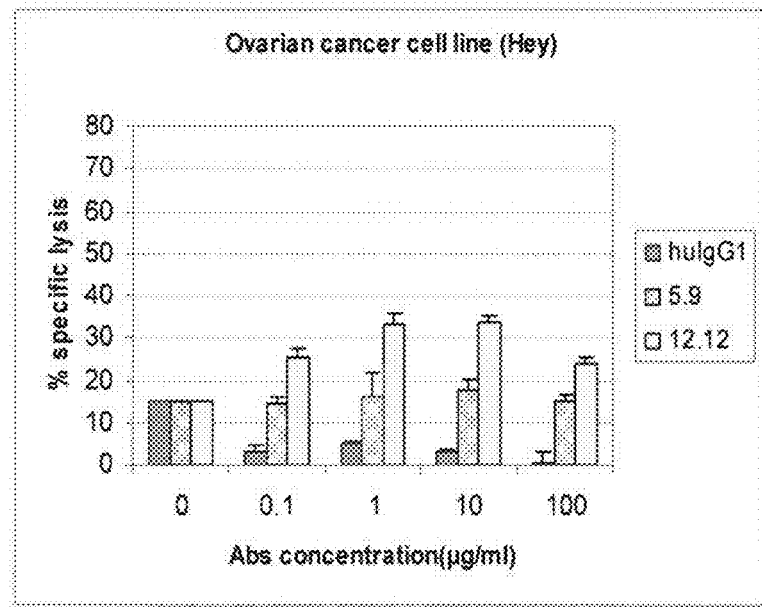
FIGURE 18B

FIGURE 19A
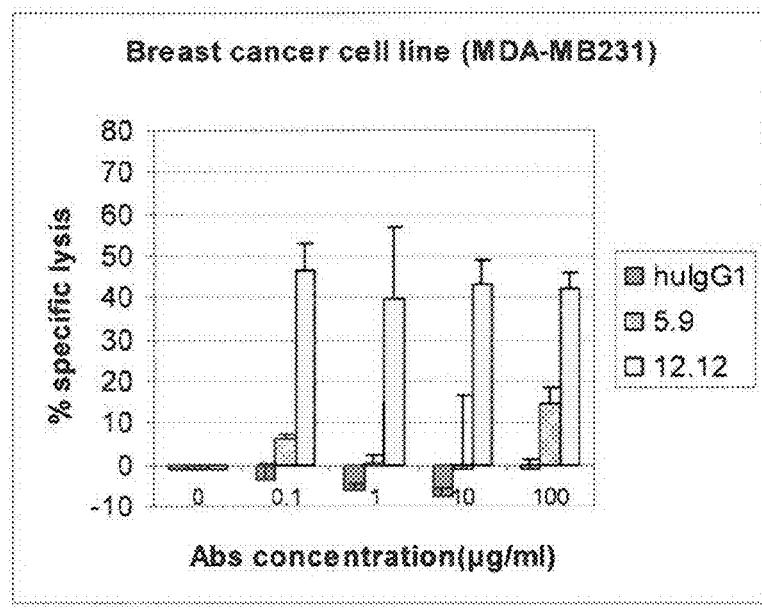
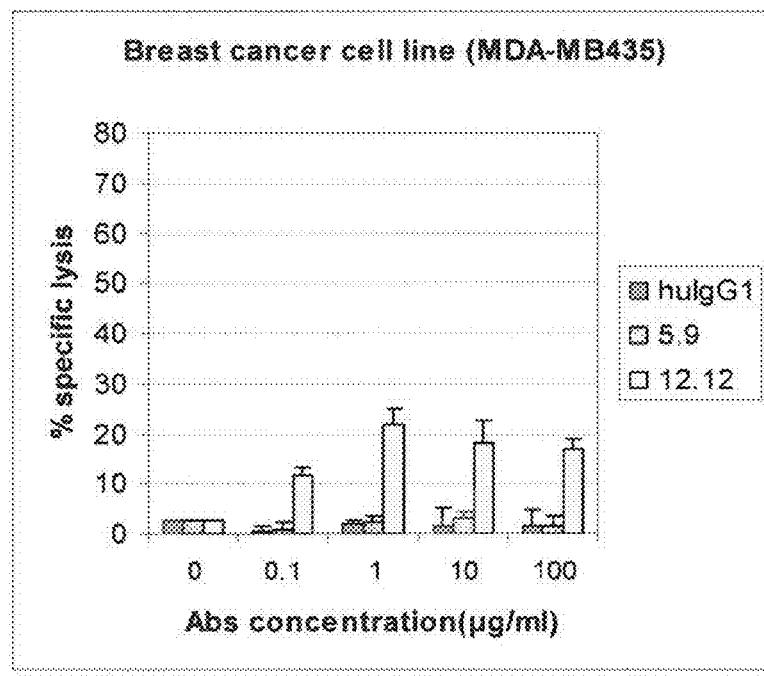
FIGURE 19B

FIGURE 19C
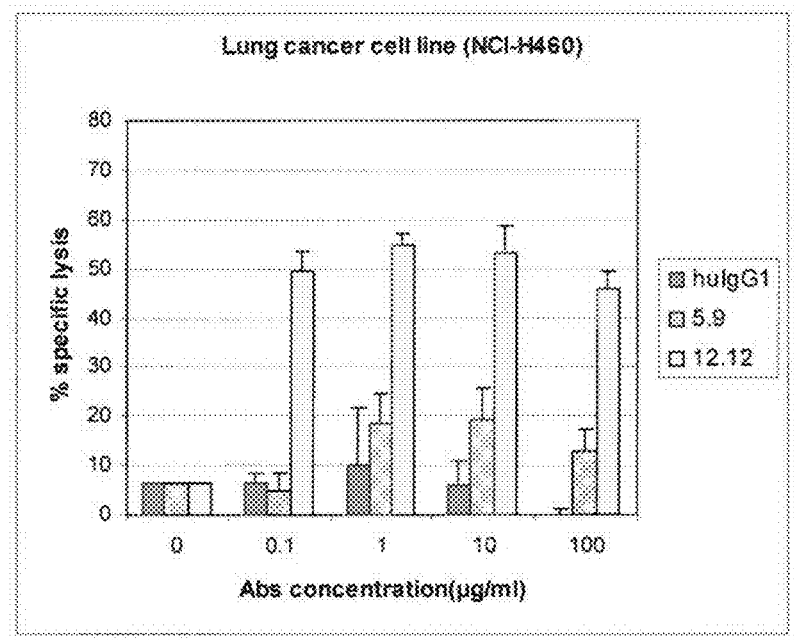
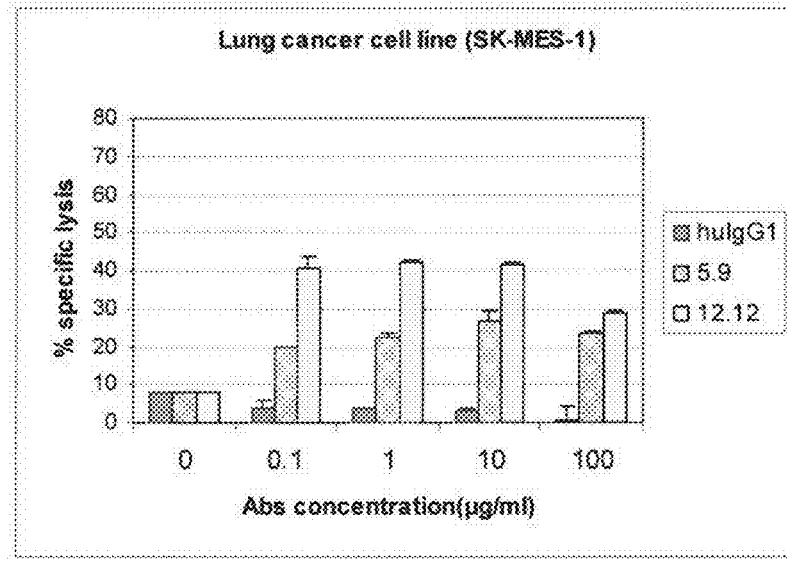
FIGURE 19D

ANTAGONIST ANTI-CD40 MONOCLONAL ANTIBODIES AND METHODS FOR THEIR USE

CROSS REFERENCE TO RELATED APPLICATIONS

This application is a divisional of U.S. application Ser. No. 11/932,472, filed Oct. 31, 2007, now U.S. Pat. No. 8,277,810, which is a continuation-in-part of U.S. application Ser. No. 10/577,390, now abandoned, which is a national-stage application of International Application No. PCT/US2004/037152, filed Nov. 4, 2004, which claims the benefit of U.S. Provisional Application Nos. 60/517,337, filed Nov. 4, 2003, 60/525,579, filed Nov. 26, 2003, and 60/565,710, filed Apr. 27, 2004. U.S. application Ser. No. 11/932,472 is also a continuation-in-part of U.S. application Ser. No. 10/578,387, now abandoned, which is a national-stage application of International Application No. PCT/US2004/037281, filed Nov. 4, 2004, which claims the benefit of U.S. Provisional Application Nos. 60/517,337, filed Nov. 4, 2003, 60/525,579, filed Nov. 26, 2003, 60/565,709, filed Apr. 26, 2004, and 60/565,710, filed Apr. 27, 2004. U.S. application Ser. No. 11/932,472 is also a continuation-in-part of U.S. application Ser. No. 10/577,642, now abandoned, which is a national-stage application of International Application No. PCT/US2004/036954, which claims the benefit of U.S. Provisional Application Nos. 60/517,337, filed Nov. 4, 2003, 60/525,579, filed Nov. 26, 2003, 60/565,710, filed Apr. 27, 2004, and 60/611,794, filed Sep. 21, 2004. U.S. application Ser. No. 11/932,472 is also a continuation-in-part of U.S. application Ser. No. 10/578,400, now abandoned, which is a national-stage application of International Application No. PCT/US2004/036955, which claims the benefit of U.S. Provisional Application Nos. 60/517,337, filed Nov. 4, 2003, 60/525,579, filed Nov. 26, 2003, 60/565,710, filed Apr. 27, 2004, and 60/565,634, also filed Apr. 27, 2004. U.S. application Ser. No. 11/932,472 is also a continuation-in-part of U.S. application Ser. No. 10/578,401, now abandoned, which is a national-stage application of International Application No. PCT/US2004/037159, filed Nov. 4, 2004, which claims the benefit of U.S. Provisional Application Nos. 60/517,337, filed Nov. 4, 2003, 60/525,579, filed Nov. 26, 2003, 60/565,710, filed Apr. 27, 2004, and 60/613,885, filed Sep. 28, 2004. U.S. application Ser. No. 11/932,472 is also a continuation-in-part of U.S. application Ser. No. 10/578,590, now abandoned, which is a national-stage application of International Application No. PCT/US2004/036958, which claims the benefit of U.S. Provisional Application Nos. 60/517,337, filed Nov. 4, 2003, 60/525,579, filed Nov. 26, 2003, and 60/565,710, filed Apr. 27, 2004. U.S. application Ser. No. 11/932,472 is also a continuation-in-part of U.S. application Ser. No. 10/576,943, now abandoned, which is a national-stage application of International Application No. PCT/US2004/036957, filed Nov. 4, 2004, which claims the benefit of U.S. Provisional Application Nos. 60/517,337, filed Nov. 4, 2003, 60/525,579, filed Nov. 26, 2003, and 60/565,710, filed Apr. 27, 2004. The contents of each of these applications are herein incorporated by reference in their entirety.

FIELD OF THE INVENTION

The invention relates to human antibodies capable of binding to CD40, methods of using the antibodies, and methods for treatment of diseases mediated by stimulation of CD40 signaling on CD40-expressing cells.

BACKGROUND OF THE INVENTION

B cells play an important role during the normal in vivo immune response. A foreign antigen will bind to surface immunoglobulins on specific B cells, triggering a chain of events including endocytosis, processing, presentation of processed peptides on MHC-class II molecules, and up-regulation of the B7 antigen on the B cell surface. A specific T cell then binds to the B cell via T cell receptor (TCR) recognition of the processed antigen presented on the MHC-class II molecule. Stimulation through the TCR activates the T cell and initiates T-cell cytokine production. A second signal that further activates the T cell is an interaction between the CD28 antigen on T cells and the B7 antigen on B cells. When the above-mentioned signals are received, the CD40 ligand (CD40L or CD154), which is not expressed on resting human T cells, is up-regulated on the T-cell surface. Binding of the CD40 ligand to the CD40 antigen on the B cell membrane provides a positive costimulatory signal that stimulates B cell activation and proliferation, causing the B cell to mature into a plasma cell secreting high levels of soluble immunoglobulin.

CD40 is a 55 kDa cell-surface antigen present on the surface of normal and neoplastic human B cells, dendritic cells, other antigen presenting cells (APCs), endothelial cells, monocytic cells, $CD8^+$ T cells, epithelial cells, some epithelial carcinomas, and many solid tumors, including lung, breast, ovary, and colon cancers. Malignant B cells from several tumors of B-cell lineage express a high level of CD40 and appear to depend on CD40 signaling for survival and proliferation. Thus, transformed cells from patients with low- and high-grade B-cell lymphomas, B-cell acute lymphoblastic leukemia, multiple myeloma, chronic lymphocytic leukemia, and Hodgkin's disease express CD40. CD40 expression is also detected in two-thirds of acute myeloblastic leukemia cases and 50% of AIDS-related lymphomas. Importantly, CD40 is found on a higher percentage of multiple myelomas compared with CD20 (Maloney et al. (1999) *Semin. Hematol.* 36(Suppl. 3):30-33).

Immunoblastic B-cell lymphomas frequently arise in immunocompromised individuals such as allograft recipients and others receiving long-term immunosuppressive therapy, AIDS patients, and patients with primary immunodeficiency syndromes such as X-linked lymphoproliferative syndrome or Wiscott-Aldrich syndrome (Thomas et al. (1991) *Adv. Cancer Res.* 57:329; Straus et al. (1993) *Ann. Intern. Med.* 118:45).

The CD40 antigen is related to the human nerve growth factor (NGF) receptor, tumor necrosis factor-α (TNF-α) receptor, and Fas, suggesting that CD40 is a receptor for a ligand with important functions in B-cell activation. It has been shown to play a critical role in normal B-cell development and function. CD40 expression on APCs plays an important co-stimulatory role in the activation of both T-helper and cytotoxic T lymphocytes. The CD40 antigen is also expressed on activated T cells, activated platelets, inflamed vascular smooth muscle cells eosinophils, synovial membranes in rheumatoid arthritis, dermal fibroblasts, and other non-lymphoid cell types. Depending on the type of cell expressing CD40, ligation can induce intercellular adhesion, differentiation, activation, and proliferation. For example, binding of CD40 to its cognate ligand, CD40L (also designated CD154), stimulates B-cell proliferation and differentiation into plasma cells, antibody production, isotype switching, and B-cell memory generation. During B-cell differentiation, CD40 is expressed on pre-B cells but lost upon differentiation into plasma cells.

Multiple myeloma (MM) is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system. Approximately 1% of all cancers, and slightly more than 10% of all hematologic malignancies, can be attributed to multiple myeloma. Incidence of MM increases in the aging population, with the median age at time of diagnosis being about 61 years. Current treatment protocols, which include a combination of chemotherapeutic agents such as vincristine, BCNU, melphalan, cyclophosphamide, Adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood progenitor cell (PBMC) transplantation have increased the complete remission rate and remission duration. Yet overall survival has only been slightly prolonged, and no evidence for a cure has been obtained. Ultimately, all MM patients relapse, even under maintenance therapy with interferon-alpha (IFN-α) alone or in combination with steroids.

Efficacy of the available chemotherapeutic treatment regimens for MM is limited by the low cell proliferation rate and development of multi-drug resistance. For more than 90% of MM patients, the disease becomes chemoresistant. As a result, alternative treatment regimens aimed at adoptive immunotherapy targeting surface antigens such as CD20 and CD40 on plasma cells are being sought. Given the poor prognosis for patients with multiple myeloma, alternative treatment protocols are needed.

Chronic lymphocytic leukemia (CLL) is a B cell malignancy characterized by neoplastic cell proliferation and accumulation in bone marrow, blood, lymph nodes, and the spleen. CLL is the most common type of adult leukemia in the Western hemisphere. Incidence of CLL increases in the aging population, with the median age at time of diagnosis being about 65 years. Current treatment protocols include chemotherapeutic agents such as fludarabine, 2-chlorodeoxyadenosine (cladribine), chlorambucil, vincristine, pentostatin, cyclophosphamide, alemtuzumab (Campath-1H), doxorubicin, and prednisone. Fludarabine is the most effective chemotherapeutic with response rates of 17 to 74%, but CLL often becomes refractory to repeated courses of the drug (Rozman and Montserrat (1995) *NEJM* 2133:1052).

The median survival rate for CLL patients is nine years, although some patients with mutated immunoglobulin genes have a more favorable prognosis. See, for example, Rozman and Montserrat (1995) *NEJM* 2133:1052) and Keating et al. (2003) *Hematol.* 2003:153. In cases where CLL has transformed into large-cell lymphoma, median survival drops to less than one year; similarly, cases of prolymphocytic leukemia have a poorer prognosis than classical CLL (Rozman and Montserrat (1995) *NEJM* 2133:1052). To date, no evidence for a cure has been obtained. Given the poor prognosis for patients with chronic lymphocytic leukemia, alternative treatment protocols are needed.

CD40-expressing carcinomas include urinary bladder carcinoma (Paulie et al. (1989) *J. Immunol.* 142:590-595; Braesch-Andersen et al. (1989) *J. Immunol.* 142:562-567), breast carcinoma (Hirano et al. (1999) *Blood* 93:2999-3007; Wingett et al. (1998) *Breast Cancer Res. Treat.* 50:27-36); prostate cancer (Rokhlin et al. (1997) *Cancer Res.* 57:1758-1768), renal cell carcinoma (Kluth et al. (1997) *Cancer Res.* 57:891-899), undifferentiated nasopharyngeal carcinoma (UNPC) (Agathanggelou et al. (1995) *Am. J. Pathol.* 147:1152-1160), squamous cell carcinoma (SCC) (Amo et al. (2000) *Eur. J. Dermatol.* 10:438-442; Posner et al. (1999) *Clin. Cancer Res.* 5:2261-2270), thyroid papillary carcinoma (Smith et al. (1999) *Thyroid* 9:749-755), cutaneous malignant melanoma (van den Oord et al. (1996) *Am. J. Pathol.* 149:1953-1961), multiple myeloma (Maloney et al. (1999) *Semin. Hematol.* 36(1 Suppl 3):30-33), Hodgkin and Reed-Sternberg cells (primed cells) (Gruss et al. (1994) *Blood* 84:2305-2314), gastric carcinoma (Yamaguchi et al. (2003) *Int. J. Oncol.* 23(6):1697-702), sarcomas (see, for example, Lollini et al. (1998) *Clin. Cancer Res.* 4(8):1843-849, discussing human osteosarcoma and Ewing's sarcoma), and liver carcinoma (see, for example, Sugimoto et al. (1999) *Hepatology* 30(4):920-26, discussing human hepatocellular carcinoma). Though some carcinoma cells exhibit high levels of CD40 expression, the role of CD40 signaling in relation to CD40 expression on these cancer cells is less well understood. A majority of the cancer cases are represented by the so-called solid tumors. Given their high incidence, methods for treating these cancers are needed.

The CD40 ligand has been identified on the cell surface of activated T cells (Fenslow et al. (1992) *J. Immunol.* 149:655; Lane et al. (1992) *Eur. J. Immunol.* 22:2573; Noelle et al. (1992) *Proc. Natl. Acad. Sci. USA* 89:6550), but is not generally expressed on resting human T cells. CD40L is a type-II transmembrane glycoprotein with homology to TNF-α (Armitage et al. (1992) *Nature* 357:80 and Spriggs et al. (1992) *J. Exp. Med.* 176:1543). The extracellular domain of CD40L contains two arginine residues proximal to the transmembrane region, providing a potential proteolytic cleavage site that gives rise to a soluble form of the ligand (sCD40L). Overexpression of CD40L causes autoimmune diseases similar to systemic lupus erythromatosus in rodent models (Higuchi et al. (2002) *J. Immunol.* 168:9-12). In contrast, absence of functional CD40L on activated T cells causes X-linked hyper-IgM syndrome (Allen et al. (1993) *Science* 259:990; and Korthauer et al. (1993) *Nature* 361:539). Further, blocking of CD40/CD40L interaction can prevent transplant rejection in non-human primate models. See, for example, Wee et al. (1992) *Transplantation* 53:501-7.

CD40 expression on APCs plays an important co-stimulatory role in the activation of these cells. For example, agonistic anti-CD40 monoclonal antibodies (mAbs) have been shown to mimic the effects of T helper cells in B-cell activation. When presented on adherent cells expressing FcγRII, these antibodies induce B-cell proliferation (Banchereau et al. (1989) *Science* 251:70). Moreover, agonistic anti-CD40 mAbs can replace the T helper signal for secretion of IgM, IgG, and IgE in the presence of IL-4 (Gascan et al. (1991) *J. Immunol.* 147:8). Furthermore, agonistic anti-CD40 mAbs can prevent programmed cell death (apoptosis) of B cells isolated from lymph nodes.

These and other observations support the current theory that the interaction of CD40 and CD40L plays a pivotal role in regulating both humoral and cell-mediated immune responses. More recent studies have revealed a much broader role of CD40/CD40L interaction in diverse physiological and pathological processes.

The CD40 signal transduction pathway depends on the coordinated regulation of many intracellular factors. Like other members of the TNF receptor family, CD40 reacts with TRAF proteins (TNF receptor factor-associated proteins) such as TRAF2 and TRAF3, which mediate an intracellular signal following engagement of CD40 with CD40L (either solid phase CD40L or soluble CD40L). The TRAFs transduce a signal into the nucleus via map kinases such as NIK (NF-κB inducing kinase) and I-kappa B kinases (IKK α/β), ultimately activating the transcription factor NF-κB (Young et al. (1998) *Immunol. Today* 19:502-06). Signaling via Ras and the MEK/ERK pathway has also been demonstrated in a subset of B cells. Additional pathways involved in CD40 cell signaling include PI3K/Akt pathway and P38 MAPK pathway (Craxton et al. (1998) *J. Immunol.* 5:439-447).

Signaling via CD40 has been shown to prevent cell death from apoptosis (Makus et al. (2002) *J. Immunol.* 14:973-982). Apoptotic signals are necessary to induce programmed cell death in a coordinated manner. Cell death signals can include intrinsic stimuli from within the cell such as endoplasmic reticulum stress or extrinsic stimuli such as receptor binding of FasL or TNFα. The signaling pathway is complex, involving activation of caspases such as caspase 3 and 9, and of poly (ADP ribose) polymerase (PARP). During the cascade, anti-apoptotic signaling proteins, such as Mcl-1 and BCLx, and members of the IAP-family proteins, such as X-Linked Inhibitor of Apoptosis (XIAP), are down-regulated (Budihardjo et al. (1999) *Annu. Rev. Cell Dev. Biol.* 15:269-90). For example, in dendritic cells, CD40 cell signaling can block apoptosis signals transduced by FasL (Bjorck et al. (1997) *Int'l Immunol.* 9:365-372).

Thus, CD40 engagement by CD40L and subsequent activation of CD40 signaling are necessary steps for normal immune responses; however, dysregulation of CD40 signaling can lead to disease. The CD40 signaling pathway has been shown to be involved autoimmune disease (Ichikawa et al. (2002) *J. Immunol.* 169:2781-7 and Moore et al. (2002) *J. Autoimmun.* 19:139-45). Additionally, the CD40/CD40L interaction plays an important role in inflammatory processes. For example, both CD40 and CD40 ligand are overexpressed in human and experimental atherosclerosis lesions. CD40 stimulation induces expression of matrix-degrading enzymes and tissue factor expression in atheroma-associated cell types, such as endothelial cells, smooth muscle cells, and macrophages. Further, CD40 stimulation induces production of proinflammatory cytokines such as IL-1, IL-6, and IL-8, and adhesion molecules such as ICAM-1, E-selectin, and VCAM. Inhibition of CD40/CD40L interaction prevents atherogenesis in animal models. In transplant models, blocking CD40/CD40L interaction prevents inflammation. It has been shown that CD40/CD40L binding acts synergistically with the Alzheimer amyloid-beta peptide to promote microglial activation, thus leading to neurotoxicity.

In patients with rheumatoid arthritis (RA), CD40 expression is increased on articular chondrocytes, thus, CD40 signaling likely contributes to production of damaging cytokines and matrix metalloproteinases. See, Gotoh et al. (2004) *J. Rheumatol.* 31:1506-12. Further, it has been shown that amplification of the synovial inflammatory response occurs through activation of mitogen-activated protein (MAP) kinases and nuclear factor kappaB (NFκB) via ligation of CD40 on CD14$^+$ synovial cells from RA patients (Harigai et al. (2004) *Arthritis. Rheum.* 50:2167-77). In an experimental model of RA, anti-CD40L antibody treatment prevented disease induction, joint inflammation, and anti-collagen antibody production (Durie et al. (1993) *Science* 261:1328). Finally, in clinical trials, it has been shown that depleting CD20$^+$ positive B cells of RA patients by administering RITUXAN® (generally indicated for B cell lymphoma) improves symptoms. (Shaw et al. (2003) *Ann. Rheum. Dis.* 62:ii55-ii59).

Blocking CD40/CD40L interactions during antigen presentation to T cells has also been shown to induce T cell tolerance. Therefore, blocking CD40/CD40L interaction prevents initial T cell activation as well as induces long term tolerance to re-exposure to the antigen.

Given the critical role of CD40L-mediated CD40 signaling in maintenance of normal immunity, methods are needed for intervention into this signaling pathway when dysregulation occurs.

BRIEF SUMMARY OF THE INVENTION

Compositions and methods are provided for treating diseases mediated by stimulation of CD40 signaling on CD40-expressing cells, including lymphomas, solid tumors, and autoimmune and inflammatory diseases, including transplant rejections. Compositions include monoclonal antibodies capable of binding to a human CD40 antigen located on the surface of a human CD40-expressing cell, wherein the binding prevents the growth or differentiation of the cell. Compositions also include monoclonal antibodies capable of specifically binding to a human CD40 antigen expressed on the surface of a human CD40-expressing cell, said monoclonal antibody being free of significant agonist activity, wherein administration of said monoclonal antibody results in significantly less tumor volume than a similar concentration of the chimeric anti-CD20 monoclonal antibody IDEC-C2B8 in a staged nude mouse xenograft tumor model using the Daudi human B cell lymphoma cell line. Compositions also include antigen-binding fragments of these monoclonal antibodies, hybridoma cell lines producing these antibodies, and isolated nucleic acid molecules encoding the amino acid sequences of these monoclonal antibodies. The invention further includes pharmaceutical compositions comprising these anti-CD40 antibodies in a pharmaceutically acceptable carrier.

Methods are provided for preventing or treating a disease mediated by stimulation of CD40 signaling, comprising treating the patient with an anti-CD40 antibody or an antigen-binding fragment thereof that is free of significant agonist activity when bound to a CD40 antigen on a human CD40-expressing cell. Diseases mediated by stimulation of CD40-expressing cells include, for example, cancers and autoimmune and inflammatory diseases, including organ and tissue graft rejections. Lymphomas that can be treated or prevented by a method of the present invention include, for example, non-Hodgkin's lymphomas (high-grade lymphomas, intermediate-grade lymphomas, and low-grade lymphomas), Hodgkin's disease, acute lymphoblastic leukemias, myelomas, chronic lymphocytic leukemias, and myeloblastic leukemias.

Particular autoimmune diseases contemplated for treatment using the methods of the invention include systemic lupus erythematosus (SLE), rheumatoid arthritis, Crohn's disease, psoriasis, autoimmune thrombocytopenic purpura, multiple sclerosis, ankylosing spondylitis, myasthenia gravis, and pemphigus vulgaris. Such antibodies could also be used to prevent rejection of organ and tissue grafts by suppressing autoimmune responses, to treat lymphomas by depriving malignant B lymphocytes of the activating signal provided by CD40, and to deliver toxins to CD40-bearing cells in a specific manner.

Methods for inhibiting the growth, differentiation, and/or proliferation of human B cells and for inhibiting antibody production by B cells in a human patient are provided, as are methods for inhibiting the growth of cancer cells of a B-cell lineage. Methods for identifying antibodies that have antagonist activity toward CD40-expressing cells are also provided.

The monoclonal antibodies disclosed herein have a strong affinity for CD40 and are characterized by a dissociation equilibrium constant ($K_D$) of at least $10^{-6}$ M, preferably at least about $10^{-7}$ M to about $10^{-8}$ M, more preferably at least about $10^{-8}$ M to about $10^{-12}$ M. Monoclonal antibodies and antigen-binding fragments thereof that are suitable for use in the methods of the invention are capable of specifically binding to a human CD40 antigen expressed on the surface of a human cell. They are free of significant agonist activity but exhibit antagonist activity when bound to CD40 antigen on human cells. In one embodiment, the anti-CD40 antibody or fragment thereof exhibits antagonist activity when bound to CD40 antigen on normal human B cells. In another embodiment, the anti-CD40 antibody or fragment thereof exhibits antagonist activity when bound to CD40 antigen on malignant human B cells. Suitable monoclonal antibodies have human constant regions; preferably they also have wholly or partially humanized framework regions; and most preferably are fully human antibodies or antigen-binding fragments thereof.

Examples of such monoclonal antibodies are the antibodies designated herein as CHIR-5.9 and CHIR-12.12; the monoclonal antibodies produced by the hybridoma cell lines designated 131.2F8.5.9 (referred to herein as the cell line 5.9) and 153.8E2.D10.D6.12.12 (referred to herein as the cell line 12.12); a monoclonal antibody comprising an amino acid sequence selected from the group consisting of the sequence shown in SEQ ID NO:6, the sequence shown in SEQ ID NO:7, the sequence shown in SEQ ID NO:8, both the sequence shown in SEQ ID NO:6 and SEQ ID NO:7, and both the sequence shown in SEQ ID NO:6 and SEQ ID NO:8; a monoclonal antibody comprising an amino acid sequence selected from the group consisting of the sequence shown in SEQ ID NO:2, the sequence shown in SEQ ID NO:4, the sequence shown in SEQ ID NO:5, both the sequence shown in SEQ ID NO:2 and SEQ ID NO:4, and both the sequence shown in SEQ ID NO:2 and SEQ ID NO:5; a monoclonal antibody comprising an amino acid sequence encoded by a nucleic acid molecule comprising a nucleotide sequence selected from the group consisting of the sequence shown in SEQ ID NO:1, the sequence shown in SEQ ID NO:3, and both the sequence shown in SEQ ID NO:1 and SEQ ID NO:3; and antigen-binding fragments of these monoclonal antibodies that retain the capability of specifically binding to human CD40, and which are free of significant agonist activity but exhibit antagonist activity when bound to CD40 antigen on human cells. Examples of such monoclonal antibodies also include a monoclonal antibody that binds to an epitope capable of binding the monoclonal antibody produced by the hybridoma cell line 12.12; a monoclonal antibody that binds to an epitope comprising residues 82-87 of the amino acid sequence shown in SEQ ID NO:10 or SEQ ID NO:12; a monoclonal antibody that competes with the monoclonal antibody CHIR-12.12 in a competitive binding assay; and a monoclonal antibody that is an antigen-binding fragment of the CHIR-12.12 monoclonal antibody or any of the foregoing monoclonal antibodies, where the fragment retains the capability of specifically binding to the human CD40 antigen. Those skilled in the art recognize that the antagonist antibodies and antigen-binding fragments of these antibodies disclosed herein include antibodies and antigen-binding fragments thereof that are produced recombinantly using methods well known in the art and described herein below, and include, for example, monoclonal antibodies CHIR-5.9 and CHIR-12.12 that have been recombinantly produced.

In one embodiment of the invention, methods of treatment comprise administering to a patient a therapeutically effective dose of a pharmaceutical composition comprising suitable antagonist anti-CD40 antibodies or antigen-binding fragments thereof. A therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody or antigen-binding fragment thereof.

The antagonist anti-CD40 antibodies identified herein as being suitable for use in the methods of the invention may be modified. Modifications of these antagonist anti-CD40 antibodies include, but are not limited to, immunologically active chimeric anti-CD40 antibodies, humanized anti-CD40 antibodies, and immunologically active murine anti-CD40 antibodies.

Thus, in one aspect of the invention, methods are provided for treating a human subject with multiple myeloma, comprising administering to the subject an anti-CD40 antibody or an antigen-binding fragment thereof that is free of significant agonist activity when bound to a CD40 antigen on a human CD40-expressing cell. Methods for inhibiting growth of multiple myeloma cells expressing CD40 antigen are also provided. Suitable antagonist anti-CD40 antibodies for use in these methods include the antagonist anti-CD40 antibodies of the invention, for example, the antibodies summarized herein above and further described herein below.

In another aspect of the invention, methods are provided for treating a human subject with chronic lymphocytic leukemia (CLL), comprising administering to the subject an anti-CD40 antibody or an antigen-binding fragment thereof that is free of significant agonist activity when bound to a CD40 antigen on a human CD40-expressing cell. Methods for inhibiting growth of CLL cells expressing CD40 antigen are also provided. Suitable antagonist anti-CD40 antibodies for use in these methods include the antagonist anti-CD40 antibodies of the invention, for example, the antibodies summarized herein above and further described herein below.

In yet another aspect of the invention, methods are provided for treating a subject for a solid tumor, where the carcinoma cells of the solid tumor express the CD40 cell-surface antigen. The methods comprise treating the subject with an antagonist anti-CD40 monoclonal antibody or an antigen-binding fragment thereof that is free of significant agonist activity when bound to CD40 antigen on a human CD40-expressing cell. Binding of the antagonist anti-CD40 monoclonal antibody (or suitable antigen-binding fragment thereof comprising the Fc portion of the antagonist anti-CD40 antibody) to CD40 antigen expressed on carcinoma cells results in antibody-dependent cell-mediated cytotoxicity (ADCC)-dependent killing of these carcinoma cells. In some embodiments, the antagonist anti-CD40 antibodies are administered in combination with one or more other cancer therapy protocols, including, but not limited to, surgery, radiation therapy, chemotherapy, cytokine therapy, or other monoclonal antibody intended for use in treatment of the solid tumor. Solid tumors that can be treated or prevented by the methods of the present invention include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas). Methods for inhibiting the growth of solid tumors comprising CD40-expressing carcinoma cells are also provided. Suitable antagonist anti-CD40 antibodies for use in these methods include the antagonist anti-CD40 antibodies of the invention, for example, the antibodies summarized herein above and further described herein below.

In still another aspect of the invention, methods of treating a subject for a cancer characterized by neoplastic B cell growth are provided. The methods comprise administering a combination of antibodies that have a therapeutic effect against neoplastic B cells expressing the CD40 and CD20 cell surface antigens. In some embodiments, a synergistic therapeutic effect occurs, making the invention especially useful for treating cancers that are refractory to antibody therapy that targets a single B cell surface antigen. In accordance with these methods of the present invention, an individual in need thereof is administered a combination of an antagonist anti-CD40 antibody (or antigen-binding fragment thereof) and an anti-CD20 antibody (or antigen-binding fragment thereof). Suitable antagonist anti-CD40 antibodies for use in these methods include the antagonist anti-CD40 antibodies of the invention, for example, the antibodies summarized herein above and further described herein below.

Suitable anti-CD20 antibodies for practicing this aspect of the invention include, but are not limited to, the chimeric monoclonal antibody IDEC-C2B8 (Rituxan® or rituximab); and anti-CD20 antibodies having the binding characteristics of IDEC-C2B8, where the anti-CD20 antibodies compete with the IDEC-C2B8 antibody in a competitive binding assay or bind to an epitope capable of binding the IDEC-C2B8 antibody. The methods of the invention are particularly effective when antagonist anti-CD40 antibodies produced by a hybridoma such as 5.9 or 12.12 are administered in combination with an anti-CD20 antibody such as IDEC-C2B8. The invention further includes pharmaceutical compositions comprising such combinations of antibodies in a pharmaceutically acceptable carrier.

These methods of the invention are useful for treating individuals with B cell lymphomas such as non-Hodgkin's lymphomas (high-grade lymphomas, intermediate-grade lymphomas, and low-grade lymphomas), Hodgkin's disease, acute lymphoblastic leukemias, myelomas, chronic lymphocytic leukemias, and myeloblastic leukemias, and are particularly useful for treatment of B cell-related cancers that are refractory to treatment with single antibody therapy that targets the CD20 cell surface antigen.

In yet another aspect of the invention, methods of treating a subject for a cancer comprising neoplastic cells expressing the CD40 cell surface antigen are provided. The methods comprise combination therapy with interleukin-2 (IL-2) or biologically active variant thereof and at least one anti-CD40 antibody or antigen-binding fragment thereof. Administering these two agents in combination provides for greater effectiveness than either agent alone, resulting in a positive therapeutic response. In some embodiments, a synergistic therapeutic effect occurs, making the invention especially useful for treating cancers that are refractory to single-agent therapy.

In accordance with the methods of the present invention, an individual in need thereof is administered a combination of an IL-2 or biologically active variant thereof and an antagonist anti-CD40 antibody or antigen-binding fragment thereof. Suitable interleukin molecules include human IL-2 and biologically active variants thereof, such as the IL-2 mutein aldesleukin (des-alanyl-1, serine-125 human interleukin-2). Suitable antagonist anti-CD40 antibodies for use in these methods include the antagonist anti-CD40 antibodies of the invention, for example, the antibodies summarized herein above and further described herein below.

In some embodiments, these two therapeutic agents are concurrently administered as two separate pharmaceutical compositions, one containing IL-2 or biologically active variant thereof, the other containing the antagonist anti-CD40 antibody or suitable antigen-binding fragment thereof, wherein each is administered according to a particular dosing regimen. The pharmaceutical composition comprising the antagonist anti-CD40 antibody or antigen-binding fragment thereof is administered according to a weekly dosing schedule, or alternatively is dosed once every two, three, or four weeks. The antagonist anti-CD40 antibody or antigen-binding fragment thereof can be dosed throughout a treatment period or for a fixed duration within a treatment period. The pharmaceutical composition comprising IL-2 or biologically active variant thereof is administered according to a constant IL-2 dosing regimen, or is administered according to a two-level IL-2 dosing regimen.

The constant IL-2 dosing regimen comprises a time period during which a constant total weekly dose of IL-2 or biologically active variant thereof is administered to the subject followed by a time period off of IL-2 dosing. One or more cycles of a constant IL-2 dosing regimen are administered to a subject in need thereof. The total weekly dose to be administered during each cycle of the constant IL-2 dosing regimen can be administered as a single dose. Alternatively, the total weekly dose administered during each cycle of the constant IL-2 dosing regimen can be partitioned into a series of equivalent doses that are administered according to a two-, three-, four-, five-, six- or seven-times-a-week dosing schedule.

The two-level IL-2 dosing regimen comprises a first time period of IL-2 dosing, wherein a higher total weekly dose of IL-2 or biologically active variant thereof is administered to the subject, followed by a second time period of IL-2 dosing, wherein a lower total weekly dose of IL-2 or biologically active variant thereof is administered to the subject. The total weekly dose of IL-2 or biologically active variant thereof during the second time period of IL-2 dosing is lower than the total weekly dose of IL-2 or biologically active variant thereof administered during the first time period of IL-2 dosing. The total weekly dose to be administered during the first time period and/or during the second time period of IL-2 dosing can be administered as a single dose. Alternatively, the total weekly dose administered during either or both of the first and second time periods of IL-2 dosing can be partitioned into a series of equivalent doses that are administered according to a two-, three-, four-, five-, six- or seven-times-a-week dosing schedule. The methods of the invention also provide for an interruption in the two-level dosing regimen of IL-2, where the subject is given a time period off of IL-2 administration, and, optionally a time period off of the anti-CD40 antibody dosing, between the first and second time periods of the two-level IL-2 dosing regimen. Concurrent therapy with these two therapeutic agents can comprise administering one or more cycles of a two-level IL-2 dosing regimen in combination with the recommended dosing regimen for the antagonist anti-CD40 antibody or suitable antigen-binding fragment thereof.

These methods of the invention are useful for treating individuals for a cancer comprising neoplastic cells expressing the CD40 cell surface antigen. Examples of such cancers include, but are not limited to, solid tumors, such as lung, ovarian, bladder, kidney, liver, gastric, prostate, skin, and breast cancer, and sarcomas, and B cell-related cancers, such as non-Hodgkin's lymphomas (high-grade lymphomas, intermediate-grade lymphomas, and low-grade lymphomas), Hodgkin's disease, acute lymphoblastic leukemias, myelomas, chronic lymphocytic leukemias, and myeloblastic leukemias.

In still another embodiment, Methods are provided for treating a human subject with an autoimmune disease and/or inflammatory disease, comprising administering to the subject an anti-CD40 antibody or an antigen-binding fragment thereof that is free of significant agonist activity when bound to a CD40 antigen on a human CD40-expressing cell. Methods for inhibiting the response of cells expressing CD40 antigen are also provided. Suitable antagonist anti-CD40 antibodies for use in the methods of the present invention have a strong affinity for CD40. These monoclonal antibodies and antigen-binding fragments thereof are capable of specifically binding to human CD40 antigen expressed on the surface of a human cell. They are free of significant agonist activity but exhibit antagonist activity when bound to CD40 antigen on human cells. In one embodiment, the anti-CD40 antibody or fragment thereof exhibits antagonist activity when bound to CD40 antigen on antigen presenting cells such as B cells.

The antagonist antibodies of the invention are especially useful in preventing, ameliorating, or treating diseases comprising an autoimmune and/or inflammatory component. These diseases include but are not limited to autoimmune and inflammatory diseases such as systemic lupus erythematosus (SLE), discoid lupus, lupus nephritis, sarcoidosis, inflammatory arthritis, including, but not limited to, juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, unwanted/unintended immune responses to therapeutic proteins, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like.

BRIEF DESCRIPTION OF THE DRAWINGS

FIG. 2A shows that binding of CHIR-5.9 and CHIR-12.12 monoclonal antibodies to cell surface CD40 prevents subsequent CD40-ligand binding. FIG. 2B shows that the CHIR-5.9 and CHIR-12.12 monoclonal antibodies can compete off CD40 ligand pre-bound to cell surface CD40.

(FIG. 3B) were used as effector cells in this assay. As NHL cells also express CD20, the target antigen for rituximab (Rituxan®), ADCC activity of the candidate mAbs was compared with that of rituximab.

FIG. 7 shows the number of CD20 and CD40 molecules on Namalwa and Daudi cells as determined using the following protocol: 1. Harvest and wash cells once with PBS w/o $Ca^{++}$/$Mg^{++}$ plus 0.5% BSA and 0.1% Sodium Azide. 2. Block $1^{e5}$ cells with 10% huSerum in PBS w/o $Ca^{++}$/$Mg^{++}$ plus 0.1% Sodium Azide on ice for 30 minutes. 3. Stain cells with FITC conjugated antibodies (12.12-FITC or Rituximab-FITC) on ice for 40 minutes. Cells were also stained with huIgG1-FITC for non-specific binding control. Antibody concentrations were 0.01, 0.1, 1, 10 and 100 μg per ml. 4. Determine Mean Channel Fluorescence (Geometric Mean) by flow cytometer using log amplifier. PI was added to exclude dead cells. 5. Determine Mean Channel Fluorescence (Geometric Means) of Quantum™24FITC (3,000 to 5,000 MESF*). Quantum™25FITC (50,000 to 2,000,000 MESF) and Quantum™26FITC (10,000 to 500,000 MESF) at the same instrument settings as for sample analysis. MESF: Molecules of Equivalent Soluble Fluorochrome. 6. Construct calibration curve by plotting MESF (y-axis) vs. the Geometric Means (x-axis). 7. The number of molecules per cell was determined using the following equation: y=ax^b where y is equal to MESF and x is equal to Mean Channel Fluorescence of the sample. Mean Channel Fluorescence used for each sample was the Geo Mean at saturation concentration (12.12FITC) or the highest concentration (rituximabFITC). 8. Dividing MESF of sample by the numbers of FITC molecules conjugated to each antibody (F:P ratio) to determine the antibody binding capacity (ABC). ABC of huIgGFITC of respected sample was corrected to obtain the final antibody binding capacity.

FIG. 9 sets forth the amino acid sequences for the light and heavy chains of the mAb CHIR-12.12. The leader (residues 1-20 of SEQ ID NO:2), variable (residues 21-132 of SEQ ID NO:2), and constant (residues 133-239 of SEQ ID NO:2) regions of the light chain are shown in FIG. 9A. The leader (residues 1-19 of SEQ ID NO:4), variable (residues 20-139 of SEQ ID NO:4), and constant (residues 140-469 of SEQ ID NO:4) regions of the heavy chain are shown in FIG. 9B. The alternative constant region for the heavy chain of the mAb CHIR-12.12 shown in FIG. 9B reflects a substitution of a serine residue for the alanine residue at position 153 of SEQ ID NO:4. The complete sequence for this variant of the heavy chain of the mAb CHIR-12.12 is set forth in SEQ ID NO:5.

FIG. 10 shows the coding sequence for the light chain (FIG. 10A; SEQ ID NO:1) and heavy chain (FIG. 10B; SEQ ID NO:3) for the mAb CHIR-12.12.

FIG. 11 sets forth the amino acid sequences for the light and heavy chains of mAb CHIR-5.9. The leader (residues 1-20 of SEQ ID NO:6), variable (residues 21-132 of SEQ ID NO:6), and constant (residues 133-239 of SEQ ID NO:6) regions of the light chain are shown in FIG. 11A. The leader (residues 1-19 of SEQ ID NO:7), variable (residues 20-144 of SEQ ID NO:7), and constant (residues 145-474 of SEQ ID NO:7) regions of the heavy chain are shown in FIG. 11B. The alternative constant region for the heavy chain of the mAb CHIR-5.9 shown in FIG. 11B reflects a substitution of a serine residue for the alanine residue at position 158 of SEQ ID NO:7. The complete sequence for this variant of the heavy chain of the mAB CHIR-5.9 is set forth in SEQ ID NO:8, where the leader is residues 1-19, the variable region is residues 20-144, and the constant region is residues 145-474.

FIG. 12 shows the coding sequence (FIG. 12A; SEQ ID NO:9) for the short isoform of human CD40 (amino acid sequence shown in FIG. 12B; SEQ ID NO:10), and the coding sequence (FIG. 12C; SEQ ID NO:11) for the long isoform of human CD40 (amino acid sequence shown in FIG. 12D).

FIG. 19 shows antibody-dependent cell-mediated cytotoxicity (ADCC) activity of monoclonal antibodies CHIR-5.9 and CHIR-12.12 on the breast cancer cell lines MDA-MB231 (FIG. 19A) and MDA-MB435 (FIG. 19B), and the lung cancer cell lines NCI-H460 (FIG. 19C) and SK-MES-1 (FIG. 19D).

DETAILED DESCRIPTION OF THE INVENTIONS

Figures 1A, 1B:
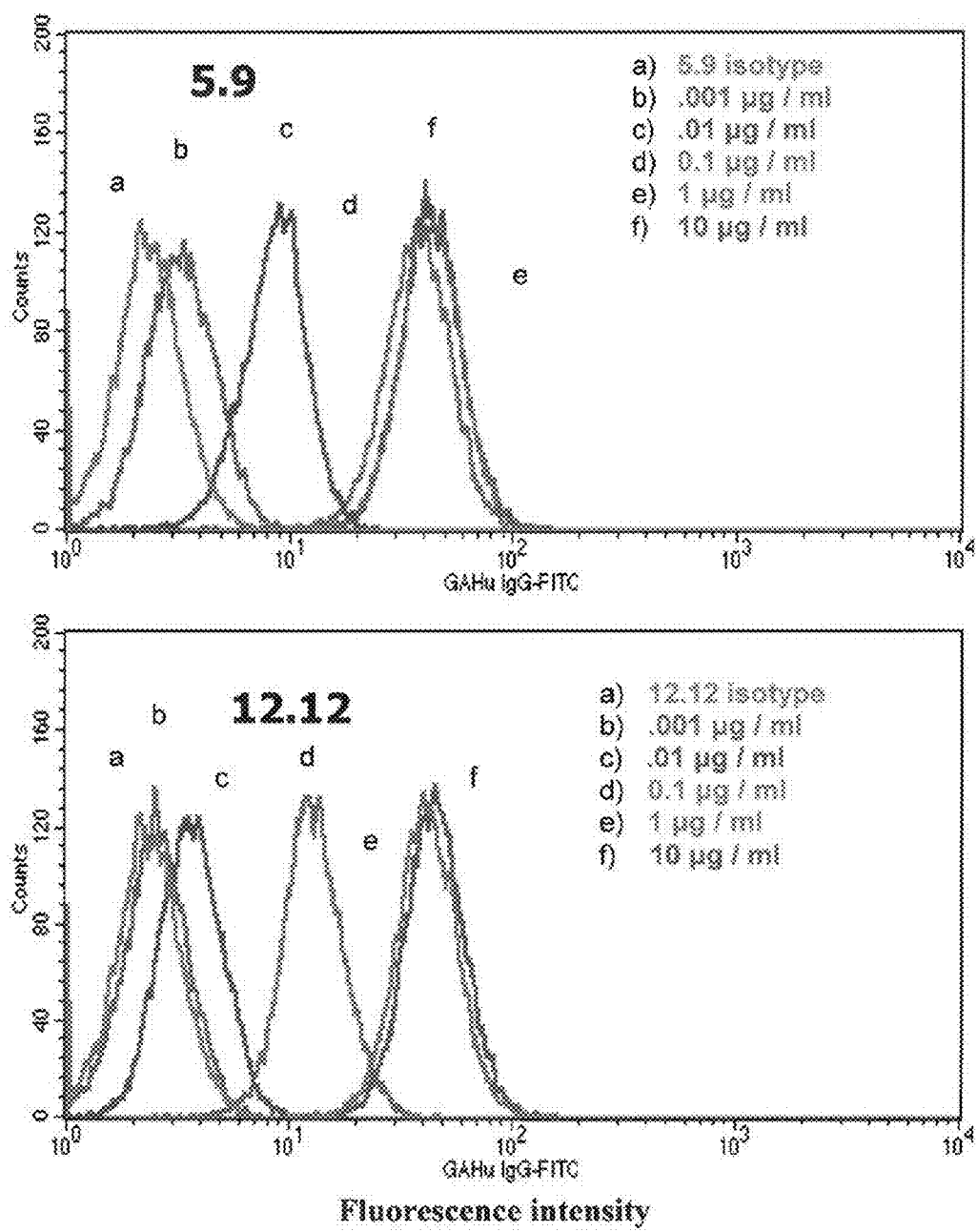
FIG. 1 shows binding of CHIR-5.9 and CHIR-12.12 monoclonal antibodies to CD40 on the surface of lymphoma cell line (Ramos).

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The following outline provides an overview of the inventions as described more fully herein below in Chapters I-VII.

Chapter I: Antagonist Anti-CD40 Antibodies and Methods for their Use
    A. Overview
    B. Antagonist Anti-CD40 Antibodies
    C. Production of Antagonist Anti-CD40 Antibodies
    D. Variants of Antagonist Anti-CD40 Antibodies
    E. Methods of Therapy
    F. Pharmaceutical Formulations and Modes of Administration
    G. Use of Antagonist Anti-CD40 Antibodies in the Manufacture of Medicaments
    H. Experimental Chapter II: Use of Antagonist Anti-CD40 Monoclonal Antibodies for Treatment of Multiple Myeloma
    A. Overview
    B. Antagonist Anti-CD40 Antibodies for Use in Methods for Treating Multiple Myeloma
    C. Methods of Therapy for Treatment of Multiple Myeloma
    D. Pharmaceutical Formulations and Modes of Administration
    E. Use of Antagonist Anti-CD40 Antibodies in the Manufacture of Medicaments for Treating Multiple Myeloma
    F. Experimental Chapter III: Use of Antagonist Anti-CD40 Monoclonal Antibodies for Treatment of Chronic Lymphocytic Leukemia (CLL)
    A. Overview
    B. Antagonist Anti-CD40 Antibodies for Use in Methods for Treating CLL
    C. Methods of Therapy for Treatment of CLL
    D. Pharmaceutical Formulations and Modes of Administration
    E. Use of Antagonist Anti-CD40 Antibodies in the Manufacture of Medicaments for Treating CLL
    F. Experimental Chapter IV: Methods of Therapy for Solid Tumors Expressing the CD40 Cell-Surface Antigen A. Overview
B. Antagonist Anti-CD40 Antibodies for Use in Methods for Treating Solid Tumors
C. Methods of Therapy for Treatment of Solid Tumors
D. Pharmaceutical Formulations and Modes of Administration
E. Use of Antagonist Anti-CD40 Antibodies in the Manufacture of Medicaments for Treating Solid Tumors
F. Experimental Chapter V: Methods of Therapy for B Cell-Related Cancers
A. Overview
B. Combination Therapy for Treatment of B Cell-Related Cancers
C. Anti-CD40 and Anti-CD20 Antibodies for Use in Combination Therapy for Treating B Cell-Related Cancers
 1. Anti-CD40 and anti-CD20 antibodies
 2. Production of anti-CD40 and anti-CD20 antibodies
 3. Variants of antagonist anti-CD40 antibodies and anti-CD20 antibodies
D. Pharmaceutical Formulations and Modes of Administration
E. Use of Antagonist Anti-CD40 Antibodies and Anti-CD20 Antibodies in the Manufacture of Medicaments for Combination Therapy for Treating B Cell-Related Cancers
F. Experimental Chapter VI: Methods of Therapy for Cancers Expressing the CD40 Antigen
A. Overview
B. Combination Therapy with Anti-CD40 Antibodies and Interleukin-2 for Treatment of Cancers Expressing the CD40 Antigen
 1. Introduction
 2. Brief Description of the Oncotherapeutic Agents
 3. Measurements of Clinical Efficacy
 4. Modes of Administration
 5. Combination Therapy
C. Exemplary Protocols for Combination IL-2/Antagonist Anti-CD40 Antibody Therapy
 1. Introduction
 2. Concurrent therapy: initiation of treatment
 3. Duration of antibody and IL-2 treatment
 4. Constant IL-2 dosing regimen
 5. Two-level IL-2 dosing regimen
 6. Interruption of IL-2 dosing
 7. Subsequent courses of combination IL-2/antagonist anti-CD40 antibody therapy
 8. IL-2 dosing schedule
D. Antagonist Anti-CD40 Antibody Dose Ranges for Use in Combination IL-2/Antagonist Anti-CD40 Antibody Therapy
E. IL-2 Dose Ranges for Use in Combination IL-2/Antagonist Anti-CD40 Antibody Therapy
 1. Recommended doses for constant IL-2 dosing regimen
 2. Recommended doses for two-level IL-2 dosing regimen
 3. Relative versus absolute doses for IL-2 dosing
 4. Calculation of IL-2 doses for different aldesleukin formulations
 5. Calculation of IL-2 doses for different IL-2 molecules
F. Additional Oncotherapy for Use with Combination IL-2/Anti-CD40 Antibody Therapy
G. Interleukin-2 and Biologically Active Variants Thereof
 1. Introduction
 2. Biologically active variants of IL-2
 3. Pharmaceutical formulations of IL-2 or variant thereof.
H. Anti-CD40 Antibodies for Use in Combination IL-2/Antagonist Anti-CD40 Antibody Therapy for Treating Cancers Expressing the CD40 Antigen
I. Use of Antagonist Anti-CD40 Antibodies and IL-2 in the Manufacture of Medicaments for Combination Therapy for Cancers Expressing the CD40 Antigen
J. Experimental Chapter VII: Use of Antagonist Anti-CD40 Antibodies for Treatment of Autoimmune and Inflammatory Diseases and Organ Transplant Rejection
A. Overview
B. Anti-CD40 Antibodies for Use in Treating Autoimmune Diseases and/or Inflammatory Diseases
C. Methods of Therapy for Treating Autoimmune Diseases and/or Inflammatory Diseases
D. Pharmaceutical Formulations and Modes of Administration
E. Use of Antagonist Anti-CD40 Antibodies in the Manufacture of Medicaments for Treating Autoimmune Diseases and/or Inflammatory Diseases
F. Experimental Chapter I: Antagonist Anti-CD40 Antibodies and Methods for their Use I. A. Overview The present invention is directed to human antibodies capable of binding to CD40, methods of using the antibodies, and methods for treatment of diseases mediated by stimulation of CD40 signaling on CD40-expressing cells, as described herein below in sections I.B-I.H and in commonly owned provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525, 579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety. Unless otherwise noted, the following definitions are applicable to the inventions described herein in Chapters I-VII.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. By "CD40 expressing neoplastic cell" is intended any neoplastic cell, whether malignant or benign, that expresses the CD40 cell surface antigen. Methods for detecting CD40 expression in cells are well known in the art and include, but are not limited to, PCR techniques, immunohistochemistry, flow cytometry, Western blot, ELISA, and the like.

The terms "cancer" and "cancerous" refer to or describe the physiological condition in mammals that is typically characterized by unregulated cell growth. Examples of cancer include but are not limited to lymphomas, leukemias, myeloma, and solid tumors. By "B cell-related cancer" is intended any type of cancer in which the dysregulated or unregulated cell growth is associated with B cells.

The term "solid tumor" refers to a cancer or carcinoma of body tissues other than blood, bone marrow, and lymphoid system. Examples of cancers that are classified as solid tumors include but are not limited to lung cancer, breast cancer, ovarian cancer, colon cancer, liver cancer and hepatic carcinomas, gastric cancer, prostate cancer, renal carcinomas, gastric carcinomas, skin cancer, sarcomas, and the like.

By "refractory" in the context of a cancer is intended the particular cancer is resistant to, or non-responsive to, therapy with a particular therapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas. For purposes of the present inventions, the terms are used synonymously. In some instances the antigen specificity of the immunoglobulin may be known.

The term "antibody" is used in the broadest sense and covers fully assembled antibodies, antibody fragments that can bind antigen (e.g., Fab', F'(ab)$_2$, Fv, single chain antibodies, diabodies), antibody chimeras, hybrid antibodies, bispecific antibodies, humanized antibodies, and the like, and recombinant peptides comprising the foregoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions both in the light-chain and the heavy-chain variable domains. The more highly conserved portions of variable domains are called the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see Kabat et al. (1991) *NIH Publ. No.* 91-3242, Vol. I, pages 647-669).

The constant domains are not involved directly in binding an antibody to an antigen, but exhibit various effector functions, such as Fc receptor (FcR) binding, participation of the antibody in antibody-dependent cellular toxicity, opsonization, initiation of complement dependent cytotoxicity, and mast cell degranulation.

The term "hypervariable region" when used herein refers to the amino acid residues of an antibody that are responsible for antigen binding. The hypervariable region comprises amino acid residues from a "complementarity determining region" or"CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) *Sequences of Proteins of Immunological Interest* (5th ed., Public Health Service, National Institute of Health, Bethesda, Md.) and/or those residues from a "hypervariable loop" (i.e., residues 26-32 (L1), 50-52 (L2), and 91-96 (L3) in the light-chain variable domain and 26-32 (H1), 53-55 (H2), and 96-101 (H3) in the heavy-chain variable domain; Clothia and Lesk (1987) *J. Mol. Biol.* 196:901-917). "Framework" or "FR" residues are those variable domain residues other than the hypervariable region residues.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$—$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have antibody-dependent cell-mediated cytotoxicity (ADCC) activity.

The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123, I-125, Y-90, Re-188, Re-186, At-211, Cu-67, Bi-212, and Pd-109. The label might also be a non-detectable entity such as a toxin.

The term "antagonist" is used in the broadest sense, and includes any molecule that partially or fully blocks, inhibits, or neutralizes a biological activity of a native target disclosed herein or the transcription or translation thereof.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, succinate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and Pluronics®. Administration "in combination with" one or more further therapeutic agents includes simultaneous (concurrent) and consecutive (i.e., sequential) administration in any order.

A "host cell," as used herein, refers to a microorganism or a eukaryotic cell or cell line cultured as a unicellular entity that can be, or has been, used as a recipient for a recombinant vector or other transfer polynucleotides, and include the progeny of the original cell that has been transfected. It is understood that the progeny of a single cell may not necessarily be completely identical in morphology or in genomic or total DNA complement as the original parent, due to natural, accidental, or deliberate mutation.

"Human effector cells" are leukocytes that express one or more FcRs and perform effector functions. Preferably, the cells express at least FcγRIII and carry out antigen-dependent cell-mediated cyotoxicity (ADCC) effector function. Examples of human leukocytes that mediate ADCC include peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Note that in addition to isolating IgG1 and IgG3 antibodies, such ADCC-mediating antibodies can be made by engineering a variable region from a non-ADCC antibody or variable region fragment to an IgG1 or IgG3 isotype constant region.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daeron (1997) *Annu. Rev. Immunol.* 15:203-234). FcRs are reviewed in Ravetch and Kinet (1991) *Annu. Rev. Immunol.* 9:457-492; Capel et al. (1994) *Immunomethods* 4:25-34; and de Haas et al. (1995) *J. Lab. Clin. Med.* 126:330-341. Other FcRs, including those to be identified in the future, are encompassed by the term "FcR" herein. The term also includes the neonatal receptor, FcRn, which is responsible for the transfer of maternal IgGs to the fetus (Guyer et al. (1976) *J. Immunol.* 117:587 and Kim et al. (1994) *J. Immunol.* 24:249).

There are a number of ways to make human antibodies. For example, secreting cells can be immortalized by infection with the Epstein-Ban virus (EBV). However, EBV-infected cells are difficult to clone and usually produce only relatively low yields of immunoglobulin (James and Bell (1987) *J. Immunol. Methods* 100:5-40). In the future, the immortalization of human B cells might possibly be achieved by introducing a defined combination of transforming genes. Such a possibility is highlighted by a recent demonstration that the expression of the telomerase catalytic subunit together with the SV40 large oncoprotein and an oncogenic allele of H-ras resulted in the tumorigenic conversion of normal human epithelial and fibroblast cells (Hahn et al. (1999) *Nature* 400: 464-468). It is now possible to produce transgenic animals (e.g., mice) that are capable, upon immunization, of producing a repertoire of human antibodies in the absence of endogenous immunoglobulin production (Jakobovits et al. (1993) *Nature* 362:255-258; Lonberg and Huszar (1995) *Int. Rev. Immunol.* 13:65-93; Fishwild et al. (1996) *Nat. Biotechnol.* 14:845-851; Mendez et al. (1997) *Nat. Genet.* 15:146-156; Green (1999) *J. Immunol. Methods* 231:11-23; Tomizuka et al. (2000) *Proc. Natl. Acad. Sci. USA* 97:722-727; reviewed in Little et al. (2000) *Immunol. Today* 21:364-370). For example, it has been described that the homozygous deletion of the antibody heavy-chain joining region ($J_H$) gene in chimeric and germ-line mutant mice results in complete inhibition of endogenous antibody production (Jakobovits et al. (1993) *Proc. Natl. Acad. Sci. USA* 90:2551-2555). Transfer of the human germ-line immunoglobulin gene array in such germ-line mutant mice results in the production of human antibodies upon antigen challenge (Jakobovits et al. (1993) *Nature* 362:255-258). Mendez et al. (1997) (*Nature Genetics* 15:146-156) have generated a line of transgenic mice that, when challenged with an antigen, generates high affinity fully human antibodies. This was achieved by germ-line integration of megabase human heavy-chain and light-chain loci into mice with deletion into endogenous $J_H$ segment as described above. These mice (XenoMouse® II technology (Abgenix; Fremont, Calif.)) harbor 1,020 kb of human heavy-chain locus containing approximately 66 $V_H$ genes, complete $D_H$ and $J_H$ regions, and three different constant regions, and also harbors 800 kb of human κ locus containing 32 Vκ genes, Jκ segments, and Cκ genes. The antibodies produced in these mice closely resemble that seen in humans in all respects, including gene rearrangement, assembly, and repertoire. The human antibodies are preferentially expressed over endogenous antibodies due to deletion in endogenous segment that prevents gene rearrangement in the murine locus. Such mice may be immunized with an antigen of particular interest.

Sera from such immunized animals may be screened for antibody reactivity against the initial antigen. Lymphocytes may be isolated from lymph nodes or spleen cells and may further be selected for B cells by selecting for CD138-negative and CD19-positive cells. In one aspect, such B cell cultures (BCCs) may be fused to myeloma cells to generate hybridomas as detailed above.

In another aspect, such B cell cultures may be screened further for reactivity against the initial antigen, preferably. Such screening includes ELISA with the target/antigen protein, a competition assay with known antibodies that bind the antigen of interest, and in vitro binding to transiently transfected CHO or other cells that express the target antigen.

The present invention is directed to compositions and methods for treating human patients with diseases mediated by stimulation of CD40 signaling on CD40-expressing cells. The methods involve treatment with an anti-CD40 antibody of the invention, or an antigen-binding fragment thereof, where administration of the antibody or antigen-binding fragment thereof promotes a positive therapeutic response within the patient undergoing this method of therapy. Anti-CD40 antibodies suitable for use in the methods of the invention specifically bind a human CD40 antigen expressed on the surface of a human cell and are free of significant agonist activity, but exhibit antagonist activity when bound to the CD40 antigen on a human CD40-expressing cell. These anti-CD40 antibodies and antigen-binding fragments thereof are referred to herein as antagonist anti-CD40 antibodies. Such antibodies include, but are not limited to, the fully human monoclonal antibodies CHIR-5.9 and CHIR-12.12 described below and monoclonal antibodies having the binding characteristics of monoclonal antibodies CHIR-5.9 and CHIR-12.12. Those skilled in the art recognize that the antagonist antibodies and antigen-binding fragments of these antibodies disclosed herein include antibodies and antigen-binding fragments thereof that are produced recombinantly using methods well known in the art and described herein below, and include, for example, monoclonal antibodies CHIR-5.9 and CHIR-12.12 that have been recombinantly produced.

Antibodies that have the binding characteristics of monoclonal antibodies CHIR-5.9 and CHIR-12.12 include antibodies that competitively interfere with binding CD40 and/or bind the same epitopes as CHIR-5.9 and CHIR-12.12. One of skill could determine whether an antibody competitively interferes with CHIR-5.9 or CHIR-12.12 using standard methods.

When these antibodies bind CD40 displayed on the surface of human cells, such as human B cells, the antibodies are free of significant agonist activity; in some embodiments, their binding to CD40 displayed on the surface of human cells results in inhibition of proliferation and differentiation of these human cells. Thus, the antagonist anti-CD40 antibodies suitable for use in the methods of the invention include those monoclonal antibodies that can exhibit antagonist activity toward normal and malignant human cells expressing the cell-surface CD40 antigen.

In some embodiments, the anti-CD40 antibodies of the invention exhibit increased anti-tumor activity relative to the chimeric anti-CD20 monoclonal antibody IDEC-C2B8, where anti-tumor activity is assayed with equivalent amounts of these antibodies in a nude mouse xenograft tumor model using human lymphoma cell lines. IDEC-C2B8 (IDEC Pharmaceuticals Corp., San Diego, Calif.; commercially available under the tradename Rituxan®, also referred to as rituximab) is a chimeric anti-CD20 monoclonal antibody containing human IgG1 and kappa constant regions with murine variable regions isolated from a murine anti-CD20 monoclonal antibody, IDEC-2B8 (Reff et al. (1994) *Blood* 83:435-445). Rituximab® is licensed for treatment of relapsed B cell low-grade or follicular non-Hodgkin's lymphoma (NHL). The discovery of antibodies with superior anti-tumor activity compared to Rituximab® could drastically improve methods of cancer therapy for B cell lymphomas, particularly B cell non-Hodgkin's lymphoma.

Suitable nude mouse xenograft tumor models include those using the human Burkitt's lymphoma cell lines known as Namalwa and Daudi. Preferred embodiments assay anti-tumor activity in a staged nude mouse xenograft tumor model using the Daudi human lymphoma cell line as described herein below in Example 17. A staged nude mouse xenograft tumor model using the Daudi lymphoma cell line is more effective at distinguishing the therapeutic efficacy of a given antibody than is an unstaged model, as in the staged model antibody dosing is initiated only after the tumor has reached a measurable size. In the unstaged model, antibody dosing is initiated generally within about 1 day of tumor inoculation and before a palpable tumor is present. The ability of an antibody to outperform Rituxan® (i.e., to exhibit increased anti-tumor activity) in a staged model is a strong indication that the antibody will be more therapeutically effective than Rituxan®. Moreover, in the Daudi model, anti-CD20, the target for Rituxan® is expressed on the cell surface at a higher level than is CD40.

By "equivalent amount" of the anti-CD40 antibody of the invention and Rituxan® is intended the same mg dose is administered on a per weight basis. Thus, where the anti-CD40 antibody of the invention is dosed at 0.01 mg/kg body weight of the mouse used in the tumor model, Rituxan® is also dosed at 0.01 mg/kg body weight of the mouse. Similarly, where the anti-CD40 antibody of the invention is dosed at 0.1, 1, or 10 mg/kg body weight of the mouse used in the tumor model, the Rituxan® is also dosed at 0.1, 1, or 10 mg/kg, respectively, of the body weight of the mouse.

When administered in the nude mouse xenograft tumor model, some antibodies of the invention result in significantly less tumor volume than an equivalent amount of Rituxan®. Thus, for example, the fully human monoclonal antibody CHIR-12.12 exhibits at least a 20% increase in anti-tumor activity relative to that observed with an equivalent dose of Rituxan when assayed in the staged nude mouse xenograft tumor model using the Daudi human lymphoma cell line in the manner described in Examples herein below, and can exhibit as much as a 50% to 60% increase in anti-tumor activity in this assay. This increased anti-tumor activity is reflected in the greater reduction in tumor volume observed with the anti-CD40 antibody of the invention when compared to the equivalent dose of Rituxan®. Thus, for example, depending upon the length of time after tumor inoculation, the monoclonal antibody CHIR-12.12 can exhibit a tumor volume that is about one-third to about one-half that observed for an equivalent dose of Rituxan®.

Another difference in antibody efficacy is to measure in vitro the concentration of antibody needed to obtain the maximum lysis of tumor cells in vitro in the presence of NK cells. For example, the anti-CD40 antibodies of the invention reach maximum lysis of Daudi cells at an EC50 of less than ½, and preferably ¼, and most preferably, ⅒ the concentration of Rituxan®.

In addition to the monoclonal antibody CHIR-12.12, other anti-CD40 antibodies that would share the characteristics of having significantly greater efficacy than equivalent amounts of Rituxan® in the assays described above include, but are not limited to: (1) the monoclonal antibody produced by the hybridoma cell line 12.12; (2) a monoclonal antibody comprising an amino acid sequence selected from the group consisting of the sequence in SEQ ID NO:2, the sequence in SEQ ID NO:4, the sequence in SEQ ID NO:5, both the sequence in SEQ ID NO:2 and SEQ ID NO:4, and both the sequence in SEQ ID NO:2 and SEQ ID NO:5; (3) a monoclonal antibody having an amino acid sequence encoded by a nucleic acid molecule comprising a nucleotide sequence selected from the group consisting of the nucleotide sequence in SEQ ID NO:1, the nucleotide sequence in SEQ ID NO:3, and both the sequence in SEQ ID NO:1 and SEQ ID NO:3; (4) a monoclonal antibody that binds to an epitope capable of binding the monoclonal antibody produced by the hybridoma cell line 12.12; (5) a monoclonal antibody that binds to an epitope comprising residues 82-87 of the amino acid sequence in SEQ ID NO:10 or SEQ ID NO:12; (6) a monoclonal antibody that competes with the monoclonal antibody CHIR-12.12 in a competitive binding assay; and (7) a monoclonal antibody that is an antigen-binding fragment of the CHIR-12.12 monoclonal antibody or the foregoing monoclonal antibodies in preceding items (1)-(6), where the fragment retains the capability of specifically binding to the human CD40 antigen.

I. B. Antagonist Anti-CD40 Antibodies

The monoclonal antibodies CHIR-5.9 and CHIR-12.12 represent suitable antagonist anti-CD40 antibodies for use in the methods of the present invention. The CHIR-5.9 and CHIR-12.12 antibodies are fully human anti-CD40 monoclonal antibodies of the IgG$_1$ isotype produced from the hybridoma cell lines 131.2F8.5.9 (referred to herein as the cell line 5.9) and 153.8E2.D10.D6.12.12 (referred to herein as the cell line 12.12). These cell lines were created using splenocytes from immunized xenotypic mice containing the human IgG$_1$ heavy chain locus and the human κ chain locus (XenoMouse® technology; Abgenix; Fremont, Calif.). The spleen cells were fused with the mouse myeloma SP2/0 cells (Sierra BioSource). The resulting hybridomas were subcloned several times to create the stable monoclonal cell lines 5.9 and 12.12. Other antibodies of the invention may be prepared similarly using mice transgenic for human immunoglobulin loci or by other methods known in the art and/or described herein.

The nucleotide and amino acid sequences of the variable regions of the CHIR-12.12 antibody, and the amino acid sequences of the variable regions of the CHIR-5.9 antibody, are disclosed. More particularly, the amino acid sequences for the leader, variable, and constant regions for the light chain and heavy chain for mAb CHIR-12.12 are set forth in FIGS. 9A and 9B, respectively. See also SEQ ID NO:2 (complete sequence for the light chain of mAb CHIR-12.12), SEQ ID NO:4 (complete sequence for the heavy chain for mAb CHIR-12.12), and SEQ ID NO:5 (complete sequence for a variant of the heavy chain for mAb CHIR-12.12 set forth in SEQ ID NO:4, where the variant comprises a serine substitution for the alanine residue at position 153 of SEQ ID NO:4). The nucleotide sequences encoding the light chain and heavy chain for mAb CHIR-12.12 are set forth in FIGS. 11A and 11B, respectively. See also SEQ ID NO:1 (coding sequence for the light chain for mAb CHIR-12.12), and SEQ ID NO:3 (coding sequence for the heavy chain for mAb CHIR-12.12). The amino acid sequences for the leader, variable, and constant regions for the light chain and heavy chain of the CHIR-5.9 mAb are set forth in FIGS. 10A and 10B, respectively. See also SEQ ID NO:6 (complete sequence for the light chain of mAb CHIR-5.9), SEQ ID NO:7 (complete sequence for the heavy chain of mAb CHIR-5.9), and SEQ ID NO:8 (complete sequence for a variant of the heavy chain of mAb CHIR-5.9 set forth in SEQ ID NO:7, where the variant comprises a serine substitution for the alanine residue at position 158 of SEQ ID NO:7). Further, hybridomas expressing CHIR-5.9 and CHIR-12.12 antibodies have been deposited with the ATCC with a patent deposit designation of PTA-5542 and PTA-5543, respectively.

In addition to antagonist activity, it is preferable that anti-CD40 antibodies of this invention have another mechanism of action against a tumor cell. For example, native CHIR-5.9 and CHIR-12.12 antibodies have ADCC activity. Alternatively, the variable regions of the CHIR-5.9 and CHIR-12.12 antibodies can be expressed on another antibody isotype that has ADCC activity. It is also possible to conjugate native forms, recombinant forms, or antigen-binding fragments of CHIR-5.9 or CHIR-12.12 to a cytotoxin, a therapeutic agent, or a radioactive metal ion or radioisotope, as noted herein below.

The CHIR-5.9 and CHIR-12.12 monoclonal antibodies bind soluble CD40 in ELISA-type assays, prevent the binding of CD40-ligand to cell-surface CD40, and displace the pre-bound CD40-ligand, as determined by flow cytometric assays. Antibodies CHIR-5.9 and CHIR-12.12 compete with each other for binding to CD40 but not with 15B8, the anti-CD40 monoclonal antibody described in U.S. Provisional Application Ser. No. 60/237,556, titled "Human Anti-CD40 Antibodies," filed Oct. 2, 2000, and PCT International Application No. PCT/US01/30857, also titled "Human Anti-CD40 Antibodies," filed Oct. 2, 2001, both of which are herein incorporated by reference in their entirety. When tested in vitro for effects on proliferation of B cells from normal human subjects, CHIR-5.9 and CHIR-12.12 act as antagonist anti-CD40 antibodies. Furthermore, CHIR-5.9 and CHIR-12.12 do not induce strong proliferation of human lymphocytes from normal subjects. These antibodies are able to kill CD40-expressing target cells by antibody dependent cellular cytotoxicity (ADCC). The binding affinity of CHIR-5.9 for human CD40 is $1.2 \times 10^{-8}$ M and the binding affinity of CHIR-12.12 is $5 \times 10^{-10}$ M, as determined by the Biacore™ assay.

Suitable antagonist anti-CD40 antibodies for use in the methods of the present invention exhibit a strong single-site binding affinity for the CD40 cell-surface antigen. The monoclonal antibodies of the invention exhibit a dissociation equilibrium constant ($K_D$) for CD40 of at least $10^{-5}$ M, at least $3 \times 10^{-5}$ M, preferably at least $10^{-6}$ M to $10^{-7}$ M, more preferably at least $10^{-8}$ M to about $10^{-12}$ M, measured using a standard assay such as Biacore™. Biacore analysis is known in the art and details are provided in the "BIAapplications handbook." Methods described in WO 01/27160 can be used to modulate the binding affinity.

By "CD40 antigen," "CD40 cell surface antigen," "CD40 receptor," or "CD40" is intended a transmembrane glycoprotein that belongs to the tumor necrosis factor (TNF) receptor family (see, for example, U.S. Pat. Nos. 5,674,492 and 4,708, 871; Stamenkovic et al. (1989) *EMBO* 8:1403; Clark (1990) *Tissue Antigens* 36:33; Barclay et al. (1997) *The Leucocyte Antigen Facts Book* (2d ed.; Academic Press, San Diego)). Two isoforms of human CD40, encoded by alternatively spliced transcript variants of this gene, have been identified. The first isoform (also known as the "long isoform" or "isoform 1") is expressed as a 277-amino-acid precursor polypeptide (SEQ ID NO:12 (first reported as GenBank Accession No. CAA43045, and identified as isoform 1 in GenBank Accession No. NP_001241), encoded by SEQ ID NO:11 (see GenBank Accession Nos. X60592 and NM_001250)), which has a signal sequence represented by the first 19 residues. The second isoform (also known as the "short isoform" or "isoform 2") is expressed as a 203-amino-acid precursor polypeptide (SEQ ID NO:10 (GenBank Accession No. NP_690593), encoded by SEQ ID NO:9 (GenBank Accession No. NM_152854)), which also has a signal sequence represented by the first 19 residues. The precursor polypeptides of these two isoforms of human CD40 share in common their first 165 residues (i.e., residues 1-165 of SEQ ID NO:10 and SEQ ID NO:12). The precursor polypeptide of the short isoform (shown in SEQ ID NO:10) is encoded by a transcript variant (SEQ ID NO:9) that lacks a coding segment, which leads to a translation frame shift; the resulting CD40 isoform contains a shorter and distinct C-terminus (residues 166-203 of SEQ ID NO:10) from that contained in the long isoform of CD40 (C-terminus shown in residues 166-277 of SEQ ID NO:12). For purposes of the present invention, the term "CD40 antigen," "CD40 cell surface antigen," "CD40 receptor," or "CD40" encompasses both the short and long isoforms of CD40. The anti-CD40 antibodies of the present invention bind to an epitope of human CD40 that resides at the same location within either the short isoform or long isoform of this cell surface antigen as noted herein below.

The CD40 antigen is displayed on the surface of a variety of cell types, as described elsewhere herein. By "displayed on the surface" and "expressed on the surface" is intended that all or a portion of the CD40 antigen is exposed to the exterior of the cell. The displayed or expressed CD40 antigen may be fully or partially glycosylated.

By "agonist activity" is intended that the substance functions as an agonist. An agonist combines with a receptor on a cell and initiates a reaction or activity that is similar to or the same as that initiated by the receptor's natural ligand. An agonist of CD40 induces any or all of, but not limited to, the following responses: B cell proliferation and differentiation, antibody production, intercellular adhesion, B cell memory generation, isotype switching, up-regulation of cell-surface expression of MHC Class II and CD80/86, and secretion of pro-inflammatory cytokines such as IL-8, IL-12, and TNF. By "antagonist activity" is intended that the substance functions as an antagonist. An antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring anti-CD40 antibody and CD40-ligand binding specificity and antagonist activity are known to one of skill in the art and include, but are not limited to, standard competitive binding assays, assays for monitoring immunoglobulin secretion by B cells, B cell proliferation assays, Banchereau-Like-B cell proliferation assays, T cell helper assays for antibody production, co-stimulation of B cell proliferation assays, and assays for up-regulation of B cell activation markers. See, for example, such assays disclosed in WO 00/75348 and U.S. Pat. No. 6,087,329, herein incorporated by reference.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B cell response. Preferably, "significant" agonist activity is an agonist activity that is at least 2-fold greater or at least 3-fold greater than the agonist activity induced by a neutral substance or negative control as measured in an assay of a B cell response. Thus, for example, where the B cell response of interest is B cell proliferation, "significant" agonist activity would be induction of a level of B cell proliferation that is at least 2-fold greater or at least 3-fold greater than the level of B cell proliferation induced by a neutral substance or negative control. In one embodiment, a non-specific immunoglobulin, for example IgG1, that does not bind to CD40 serves as the negative control. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in an assay of a B cell response. The antagonist anti-CD40 antibodies useful in the methods of the present invention are free of significant agonist activity as noted above when bound to a CD40 antigen on a human cell. In one embodiment of the invention, the antagonist anti-CD40 antibody is free of significant agonist activity in one B cell response. In another embodiment of the invention, the antagonist anti-CD40 antibody is free of significant agonist activity in assays of more than one B cell response (e.g., proliferation and differentiation, or proliferation, differentiation, and antibody production).

As used herein "anti-CD40 antibody" encompasses any antibody that specifically recognizes the CD40 B cell surface antigen, including polyclonal antibodies, monoclonal antibodies, single-chain antibodies, and fragments thereof such as Fab, F(ab')$_2$, F$_v$, and other fragments which retain the antigen binding function of the parent anti-CD40 antibody. Of particular interest to the present invention are the antagonist anti-CD40 antibodies disclosed herein that share the binding characteristics of the monoclonal antibodies CHIR-5.9 and CHIR-12.12 described above. Such antibodies include, but are not limited to the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen.

I. B. Production of Antagonist Anti-CD40 Antibodies

The antagonist anti-CD40 antibodies disclosed herein and for use in the methods of the present invention can be produced using any antibody production method known to those of skill in the art. Thus, polyclonal sera may be prepared by conventional methods. In general, a solution containing the CD40 antigen is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 cells expressing CD40 are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf 9 (*Spodoptera frugiperda*) cells is disclosed in U.S. Pat. No. 6,004,552, incorporated herein by reference. Briefly, sequences encoding human CD40 were recombined into a baculovirus using transfer vectors. The plasmids were co-transfected with wild-type baculovirus DNA into Sf 9 cells. Recombinant baculovirus-infected Sf 9 cells were identified and clonally purified.

Preferably the antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site, i.e., the CD40 cell surface antigen in the present invention. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Where the antagonist anti-CD40 antibodies of the invention are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. (1993) *Curr. Opinion in Immunol.* 5:256 and Phickthun (1992) *Immunol. Revs.* 130:151. Alternatively, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

In some embodiments, the antagonist anti-CD40 antibody, for example, the CHIR-12.12 or CHIR-5.9 antibody, or antigen-binding fragment thereof is produced in CHO cells using the GS gene expression system (Lonza Biologics, Portsmouth, N.H.), which uses glutamine synthetase as a marker. See, also U.S. Pat. Nos. 5,122,464; 5,591,639; 5,658,759; 5,770,359; 5,827,739; 5,879,936; 5,891,693; and 5,981,216; the contents of which are herein incorporated by reference in their entirety.

Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674,492; 5,874,082; 5,677,165; 6,056,959; WO 00/63395; International Publication Nos. WO 02/28905 and WO 02/28904; Gordon et al. (1988) *J. Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J. Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference. Of particular interest to the present invention are the antagonist anti-CD40 antibodies disclosed herein that share the binding characteristics of the monoclonal antibodies CHIR-5.9 and CHIR-12.12 described above.

The term "CD40-antigen epitope" as used herein refers to a three dimensional molecular structure (either linear or conformational) that is capable of immunoreactivity with the anti-CD40 monoclonal antibodies of this invention, excluding the CD40 antigen itself. CD40-antigen epitopes may comprise proteins, protein fragments, peptides, carbohydrates, lipids, and other molecules, but for the purposes of the present invention are most commonly proteins, short oligopeptides, oligopeptide mimics (i e, organic compounds which mimic the antibody binding properties of the CD40 antigen), or combinations thereof. Suitable oligopeptide mimics are described, inter alia, in PCT application US 91/04282.

Additionally, the term "anti-CD40 antibody" as used herein encompasses chimeric anti-CD40 antibodies; such chimeric anti-CD40 antibodies for use in the methods of the invention have the binding characteristics of the CHIR-5.9 and CHIR-12.12 monoclonal antibodies described herein. By "chimeric" antibodies is intended antibodies that are most preferably derived using recombinant deoxyribonucleic acid techniques and which comprise both human (including immunologically "related" species, e.g., chimpanzee) and non-human components. Rituxan® is an example of a chimeric antibody with a murine variable region and a human constant region. For purposes of the present invention, the constant region of the chimeric antibody is most preferably substantially identical to the constant region of a natural human antibody; the variable region of the chimeric antibody is most preferably derived from a non-human source and has the desired antigenic specificity to the CD40 cell-surface antigen. The non-human source can be any vertebrate source that can be used to generate antibodies to a human CD40 cell-surface antigen or material comprising a human CD40 cell-surface antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). As used herein, the phrase "immunologically active" when used in reference to chimeric anti-CD40 antibodies means a chimeric antibody that binds human CD40.

Humanized anti-CD40 antibodies represent additional anti-CD40 antibodies suitable for use in the methods of the present invention. By "humanized" is intended forms of anti-CD40 antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, e.g., Chothia et al (1987) *J. Mol. Biol.* 196:901-917; Kabat et al (1991) U.S. Dept. of Health and Human Services, NIH Publication No. 91-3242). The phrase "constant region" refers to the portion of the antibody molecule that confers effector functions. In previous work directed towards producing non-immunogenic antibodies for use in therapy of human disease, mouse constant regions were substituted by human constant regions. The constant regions of the subject humanized antibodies were derived from human immunoglobulins. However, these humanized antibodies still elicited an unwanted and potentially dangerous immune response in humans and there was a loss of affinity. Humanized anti-CD40 antibodies for use in the methods of the present invention have binding characteristics similar to those exhibited by the CHIR-5.9 and CHIR-12.12 monoclonal antibodies described herein.

Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-

596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

Also encompassed by the term anti-CD40 antibodies are xenogeneic or modified anti-CD40 antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

Preferably, fully human antibodies to CD40 are obtained by immunizing transgenic mice. One such mouse is obtained using XenoMouse® technology (Abgenix; Fremont, Calif.), and is disclosed in U.S. Pat. Nos. 6,075,181, 6,091,001, and 6,114,598, all of which are incorporated herein by reference. To produce the antibodies disclosed herein, mice transgenic for the human IgG$_1$ heavy chain locus and the human κ light chain locus can be immunized with Sf 9 cells expressing human CD40. Mice can also be transgenic for other isotypes. Fully human antibodies useful in the methods of the present invention are characterized by binding properties similar to those exhibited by the CHIR-5.9 and CHIR-12.12 monoclonal antibodies.

Fragments of the anti-CD40 antibodies are suitable for use in the methods of the invention so long as they retain the desired affinity of the full-length antibody. Thus, a fragment of an anti-CD40 antibody will retain the ability to bind to the CD40 B cell surface antigen. Such fragments are characterized by properties similar to the corresponding full-length antagonist anti-CD40 antibody, that is, the fragments will specifically bind a human CD40 antigen expressed on the surface of a human cell, and are free of significant agonist activity but exhibit antagonist activity when bound to a CD40 antigen on a human CD40-expressing cell. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the V$_H$ and V$_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the V$_H$ and V$_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315. Antigen-binding fragments of the antagonist anti-CD40 antibodies disclosed herein can also be conjugated to a cytotoxin to effect killing of the target cancer cells, as described herein below.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Antagonist anti-CD40 antibodies useful in the methods of the present invention include the CHIR-5.9 and CHIR-12.12 monoclonal antibodies disclosed herein as well as antibodies differing from this antibody but retaining the CDRs; and antibodies with one or more amino acid addition(s), deletion(s), or substitution(s), wherein the antagonist activity is measured by inhibition of B-cell proliferation and/or differentiation. The invention also encompasses de-immunized (humanized) antagonist anti-CD40 antibodies, which can be produced as described in, for example, International Publication Nos. WO 98/52976 and WO 0034317; herein incorporated by reference. In this manner, residues within the antagonist anti-CD40 antibodies of the invention are modified so as to render the antibodies non- or less immunogenic to humans while retaining their antagonist activity toward human CD40-expressing cells, wherein such activity is measured by assays noted elsewhere herein. Also included within the scope of the claims are fusion proteins comprising an antagonist anti-CD40 antibody of the invention, or a fragment thereof, which fusion proteins can be synthesized or expressed from corresponding polynucleotide vectors, as is known in the art. Such fusion proteins are described with reference to conjugation of antibodies as noted below.

The antibodies of the present invention can have sequence variations produced using methods described in, for example, Patent Publication Nos. EP 0 983 303 A1, WO 00/34317, and WO 98/52976, incorporated herein by reference. For example, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Any such conservative or non-conservative substitutions can be made using art-recognized methods, such as those noted elsewhere herein, and the resulting antibodies will fall within the scope of the invention. The variant antibodies can be routinely tested for antagonist activity, affinity, and specificity using methods described herein.

An antibody produced by any of the methods described above, or any other method not disclosed herein, will fall within the scope of the invention if it possesses at least one of the following biological activities: inhibition of immunoglobulin secretion by normal human peripheral B cells stimulated by T cells; inhibition of survival and/or proliferation of normal human peripheral B cells stimulated by Jurkat T cells; inhibition of survival and/or proliferation of normal human peripheral B cells stimulated by CD40L-expressing cells or soluble CD40 ligand (sCD40L); inhibition of "survival" anti-apoptotic intracellular signals in any cell stimulated by sCD40L or solid-phase CD40L; inhibition of CD40 signal transduction in any cell upon ligation with sCD40L or solid-phase CD40L; and inhibition of proliferation of human malignant B cells as noted below. These assays can be performed as described in the Examples herein. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674, 492 and 5,847,082; herein incorporated by reference.

A representative assay to detect antagonist anti-CD40 antibodies specific to the CD40-antigen epitopes identified herein is a "competitive binding assay." Competitive binding assays are serological assays in which unknowns are detected and quantitated by their ability to inhibit the binding of a labeled known ligand to its specific antibody. This is also referred to as a competitive inhibition assay. In a representative competitive binding assay, labeled CD40 polypeptide is precipitated by candidate antibodies in a sample, for example, in combination with monoclonal antibodies raised against one or more epitopes of the monoclonal antibodies of the invention. Anti-CD40 antibodies that specifically react with an epitope of interest can be identified by screening a series of antibodies prepared against a CD40 protein or fragment of the protein comprising the particular epitope of the CD40 protein of interest. For example, for human CD40, epitopes of interest include epitopes comprising linear and/or nonlinear amino acid residues of the short isoform of human CD40 (see GenBank Accession No. NP_690593) set forth in FIG. 12B (SEQ ID NO:10), encoded by the sequence set forth in FIG. 12A (SEQ ID NO:9; see also GenBank Accession No. NM_152854), or of the long isoform of human CD40 (see GenBank Accession Nos. CAA43045 and NP_001241) set forth in FIG. 12D (SEQ ID NO:12), encoded by the sequence set forth in FIG. 12C (SEQ ID NO:11; see GenBank Accession Nos. X60592 and NM_001250). Alternatively, competitive binding assays with previously identified suitable antagonist anti-CD40 antibodies could be used to select monoclonal antibodies comparable to the previously identified antibodies.

Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-CD40 antibody and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Any of the previously described antagonist anti-CD40 antibodies or antibody fragments thereof may be conjugated prior to use in the methods of the present invention. Methods for producing conjugated antibodies are known in the art. Thus, the anti-CD40 antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivastava and Mease (1991) *Nucl. Med. Bio.* 18:589-603, herein incorporated by reference. Suitable labels include fluorophores, chromophores, radioactive atoms (particularly $^{32}$P and $^{125}$I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefore. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labeled with $^{125}$I, or with an anti-biotin mAb labeled with HRP. Other permutations and possibilities will be readily apparent to those of ordinary skill in the art, and are considered as equivalents within the scope of the instant invention.

Alternatively, the anti-CD40 antibody may be labeled using "direct labeling" or a "direct labeling approach," where a radionuclide is covalently attached directly to an antibody (typically via an amino acid residue). Preferred radionuclides are provided in Srivastava and Mease (1991) supra. The indirect labeling approach is particularly preferred. See also, for example, International Publication Nos. WO 00/52031 and WO 00/52473, where a linker is used to attach a radioactive label to antibodies; and the labeled forms of antibodies described in U.S. Pat. No. 6,015,542; herein incorporated by reference.

Further, an antibody (or fragment thereof) may be conjugated to a therapeutic moiety such as a cytotoxin, a therapeutic agent, or a radioactive metal ion or radioisotope. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., fludarabine, 2-chlorodeoxyadenosine, methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Radioisotopes include, but are not limited to, I-131, I-123, I-125, Y-90, Re-188, Re-186, At-211, Cu-67, Bi-212, Bi-213, Pd-109, Tc-99, In-111, and the like. The conjugates of the invention can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-alpha, interferon-beta, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known. See, for example, Arnon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; Thorpe (1985) "Antibody Carriers of Cytotoxic Agents in Cancer Therapy: A Review," in *Monoclonal Antibodies '84: Biological and Clinical Applications*, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316; and Thorpe et al. (1982) Immunol. Rev. 62:119-158.

Alternatively, an antibody can be conjugated to a second antibody to form an antibody heteroconjugate as described in U.S. Pat. No. 4,676,980. In addition, linkers may be used between the labels and the antibodies of the invention (see U.S. Pat. No. 4,831,175). Antibodies or, antigen-binding fragments thereof may be directly labeled with radioactive iodine, indium, yttrium, or other radioactive particle known in the art (U.S. Pat. No. 5,595,721). Treatment may consist of a combination of treatment with conjugated and nonconjugated antibodies administered simultaneously or sequentially, in either order, on the same or different days (WO 00/52031 and WO 00/52473).

I. D. Variants of Antagonist Anti-CD40 Antibodies

Suitable biologically active variants of the antagonist anti-CD40 antibodies can be used in the methods of the present invention. Such variants will retain the desired binding properties of the parent antagonist anti-CD40 antibody. Methods for making antibody variants are generally available in the art.

For example, amino acid sequence variants of an antagonist anti-CD40 antibody, for example, the CHIR-5.9 or CHIR-12.12 monoclonal antibody described herein, can be prepared by mutations in the cloned DNA sequence encoding the antibody of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly$\Leftrightarrow$Ala, Val$\Leftrightarrow$Ile$\Leftrightarrow$Leu, Asp$\Leftrightarrow$Glu, Lys$\Leftrightarrow$Arg, Asn$\Leftrightarrow$Gln, and Phe$\Leftrightarrow$Trp$\Leftrightarrow$Tyr.

In constructing variants of the antagonist anti-CD40 antibody polypeptide of interest, modifications are made such that variants continue to possess the desired activity, i.e., similar binding affinity and are capable of specifically binding to a human CD40 antigen expressed on the surface of a human cell, and being free of significant agonist activity but exhibiting antagonist activity when bound to a CD40 antigen on a human CD40-expressing cell. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an antagonist anti-CD40 antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference antagonist anti-CD40 antibody have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antagonist anti-CD40 antibody molecule, for example, the CHIR-5.9 or CHIR-12.12 monoclonal antibody described herein, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antagonist anti-CD40 antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The precise chemical structure of a polypeptide capable of specifically binding CD40 and retaining antagonist activity, particularly when bound to CD40 antigen on malignant B cells, depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of antagonist anti-CD40 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CD40 antibody used herein so long as the antagonist properties of the anti-CD40 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy antagonist activity do not remove the polypeptide sequence from the definition of anti-CD40 antibodies of interest as used herein.

The art provides substantial guidance regarding the preparation and use of polypeptide variants. In preparing the anti-CD40 antibody variants, one of skill in the art can readily determine which modifications to the native protein nucleotide or amino acid sequence will result in a variant that is suitable for use as a therapeutically active component of a pharmaceutical composition used in the methods of the present invention.

I. E. Methods of Therapy Using the Antagonist Anti-CD40 Antibodies of the Invention Methods of the invention are directed to the use of antagonist anti-CD40 antibodies to treat patients having a disease mediated by stimulation of CD40 signaling on CD40-expressing cells. By "CD40-expressing cell" is intended normal and malignant B cells expressing CD40 antigen. Methods for detecting CD40 expression in cells are well known in the art and include, but are not limited to, PCR techniques, immunohistochemistry, flow cytometry, Western blot, ELISA, and the like. By "malignant" B cell is intended any neoplastic B cell, including but not limited to B cells derived from lymphomas including low-, intermediate-, and high-grade B cell lymphomas, immunoblastic lymphomas, non-Hodgkin's lymphomas, Hodgkin's disease, Epstein-Ban Virus (EBV) induced lymphomas, and AIDS-related lymphomas, as well as B cell acute lymphoblastic leukemias, myelomas, chronic lymphocytic leukemias, acute myeloblastic leukemias, and the like.

"Treatment" is herein defined as the application or administration of an antagonist anti-CD40 antibody or antigen-binding fragment thereof to a patient, or application or administration of an antagonist anti-CD40 antibody or fragment thereof to an isolated tissue or cell line from a patient, where the patient has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the application or administration of a pharmaceutical composition comprising the antagonist anti-CD40 antibodies or fragments thereof to a patient, or application or administration of a pharmaceutical composition comprising the anti-CD40 antibodies or fragments thereof to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 antibody (or antigen-binding fragment thereof) causes a physiological response that is beneficial with respect to treatment of disease states associated with stimulation of CD40 signaling on CD40-expressing cells in a human.

The methods of the invention find use in the treatment of non-Hodgkin's lymphomas related to abnormal, uncontrollable B cell proliferation or accumulation. For purposes of the present invention, such lymphomas will be referred to according to the Working Formulation classification scheme, that is those B cell lymphomas categorized as low grade, intermediate grade, and high grade (see "The Non-Hodgkin's Lymphoma Pathologic Classification Project," *Cancer* 49(1982): 2112-2135). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the methods of the invention are useful in the therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), hairy cell leukemia, plasmacytoma/myeloma, diffuse large cell B cell lymphoma of the subtype primary mediastinal (thymic), Burkitt's lymphoma, and Burkitt's like high grade B cell lymphoma; acute leukemias; acute lymphocytic leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); chronic lymphocytic leukemia; polycythemia vera; multiple myeloma; Waldenstrom's macroglobulinemia; heavy chain disease; and unclassifiable low-grade or high-grade B cell lymphomas.

It is recognized that the methods of the invention may be useful in preventing further tumor outgrowths arising during therapy. The methods of the invention are particularly useful in the treatment of subjects having low-grade B cell lymphomas, particularly those subjects having relapses following standard chemotherapy. Low-grade B cell lymphomas are more indolent than the intermediate- and high-grade B cell lymphomas and are characterized by a relapsing/remitting course. Thus, treatment of these lymphomas is improved using the methods of the invention, as relapse episodes are reduced in number and severity.

The antagonist anti-CD40 antibodies described herein may also find use in the treatment of inflammatory diseases and deficiencies or disorders of the immune system including, but not limited to, systemic lupus erythematosus, psoriasis, scleroderma, CREST syndrome, inflammatory myositis, Sjogren's syndrome, mixed connective tissue disease, rheumatoid arthritis, multiple sclerosis, inflammatory bowel disease, acute respiratory distress syndrome, pulmonary inflammation, idiopathic pulmonary fibrosis, osteoporosis, delayed type hypersensitivity, asthma, primary biliary cirrhosis, and idiopathic thrombocytopenic purpura.

In accordance with the methods of the present invention, at least one antagonist anti-CD40 antibody (or antigen-binding fragment thereof) as defined elsewhere herein is used to promote a positive therapeutic response with respect to a malignant human B cell. By "positive therapeutic response" with respect to cancer treatment is intended an improvement in the disease in association with the anti-tumor activity of these antibodies or fragments thereof, and/or an improvement in the symptoms associated with the disease. That is, an anti-proliferative effect, the prevention of further tumor outgrowths, a reduction in tumor size, a reduction in the number of cancer cells, and/or a decrease in one or more symptoms mediated by stimulation of CD40-expressing cells can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bioluminescent imaging, for example, luciferase imaging, bone scan imaging, and tumor biopsy sampling including bone marrow aspiration (BMA). In addition to these positive therapeutic responses, the subject undergoing therapy with the antagonist anti-CD40 antibody or antigen-binding fragment thereof may experience the beneficial effect of an improvement in the symptoms associated with the disease. Thus for B cell tumors, the subject may experience a decrease in the so-called B symptoms, i.e., night sweats, fever, weight loss, and/or urticaria.

By "therapeutically effective dose or amount" or "effective amount" is intended an amount of antagonist anti-CD40 antibody or antigen-binding fragment thereof that, when administered brings about a positive therapeutic response with respect to treatment of a patient with a disease comprising stimulation of CD40-expressing cells. In some embodiments of the invention, a therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody or antigen-binding fragment thereof.

A further embodiment of the invention is the use of antagonist anti-CD40 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

The anti-CD40 antibodies described herein can further be used to provide reagents, e.g., labeled antibodies that can be used, for example, to identify cells expressing CD40. This can be very useful in determining the cell type of an unknown sample. Panels of monoclonal antibodies can be used to identify tissue by species and/or by organ type. In a similar fashion, these anti-CD40 antibodies can be used to screen tissue culture cells for contamination (i.e., screen for the presence of a mixture of CD40-expressing and non-CD40 expressing cells in a culture).

The antagonist anti-CD40 antibodies can be used in combination with known chemotherapeutics and cytokines for the treatment of disease states comprising stimulated CD40-expressing cells. For example, the anti-CD40 antibodies of the invention can be used in combination with cytokines such as interleukin-2. In another embodiment, the anti-CD40 antibodies of the invention can be used in combination with rituximab (IDEC-C2B8; Rituxan®; IDEC Pharmaceuticals Corp., San Diego, Calif.).

In this manner, the antagonist anti-CD40 antibodies described herein, or antigen-binding fragments thereof, are administered in combination with at least one other cancer therapy, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, and IL-21 therapy; steroid therapy; or other cancer therapy; where the additional cancer therapy is administered prior to, during, or subsequent to the antagonist anti-CD40 antibody therapy. Thus, where the combined therapies comprise administration of an antagonist anti-CD40 antibody or antigen-binding fragment thereof in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass coadministration, using separate formulations or a single pharmaceutical formulation, or and consecutive administration in either order. Where the methods of the present invention comprise combined therapeutic regimens, these therapies can be given simultaneously, i.e., the antagonist anti-CD40 antibody or antigen-binding fragment thereof is administered concurrently or within the same time frame as the other cancer therapy (i.e., the therapies are going on concurrently, but the antagonist anti-CD40 antibody or antigen-binding fragment thereof is not administered precisely at the same time as the other cancer therapy). Alternatively, the antagonist anti-CD40 antibody of the present invention or antigen-binding fragment thereof may also be administered prior to or subsequent to the other cancer therapy. Sequential administration of the different cancer therapies may be performed regardless of whether the treated subject responds to the first course of therapy to decrease the possibility of remission or relapse. Where the combined therapies comprise administration of the antagonist anti-CD40 antibody or antigen-binding fragment thereof in combination with administration of a cytotoxic agent, preferably the antagonist anti-CD40 antibody or antigen-binding fragment thereof is administered prior to administering the cytotoxic agent.

In some embodiments of the invention, the antagonist anti-CD40 antibodies described herein, or antigen-binding fragments thereof, are administered in combination with chemotherapy, and optionally in combination with autologous bone marrow transplantation, wherein the antibody and the chemotherapeutic agent(s) may be administered sequentially, in either order, or simultaneously (i.e., concurrently or within the same time frame). Examples of suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine. In some embodiments, the antagonist anti-CD40 antibody, for example, the monoclonal antibody CHIR-12.12 or CHIR-5.9, or an antigen-binding fragment thereof is administered prior to treatment with the chemotherapeutic agent. In alternative embodiments, the antagonist anti-CD40 antibody is administered after treatment with the chemotherapeutic agent. In yet other embodiments, the chemotherapeutic agent is administered simultaneously with the antagonist anti-CD40 antibody or antigen-binding fragment thereof.

Thus, for example, in some embodiments, the antagonist anti-CD40 antibody, for example, the monoclonal antibody CHIR-12.12 or CHIR-5.9, or antigen-binding fragment thereof is administered in combination with fludarabine or fludarabine phosphate. In one such embodiment, the antagonist anti-CD40 antibody or antigen-binding fragment thereof is administered prior to administration of fludarabine or fludarabine phosphate. In alternative embodiments, the antagonist anti-CD40 antibody or antigen-binding fragment thereof is administered after treatment with fludarabine or fludarabine phosphate. In yet other embodiments, the fludarabine or fludarabine phosphate is administered simultaneously with the antagonist anti-CD40 antibody or antigen-binding fragment thereof.

In other embodiments of the invention, chlorambucil, an alkylating drug, is administered in combination with an antagonist anti-CD40 antibody described herein, for example, the monoclonal antibody CHIR-12.12 or CHIR-5.9, or an antigen-binding fragment thereof. In one such embodiment, the antagonist anti-CD40 antibody or antigen-binding fragment thereof is administered prior to administration of chlorambucil. In alternative embodiments, the antagonist anti-CD40 antibody or antigen-binding fragment thereof is administered after treatment with chlorambucil. In yet other embodiments, the chlorambucil is administered simultaneously with the antagonist anti-CD40 antibody or antigen-binding fragment thereof.

In yet other embodiments, anthracycline-containing regimens such as CAP (cyclophosphamide, doxorubicin plus prednisone) and CHOP (cyclophosphamide, vincristine, prednisone plus doxorubicin) may be combined with administration of an antagonist anti-CD40 antibody described herein, for example, the monoclonal antibody CHIR-12.12 or CHIR-5.9, or antigen-binding fragment thereof. In one such embodiment, the antagonist anti-CD40 antibody or antigen-binding fragment thereof is administered prior to administration of anthracycline-containing regimens. In other embodiments, the antagonist anti-CD40 antibody or antigen-binding fragment thereof is administered after treatment with anthracycline-containing regimens. In yet other embodiments, the anthracycline-containing regimen is administered simultaneously with the antagonist anti-CD40 antibody or antigen-binding fragment thereof.

In alternative embodiments, an antagonist anti-CD40 antibody described herein, for example, the monoclonal antibody CHIR-12.12 or CHIR-5.9, or an antigen-binding fragment thereof, is administered in combination with alemtuzumab (Campath®; distributed by Berlex Laboratories, Richmond, Calif.). Alemtuzumab is a recombinant humanized monoclonal antibody (Campath-1H) that targets the CD52 antigen expressed on malignant B cells. In one such embodiment, the antagonist anti-CD40 antibody or antigen-binding fragment thereof is administered prior to administration of alemtuzumab. In other embodiments, the antagonist anti-CD40 antibody or antigen-binding fragment thereof is administered after treatment with alemtuzumab. In yet other embodiments, the alemtuzumab is administered simultaneously with the antagonist anti-CD40 antibody or antigen-binding fragment thereof.

In alternative embodiments, an antagonist anti-CD40 antibody described herein, for example, the monoclonal antibody CHIR-12.12 or CHIR-5.9, or antigen-binding fragment thereof, is administered in combination with a therapeutic anti-CD20 antibody targeting the CD20 antigen on malignant B cells, for example, rituximab (Rituxan®), the fully human antibody HuMax-CD20, R-1594, IMMU-106, TRU-015, AME-133, tositumomab/I-131 tositumomab (Bexxar®), or ibritumomab tiuxetan (Zevalin®). In one such embodiment, the antagonist anti-CD40 antibody or antigen-binding fragment thereof is administered prior to administration of the anti-CD20 antibody. In other embodiments, the antagonist anti-CD40 antibody or antigen-binding fragment thereof is administered after treatment with the anti-CD20 antibody. In yet other embodiments, the anti-CD20 antibody is administered simultaneously with the antagonist anti-CD40 antibody or antigen-binding fragment thereof.

In alternative embodiments, an antagonist anti-CD40 antibody described herein, for example, the monoclonal antibody CHIR-12.12 or CHIR-5.9, or antigen-binding fragment thereof, is administered in combination with a small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium). In one such embodiment, the antagonist anti-CD40 antibody or antigen-binding fragment thereof is administered prior to administration of the small molecule-based cancer therapy. In other embodiments, the antagonist anti-CD40 antibody or antigen-binding fragment thereof is administered after treatment with the small molecule-based cancer therapy. In yet other embodiments, the small molecule-based cancer therapy is administered simultaneously with the antagonist anti-CD40 antibody or antigen-binding fragment thereof.

In yet other embodiments, an antagonist anti-CD40 antibody described herein, for example, the monoclonal antibody CHIR-12.12 or CHIR-5.9 or an antigen-binding fragment thereof, can be used in combination with vaccine/immunotherapy-based cancer therapy, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, or IL-21 therapy; or steroid therapy. In one such embodiment, the antagonist anti-CD40 antibody or antigen-binding fragment thereof is administered prior to administration of the vaccine/immunotherapy-based cancer therapy. In other embodiments, the antagonist anti-CD40 antibody or antigen-binding fragment thereof is administered after treatment with the vaccine/immunotherapy-based cancer therapy. In yet other embodiments, the vaccine/immunotherapy-based cancer therapy is administered simultaneously with the antagonist anti-CD40 antibody or antigen-binding fragment thereof.

In one such embodiment, an antagonist anti-CD40 antibody described herein, for example, the monoclonal antibody CHIR-12.12 or CHIR-5.9, or an antigen-binding fragment thereof, can be used in combination with IL-2. IL-2, an agent known to expand the number of natural killer (NK) effector cells in treated patients, can be administered prior to, or concomitantly with, the antagonist anti-CD40 antibody of the invention or antigen-binding fragment thereof. This expanded number of NK effector cells may lead to enhanced ADCC activity of the administered antagonist anti-CD40 antibody or antigen-binding fragment thereof. In other embodiments, IL-21 serves as the immunotherapeutic agent to stimulate NK cell activity when administered in combination with an antagonist anti-CD40 antibody described herein, for example, the monoclonal antibody CHIR-12.12 or CHIR-5.9, or an antigen-binding fragment thereof.

Further, combination therapy with two or more therapeutic agents and an antagonist anti-CD40 antibody described herein can also be used for treatment of a treatment of disease states comprising stimulated CD40-expressing cells, for example, B cell-related cancers, and autoimmune and/or inflammatory disorders. Without being limiting, examples include triple combination therapy, where two chemotherapeutic agents are administered in combination with an antagonist anti-CD40 antibody described herein, and where a chemotherapeutic agent and another anti-cancer monoclonal antibody (for example, alemtuzumab, rituximab, or anti-CD23 antibody) are administered in combination with an antagonist anti-CD40 antibody described herein. Examples of such combinations include, but are not limited to, combinations of fludarabine, cyclophosphamide, and the antagonist anti-CD40 antibody, for example, the monoclonal antibody CHIR-12.12 or CHIR-5.9 or an antigen-binding fragment thereof; and combinations of fludarabine, an anti-CD20 antibody, for example, rituximab (Rituxan®; IDEC Pharmaceuticals Corp., San Diego, Calif.), and the antagonist anti-CD40 antibody, for example, the monoclonal antibody CHIR-12.12 or CHIR-5.9 or an antigen-binding fragment thereof.

I. F. Pharmaceutical Formulations and Modes of Administration

The antagonist anti-CD40 antibodies of this invention are administered at a concentration that is therapeutically effective to prevent or treat CD40-expressing cell-mediated diseases such as SLE, PBC, ITP, multiple sclerosis, psoriasis, Crohn's disease, graft rejection, and B-cell lymphoma. To accomplish this goal, the antibodies may be formulated using a variety of acceptable excipients known in the art. Typically, the antibodies are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Intravenous administration occurs preferably by infusion over a period of about 1 to about 10 hours, more preferably over about 1 to about 8 hours, even more preferably over about 2 to about 7 hours, still more preferably over about 4 to about 6 hours, depending upon the anti-CD40 antibody being administered. The initial infusion with the pharmaceutical composition may be given over a period of about 4 to about 6 hours with subsequent infusions delivered more quickly. Subsequent infusions may be administered over a period of about 1 to about 6 hours, including, for example, about 1 to about 4 hours, about 1 to about 3 hours, or about 1 to about 2 hours.

A pharmaceutical composition of the invention is formulated to be compatible with its intended route of administration. Examples of possible routes of administration include parenteral, (e.g., intravenous (IV), intramuscular (IM), intradermal, subcutaneous (SC), or infusion), oral and pulmonary (e.g., inhalation), nasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The anti-CD40 antibodies are typically provided by standard technique within a pharmaceutically acceptable buffer, for example, sterile saline, sterile buffered water, propylene glycol, combinations of the foregoing, etc. Methods for preparing parenterally administrable agents are described in *Remington's Pharmaceutical Sciences* (18$^{th}$ ed.; Mack Publishing Company, Eaton, Pa., 1990), herein incorporated by reference. See also, for example, WO 98/56418, which describes stabilized antibody pharmaceutical formulations suitable for use in the methods of the present invention.

The amount of at least one anti-CD40 antibody or fragment thereof to be administered is readily determined by one of ordinary skill in the art without undue experimentation. Factors influencing the mode of administration and the respective amount of at least one antagonist anti-CD40 antibody (or fragment thereof) include, but are not limited to, the severity of the disease, the history of the disease, and the age, height, weight, health, and physical condition of the individual undergoing therapy. Similarly, the amount of antagonist anti-CD40 antibody or fragment thereof to be administered will be dependent upon the mode of administration and whether the subject will undergo a single dose or multiple doses of this anti-tumor agent. Generally, a higher dosage of anti-CD40 antibody or fragment thereof is preferred with increasing weight of the subject undergoing therapy. The dose of anti- CD40 antibody or fragment thereof to be administered is in the range from about 0.003 mg/kg to about 50 mg/kg, preferably in the range of 0.01 mg/kg to about 40 mg/kg. Thus, for example, the dose can be 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg.

In another embodiment of the invention, the method comprises administration of multiple doses of antagonist anti-CD40 antibody or fragment thereof. The method may comprise administration of 1, 2, 3, 4, 5, 6, 7, 8, 9, 10, 15, 20, 25, 30, 35, 40, or more therapeutically effective doses of a pharmaceutical composition comprising an antagonist anti-CD40 antibody or fragment thereof. The frequency and duration of administration of multiple doses of the pharmaceutical compositions comprising anti-CD40 antibody or fragment thereof can be readily determined by one of skill in the art without undue experimentation. Moreover, treatment of a subject with a therapeutically effective amount of an antibody can include a single treatment or, preferably, can include a series of treatments. In a preferred example, a subject is treated with antagonist anti-CD40 antibody or antigen-binding fragment thereof in the range of between about 0.1 to 20 mg/kg body weight, once per week for between about 1 to 10 weeks, preferably between about 2 to 8 weeks, more preferably between about 3 to 7 weeks, and even more preferably for about 4, 5, or 6 weeks. Treatment may occur annually to prevent relapse or upon indication of relapse. It will also be appreciated that the effective dosage of antibody or antigen-binding fragment thereof used for treatment may increase or decrease over the course of a particular treatment. Changes in dosage may result and become apparent from the results of diagnostic assays as described herein.

Thus, in one embodiment, the dosing regimen includes a first administration of a therapeutically effective dose of at least one anti-CD40 antibody or fragment thereof on days 1, 7, 14, and 21 of a treatment period. In another embodiment, the dosing regimen includes a first administration of a therapeutically effective dose of at least one anti-CD40 antibody or fragment thereof on days 1, 2, 3, 4, 5, 6, and 7 of a week in a treatment period. Further embodiments include a dosing regimen having a first administration of a therapeutically effective dose of at least one anti-CD40 antibody or fragment thereof on days 1, 3, 5, and 7 of a week in a treatment period; a dosing regimen including a first administration of a therapeutically effective dose of at least one anti-CD40 antibody or fragment thereof on days 1 and 3 of a week in a treatment period; and a preferred dosing regimen including a first administration of a therapeutically effective dose of at least one anti-CD40 antibody or fragment thereof on day 1 of a week in a treatment period. The treatment period may comprise 1 week, 2 weeks, 3 weeks, a month, 3 months, 6 months, or a year. Treatment periods may be subsequent or separated from each other by a day, a week, 2 weeks, a month, 3 months, 6 months, or a year.

In some embodiments, the therapeutically effective doses of antagonist anti-CD40 antibody or antigen-binding fragment thereof ranges from about 0.003 mg/kg to about 50 mg/kg, from about 0.01 mg/kg to about 40 mg/kg, from about 0.01 mg/kg to about 30 mg/kg, from about 0.1 mg/kg to about 30 mg/kg, from about 0.5 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. Thus, for example, the dose of any one antagonist anti-CD40 antibody or antigen-binding fragment thereof, for example the anti-CD40 monoclonal antibody CHIR-12.12 or CHIR-5.9 or antigen-binding fragment thereof, can be 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.003 mg/kg to about 50 mg/kg. The same therapeutically effective dose of an antagonist anti-CD40 antibody or antigen-binding fragment thereof can be administered throughout each week of antibody dosing. Alternatively, different therapeutically effective doses of an antagonist anti-CD40 antibody or antigen-binding fragment thereof can be used over the course of a treatment period.

In other embodiments, the initial therapeutically effective dose of an antagonist anti-CD40 antibody or antigen-binding fragment thereof as defined elsewhere herein can be in the lower dosing range (i.e., about 0.003 mg/kg to about 20 mg/kg) with subsequent doses falling within the higher dosing range (i.e., from about 20 mg/kg to about 50 mg/kg).

In alternative embodiments, the initial therapeutically effective dose of an antagonist anti-CD40 antibody or antigen-binding fragment thereof as defined elsewhere herein can be in the upper dosing range (i.e., about 20 mg/kg to about 50 mg/kg) with subsequent doses falling within the lower dosing range (i.e., 0.003 mg/kg to about 20 mg/kg). Thus, in one embodiment, the initial therapeutically effective dose of the antagonist anti-CD40 antibody or antigen-binding fragment thereof is about 20 mg/kg to about 35 mg/kg, including about 20 mg/kg, about 25 mg/kg, about 30 mg/kg, and about 35 mg/kg, and subsequent therapeutically effective doses of the antagonist anti-CD40 antibody or antigen binding fragment thereof are about 5 mg/kg to about 15 mg/kg, including about 5 mg/kg, 8 mg/kg, 10 mg/kg, 12 mg/kg, and about 15 mg/kg.

In some embodiments of the invention, antagonist anti-CD40 antibody therapy is initiated by administering a "loading dose" of the antibody or antigen-binding fragment thereof to the subject in need of antagonist anti-CD40 antibody therapy. By "loading dose" is intended an initial dose of the antagonist anti-CD40 antibody or antigen-binding fragment thereof that is administered to the subject, where the dose of the antibody or antigen-binding fragment thereof administered falls within the higher dosing range (i.e., from about 20 mg/kg to about 50 mg/kg). The "loading dose" can be administered as a single administration, for example, a single infusion where the antibody or antigen-binding fragment thereof is administered IV, or as multiple administrations, for example, multiple infusions where the antibody or antigen-binding fragment thereof is administered IV, so long as the complete "loading dose" is administered within about a 24-hour period. Following administration of the "loading dose," the subject is then administered one or more additional therapeutically effective doses of the antagonist anti-CD40 antibody or antigen-binding fragment thereof. Subsequent therapeutically effective doses can be administered, for example, according to a weekly dosing schedule, or once every two weeks, once every three weeks, or once every four weeks. In such embodiments, the subsequent therapeutically effective doses generally fall within the lower dosing range (i.e., 0.003 mg/kg to about 20 mg/kg).

Alternatively, in some embodiments, following the "loading dose," the subsequent therapeutically effective doses of the antagonist anti-CD40 antibody or antigen-binding fragment thereof are administered according to a "maintenance schedule," wherein the therapeutically effective dose of the antibody or antigen-binding fragment thereof is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the antagonist anti-CD40 antibody or antigen-binding fragment thereof fall within the lower dosing range (i.e., 0.003 mg/kg to about 20 mg/kg), particularly when the subsequent doses are administered at more frequent intervals, for example, once every two weeks to once every month, or within the higher dosing range (i.e., from about 20 mg/kg to about 50 mg/kg), particularly when the subsequent doses are administered at less frequent intervals, for example, where subsequent doses are administered about one month to about 12 months apart.

The antagonist anti-CD40 antibodies present in the pharmaceutical compositions described herein for use in the methods of the invention may be native or obtained by recombinant techniques, and may be from any source, including mammalian sources such as, e.g., mouse, rat, rabbit, primate, pig, and human. Preferably such polypeptides are derived from a human source, and more preferably are recombinant, human proteins from hybridoma cell lines.

The pharmaceutical compositions useful in the methods of the invention may comprise biologically active variants of the antagonist anti-CD40 antibodies of the invention. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant anti-CD40 antibody will serve as a therapeutically active component in the pharmaceutical composition in a manner similar to that observed for the native antagonist antibody, for example CHIR-5.9 or CHIR-12.12 as expressed by the hybridoma cell line 5.9 or 12.12, respectively. Methods are available in the art for determining whether a variant anti-CD40 antibody retains the desired biological activity, and hence serves as a therapeutically active component in the pharmaceutical composition. Biological activity of antibody variants can be measured using assays specifically designed for measuring activity of the native antagonist antibody, including assays described in the present invention.

Any pharmaceutical composition comprising an antagonist anti-CD40 antibody having the binding properties described herein as the therapeutically active component can be used in the methods of the invention. Thus liquid, lyophilized, or spray-dried compositions comprising one or more of the antagonist anti-CD40 antibodies of the invention may be prepared as an aqueous or nonaqueous solution or suspension for subsequent administration to a subject in accordance with the methods of the invention. Each of these compositions will comprise at least one of the antagonist anti-CD40 antibodies of the present invention as a therapeutically or prophylactically active component. By "therapeutically or prophylactically active component" is intended the anti-CD40 antibody is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

Formulants may be added to pharmaceutical compositions comprising an antagonist anti-CD40 antibody of the invention. These formulants may include, but are not limited to, oils, polymers, vitamins, carbohydrates, amine acids, salts, buffers, albumin, surfactants, or bulking agents. Preferably carbohydrates include sugar or sugar alcohols such as mono-, di-, or polysaccharides, or water soluble glucans. The saccharides or glucans can include fructose, glucose, mannose, sorbose, xylose, maltose, sucrose, dextran, pullulan, dextrin, $\alpha$ and $\beta$ cyclodextrin, soluble starch, hydroxyethyl starch, and carboxymethylcellulose, or mixtures thereof. "Sugar alcohol" is defined as a $C_4$ to $C_8$ hydrocarbon having a hydroxyl group and includes galactitol, inositol, mannitol, xylitol, sorbitol, glycerol, and arabitol. These sugars or sugar alcohols may be used individually or in combination. The sugar or sugar alcohol concentration is between 1.0% and 7% w/v., more preferably between 2.0% and 6.0% w/v. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546; which are all hereby incorporated by reference in their entireties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al. (1988) *J. Bio. Chem.* 263:15064-15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al. (1982) *Cancer Research* 42:4734; Cafiso (1981) *Biochem Biophys Acta* 649:129; and Szoka (1980) *Ann. Rev. Biophys. Eng.* 9:467. Other drug delivery systems are known in the art and are described in, e.g., Poznansky et al. (1980) *Drug Delivery Systems* (R.L. Juliano, ed., Oxford, N.Y.) pp. 253-315; Poznansky (1984) *Pharm Revs* 36:277.

The formulants to be incorporated into a pharmaceutical composition should provide for the stability of the antagonist anti-CD40 antibody or antigen-binding fragment thereof. That is, the antagonist anti-CD40 antibody or antigen-binding fragment thereof should retain its physical and/or chemical stability and have the desired biological activity, i.e., one or more of the antagonist activities defined herein above, including, but not limited to, inhibition of immunoglobulin secretion by normal human peripheral B cells stimulated by T cells; inhibition of survival and/or proliferation of normal human peripheral B cells stimulated by Jurkat T cells; inhibition of survival and/or proliferation of normal human peripheral B cells stimulated by CD40L-expressing cells or soluble CD40 ligand (sCD40L); inhibition of "survival" anti-apoptotic intracellular signals in any cell stimulated by sCD40L or solid-phase CD40L; inhibition of CD40 signal transduction in any cell upon ligation with sCD40L or solid-phase CD40L; and inhibition of proliferation of human malignant B cells as noted elsewhere herein.

Methods for monitoring protein stability are well known in the art. See, for example, Jones (1993) *Adv. Drug Delivery Rev.* 10:29-90; Lee, ed. (1991) *Peptide and Protein Drug Delivery* (Marcel Dekker, Inc., New York, N.Y.); and the stability assays disclosed herein below. Generally, protein stability is measured at a chosen temperature for a specified period of time. In preferred embodiments, a stable antibody pharmaceutical formulation provides for stability of the antagonist anti-CD40 antibody or antigen-binding fragment thereof when stored at room temperature (about 25° C.) for at least 1 month, at least 3 months, or at least 6 months, and/or is stable at about 2-8° C. for at least 6 months, at least 9 months, at least 12 months, at least 18 months, at least 24 months.

A protein such as an antibody, when formulated in a pharmaceutical composition, is considered to retain its physical stability at a given point in time if it shows no visual signs (i.e., discoloration or loss of clarity) or measurable signs (for example, using size-exclusion chromatography (SEC) or UV light scattering) of precipitation, aggregation, and/or denaturation in that pharmaceutical composition. With respect to chemical stability, a protein such as an antibody, when formulated in a pharmaceutical composition, is considered to retain its chemical stability at a given point in time if measurements of chemical stability are indicative that the protein (i.e., antibody) retains the biological activity of interest in that pharmaceutical composition. Methods for monitoring changes in chemical stability are well known in the art and include, but are not limited to, methods to detect chemically altered forms of the protein such as result from clipping, using, for example, SDS-PAGE, SEC, and/or matrix-assisted laser desorption ionization/time of flight mass spectrometry; and degradation associated with changes in molecular charge (for example, associated with deamidation), using, for example, ion-exchange chromatography. See, for example, the methods disclosed herein below.

An antagonist anti-CD40 antibody or antigen-binding fragment thereof, when formulated in a pharmaceutical composition, is considered to retain a desired biological activity at a given point in time if the desired biological activity at that time is within about 30%, preferably within about 20% of the desired biological activity exhibited at the time the pharmaceutical composition was prepared as determined in a suitable assay for the desired biological activity. Assays for measuring the desired biological activity of the antagonist anti-CD40 antibodies disclosed herein, and antigen-binding fragments thereof, can be performed as described in the Examples herein. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

In some embodiments of the invention, the antagonist anti-CD40 antibody, for example, the CHIR-12.12 or CHIR-5.9 monoclonal antibody, or antigen-binding fragment thereof is formulated in a liquid pharmaceutical formulation. The antagonist anti-CD40 antibody or antigen binding fragment thereof can be prepared using any method known in the art, including those methods disclosed herein above. In one embodiment, the antagonist anti-CD40 antibody, for example, the CHIR-12.12 or CHIR-5.9 monoclonal antibody, or antigen-binding fragment thereof is recombinantly produced in a CHO cell line.

Following its preparation and purification, the antagonist anti-CD40 antibody or antigen-binding fragment thereof can be formulated as a liquid pharmaceutical formulation in the manner set forth herein. Where the antagonist anti-CD40 antibody or antigen-binding fragment thereof is to be stored prior to its formulation, it can be frozen, ro example, at ≤−20° C., and then thawed at room temperature for further formulation. The liquid pharmaceutical formulation comprises a therapeutically effective amount of the antagonist anti-CD40 antibody or antigen-binding fragment thereof. The amount of antibody or antigen-binding fragment thereof present in the formulation takes into consideration the route of administration and desired dose volume.

In this manner, the liquid pharmaceutical composition comprises the antagonist anti-CD40 antibody, for example, the CHIR-12.12 or CHIR-5.9 antibody, or antigen-binding fragment thereof at a concentration of about 0.1 mg/ml to about 50.0 mg/ml, about 0.5 mg/ml to about 40.0 mg/ml, about 1.0 mg/ml to about 30.0 mg/ml, about 5.0 mg/ml to about 25.0 mg/ml, about 5.0 mg/ml to about 20.0 mg/ml, or about 15.0 mg/ml to about 25.0 mg/ml. In some embodiments, the liquid pharmaceutical composition comprises the antagonist anti-CD40 antibody or antigen-binding fragment thereof at a concentration of about 0.1 mg/ml to about 5.0 mg/ml, about 5.0 mg/ml to about 10.0 mg/ml, about 10.0 mg/ml to about 15.0 mg/ml, about 15.0 mg/ml to about 20.0 mg/ml, about 20.0 mg/ml to about 25.0 mg/ml, about 25.0 mg/ml to about 30.0 mg/ml, about 30.0 mg/ml to about 35.0 mg/ml, about 35.0 mg/ml to about 40.0 mg/ml, about 40.0 mg/ml to about 45.0 mg/ml, or about 45.0 mg/ml to about 50.0 mg/ml. In other embodiments, the liquid pharmaceutical composition comprises the antagonist anti-CD40 antibody or antigen-binding fragment thereof at a concentration of about 15.0 mg/ml, about 16.0 mg/ml, about 17.0 mg/ml, about 18.0 mg/ml, about 19.0 mg/ml, about 20.0 mg/ml, about 21.0 mg/ml, about 22.0 mg/ml, about 23.0 mg/ml, about 24.0 mg/ml, or about 25.0 mg/ml. The liquid pharmaceutical composition comprises the antagonist anti-CD40 antibody, for example, the CHIR-12.12 or CHIR-5.9 antibody, or antigen-binding fragment thereof and a buffer that maintains the pH of the formulation in the range of about pH 5.0 to about pH 7.0, including about pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and other such values within the range of about pH 5.0 to about pH 7.0. In some embodiments, the buffer maintains the pH of the formulation in the range of about pH 5.0 to about pH 6.5, about pH 5.0 to about pH 6.0, about pH 5.0 to about pH 5.5, about pH 5.5 to about 7.0, about pH 5.5 to about pH 6.5, or about pH 5.5 to about pH 6.0.

Any suitable buffer that maintains the pH of the liquid anti-CD40 antibody formulation in the range of about pH 5.0 to about pH 7.0 can be used in the formulation, so long as the physicochemical stability and desired biological activity of the antibody are retained as noted herein above. Suitable buffers include, but are not limited to, conventional acids and salts thereof, where the counter ion can be, for example, sodium, potassium, ammonium, calcium, or magnesium. Examples of conventional acids and salts thereof that can be used to buffer the pharmaceutical liquid formulation include, but are not limited to, succinic acid or succinate, citric acid or citrate, acetic acid or acetate, tartaric acid or tartarate, phosphoric acid or phosphate, gluconic acid or gluconate, glutamic acid or glutamate, aspartic acid or aspartate, maleic acid or maleate, and malic acid or malate buffers. The buffer concentration within the formulation can be from about 1 mM to about 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of about 1 mM to about 50 mM. In some embodiments, the buffer concentration within the formulation is from about 5 mM to about 15 mM, including about 5 mM, 6 mM, 7 mM, 8 mM, 9 mM, 10 mM, 11 mM, 12 mM, 13 mM, 14 mM, 15 mM, or other such values within the range of about 5 mM to about 15 mM.

In some embodiments of the invention, the liquid pharmaceutical formulation comprises a therapeutically effective amount of the antagonist anti-CD40 antibody, for example, the CHIR-12.12 or CHIR-5.9 monoclonal antibody, or antigen-binding fragment thereof and succinate buffer or citrate buffer at a concentration that maintains the pH of the formulation in the range of about pH 5.0 to about pH 7.0, preferably about pH 5.0 to about pH 6.5. By "succinate buffer" or "citrate buffer" is intended a buffer comprising a salt of succinic acid or a salt of citric acid, respectively. In a preferred embodiment, the succinate or citrate counterion is the sodium cation, and thus the buffer is sodium succinate or sodium citrate, respectively. However, any cation is expected to be effective. Other possible succinate or citrate cations include, but are not limited to, potassium, ammonium, calcium, and magnesium. As noted above, the succinate or citrate buffer concentration within the formulation can be from about 1 mM to about 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of about 1 mM to about 50 mM. In some embodiments, the buffer concentration within the formulation is from about 5 mM to about 15 mM, including about 5 mM, 6 mM, 7 mM, 8 mM, 9 mM, 10 mM, 11 mM, 12 mM, 13 mM, 14 mM, or about 15 mM. In other embodiments, the liquid pharmaceutical formulation comprises the antagonist anti-CD40 antibody, for example, the CHIR-12.12 or CHIR-5.9 monoclonal antibody, or antigen-binding fragment thereof at a concentration of about 0.1 mg/ml to about 50.0 mg/ml, or about 5.0 mg/ml to about 25.0 mg/ml, and succinate or citrate buffer, for example, sodium succinate or sodium citrate buffer, at a concentration of about 1 mM to about 20 mM, about 5 mM to about 15 mM, preferably about 10 mM.

Where it is desirable for the liquid pharmaceutical formulation to be near isotonic, the liquid pharmaceutical formulation comprising a therapeutically effective amount of the antagonist anti-CD40 antibody, for example, the CHIR-12.12 or CHIR-5.9 monoclonal antibody, or antigen-binding fragment thereof, and a buffer to maintain the pH of the formulation within the range of about pH 5.0 to about pH 7.0 can further comprise an amount of an isotonizing agent sufficient to render the formulation near isotonic. By "near isotonic" is intended the aqueous formulation has an osmolarity of about 240 mmol/kg to about 360 mmol/kg, preferably about 240 to about 340 mmol/kg, more preferably about 250 to about 330 mmol/kg, even more preferably about 260 to about 320 mmol/kg, still more preferably about 270 to about 310 mmol/kg. Methods of determining the isotonicity of a solution are known to those skilled in the art. See, for example, Setnikar et al. (1959) *J. Am. Pharm. Assoc.* 48:628.

Those skilled in the art are familiar with a variety of pharmaceutically acceptable solutes useful in providing isotonicity in pharmaceutical compositions. The isotonizing agent can be any reagent capable of adjusting the osmotic pressure of the liquid pharmaceutical formulation of the present invention to a value nearly equal to that of a body fluid. It is desirable to use a physiologically acceptable isotonizing agent. Thus, the liquid pharmaceutical formulation comprising a therapeutically effective amount of the antagonist anti-CD40 antibody, for example, the CHIR-12.12 or CHIR-5.9 monoclonal antibody, or antigen-binding fragment thereof, and a buffer to maintain the pH of the formulation within the range of about pH 5.0 to about pH 7.0, can further comprise components that can be used to provide isotonicity, for example, sodium chloride; amino acids such as alanine, valine, and glycine; sugars and sugar alcohols (polyols), including, but not limited to, glucose, dextrose, fructose, sucrose, maltose, mannitol, trehalose, glycerol, sorbitol, and xylitol; acetic acid, other organic acids or their salts, and relatively minor amounts of citrates or phosphates. The ordinary skilled person would know of additional agents that are suitable for providing optimal tonicity of the liquid formulation.

In some preferred embodiments, the liquid pharmaceutical formulation comprising a therapeutically effective amount of the antagonist anti-CD40 antibody, for example, the CHIR-12.12 or CHIR-5.9 monoclonal antibody, or antigen-binding fragment thereof, and a buffer to maintain the pH of the formulation within the range of about pH 5.0 to about pH 7.0, further comprises sodium chloride as the isotonizing agent. The concentration of sodium chloride in the formulation will depend upon the contribution of other components to tonicity. In some embodiments, the concentration of sodium chloride is about 50 mM to about 300 mM, about 50 mM to about 250 mM, about 50 mM to about 200 mM, about 50 mM to about 175 mM, about 50 mM to about 150 mM, about 75 mM to about 175 mM, about 75 mM to about 150 mM, about 100 mM to about 175 mM, about 100 mM to about 200 mM, about 100 mM to about 150 mM, about 125 mM to about 175 mM, about 125 mM to about 150 mM, about 130 mM to about 170 mM, about 130 mM to about 160 mM, about 135 mM to about 155 mM, about 140 mM to about 155 mM, or about 145 mM to about 155 mM. In one such embodiment, the concentration of sodium chloride is about 150 mM. In other such embodiments, the concentration of sodium chloride is about 150 mM, the buffer is sodium succinate or sodium citrate buffer at a concentration of about 5 mM to about 15 mM, the liquid pharmaceutical formulation comprises a therapeutically effective amount of the antagonist anti-CD40 antibody, for example, the CHIR-12.12 or CHIR-5.9 monoclonal antibody, or antigen-binding fragment thereof, and the formulation has a pH of about pH 5.0 to about pH 7.0, about pH 5.0 to about pH 6.0, or about pH 5.5 to about pH 6.5. In other embodiments, the liquid pharmaceutical formulation comprises the antagonist anti-CD40 antibody, for example, the CHIR-12.12 or CHIR-5.9 monoclonal antibody, or antigen-binding fragment thereof, at a concentration of about 0.1 mg/ml to about 50.0 mg/ml or about 5.0 mg/ml to about 25.0 mg/ml, about 150 mM sodium chloride, and about 10 mM sodium succinate or sodium citrate, at a pH of about pH 5.5.

Protein degradation due to freeze thawing or mechanical shearing during processing of a liquid pharmaceutical formulations of the present invention can be inhibited by incorporation of surfactants into the formulation in order to lower the surface tension at the solution-air interface. Thus, in some embodiments, the liquid pharmaceutical formulation comprises a therapeutically effective amount of the antagonist anti-CD40 antibody, for example, the CHIR-12.12 or CHIR-5.9 monoclonal antibody, or antigen-binding fragment thereof, a buffer to maintain the pH of the formulation within the range of about pH 5.0 to about pH 7.0, and further comprises a surfactant. In other embodiments, the liquid pharmaceutical formulation comprises a therapeutically effective amount of the antagonist anti-CD40 antibody, for example, the CHIR-12.12 or CHIR-5.9 monoclonal antibody, or antigen-binding fragment thereof, a buffer to maintain the pH of the formulation within the range of about pH 5.0 to about pH 7.0, an isotonizing agent such as sodium chloride at a concentration of about 50 mM to about 300 mM, and further comprises a surfactant.

Typical surfactants employed are nonionic surfactants, including polyoxyethylene sorbitol esters such as polysorbate 80 (Tween 80) and polysorbate 20 (Tween 20); polyoxypropylene-polyoxyethylene esters such as Pluronic F68; polyoxyethylene alcohols such as Brij 35; simethicone; polyethylene glycol such as PEG400; lysophosphatidylcholine; and polyoxyethylene-p-t-octylphenol such as Triton X-100. Classic stabilization of pharmaceuticals by surfactants or emulsifiers is described, for example, in Levine et al. (1991) *J. Parenteral Sci. Technol.* 45(3):160-165, herein incorporated by reference. A preferred surfactant employed in the practice of the present invention is polysorbate 80. Where a surfactant is included, it is typically added in an amount from about 0.001% to about 1.0% (w/v), about 0.001% to about 0.5%, about 0.001% to about 0.4%, about 0.001% to about 0.3%, about 0.001% to about 0.2%, about 0.005% to about 0.5%, about 0.005% to about 0.2%, about 0.01% to about 0.5%, about 0.01% to about 0.2%, about 0.03% to about 0.5%, about 0.03% to about 0.3%, about 0.05% to about 0.5%, or about 0.05% to about 0.2%.

Thus, in some embodiments, the liquid pharmaceutical formulation comprises a therapeutically effective amount of the antagonist anti-CD40 antibody, for example, the CHIR-12.12 or CHIR-5.9 monoclonal antibody, or antigen-binding fragment thereof, the buffer is sodium succinate or sodium citrate buffer at a concentration of about 1 mM to about 50 mM, about 5 mM to about 25 mM, or about 5 mM to about 15 mM; the formulation has a pH of about pH 5.0 to about pH 7.0, about pH 5.0 to about pH 6.0, or about pH 5.5 to about pH 6.5; and the formulation further comprises a surfactant, for example, polysorbate 80, in an amount from about 0.001% to about 1.0% or about 0.001% to about 0.5%. Such formulations can optionally comprise an isotonizing agent, such as sodium chloride at a concentration of about 50 mM to about 300 mM, about 50 mM to about 200 mM, or about 50 mM to about 150 mM. In other embodiments, the liquid pharmaceutical formulation comprises the antagonist anti-CD40 antibody, for example, the CHIR-12.12 or CHIR-5.9 monoclonal antibody, or antigen-binding fragment thereof, at a concentration of about 0.1 mg/ml to about 50.0 mg/ml or about 5.0 mg/ml to about 25.0 mg/ml, including about 20.0 mg/ml; about 50 mM to about 200 mM sodium chloride, including about 150 mM sodium chloride; sodium succinate or sodium citrate at about 5 mM to about 20 mM, including about 10 mM sodium succinate or sodium citrate; sodium chloride at a concentration of about 50 mM to about 200 mM, including about 150 mM; and optionally a surfactant, for example, polysorbate 80, in an amount from about 0.001% to about 1.0%, including about 0.001% to about 0.5%; where the liquid pharmaceutical formulation has a pH of about pH 5.0 to about pH 7.0, about pH 5.0 to about pH 6.0, about pH 5.0 to about pH 5.5, about pH 5.5 to about pH 6.5, or about pH 5.5 to about pH 6.0.

The liquid pharmaceutical formulation can be essentially free of any preservatives and other carriers, excipients, or stabilizers noted herein above. Alternatively, the formulation can include one or more preservatives, for example, antibacterial agents, pharmaceutically acceptable carriers, excipients, or stabilizers described herein above provided they do not adversely affect the physicochemical stability of the antagonist anti-CD40 antibody or antigen-binding fragment thereof. Examples of acceptable carriers, excipients, and stabilizers include, but are not limited to, additional buffering agents, co-solvents, surfactants, antioxidants including ascorbic acid and methionine, chelating agents such as EDTA, metal complexes (for example, Zn-protein complexes), and biodegradable polymers such as polyesters. A thorough discussion of formulation and selection of pharmaceutically acceptable carriers, stabilizers, and isomolytes can be found in *Remington's Pharmaceutical Sciences* (18$^{th}$ ed.; Mack Publishing Company, Eaton, Pa., 1990), herein incorporated by reference.

After the liquid pharmaceutical formulation or other pharmaceutical composition described herein is prepared, it can be lyophilized to prevent degradation. Methods for lyophilizing liquid compositions are known to those of ordinary skill in the art. Just prior to use, the composition may be reconstituted with a sterile diluent (Ringer's solution, distilled water, or sterile saline, for example) that may include additional ingredients. Upon reconstitution, the composition is preferably administered to subjects using those methods that are known to those skilled in the art.

I. G. Use of Antagonist Anti-CD40 Antibodies in the Manufacture of Medicaments

The present invention also provides for the use of an antagonist anti-CD40 antibody or antigen-binding fragment thereof in the manufacture of a medicament for treating a subject for a cancer characterized by neoplastic B cell growth, wherein the medicament is coordinated with treatment with at least one other cancer therapy. Cancers characterized by neoplastic B cell growth include, but are not limited to, the B cell-related cancers discussed herein above, for example, non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, myeloblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, and mantle cell lymphoma.

By "coordinated" is intended the medicament comprising the antagonist anti-CD40 antibody or antigen-binding fragment thereof is to be used either prior to, during, or after treatment of the subject with at least one other cancer therapy. Examples of other cancer therapies include, but are not limited to, surgery; radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy; IL-15 therapy, and IL-21 therapy; steroid therapy; or other cancer therapy; where treatment with the additional cancer therapy, or additional cancer therapies, occurs prior to, during, or subsequent to treatment of the subject with the medicament comprising the antagonist anti-CD40 antibody or antigen-binding fragment thereof, as noted herein above.

In some embodiments, the present invention provides for the use of the anti-CD40 antibody, for example, the monoclonal antibody CHIR-12.12 or CHIR-5.9, or antigen-binding fragment thereof in the manufacture of a medicament for treating a B cell lymphoma, for example non-Hodgkin's lymphoma, in a subject, wherein the medicament is coordinated with treatment with at least one other cancer therapy selected from the group consisting of chemotherapy, anti-cancer antibody therapy, small molecule-based cancer therapy, and vaccine/immunotherapy-based cancer therapy, wherein the medicament is to be used either prior to, during, or after treatment of the subject with the other cancer therapy or, in the case of multiple combination therapies, either prior to, during, or after treatment of the subject with the other cancer therapies.

Thus, for example, in some embodiments, the invention provides for the use of the monoclonal antibody CHIR-12.12 or CHIR-5.9, or antigen-binding fragment thereof, in the manufacture of a medicament for treating a B cell lymphoma, for example, non-Hodgkin's lymphoma, in a subject, wherein the medicament is coordinated with treatment with chemotherapy, where the chemotherapeutic agent is selected from the group consisting of cytoxan, doxorubicin, vincristine, prednisone, and combinations thereof, for example CHOP. In other embodiments, the invention provides for the use of the monoclonal antibody CHIR-12.12 or CHIR-5.9, or antigen-binding fragment thereof, in the manufacture of a medicament for treating a B cell lymphoma, for example non-Hodgkin's lymphoma, in a subject, wherein the medicament is coordinated with treatment with at least one other anti-cancer antibody selected from the group consisting of alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; and any combinations thereof; wherein the medicament is to be used either prior to, during, or after treatment of the subject with the other cancer therapy or, in the case of multiple combination therapies, either prior to, during, or after treatment of the subject with the other cancer therapies.

In yet other embodiments, the present invention provides for the use of the monoclonal antibody CHIR-12.12 or CHIR-5.9, or antigen-binding fragment thereof, in the manufacture of a medicament for treating a B cell lymphoma, for example non-Hodgkin's lymphoma, in a subject, wherein the medicament is coordinated with treatment with at least one other small molecule-based cancer therapy selected from the group consisting of microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), an apoptotic agent such as Xcytrin® (motexafin gadolinium), inhibitors of production of the protein Bcl-2 by cancer cells (for example, the antisense agents oblimersen and Genasense®), nelarabine, and any combinations thereof; wherein the medicament is to be used either prior to, during, or after treatment of the subject with the other cancer therapy or, in the case of multiple combination therapies, either prior to, during, or after treatment of the subject with the other cancer therapies.

In still other embodiments, the present invention provides for the use of the monoclonal antibody CHIR-12.12 or CHIR-5.9, or antigen-binding fragment thereof, in the manufacture of a medicament for treating a B cell lymphoma, for example non-Hodgkin's lymphoma, in a subject, wherein the medicament is coordinated with treatment with at least one other vaccine/immunotherapy-based cancer therapy selected from the group consisting of vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interleukin-2 (IL-2) therapy, IL-12 therapy; IL-15 therapy, and IL-21 therapy, and any combinations thereof; wherein the medicament is to be used either prior to, during, or after treatment of the subject with the other cancer therapy or, in the case of multiple combination therapies, either prior to, during, or after treatment of the subject with the other cancer therapies.

In some embodiments, the present invention provides for the use of the anti-CD40 antibody, for example, the monoclonal antibody CHIR-12.12 or CHIR-5.9, or antigen-binding fragment thereof in the manufacture of a medicament for treating a B cell-related leukemia, for example B-cell acute lymphocytic leukemia (B-ALL), in a subject, wherein the medicament is coordinated with treatment with at least one other cancer therapy selected from the group consisting of chemotherapy and anti-metabolite therapy, wherein the medicament is to be used either prior to, during, or after treatment of the subject with the other cancer therapy or, in the case of multiple combination therapies, either prior to, during, or after treatment of the subject with the other cancer therapies. Examples of such embodiments include, but are not limited to, those instances where the medicament comprising the antagonist anti-CD40 antibody, for example, the monoclonal antibody CHIR-12.12 or CHIR-5.9, or antigen-binding fragment thereof is coordinated with treatment with a chemotherapeutic agent or anti-metabolite selected from the group consisting of cytoxan, doxorubicin, vincristine, prednisone, cytarabine, mitoxantrone, idarubicin, asparaginase, methotrexate, 6-thioguanine, 6-mercaptopurine, and combinations thereof; wherein the medicament is to be used either prior to, during, or after treatment of the subject with the other cancer therapy or, in the case of multiple combination therapies, either prior to, during, or after treatment of the subject with the other cancer therapies. In one such example, the medicament is coordinated with treatment with cytarabine plus daunorubicin, cytarabine plus mitoxantrone, and/or cytarabine plus idarubicin; wherein the medicament is to be used either prior to, during, or after treatment of the B-ALL subject with the other cancer therapy or, in the case of multiple combination therapies, either prior to, during, or after treatment of the subject with the other cancer therapies.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating a subject for a cancer characterized by neoplastic B cell growth, including the B cell-related cancers described herein above, wherein the medicament is used in a subject that has been pretreated with at least one other cancer therapy. By "pretreated" or "pretreatment" is intended the subject has received one or more other cancer therapies (i.e., been treated with at least one other cancer therapy) prior to receiving the medicament comprising the antagonist anti-CD40 antibody or antigen-binding fragment thereof. "Pretreated" or "pretreatment" includes subjects that have been treated with at least one other cancer therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior cancer therapy, or prior cancer therapies. Thus, the subject that receives the medicament comprising the antagonist anti-CD40 antibody or antigen-binding fragment thereof could have responded, or could have failed to respond (i.e. the cancer was refractory), to pretreatment with the prior cancer therapy, or to one or more of the prior cancer therapies where pretreatment comprised multiple cancer therapies. Examples of other cancer therapies for which a subject can have received pretreatment prior to receiving the medicament comprising the antagonist anti-CD40 antibody or antigen-binding fragment thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy, including, but not limited to, those anti-cancer antibodies listed herein above; small molecule-based cancer therapy, including, but not limited to, the small molecules listed herein above; vaccine/immunotherapy-based cancer therapies, including, but limited to, those listed herein above; steroid therapy; other cancer therapy; or any combination thereof.

"Treatment" in the context of coordinated use of a medicament described herein with one or more other cancer therapies is herein defined as the application or administration of the medicament or of the other cancer therapy to a subject, or application or administration of the medicament or other cancer therapy to an isolated tissue or cell line from a subject, where the subject has a cancer characterized by neoplastic B cell growth, a symptom associated with such a cancer, or a predisposition toward development of such a cancer, where the purpose is to cure, heal, alleviate, relieve, alter, remedy, ameliorate, improve, or affect the cancer, any associated symptoms of the cancer, or the predisposition toward the development of the cancer.

The following examples for this invention are offered by way of illustration and not by way of limitation.

I. H. EXPERIMENTAL

The antagonist anti-CD40 antibodies used in the examples below are CHIR-5.9 and CHIR-12.12. The CHIR-5.9 and CHIR-12.12 anti-CD40 antibodies are human $IgG_1$ subtype anti-human CD40 monoclonal antibodies (mAbs) generated by immunization of transgenic mice bearing the human $IgG_1$ heavy chain locus and the human κ light chain locus (XenoMouse® technology; Abgenix; Fremont, Calif.). As shown by FACS analysis, CHIR-5.9 and CHIR-12.12 bind specifically to human CD40 and can prevent CD40 ligand binding. Both mAbs can compete off CD40-ligand pre-bound to cell surface CD40. Both antibodies are strong antagonists and inhibit in vitro CD40 ligand-mediated proliferation of normal B cells, as well as cancer cells from NHL and CLL patients. In vitro, both antibodies kill cancer cell lines as well as primary cancer cells from NHL patients by ADCC. Dose-dependent anti-tumor activity was seen in a xenograft human lymphoma model. The binding affinity of CHIR-5.9 to human CD40 is $1.2 \times 10^{-8}$ M and the binding affinity of CHIR-12.12 to human CD40 is $5 \times 10^{-10}$ M.

Mouse hybridoma line 131.2F8.5.9 (CMCC#12047) and hybridoma line 153.8E2.D10.D6.12.12 (CMCC#12056) have been deposited with the American Type Culture Collection [ATCC; 10801 University Blvd., Manassas, Va. 20110-2209 (USA)] on Sep. 17, 2003, under Patent Deposit Number PTA-5542 and PTA-5543, respectively.

The following protocols have been used in the examples described below.

ELISA Assay for Immunoglobulin Quantification

The concentrations of human IgM and IgG were estimated by ELISA. 96-well ELISA plates were coated with 2 μg/ml goat anti-human IgG MAb (The Jackson Laboratory, Bar Harbor, Me.) or with 2 μg/ml goat anti-human IgM MAb 4102 (Bio Source International, California) in 0.05 M carbonate buffer (pH 9.6), by incubation for 16 hours at 4° C. Plates were washed 3 times with PBS-0.05% Tween-20 (PBS-Tween) and saturated with BSA for 1 hour. After 2 washes the plates were incubated for 2 hour at 37° C. with different dilutions of the test samples. After 3 washes, bound Ig was detected by incubation for 2 hour at 37° C. with 1 μg/ml peroxidase-labeled goat anti-human IgG MAb or goat anti-human IgM Mab. Plates were washed 4 times, and bound peroxidase activity was revealed by the addition of O-phenylenediamine as a substrate. Human IgG or IgM standards (Caltaq, Burlingame, Calif.) was used to establish a standard curve for each assay.

Isolation of the Peripheral Blood Mononuclear Cells (PBMC) from Human Peripheral Blood 20 ml of Ficoll-Paque solution (low endotoxin; Pharmacia) was added per 50 ml polystyrene tube, in 3 tubes, 30 minutes before adding the blood. The Ficoll-Paque solution was warmed up to room temperature. 3 L of bleach in 1:10 dilution was prepared, and used to wash all the tubes and pipettes contacting the blood. The blood was layered on the top of the Ficoll-Paque solution without disturbing the Ficoll layer, at 1.5 ml blood/1 ml of Ficoll-Paque. The tubes were centrifuged at 1700 rpm for 30 minutes at room temperature with the brake on the centrifuge turned off. As much of the top layer (plasma) as possible was removed, minimizing the vacuum in order to avoid removing the second layer of solution. The second layer, which contains the B and T lymphocytes, was collected using a sterile Pasteur pipette, and place in two 50-ml polystyrene tubes. The collection was diluted with 3× the volume of cold RPMI with no additives, and the tubes were centrifuged at 1000 RPM for 10 minutes. The media was removed by aspiration, and the cells from both 50-ml tubes were resuspended in a total of 10 ml cold RPMI (with additives) and transferred to a 15-ml tube. The cells were counted using the hemacytometer, then centrifuged at 1000 RPM for 10 minutes. The media was removed and the cells resuspended in 4 ml RPMI. This fraction contained the PBMC.

Isolation of the B Cells from PBMC

100 μl of Dynabeads (anti-h CD19) were placed in a 5-ml plastic tube. 3 ml of sterile PBS were added to the beads and mixed, and placed in the magnetic holder, then allowed to sit for 2 minutes. The solution was removed using a Pasteur pipette. 3 ml of sterile PBS were added, mixed, and placed in the magnetic holder, then allowed to sit for 2 minutes. This procedure with sterile PBS was repeated one more time for a total of 3 washes. The PBMC was added into the beads and incubated, while mixing, for 30 minutes at 40° C. The tube containing the PBMC and beads was placed into the magnetic holder for 2 minutes, then the solution was transferred to a new 5-ml tube in the magnetic holder. After 2 minutes, the solution was transferred to a new 15-ml tube. This step was repeated four more times, and the solutions of the first four times were collected in the 15-ml tube, then centrifuged at 1000 RPM for 5 minutes. This step produced the pellet for T-cell separation.

100 μl RPMI (with additives) was added to collect the beads, and the solution was transferred into a 0.7-ml tube. 10 μl of Dynal Detacha Beads were added into the suspension at room temperature, and it was allowed to rotate for 45 minutes. The suspension was transferred into a new 5-ml tube and 3-ml of RPMI (with additives) were added. The tube was placed in the magnetic holder for 2 minutes. The solution was transferred into a new 5-ml tube in the holder for 2 minutes, then to a 15-ml tube. The previous step was repeated three more times, collecting the solution in the 15-ml tube. The 15-ml tube was centrifuged at 1000 RPM for 10 minutes, and the cells resuspended in 10 ml RMPI. The washing step was repeated 2 more times for a total of 3 washes. The cells were counted before the last centrifugation. This step completed the B-cell purification. Cells were stored in 90% FCS and 10% DMSO and frozen at −800° C.

Isolation of the T Cells

The human T cell Enrichment Column (R&D systems, anti-h CD 3 column kit) was prepared using 20 ml of 1× column wash buffer by mixing 2 ml of 10× column wash buffer and 18 ml of sterile distilled water. The column was cleaned with 70% ethanol and placed on top of a 15-ml tube. The top cap of the column was removed first to avoid drawing air into the bottom of the column. Next, the bottom cap was removed, and the tip was cleaned with 70% ethanol. The fluid within the column was allowed to drain into the 15-ml tube. A new sterile 15-ml tube was placed under the column after the column buffer had drained to the level of the white filter. The B-cell depleted PBMC fraction was suspended in 1 ml of buffer and added to the top of the column. The cells were allowed to incubate with the column at room temperature for 10 minutes. The T-cells were eluted from the column with 4 aliquots of 2 ml each of 1× column wash buffer. The collected T-cells were centrifuged at 1000 RPM for 5 minutes. The supernatant was removed and the cells resuspended in 10 ml RPMI. Cells were counted and centrifuged one more time. The supernatant was removed, completing the T-cell purification. Cells were stored in 90% FCS and 10% DMSO and frozen at −80° C.

For the above procedures, the RPMI composition contained 10% FCS (inactivated at 56° C. for 45 min), 1% Pen/Strep (100 u/ml Penicillin, 0.1 µg/ml Streptomycin), 1% Glutamate, 1% sodium puravate, 50 µM 2-ME.

Flow Cytofluorometric Assay

Ramos cells (106 cells/sample) were incubated in 100 µl primary antibody (10 µg/ml in PBS-BSA) for 20 min at 4° C. After 3 washes with PBS-BSA or HBSS-BSA, the cells were incubated in 100 µl FITC-labeled F(ab')$_2$ fragments of goat anti-(human IgG) antibodies (Caltaq) for 20 min at 4° C. After 3 washes with PBS-BSA and 1 wash with PBS, the cells were resuspended in 0.5-ml PBS. Analyses were performed with a FACSCAN V (Becton Dickinson, San Jose, Calif.).

Generation of Hybridoma Clones

Splenocytes from immunized mice were fused with SP 2/0 or P 3×63Ag8.653 murine myeloma cells at a ratio of 10:1 using 50% polyethylene glycol as previously described by de Boer et al. (1988) *J. Immunol. Meth.* 113:143. The fused cells were resuspended in complete IMDM medium supplemented with hypoxanthine (0.1 mM), aminopterin (0.01 mM), thymidine (0.016 mM), and 0.5 ng/ml hIL-6 (Genzyme, Cambridge, Mass.). The fused cells were then distributed between the wells of 96-well tissue culture plates, so that each well contained 1 growing hybridoma on average.

After 10-14 days the supernatants of the hybridoma populations were screened for specific antibody production. For the screening of specific antibody production by the hybridoma clones, the supernatants from each well were pooled and tested for anti-CD 40 activity specificity by ELISA first. The positives were then used for fluorescent cell staining of EBV-transformed B cells as described for the FACS assay above. Positive hybridoma cells were cloned twice by limiting dilution in IMDM/FBS containing 0.5 ng/ml hIL-6.

Example 1

Production of Anti-CD40 Antibodies

Several fully human, antagonist anti-CD40 monoclonal antibodies of IgG1 isotype were generated. Transgenic mice bearing the human IgG1 heavy chain locus and the human κ chain locus (Abgenix γ-1 XenoMouse® technology (Abgenix; Fremont, Calif.)) were used to generate these antibodies. SF9 insect cells expressing CD40 extracellular domain were used as immunogen. A total of 31 mice spleens were fused with the mouse myeloma SP2/0 cells to generate 895 antibodies that recognize recombinant CD40 in ELISA (Tables 1A and 1B). On average approximately 10% of hybridomas produced using Abgenix XenoMouse® technology may contain mouse lambda light chain instead of human kappa chain. The antibodies containing mouse light lambda chain were selected out. A subset of 260 antibodies that also showed binding to cell-surface CD40 were selected for further analysis. Stable hybridomas selected during a series of subcloning procedures were used for further characterization in binding and functional assays.

TABLE 1A

A Typical Fusion

| Fusion # | anti-CD40 titer (1:100K) | Fusion Efficiency | # of wells screened | # of ELISA+ | # of cell surface+ |
|---|---|---|---|---|---|
| 153 | 3 | 100% | 960 | 123 | 33 |
| 154 | 4.67 | 15% | 140 | 0 | 0 |
| 155 | 6 | ~40% | 960 | 3 | 3 |
| 156 | 3.17 | ~25% | 220 | 1 | 0 |
| 157 | 4.67 | 90% | 960 | 32 | 6 |
| 158 | 4.4 | 90% | 960 | 23 | 8 |
| 159 | 1.17 | 100% | 960 | 108 | 18 |
| 160 | 1.78 | 90% | 960 | 30 | 5 |
| Total | | | 6120 | 320 | 73 |

TABLE 1B

Summary of Four Sets of Fusions

| # of mice | ELISA-positive hybridomas | Cell surface positive Hybridomas |
|---|---|---|
| 31 | 895 | 260 |

TABLE 2

Summary of initial set of data with anti-CD40 IgG1 antibodies

| Mother Hybridoma | Hybridoma clones | cell surface binding | Antagonist | ADCC | CDC | CMCC# | V-region DNA sequence |
|---|---|---|---|---|---|---|---|
| 131.2F5 | 131.2F5.8.5.1 | +++ | ++ | ND | ND | ND | |
| | 131.2F5.8.5.9 | +++ | +++ | ++ | − | 12047 | Yes |
| | 131.2F5.8.5.11 | +++ | +++ | ++ | − | 12055 | Yes |
| 153.3C5 | 153.3C5D8D7.8.4.7.1 | ++ | ND | ND | ND | ND | |
| | 153.3C5D8D7.8.4.7.8 | ++ | ND | ND | ND | ND | |
| | 153.3C5D8D7.8.4.7.11 | +++ | +++ | + | ND | ND | |
| 153.1D2 | 153.1D2.9.1 | +++ | ND | ND | ND | 12067 | |
| | 153.1D2.9.8 | +++ | +++ | ++ | − | 12057 | |
| | 153.1D2.9.12 | +++ | ND | ND | ND | 12068 | |
| 158.6F3 | 158.6F3.5.1 | +++ | +++ | ++ | − | 12054 | Yes |
| | 158.6F3.5.7 | +++ | ND | ND | ND | 12061 | |
| | 158.6F3.5.10 | +++ | ND | ND | ND | 12062 | |
| | 153.8E2D10D6.12.7 | +++ | ND | ND | ND | 12075 | |

TABLE 2-continued

Summary of initial set of data with anti-CD40 IgG1 antibodies

| Mother Hybridoma | Hybridoma clones | cell surface binding | Antagonist | ADCC | CDC | CMCC# | V-region DNA sequence |
|---|---|---|---|---|---|---|---|
| 153.8E2 | 153.8E2D10D6.12.9 | +++ | ND | ND | ND | 12063 | |
| | 153.8E2D10D6.12.12 | +++ | +++ | ++++ | − | 12056 | Yes |
| | 155.2C2E9F12.2.10.4 | +++ | +/− | ND | ND | 12064 | |
| 155.2C2 | 155.2C2E9F12.2.10.5 | +++ | ND | ND | ND | 12065 | |
| | 155.2C2E9F12.2.10.6 | +/− | ND | ND | ND | 12066 | |
| | 166.5E6G12.1 | +++ | ND | ND | ND | 12069 | |
| 166.5E6 | 166.5E6G12.3 | +++ | ND | ND | ND | 12070 | |
| | 166.5E6G12.4 | +++ | + | ND | ND | 12071 | |
| 177.8C10 | 177.8C10B3H9 | +++ | ++ | ND | ND | ND | |
| | 183.4B3E11.6.1.5 | ++ | ND | ND | ND | ND | |
| 183.4B3 | 183.4B3E11.6.1.9 | ++ | ND | ND | ND | ND | |
| | 183.4B3E11.6.1.10 | +++ | ++ | ND | ND | ND | |
| | 183.2G5D2.8.7 | +++ | +/− | ND | ND | ND | |
| 183.2G5 | 183.2G5D2.8.8 | +++ | ND | ND | ND | ND | |
| | 183.2G5D2.8.9 | +++ | ND | ND | ND | ND | |
| | 184.6C11D3.2 | ++ | ND | ND | ND | 12078 | |
| 184.6C11 | 184.6C11D3.3 | ++ | ND | ND | ND | 12080 | |
| | 184.6C11D3.6 | +/− | +/− | ND | ND | 12079 | |
| | 185.3E4F12.5.6 | +++ | ND | ND | ND | 12072 | |
| 185.3E4 | 185.3E4F12.5.11 | +++ | ND | ND | ND | 12073 | |
| | 185.3E4F12.5.12 | +++ | + | ND | ND | 12074 | |
| | 185.1A9E9.6.1 | + | ND | ND | ND | ND | |
| 185.1A9 | 185.1A9E9.6.6 | +++ | +++ | + | ND | ND | |
| | 185.9F11E10.3B5.1 | +++ | ND | ND | ND | ND | |
| 185.9F11 | 185.9F11E10.3B5.8 | +++ | ND | ND | ND | ND | |
| | 185.9F11E10.3B5.12 | +++ | +++ | ND | ND | ND | |

Clones from 7 mother hybridomas were identified to have antagonist activity. Based on their relative antagonist potency and ADCC activities, two hybridoma clones were selected. Their names are: 131.2F8.5.9 (5.9) and 153.8E2.D10.D6.12.12 (12.12).

Clones from 7 other hybridomas were identified as having antagonist activity (Table 2 above). Based on their relative antagonistic potency and ADCC activities, two hybridoma clones were selected for further evaluation. They are named 131.2F8.5.9 (5.9) and 153.8E2.D10.D6.12.12 (12.12). The binding profile of these two antibodies to CD40+ lymphoma cell line is shown as a flow cytometric histogram in FIG. 1.

Example 2

Polynucleotide and Amino Acid Sequences of Human Anti-CD40 Antibodies

The cDNAs encoding the variable regions of the candidate antibodies were amplified by PCR, cloned, and sequenced. The amino acid sequences for the light chain and heavy chain of the CHIR-12.12 antibody are set forth in FIGS. 9A and 9B, respectively. See also SEQ ID NO:2 (light chain for mAb CHIR-12.12) and SEQ ID NO:4 (heavy chain for mAb CHIR-12.12). A variant of the heavy chain for mAb CHIR-12.12 is shown in FIG. 9B (see also SEQ ID NO:5), which differs from SEQ ID NO:4 in having a serine residue substituted for the alanine residue at position 153 of SEQ ID NO:4. The nucleotide sequences encoding the light chain and heavy chain of the CHIR-12.12 antibody are set forth in FIGS. 10A and 10B, respectively. See also SEQ ID NO:1 (coding sequence for light chain for mAb CHIR-12.12) and SEQ ID NO:3 (coding sequence for heavy chain for mAb CHIR-12.12). The amino acid sequences for the light chain and heavy chain of the CHIR-5.9 antibody are set forth in FIGS. 11A and 11B, respectively. See also SEQ ID NO:6 (light chain for mAb CHIR-5.9) and SEQ ID NO:7 (heavy chain for mAb CHIR-5.9). A variant of the heavy chain for mAb CHIR-5.9 is shown in FIG. 11B (see also SEQ ID NO:8), which differs from SEQ ID NO:7 in having a serine residue substituted for the alanine residue at position 158 of SEQ ID NO:7.

As expected for antibodies derived from independent hybridomas, there is substantial variation in the nucleotide sequences in the complementarity determining regions (CDRs). The diversity in the CDR3 region of $V_H$ is believed to most significantly determine antibody specificity.

Example 3

Effect of CHIR-5.9 and CHIR-12.12 on the CD40/CD40L Interaction In Vitro

Figure 2A:
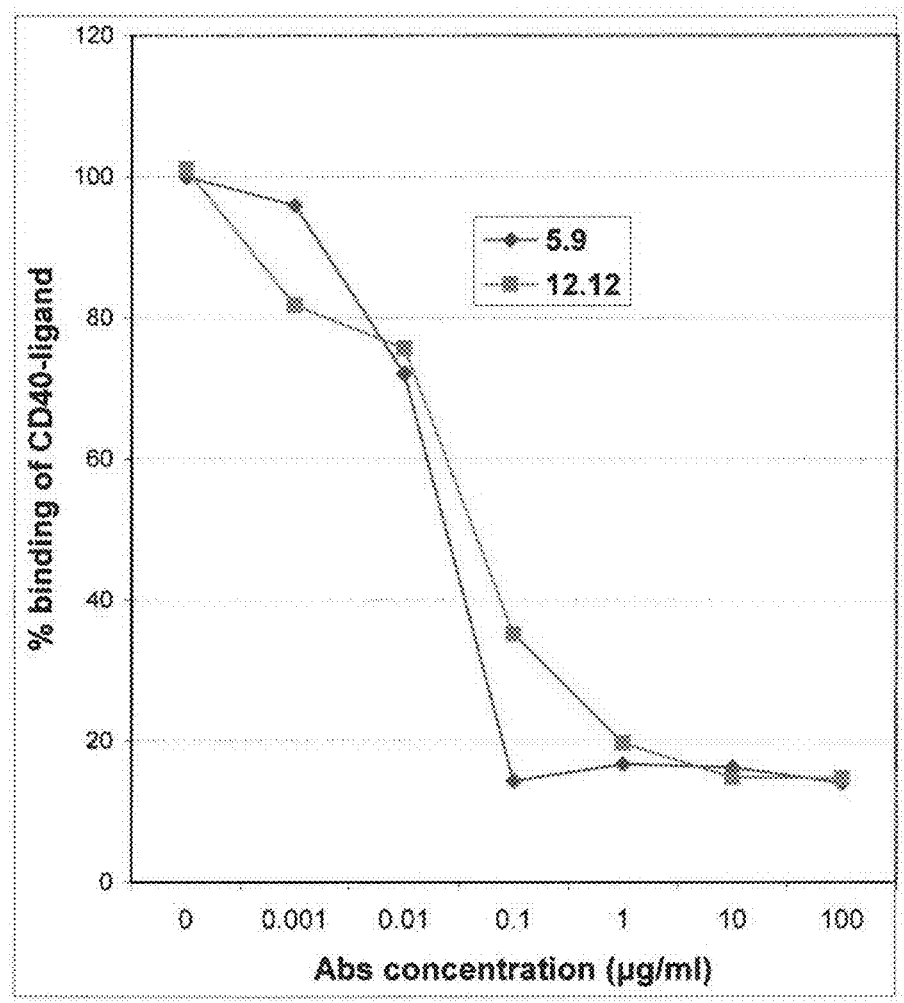
FIGS. 2A and 2B illustrate binding properties of the CHIR-5.9 and CHIR-12.12 monoclonal anti-CD40 antibodies relative to CD40 ligand.
Figure 2B:
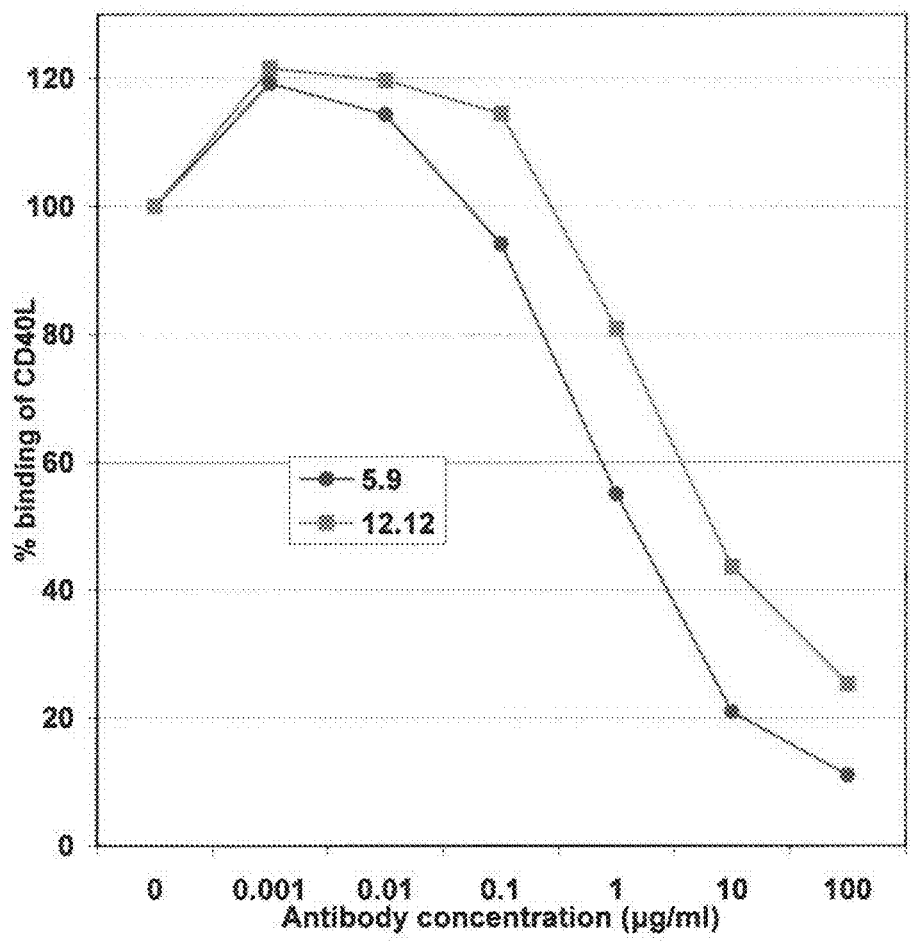

The candidate antibodies CHIR-5.9 and CHIR-12.12 prevent the binding of CD40 ligand to cell surface CD40 and displace the pre-bound CD40 ligand. Antibodies CHIR-5.9 and CHIR-12.12 were tested for their ability to prevent CD40-ligand binding to CD40 on the surface of a lymphoma cell line (Ramos). Binding of both antibodies (unlabeled) prevented the subsequent binding of PE-CD40 ligand as measured by flow cytometric assays (FIG. 2A). In a second set of assays the two antibodies were tested for their ability to replace CD40 ligand pre-bound to cell surface CD40. Both antibodies were effective for competing out pre-bound CD40 ligand, with CHIR-5.9 being slightly more effective than CHIR-12.12 (FIG. 2B).

Example 4

CHIR-5.9 and CHIR-12.12 Bind to a Different Epitope on CD40 than 15B8

The candidate monoclonal antibodies CHIR-5.9 and CHIR-12.12 compete with each other for binding to CD40 but not with 15B8, an IgG₂ anti-CD40 mAb (see International Publication No. WO 02/28904). Antibody competition binding studies using Biacore™ were designed using CM5 biosensor chips with protein A immobilized via amine coupling, which was used to capture either anti-CD40, CHIR-12.12, or 15B8. Normal association/dissociation binding curves are observed with varying concentrations of CD40-his (data not shown). For competition studies, either CHIR-12.12 or 15B8 were captured onto the protein A surface. Subsequently a CD40-his/CHIR-5.9 Fab complex (100 nM CD40:1 µM CHIR-5.9 Fab), at varying concentrations, was flowed across the modified surface. In the case of CHIR-12.12, there was no association of the complex observed, indicating CHIR-5.9 blocks binding of CHIR-12.12 to CD40-his. For 15B8, association of the Fab CHIR-5.9 complex was observed indicating CHIR-5.9 does not block binding of 15B8 to CD40 binding site. However, the off rate of the complex dramatically increased (data not shown).

It has also been determined that 15B8 and CHIR-12.12 do not compete for CD40-his binding. This experiment was set up by capturing CHIR-12.12 on the protein A biosensor chip, blocking residual protein A sites with control hIgG$_1$, binding CD40-his and then flowing 15B8 over the modified surface. 15B8 did bind under these conditions indicating CHIR-12.12 does not block 15B8 from binding to CD40.

Example 5

Binding Properties of Selected Hybridomas

Protein A was immobilized onto CM5 biosensor chips via amine coupling. Human anti-CD40 monoclonal antibodies, at 1.5 µg/ml, were captured onto the modified biosensor surface for 1.5 minutes at 10 µl/min. Recombinant soluble CD40-his was flowed over the biosensor surface at varying concentrations. Antibody and antigen were diluted in 0.01 M HEPES pH 7.4, 0.15 M NaCl, 3 mM EDTA, 0.005% Surfactant P20 (HBS-EP). Kinetic and affinity constants were determined using the Biaevaluation software with a 1:1 interaction model/global fit.

As shown in Table 3 below, there is 121-fold difference in the off rate of CHIR-5.9 and CHIR-12.12 resulting in 24-fold higher affinity for CHIR-12.12.

| Antibody | ka (M−1 sec−1)) | kd (sec−1) | KD (nM) |
|---|---|---|---|
| Anti-CD40, CHIR-5.9 | $(12.35 \pm 0.64) \times 10^5$ | $(15.0 \pm 1.3) \times 10^{-3}$ | $12.15 \pm 0.35$ |
| Anti-CD40, CHIR-12.12 | $(2.41 \pm 0.13) \times 10^5$ | $(1.24 \pm 0.06) \times 10^{-4}$ | $0.51 \pm 0.02$ |

Example 6

CHIR-5.9 and CHIR-12.12 are Potent Antagonists for CD40-Mediated Proliferation of Human Lymphocytes from Normal Subjects Engagement of CD40 by CD40 ligand induces proliferation of human B cells. An antagonist anti-CD40 antibody is expected to inhibit this proliferation. Two candidate antibodies (CHIR-5.9 and CHIR-12.12) were tested for their ability to inhibit CD40 ligand-induced proliferation of PBMC from normal human subjects. Formaldehyde-fixed CHO cells transfectant-expressing CD40 ligand (CD40L) were used as a source of CD40 ligand. Human PBMC were cultured for 4 days with the formaldehyde-fixed CHO cells expressing CD40-ligand in the presence of varying concentrations of anti-CD40 mAb CHIR-5.9 or CHIR-12.12. The proliferation was measured by tritiated-thymidine incorporation. Cells were pulsed with tritiated-labeled thymidine at 37° C. for 14-18 hours.

Both antibodies were found to be very effective for inhibiting CD40 ligand-induced proliferation of human PBMC (Table 4A, mAb CHIR-5.9, Table 4B, mAb CHIR-12.12). The experiment was performed with multiple donors of PBMC (n=12 for CHIR-5.9 and n=2 for CHIR-12.12) to ensure that the observed inhibition was not a peculiarity of cells from a single donor. Follow-up assessments with 4 additional donors of PBMC were carried out for mAb CHIR-12.12 with similar trends observed. A wide range of antibody concentrations (0.01 µg/ml to 100 µg/ml) was used in these assays. Nearly complete inhibition of CD40 ligand-induced proliferation could be achieved at 0.1 µg/ml concentration of antibodies in most cases. Antibody concentration (pM) to inhibit 50% of CD-40 ligand-induced lymphocyte proliferation (IC50) for lymphocytes from 6 donors yielded an average IC50 (pM) of 47 (SD=21; donor 1, 24; donor 2, 66; donor 3, 45; donor 4, 84; donor 5, 30; donor 6, 35), which compares favorably with the average IC50 (pM) of 49.65 shown in Table 4B. Based on the current data set, both candidate antibodies seem similar in their potency for inhibition of CD40 ligand-induced proliferation of normal PBMC.

TABLE 4A

Effect of mAb CHIR-5.9 on CD40L-induced PBMC proliferation.

| Exp# | | PBMC alone | CHO-CD40L alone | PBMC + CHO-CD40L | Abs Conc (µg/ml) | huIgG1 | | CHIR-5.9 | |
|---|---|---|---|---|---|---|---|---|---|
| | | | | | | CPM | % of inhibition | CPM | % of inhibition |
| PBMC-010 | | 1851 | 121 | 4436 | 1 | 5080 | −26 | 2622 | 74 |
| | | 1851 | 121 | 4436 | 0.25 | 5498 | −43 | 2907 | 62 |
| | | 1851 | 121 | 4436 | 0.0625 | 6029 | −65 | 2619 | 74 |
| | | 1851 | 121 | 4436 | 0.0156 | 5814 | −56 | 1199 | 131 |
| PBMC-011 | Donor#1 | 2162 | 178 | 8222 | 10 | 13137 | −84 | 2252 | 101 |
| | | 2162 | 178 | 8222 | 1 | 11785 | −61 | 1438 | 115 |
| | | 2162 | 178 | 8222 | 0.1 | 10758 | −43 | 1249 | 119 |
| | | 2162 | 178 | 8222 | 0.01 | 11322 | −53 | 4705 | 60 |
| | Donor#2 | 2216 | 294 | 7873 | 10 | 16679 | −164 | 2362 | 103 |
| | | 2216 | 294 | 7873 | 1 | 14148 | −117 | 1202 | 124 |
| | | 2216 | 294 | 7873 | 0.1 | 12422 | −85 | 756 | 133 |
| | | 2216 | 294 | 7873 | 0.01 | 13870 | −112 | 6606 | 24 |
| | Donor#3 | 2396 | 241 | 11021 | 10 | 11641 | −7 | 2631 | 100 |
| | | 2396 | 241 | 11021 | 1 | 13528 | −30 | 1450 | 114 |
| | | 2396 | 241 | 11021 | 0.1 | 12176 | −14 | 990 | 120 |
| | | 2396 | 241 | 11021 | 0.01 | 11895 | −10 | 5357 | 68 |

TABLE 4A-continued

Effect of mAb CHIR-5.9 on CD40L-induced PBMC proliferation.

| Exp# | | PBMC alone | CHO-CD40L alone | PBMC + CHO-CD40L | Abs Conc (µg/ml) | huIgG1 CPM | % of inhibition | CHIR-5.9 CPM | % of inhibition |
|---|---|---|---|---|---|---|---|---|---|
| | Donor#4 | 4552 | 133 | 15301 | 10 | 22098 | −64 | 3768 | 109 |
| | | 4552 | 133 | 15301 | 1 | 19448 | −39 | 2040 | 125 |
| | | 4552 | 133 | 15301 | 0.1 | 18398 | −29 | 1728 | 128 |
| | | 4552 | 133 | 15301 | 0.01 | 22767 | −70 | 9481 | 55 |
| PBMC-012 | | 777 | 117 | 6041 | 10 | 7327 | −25 | 2150 | 76 |
| | | 777 | 117 | 6041 | 1 | 6212 | −3 | 1550 | 87 |
| | | 777 | 117 | 6041 | 0.1 | 7006 | −19 | 828 | 101 |
| | | 777 | 117 | 6041 | 0.01 | 7524 | −29 | 1213 | 94 |
| PBMC-014 | | 1857 | 73 | 7889 | 100 | 9399 | −25 | 3379 | 76 |
| | | 1857 | 73 | 7889 | 20 | 8120 | −4 | 3870 | 67 |
| | | 1857 | 73 | 7889 | 4 | 8368 | −8 | 2552 | 90 |
| | | 1857 | 73 | 7889 | 0.8 | 9564 | −28 | 1725 | 103 |
| PBMC-015 | Donor#1 | 3203 | 127 | 10485 | 100 | 15425 | −69 | 1497 | 126 |
| | | 3203 | 127 | 10485 | 20 | 11497 | −14 | 1611 | 124 |
| | | 3203 | 127 | 10485 | 4 | 11641 | −16 | 1359 | 128 |
| | | 3203 | 127 | 10485 | 0.8 | 12807 | −32 | 1490 | 126 |
| | Donor#2 | 3680 | 175 | 15145 | 100 | 21432 | −56 | 1792 | 118 |
| | | 3680 | 175 | 15145 | 20 | 16998 | −16 | 1779 | 118 |
| | | 3680 | 175 | 15145 | 4 | 17729 | −23 | 1965 | 117 |
| | | 3680 | 175 | 15145 | 0.8 | 17245 | −19 | 2217 | 115 |
| | Donor#3 | 2734 | 152 | 19775 | 100 | 22967 | −19 | 1664 | 107 |
| | | 2734 | 152 | 19775 | 20 | 21224 | −9 | 1848 | 106 |
| | | 2734 | 152 | 19775 | 4 | 20658 | −5 | 1534 | 108 |
| | | 2734 | 152 | 19775 | 0.8 | 18923 | 5 | 1262 | 110 |
| PBMC-016 | | 1118 | 36 | 13531 | 0.1 | 10928 | 21 | 745 | 103 |
| | | 1118 | 36 | 13531 | 0.05 | 11467 | 17 | 962 | 102 |
| | | 1118 | 36 | 13531 | 0.01 | 11942 | 13 | 3013 | 85 |
| PBMC-017 | | 962 | 75 | 12510 | 1 | 13597 | −9 | 258 | 107 |
| | Average % inhibition of human PBMC at 100 µg/ml | | | | | | −42 | | 107 |
| | Average % inhibition of human PBMC at 10 µg/ml | | | | | | −69 | | 98 |
| | Average % inhibition of human PBMC at 1 µg/ml | | | | | | −41 | | 107 |
| | Average % inhibition of human PBMC at 0.1 µg/ml | | | | | | −28 | | 117 |
| | Average % inhibition of human PBMC at 0.01 µg/ml | | | | | | −44 | | 64 |
| | Average % inhibition of human PBMC | | | | | | −35 | | 101 |

% of inhibition: 100 − (CPM with Abs − PBMC alone − CHO-CD40L alone)/(CPM of PBMC + CHO-CD40L − PBMC alone − CHO-CD40L alone)*100%

TABLE 4B

Effect of mAb CHIR-12.12 on CD40L-induced PBMC proliferation.

| Exp# | | PBMC alone | CHO-CD40L alone | PBMC + CHO-CD40L | Abs Conc (µg/ml) | HuIgG1 CPM | % of inhibition | CHIR-12.12 CPM | % of inhibition | IC50(nM) |
|---|---|---|---|---|---|---|---|---|---|---|
| PBMC-025 | Donor#1 | 4051 | 32 | 42292 | 0.1 | 33354 | 23 | 440 | 110 | 24.22 |
| | | 4051 | 32 | 42292 | 0.01 | 37129 | 14 | 8696 | 88 | |
| | | 4051 | 32 | 42292 | 0.001 | 40271 | 5 | 32875 | 25 | |
| | | 4051 | 32 | 42292 | 0.0001 | 40034 | 6 | 37261 | 13 | |
| | Donor#2 | 2260 | 31 | 14987 | 0.1 | 15767 | −6 | 365 | 115 | 65.96 |
| | | 2260 | 31 | 14987 | 0.01 | 17134 | −17 | 6734 | 65 | |
| | | 2260 | 31 | 14987 | 0.001 | 20142 | −41 | 16183 | −9 | |
| | | 2260 | 31 | 14987 | 0.0001 | 17847 | −23 | 16187 | −9 | |
| PBMC-026 | Donor#1 | 2039 | 35 | 19071 | 0.1 | 17136 | 11 | 624 | 109 | 45 |
| | | 2039 | 35 | 19071 | 0.01 | 16445 | 15 | 6455 | 74 | |
| | | 2039 | 35 | 19071 | 0.001 | 16195 | 17 | 17833 | 7 | |
| | | 2039 | 35 | 19071 | 0.0001 | 18192 | 5 | 17924 | 7 | |
| | Donor#2 | 2016 | 64 | 17834 | 0.1 | 17181 | 4 | 2078 | 100 | 84 |
| | | 2016 | 64 | 17834 | 0.01 | 16757 | 7 | 10946 | 44 | |
| | | 2016 | 64 | 17834 | 0.001 | 18613 | −5 | 17924 | −1 | |
| | | 2016 | 64 | 17834 | 0.0001 | 17169 | 4 | 18569 | −5 | |
| PBMC-028 | Donor#1 | 4288 | 45 | 22547 | 1 | 18204 | 24 | 2098 | 112 | 30.07 |
| | | 4288 | 45 | 22547 | 0.1 | 20679 | 10 | 1827 | 114 | |
| | | 4288 | 45 | 22547 | 0.01 | 22799 | −1 | 6520 | 88 | |
| | | 4288 | 45 | 22547 | 0.001 | 23547 | −5 | 22327 | 1 | |
| | | 4288 | 45 | 22547 | 0.0001 | 24778 | −12 | 24124 | −9 | |
| | Donor#2 | 2148 | 58 | 54894 | 1 | 48545 | 12 | 5199 | 94 | 34.68 |
| | | 2148 | 58 | 54894 | 0.1 | 45708 | 17 | 5091 | 95 | |
| | | 2148 | 58 | 54894 | 0.01 | 51741 | 6 | 18890 | 68 | |
| | | 2148 | 58 | 54894 | 0.001 | 52421 | 5 | 50978 | 7 | |
| | | 2148 | 58 | 54894 | 0.0001 | 54778 | 0 | 52581 | 4 | |

TABLE 4B-continued

Effect of mAb CHIR-12.12 on CD40L-induced PBMC proliferation.

|  |  |  |  |  | Abs Conc | HuIgG1 | | CHIR-12.12 | | |
|---|---|---|---|---|---|---|---|---|---|---|
| Exp# | | PBMC alone | CHO-CD40L alone | PBMC + CHO-CD40L | (µg/ml) | CPM | % of inhibition | CPM | % of inhibition | IC50(nM) |
| PBMC-029 | Donor#1 | 609 | 69 | 10054 | 0.1 | 11027 | −10 | 2098 | 85 | 28.06 |
| | | 609 | 69 | 10054 | 0.01 | 10037 | 0 | 1827 | 88 | |
| | | 609 | 69 | 10054 | 0.001 | 10222 | −2 | 6520 | 38 | |
| | | 609 | 69 | 10054 | 0.0001 | 11267 | −13 | 22327 | −131 | |
| | Donor#2 | 7737 | 57 | 23132 | 0.1 | 21254 | 12 | 2536 | 134 | 55.35 |
| | | 7737 | 57 | 23132 | 0.01 | 21726 | 9 | 10249 | 84 | |
| | | 7737 | 57 | 23132 | 0.001 | 22579 | 4 | 23380 | −2 | |
| | | 7737 | 57 | 23132 | 0.0001 | 22491 | 4 | 23183 | 0 | |
| PBMC-030 | Donor#1 | 2739 | 47 | 53426 | 0.1 | 60116 | −13 | 2132 | 101 | 35.52 |
| | | 2739 | 47 | 53426 | 0.01 | 56411 | −6 | 14297 | 77 | |
| | | 2739 | 47 | 53426 | 0.001 | 59167 | −11 | 55868 | −5 | |
| | | 2739 | 47 | 53426 | 0.0001 | 59290 | −12 | 60865 | −15 | |
| | Donor#2 | 4310 | 50 | 53781 | 0.1 | 52881 | 2 | 3208 | 102 | 102.88 |
| | | 4310 | 50 | 53781 | 0.01 | 51741 | 4 | 30716 | 47 | |
| | | 4310 | 50 | 53781 | 0.001 | 53072 | 1 | 53628 | 0 | |
| | | 4310 | 50 | 53781 | 0.0001 | 58045 | −9 | 54343 | −1 | |
| PBMC-032 | Donor#1 | 2458 | 42 | 14058 | 0.1 | 16579 | −22 | 636 | 116 | 40.36 |
| | | 2458 | 42 | 14058 | 0.01 | 19250 | −45 | 3358 | 93 | |
| | | 2458 | 42 | 14058 | 0.001 | 19852 | −50 | 20639 | −57 | |
| | | 2458 | 42 | 14058 | 0.0001 | 19161 | −44 | 18907 | −42 | |
| | Average % inhibition of human PBMC at 0.1 µg/ml | | | | | | 3 | | 107 | 49.65 |
| | Average % inhibition of human PBMC at 0.01 µg/ml | | | | | | −1 | | 74 | |
| | Average % inhibition of human PBMC at 0.001 µg/ml | | | | | | −7 | | 0 | |
| | Average % inhibition of human PBMC at 0.0001 µg/ml | | | | | | −8 | | −17 | |

% of inhibition: 100 − (CPM with Abs − PBMC alone − CHO-CD40L alone)/(CPM of PBMC + CHO-CD40L − PBMC alone − CHO-CD40L alone)*100%

In addition to B cells, human PBMC also contain natural killer cells that can mediate antibody dependent cytotoxicity (ADCC). To clarify the mechanism of antibody-mediated inhibition of proliferation, assays were performed with B cells purified from human PBMC. Similar to results obtained with PBMC, both antibodies potently inhibited the CD40 ligand-induced proliferation of purified B cells (Table 5, n=3). These data demonstrate that the antagonist activity of the candidate antibodies, and not the mechanism of ADCC, is the cause of proliferation inhibition in these assays.

Example 7

CHIR-5.9 and CHIR-12.12 do not Induce Strong Proliferation of Human B Cells from Normal Subjects CD40 ligand activates normal B cells and B-cell lymphoma cells to proliferate. Binding of some anti-CD40 anti-

TABLE 5

Effect of anti-CD40 antibodies on CD40 ligand-induced proliferation of purified human B cells

|  |  | CPM | | | | HuIgG1 | | CHIR-5.9 | | CHIR-12.12 | |
|---|---|---|---|---|---|---|---|---|---|---|---|
| Exp# | Donor # | B cells | CHO-CD40L | B cells + CHO-CD40L | Abs Conc (µg/ml) | CPM | % inhibition | CPM | % inhibition | CPM | % inhibition |
| B cell-004 | 1 | 418 | 89 | 3132 | 100 | 429 | 103 | 271 | 109 | 152 | 114 |
| | | 418 | 89 | 3132 | 20 | 3193 | −2 | 316 | 107 | 222 | 111 |
| | | 418 | 89 | 3132 | 4 | 3175 | −2 | 144 | 114 | 235 | 110 |
| | | 418 | 89 | 3132 | 0.8 | 6334 | −122 | 245 | 110 | 63 | 117 |
| | 2 | 81 | 73 | 27240 | 100 | 28311 | −4 | 85 | 100 | 77 | 100 |
| | | 81 | 73 | 27240 | 20 | 24707 | 9 | 65 | 100 | 94 | 100 |
| | | 81 | 73 | 27240 | 4 | 23081 | 15 | 108 | 100 | 68 | 100 |
| | | 81 | 73 | 27240 | 0.8 | 26252 | 4 | 87 | 100 | 77 | 100 |
| B cell-005 | 3 | 267 | 75 | 24552 | 1 | 25910 | −6 | 291 | 100 | 102 | 101 |
| | | 267 | 75 | 24552 | 0.1 | 28447 | −16 | 259 | 100 | 108 | 101 |
| | | 267 | 75 | 24552 | 0.01 | 26706 | −9 | 2957 | 89 | 4922 | 81 |
| | Average % inhibition | | | | | | −3 | | 103 | | 103 |

% of inhibition: 100 − (CPM with Abs − B cells alone − CHO-CD40L alone)/(CPM of B cell with CHO-CD40L − B cells alone − CHO-CD40L alone)*100% bodies (agonist) can provide a similar stimulatory signal for the proliferation of normal and cancer B cells. Antibodies with strong B cell stimulatory activity are not suitable candidates for therapeutic treatment of B cell lymphomas. The two candidate antibodies were tested for their ability to induce proliferation of B cells from normal volunteer donors. The B cells purified by Ficoll-Hypaque Plus gradient centrifugation from normal donor PBMC were cultured in 96-well plates with varying concentrations of candidate antibodies (range of 0.001 to 100 μg/ml) for a total of 4 days. In the positive control group, PBMC were cultured with formaldehyde-fixed CHO cells expressing CD40-ligand. The B cell proliferation was measured by incorporation of tritiated-labeled thymidine at 37° C. for 14-18 hours. While the CD40 ligand presented on CHO cells induced vigorous proliferation of B cells resulting in an average stimulation index (SI) of 145, the candidate antibodies induced only a weak proliferation with a stimulation index of 2.89 and 5.08 for CHIR-12.12 and CHIR-5.9, respectively (n=3) (Table 6).

tory activity of anti-CD40 antibodies. To confirm the lack of B cell stimulatory activity of CHIR-5.9 and CHIR-12.12 antibodies in the presence of cross-linking cells, proliferation experiments were performed with total PBMC containing B cells as well as FcR+ cells. Data from these experiments (Table 7A, mAb CHIR-5.9; Table 7B, mAb CHIR-12.12) confirm that these candidate antibodies even in the presence of FcR-bearing cells in general do not stimulate B cells to proliferate over background proliferation induced by control human IgG1 (n=10). The CD40 ligand induced an average stimulation index (SI) SI of 7.41. The average SI with candidate antibodies were 0.55 and 1.05 for CHIR-12.12 and CHIR-5.9, respectively. Only one of the 10 donor PBMC tested showed some stimulatory response to CHIR-5.9 antibody (donor #2 in Table 7). The lack of stimulatory activity by candidate mAbs was further confirmed by measuring the PBMC proliferation in response to candidate anti-CD40 antibodies immobilized on the plastic surface of the culture wells (n=2). The average SI with CD40 ligand, CHIR-12.12, and

TABLE 6

Proliferation of B cells purified from normal human subjects in response to candidate anti-CD40 mAbs

| Exp# | Donor# | B cells CPM | Bcells + CHO-CD40L CPM | S. index (1) | Abs conc (μg/ml) | B cells + huIgG1 CPM | S. index (2) | B cells + CHIR-5.9 CPM | S. index (2) | B cells + CHIR-12.12 CPM | S. index (2) |
|---|---|---|---|---|---|---|---|---|---|---|---|
| B cell-004 | 1 | 418 | 3132 | 7.49 | 100 | 498 | 1.19 | 401 | 0.96 | 458 | 1.10 |
| Frozen | | 418 | 3132 | | 20 | 245 | 0.59 | 232 | 0.56 | 370 | 0.89 |
| | | 418 | 3132 | | 4 | 241 | 0.58 | 232 | 0.56 | 211 | 0.50 |
| | | 418 | 3132 | | 0.8 | 376 | 0.90 | 298 | 0.71 | 230 | 0.55 |
| Frozen | 2 | 81 | 27240 | 336.30 | 100 | 34 | 0.42 | 454 | 5.60 | 122 | 1.51 |
| | | 81 | 27240 | | 20 | 48 | 0.59 | 706 | 8.72 | 255 | 3.15 |
| | | 81 | 27240 | | 4 | 41 | 0.51 | 567 | 7.00 | 367 | 4.53 |
| | | 81 | 27240 | | 0.8 | 34 | 0.42 | 736 | 9.09 | 408 | 5.04 |
| B cell-005 | 3 | 267 | 24552 | 91.96 | 1 | 691 | 2.59 | 2101 | 7.87 | 1223 | 4.58 |
| | | 267 | 24552 | | 0.1 | 686 | 2.57 | 2267 | 8.49 | 1557 | 5.83 |
| | | 267 | 24552 | | 0.01 | 808 | 3.03 | 2203 | 8.25 | 1027 | 3.85 |
| | | 267 | 24552 | | 0.001 | 567 | 2.12 | 846 | 3.17 | 826 | 3.09 |
| Average Stimulation Index (SI) | | | | 145.25 | | | 1.29 | | 5.08 | | 2.88 |

S. index(1): = CPM (B cells + CHO-CD40L)/CPM (B cells alone)

S. index(2): = CPM (B cells + Abs)/CPM (PBMC alone)

In addition to B cells, human PBMC contain cell types that bear Fc receptors (FcR) for IgG1 molecules that can provide cross linking of anti-CD40 antibodies bound to CD40 on B cells. This cross-linking could potentially enhance stimula- CHIR-5.9 stimulation were 22, 0.67, and 1.2, respectively (Table 8). Taken together these data show that the candidate antiCD40 antibodies do not possess strong B cell stimulatory properties.

TABLE 7A

Proliferation of PBMC from normal human subjects in response to mAb CHIR-5.9.

| Exp# | | PBMC | PBMC + CHO-CD40L CPM | index(1) | Abs conc (µg/ml) | PBMC + huIgG1 CPM | index(2) | PBMC + CHIR-5.9 CPM | index(2) |
|---|---|---|---|---|---|---|---|---|---|
| PBMC-010 | | 1417 | 5279 | 3.73 | 1 | 1218 | 0.86 | 5973 | 4.22 |
| | | 1417 | 5279 | | 0.25 | 1712 | 1.21 | 4815 | 3.40 |
| | | 1417 | 5279 | | 0.0625 | 1449 | 1.02 | 3642 | 2.57 |
| | | 1417 | 5279 | | 0.0156 | 1194 | 0.84 | 3242 | 2.29 |
| PBMC-011 | Donor#1 | 2138 | 8247 | 3.86 | 10 | 3047 | 1.43 | 3177 | 1.49 |
| | | 2138 | 8247 | | 1 | 2726 | 1.28 | 3617 | 1.69 |
| | | 2138 | 8247 | | 0.1 | 2026 | 0.95 | 2011 | 0.94 |
| | | 2138 | 8247 | | 0.01 | 2424 | 1.13 | 1860 | 0.87 |
| | Donor#2 | 2374 | 11561 | 4.87 | 10 | 4966 | 2.09 | 4523 | 1.91 |
| | | 2374 | 11561 | | 1 | 2544 | 1.07 | 2445 | 1.03 |
| | | 2374 | 11561 | | 0.1 | 2177 | 0.92 | 1462 | 0.62 |
| | | 2374 | 11561 | | 0.01 | 4672 | 1.97 | 1896 | 0.80 |
| | Donor#3 | 3229 | 7956 | 2.46 | 10 | 5035 | 1.56 | 2119 | 0.66 |
| | | 3229 | 7956 | | 1 | 2826 | 0.88 | 1099 | 0.34 |
| | | 3229 | 7956 | | 0.1 | 2277 | 0.71 | 1052 | 0.33 |
| | | 3229 | 7956 | | 0.01 | 3078 | 0.95 | 1899 | 0.59 |
| | Donor#4 | 4198 | 14314 | 3.41 | 10 | 5012 | 1.19 | 5176 | 1.23 |
| | | 4198 | 14314 | | 1 | 3592 | 0.86 | 4702 | 1.12 |
| | | 4198 | 14314 | | 0.1 | 5298 | 1.26 | 4319 | 1.03 |
| | | 4198 | 14314 | | 0.01 | 5758 | 1.37 | 5400 | 1.29 |
| PBMC-014 | | 2350 | 8787 | 3.74 | 100 | 2722 | 1.16 | 2471 | 1.05 |
| | | 2350 | 8787 | | 20 | 2315 | 0.99 | 2447 | 1.04 |
| | | 2350 | 8787 | | 4 | 2160 | 0.92 | 1659 | 0.71 |
| | | 2350 | 8787 | | 0.8 | 2328 | 0.99 | 1671 | 0.71 |
| PBMC-015 | Donor#1 | 3284 | 12936 | 3.94 | 100 | 3598 | 1.10 | 1682 | 0.51 |
| | | 3284 | 12936 | | 20 | 2751 | 0.84 | 1562 | 0.48 |
| | | 3284 | 12936 | | 4 | 3135 | 0.95 | 1105 | 0.34 |
| | | 3284 | 12936 | | 0.8 | 4027 | 1.23 | 1419 | 0.43 |
| | Donor#2 | 6099 | 19121 | 3.14 | 100 | 2999 | 0.49 | 5104 | 0.84 |
| | | 6099 | 19121 | | 20 | 4025 | 0.66 | 3917 | 0.64 |
| | | 6099 | 19121 | | 4 | 4496 | 0.74 | 3341 | 0.55 |
| | | 6099 | 19121 | | 0.8 | 3834 | 0.63 | 4139 | 0.68 |
| | Donor#3 | 2479 | 19826 | 8.00 | 100 | 3564 | 1.44 | 1204 | 0.49 |
| | | 2479 | 19826 | | 20 | 1874 | 0.76 | 782 | 0.32 |
| | | 2479 | 19826 | | 4 | 1779 | 0.72 | 634 | 0.26 |
| | | 2479 | 19826 | | 0.8 | 2274 | 0.92 | 937 | 0.38 |
| PBMC-016 | | 1148 | 15789 | 13.75 | 0.1 | 1255 | 1.09 | 1036 | 0.90 |
| | | 1148 | 15789 | | 0.05 | 1284 | 1.12 | 871 | 0.76 |
| | | 1148 | 15789 | | 0.01 | 1446 | 1.26 | 952 | 0.83 |
| Average SI of PBMC | | | | 5.09 | | | 1.06 | | 1.03 | index(1): = (PBMC + CHO-CD40L)/PBMC
index(2): = (PBMC + Abs)/PBMC

TABLE 7B

Proliferation of PBMC from normal human subjects in response to mAb CHIR-12.12.

| Exp# | | PBMC | PBMC + CHO-CD40L CPM | index(1) | Abs conc (µg/ml) | PBMC + huIgG1 CPM | index(2) | PBMC + CHIR-12.12 CPM | index(2) |
|---|---|---|---|---|---|---|---|---|---|
| PBMC-025 | Donor#1 | 4051 | 42292 | 10.44 | 0.1 | 2909 | 0.72 | 2451 | 0.61 |
| | | 4051 | 42292 | | 0.01 | 4725 | 1.17 | 8924 | 2.20 |
| | | 4051 | 42292 | | 0.001 | 8080 | 1.99 | 8782 | 2.17 |
| | | 4051 | 42292 | | 0.0001 | 4351 | 1.07 | 4342 | 1.07 |
| | Donor#2 | 2260 | 14987 | 6.63 | 0.1 | 2538 | 1.12 | 6741 | 2.98 |
| | | 2260 | 14987 | | 0.01 | 3524 | 1.56 | 8921 | 3.95 |
| | | 2260 | 14987 | | 0.001 | 3159 | 1.40 | 4484 | 1.98 |
| | | 2260 | 14987 | | 0.0001 | 2801 | 1.24 | 2533 | 1.12 |
| PBMC-026 | Donor#1 | 2085 | 18313 | 8.78 | 0.1 | 1386 | 0.66 | 2761 | 1.32 |
| | | 2085 | 18313 | | 0.01 | 2871 | 1.38 | 3162 | 1.52 |
| | | 2085 | 18313 | | 0.001 | 2602 | 1.25 | 3233 | 1.55 |
| | | 2085 | 18313 | | 0.0001 | 1709 | 0.82 | 1766 | 0.85 |
| | Donor#2 | 676 | 18054 | 26.71 | 0.1 | 660 | 0.98 | 2229 | 3.30 |
| | | 676 | 18054 | | 0.01 | 2864 | 4.24 | 1238 | 1.83 |
| | | 676 | 18054 | | 0.001 | 693 | 1.03 | 1507 | 2.23 |
| | | 676 | 18054 | | 0.0001 | 984 | 1.46 | 811 | 1.20 |
| PBMC-027 | Donor#1 | 2742 | 13028 | 4.75 | 0.1 | 4725 | 1.72 | 2795 | 1.02 |
| | | 2742 | 13028 | | 0.01 | 4575 | 1.67 | 5353 | 1.95 |
| | | 2742 | 13028 | | 0.001 | 3218 | 1.17 | 3501 | 1.28 |
| | | 2742 | 13028 | | 0.0001 | 5107 | 1.86 | 4272 | 1.56 |

TABLE 7B-continued

Proliferation of PBMC from normal human subjects in response to mAb CHIR-12.12.

| Exp# | | PBMC | PBMC + CHO-CD40L CPM | index(1) | Abs conc (µg/ml) | PBMC + huIgG1 CPM | index(2) | PBMC + CHIR-12.12 CPM | index(2) |
|---|---|---|---|---|---|---|---|---|---|
| | Donor#2 | 1338 | 11901 | 8.89 | 0.1 | 1633 | 1.22 | 1943 | 1.45 |
| | | 1338 | 11901 | | 0.01 | 1520 | 1.14 | 5132 | 3.84 |
| | | 1338 | 11901 | | 0.001 | 1517 | 1.13 | 2067 | 1.54 |
| | | 1338 | 11901 | | 0.0001 | 1047 | 0.78 | 2076 | 1.55 |
| PBMC-028 | Donor#1 | 4288 | 22547 | 5.26 | 0.1 | 3686 | 0.86 | 2525 | 0.59 |
| | | 4288 | 22547 | | 0.01 | 3113 | 0.73 | 2047 | 0.48 |
| | | 4288 | 22547 | | 0.001 | 4414 | 1.03 | 3515 | 0.82 |
| | | 4288 | 22547 | | 0.0001 | 2452 | 0.57 | 4189 | 0.98 |
| | Donor#2 | 2148 | 54894 | 25.56 | 0.1 | 9127 | 4.25 | 5574 | 2.59 |
| | | 2148 | 54894 | | 0.01 | 4566 | 2.13 | 6515 | 3.03 |
| | | 2148 | 54894 | | 0.001 | 5285 | 2.46 | 5919 | 2.76 |
| | | 2148 | 54894 | | 0.0001 | 4667 | 2.17 | 4298 | 2.00 |
| PBMC-029 | Donor#1 | 609 | 10054 | 16.51 | 0.1 | 359 | 0.59 | 363 | 0.60 |
| | | 609 | 10054 | | 0.01 | 473 | 0.78 | 956 | 1.57 |
| | | 609 | 10054 | | 0.001 | 461 | 0.76 | 1159 | 1.90 |
| | | 609 | 10054 | | 0.0001 | 625 | 1.03 | 558 | 0.92 |
| | Donor#2 | 7737 | 23132 | 2.99 | 0.1 | 4940 | 0.64 | 3493 | 0.45 |
| | | 7737 | 23132 | | 0.01 | 6041 | 0.78 | 3644 | 0.47 |
| | | 7737 | 23132 | | 0.001 | 5098 | 0.66 | 5232 | 0.68 |
| | | 7737 | 23132 | | 0.0001 | 5135 | 0.66 | 5241 | 0.68 |
| PBMC-030 | Donor#1 | 4164 | 57205 | 13.74 | 10 | 2713 | 0.65 | 1046 | 0.25 |
| | | 4164 | 57205 | | 1 | 3627 | 0.87 | 1576 | 0.38 |
| | | 4164 | 57205 | | 0.1 | 4590 | 1.10 | 1512 | 0.36 |
| | | 4164 | 57205 | | 0.01 | 4384 | 1.05 | 2711 | 0.65 |
| | Donor#2 | 3324 | 53865 | 16.20 | 10 | 6376 | 1.92 | 4731 | 1.42 |
| | | 3324 | 53865 | | 1 | 4720 | 1.42 | 5219 | 1.57 |
| | | 3324 | 53865 | | 0.1 | 3880 | 1.17 | 5869 | 1.77 |
| | | 3324 | 53865 | | 0.01 | 3863 | 1.16 | 5657 | 1.70 |
| PBMC-032 | Donor#1 | 1808 | 15271 | 8.45 | 10 | 2349 | 1.30 | 4790 | 2.65 |
| | | 1808 | 15271 | | 1 | 3820 | 2.11 | 5203 | 2.88 |
| | | 1808 | 15271 | | 0.1 | 2098 | 1.16 | 6332 | 3.50 |
| | | 1808 | 15271 | | 0.01 | 1789 | 0.99 | 5005 | 2.77 |
| | Average SI of PBMC | | | 11.92 | | | 1.30 | | 1.62 | index(1): = CPM of (PBMC + CHO-CD40L)/CPM of PBMC
index(2): = CPM of (PBMC + Abs)/CPM of PBMC

TABLE 8

Proliferation of PBMC from normal human subjects in response to immobilized anti-CD40 antibodies

| Exp# | PBMC CPM | PBMC + CHO-CD40L CPM | S. index (1) | Abs conc (ug/ml) | PBMC + huIgG1 CPM | S. index (2) | PBMC + CHIR-5.9 CPM | S. index (2) | PBMC + CHIR-12.12 CPM | S. index (2) |
|---|---|---|---|---|---|---|---|---|---|---|
| PBMC-012 | 225 | 6808 | 30.26 | 10 | 279 | 1.24 | 734 | 3.26 | 200 | 0.89 |
| | 225 | 6808 | | 1 | 175 | 0.78 | 178 | 0.79 | 161 | 0.72 |
| | 225 | 6808 | | 0.1 | 156 | 0.69 | 226 | 1.00 | 249 | 1.11 |
| | 225 | 6808 | | 0.01 | 293 | 1.30 | 232 | 1.03 | 254 | 1.13 |
| Immoblize-004 | 857 | 11701 | 13.65 | 1000 | 479 | 0.56 | 1428 | 1.67 | 384 | 0.45 |
| | 857 | 11701 | | 100 | 543 | 0.63 | 839 | 0.98 | 265 | 0.31 |
| | 857 | 11701 | | 10 | 487 | 0.57 | 411 | 0.48 | 262 | 0.31 |
| | 857 | 11701 | | 1 | 632 | 0.74 | 372 | 0.43 | 376 | 0.44 |
| Average Stimulation index | | | 21.96 | | | 0.81 | | 1.21 | | 0.67 |

S. index (1): = CPM (PBMC + CHO-CD40L)/CPM (PBMC)
S. index (2): = CPM (PBMC + mAbs)/CPM (PBMC)

Example 8

CHIR-5.9 and CHIR-12.12 are Able to Kill CD40-Bearing Target Cells by ADCC

The candidate antibodies can kill CD40-bearing target cells (lymphoma lines) by the mechanism of ADCC. Both CHIR-5.9 and CHIR-12.12 are fully human antibodies of IgG1 isotype and are expected to have the ability to induce the killing of target cells by the mechanism of ADCC. They were tested for their ability to kill cancer cell lines in vitro assays. Two human lymphoma cell lines (Ramos and Daudi) were selected as target cells for these assays. PBMC or enriched NK cells from 8 normal volunteer donors were used as effector cells in these assays. A more potent ADCC response was observed with CHIR-12.12 compared with CHIR-5.9 against both the lymphoma cancer cell line target cells. Lymphoma cell lines also express CD20, the target antigen for rituximab (Rituxan®), which allowed for comparison of the ADCC activity of these two candidate mAbs with rituximab ADCC activity. For lymphoma cell line target, an average specific lysis of 35%, 59%, and 47% was observed for CHIR-5.9, CHIR-12.12, and rituximab respectively when used at 1 µg/ml concentration (Table 9). The two antibodies did not show much activity in complement dependent cytotoxicity (CDC) assays.

TABLE 9

Anti-CD40 mAB dependent killing of lymphoma cell lines by ADCC.
Anti-CD40 mAb dependent killing of lymphoma cell lines by ADCC Target cells: Human lymphoma cell line (Ramos or Daudi)

| Exp# | Effector cell | E:T ratio | % lysis IgG1 | Abs conc (µg/ml) | CHIR-5.9 % lysis | CHIR-5.9 % lysis – % lysis IgG1 | CHIR-12.12 % lysis | CHIR-12.12 % lysis – % lysis IgG1 | Rituxan % lysis | Rituxan % lysis – % lysis IgG1 |
|---|---|---|---|---|---|---|---|---|---|---|
| ADCC-005 Alarmor Blue | huNK | 3 | 17.05 | 5 | 30.75 | 13.70 | 65.22 | 48.17 | ND | ND |
| | huNK | 3 | 40.81 | 5 | 58.62 | 17.81 | 87.87 | 47.06 | ND | ND |
| ADCC-006 Alarmor Blue | huNK | 2 | −3.09 | 10 | 3.50 | 6.59 | 43.71 | 46.8 | 34.82 | 37.91 |
| | | | −8.62 | 1 | −10.10 | −1.48 | 45.13 | 53.75 | 37.07 | 45.69 |
| | | | −11 | 0.1 | −14.80 | −3.80 | 39.82 | 50.82 | 33.61 | 44.61 |
| | | | −4.54 | 0.01 | 2.53 | 7.07 | 50.07 | 54.61 | 28.49 | 33.03 |
| 51Cr | huNK | 5 | 1.5 | 10 | 32.09 | 30.59 | 47.24 | 45.742 | ND | ND |
| | | | 2.4 | 1 | 18.01 | 15.61 | 37.42 | 35.022 | ND | ND |
| | | | 2.5 | 0.1 | 14.67 | 12.17 | 37.63 | 35.131 | ND | ND |
| ADCC-009 Calcein AM | huNK | 10 | 2.32 | 5 | 66.20 | 63.88 | 97.70 | 95.38 | 86.2 | 83.88 |
| | | | 0.48 | 1 | 67.20 | 66.72 | 123.00 | 122.52 | 88.2 | 87.72 |
| | | | −1.43 | 0.2 | 78.40 | 79.83 | 118.00 | 119.43 | 88.8 | 90.23 |
| | | | 3.39 | 0.04 | 69.10 | 65.71 | 109.00 | 105.61 | 84.9 | 81.51 |
| ADCC-011 Calcein AM | huNK | 8 | 3.18 | 1 | 15.36 | 12.19 | 51.59 | 48.42 | 22.44 | 19.27 |
| | | | 4.58 | 0.01 | 7.39 | 2.81 | 46.80 | 42.22 | 14.68 | 10.10 |
| | | | 5.41 | 0.002 | 6.35 | 0.94 | 5.10 | −0.31 | 9.58 | 4.16 |
| | | | 7.03 | 0.0004 | 7.76 | 0.73 | 5.99 | −1.04 | 5.99 | −1.04 |
| ADCC-012 Calcein AM | huNK | 10 | 13.34 | 10 | 73.31 | 59.97 | 117.80 | 104.46 | 50.75 | 37.41 |
| | | | 13.50 | 1 | 74.76 | 61.26 | 88.64 | 75.14 | 65.97 | 52.47 |
| | | | 12.27 | 0.01 | 58.52 | 46.25 | 72.88 | 60.61 | 50.16 | 37.89 |
| | | | 13.61 | 0.005 | 57.50 | 43.89 | 69.45 | 55.84 | 39.28 | 25.67 |
| | | | 11.95 | 0.001 | 56.81 | 44.86 | 65.17 | 53.22 | 33.07 | 21.12 |
| ADCC-013 51Cr | PBMC | 100 | 2.54 | 1 | 21.03 | 18.49 | 37.94 | 35.40 | 32.28 | 29.74 |
| | | | 2.45 | 0.1 | 15.50 | 13.05 | 30.82 | 28.37 | 27.18 | 24.73 |
| | | | 2.92 | 0.01 | 14.53 | 11.61 | 22.59 | 19.67 | 12.79 | 9.87 |
| | | | 2.78 | 0.001 | 3.90 | 1.12 | 8.99 | 6.21 | 3.13 | 0.35 |
| ADCC-014 51Cr | PBMC | 100 | 4.64 | 10 | 53.54 | 48.90 | 56.12 | 51.48 | ND | ND |
| | | | 4.64 | 1 | 46.84 | 42.20 | 43.00 | 38.36 | ND | ND |
| | | | 4.64 | 0.1 | 45.63 | 40.99 | 39.94 | 35.30 | ND | ND |
| | | | 4.64 | 0.01 | 7.73 | 3.09 | 9.79 | 5.15 | ND | ND |
| | | | 4.64 | 0.001 | 8.83 | 4.19 | 10.81 | 6.17 | ND | ND |
| Average % lysis at 1 µg/ml concentration of mAbs | | | | | | 35.31 | | 59.03 | | 47.23 |

* The greater than 100% killing are due to incomplete killing by detergent used for 100% killing control.

Example 9

CD40 is Present on the Surface of NHL Cells from Lymph Node Biopsy Patients

NHL cells were isolated from biopsied lymph nodes from patients and were preserved in liquid nitrogen until use. Cell viability at the time of analysis exceeded 90%. The cells from two rituximab-sensitive and three rituximab-resistant patients (five patients in total) were stained with either a direct labeled 15B8-FITC or 15B8 plus anti-huIgG$_2$-FITC and analyzed by Flow cytometry. NHL cells from all the patients were found to express CD40. Table 10 shows that an average of 76% of NHL cells express CD40 (a range of 60-91%).

TABLE 10

| Patient ID[a] | Patient type[b] | % positive[c] MS81[d] | % positive[c] 15B8[e] |
|---|---|---|---|
| B | CR | n.d.[f] | 91.02 |
| J | CR | n.d. | 60.36 |
| H | NR | n.d. | 85.08 |
| H | NR | 72.24 | 81.19 |
| K | NR | n.d. | 70.69 |
| L | NR | n.d. | 66.82 |
| Average % positive | | | 76 |

[a] NHL patients treated with anti-CD20 mAb
[b] patient response to anti-CD20 mAb; CR = complete responder; NR = nonresponder
[c] % of cells in lymphocyte gate that stain positive
[d] MS81, agonist anti-CD40 mAb
[e] 15B8, antagonist anti-CD40 Mab
[f] n.d., not done

Example 10

CHIR-5.9 and CHIR-12.12 Do Not Stimulate Proliferation of Cancer Cells from the Lymph Nodes of NHL Patients CD40 ligand is known to provide a stimulatory signal for the survival and proliferation of lymphoma cells from NHL patients. Binding of some anti-CD40 antibodies (agonist) can provide a similar stimulatory signal for the proliferation of patient cancer cells. Antibodies with strong B cell stimulatory activity are not suitable candidate for therapeutic treatment of B cell lymphomas. The two candidate antibodies were tested for their ability to induce proliferation of NHL cells from 3 patients. The cells isolated from lymph node (LN) biopsies were cultured with varying concentrations of candidate antibodies (range of 0.01 to 300 µg/ml) for a total of 3 days. The cell proliferation was measured by incorporation of tritiated thymidine. Neither of the two candidate mAbs induced any proliferation of cancer cells at any concentration tested (Table 11). Antibodies even in the presence of exogenously added IL-4, a B cell growth factor, did not induce proliferation of NHL cells (tested in one of the thee patient cells. These results indicate that CHIR-5.9 and CHIR-12.12 are not agonist anti-CD40 antibodies and do not stimulate proliferation in vitro of NHL cells from patients.

two candidate anti-CD40 antibodies were tested at varying concentrations (0.01 µg/ml to 100 µg/ml) for their ability to inhibit CD40 ligand-induced proliferation of NHL cells from patients. NHL cells from patients were cultured in suspension over CD40L-expressing feeder in the presence of IL-4. The NHL cell proliferation was measured by $^3$H-thymidine incorporation. Both antibodies were found to be very effective for inhibiting CD40 ligand-induced proliferation of NHL cells (Table 12, n=2). Nearly complete inhibition of CD40 ligand-induced proliferation could be achieved at 1.0 to 10 µg/ml concentration of antibodies.

TABLE 11

Proliferation of cancer cells from LN of NHL patients in response to candidate anti-CD40 mAbs

| Donor# | Abs conc (ug/ml) | CPM Cells + IgG1 | cells + CHIR-5.9 | S. index CHIR-5.9 | CPM cells + CHIR-12.12 | S. index CHIR-12.12 | CPM cells + MS81 | S. index MS81 |
|---|---|---|---|---|---|---|---|---|
| PP | 0.01 | 180 | 203 | 1.23 | 133.67 | 0.74 | ND | ND |
|  | 0.1 | 107.5 | 151.67 | 1.41 | 136 | 1.27 | ND | ND |
|  | 1 | 130.67 | 206.67 | 1.58 | 197.33 | 1.51 | 179 | 1.37 |
|  | 10 | 152.5 | 245 | 1.61 | 137.33 | 0.90 | 871.67 | 5.71 |
|  | 100 | 137.67 | 332.33 | 2.41 | 157.33 | 1.14 | ND | ND |
|  | 300 | 137.67 | 254.33 | 1.85 | 100.67 | 0.73 | ND | ND |
| MM | 0.01 | 165 | 180.33 | 1.09 | 124 | 0.75 | ND | ND |
|  | 0.1 | 180.5 | 149.67 | 0.83 | 111.33 | 0.62 | ND | ND |
|  | 1 | 62 | 109.67 | 1.77 | 104.67 | 1.69 | ND | ND |
|  | 10 | 91.5 | 93.33 | 1.02 | 100 | 1.09 | 763 | 8.34 |
|  | 100 | 123 | 173 | 1.41 | 105.33 | 0.86 | ND | ND |
|  | 300 | 109 | 183.67 | 1.69 | 157 | 1.44 | ND | ND |
| BD (IL-4) | 0.01 | 1591.5 | 1623.67 | 1.02 | 1422 | 0.89 | ND | ND |
|  | 0.1 | 1405 | 1281 | 0.91 | 1316.33 | 0.94 | ND | ND |
|  | 1 | 1526 | 1352.33 | 0.89 | 1160 | 0.76 | 1508.33 | 0.99 |
|  | 10 | 1450 | 1424 | 0.98 | 1244 | 0.86 | 4146.67 | 2.86 |
|  | 100 | 1406.67 | 1497.67 | 1.06 | 1255.33 | 0.89 | ND | ND |
|  | 300 | 1410.33 | 1466.67 | 1.04 | 1233 | 0.87 | ND | ND |

Example 11

CHIR-5.9 and CHIR-12.12 Can Block CD40 Ligand-Mediated Proliferation of Cancer Cells from Non-Hodgkin's Lymphoma Patients Engagement of CD40 by CD40 ligand induces proliferation of cancer cells from NHL patients. An antagonist anti-CD40 antibody is expected to inhibit this proliferation. The

TABLE 12

Inhibition of CD40 ligand-induced proliferation of cancer cells from the LN of NHL patients.

| Patient | Abs Conc (ug/ml) | CPM IgG1 | CHIR-5.9 CPM | % inhibition | CHIR-12.12 CPM | % inhibition | Rituximab CPM | % inhibition |
|---|---|---|---|---|---|---|---|---|
| BD | 0.01 | 29525.5 | 25369 | 14 | 24793 | 16 | 29490.3 | 0 |
|  | 0.1 | 29554 | 20265.33 | 31 | 13671 | 54 | 29832.7 | −1 |
|  | 1 | 29486.67 | 6785.33 | 77 | 453 | 98 | 26355.3 | 11 |
|  | 10 | 29710 | 506.33 | 98 | 371 | 99 | 29427.3 | 1 |
|  | 100 | 29372.33 | 512.33 | 98 | 386.67 | 99 | ND | ND |
| PP | 0.01 | 23572 | 23229.33 | 1 | 23666 | 0 | 25317.3 | −7 |
|  | 0.1 | 22520 | 19092.33 | 15 | 17197 | 24 | 26349.7 | −17 |
|  | 1 | 23535.67 | 1442.33 | 94 | 802.67 | 97 | 26515.7 | −13 |
|  | 10 | 23101.5 | 608.67 | 97 | 221.33 | 99 | 25478.3 | −10 |
|  | 100 | 23847.33 | ND | ND | 252 | 99 | ND | ND |

% inhibition: 100 − (CPM with test Abs/CPM with control mAb) *100%

Example 12

Effect of CHIR-5.9 on Number of Viable NHL Cells when Cultured with CD40-Ligand Bearing Cells Effects of CHIR-5.9 on the viable NHL cell numbers when cultured with CD40-ligand bearing cells over an extended period of time (days 7, 10, and 14) were investigated. CD40 ligand-mediated signaling through CD40 is important for B cell survival. This set of experiments evaluated the effect of anti-CD40 antibodies on NHL cell numbers at days 7, 10, and 14. NHL cells from five patients were cultured in suspension over CD40L-expressing irradiated feeder cells in the presence of IL-4. The control human IgG and CHIR-5.9 antibodies were added at concentrations of 10 µg/ml at day 0 and day 7. The viable cells under each condition were counted on the specified day. Cell numbers in the control group (IgG) increased with time as expected. Reduced numbers of cells were recovered from CHIR-5.9-treated cultures compared to control group. The greatest levels of reduction in cell numbers by CHIR-5.9 antibody were observed at day 14 and were on average 80.5% (a range of 49-94%) compared to isotype control (n=5). These data are summarized in Table 13.

TABLE 13

Effect of anti-CD40 antibody (CHIR-5.9/5.11) on NHL patient cell numbers over prolonged culture period (day 7, 10, and 14)

| Patient | Days in culture | Viable cell numbers IgG | mAb CHIR-5.9/5.11 | % reduction compared to IgG control |
|---------|-----------------|-------------------------|-------------------|-------------------------------------|
| PS      | 0               | 1000000                 | 1000000           | 0.00                                |
|         | 7               | 935000                  | 447500            | 52.14                               |
|         | 10              | 1270900                 | 504100            | 60.34                               |
|         | 14              | 1029100                 | 525000            | 48.98                               |
| MT      | 0               | 1000000                 | 1000000           | 0.00                                |
|         | 7               | 267600                  | 182500            | 31.80                               |
|         | 10              | 683400                  | 191600            | 71.96                               |
|         | 14              | 1450000                 | 225000            | 84.48                               |
| BRF     | 0               | 250000                  | 250000            | 0.00                                |
|         | 7               | 145000                  | 86667             | 40.23                               |
|         | 10              | 207500                  | 65000             | 68.67                               |
|         | 14              | 570500                  | 33330             | 94.16                               |
| DP      | 0               | 250000                  | 250000            | 0.00                                |
|         | 7               | 188330                  | 136670            | 27.43                               |
|         | 10              | 235000                  | 128330            | 45.39                               |
|         | 14              | 428330                  | 58330             | 86.38                               |
| PP      | 0               | 250000                  | 250000            | 0.00                                |
|         | 7               | 270000                  | 176670            | 34.57                               |
|         | 10              | 311670                  | 128330            | 58.83                               |
|         | 14              | 458330                  | 53330             | 88.36                               |

*% reduction compare to ctrl Abs = 100 − (test Abs/ctrl Abs) * 100

Example 13

Figure 3A:
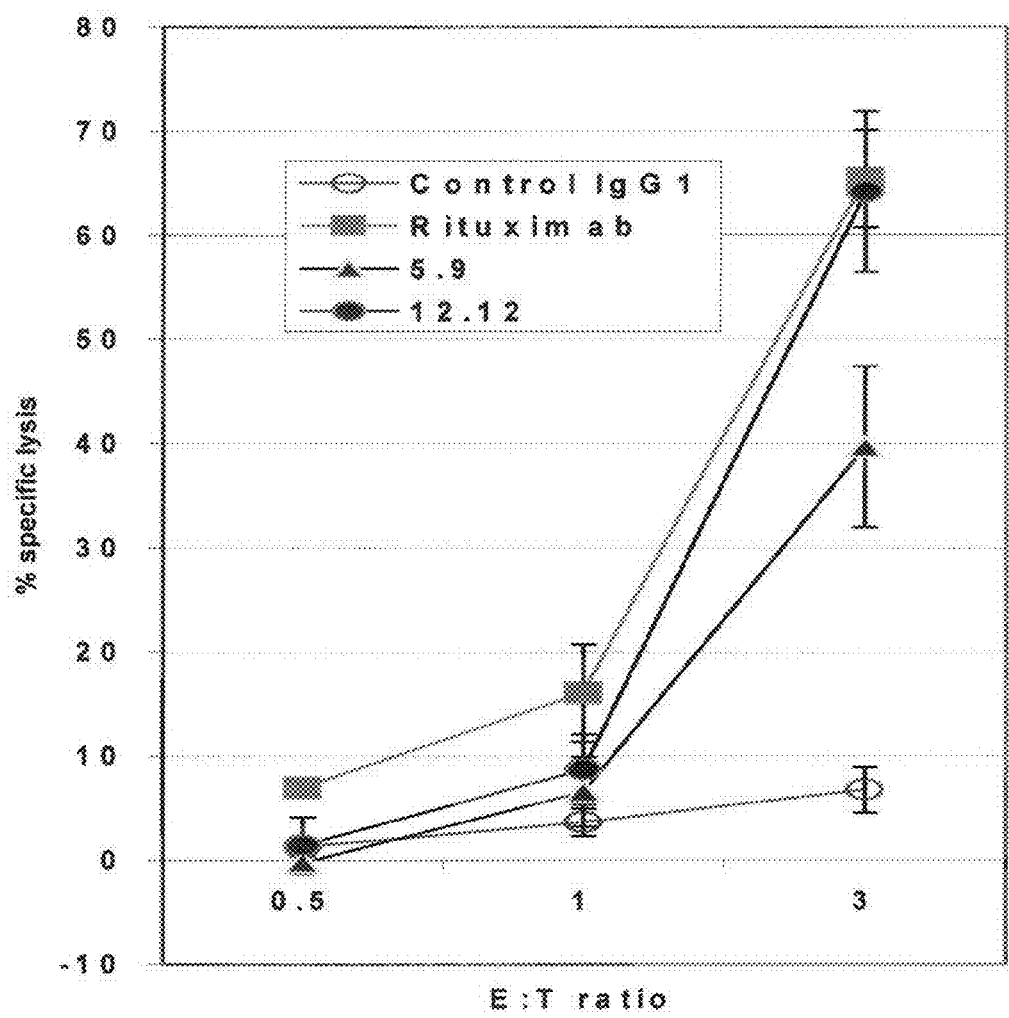
FIGS. 3A and 3B show ADCC activity of the candidate monoclonal antibodies CHIR-5.9 and CHIR-12.12 against cancer cells from the lymph nodes of non-Hodgkin's lymphoma (NHL) patients. Enriched NK cells from a normal volunteer donor either fresh after isolation (FIG. 3A) or after culturing overnight at 37° C.
Figure 3B:
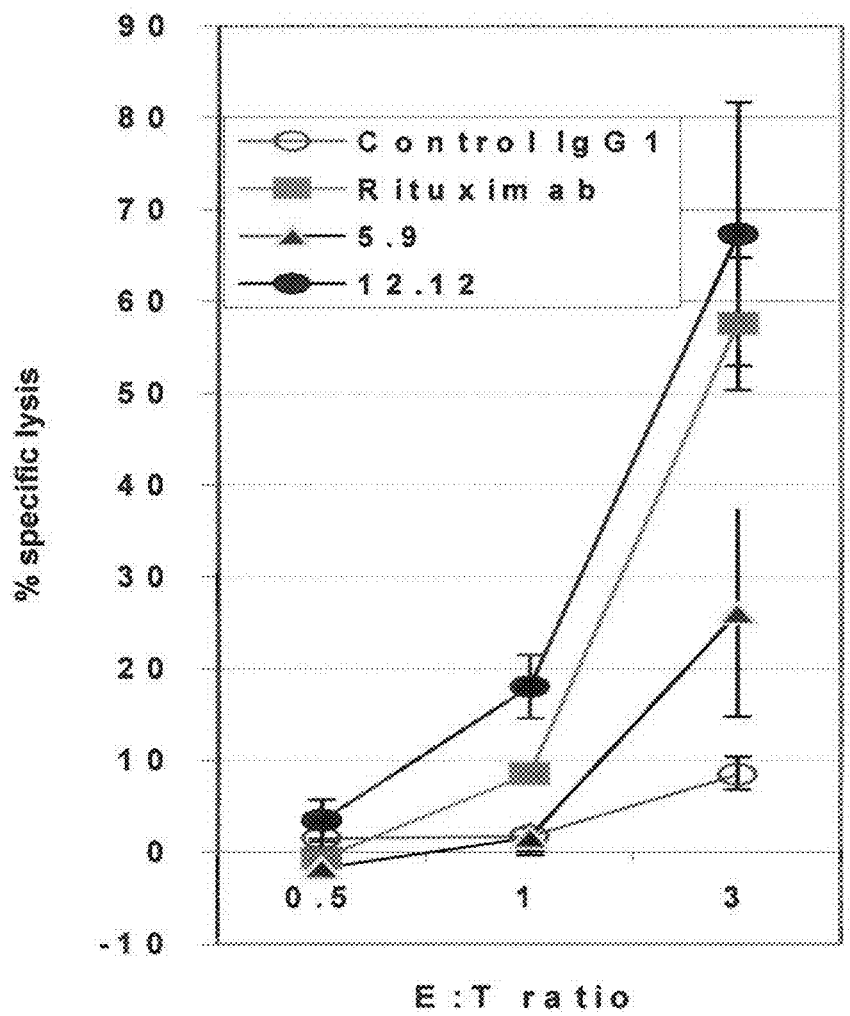

CHIR-5.9 and CHIR-12.12 are Able to Kill Cancer Cells from the Lymph Nodes of NHL Patients by ADCC Both CHIR-5.9 and CHIR-12.12 are fully human antibodies of IgG$_1$ isotype and were shown to induce the killing of lymphoma cell lines in vitro by the mechanism of ADCC (Table 9). They were tested for their ability to kill cancer cells from a single NHL patient in vitro assays. Enriched NK cells from normal volunteer donor either fresh after isolation or after culturing overnight at 37° C. were used as effector cells in this assay. Similar results were obtained with both freshly isolated NK cells and NK cells used after overnight culture. The higher level of ADCC was observed with CHIR-12.12 compared with CHIR-5.9 against the NHL cells from the patient. NHL cells also express CD20, the target antigen for rituximab (Rituxan®), which allowed for comparison of the ADCC activity of these two candidate mAbs with rituximab. Antibody CHIR-12.12 and rituximab show similar level of ADCC activity with CHIR-5.9 scoring lower in this assay. These data are shown in FIGS. 3A and 3B.

Example 14

CHIR-5.9 and CHIR-12.12 Can Block CD40-Mediated Survival and Proliferation of Cancer Cells from CLL Patients The candidate antibodies can block CD40-mediated survival and proliferation of cancer cells from CLL patients. CLL cells from patients were cultured in suspension over CD40L-expressing formaldehyde-fixed CHO cells under two different conditions: addition of human isotype antibody IgG (control); and addition of either CHIR-5.9 or CHIR-12.12 monoclonal antibody. All antibodies were added at concentrations of 1, 10, and 100 µg/mL in the absence of IL-4. The cell counts were performed at 24 and 48 h by MTS assay. Reduced numbers of cells were recovered from CHIR-5,9-(n=6) and CHIR-12.12-(n=2) treated cultures compared to control group. The greater differences in cell numbers between anti-CD40 mAb-treated and control antibody-treated cultures were seen at the 48-h time point. These data are summarized in Table 14.

TABLE 14

The effect of candidate antibodies on CD40-induced survival and proliferation of cancer cells from CLL patients measured at 48 h after the culture initiation

| Patient# | Ab conc (µg/ml) | Relative cell numbers IgG1 | CHIR-5.9/5.11 | CHIR-12.12 | % reduction in cell numbers* CHIR-5.9/5.11 | CHIR-12.12 |
|----------|-----------------|----------------------------|---------------|------------|--------------------------------------------|------------|
| 1        | 1               | 269.31                     | 25.27         | ND         | 90.62                                      | ND         |
|          | 10              | 101.58                     | 33.07         | ND         | 67.44                                      | ND         |
|          | 100             | 130.71                     | 40.16         | ND         | 69.28                                      | ND         |
| 2        | 1               | 265.55                     | 75.8          | ND         | 71.46                                      | ND         |
|          | 10              | 227.57                     | 128.5         | ND         | 43.53                                      | ND         |
|          | 100             | 265.99                     | 6.4           | ND         | 97.59                                      | ND         |
| 3        | 1               | 85.9                       | 35.39         | ND         | 58.80                                      | ND         |
|          | 10              | 70.44                      | 39.51         | ND         | 43.91                                      | ND         |
|          | 100             | 77.65                      | 20.95         | ND         | 73.02                                      | ND         |
| 4        | 1               | 80.48                      | 15.03         | ND         | 81.32                                      | ND         |
|          | 10              | 63.01                      | 19.51         | ND         | 69.04                                      | ND         |
|          | 100             | 55.69                      | 3.65          | ND         | 93.45                                      | ND         |
| 5        | 1               | 90.63                      | 91.66         | 89.59      | −1.14                                      | 1.15       |
|          | 10              | 78.13                      | 82.28         | 60.41      | −5.31                                      | 22.68      |
|          | 100             | 63.53                      | 86.47         | 39.59      | −36.11                                     | 37.68      |
| 6        | 1               | 130.21                     | 77.6          | 71.88      | 40.40                                      | 44.80      |
|          | 10              | 131.77                     | 78.13         | 73.96      | 40.71                                      | 43.87      |
|          | 100             | 127.08                     | 76.56         | 82.29      | 39.75                                      | 35.25      |

*% reduction compared to control Abs = 100 − (test Abs/control Abs)*100

Example 15

CHIR-5.9 and CHIR-12.12 Show Anti-Tumor Activity in Animal Models Pharmacology/In Vivo Efficacy The candidate mAbs are expected to produce desired pharmacological effects to reduce tumor burden by either/both of two anti-tumor mechanisms, blockade of proliferation/survival signal and induction of ADCC. The currently available human lymphoma xenograft models use long-term lymphoma cell lines that, in contrast to primary cancer cells, do not depend on CD40 stimulation for their growth and survival. Therefore the component of these mAbs' anti-tumor activity based on blocking the tumor proliferation/survival signal is not expected to contribute to anti-tumor efficacy in these models. The efficacy in these models is dependent on the ADCC, the second anti-tumor mechanism associated with the CHIR-5.9 and CHIR-12.12 mAbs. Two xenograft human lymphoma models based on Namalwa and Daudi cell lines were assessed for anti-tumor activities of candidate mAbs. To further demonstrate their therapeutic activity, these candidate mAbs were evaluated in an unstaged and staged xenograft human lymphoma model based on the Daudi cell line.

Summary of In Vivo Efficacy Data

Figure 4:
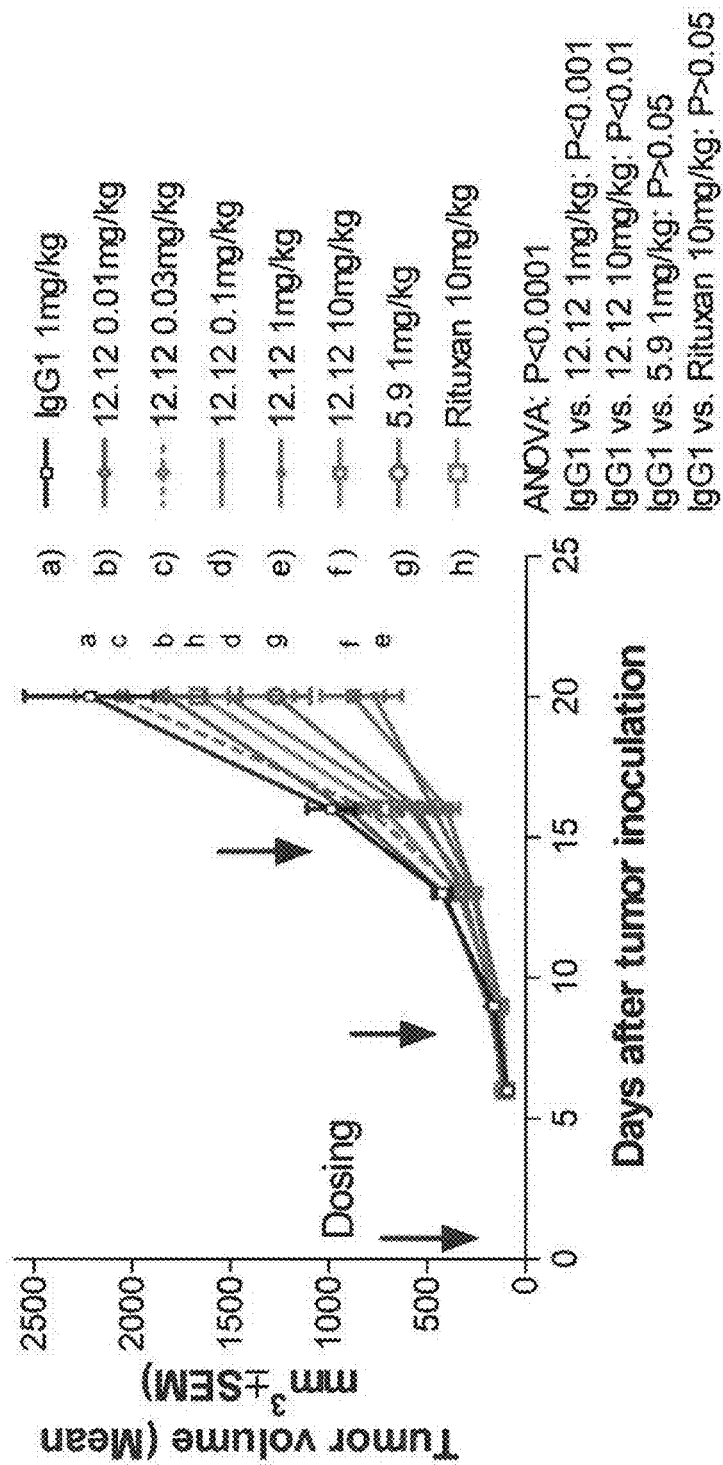
FIG. 4 demonstrates in vivo anti-tumor activity of monoclonal antibodies CHIR-5.9 and CHIR-12.12 compared to that of rituximab using an unstaged nude mouse xenograft B cell lymphoma (Namalwa) model.
Figure 5:
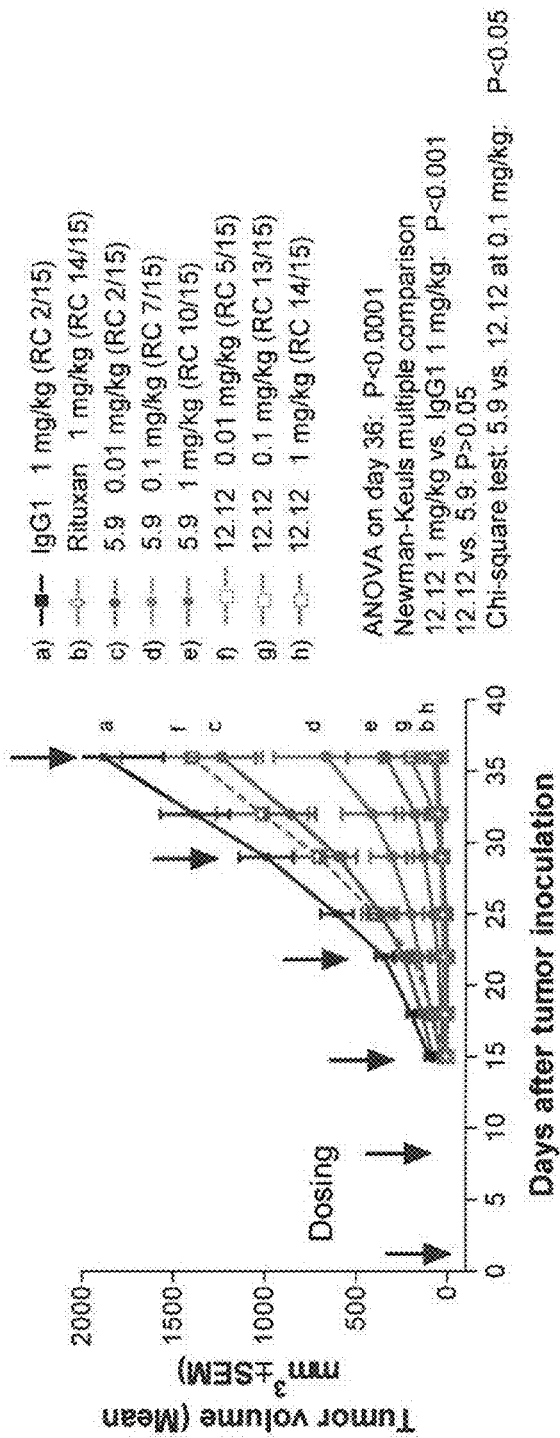
FIG. 5 demonstrates in vivo anti-tumor activity of monoclonal antibodies CHIR-5.9 and CHIR-12.12 compared to that of rituximab using an unstaged nude mouse xenograft B cell lymphoma (Daudi) model. RC, resistance to tumor challenge.
Figure 6:
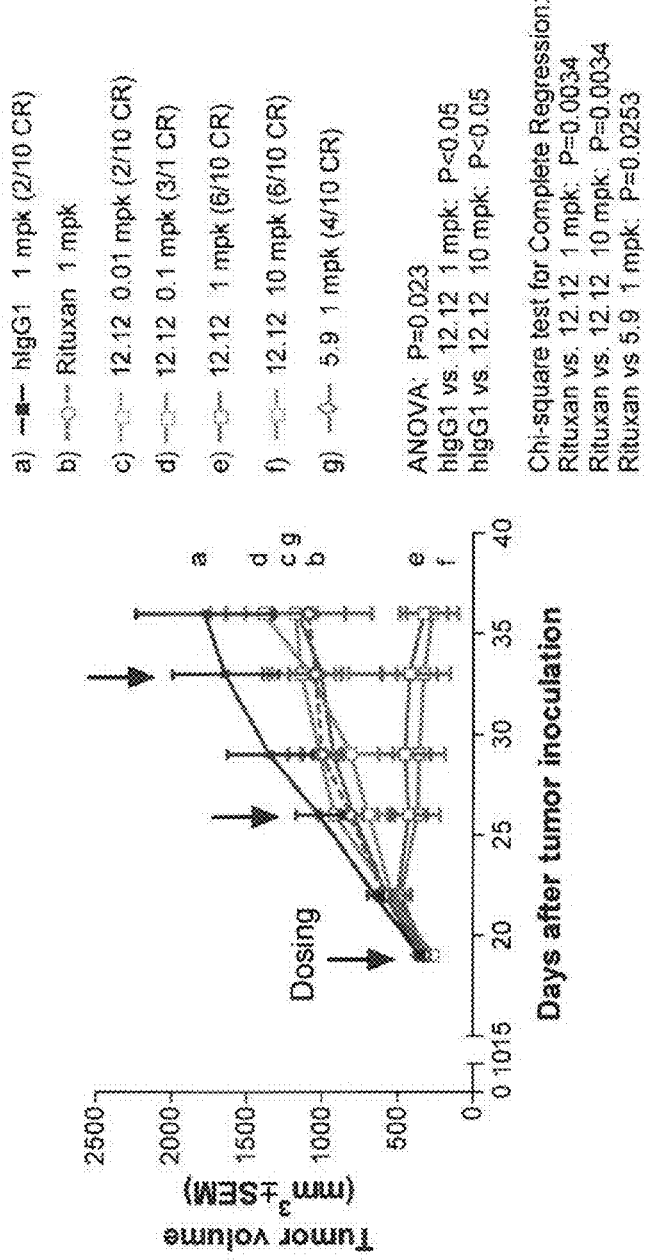
FIG. 6 demonstrates in vivo anti-tumor activity of monoclonal antibodies CHIR-5.9 and CHIR-12.12 compared to that of rituximab using a staged nude mouse xenograft B cell lymphoma (Daudi) model. CR, complete regression.

When administered intraperitoneally (i.p.) once a week for a total of 3 doses, CHIR-12.12, one of the two candidate mAbs, significantly inhibited the growth of aggressive unstaged B cell lymphoma (Namalwa) in a dose-dependent manner (FIG. 4). The second candidate mAb, CHIR-5.9, was tested only at a single dose in this study and was less effective than CHIR-12.12 at the same dose. Interestingly, CHIR-12.12 was found to be more efficacious in this model than rituximab. It is possible that lower efficacy by rituximab could be due to low CD20 expression on the Namalwa lymphoma cell line. The efficacy observed with candidate mAbs has greater importance because only one of the two cancer cell killing mechanisms (ADCC) is operative in the current xenograft lymphoma model. Two killing mechanisms, ADCC and blocking of survival signal, are expected to contribute to anti-tumor activities in human lymphoma patients. This is likely to increase the chance of achieving efficacy in human lymphoma patients. The candidate anti-CD40 mAbs also showed a trend toward tumor growth inhibition in a second B cell lymphoma model (non-validated Daudi model, data not shown). In follow-up studies, the two candidate antibodies were shown to have dose-dependent anti-tumor efficacy in both the unstaged and staged Daudi lymphoma models (FIGS. 5 and 6, respectively). In the staged Daudi model, the CHIR-12.12 mAb was more efficacious at reducing tumor volume than was a similar dose of Rituxan®.

Xenograft Human B Cell Lymphoma Models

To ensure consistent tumor growth, T cell-deficient nude mice were whole-body irradiated at 3 Gy to further suppress the immune system one day before tumor inoculation. Tumor cells were inoculated subcutaneously in the right flank at $5 \times 10^6$ cells per mouse. Treatment was initiated either one day after tumor implantation (unstaged subcutaneous xenograft human B cell lymphoma models, Namalwa and Daudi) or when tumor volume reached 200-400 mm$^3$ (staged Daudi model, usually 15 days after tumor inoculation). Tumor-bearing mice were injected anti-CD40 mAbs intraperitoneally (i.p.) once a week at the indicated doses. Tumor volumes were recorded twice a week. When tumor volume in any group reached 2500 mm$^3$, the study was terminated. Note that in the staged Daudi model, tumor volume data was analyzed up to day 36 due to the death of some mice after that day. Complete regression (CR) was counted until the end of the study. Data were analyzed using ANOVA or Kruskal-Wallis test and corresponding post-test for multi-group comparison.

In the unstaged Namalwa model, anti-CD40 mAb CHIR-12.12, but not Rituxan® (rituximab), significantly (p=<0.01) inhibited the growth of Namalwa tumors (tumor volume reduction of 60% versus 25% for rituxamab, n=10 mice/group) (FIG. 4). Thus, in this model, anti-CD40 mAb CHIR-12.12 was more potent than rituximab. It is noteworthy that the second candidate mAb, CHIR-5.9, was at least as efficacious as rituximab at a dose 1/10 that of rituximab. Both anti-CD40 mAb CHIR-12.12 and rituxan significantly prevented tumor development in the unstaged Daudi tumor model (14/15 resistance to tumor challenge) (FIG. 5).

When these anti-CD40 monoclonal antibodies were further compared in a staged xenograft Daudi model, in which treatment started when the subcutaneous tumor was palpable, anti-CD40 mAb CHIR-12.12 at 1 mg/kg caused significant tumor reduction (p=0.003) with 60% complete regression (6/10), while rituximab at the same dose did not significantly inhibit the tumor growth nor did it cause complete regression (0/10). See FIG. 6.

In summary, the anti-CD40 mAb CHIR-12.12 significantly inhibited tumor growth in experimental lymphoma models. At the same dose and regimen, mAb CHIR-12.12 showed better anti-cancer activity than did Rituxan® (rituximab). Further, no clinical sign of toxicity was observed at this dose and regimen. These data suggest that the anti-CD40 mAb CHIR-12.12 has potent anti-human lymphoma activity in vitro and in xenograft models and could be clinically effective for the treatment of lymphoma.

Example 16

Pharmacokinetics of CHIR-5.9 and CHIR-12.12

The pharmacokinetics of anti-CD40 mAb in mice was studied after single IV and IP dose administration. Anti-CD40 mAb exhibited high systemic bioavailability after IP administration, and prolonged terminal half-life (>5 days) (data not shown). This pilot study was conducted to aid in the design of pharmacology studies; however, it is of little to no importance for the development activity of this mAb since this fully human mAb does not cross react with mouse CD40.

Example 17

Characterization of Epitope for Monoclonal Antibodies CHIR-12.12 and CHIR-5.9

To determine the location of the epitope on CD40 recognized by monoclonal antibodies CHIR-12.12 and CHIR-5.9, SDS-PAGE and Western blot analysis were performed. Purified CD40 (0.5 µg) was separated on a 4-12% NUPAGE gel under reducing and non-reducing conditions, transferred to PVDF membranes, and probed with monoclonal antibodies at 10 µg/ml concentration. Blots were probed with alkaline phosphatase conjugated anti-human IgG and developed using the Western Blue$^R$ stabilized substrate for alkaline phosphatase (Promega).

Results indicate that anti-CD40 monoclonal antibody CHIR-12.12 recognizes epitopes on both the non-reduced and reduced forms of CD40, with the non-reduced form of CD40 exhibiting greater intensity than the reduced form of CD40 (Table 15; blots not shown). The fact that recognition was positive for both forms of CD40 indicates that this antibody interacts with a conformational epitope part of which is a linear sequence. Monoclonal antibody CHIR-5.9 primarily recognizes the non-reduced form of CD40 suggesting that this antibody interacts with a primarily conformational epitope (Table 15; blots not shown).

TABLE 15

Domain identification.

|  | Domain 1 | Domain 2 | Domain 3 | Domain 4 |
|---|---|---|---|---|
| mAb CHIR-12.12 | − | + | − | − |
| mAb CHIR-5.9 | − | + | − | − |
| mAb 15B8 | + | − | − | − |

To map the antigenic region on CD40, the four extracellular domains of CD40 were cloned and expressed in insect cells as GST fusion proteins. The secretion of the four domains was ensured with a GP67 secretion signal. Insect cell supernatant was analyzed by SDS-PAGE and western blot analysis to identify the domain containing the epitope.

Monoclonal antibody CHIR-12.12 recognizes an epitope on Domain 2 under both reducing and non-reducing conditions (Table 16; blots not shown). In contrast, monoclonal antibody CHIR-5.9 exhibits very weak recognition to Domain 2 (Table 16; blots not shown). Neither of these antibodies recognize Domains 1, 3, or 4 in this analysis.

TABLE 16

Domain 2 analysis.

|  | Reduced | Non-reduced |
|---|---|---|
| mAb CHIR-12.12 | ++ | +++ |
| mAb CHIR-5.9 | + | + |

To define more precisely the epitope recognized by mAb CHIR-12.12, peptides were synthesized from the extracellular Domain 2 of CD40, which corresponds to the sequence PCGESEFLDTWNRETHCHQHKYCDPN-LGLRVQQKGTSETDTICT (residues 61-104 of the sequence shown in SEQ ID NO:10 or SEQ ID NO:12). SPOTs membranes (Sigma) containing thirty-five 10mer peptides with a 1-amino-acid offset were generated. Western blot analysis with mAb CHIR-12.12 and anti-human IgG beta-galactosidase as secondary antibody was performed. The blot was stripped and reprobed with mAb CHIR-5.9 to determine the region recognized by this antibody SPOTs analysis probing with anti-CD40 monoclonal antibody CHIR-12.12 at 10 μg/ml yielded positive reactions with spots 18 through 22. The sequence region covered by these peptides is shown in Table 17.

TABLE 17

Results of SPOTs analysis probing with anti-CD40 monoclonal antibody CHIR-12.12.

| Spot Number | Sequence Region |
|---|---|
| 18 | HQHKYCDPNL (residues 78-87 of SEQ ID NO: 10 or SEQ ID NO: 12) |
| 19 | QHKYCDPNLG (residues 79-88 of SEQ ID NO: 10 or SEQ ID NO: 12) |
| 20 | HKYCDPNLGL (residues 80-89 of SEQ ID NO: 10 or SEQ ID NO: 12) |
| 21 | KYCDPNLGLR (residues 81-90 of SEQ ID NO: 10 or SEQ ID NO: 12) |
| 22 | YCDPNLGLRV (residues 82-91 of SEQ ID NO: 10 or SEQ ID NO: 12) |

These results correspond to a linear epitope of: YCDPNL (residues 82-87 of the sequence shown in SEQ ID NO:10 or SEQ ID NO:12). This epitope contains Y82, D84, and N86, which have been predicted to be involved in the CD40-CD40 ligand interaction.

SPOTs analysis with mAb CHIR-5.9 showed a weak recognition of peptides represented by spots 20-22 shown in Table 18, suggesting involvement of the region YCDPNLGL (residues 82-89 of the sequence shown in SEQ ID NO:10 or SEQ ID NO:12) in its binding to CD40. It should be noted that the mAbs CHIR-12.12 and CHIR-5.9 compete with each other for binding to CD40 in BIACORE analysis.

TABLE 18

Results of SPOTs analysis probing with anti-CD40 monoclonal antibody CHIR-5.9.

| Spot Number | Sequence Region |
|---|---|
| 20 | HKYCDPNLGL (residues 80-89 of SEQ ID NO: 10 or SEQ ID NO: 12) |
| 21 | KYCDPNLGLR (residues 81-90 of SEQ ID NO: 10 or SEQ ID NO: 12) |
| 22 | YCDPNLGLRV (residues 82-91 of SEQ ID NO: 10 or SEQ ID NO: 12) |

The linear epitopes identified by the SPOTs analyses are within the CD40 B1 module. The sequence of the CD40 B1 module is:

(residues 80-103 of
SEQ ID NO: 10 or SEQ ID NO: 12)
HKYCDPNLGLRVQQKGTSETDTIC.

Within the linear epitope identified for CHIR-12.12 is C83. It is known that this cysteine residue forms a disulphide bond with C103. It is likely that the conformational epitope of the CHIR-12.12 mAb contains this disulfide bond (C83-C103) and/or surrounding amino acids conformationally close to C103.

Example 18

Number of CD20 and CD40 Molecules on Namalwa and Daudi Cells

The number of CD20 and CD40 molecules on Namalwa and Daudi cells was determined as outlined in FIG. 7, using antibody concentrations of 0.01, 0.1, 1, 10, and 100 µg/ml. As can be seen in FIG. 7, the average number of CD20 molecules (target for rituximab) is greater on both the Namalwa and Daudi cell lines than is the number of CD40 molecules (target for mAb CHIR-12.12).

Example 19

ADCC of mAb CHIR-12.12 and Rituximab Against Daudi Lymphoma Cells

The rituximab and candidate mAb CHIR-12.12 were tested in vitro for ADCC activity at variable concentrations against lymphoma cell line Daudi as target (T) cells and purified NK cells from healthy human volunteers as effector (E) cells. Freshly isolated human NK cells were mixed with calcein-labeled Daudi lymphoma cells at an E:T ratio of 10. The cell mixture was incubated for 4 hours at 37° C. in the presence of the stated concentrations of either mAb CHIR-12.12 or rituximab. The calcein level released from lysed target cells in the supernatant was measured as Arbitrary Fluorescent Units (AFU). The percent specific lysis was calculated as: 100×(AFU test−AFU spontaneous release)/(AFU maximal release−AFU spontaneous release), where AFU spontaneous release is the calcein released by target cells in the absence of antibody or NK cells, and AFU maximal release is the calcein released by target cells upon lysis by detergent.

Figure 8:
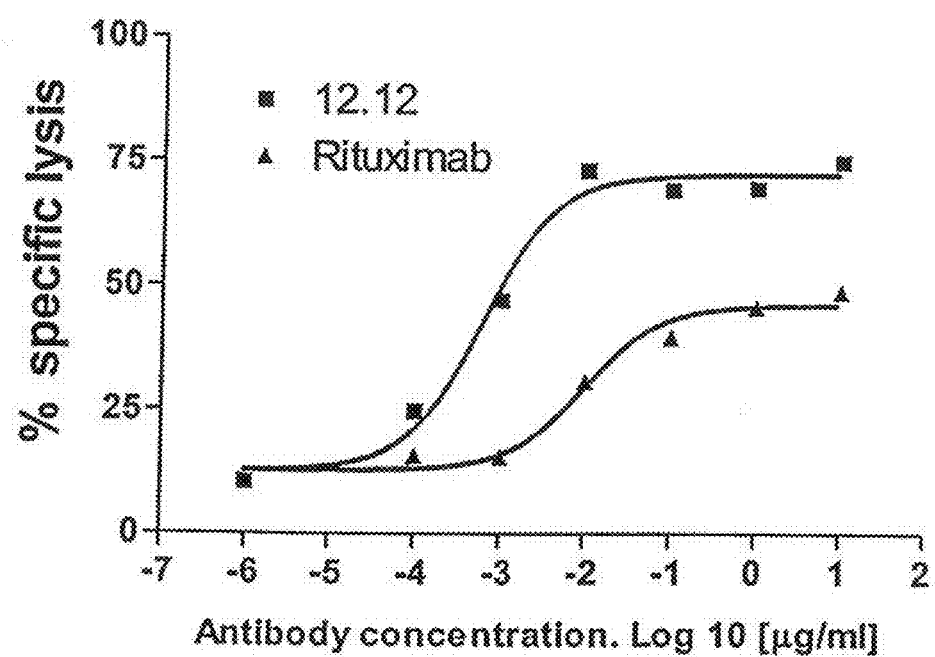
FIG. 8 shows comparative ADCC of the mAb CHIR-12.12 and rituximab against Daudi lymphoma cells.

Antibody concentration-dependent Daudi cell lysis was observed (FIG. 8; Table 19 below). The maximum specific lysis of target lymphoma cells induced by anti-CD40 mAb was greater compared to the lysis induced by rituximab (63.6% versus 45.9%, n=6; paired t test of mAb CHIR-12.12 versus rituximab, p=0.0002). In addition, ED50 for rituximab was on average (n=6) 51.6 pM, 13-fold higher than ED50 for the anti-CD40 mAb CHIR-12.12 for this activity.

TABLE 19

Comparative ADCC of mAb CHIR-12.12 and rituximab against Daudi lymphoma cells.

| NK Cell Donor | Maximal Killing (%) | | ED50 (pM) | |
| --- | --- | --- | --- | --- |
| | mAb CHIR-12.12 | Rituximab | mAb CHIR-12.12 | Rituximab |
| 1 | 50.2 | 34.9 | 3.2 | 14.2 |
| 2 | 83.1 | 68.6 | 2.2 | 27.2 |
| 3 | 64.2 | 36.9 | 4.1 | 66.9 |
| 4 | 53.3 | 39.5 | 2.4 | 47.6 |
| 5 | 74.8 | 56.6 | 2.8 | 24.1 |
| 6 | 56.2 | 38.9 | 7.9 | 129.5 |
| Average | 63.6 | 45.9 | 3.8 | 51.6 |

Example 20

CHIR-12.12 Blocks CD40L-Mediated CD40 Survival and Signaling Pathways in Normal Human B Cells Soluble CD40 ligand (CD40L) activates B cells and induces various aspects of functional responses, including enhancement of survival and proliferation, and activation of NFκB, ERK/MAPK, PI3K/Akt, and p38 signaling pathways. In addition, CD40L-mediated CD40 stimulation provides survival signals by reduction of cleaved PARP and induction of the anti-apoptotic proteins, XIAP and Mcl-1, in normal B cells. CD40L-mediated CD40 stimulation also recruits TRAF2 and TRAF3 to bind CD40 cytoplasmic domain.

The following studies demonstrate that CHIR-12.12 directly inhibited all of these stimulation effects on normal human B cells. For example, CHIR-12.12 treatment resulted in increased cleavage of caspase-9, caspase-3, and PARP as well as reduction of XIAP and Mcl-1 in a time- and dose-dependent manner, restoring B cell apoptosis. Treatment with CHIR-12.12 also inhibited phosphorylation of IκB kinase (IKK) α and β (NFκB pathway), ERK, Akt, and p38 in response to CD40L-mediated CD40 stimulation. Further, it was found that CHIR-12.12 did not trigger these apoptotic effects without initial CD40L-mediated CD40 stimulation.

CHIR-12.12 Inhibited Survival Mediated by CD40 Ligand by Inducing Cleavage of PARP.

In these experiments, 0.6×10$^6$ normal human B cells from healthy donors (percent purity between 85-95%) were stimulated with 1 µg/ml sCD40L (Alexis Corp., Bingham, Nottinghamshire, UK). CHIR-12.12 (10 µg/ml) and control IgG were then added. Cells were collected at 0, 20 minutes, 2 hours, 6 hours, 18 hours, and 26 hours. Cleaved caspase-9, cleaved caspase-3, cleaved PARP, and β-actin controls were detected in cell lysates by Western blot.

Briefly, it was observed that CD40L-mediated CD40 stimulation provided survival signals as it did not result in increases of cleaved caspase-9, cleaved caspase-3, or cleaved PARP over time, indicating that the cells were not undergoing apoptosis. However, treatment with CHIR-12.12 resulted in an increase of these cleavage products, indicating that CHIR-12.12 treatment abrogated the effects of CD40L binding on survival signaling in sCD40L-stimulated normal B cells, restoring B cell apoptosis (data not shown).

CHIR-12.12 Inhibited Expression of "Survival" Anti-Apoptotic Proteins.

In these experiments, 0.6×10$^6$ normal human B cells from healthy donors (percent purity between 85-95%) were stimulated with 1 µg/ml sCD40L (Alexis Corp., Bingham, Nottinghamshire, UK). CHIR-12.12 (10 µg/ml) and control IgG were then added. Cells were collected at 0, 20 minutes, 2 hours, 6 hours, 18 hours, and 26 hours. Mcl-1, XIAP, CD40, and β-actin controls were detected in cell lysates by Western blot.

Briefly, sCD40L stimulation resulted in sustained expression of Mcl-1 and XIAP over time. However, treatment of the sCD40L-stimulated cells with CHIR 12.12 resulted in a decrease in expression of these proteins overtime (data not shown). Since Mcl-1 and XIAP are "survival" signals capable of blocking the apoptotic pathway, these results demonstrate that CHIR-12.12 treatment removes the blockade against apoptosis in sCD40L-stimulated normal B cells.

CHIR-12.12 Treatment Inhibited Phosphorylation of IKKα (Ser180) and IKK β (Ser 181) in Normal B Cells.

In these experiments, $1.0 \times 10^6$ normal human B cells from healthy donors (percent purity between 85-95%) were stimulated with 1 μg/ml sCD40L (Alexis Corp., Bingham, Nottinghamshire, UK). CHIR-12.12 (10 μg/ml) and control IgG were then added. Cells were collected at 0 and 20 minutes. Phosphorylated IKKα (Ser180) and IKK β (Ser 181) and total IKKβ controls were detected in cell lysates by Western blot.

Briefly, stimulation by sCD40L resulted in phosphorylation of IKKα (Ser180) and IKK β (Ser 181) over time; however, treatment with CHIR-12.12 abrogated this response to sCD40L stimulation in normal B cells (data not shown).

CHIR-12.12 Treatment Inhibited Survival Mediated by CD40 Ligand in a Dose-Dependent Manner.

In these experiments, $0.6 \times 10^6$ normal human B cells from healthy donors percent purity between 85-95%) were stimulated with 1 μg/ml sCD40L (Alexis Corp., Bingham, Nottinghamshire, UK). CHIR-12.12 (0.01, 0.1, 0.2, 0.5, 1.0 μg/ml) and control IgG were then added. Cells were collected at 24 hours. Cleaved PARP, and β-actin controls were detected in cell lysates by Western blot.

Briefly, CHIR-12.12 treatment resulted in increase of PARP cleavage in sCD40L stimulated cells in a dose-dependent manner and therefore abrogated the survival signaling pathway in sCD40L-stimulated normal B cells (data not shown).

CHIR-12.12 Inhibited Expression of "Survival" Anti-Apoptotic Proteins in a Dose-Dependent Manner.

In these experiments, $0.6 \times 10^6$ normal human B cells from healthy donors (percent purity between 85-95%) were stimulated with 1 μg/ml sCD40L (Alexis Corp., Bingham, Nottinghamshire, UK). CHIR-12.12 (0.5, 2, and 10 μg/ml) and control IgG were then added. Cells were collected at 22 hours. Mcl-1, XIAP, cleaved PARP, and β-actin controls were detected in cell lysates by Western blot.

Briefly, CHIR-12.12 treatment reduced Mcl-1 and XIAP expression and increased cleaved PARP expression in sCD40L-stimulated cells in a dose-dependent manner, and thus abrogated these blockades to the apoptotic pathway in sCD40L-stimulated normal B cells (data not shown).

CHIR-12.12 did not Affect Expression of Anti-Apoptotic Proteins, Cleaved-PARP, and XIAP, in the Absence of Soluble CD40L Signaling.

In these experiments, $1.0 \times 10^6$ normal human B cells from healthy donors (percent purity between 85-95%) were treated with CHIR-12.12 (10 μg/ml) and control IgG only (i.e., cells were not pre-stimulated with sCD40L before adding antibody). Cells were collected at 0, 4, 14, and 16 hours. XIAP, cleaved PARP, and β-actin controls were detected in cell lysates by Western blot.

Briefly, the results show that without sCD40L stimulation, the cells expressed increased concentrations of cleaved PARP, while expression of XIAP remained constant, in both IgG treated control cells and CHIR-12.12 cells (data not shown). These data indicate that CHIR-12.12 does not trigger apoptosis in normal human B cells without CD40L stimulation.

CHIR-12.12 Inhibits Phosphorylation of IKKα (Ser180) and IKKβ (Ser181), Akt, ERK, and p38 in Normal B Cells.

In these experiments, $1.0 \times 10^6$ normal human B cells from healthy donors (percent purity between 85-95%) were serum starved in 1% FBS-containing media and stimulated with 1 μg/ml sCD40L (Alexis Corp., Bingham, Nottinghamshire, UK). The cultures were treated with CHIR-12.12 (1 and 10 μg/ml) and control IgG. Cells were collected at 0 and 20 minutes. Phospho-IKKα, phospho-IKKβ, total IKKβ, phospho-ERK, total ERK, phospho-Akt, total Akt, phospho-p38, and total p38 were detected in cell lysates by Western blot.

Briefly, sCD40L stimulation resulted in increases in IKKα/β phosphorylation, ERK phosphorylation, Akt phosphorylation, and p38 phosphorylation, thus leading to survival and or proliferation of the cells. Treatment of the cells with CHIR-12.12 abrogated the effects of sCD40L stimulation on these signaling pathways in normal B cells (data not shown).

CHIR 12.12 Inhibits Multiple Signaling Pathways Such as PI3K and MEK/ERK in the CD40 Signaling Cascade.

In these experiments, $1.0 \times 10^6$ normal human B cells from healthy donors (percent purity between 85-95%) were serum starved in 1% FBS-containing media and stimulated with 1 μg/ml sCD40L (Alexis Corp., Bingham, Nottinghamshire, UK). The cultures were also treated with CHIR-12.12 (1 and 10 μg/ml), Wortmanin, (a PI3K/Akt inhibitor; 1 and 10 μM), LY 294002 (a PI3K/Akt inhibitor; 10 and 30 μM), and PD 98095 (a MEK inhibitor; 10 and 30 μg/ml). Cells were collected at 0 and 20 minutes. Phospho-ERK, phospho-Akt, total Akt, phospho-IKKα/β, and total were detected in cell lysates by Western blot.

Briefly, the results show that CHIR-12.12 abrogated the phosphorylation of all of these signal transduction molecules, whereas the signal transduction inhibitors showed only specific abrogation of signaling, indicating that CHIR-12.12 likely inhibits upstream of these signal transduction molecules mediated by CD40L stimulation (data not shown).

CHIR-12.12 Inhibits the Binding of Signaling Molecules TRAF2 and TRAF3 to the Cytoplasmic Domain of CD40 in Normal B Cells.

In these experiments, $4.0 \times 10^6$ normal human B cells from healthy donors (percent purity between 85-95%) were serum starved for four hours in 1% FBS-containing media and stimulated with 1 μg/ml sCD40L (Alexis Corp., Bingham, Nottinghamshire, UK) for 20 minutes. Cells were collected at 0 and 20 minutes. CD40 was immunoprecipitated using polyclonal anti-CD40 (Santa Cruz Biotechnology, CA), and was probed in a Western blot with anti-TRAF2 mAb (Santa Cruz Biotechnology, CA), anti-TRAF3 mAb (Santa Cruz Biotechnology, CA), and anti-CD40 mAb (Santa Cruz Biotechnology, CA).

Briefly, the results show that TRAF2 and TRAF3 co-precipitated with CD40 after sCD40L stimulation. In contrast, treatment with CHIR-12.12 abrogated formation of the CD40-TRAF2/3 signaling complex in sCD40L-stimulated normal B cells. There were no changes in CD40 expression (data not shown).

Without being bound by theory, the results of these experiments, and the results in the examples outlined above, indicate that the CHIR-12.12 antibody is a dual action antagonist anti-CD40 monoclonal antibody having a unique combination of attributes. This fully human monoclonal antibody blocks CD40L-mediated CD40 signaling pathways for survival and proliferation of B cells; this antagonism leads to ultimate cell death. CHIR-12.12 also mediates recognition and binding by effector cells, initiating antibody dependent cellular cytotoxicity (ADCC). Once CHIR-12.12 is bound to effector cells, cytolytic enzymes are released, leading to B-cell apoptosis and lysis. CHIR-12.12 is a more potent anti-tumor antibody than is rituximab when compared in pre-clinical tumor models.

Example 21

Agonist and Antagonist Activity Against Primary Cancer Cell from NHL, CLL, and NM Patients In collaboration with clinical investigators, the candidate mAbs is tested for a variety of activities (listed below) against primary cancer cells from NHL and CLL and multiple myeloma patients.
  Agonist effect in proliferation assays (8 NHL patients, 8 CLL patients and 8 mM patients)
  Antagonist effect in proliferation assays (8 NHL patients, 8 CLL patients and 8 MM patients)
  Apoptotic effect by Annexin V assay (3-4 NHL patients, 4 CLL patients, and 4 MM patients)
  Reversing survival signal by Annexin V assay (3 NHL patients, 3 CLL patients and 3 mM patients)
  Complement dependent cytotoxicity (4 NHL patients, 4 CLL patients, and 4mM patients)
  Antibody dependent cytotoxicity (6 NHL patients, 6 CLL patients and 6 mM patients)

Example 22

Identification of Relevant Animal Species for Toxicity Studies

As these two candidate antibodies do not cross-react with rodent CD40, other species must be identified for testing toxicologic effects.

The ability of the two candidate anti-CD40 antibodies to cross-react with animal CD40 is tested by flow cytometric assays. Rat, rabbit, dog, cynomolgus monkeys and marmoset monkeys are tested for this study.

The candidate antibodies show antagonist activity upon binding to CD40 on human B cells. To identify an animal species that has similar response to candidate antibodies, lymphocytes from species that show binding to candidate antibodies are tested in proliferation assays for antagonist activity. The lymphocytes from the species selected for antagonistic binding of candidate antibodies are further tested for their ability to serve as effector cells for killing CD40-expressing lymphoma cell lines through the mechanism of ADCC. Finally the selected animal species are tested in an IHC study for the tissue-binding pattern of candidate antibodies. The animal species responding to the candidate antibodies in these assays in a manner similar to that observed for human cells are chosen for toxicology studies.

Initial studies indicate that the candidate anti-CD40 mAbs cross-react with cynomolgus monkey CD40.

Example 23

Tumor Targeting Profile of CHIR-5.9 and CHIR-12.12

To determine the relative tumor targeting profile of CHIR-12.12 and CHIR-5.9 mAbs, fluorescent-labeled candidate mAbs and isotype control antibodies are administered into tumor-bearing mice. Tumor specimens and normal organs are harvested at different time points after dosing. The accumulation of labeled antibody in tumors and normal organs is analyzed.

Example 24

Mechanism of Action of CHIR-5.9 and CHIR-12.12

To elucidate the mechanism(s) that mediates the tumor growth inhibition by the CHIR-5.9 and CHIR-12.12 mAbs, the following studies are undertaken:

Fc-receptor knock-out or blockage model: ADCC is mediated by binding of effecter cells such as NK, marcrophage, and monocytes to the Fc portion of antibody through Fc receptor. Mice deficient in activating Fc receptors as well as antibodies engineered to disrupt Fc binding to those receptors will block the ADCC mediated tumor growth inhibition. Loss or significantly reduced tumor inhibition in this model will suggest that the tumor growth inhibition by these two candidate mAbs is mainly mediated by ADCC mechanism.

Example 25

Liquid Pharmaceutical Formulation for Antagonist Anti-CD40 Antibodies

The objective of this study was to investigate the effects of solution pH on stability of the antagonist anti-CD40 antibody CHIR-12.12 by both biophysical and biochemical methods in order to select the optimum solution environment for this antibody. Differential Scanning calorimetry (DSC) results showed that the conformation stability of CHIR-12.12 is optimal in formulations having pH 5.5-6.5. Based on a combination of SDS-PAGE, Size-Exclusion HPLC (SEC-HPLC), and Cation-Exchange HPLC (CEX-HPLC) analysis, the physicochemical stability of CHIR-12.12 is optimal at about pH 5.0-5.5. In view of these results, one recommended liquid pharmaceutical formulation comprising this antibody is a formulation comprising CHIR-12.12 at about 20 mg/ml formulated in about 10 mM sodium succinate, about 150 mM sodium chloride, and having a pH of about pH 5.5.

Materials and Methods

The CHIR-12.12 antibody used in the formulation studies is a human monoclonal antibody produced by a CHO cell culture process. This MAb has a molecular weight of 150 kDa and consists of two light chains and two heavy chains linked together by disulfide bands. It is targeted against the CD40 cell surface receptor on CD40-expressing cells, including normal and malignant B cells, for treatment of various cancers and autoimmune/inflammatory diseases.

The anti-CD40 drug substance used for this study was a CHO-derived purified anti-CD40 (CHIR-12.12) bulk lot. The composition of the drug substance was 9.7 mg/ml CHIR-12.12 antibody in 10 mM sodium citrate, 150 mM sodium chloride, at pH 6.5. The control sample in the study was the received drug substance, followed by freezing at ≤−60° C., thawing at RT and testing along with stability samples at predetermined time points. The stability samples were prepared by dialysis of the drug substance against different pH solutions and the CHIR-12.12 concentration in each sample was determined by UV 280 as presented in Table 20.

TABLE 20

CHIR-12.12 formulations.

| Buffer Composition | pH | CHIR-12.12 Concentration (mg/ml) |
|---|---|---|
| 10 mM sodium citrate, 150 mM sodium chloride | 4.5 | 9.0 |
| 10 mM sodium succinate, 150 mM sodium chloride | 5.0 | 9.3 |
| 10 mM sodium succinate, 150 mM sodium chloride | 5.5 | 9.2 |
| 10 mM sodium citrate, 150 mM sodium chloride | 6.0 | 9.7 |
| 10 mM sodium citrate, 150 mM sodium chloride | 6.5 | 9.4 |
| 10 mM sodium phosphate, 150 mM sodium chloride | 7.0 | 9.4 |
| 10 mM sodium phosphate, 150 mM sodium chloride | 7.5 | 9.5 |
| 10 mM glycine, 150 mM sodium chloride | 9.0 | 9.5 |

Physicochemical stability of the CHIR-12.12 antibody in the various formulations was assayed using the following protocols.

Differential Scanning Calorimetry (DSC

Conformational stability of different formulation samples was monitored using a MicroCal VP-DSC upon heating 15° C. to 90° C. at 1° C./min.

SDS-PAGE

Fragmentation and aggregation were estimated using 4-20% Tris-Glycine Gel under non-reducing and reducing conditions. Protein was detected by Coomassie blue staining.

Size Exclusion Chromatograph (SEC-HPLC)

Protein fragmentation and aggregation were also measured by a Water Alliance HPLC with a Tosohaas TSK-GEL 3000SWXL column, 100 mM sodium phosphate, pH 7.0 as mobile phase at a flow rate of 0.7 ml/min.

Cation Exchange Chromatography (CEX-HPLC)

Charge change related degradation was measured using Waters 600s HPLC system with a Dionex Propac WCX-10 column, 50 mM HEPEs, pH 7.3 as mobile phase A and 50 mM HEPES containing 500 mM NaCl, pH 7.3 as mobile phase B at a flow rate of 0.5° C./min.

Results and Discussion

Conformational Stability Study.

Figure 13:
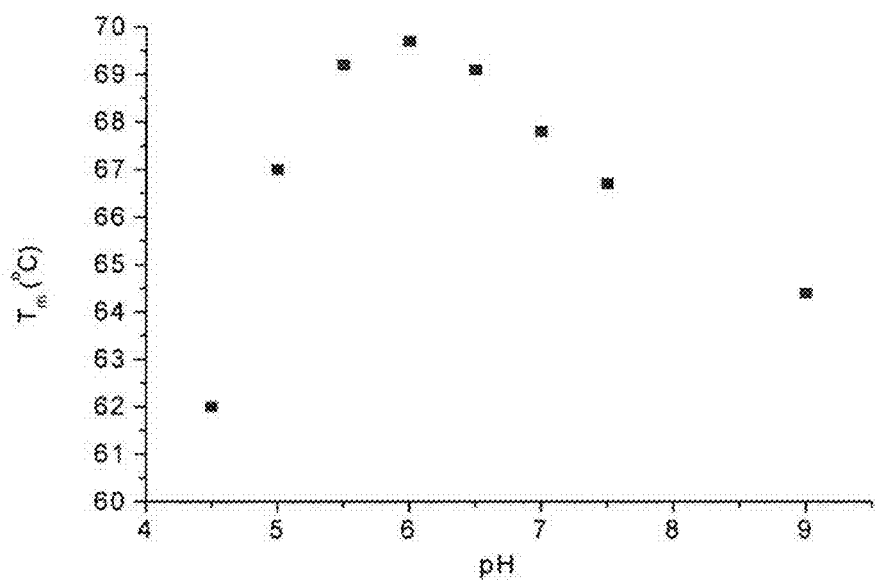
FIG. 13 shows thermal melting temperature of CHIR-12.12 in different pH formulations measured by differential scanning calorimetry (DSC).

Thermal unfolding of CHIR-12.12 revealed at least two thermal transitions, probably representing unfolding melting of the Fab and the Fc domains, respectively. At higher temperatures, the protein presumably aggregated, resulting in loss of DSC signal. For the formulation screening purpose, the lowest thermal transition temperature was defined as the melting temperature, Tm, in this study. FIG. 13 shows the thermal melting temperature as a function of formulation pHs. Formulations at pH 5.5-6.5 provided anti-CD40 with higher conformational stability as demonstrated by the higher thermal melting temperatures.

SDS-PAGE Analysis.

The CHIR-12.12 formulation samples at pH 4.5-9.0 were incubated at 40° C. for 2 months and subjected to SDS-PAGE analysis (data not shown). Under non-reducing conditions, species with molecular weight (MW) of 23 kDa and 27 kDa were observed in formulations above pH 5.5, and species with MW of 51 kDa were observed in all formulations, but appeared less at pH 5.0-5.5. A species with MW of 100 kDa could be seen at pH 7.5 and pH 9.0.

Under reducing conditions, CHIR-12.12 was reduced into free heavy chains and light chains with MW of 50 kDa and 24 kDa, respectively. The 100 kDa species seemed not fully reducible and increased with increasing solution pH, suggesting non-disulfide covalent association might occur in the molecules. Since there were other species with unknown identities on SDS-PAGE, stability comparison of each formulation is based on the remaining purity of CHIR-12.12. Formulations at pH 5.0-6.0 provided a more stable environment to CHIR-12.12. Few aggregates were detected by SDS-PAGE (data not shown).

SEC-HPLC Analysis

SEC-HPLC analysis detected the intact CHIR-12.12 as the main peak species, an aggregation species as a front peak species separate from the main peak species, a large fragment species as a shoulder peak on the back of the main peak species, and small fragment species were detected post-main peak species. After incubation at 5° C. and 25° C. for 3 months, negligible amounts of protein fragments and aggregates (<1.0%) were detected in the above formulations and the CHIR-12.12 main peak species remained greater than 99% purity (data not shown). However, protein fragments gradually developed upon storage at 40° C. and more fragments formed at pH 4.5 and pH 6.5-9.0, as shown in Table 21. After incubating the CHIR-12.12 formulations at 40° C. for 3 months, about 2-3% aggregates were detected in pH 7.5 and pH 9.0, while less than 1% aggregates were detected in other pH formulations (data not shown). The SEC-HPLC results indicate CHIR-12.12 is more stable at about pH 5.0-6.0.

TABLE 21

SEC-HPLC results of CHIR-12.12 stability samples under real-time and accelerated storage conditions.

| | Main peak % | | | | Fragments % | | | |
|---|---|---|---|---|---|---|---|---|
| Sample | t = 0 | 40° C. 1 m | 40° C. 2 m | 40° C. 3 m | t = 0 | 40° C. 1 m | 40° C. 2 m | 40° C. 3 m |
| Control | 99.4 | 99.2 | 99.9 | 99.5 | <1.0 | <1.0 | <1.0 | <1.0 |
| pH 4.5 | 99.4 | 93.2 | 86.0 | 81.3 | <1.0 | 6.4 | 13.2 | 18.1 |
| pH 5.0 | 99.8 | 98.7 | 91.3 | 89.2 | <1.0 | <1.0 | 7.8 | 10.2 |
| pH 5.5 | 99.8 | 98.9 | 91.4 | 90.6 | <1.0 | <1.0 | 7.6 | 8.8 |
| pH 6.0 | 99.6 | 97.7 | 90.4 | 87.3 | <1.0 | 1.9 | 8.2 | 11.7 |
| pH 6.5 | 99.3 | 93.4 | 89.0 | 86.9 | <1.0 | 5.6 | 9.9 | 12.4 |
| pH 7.0 | 99.2 | 93.9 | 87.4 | 85.1 | <1.0 | 5.5 | 11.1 | 13.5 |
| pH 7.5 | 99.1 | 92.8 | 84.4 | 81.9 | <1.0 | 6.4 | 12.9 | 16.2 |
| pH 9.0 | 99.3 | 82.4 | 61.6 | 50.6 | <1.0 | 15.4 | 36.2 | 47.6 |

CEX-HPLC Analysis.

CEX-HPLC analysis detected the intact CHIR-12.12 as the main peak species, acidic variants eluted earlier than the main peak species, and C-terminal lysine addition variants eluted post-main peak species. Table 22 shows the dependence of the percentages of the remaining main peak CHIR-12.12 species and acidic variants on solution pH. The control sample already contained a high degree of acidic species (~33%), probably due to early-stage fermentation and purification processes. The susceptibility of CHIR-12.12 to higher pH solutions is evidenced by two facts. First, the initial formulation sample at pH 9.0 (t=0) already generated 12% more acidic species than the control. Second, the percentage of acidic species increased sharply with increasing pH. The charge change-related degradation is likely due to deamidation. The above data indicate that this type of degradation of CHIR-12.12 was minimized at about pH 5.0-5.5.

TABLE 22

Percentage of peak area by CEX-HPLC for CHIR-12.12 in different pH formulations under real-time and accelerated storage conditions.

| | Main peak % | | | | | Acidic variants % | | | |
|---|---|---|---|---|---|---|---|---|---|
| Sample | 5° C. t = 0 | 5° C. 3 m | 25° C. 3 m | 40° C. 1 m | 40° C. 2 m | t = 0 | 5° C. 3 m | 25° C. 3 m | 40° C. 1 m | 40° C. 2 m |
| Control | 49.2 | 49.8 | 49.8 | 49.2 | 50.3 | 32.0 | 33.7 | 33.7 | 32.0 | 33.6 |
| pH 4.5 | 48.5 | 49.7 | 43.7 | 39.7 | 30.0 | 32.5 | 32.6 | 38.0 | 44.2 | 56.4 |
| pH 5.0 | 49.6 | 49.8 | 48.3 | 40.6 | 31.4 | 32.7 | 31.8 | 35.0 | 44.3 | 57.1 |
| pH 5.5 | 50.7 | 50.3 | 48.1 | 40.0 | 30.2 | 32.6 | 31.8 | 37.8 | 48.9 | 63.3 |
| pH 6.0 | 50.2 | 49.9 | 47.9 | 37.4 | 23.9 | 33.1 | 33.6 | 38.5 | 54.9 | 72.7 |
| pH 6.5 | 49.4 | 49.9 | 42.3 | 29.7 | 14.6 | 33.3 | 33.6 | 47.7 | 65.2 | 84.6 |
| pH 7.0 | 49.7 | 49.9 | 21.9 | — | — | 34.4 | 36.4 | 64.4 | — | — |
| pH 7.5 | 49.3 | 48.3 | 12.7 | — | — | 35.5 | 40.1 | 79.2 | — | — |
| pH 9.0 | 41.3 | 31.8 | — | — | — | 44.7 | 59.9 | — | — | — |

Conclusion

The pH has a significant effect on conformational and physicochemical stabilities of CHIR-12.12. Charge change-related degradation was determined to be the main degradation pathway for CHIR-12.12, which was minimized at pH 5.0-5.5. Based on overall stability data, one recommended liquid pharmaceutical formulation comprising this antibody is a formulation comprising CHIR-12.12 at about 20 mg/ml formulated in about 10 mM sodium succinate, about 150 mM sodium chloride, and having a pH of about pH 5.5.

Example 26

Clinical Studies with CHIR-5.9 and CHIR-12.12

Clinical Objectives

The overall objective is to provide an effective therapy for B cell tumors by targeting them with an anti-CD40 IgG1. These tumors include B-cell lymphoma, Chronic Lymphocytic Lyphoma (CLL), Acute Lymphoblastic Leukemia (ALL), Multiple Myeloma (MM), Waldenstrom's Macroglobulinemia, and Systemic Castleman's Disease. The signal for these diseases is determined in phase II although some measure of activity may be obtained in phase I. Initially the agent is studied as a single agent, but will be combined with other agents, chemotherapeutics, and other antibodies, as development proceeds.

Phase I
  Evaluate safety and pharmacokinetics—dose escalation in subjects with B cell malignancies.
  Choose dose based on safety, tolerability, and change in serum markers of CD40. In general an MTD is sought but other indications of efficacy (depletion of CD40+ B cells, etc.) may be adequate for dose finding.
  Consideration of more than one dose especially for different indications, e.g., the CLL dose may be different than the NHL. Thus, some dose finding may be necessary in phase II.
  Patients are dosed weekly with real-time pharmacokinetic (Pk) sampling. Initially a 4-week cycle is the maximum dosing allowed. The Pk may be highly variable depending on the disease studied, density of CD40 etc.
  This trial(s) is open to subjects with B-cell lymphoma, CLL, and potentially other B cell malignancies.
  Decision to discontinue or continue studies is based on safety, dose, and preliminary evidence of anti-tumor activity.
  Activity of drug as determined by response rate is determined in Phase II.
  Identify dose(s) for Phase II.

Phase II
  Several trials will be initiated in the above-mentioned tumor types with concentration on B-cell lymphoma, CLL, and Multiple Myeloma (MM). Separate trials may be required in low grade and intermediate/high grade NHL as CD40 may have a different function depending on the grade of lymphoma. In low-grade disease, CD40 acts more as a survival factor, preventing apoptosis. In higher-grade disease, interruption of CD40 signaling may lead to cell death. More than one dose, and more than one schedule may be tested in a randomized phase II setting.
  In each disease, target a population that has failed current standard of care:
    CLL: patients who were resistant to Campath® and chemotherapy.
    Low grade NHL: Rituxan® or CHOP-R failures
    Intermediate NHL: CHOP-R failures
    Multiple Myeloma: Chemotherapy failures
      Decision to discontinue or continue with study is based on proof of therapeutic concept in Phase II
      Determine whether surrogate marker can be used as early indication of clinical efficacy
      Identify doses for Phase III Phase III
  Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.

Chapter II: Use of Antagonist Anti-CD40 Monoclonal Antibodies for Treatment of Multiple Myeloma II. A. Overview This invention is directed to methods for treating human subjects with multiple myeloma, as described herein below in sections II.B-II.F and in commonly owned U.S. Provisional Application No. 60/565,709, filed Apr. 26, 2004 and International Application No. PCT/US2004/037281, filed Nov. 4, 2004 and published as WO 2005/044855, which corresponds to copending U.S. National-Phase application Ser. No. 10/578,387, which published as U.S. Application Publication No. 2007-0218060, all of which are entitled "Use of Antagonist Anti-CD40 Moncolonal Antibodies for Treatment of Multiple Myeloma"; the contents of each of which are herein incorporated by reference in their entirety. The methods involve treatment with an anti-CD40 antibody described herein, or an antigen-binding fragment thereof, where administration of the antibody or antigen-binding fragment thereof promotes a positive therapeutic response within the subject undergoing this method of therapy to treat multiple myeloma.

II. B. Antagonist Anti-CD40 Antibodies for Use in Methods of Treating Multiple Myeloma Anti-CD40 antibodies suitable for use in these methods of the invention specifically bind a human CD40 antigen expressed on the surface of a human cell and are free of significant agonist activity, but exhibit antagonist activity when bound to the CD40 antigen on a human CD40-expressing cell, as demonstrated for CD40-expressing normal and neoplastic human B cells, and as described herein above in Chapter I. These anti-CD40 antibodies and antigen-binding fragments thereof are referred to herein as antagonist anti-CD40 antibodies. Such antibodies include, but are not limited to, the fully human monoclonal antibodies 5.9 and CHIR-12.12, and monoclonal antibodies having the binding characteristics of monoclonal antibodies 5.9 and CHIR-12.12, as described herein above in Chapter I. These monoclonal antibodies, which can be recombinantly produced, are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety.

Antibodies that have the binding characteristics of monoclonal antibodies CHIR-5.9 and CHIR-12.12 include antibodies that competitively interfere with binding CD40 and/or bind the same epitopes as CHIR-5.9 and CHIR-12.12. One of skill in the art could determine whether an antibody competitively interferes with CHIR-5.9 or CHIR-12.12 using standard methods known in the art.

Thus, in addition to the monoclonal antibodies CHIR-5.9 and CHIR-12.12, other antibodies that would be useful in practicing the methods of the invention described herein in Chapter II include, but are not limited to, the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen. Those skilled in the art recognize that the antagonist anti-CD40 antibodies and antigen-binding fragments of these antibodies suitable for use in the methods disclosed herein include antagonist anti-CD40 antibodies and antigen-binding fragments thereof that are produced recombinantly using methods well known in the art and described herein below, and include, for example, monoclonal antibodies CHIR-5.9 and CHIR-12.12 that have been recombinantly produced.

Any of these antagonist anti-CD40 antibodies or antibody fragments thereof may be conjugated (e.g., labeled or conjugated to a therapeutic moiety or to a second antibody) prior to use in these methods for treating multiple myeloma in a human patient, as described herein above in Chapter I. Furthermore, suitable biologically variants of the antagonist anti-CD40 antibodies described elsewhere herein can be used in the methods of the present invention. Such variants, including those described herein above in Chapter I, will retain the desired binding properties of the parent antagonist anti-CD40 antibody. Methods for making antibody variants are generally available in the art; see, for example, the methods described herein above in Chapter I.

II. C. Methods of Therapy for Multiple Myeloma

Methods of the invention are directed to the use of antagonist anti-CD40 antibodies to treat subjects (i.e., patients) having multiple myeloma, where the cells of this cancer express the CD40 antigen. By "CD40-expressing multiple myeloma cell" is intended multiple myeloma cells that express the CD40 antigen. The successful treatment of multiple myeloma depends on how advanced the cancer is at the time of diagnosis, and whether the subject has or will undergo other methods of therapy in combination with anti-CD40 antibody administration.

A number of criteria can be used to classify stage of multiple myeloma. The methods of the present invention can be utilized to treatment multiple myelomas classified according to the Durie-Salmon classification system, which includes three stages. In accordance with this classification system, a subject having Stage I multiple myeloma has a low "M component," no sign of anemia or hypercalcemia, no bone lesions as revealed by X-rays, or only a single lesion. By "M component" is intended the presence of an overabundance of one immunoglobulin type. As multiple myeloma progresses, a subject develops a high M component of IgA or IgG antibodies, and low levels of other immunoglobulins. Stage II represents an intermediate condition, more advanced than Stage I but still lacking characteristics of Stage III. This third stage is reached where one or more of the following is detected: hypercalcemia, anemia, multiple bone lesions, or high M component.

The Durie-Salmon classification system can be combined with measurements of creatinine levels to provide a more accurate characterization of the state of the disease. Creatinine levels in multiple myeloma subjects are classified as "A" or "B" with a "B" result indicating a poorer prognosis than "A." "B" indicates high creatinine levels and failing kidney function. In this manner, a "Stage IA" case of multiple myeloma would indicate no anemia, hypercalcemia or other symptoms, combined with low creatinine levels. As a further means of assessing prognosis, these foregoing criteria can be utilized in combination with monitoring of the blood level of beta-2-microglobulin, which is produced by the multiple myeloma cells. High levels of the protein indicate that cancer cells are present in large numbers.

The methods of the present invention are applicable to treatment of multiple myeloma classified according to any of the foregoing criteria. Just as these criteria can be utilized to characterize progressive stages of the disease, these same criteria, i.e., anemia, hypercalcemia, creatinine level, and beta-2-microglobulin level, number of bone lesions, and M component, can be monitored to assess treatment efficacy.

"Treatment" is herein defined as the application or administration of an antagonist anti-CD40 antibody or antigen-binding fragment thereof to a subject, or application or administration of an antagonist anti-CD40 antibody or fragment thereof to an isolated tissue or cell line from a subject, where the subject has multiple myeloma, a symptom associated with multiple myeloma, or a predisposition toward development of multiple myeloma, where the purpose is to cure, heal, alleviate, relieve, alter, remedy, ameliorate, improve, or affect the multiple myeloma, any associated symptoms of multiple myeloma, or the predisposition toward the development of multiple myeloma. By "treatment" is also intended the application or administration of a pharmaceutical composition comprising the antagonist anti-CD40 antibodies or fragments thereof to a subject, or application or administration of a pharmaceutical composition comprising the anti-CD40 antibodies or fragments thereof to an isolated tissue or cell line from a subject, has multiple myeloma, a symptom associated with multiple myeloma, or a predisposition toward development of multiple myeloma, where the purpose is to cure, heal, alleviate, relieve, alter, remedy, ameliorate, improve, or affect the multiple myeloma, any associated symptoms of multiple myeloma, or the predisposition toward the development of multiple myeloma.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 antibody (or antigen-binding fragment thereof) causes a physiological response that is beneficial with respect to treatment of multiple myeloma, where the disease comprises cells expressing the CD40 antigen. It is recognized that the methods of the invention may be useful in preventing further proliferation and outgrowths of multiple myeloma cells arising during therapy.

In accordance with the methods of the present invention, at least one antagonist anti-CD40 antibody (or antigen-binding fragment thereof) as defined elsewhere herein is used to promote a positive therapeutic response with respect to treatment or prevention of multiple myeloma. By "positive therapeutic response" with respect to cancer treatment is intended an improvement in the disease in association with the anti-tumor activity of these antibodies or fragments thereof, and/or an improvement in the symptoms associated with the disease. That is, an anti-proliferative effect, the prevention of further tumor outgrowths, a reduction in tumor size, a reduction in the number of cancer cells, and/or a decrease in one or more symptoms mediated by stimulation of CD40-expressing cells can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bioluminescent imaging, for example, luciferase imaging, bone scan imaging, and tumor biopsy sampling including bone marrow aspiration (BMA). In addition to these positive therapeutic responses, the subject undergoing therapy with the antagonist anti-CD40 antibody or antigen-binding fragment thereof may experience the beneficial effect of an improvement in the symptoms associated with the disease.

By "therapeutically effective dose or amount" or "effective amount" is intended an amount of antagonist anti-CD40 antibody or antigen-binding fragment thereof that, when administered brings about a positive therapeutic response with respect to treatment of a subject with multiple myeloma. In some embodiments of the invention, a therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody or antigen-binding fragment thereof.

A further embodiment of the invention is the use of antagonist anti-CD40 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

The antagonist anti-CD40 antibodies can be used in combination with known chemotherapeutics, alone or in combination with bone marrow transplantation, radiation therapy, steroids, and interferon-alpha for the treatment of multiple myeloma. In this manner, the antagonist anti-CD40 antibodies described herein, or antigen-binding fragments thereof, are administered in combination with at least one other cancer therapy, including, but not limited to, radiation therapy, chemotherapy, interferon-alpha therapy, or steroid therapy, where the additional cancer therapy is administered prior to, during, or subsequent to the anti-CD40 antibody therapy. Thus, where the combined therapies comprise administration of an anti-CD40 antibody or antigen-binding fragment thereof in combination with administration of another therapeutic agent, as with chemotherapy, radiation therapy, or therapy with interferon-alpha and/or steroids, the methods of the invention encompass coadministration, using separate formulations or a single pharmaceutical formulation, and consecutive administration in either order, wherein preferably there is a time period where both (or all) active agents simultaneously exert their therapeutic activities. Where the methods of the present invention comprise combined therapeutic regimens, these therapies can be given simultaneously, i.e., the anti-CD40 antibody or antigen-binding fragment thereof is administered concurrently or within the same time frame as the other cancer therapy (i.e., the therapies are going on concurrently, but the anti-CD40 antibody or antigen-binding fragment thereof is not administered precisely at the same time as the other cancer therapy). Alternatively, the anti-CD40 antibody of the present invention or antigen-binding fragment thereof may also be administered prior to or subsequent to the other cancer therapy. Sequential administration of the different cancer therapies may be performed regardless of whether the treated subject responds to the first course of therapy to decrease the possibility of remission or relapse.

In some embodiments of the invention, the anti-CD40 antibodies described herein, or antigen-binding fragments thereof, are administered in combination with chemotherapy, and optionally in combination with autologous bone marrow transplantation, wherein the antibody and the chemotherapeutic agent(s) may be administered sequentially, in either order, or simultaneously (i.e., concurrently or within the same time frame). Examples of suitable chemotherapeutic agents include, but are not limited to, vincristine, BCNU, melphalan, cyclophosphamide, Adriamycin, and prednisone or dexamethasone.

Thus, for example, in one embodiment, the anti-CD40 antibody is administered in combination with melphalan, an alkylating drug, and the steroid prednisone (as referred to as MP). Alternatively, the alkylating medications cyclophosphamide and chlorambucil may be used instead of melphalan, in combination with steroids and the anti-CD40 antibodies of the invention. Where subjects have not responded to MP or its alternatives, and for subjects who relapse after MP treatment, the anti-CD40 antibodies of the invention can be administered in combination with a chemotherapy regimen that includes administration of vincristine, doxorubicin, and high-dose dexamethasone (also referred to as "VAD"), which may further include coadministration of cyclophosphamide. In other embodiments, the anti-CD40 antibodies can be used in combination with another agent having anti-angiogenic properties, such as thalidomide, or interferon-alpha. These later agents can be effective where a subject is resistant to MP and/or VAD therapy. In yet other embodiments, the anti-CD40 antibody can be administered in combination with a proteasome inhibitor such as bortezomib (Velcade™), where the latter is administered in subjects whose disease has relapsed after two prior treatments and who have demonstrated resistance to their last treatment. Alternatively, the anti-CD40 antibodies can be administered to a subject in combination with high dose chemotherapy, alone or with autologous bone marrow transplantation.

The anti-CD40 antibodies described herein can further be used to provide reagents, e.g., labeled antibodies that can be used, for example, to identify cells expressing CD40. This can be very useful in determining the cell type of an unknown sample. Panels of monoclonal antibodies can be used to identify tissue by species and/or by organ type. In a similar fashion, these anti-CD40 antibodies can be used to screen tissue culture cells for contamination (i.e., screen for the presence of a mixture of CD40-expressing and non-CD40 expressing cells in a culture).

II. D. Pharmaceutical Formulations and Modes of Administration

The antagonist anti-CD40 antibodies of this invention are administered at a concentration that is therapeutically effective to prevent or treat multiple myeloma. To accomplish this goal, the antibodies may be formulated using a variety of acceptable excipients known in the art, as noted herein above in Chapter I. Typically, the antibodies are administered by injection, either intravenously, intraperitoneally, or subcutaneously. Methods to accomplish this administration are known to those of ordinary skill in the art, and include those methods described hereinabove in Chapter I. It may also be possible to obtain compositions that may be topically or orally administered, or which may be capable of transmission across mucous membranes. Intravenous administration occurs preferably by infusion over a period of time, as described herein above in Chapter I. Possible routes of administration, preparation of suitable formulations, therapeutically effective amounts to be administered, and suitable dosing regimens are as described herein above in Chapter I. See also commonly owned U.S. Provisional Application No. 60/565,709, filed Apr. 26, 2004 and International Application No. PCT/US2004/037281, filed Nov. 4, 2004 and published as WO 2005/044855, which corresponds to copending U.S. National-Phase application Ser. No. 10/578,387, which published as U.S. Application Publication No. 2007-0218060; the contents of each of which are herein incorporated by reference in their entirety.

II. E. Use of Antagonist Anti-CD40 Antibodies in the Manufacture of Medicaments for Treating Multiple Myeloma The present invention also provides for the use of an antagonist anti-CD40 antibody or antigen-binding fragment thereof in the manufacture of a medicament for treating multiple myeloma in a subject, wherein the medicament is coordinated with treatment with at least one other cancer therapy. By "coordinated" is intended the medicament is to be used either prior to, during, or after treatment of the subject with at least one other cancer therapy.

Examples of other cancer therapies include, but are not limited to, surgery; radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy; IL-15 therapy, and IL-21 therapy; steroid therapy; or other cancer therapy; where treatment with the additional cancer therapy, or additional cancer therapies, occurs prior to, during, or subsequent to treatment of the subject with the medicament comprising the antagonist anti-CD40 antibody or antigen-binding fragment thereof, as noted herein above.

Thus, for example, in some embodiments, the invention provides for the use of the monoclonal antibody CHIR-12.12 or CHIR-5.9, or antigen-binding fragment thereof, in the manufacture of a medicament for treating multiple myeloma in a subject, wherein the medicament is coordinated with treatment with chemotherapy, where the chemotherapeutic agent is selected from the group consisting of vincristine, doxorubicin, BCNU, melphalan, cyclophosphamide, Adriamycin, and prednisone or dexamethasone. In one such embodiment, the chemotherapy is melphalan plus prednisone; in other embodiments, the chemotherapy is VAD (vincristine, doxorubicin, and dexamethasone).

In other embodiments, the invention provides for the use of the monoclonal antibody CHIR-12.12 or CHIR-5.9, or antigen-binding fragment thereof, in the manufacture of a medicament for treating multiple myeloma in a subject, wherein the medicament is coordinated with treatment with at least one other anti-cancer antibody selected from the group consisting of the fully human antibody HuMax-CD20, α-M-CSF antibody targeting macrophage colony stimulating factor; antibodies targeting the receptor activator of nuclear factor-kappaB (RANK) and its ligand (RANKL), which are over-expressed in multiple myeloma; anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of tumors of hematopoietic origin); and any combinations thereof; wherein the medicament is to be used either prior to, during, or after treatment of the subject with the other cancer therapy or, in the case of multiple combination therapies, either prior to, during, or after treatment of the subject with the other cancer therapies.

In yet other embodiments, the present invention provides for the use of the monoclonal antibody CHIR-12.12 or CHIR-5.9, or antigen-binding fragment thereof, in the manufacture of a medicament for treating multiple myeloma in a subject, wherein the medicament is coordinated with treatment with at least one other small molecule-based cancer therapy selected from the group consisting of Thalomid® (thalidomide), immunomodulatory derivatives of thalidomide (for example, revlimid (formerly revimid)), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide), and any combinations thereof; wherein the medicament is to be used either prior to, during, or after treatment of the subject with the other cancer therapy or, in the case of multiple combination therapies, either prior to, during, or after treatment of the subject with the other cancer therapies.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating a subject for multiple myeloma, wherein the medicament is used in a subject that has been pretreated with at least one other cancer therapy. By "pretreated" or "pretreatment" is intended the subject has received one or more other cancer therapies (i.e., been treated with at least one other cancer therapy) prior to receiving the medicament comprising the antagonist anti-CD40 antibody or antigen-binding fragment thereof. "Pretreated" or "pretreatment" includes subjects that have been treated with at least one other cancer therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior cancer therapy, or prior cancer therapies. Thus, the subject that receives the medicament comprising the antagonist anti-CD40 antibody or antigen-binding fragment thereof could have responded, or could have failed to respond (i.e. the cancer was refractory), to pretreatment with the prior cancer therapy, or to one or more of the prior cancer therapies where pretreatment comprised multiple cancer therapies. Examples of other cancer therapies for which a subject can have received pretreatment prior to receiving the medicament comprising the antagonist anti-CD40 antibody or antigen-binding fragment thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy, including, but not limited to, those anti-cancer antibodies listed herein above; small molecule-based cancer therapy, including, but not limited to, the small molecules listed herein above; vaccine/immunotherapy-based cancer therapies, including, but limited to, those listed herein above; steroid therapy; other cancer therapy; or any combination thereof.

"Treatment" in the context of coordinated use of a medicament described herein with one or more other cancer therapies is herein defined as the application or administration of the medicament or of the other cancer therapy to a subject, or application or administration of the medicament or other cancer therapy to an isolated tissue or cell line from a subject, where the subject has multiple myeloma, a symptom associated with such a cancer, or a predisposition toward development of such a cancer, where the purpose is to cure, heal, alleviate, relieve, alter, remedy, ameliorate, improve, or affect the cancer, any associated symptoms of the cancer, or the predisposition toward the development of the cancer.

The following examples for this invention are offered by way of illustration and not by way of limitation.

II. F. EXPERIMENTAL

The antagonist anti-CD40 antibodies used in the examples below are 5.9 and CHIR-12.12, described in Chapter I above, and in commonly owned U.S. Provisional Application No. 60/565,709, filed Apr. 26, 2004 and International Application No. PCT/US2004/037281, filed Nov. 4, 2004 and published as WO 2005/044855, which corresponds to copending U.S. National-Phase application Ser. No. 10/578,387, which published as U.S. Application Publication No. 2007-0218060; the contents of each of which are herein incorporated by reference in their entirety.

Studies are undertaken to determine if antagonist anti-CD40 mAbs 5.9 and CHIR-12.12 exhibit the following properties: (1) bind to multiple myeloma patient cells (as determined using flow cytometry); (2) promote cell death in multiple myeloma patient cells by blocking CD40-ligand induced survival signals; (3) have any stimulatory/inhibitory activity by themselves for multiple myeloma (MM) cells; and/or (4) mediate ADCC as a mode of action.

Example 1

Binding of mAbs 5.9 and CHIR-12.12 to $CD40^+$ Multiple Myeloma (MM) Cells from MM Patients FITC-labeled anti-CD40 mAb 5.9 and CHIR-12.12 are tested along with control FITC-labeled human IgG1 for staining of multiple myeloma (MM) cells. $CD40^+$ mM cells obtained from 8 patients are incubated with FITC-labeled anti-CD40 mAb 5.9 or CHIR-12.12, or FITC-labeled human IgG1. Flow cytometric analyses are performed with a FAC-SCAN V (Becton Dickinson, San Jose, Calif.).

Example 2

Anti-CD40 mAb 5.9 and CHIR-12.12 Block CD40-Ligand-Mediated Survival Signals in Multiple Myeloma (MM) Cells Multiple myeloma cells obtained from 8 patients are cultured separately with antagonist anti-CD40 mAb 5.9 or CHIR-12.12 and control human IgG1, under the following conditions:

| Antibody concentration (µg/ml) | MM cells | MM cells plus CD40-ligand expressing fixed CHO cells |
|---|---|---|
| 0 | + | − |
| 0 | + | + |
| 1.0 (anti-CD40) | + | + |
| 10.0 (anti-CD40) | + | + |
| 100.0 (anti-CD40) | + | + |
| 1.0 (control IgG) | + | + |
| 10.0 (control IgG) | + | + |
| 100.0 (control IgG) | + | + |

After 72 hours, the cultures are analyzed as follows:
Viable cell counts and measurement of cell death by staining with PI and Annexine V
Overnight pulse with tritiated thymidine to measure proliferation

Example 3

Assessment of Anti-CD40 mAb Stimulatory/Inhibitory Activity for Multiple Myeloma (MM) Cells Multiple myeloma cells from 8 patients are cultured under the following conditions in the presence of anti-CD40 mAb CHIR-12.12 or 5.9, using IgG as control:

| Antibodies concentration (μg/ml) | MM cells | MM cells plus CD40-ligand expressing fixed CHO cells |
|---|---|---|
| 0 | + | − |
| 0 | + | + |
| 1.0 (anti-CD40) | + | − |
| 10.0 (anti-CD40) | + | − |
| 100.0 (anti-CD40) | + | − |
| 1.0 (control IgG) | + | − |
| 10.0 (control IgG) | + | − |
| 100.0 (control IgG) | + | − |

After 72 hours, the cultures are analyzed as follows:
Viable cell counts and measurement of cell death by staining with PI and Annexine V
Overnight pulse with tritiated thymidine to measure proliferation Example 4

Ability of Anti-CD40 mAb CHIR-12.12 and 5.9 to Lyse Patient-Derived Multiple Myeloma (MM) Cells by Antibody-Dependent Cellular Cytotoxicity (ADCC)

Multiple myeloma cells obtained from 8 patients are cultured separately with antagonist anti-CD40 mAb 5.9 or CHIR-12.12 and control human IgG1, under the following conditions:

| Antibodies concentration (μg/ml) | $^{51}Cr$ or Calcein AM loaded MM cells with NK cells from healthy donor |
|---|---|
| 0 | + |
| 0.1 (anti-CD40) | + |
| 1.0 (anti-CD40) | + |
| 10.0 (anti-CD40) | + |
| 0.1 (control IgG) | + |
| 1.0 (control IgG) | + |
| 10.0 (control IgG) | + |
| 0.1 (rituximab) | + |
| 1.0 (rituximab) | + |
| 10.0 (rituximab) | + |

At 4 hours, specific cell lysis is calculated by measuring the levels of released $^{51}Cr$ or fluorescent dye.

Example 5

CHIR-12.12 Anti-Tumor Activity in Multiple Myeloma Animal Models

When administered intraperitoneally (i.p.) once a week for a total of 3 doses, CHIR-12.12 significantly inhibited the growth of aggressive staged and unstaged multiple myeloma in a dose-dependent manner. Efficacy could be further improved by combining the antibody therapy with bortezomib (VELCADE®) treatment.
IM-9 Multiple Myeloma Xenograft Models
SCID mice were inoculated subcutaneously with IM-9 tumor cells (a human multiple myeloma cell line expressing both CD40 and CD20) in 50% MATRIGEL™ at $5 \times 10^6$ cells per mouse. In unstaged models, treatment was initiated one day after tumor implantation. In staged models, treatment was initiated when tumor volume reached 150-200 mm³. Tumor-bearing mice were injected with anti-CD40 mAb intraperitoneally once a week at the indicated doses. Data were analyzed using the log-rank test.

In an unstaged conditional survival model, CHIR-12.12 significantly prolonged the survival of tumor-bearing mice in a dose-dependent manner with 60% survival in the 0.1 mg/kg CHIR-12.12 treated group and 80% survival in the 1 and 10 mg/kg CHIR-12.12 treated groups, respectively, on day 56 ($p<0.01$ and $p<0.001$, respectively) (data not shown). All animals in the control $IgG_1$ and bortezomib treated groups were euthanized between day 18 and day 26 due to disease related to tumor development.

Figure 14:
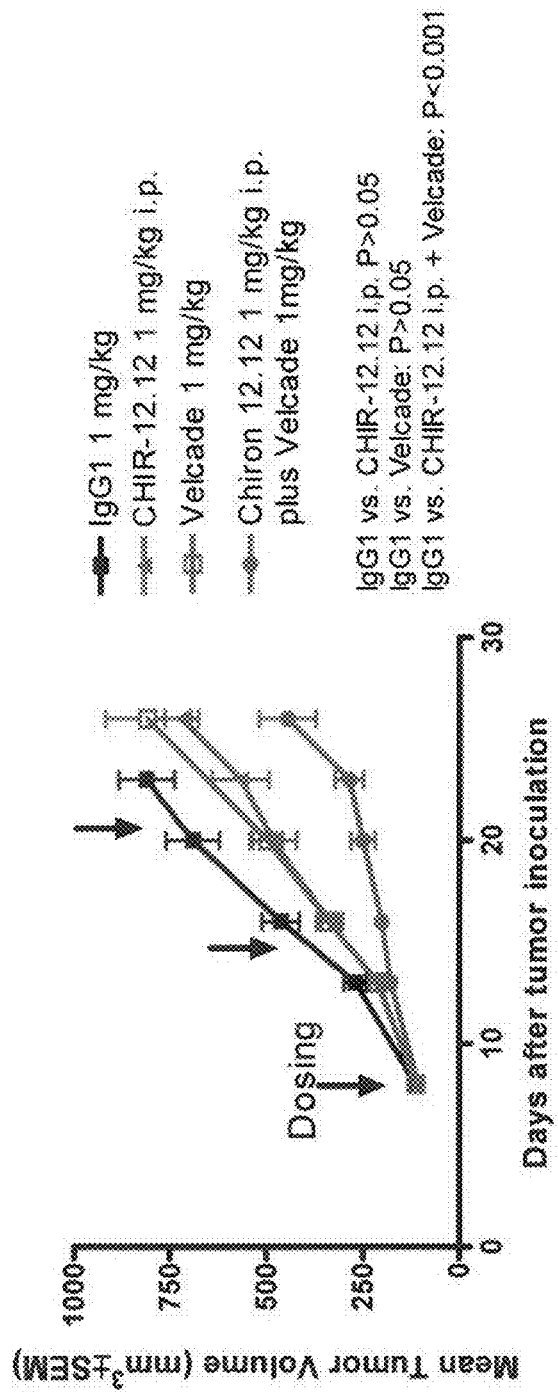
FIG. 14 demonstrates enhanced in vivo anti-tumor activity of combination treatment with the monoclonal antibody CHIR-12.12 and bortezomib (VELCADE®) using a human multiple myeloma IM-9 xenograft model.

In a staged subcutaneous model, CHIR-12.12 administered weekly at 0.1, 1 and 10 mg/kg significantly inhibited tumor growth with a tumor volume reduction of 17% ($p>0.05$; data not shown), 34% ($p<0.01$; FIG. 14) and 44% ($p<0.001$; data not shown) respectively. Bortezomib, when tested at 0.5 mg/kg twice a week did not inhibit tumor growth (data not shown). At the maximally tolerated dose (MTD) of 1 mg/kg twice a week, bortezomib inhibited tumor growth by 30% ($p<0.01$) as shown in FIG. 14. However, when CHIR-12.12 was administered weekly (1 mg/kg) in combination with the maximally tolerated dose of bortezomib, a tumor volume reduction of over 50% was observed ($p<0.001$).

In summary, the anti-CD40 mAb CHIR-12.12 significantly inhibited tumor growth in experimental multiple myeloma models. Further, combining CHIR-12.12 with bortezomib treatment further increases efficacy over any one single treatment. These data suggest that the anti-CD40 mAb CHIR-12.12 has potent anti-tumor activity and could be clinically effective for the treatment of multiple myeloma, either alone or in combination with other chemotherapeutic agents.

Example 6

Clinical Studies with 5.9 and CHIR-12.12

Clinical Objectives
The overall objective is to provide an effective therapy for multiple myeloma by targeting these cancer cells with an anti-CD40 IgG1. The signal for this disease is determined in phase II although some measure of activity may be obtained in phase I. Initially the agent is studied as a single agent, but will be combined with other agents, chemotherapeutics, and radiation therapy, as development proceeds.
Phase I
  Evaluate safety and pharmacokinetics—dose escalation in subjects with multiple myeloma.
  Choose dose based on safety, tolerability, and change in serum markers of CD40. In general an MTD is sought but other indications of efficacy (depletion of CD40+ multiple myeloma cells, etc.) may be adequate for dose finding.
  Consideration of more than one dose, as some dose finding may be necessary in phase II.
  Patients are dosed weekly with real-time pharmacokinetic (Pk) sampling. Initially a 4-week cycle is the maximum dosing allowed. The Pk may be highly variable depending on the disease state, density of CD40 etc.
  This trial(s) is open to subjects with multiple myeloma.
  Decision to discontinue or continue studies is based on safety, dose, and preliminary evidence of anti-tumor activity.

Activity of drug as determined by response rate is determined in Phase II.

Identify dose(s) for Phase II.

Phase II

Several trials will be initiated in subjects with multiple myeloma. More than one dose, and more than one schedule may be tested in a randomized phase II setting.

Target a multiple myeloma population that has failed current standard of care (chemotherapy failures)

Decision to discontinue or continue with study is based on proof of therapeutic concept in Phase II Determine whether surrogate marker can be used as early indication of clinical efficacy Identify doses for Phase III Phase III Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.

Chapter III: Use of Antagonist Anti-CD40 Monoclonal Antibodies for Treatment of Chronic Lymphocytic Leukemia

III. A. Overview

This aspect of the invention is directed to methods for treating human subjects having chronic lymphocytic leukemia, as described herein below in sections III.B-III.F and in commonly owned U.S. Provisional Application No. 60/611,794, filed Sep. 21, 2004 and International Application No. PCT/US2004/036954, filed Nov. 4, 2004 and published as WO 2005/044304, which corresponds to copending U.S. National-Phase application Ser. No. 10/577,642, which published as U.S. Application Publication No. 20070110754, all of which are entitled "Use of Antagonist Anti-CD40 Antibodies for Treatment of Chronic Lymphocytic Leukemia"; the contents of each of which are herein incorporated by reference in their entirety. The methods involve treatment with an anti-CD40 antibody described herein, or an antigen-binding fragment thereof, where administration of the antibody or antigen-binding fragment thereof promotes a positive therapeutic response within the subject undergoing this method of therapy to treat chronic lymphocytic leukemia.

III. B. Antagonist Anti-CD40 Antibodies for Use in Methods of Treating Chronic Lymphocytic Leukemia Anti-CD40 antibodies suitable for use in these methods of the invention specifically bind a human CD40 antigen expressed on the surface of a human cell and are free of significant agonist activity, but exhibit antagonist activity when bound to the CD40 antigen on a human CD40-expressing cell, as demonstrated for CD40-expressing normal and neoplastic human B cells. These anti-CD40 antibodies and antigen-binding fragments thereof are referred to herein as antagonist anti-CD40 antibodies. Such antibodies include, but are not limited to, the fully human monoclonal antibodies 5.9 and CHIR-12.12, and monoclonal antibodies having the binding characteristics of monoclonal antibodies 5.9 and CHIR-12.12, as described herein above in Chapter I. These monoclonal antibodies, which can be recombinantly produced, are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety. Antibodies that have the binding characteristics of monoclonal antibodies CHIR-5.9 and CHIR-12.12 include antibodies that competitively interfere with binding CD40 and/or bind the same epitopes as CHIR-5.9 and CHIR-12.12. One of skill in the art could determine whether an antibody competitively interferes with CHIR-5.9 or CHIR-12.12 using standard methods known in the art.

Thus, in addition to the monoclonal antibodies CHIR-5.9 and CHIR-12.12, other antibodies that would be useful in practicing the methods of the invention described herein in Chapter II include, but are not limited to, the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen. Those skilled in the art recognize that the antagonist anti-CD40 antibodies and antigen-binding fragments of these antibodies suitable for use in the methods disclosed herein include antagonist anti-CD40 antibodies and antigen-binding fragments thereof that are produced recombinantly using methods well known in the art and described herein below, and include, for example, monoclonal antibodies CHIR-5.9 and CHIR-12.12 that have been recombinantly produced.

Any of these antagonist anti-CD40 antibodies or antibody fragments thereof may be conjugated (e.g., labeled or conjugated to a therapeutic moiety or to a second antibody) prior to use in these methods for treating chronic lymphocytic leukemia in a human patient, as described herein above in Chapter I. Furthermore, suitable biologically variants of the antagonist anti-CD40 antibodies described elsewhere herein can be used in the methods of the present invention. Such variants, including those described herein above in Chapter I, will retain the desired binding properties of the parent antagonist anti-CD40 antibody. Methods for making antibody variants are generally available in the art; see, for example, the methods described herein above in Chapter I.

III. C. Methods of Therapy for CLL

Methods of the invention are directed to the use of antagonist anti-CD40 antibodies to treat subjects (i.e., patients) having chronic lymphocytic leukemia (CLL), where the cells of this cancer express the CD40 antigen. By "CD40-expressing chronic lymphocytic leukemia cell" is intended CLL cells that express the CD40 antigen. The successful treatment of CLL depends on how advanced the cancer is at the time of diagnosis, and whether the subject has or will undergo other methods of therapy in combination with anti-CD40 antibody administration. Methods for detecting CD40 expression in cells are well known in the art and include, but are not limited to, PCR techniques, immunohistochemistry, flow cytometry, Western blot, ELISA, and the like.

A number of criteria can be used to classify stage of CLL. The methods of the present invention can be utilized to treat CLLs classified according to the Rai-Binet classification system. In the Rai system, there are five stages: stage 0 wherein only lymphocytosis is present; stage I wherein lymphadenopathy is present; stage II wherein splenomegaly, lymphadenopathy, or both are present; stage III wherein anemia, organomegaly, or both are present (progression is defined by weight loss, fatigue, fever, massive organomegaly, and a rapidly increasing lymphocyte count); and stage IV wherein anemia, thrombocytopenia, organomegaly, or a combination thereof are present. Under the Binet staging system there are only three categories: stage A wherein lymphocytosis is present and less than three lymph nodes are enlarged (this stage is inclusive of all Rai stage 0 patients, one-half of Rai stage I patients, and one-third of Rai stage II patients); stage B wherein three or more lymph nodes are involved; and stage C wherein anemia or thrombocytopenia, or both are present. The Rai-Binet classification system can be combined with measurements of mutation of the immunoglobulin genes to provide a more accurate characterization of the state of the disease. The presence of mutated immunoglobulin genes correlates to improved prognosis.

The methods of the present invention are applicable to treatment of CLL classified according to any of the foregoing criteria. Just as these criteria can be utilized to characterize progressive stages of the disease, these same criteria, i.e., anemia, lymphadenopathy, organomegaly, thrombocytopenia, and immunoglobulin gene mutation, can be monitored to assess treatment efficacy.

"Treatment" is herein defined as the application or administration of an antagonist anti-CD40 antibody or antigen-binding fragment thereof to a subject, or application or administration of an antagonist anti-CD40 antibody or antigen-binding fragment thereof to an isolated tissue or cell line from a subject, where the subject has CLL, a symptom associated with CLL, or a predisposition toward development of CLL, where the purpose is to cure, heal, alleviate, relieve, alter, remedy, ameliorate, improve, or affect the CLL, any associated symptoms of CLL, or the predisposition toward the development of CLL. By "treatment" is also intended the application or administration of a pharmaceutical composition comprising an antagonist anti-CD40 antibodies or antigen-binding fragment thereof to a subject, or application or administration of a pharmaceutical composition comprising an antagonist anti-CD40 antibody or antigen-binding fragment thereof to an isolated tissue or cell line from a subject, where the subject has CLL, a symptom associated with CLL, or a predisposition toward development of CLL, where the purpose is to cure, heal, alleviate, relieve, alter, remedy, ameliorate, improve, or affect the CLL, any associated symptoms of CLL, or the predisposition toward the development of CLL.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 antibody (or antigen-binding fragment thereof) causes a physiological response that is beneficial with respect to treatment of CLL, where the disease comprises cells expressing the CD40 antigen. It is recognized that the methods of the invention may be useful in preventing further proliferation and outgrowths of CLL cells arising during therapy.

In accordance with the methods of the present invention, at least one antagonist anti-CD40 antibody (or antigen-binding fragment thereof) as defined elsewhere herein is used to promote a positive therapeutic response with respect to treatment or prevention of CLL. By "positive therapeutic response" with respect to cancer treatment is intended an improvement in the disease in association with the anti-tumor activity of these antibodies or antigen-binding fragments thereof, and/or an improvement in the symptoms associated with the disease. That is, an anti-proliferative effect, the prevention of further tumor outgrowths, a reduction in tumor size, a reduction in the number of cancer (i.e., neoplastic) cells, an increase in neoplastic cell death, inhibition of neoplastic cell survival, an increased patient survival rate, and/or a decrease in one or more symptoms mediated by stimulation of CD40-expressing cells can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, flow cytometry or fluorescence-activated cell sorter (FACS) analysis, bioluminescent imaging, for example, luciferase imaging, bone scan imaging, and tumor biopsy sampling including bone marrow aspiration (BMA). In addition to these positive therapeutic responses, the subject undergoing therapy with the antagonist anti-CD40 antibody or antigen-binding fragment thereof may experience the beneficial effect of an improvement in the symptoms associated with the disease.

By "therapeutically effective dose or amount" or "effective amount" is intended an amount of antagonist anti-CD40 antibody or antigen-binding fragment thereof that, when administered brings about a positive therapeutic response with respect to treatment of a subject with CLL. In some embodiments of the invention, a therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody or antigen-binding fragment thereof.

A further embodiment of the invention is the use of antagonist anti-CD40 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

The antagonist anti-CD40 antibodies can be used in combination with known chemotherapeutics, alone or in combination with surgery or surgical procedures (e.g. splenectomy, hepatectomy, lymphadenectomy, leukophoresis, bone marrow transplantation, and the like), radiation therapy, chemotherapy, other anti-cancer monoclonal antibody therapy, steroids, IL-2 therapy, and interferon-alpha for the treatment of CLL. In this manner, the antagonist anti-CD40 antibodies described herein, or antigen-binding fragments thereof, are administered in combination with at least one other cancer therapy, including, but not limited to, surgery, radiation therapy, chemotherapy, other anti-cancer monoclonal antibody therapy (for example, alemtuzumab (Campath®), targeting the CD52 cell surface antigen on malignant B cells; rituximab (Rituxan®), targeting the CD20 cell surface antigen on malignant B cells, or other therapeutic anti-CD20 antibody, for example, the fully human antibody HuMax-CD20, R-1594, IMMU-106, TRU-015, AME-133, tositumomab/I-131 tositumomab (Bexxar®), ibritumomab tiuxetan (Zevalin®); or anti-CD23 antibody targeting the CD23 antigen on malignant B cells); interferon-alpha therapy, interleukin-2 (IL-2) therapy, therapy with IL-12, IL-15, or IL-21, or steroid therapy, where the additional cancer therapy is administered prior to, during, or subsequent to the anti-CD40 antibody therapy. Thus, where the combined therapies comprise administration of an anti-CD40 antibody or antigen-binding fragment thereof in combination with administration of another therapeutic agent, as with chemotherapy, radiation therapy, or therapy with interferon-alpha, IL-2, and/or steroids, the methods of the invention encompass coadministration, using separate formulations or a single pharmaceutical formulation, and consecutive administration in either order. Where the methods of the present invention comprise combined therapeutic regimens, these therapies can be given simultaneously, i.e., the anti-CD40 antibody or antigen-binding fragment thereof is administered concurrently or within the same time frame as the other cancer therapy (i.e., the therapies are going on concurrently, but the anti-CD40 antibody or antigen-binding fragment thereof is not administered precisely at the same time as the other cancer therapy). Alternatively, the anti-CD40 antibody of the present invention or antigen-binding fragment thereof may also be administered prior to or subsequent to the other cancer therapy. Sequential administration of the different cancer therapies may be performed regardless of whether the treated subject responds to the first course of therapy to decrease the possibility of remission or relapse. Where the combined therapies comprise administration of the anti-CD40 antibody or antigen-binding fragment thereof in combination with administration of a cytotoxic agent, preferably the anti-CD40 antibody or antigen-binding fragment thereof is administered prior to administering the cytotoxic agent.

In some embodiments of the invention, the antagonist anti-CD40 antibodies described herein, or antigen-binding fragments thereof, are administered in combination with chemotherapy, and optionally in combination with autologous bone marrow transplantation, wherein the antibody and the chemotherapeutic agent(s) may be administered sequentially, in either order, or simultaneously (i.e., concurrently or within the same time frame). Examples of suitable chemotherapeutic agents include, but are not limited to, fludarabine, chlorambucil, vincristine, pentostatin, 2-chlorodeoxyadenosine (cladribine), cyclophosphamide, doxorubicin, and prednisone.

Thus, for example, in some embodiments, the antagonist anti-CD40 antibody, for example, the monoclonal antibody CHIR-12.12 or CHIR-5.9 or antigen-binding fragment thereof, is administered in combination with fludarabine. In one such embodiment, the antagonist anti-CD40 antibody is administered prior to administration of fludarabine. In alternative embodiments, the antagonist anti-CD40 antibody is administered after treatment with fludarabine. In yet other embodiments, the fludarabine is administered simultaneously with the antagonist anti-CD40 antibody.

In other embodiments of the invention, chlorambucil, an alkylating drug, is administered in combination with an antagonist anti-CD40 antibody described herein, for example, the monoclonal antibody CHIR-12.12 or CHIR-5.9 or an antigen-binding fragment thereof. In one such embodiment, the antagonist anti-CD40 antibody is administered prior to administration of chlorambucil. In alternative embodiments, the antagonist anti-CD40 antibody is administered after treatment with chlorambucil. In yet other embodiments, the chlorambucil is administered simultaneously with the antagonist anti-CD40 antibody.

In yet other embodiments, anthracycline-containing regimens such as CAP (cyclophosphamide, doxorubicin plus prednisone) and CHOP (cyclophosphamide, vincristine, prednisone plus doxorubicin) may be combined with administration of an antagonist anti-CD40 antibody described herein, for example, the monoclonal antibody CHIR-12.12 or CHIR-5.9 or an antigen-binding fragment thereof. In one such embodiment, the antagonist anti-CD40 antibody is administered prior to administration of anthracycline-containing regimens. In other embodiments, the antagonist anti-CD40 antibody is administered after treatment with anthracycline-containing regimens. In yet other embodiments, the anthracycline-containing regimen is administered simultaneously with the antagonist anti-CD40 antibody.

In alternative embodiments, an antagonist anti-CD40 antibody described herein, for example, the monoclonal antibody CHIR-12.12 or CHIR-5.9 or an antigen-binding fragment thereof, is administered in combination with alemtuzumab (Campath®; distributed by Berlex Laboratories, Richmond, Calif.). Alemtuzumab is a recombinant humanized monoclonal antibody (Campath-1H) that targets the CD52 antigen expressed on malignant B cells. In one such embodiment, the antagonist anti-CD40 antibody is administered prior to administration of alemtuzumab. In other embodiments, the antagonist anti-CD40 antibody is administered after treatment with alemtuzumab. In yet other embodiments, the alemtuzumab is administered simultaneously with the antagonist anti-CD40 antibody.

In other embodiments, the antagonist anti-CD40 antibodies described herein, for example, the monoclonal antibody CHIR-12.12 or CHIR-5.9 or antigen-binding fragment thereof, can be used in combination with another agent that has anti-angiogenic properties, such as thalidomide, or interferon-alpha. These latter agents can be effective where a subject is resistant to first-line therapy. Alternatively, the antagonist anti-CD40 antibodies can be administered to a subject in combination with high dose chemotherapy, alone or with autologous bone marrow transplantation.

In alternative embodiments, an antagonist anti-CD40 antibody described herein, for example, the monoclonal antibody CHIR-12.12 or CHIR-5.9 or an antigen-binding fragment thereof, can be used in combination with other immunotherapeutic agents, notably IL-2. IL-2, an agent known to expand the number of natural killer (NK) effector cells in treated patients, can be administered prior to, or concomitantly with, the antagonist anti-CD40 antibody of the invention. This expanded number of NK effector cells may lead to enhanced ADCC activity of the administered antagonist anti-CD40 antibody.

Further, combination therapy with two or more therapeutic agents and an antagonist anti-CD40 antibody described herein can also be used for treatment of CLL. Without being limiting, examples include triple combination therapy, where two chemotherapeutic agents are administered in combination with an antagonist anti-CD40 antibody described herein, and where a chemotherapeutic agent and another anti-cancer monoclonal antibody (for example, alemtuzumab; rituximab or other anti-CD20 antibody, for example, the fully human antibody HuMax-CD20, R-1594, IMMU-106, TRU-015, AME-133, tositumomab/I-131 tositumomab (Bexxar®), ibritumomab tiuxetan (Zevalin®); or anti-CD23 antibody) are administered in combination with an antagonist anti-CD40 antibody described herein. Examples of such combinations include, but are not limited to, combinations of fludarabine, cyclophosphamide, and the antagonist anti-CD40 antibody, for example, the monoclonal antibody CHIR-12.12 or CHIR-5.9 or an antigen-binding fragment thereof; and combinations of fludarabine, an anti-CD20 antibody, for example, rituximab (Rituxan®; IDEC Pharmaceuticals Corp., San Diego, Calif.), and the antagonist anti-CD40 antibody, for example, the monoclonal antibody CHIR-12.12 or CHIR-5.9 or an antigen-binding fragment thereof.

III. D. Pharmaceutical Formulations and Modes of Administration

The antagonist anti-CD40 antibodies of this invention are administered at a concentration that is therapeutically effective to prevent or treat chronic lymphocytic leukemia. To accomplish this goal, the antibodies may be formulated using a variety of acceptable excipients known in the art, as noted herein above in Chapter I. Typically, the antibodies are administered by injection, either intravenously, intraperitoneally, or subcutaneously. Methods to accomplish this administration are known to those of ordinary skill in the art, and include those methods described hereinabove in Chapter I. It may also be possible to obtain compositions that may be topically or orally administered, or which may be capable of transmission across mucous membranes. Intravenous administration occurs preferably by infusion over a period of time, as described herein above in Chapter I. Possible routes of administration, preparation of suitable formulations, therapeutically effective amounts to be administered, and suitable dosing regimens are as described herein above in Chapter I. See also commonly owned U.S. Provisional Application No. 60/611,794, filed Sep. 21, 2004 and International Application No. PCT/US2004/036954, filed Nov. 4, 2004 and published as WO 2005/044304, which corresponds to copending U.S. National-Phase application Ser. No. 10/577,642, which published as U.S. Application Publication No. 20070110754; the contents of each of which are herein incorporated by reference in their entirety.

III. E. Use of Antagonist Anti-CD40 Antibodies in the Manufacture of Medicaments for Treating CLL The present invention also provides for the use of an antagonist anti-CD40 antibody or antigen-binding fragment thereof in the manufacture of a medicament for treating CLL in a subject, wherein the medicament is coordinated with treatment with at least one other cancer therapy. By "coordinated" is intended the medicament is to be used either prior to, during, or after treatment of the subject with at least one other cancer therapy. Examples of other cancer therapies include, but are not limited to, those described herein above, i.e., surgery; radiation therapy; chemotherapy, optionally in combination with autologous bone marrow transplant, where Examples of other cancer therapies include, but are not limited to, surgery; radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL); anti-CD23 antibody targeting the CD23 antigen on malignant B cells (for example, IDEC-152); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) expressed on a number of tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy; IL-15 therapy, and IL-21 therapy; steroid therapy; or other cancer therapy; where treatment with the additional cancer therapy, or additional cancer therapies, occurs prior to, during, or subsequent to treatment of the subject with the medicament comprising the antagonist anti-CD40 antibody or antigen-binding fragment thereof, as noted herein above. In one such embodiment, the present invention provides for the use of the monoclonal antibody CHIR-12.12 or CHIR-5.9 in the manufacture of a medicament for treating CLL in a subject, wherein the medicament is coordinated with treatment with at least one other cancer therapy as noted herein above.

Thus, for example, in some embodiments, the invention provides for the use of the monoclonal antibody CHIR-12.12 or CHIR-5.9, or antigen-binding fragment thereof, in the manufacture of a medicament for treating CLL in a subject, wherein the medicament is coordinated with treatment with chemotherapy, where the chemotherapy is selected from the group consisting of fludarabine, chlorambucil, vincristine, pentostatin, 2-chlorodeoxyadenosine (cladribine), cyclophosphamide, doxorubicin, and prednisone, and anthracycline-containing regimens such as CAP (cyclophosphamide, doxorubicin plus prednisone) and CHOP (cyclophosphamide, vincristine, prednisone plus doxorubicin), and any combinations thereof; wherein the medicament is to be used either prior to, during, or after treatment of the subject with the other cancer therapy or, in the case of multiple combination therapies, either prior to, during, or after treatment of the subject with the other cancer therapies.

In other embodiments, the invention provides for the use of the monoclonal antibody CHIR-12.12 or CHIR-5.9, or antigen-binding fragment thereof, in the manufacture of a medicament for treating multiple myeloma in a subject, wherein the medicament is coordinated with treatment with at least one other anti-cancer antibody selected from the group consisting of alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/I-131 tositumomab (Bexxar®), ibritumomab tiuxetan (Zevalin®), or any other therapeutic anti-CD20 antibody targeting the CD20 antigen on malignant B cells; anti-CD23 antibody targeting the CD23 antigen on malignant B cells (for example, IDEC-152); and anti-CD22 antibody targeting the CD22 antigen on malignant B cells (for example, the monoclonal antibody BL-22, an alphaCD22 toxin), and any combinations thereof; wherein the medicament is to be used either prior to, during, or after treatment of the subject with the other cancer therapy or, in the case of multiple combination therapies, either prior to, during, or after treatment of the subject with the other cancer therapies.

In yet other embodiments, the present invention provides for the use of the monoclonal antibody CHIR-12.12 or CHIR-5.9, or antigen-binding fragment thereof, in the manufacture of a medicament for treating CLL in a subject, wherein the medicament is coordinated with treatment with at least one other small molecule-based cancer therapy selected from the group consisting of SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule inhibitors of histone deacetylases (for example, hybrid/polar cytodifferentiation HPC) agents such as suberanilohydroxamic acid (SAHA), and FR-901228), and any combinations thereof; or with other cancer therapy, for example, CD154 gene immunization (for example, ISF-154); wherein the medicament is to be used either prior to, during, or after treatment of the subject with the other cancer therapy or, in the case of multiple combination therapies, either prior to, during, or after treatment of the subject with the other cancer therapies.

In some embodiments, the medicament comprising the antagonist anti-CD40 antibody, for example, the monoclonal antibody CHIR-12.12 or CHIR-5.9 disclosed herein, or antigen-binding fragment thereof is coordinated with treatment with two other cancer therapies. Without being limiting, examples include coordination of the medicament with treatment with two chemotherapeutic agents, for example, coordination with treatment with fludarabine and cyclophosphamide; and coordination of the medicament with treatment with a chemotherapeutic agent, for example, fludarabine, and another anti-cancer monoclonal antibody, for example, alemtuzumab, rituximab or other anti-CD20 antibody including the fully human antibody HuMax-CD20, R-1594, IMMU- 106, TRU-015, AME-133, tositumomab/I-131 tositumomab (Bexxar®), and ibritumomab tiuxetan (Zevalin®), or anti-CD23 antibody. Where the medicament comprising the antagonist anti-CD40 antibody is coordinated with two other cancer therapies, use of the medicament can be prior to, during, or after treatment of the subject with either or both of the other cancer therapies.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating CLL in a subject, wherein the medicament is used in a subject that has been pretreated with at least one other cancer therapy. By "pretreated" or "pretreatment" is intended the subject has been treated with one or more other cancer therapies prior to receiving the medicament comprising the antagonist anti-CD40 antibody or antigen-binding fragment thereof. "Pretreated" or "pretreatment" includes subjects that have been treated with the other cancer therapy, or other cancer therapies, within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior cancer therapy, or prior cancer therapies. Thus, the subject that receives the medicament comprising the antagonist anti-CD40 antibody or antigen-binding fragment thereof could have responded, or could have failed to respond, to pretreatment with the prior cancer therapy, or to one or more of the prior cancer therapies where pretreatment comprised multiple cancer therapies, for example, surgery and chemotherapy; surgery and other anti-cancer antibody therapy; chemotherapy and other anti-cancer antibody therapy; or surgery, chemotherapy, and other anti-cancer antibody therapy.

Thus, in some embodiments, the invention provides for the use of an antagonist anti-CD40 antibody, for example the monoclonal antibody CHIR-12.12 or CHIR-5.9 disclosed herein, or antigen-binding fragment thereof in the manufacture of a medicament that is used in a subject in need of treatment for CLL, where the subject has been pretreated with one or more of the following other cancer therapies: surgery; radiation therapy; chemotherapy, optionally in combination with autologous bone marrow transplant, where suitable chemotherapeutic agents include, but are not limited to, fludarabine, chlorambucil, cladrabine, vincristine, pentostatin, 2-chlorodeoxyadenosine, cyclophosphamide, doxorubicin, prednisone, and combinations thereof, for example, anthracycline-containing regimens such as CAP (cyclophosphamide, doxorubicin plus prednisone) and CHOP (cyclophosphamide, vincristine, prednisone plus doxorubicin); other anti-cancer monoclonal antibody therapy (for example, alemtuzumab (Campath®); rituximab (Rituxan®) or any other therapeutic anti-CD20 antibody; or anti-CD23 antibody targeting the CD23 antigen on malignant B cells); interferon-alpha therapy; interleukin-2 (IL-2) therapy; therapy with IL-12, IL-15, or IL-21; or steroid therapy.

"Treatment" in the context of coordinated use of a medicament described herein with one or more other cancer therapies is herein defined as the application or administration of the medicament or of the other cancer therapy to a subject, or application or administration of the medicament or other cancer therapy to an isolated tissue or cell line from a subject, where the subject has chronic lymphocytic leukemia, a symptom associated with such a cancer, or a predisposition toward development of such a cancer, where the purpose is to cure, heal, alleviate, relieve, alter, remedy, ameliorate, improve, or affect the cancer, any associated symptoms of the cancer, or the predisposition toward the development of the cancer.

The following examples for this invention are offered by way of illustration and not by way of limitation.

III. F. EXPERIMENTAL

Introduction

The antagonist anti-CD40 antibodies used in the examples below are CHIR-5.9 and CHIR-12.12, described in Chapter I above, and in commonly owned U.S. Provisional Application No. 60/611,794, filed Sep. 21, 2004 and International Application No. PCT/US2004/036954, filed Nov. 4, 2004 and published as WO 2005/044304, which corresponds to copending U.S. National-Phase application Ser. No. 10/577,642, which published as U.S. Application Publication No. 20070110754; the contents of each of which are herein incorporated by reference in their entirety.

B-cell chronic lymphocytic leukemia (CLL) is characterized by in vivo accumulation of long-lived $CD5^+$ B cells. However, when cultured in vitro, CLL cells die quickly by apoptosis. Protection from apoptosis in vivo is believed to result from supply of survival signals from the microenvironment. CD40 stimulation of CLL cells by CD40-ligand is identified to be one such survival signal.

The following studies were undertaken to determine if antagonist anti-CD40 mAbs CHIR-5.9 and CHIR-12.12 exhibit the following properties: (1) bind to chronic lymphocytic leukemia (CLL) patient cells; (2) promote cell death in CLL patient cells by blocking CD40-ligand induced survival signals; (3) have any stimulatory/inhibitory activity by themselves for chronic lymphocytic leukemia (CLL) cells; and/or (4) mediate ADCC as a mode of action.

Example 1

CHIR-5.9 and CHIR-12.12 can Block CD40-Mediated Survival and Proliferation of Cancer Cells from CLL Patients The candidate antibodies can block CD40-mediated survival and proliferation of cancer cells from CLL patients. CLL cells from patients were cultured in suspension over CD40L-expressing formaldehyde-fixed CHO cells under two different conditions: addition of human isotype antibody IgG (control); and addition of either CHIR-5.9 or CHIR-12.12 monoclonal antibody. All antibodies were added at concentrations of 1, 10, and 100 μg/mL in the absence of IL-4. The cell counts were performed at 24 and 48 h by MTS assay. Reduced numbers of cells were recovered from CHIR-5.9-(n=6) and CHIR-12.12-(n=2) treated cultures compared to control group. The greater differences in cell numbers between anti-CD40 mAb-treated and control antibody-treated cultures were seen at the 48-h time point. These data are summarized in Table 1.

TABLE 1

The effect of candidate antibodies on CD40-induced survival and proliferation of cancer cells from CLL patients measured at 48 h after the culture initiation

| Patient# | Ab conc (µg/ml) | Relative cell numbers IgG1 | CHIR-5.9/5.11 | CHIR-12.12 | % reduction in cell numbers* CHIR-5.9/5.11 | CHIR-12.12 |
|---|---|---|---|---|---|---|
| 1 | 1 | 269.31 | 25.27 | ND | 90.62 | ND |
|   | 10 | 101.58 | 33.07 | ND | 67.44 | ND |
|   | 100 | 130.71 | 40.16 | ND | 69.28 | ND |
| 2 | 1 | 265.55 | 75.8 | ND | 71.46 | ND |
|   | 10 | 227.57 | 128.5 | ND | 43.53 | ND |
|   | 100 | 265.99 | 6.4 | ND | 97.59 | ND |
| 3 | 1 | 85.9 | 35.39 | ND | 58.80 | ND |
|   | 10 | 70.44 | 39.51 | ND | 43.91 | ND |
|   | 100 | 77.65 | 20.95 | ND | 73.02 | ND |
| 4 | 1 | 80.48 | 15.03 | ND | 81.32 | ND |
|   | 10 | 63.01 | 19.51 | ND | 69.04 | ND |
|   | 100 | 55.69 | 3.65 | ND | 93.45 | ND |
| 5 | 1 | 90.63 | 91.66 | 89.59 | −1.14 | 1.15 |
|   | 10 | 78.13 | 82.28 | 60.41 | −5.31 | 22.68 |
|   | 100 | 63.53 | 86.47 | 39.59 | −36.11 | 37.68 |
| 6 | 1 | 130.21 | 77.6 | 71.88 | 40.40 | 44.80 |
|   | 10 | 131.77 | 78.13 | 73.96 | 40.71 | 43.87 |
|   | 100 | 127.08 | 76.56 | 82.29 | 39.75 | 35.25 |

*% reduction compared to control Abs = 100 − (test Abs/control Abs)*100

Figures 15A, 15B:
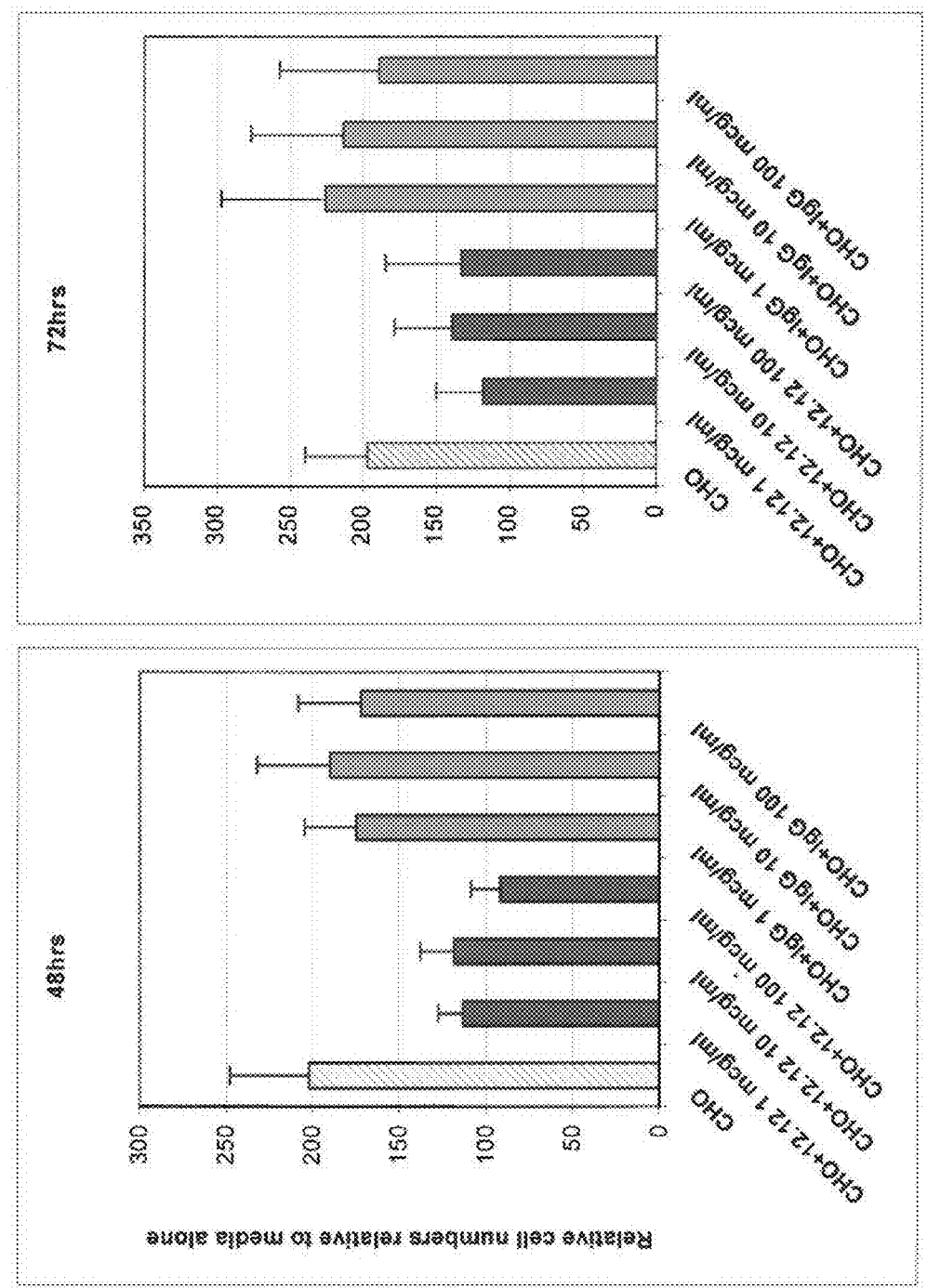
FIG. 15 shows that monoclonal antibody CHIR-12.12 inhibits CD40L-mediated proliferation of cancer cells from patients with CLL(n=9) at 48 h (FIG. 15A) and 72 h (FIG. 15B).

A second study revealed similar results. In this study, primary CLL cells from 9 patients were cultured in suspension over CD40L-expressing formaldehyde-fixed CHO cells in the presence or absence of 1, 10, or 100 µg/ml anti-CD40 mAb CHIR-12.12 in a manner described above, using nonspecific IgG as the control. After 48 and 72 hours, proliferation of the cultures was measured as noted above. In the absence of anti-CD40 mAb CHIR-12.12, the primary CLL cells either resisted spontaneous cell death or proliferated. This effect was inhibited in the presence of mAb CHIR-12.12, which restored CLL cell death. Thus, these results demonstrate inhibition of CD40-induced CLL cell proliferation by the anti-CD40 mAb CHIR-12.12 at both 48 and 72 hours. See FIGS. 15A and 15B.

Figures 16A, 16B:
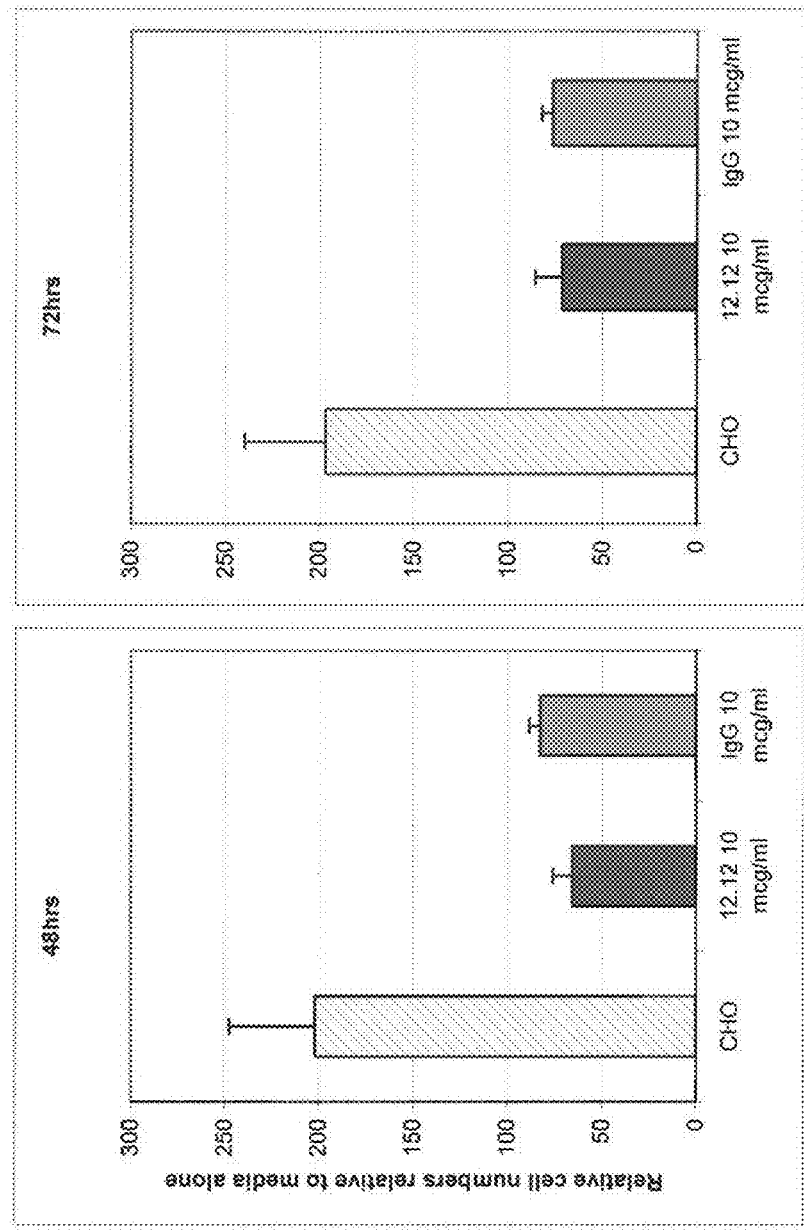
FIG. 16 shows that monoclonal antibody CHIR-12.12 does not have a stimulatory effect on CLL patient cells (n=9) at 48 h (FIG. 16A) and 72 h (FIG. 16B).

Similar experiments were performed on unstimulated CLL cells in the presence of mAb CHIR-12.12 alone. The mAb CHIR-12.12 (10 µg/ml) alone did not induce CLL proliferation and thus did not have a stimulatory effect on CLL cells as compared to control IgG (10 µg/ml) at 48 and 72 hours. See FIGS. 16A and 16B.

Example 2

Ability of Anti-CD40 mAb CHIR-12.12 to Lyse Chronic Lymphocytic Leukemia (CLL) Cell Lines by Antibody-Dependent Cellular Cytotoxicity (ADCC)

The CLL cell line EHEB was cultured with antagonist anti-CD40 mAb CHIR-12.12 or the anti-CD20 antibody Rituxan® (IDEC Pharmaceuticals Corp., San Diego, Calif.) and freshly isolated human NK cells from normal volunteer blood donors as effector cells. The percent specific lysis was measured based on the release of marker from target cells.

Figure 17:
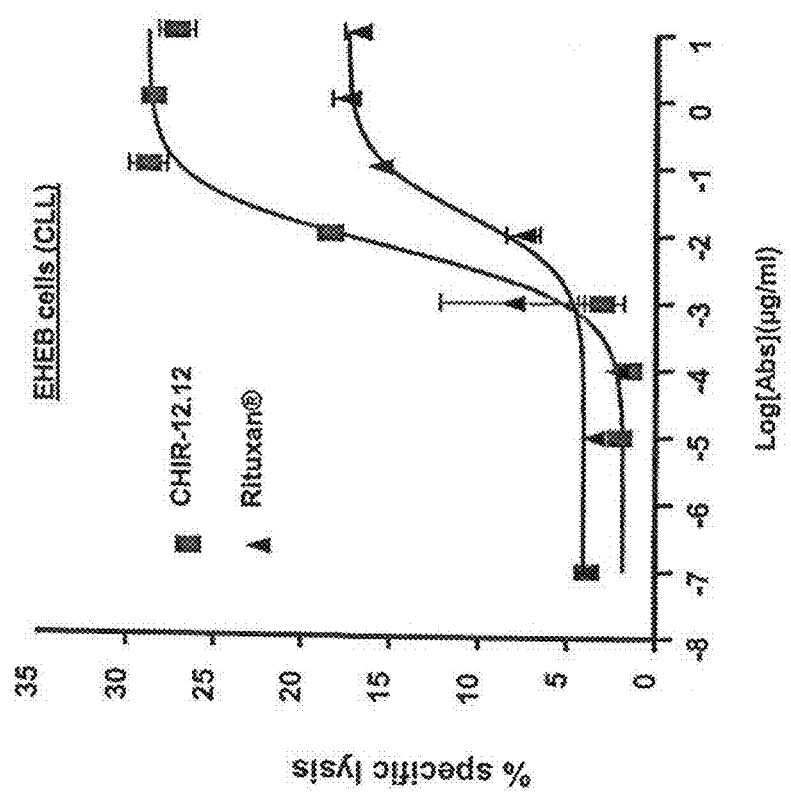
FIG. 17 shows more efficient ADCC-mediated cell lysis of CLL cell line EHEB by monoclonal antibody CHIR-12.12 versus the monoclonal antibody Rituxan®.
Figure 18C:
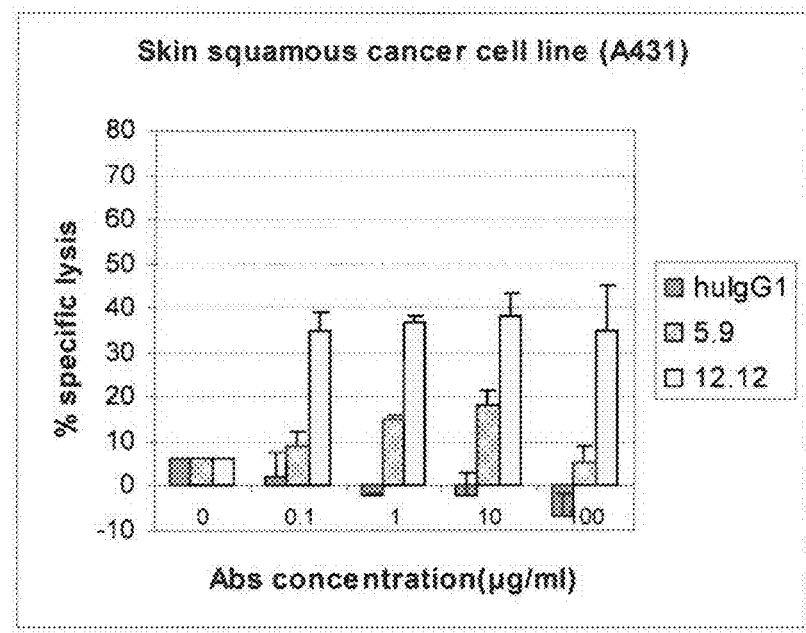
FIG. 18 shows antibody-dependent cell-mediated cytotoxicity (ADCC) activity of monoclonal antibodies CHIR-5.9 and CHIR-12.12 on the ovarian cancer cell lines SKO3 (FIG. 18A) and Hey (FIG. 18B), the skin squamous cancer cell line A431 (FIG. 18C), and the colon cancer cell line HCT116 (FIG. 18D).
Figure 18D:
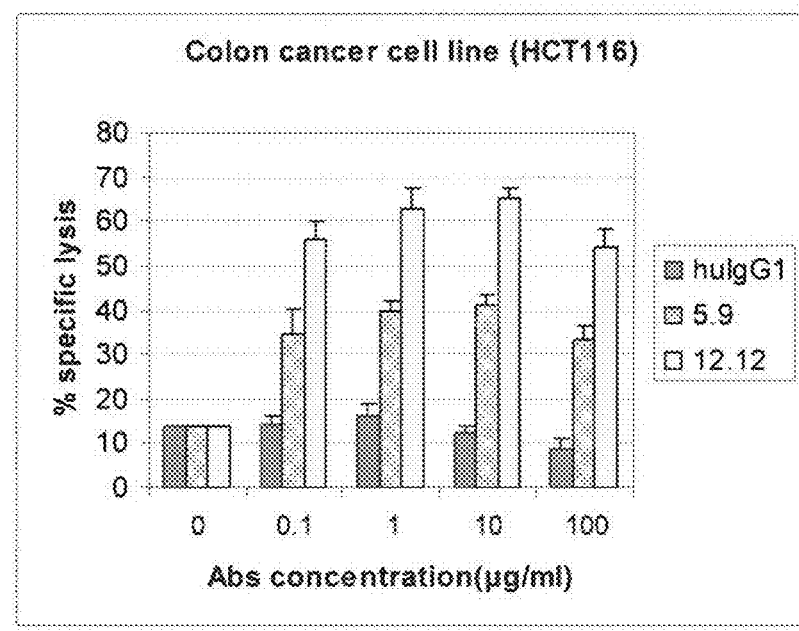

The anti-CD40 mAb CHIR-12.12 showed lysis activity in a dose-dependent manner and reached maximum lysis levels at 0.1 µg/ml (FIG. 17). As shown in FIG. 17, mAb CHIR-12.12 induced greater ADCC-mediated cell lysis than Rituxan® (maximum specific lysis with mAb CHIR-12.12=27.2% versus maximum specific lysis with Rituxan®=16.2%; p=0.007). Based on these results, approximately 10-fold more binding sites for anti-CD20 antibody than for anti-CD40 antibody were present on the target cells (see Table 2), indicative of fewer CD40 molecules being expressed on CLL cell line EHEB when compared to CD20 expression. In fact, the CLL target cell line expressed 509,053±13,560 CD20 molecules compared to 48,416±584 CD40 molecules. Thus, the greater ADCC mediated by mAb CHIR-12.12 was not due to higher density of CD40 molecules on this CLL cell line compared to CD20 molecules.

TABLE 2

EHEB cell line target binding site ratio.

| Cell Line | % Maximum Lysis mAb CHIR-12.12 | Rituxan ® | Ratio of Maximum Binding Sites CD20/CD40 |
|---|---|---|---|
| EHEB | 27.19 | 16.21 | 10.51 |

Example 3

Clinical Studies with CHIR-5.9 and CHIR-12.12

Clinical Objectives

The overall objective is to provide an effective therapy for chronic lymphocytic leukemia (CLL) by targeting these cancer cells with an anti-CD40 IgG1. The signal for this disease is determined in phase I although some measure of activity may be obtained in phase I. Initially the agent is studied as a single agent, but will be combined with other agents, chemotherapeutics, and radiation therapy, as development proceeds.

Phase I
  Evaluate safety and pharmacokinetics—dose escalation in subjects with chronic lymphocytic leukemia (CLL).
  Choose dose based on safety, tolerability, and change in serum markers of CD40.
  In general an MTD is sought but other indications of efficacy (depletion of CD40+ CLL cells, etc.) may be adequate for dose finding.
  Consideration of more than one dose, as some dose finding may be necessary in phase II.
  Patients are dosed weekly with real-time pharmacokinetic (Pk) sampling. Initially a 4-week cycle is the maximum dosing allowed. The Pk may be highly variable depending on the disease state, density of CD40 etc.
  This trial(s) is open to subjects with CLL.
  Decision to discontinue or continue studies is based on safety, dose, and preliminary evidence of anti-tumor activity.
  Activity of drug as determined by response rate is determined in Phase II.
  Identify dose(s) for Phase II.

Phase II
  Several trials will be initiated in subjects with CLL. More than one dose, and more than one schedule may be tested in a randomized phase II setting.
    Target a CLL population that has failed current standard of care (chemotherapy failures)
      Decision to discontinue or continue with study is based on proof of therapeutic concept in Phase II
      Determine whether surrogate marker can be used as early indication of clinical efficacy
      Identify doses for Phase III Phase III Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.

Chapter IV: Methods of Therapy for Solid Tumors Expressing the CD40 Cell-Surface Antigen IV. A. Overview This aspect of the invention is directed to methods for treating human subjects with solid tumors that comprise CD40-expressing carcinoma cells, including, but not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas), as described herein below in sections IV.B-IV.F and in commonly owned U.S. Provisional Application No. 60/565,634, filed Apr. 26, 2004 and International Application No. PCT/US2004/036955, filed Nov. 4, 2004 and published as WO 2005/044305, which corresponds to copending U.S. National-Phase application Ser. No. 10/578,400, which published as U.S. Application Publication No. 20070098717, all of which are entitled "Methods of Therapy for Solid Tumors Expressing the CD40 Cell-Surface Antigen"; the contents of each of which are herein incorporated by reference in their entirety. The methods involve treatment with an anti-CD40 antibody described herein, or an antigen-binding fragment thereof, where administration of the antibody or antigen-binding fragment thereof promotes a positive therapeutic response within the subject undergoing this method of therapy to treat a solid tumor.

IV. B. Antagonist Anti-CD40 Antibodies for Use in Methods for Treating Solid Tumors Anti-CD40 antibodies suitable for use in these methods of the invention specifically bind a human CD40 antigen expressed on the surface of a human carcinoma cell and are free of significant agonist activity, but exhibit antagonist activity when bound to the CD40 antigen on a human CD40-expressing cell, as demonstrated for CD40-expressing normal and neoplastic human B cells. These anti-CD40 antibodies and antigen-binding fragments thereof are referred to herein as antagonist anti-CD40 antibodies. Such antibodies include, but are not limited to, the fully human monoclonal antibodies 5.9 and CHIR-12.12, and monoclonal antibodies having the binding characteristics of monoclonal antibodies 5.9 and CHIR-12.12, as described herein above in Chapter I. These monoclonal antibodies, which can be recombinantly produced, are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety.

When these antibodies bind CD40 displayed on the surface of CD40-expressing cells of a solid tumor (also referred to herein as CD40-expressing carcinoma cells), the antibodies are free of significant agonist activity; in some embodiments, their binding to CD40 displayed on the surface of CD40-expressing carcinoma cells results in ADCC-dependent killing of these carcinoma cells, and hence a reduction in tumor volume. Thus, the antagonist anti-CD40 antibodies suitable for use in the methods of the invention include those monoclonal antibodies that can exhibit antagonist activity toward human cells expressing the cell-surface CD40 antigen, as demonstrated for CD40-expressing normal and neoplastic human B cells.

Antibodies that have the binding characteristics of monoclonal antibodies CHIR-5.9 and CHIR-12.12 include antibodies that competitively interfere with binding CD40 and/or bind the same epitopes as CHIR-5.9 and CHIR-12.12. One of skill in the art could determine whether an antibody competitively interferes with CHIR-5.9 or CHIR-12.12 using standard methods known in the art.

Thus, in addition to the monoclonal antibodies CHIR-5.9 and CHIR-12.12, other antibodies that would be useful in practicing the methods of the invention described herein in Chapter II include, but are not limited to, the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen. Those skilled in the art recognize that the antagonist anti-CD40 antibodies and antigen-binding fragments of these antibodies suitable for use in the methods disclosed herein include antagonist anti-CD40 antibodies and antigen-binding fragments thereof that are produced recombinantly using methods well known in the art and described herein below, and include, for example, monoclonal antibodies CHIR-5.9 and CHIR-12.12 that have been recombinantly produced.

Any of these antagonist anti-CD40 antibodies or antibody fragments thereof may be conjugated (e.g., labeled or conjugated to a therapeutic moiety or to a second antibody), as described herein above in Chapter I, prior to use in these methods for treating a solid tumor in a human patient. Furthermore, suitable biologically variants of the antagonist anti-CD40 antibodies described elsewhere herein can be used in the methods of the present invention. Such variants, including those described herein above in Chapter I, will retain the desired binding properties of the parent antagonist anti-CD40 antibody. Methods for making antibody variants are generally available in the art; see, for example, the methods described herein above in Chapter I.

IV. C. Methods of Therapy for Treatment of Solid Tumors

Methods of the invention are directed to the use of antagonist anti-CD40 antibodies to treat subjects (i.e., patients) having solid tumors that comprise cells expressing the CD40 cell-surface antigen. By "CD40-expressing carcinoma cell" is intended any malignant (i.e., neoplastic) or pre-malignant cell of a solid tumor that expresses the CD40 cell-surface antigen. Methods for detecting CD40 expression in cells are well known in the art and include, but are not limited to, PCR techniques, immunohistochemistry, flow cytometry, Western blot, ELISA, and the like. Solid tumors that can be treated using the methods of the present invention include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas).

"Treatment" is herein defined as the application or administration of an antagonist anti-CD40 antibody or antigen-binding fragment thereof to a subject, or application or administration of an antagonist anti-CD40 antibody or fragment thereof to an isolated tissue or cell line from a subject, where the subject has a solid tumor, a symptom associated with a solid tumor, or a predisposition toward development of a solid tumor, where the purpose is to cure, heal, alleviate, relieve, alter, remedy, ameliorate, improve, or affect the solid tumor, any associated symptoms of the solid tumor, or the predisposition toward development of the solid tumor. By "treatment" is also intended the application or administration of a pharmaceutical composition comprising the antagonist anti-CD40 antibodies or fragments thereof to a subject, or application or administration of a pharmaceutical composition comprising the anti-CD40 antibodies or fragments thereof to an isolated tissue or cell line from a subject, who has a solid tumor, a symptom associated with a solid tumor, or a predisposition toward development of the solid tumor, where the purpose is to cure, heal, alleviate, relieve, alter, remedy, ameliorate, improve, or affect the solid tumor, any associated symptoms of the solid tumor, or the predisposition toward development of the solid tumor.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 antibody (or antigen-binding fragment thereof) causes a physiological response that is beneficial with respect to treatment of solid tumors in a human, where the solid tumors comprise CD40-expressing carcinoma cells. It is recognized that the methods of the invention may be useful in preventing further tumor outgrowths arising during therapy.

In accordance with the methods of the present invention, at least one antagonist anti-CD40 antibody (or antigen-binding fragment thereof) as defined elsewhere herein is used to promote a positive therapeutic response with respect to a solid tumor. By "positive therapeutic response" with respect to cancer treatment is intended an improvement in the disease in association with the anti-tumor activity of these antibodies or fragments thereof, and/or an improvement in the symptoms associated with the disease. That is, an anti-proliferative effect, the prevention of further tumor outgrowths, a reduction in tumor size, a reduction in the number of cancer cells, and/or a decrease in one or more symptoms mediated by stimulation of CD40-expressing cells can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bioluminescent imaging, for example, luciferase imaging, bone scan imaging, and tumor biopsy sampling including bone marrow aspiration (BMA). In addition to these positive therapeutic responses, the subject undergoing therapy with the antagonist anti-CD40 antibody or antigen-binding fragment thereof may experience the beneficial effect of an improvement in the symptoms associated with the disease.

By "therapeutically effective dose or amount" or "effective amount" is intended an amount of antagonist anti-CD40 antibody or antigen-binding fragment thereof that, when administered brings about a positive therapeutic response with respect to treatment of a patient with a solid tumor comprising CD40-expressing carcinoma cells. In some embodiments of the invention, a therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody or antigen-binding fragment thereof.

A further embodiment of the invention is the use of antagonist anti-CD40 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

In some preferred embodiments, the antagonist anti-CD40 antibodies of the invention, or antigen-binding fragments thereof, are administered in combination with at least one other cancer therapy, including, but not limited to, surgery, radiation therapy, chemotherapy, cytokine therapy, or other monoclonal antibody intended for use in treatment of the solid tumor of interest, where the additional cancer therapy is administered prior to, during, or subsequent to the anti-CD40 antibody therapy. Thus, where the combined therapies comprise administration of an anti-CD40 antibody or antigen-binding fragment thereof in combination with administration of another therapeutic agent, as with chemotherapy, cytokine therapy, or other monoclonal antibody, the methods of the invention encompass coadministration, using separate formulations or a single pharmaceutical formulation, and consecutive administration in either order, wherein preferably there is a time period where both (or all) active agents simultaneously exert their therapeutic activities. Where the methods of the present invention comprise combined therapeutic regimens, these therapies can be given simultaneously, i.e., the anti-CD40 antibody or antigen-binding fragment thereof is administered concurrently or within the same time frame as the other cancer therapy (i.e., the therapies are going on concurrently, but the anti-CD40 antibody or antigen-binding fragment thereof is not administered precisely at the same time as the other cancer therapy). Alternatively, the anti-CD40 antibody of the present invention or antigen-binding fragment thereof may also be administered prior to or subsequent to the other cancer therapy. Sequential administration of the different cancer therapies may be performed regardless of whether the treated subject responds to the first course of therapy to decrease the possibility of remission or relapse.

In some embodiments of the invention, the anti-CD40 antibodies described herein, or antigen-binding fragments thereof, are administered in combination with chemotherapy or cytokine therapy, wherein the antibody and the chemotherapeutic agent(s) or cytokine(s) may be administered sequentially, in either order, or simultaneously (i.e., concurrently or within the same time frame). Examples of suitable chemotherapeutic agents include, but are not limited to, CPT-11 (Irinotecan), which can be used, for example, in treating colorectal cancer and non-small cell lung cancer; gemcitabine, which can be used, for example, in treating lung cancer, breast cancer, and epithelial ovarian cancer; and other chemotherapeutic agents suitable for treatment of solid tumors. Cytokines of interest include, but are not limited to, alpha interferon, gamma interferon, interleukin-2 (IL-2), IL-12, IL-15, and IL-21, granulocyte macrophage colony stimulating factor (GM-CSF), granulocyte colony stimulating factor (G-CSF), or biologically active variants of these cytokines.

In other embodiments of the invention, the anti-CD40 antibodies described herein, or antigen-binding fragments thereof, are administered in combination with other monoclonal antibodies intended for treatment of the solid tumor. Thus, for example, where the subject is undergoing treatment for a breast cancer comprising CD40-expressing carcinoma cells, therapy could include administration of effective amounts of an antagonist anti-CD40 antibody described herein, or antigen-binding fragment thereof, in combination with administration of effective amounts of Herceptin® (Genentech, Inc., San Francisco, Calif.), which targets the Her2 receptor protein on Her2+ breast cancer cells. Similarly, where the subject is undergoing treatment for colorectal cancer comprising CD40-expressing carcinoma cells, therapy could include administration of effective amounts of an antagonist anti-CD40 antibody described herein, or antigen-binding fragment thereof, in combination with administration of effective amounts of the humanized monoclonal antibody Avastin™ (also known as bevacizumab; Genentech, Inc., San Francisco, Calif.), which binds to and inhibits vascular endothelial growth factor (VEGF), a protein that plays a critical role in tumor angiogenesis. Other examples of monoclonal antibodies intended for treatment of solid tumors that can be used in combination with the anti-CD40 antibodies of the present invention include, but are not limited to, anti-EGFR antibody targeting the epidermal growth factor receptor (for example, IMC-C225 (ImClone Systems, New York, N.Y.) (see, for example, Mendelsohn and Baselga (2000) *Oncogene* 19:6550-6565 and Solbach et al. (2002) *Int. J. Cancer* 101: 390-394); anti-IGF-1 receptor antibody, targeting the IGF-1 receptor protein (see, for example, Maloney et al. (2003) *Cancer Res.* 63:5073-5083 and Hailey et al. (2002) *Mol. Cancer. Ther.* 1:1349-1353; anti-MUC1 antibody, targeting the tumor-associated antigen MUC1; anti-α5β1, anti-αvβ5, and anti-αvβ3, targeting these respective integrins, which regulate cell adhesion and signaling processes involved in cell proliferation and survival (see, for example, Laidler et al. (2000) *Acta Biochimica Polonica* 47(4):1159-1170 and Cruet-Hennequart et al. (2003) *Oncogene* 22(11):1688-1702); anti-P-cadherin antibody, targeting this cadherin family member (see, for example, copending U.S. Patent Application 20030194406); and anti-VE-cadherin antibody, targeting angiogenic-related function of this endothelial cell-specific adhesion molecule (see, for example, Liao et al. (2002) *Cancer Res.* 62:2567-2575).

The anti-CD40 antibodies of the invention and the other monoclonal antibody can be administered sequentially, in either order, or simultaneously (i.e., concurrently or within the same time frame). Where more than one type of monoclonal antibody is administered, the methods of the present invention can further comprise exposure to radiation and/or chemotherapy as warranted for the cancer undergoing treatment and as recommended by the supervising medical practitioner.

IV. D. Pharmaceutical Formulations and Modes of Administration

The antagonist anti-CD40 antibodies of this invention are administered at a concentration that is therapeutically effective to prevent or treat solid tumors comprising CD40-expressing carcinoma cells, including ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas). To accomplish this goal, the antibodies may be formulated using a variety of acceptable excipients known in the art, as noted herein above in Chapter I. Typically, the antibodies are administered by injection, either intravenously, intraperitoneally, or intratumorally. Methods to accomplish this administration are known to those of ordinary skill in the art, and include those methods described hereinabove in Chapter I. It may also be possible to obtain compositions that may be topically or orally administered, or which may be capable of transmission across mucous membranes. Intravenous administration occurs preferably by infusion over a period of time, as described herein above in Chapter I. Possible routes of administration, preparation of suitable formulations, therapeutically effective amounts to be administered, and suitable dosing regimens are as described herein above in Chapter I. See also commonly owned U.S. Provisional Application No. 60/565,634, filed Apr. 26, 2004 and International Application No. PCT/US2004/036955, filed Nov. 4, 2004 and published as WO 2005/044305, which corresponds to copending U.S. National-Phase application Ser. No. 10/578,400, which published as U.S. Application Publication No. 20070098717; the contents of each of which are herein incorporated by reference in their entirety.

IV. E. Use of Antagonist Anti-CD40 Antibodies in the Manufacture of Medicaments for Treating Solid Tumors The present invention also provides for the use of an antagonist anti-CD40 antibody or antigen-binding fragment thereof in the manufacture of a medicament for treating a subject for a solid tumor comprising carcinoma cells expressing CD40 antigen, wherein the medicament is coordinated with treatment with at least one other cancer therapy. Examples of such tumors include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas).

By "coordinated" is intended the medicament is to be used either prior to, during, or after treatment of the subject with at least one other cancer therapy. Examples of other cancer therapies include, but are not limited to, surgery; radiation therapy; chemotherapy, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; cytokine therapy, including, but not limited to, alpha-interferon therapy, gamma-interferon therapy, therapy with interleukin-2 (IL-2), IL-12, IL-15, and IL-21, granulocyte macrophage colony stimulating factor (GM-CSF), granulocyte colony stimulating factor (G-CSF), or biologically active variants of these cytokines; or other monoclonal antibody intended for use in treatment of the solid tumor of interest, for example, Herceptin® (Genentech, Inc., San Francisco, Calif.), which targets the Her2 receptor protein on Her2+ breast cancer cells; the humanized monoclonal antibody Avastin™ (also known as bevacizumab; Genentech, Inc., San Francisco, Calif.), which binds to and inhibits vascular endothelial growth factor (VEGF), and has use in treatment of colon cancer; anti-EGFR antibody targeting the epidermal growth factor receptor (for example, IMC-C225 (ImClone Systems, New York, N.Y.); anti-IGF-1 receptor antibody, targeting the IGF-1 receptor protein; anti-MUC1 antibody, targeting the tumor-associated antigen MUC1; anti-α5β1, anti-αvβ5, and anti-αvβ3, targeting these respective integrins, which regulate cell adhesion and signaling processes involved in cell proliferation and survival; anti-P-cadherin antibody, targeting this cadherin family member (see, for example, copending U.S. Patent Application Publication No. 20030194406); and anti-VE-cadherin antibody, targeting angiogenic-related function of this endothelial cell-specific adhesion molecule; where treatment with the additional cancer therapy, or additional cancer therapies, occurs prior to, during, or subsequent to treatment of the subject with the medicament comprising the antagonist anti-CD40 antibody or antigen-binding fragment thereof, as noted herein above.

Thus, for example, in some embodiments, the invention provides for the use of the monoclonal antibody CHIR-12.12 or CHIR-5.9, or antigen-binding fragment thereof, in the manufacture of a medicament for treating a subject for a solid tumor comprising carcinoma cells expressing CD40 antigen, wherein the medicament is coordinated with treatment with chemotherapy, where the chemotherapeutic agent is selected from the group consisting of CPT-11 (Irinotecan), which can be used, for example, in treating colorectal cancer and non-small cell lung cancer; gemcitabine, which can be used, for example, in treating lung cancer, breast cancer, and epithelial ovarian cancer; and other chemotherapeutic agents suitable for treatment of solid tumors; where treatment with the additional cancer therapy, or additional cancer therapies, occurs prior to, during, or subsequent to treatment of the subject with the medicament comprising the antagonist anti-CD40 antibody or antigen-binding fragment thereof, as noted herein above.

In other embodiments, the invention provides for the use of the monoclonal antibody CHIR-12.12 or CHIR-5.9, or antigen-binding fragment thereof, in the manufacture of a medicament for treating a subject for a solid tumor comprising carcinoma cells expressing CD40 antigen, wherein the medicament is coordinated with treatment with at least one other anti-cancer antibody selected from the group consisting of Herceptin® (Genentech, Inc., San Francisco, Calif.), which targets the Her2 receptor protein on Her2+ breast cancer cells; the humanized monoclonal antibody Avastin™ (also known as bevacizumab; Genentech, Inc., San Francisco, Calif.), which binds to and inhibits vascular endothelial growth factor (VEGF), and has use in treatment of colon cancer; anti-EGFR antibody targeting the epidermal growth factor receptor (for example, IMC-C225 (ImClone Systems, New York, N.Y.); anti-IGF-1 receptor antibody, targeting the IGF-1 receptor protein; anti-MUC1 antibody, targeting the tumor-associated antigen MUC1; anti-α5β1, anti-αvβ5, and anti-αvβ3, targeting these respective integrins, which regulate cell adhesion and signaling processes involved in cell proliferation and survival; anti-P-cadherin antibody, targeting this cadherin family member (see, for example, copending U.S. Patent Application Publication No. 20030194406); and anti-VE-cadherin antibody, targeting angiogenic-related function of this endothelial cell-specific adhesion molecule; where treatment with the additional cancer therapy, or additional cancer therapies, occurs prior to, during, or subsequent to treatment of the subject with the medicament comprising the antagonist anti-CD40 antibody or antigen-binding fragment thereof, as noted herein above.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating a subject for a solid tumor comprising carcinoma cells expressing CD40 antigen, wherein the medicament is used in a subject that has been pretreated with at least one other cancer therapy. By "pretreated" or "pretreatment" is intended the subject has received one or more other cancer therapies (i.e., been treated with at least one other cancer therapy) prior to receiving the medicament comprising the antagonist anti-CD40 antibody or antigen-binding fragment thereof. "Pretreated" or "pretreatment" includes subjects that have been treated with at least one other cancer therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior cancer therapy, or prior cancer therapies. Thus, the subject that receives the medicament comprising the antagonist anti-CD40 antibody or antigen-binding fragment thereof could have responded, or could have failed to respond (i.e. the cancer was refractory), to pretreatment with the prior cancer therapy, or to one or more of the prior cancer therapies where pretreatment comprised multiple cancer therapies. Examples of other cancer therapies for which a subject can have received pretreatment prior to receiving the medicament comprising the antagonist anti-CD40 antibody or antigen-binding fragment thereof include, but are not limited to, surgery; radiation therapy; chemotherapy, where suitable chemotherapeutic agents include, but are not limited to, those listed herein above; other anti-cancer monoclonal antibody therapy, including, but not limited to, those anti-cancer antibodies listed herein above; cytokine therapy, including the cytokine therapies listed herein above; or any combination thereof.

"Treatment" in the context of coordinated use of a medicament described herein with one or more other cancer therapies is herein defined as the application or administration of the medicament or of the other cancer therapy to a subject, or application or administration of the medicament or other cancer therapy to an isolated tissue or cell line from a subject, where the subject has a solid tumor comprising carcinoma cells expressing CD40 antigen, a symptom associated with such a cancer, or a predisposition toward development of such a cancer, where the purpose is to cure, heal, alleviate, relieve, alter, remedy, ameliorate, improve, or affect the cancer, any associated symptoms of the cancer, or the predisposition toward the development of the cancer.

The following examples for this invention are offered by way of illustration and not by way of limitation.

IV. F. EXPERIMENTAL

The antagonist anti-CD40 antibodies used in the examples below are 5.9 and CHIR-12.12, described in Chapter I above, and in commonly owned U.S. Provisional Application No. 60/565,634, filed Apr. 26, 2004 and International Application No. PCT/US2004/036955, filed Nov. 4, 2004 and published as WO 2005/044305, which corresponds to copending U.S. National-Phase application Ser. No. 10/578,400, which published as U.S. Application Publication No. 20070098717; the contents of each of which are herein incorporated by reference in their entirety.

Example 1

CD40 is Expressed on a High Proportion of Solid Tumors

A variety of solid tumor-derived cultured cancer cell lines and patient biopsies have been found to express CD40. A high % of biopsied samples from breast, lung, ovary, and skin cancer patients were found to express CD40.

Example 2

Ability of Candidate Monoclonal Antibody CHIR-12.12 to Bind to CD40 Expressed on Several Human Carcinomas Carcinoma tissue samples were obtained from individuals (N=10) with ovarian, lung, mammary, or colon cancer and frozen for subsequent analysis of antibody binding using immunohistochemistry. The percent of neoplastic cells in the various human carcinomas able to bind to the CHIR-12.12 mAb was determined. As can be seen from Table 1, 60% of the ovarian and lung carcinoma samples fell into the highest category of percent binding (i.e., 50-100% of the cells in these samples were able to bind to the CHIR-12.12 mAb). Thirty percent of the mammary and 10% of the colon carcinoma samples fell into the highest category of percent binding.

TABLE 1

Ability of CHIR-12.12 mAb to bind to several human carcinomas.

| | Percent of Neoplastic Cells Binding to CHIR-12.12 mAb | | | | |
|---|---|---|---|---|---|
| Carcinomas | Negative | <5% | 5-25% | 25-50% | 50-100% |
| Ovarian n = 10 | 0% | 0% | 30% | 10% | 60% |
| Lung n = 10 | 0% | 20% | 20% | 0% | 60% |
| Mammary N = 10 | 0% | 30% | 20% | 20% | 30% |
| Colon N = 10 | 0% | 70% | 10% | 10% | 10% |

Example 3

CHIR-5.9 and CHIR-12.12 Are Able to Kill CD40-Bearing Target Cells by ADCC

The candidate antibodies can kill CD40-bearing target cells (lymphoma lines and solid tumor cell lines) by the mechanism of ADCC. Both CHIR-5.9 and CHIR-12.12 are fully human antibodies of IgG1 isotype and are expected to have the ability to induce the killing of target cells by the mechanism of ADCC. They were tested for their ability to kill cancer cell lines in vitro assays. Two human lymphoma cell lines (Ramos and Daudi) and one human colon cancer cell line (HCT116) were initially selected as target cells for these assays. PBMC or enriched NK cells from 8 normal volunteer donors were used as effector cells in these assays. Higher ADCC was seen against lymphoma cell lines that the colon cancer cell line. A more potent ADCC response was observed with CHIR-12.12 compared with CHIR-5.9 against both the lymphoma and colon cancer cell line target cells. Lymphoma cell lines also express CD20, the target antigen for rituximab (Rituxan®; IDEC Pharmaceuticals Corp., San Diego, Calif.), which allowed for comparison of the ADCC activity of these two candidate mAbs with rituximab ADCC activity. For lymphoma cell line target, an average specific lysis of 35%, 59%, and 47% was observed for CHIR-5.9, CHIR-12.12, and rituximab respectively when used at 1 μg/ml concentration. For colon cancer cell line target, an average specific lysis of 20% and 39% were observed for CHIR-5.9 and CHIR-12.12, respectively. See Table 3 below. The two antibodies did not show much activity in complement dependent cytotoxicity (CDC) assays.

TABLE 3

Anti-CD40 mAB dependent killing of lymphoma and colon cancer cell lines by ADCC.
Anti-CD40 mAb dependent killing of lymphoma and colon cancer cell lines by ADCC

| | | | | | Target cells: Human lymphoma cell line (Ramos or Daudi) | | | | | |
|---|---|---|---|---|---|---|---|---|---|---|
| | | | | | 5.9 | | 12.12 | | Rituxan | |
| Exp# | Effector cell | E:T ratio | % lysis IgG1 | Abs conc (ug/ml) | % lysis | % lysis – % lysis IgG1 | % lysis | % lysis – % lysis IgG1 | % lysis | % lysis – % lysis IgG1 |
| ADCC-005 Alarmor Blue | huNK | 3 | 17.05 | 5 | 30.75 | 13.70 | 65.22 | 48.17 | ND | ND |
| | huNK | 3 | 40.81 | 5 | 58.62 | 17.81 | 87.87 | 47.06 | ND | ND |
| ADCC-006 Alarmor Blue | huNK | 2 | −3.09 | 10 | 3.50 | 6.59 | 43.71 | 46.8 | 34.82 | 37.91 |
| | | | −8.62 | 1 | −10.10 | −1.48 | 45.13 | 53.75 | 37.07 | 45.69 |
| | | | −11 | 0.1 | −14.80 | −3.80 | 39.82 | 50.82 | 33.61 | 44.61 |
| | | | −4.54 | 0.01 | 2.53 | 7.07 | 50.07 | 54.61 | 28.49 | 33.03 |
| 51Cr | huNK | 5 | 1.5 | 10 | 32.09 | 30.59 | 47.24 | 45.742 | ND | ND |
| | | | 2.4 | 1 | 18.01 | 15.61 | 37.42 | 35.022 | ND | ND |
| | | | 2.5 | 0.1 | 14.67 | 12.17 | 37.63 | 35.131 | ND | ND |
| ADCC-009 Calcien AM | huNK | 10 | 2.32 | 5 | 66.20 | 63.88 | 97.70 | 95.38 | 86.2 | 83.88 |
| | | | 0.48 | 1 | 67.20 | 66.72 | 123.00 | 122.52 | 88.2 | 87.72 |
| | | | −1.43 | 0.2 | 78.40 | 79.83 | 118.00 | 119.43 | 88.8 | 90.23 |
| | | | 3.39 | 0.04 | 69.10 | 65.71 | 109.00 | 105.61 | 84.9 | 81.51 |
| ADCC-011 Calcien AM | huNK | 8 | 3.18 | 1 | 15.36 | 12.19 | 51.59 | 48.42 | 22.44 | 19.27 |
| | | | 4.58 | 0.01 | 7.39 | 2.81 | 46.80 | 42.22 | 14.68 | 10.10 |
| | | | 5.41 | 0.002 | 6.35 | 0.94 | 5.10 | −0.31 | 9.58 | 4.16 |
| | | | 7.03 | 0.0004 | 7.76 | 0.73 | 5.99 | −1.04 | 5.99 | −1.04 |
| ADCC-012 Calcien AM | huNK | 10 | 13.34 | 10 | 73.31 | 59.97 | 117.80 | 104.46 | 50.75 | 37.41 |
| | | | 13.50 | 1 | 74.76 | 61.26 | 88.64 | 75.14 | 65.97 | 52.47 |
| | | | 12.27 | 0.01 | 58.52 | 46.25 | 72.88 | 60.61 | 50.16 | 37.89 |
| | | | 13.61 | 0.005 | 57.50 | 43.89 | 69.45 | 55.84 | 39.28 | 25.67 |
| | | | 11.95 | 0.001 | 56.81 | 44.86 | 65.17 | 53.22 | 33.07 | 21.12 |
| ADCC-013 51Cr | PBMC | 100 | 2.54 | 1 | 21.03 | 18.49 | 37.94 | 35.40 | 32.28 | 29.74 |
| | | | 2.45 | 0.1 | 15.50 | 13.05 | 30.82 | 28.37 | 27.18 | 24.73 |
| | | | 2.92 | 0.01 | 14.53 | 11.61 | 22.59 | 19.67 | 12.79 | 9.87 |
| | | | 2.78 | 0.001 | 3.90 | 1.12 | 8.99 | 6.21 | 3.13 | 0.35 |
| ADCC-014 51Cr | PBMC | 100 | 4.64 | 10 | 53.54 | 48.90 | 56.12 | 51.48 | ND | ND |
| | | | 4.64 | 1 | 46.84 | 42.20 | 43.00 | 38.36 | ND | ND |
| | | | 4.64 | 0.1 | 45.63 | 40.99 | 39.94 | 35.30 | ND | ND |
| | | | 4.64 | 0.01 | 7.73 | 3.09 | 9.79 | 5.15 | ND | ND |
| | | | 4.64 | 0.001 | 8.83 | 4.19 | 10.81 | 6.17 | ND | ND |
| Average % lysis at 1 ug/ml concentration of mAbs | | | | | | 35.31 | | 59.03 | | 47.23 | |

| | | | Target cells: Human Colon Carcinoma (HCT116) | | | |
|---|---|---|---|---|---|---|
| | | | 5.9 | | 12.12 | |
| Exp# | % lysis IgG1 | Abs conc (ug/ml) | % lysis | % lysis – % lysis ctrl | % lysis | % lysis – % lysis ctrl |
| ADCC-005 Alarmor Blue | ND | ND | ND | ND | ND | ND |
| | ND | ND | ND | ND | ND | ND |
| ADCC-006 Alarmor Blue | 11.14 | 10 | 12.78 | 1.64 | 33.6 | 22.46 |
| | 13.6 | 1 | 8.921 | −4.68 | 21.99 | 8.39 |
| | 15.49 | 0.1 | 8.82 | −6.67 | 26.15 | 10.66 |
| | 13.62 | 0.01 | 17.24 | 3.62 | 28.07 | 14.45 |
| 51Cr | 33.1 | 10 | 120.02 | 86.92 | 170.41 | 137.31 |
| | 23.1 | 2 | 138.4 | 115.3 | 166.62 | 143.52 |
| | 46.4 | 0.4 | 141.41 | 95.01 | 159.45 | 113.05 |
| ADCC-009 Calcien AM | 26.4 | 5 | 41.3 | 14.9 | 62.3 | 35.9 |
| | 32.8 | 1 | 43.8 | 11 | 73.8 | 41 |
| | 33.5 | 0.2 | 42.6 | 9.1 | 71.4 | 37.9 |
| | 26 | 0.04 | 54.8 | 28.8 | 66 | 40 |

TABLE 3-continued

Anti-CD40 mAB dependent killing of lymphoma and colon cancer cell lines by ADCC.
Anti-CD40 mAb dependent killing of lymphoma and colon cancer cell lines by ADCC

| | ADCC-011 | 11.63 | 1 | 6.31 | −5.32 | 19.96 | 8.33 |
|---|---|---|---|---|---|---|---|
| | Calcien AM | 5.885 | 0.01 | −0.05 | −5.94 | 15.25 | 9.37 |
| | | 4.379 | 0.002 | 3.96 | −0.42 | −0.75 | −5.13 |
| | | 1.883 | 0.0004 | 5.13 | 3.25 | 2.825 | 0.94 |
| | ADCC-012 | 0.132 | 10 | 18.42 | 18.29 | 36.1 | 35.97 |
| | Calcien AM | 11.15 | 1 | 28.60 | 17.45 | 42.22 | 31.07 |
| | | 10.89 | 0.01 | 15.51 | 4.62 | 31.07 | 20.18 |
| | | 14.01 | 0.005 | 23.31 | 9.3 | 27.55 | 13.54 |
| | | 14.63 | 0.001 | 24.68 | 10.05 | 32.53 | 17.9 |
| | ADCC-013 | 13.53 | 1 | 22.04 | 8.51 | 43.98 | 30.45 |
| | 51Cr | 15.88 | 0.1 | 21.89 | 6.01 | 43.14 | 27.26 |
| | | 16.85 | 0.01 | 19.75 | 2.9 | 37.16 | 20.31 |
| | | 15.45 | 0.001 | 14.36 | −1.09 | 19.22 | 3.77 |
| | ADCC-014 | 24.12 | 10 | 25.24 | 1.12 | 43.09 | 18.97 |
| | 51Cr | 24.12 | 1 | 22.68 | −1.44 | 32.12 | 8 |
| | | 24.12 | 0.1 | 24.95 | 0.83 | 31.48 | 7.36 |
| | | 24.12 | 0.01 | 23.67 | −0.45 | 26.14 | 2.02 |
| | | 24.12 | 0.001 | 21.55 | −2.57 | 21.84 | −2.28 |
| Average % lysis at 1 ug/ml concentration of mAbs | | | | | | 20.12 | 38.68 |

* The greater than 100% killing are due to incomplete killing by detergent used for 100% killing control.

Further testing of the ADCC activity of these two monoclonal anti-CD40 antibodies was carried out on the colon cancer cell line HCT116 and seven other carcinoma cell lines, including the ovarian cancer cell lines SKOV3 and HEY, the skin squamous cancer cell line A431, the breast cancer cell lines MDA-MB231 and MDA-MB435, and the lung cancer cell lines NCI-H460 and SK-MES-1 using the procedures outlined above. As seen in FIGS. 5A-D and 6A-D, the CHIR-12.12 monoclonal antibody generally exhibited greater ADCC activity than the CHIR-5.9 monoclonal antibody at any given concentration and for any given cell line tested.

Example 4

CHIR-5.9 and CHIR-12.12 Show Anti-Tumor Activity in Animal Models

Pharmacology/in vivo Efficacy

The candidate mAbs are expected to produce desired pharmacological effects to reduce tumor burden by either/both of two anti-tumor mechanisms, blockade of proliferation/survival signal and induction of ADCC. The currently available xenograft human lymphoma models use long-term lymphoma cell lines that, in contrast to primary cancer cells, do not depend on CD40 stimulation for their growth and survival. Therefore the component of these mAbs' anti-tumor activity based on blocking the tumor proliferation/survival signal is not expected to contribute to anti-tumor efficacy in these models. The efficacy in these models is dependent on the ADCC, the second anti-tumor mechanism associated with the CHIR-5.9 and CHIR-12.12 mAbs.

Xenograft Human B Cell Lymphoma Models

Two xenograft human lymphoma models based on Namalwa and Daudi cell lines were assessed for anti-tumor activities of candidate mAbs. To further demonstrate their therapeutic activity, these candidate mAbs were evaluated in an unstaged (i.e., prophylactic) and staged (i.e., therapeutic) xenograft human lymphoma model based on the Daudi cell line. Details of the results and experimental analyses for these xenograft human lymphoma models are disclosed in copending provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively; the contents of each of which are herein incorporated by reference in their entirety.

To summarize, T cell-deficient nude mice were wholebody irradiated at 3 Gy to further suppress the immune system one day before tumor inoculation. Tumor cells were inoculated subcutaneously in the right flank at $5 \times 10^6$ cells per mouse. Treatment was initiated either one day after tumor implantation (unstaged (prophylactic) subcutaneous xenograft human B cell lymphoma models, Namalwa and Daudi) or when tumor volume reached 200 mm$^3$ (staged (therapeutic) Daudi model, usually 15 days after tumor inoculation). Tumor-bearing mice were injected anti-CD40 mAbs intraperitoneally (i.p.) once a week. Doses for the unstaged Namalwa model were as follows: 0.01 mg/kg, 0.03 mg/kg, 0.1 mg/kg, 1 mg/kg, and 10 mg/kg (mAb CHIR-12.12); 1 mg/kg (mAb CHIR-5.9); and 10 mg/kg (rituximab). Doses for the unstaged Daudi model were as follows: 0.01 mg/kg, 0.1 mg/kg, and 1 mg/kg (mAb CHIR-12.12 and mAb CHIR-5.9); 1 mg/kg (rituximab). Doses for the staged Daudi model were as follows: 0.01 mg/kg, 0.1 mg/kg, 1 mg/kg, and 10 mg/kg (mAb CHIR-12.12); 1 mg/kg (mAb CHIR-5.9); and 1 mg/kg (rituximab). Tumor volumes were recorded twice a week. When tumor volume in any group reached 2500 mm$^3$, the study was terminated. Note that in the staged Daudi model, tumor volume data was analyzed up to day 36 due to the death of some mice after that day. Complete regression (CR) was counted until the end of the study. Data were analyzed using ANOVA or Kruskal-Wallis test and corresponding post-test for multi-group comparison.

In the unstaged Namalwa model, anti-CD40 mAb CHIR-12.12, but not rituximab, significantly (p=<0.01) inhibited the growth of Namalwa tumors (tumor volume reduction of 60% versus 25% for rituxamab, n=10 mice/group) (data not shown). Thus, in this model, anti-CD40 mAb CHIR-12.12 was more potent than rituximab. It is noteworthy that the second candidate mAb, CHIR-5.9, was at least as efficacious as rituximab at a dose $\frac{1}{10}^{th}$ that of rituximab. Both anti-CD40 mAb CHIR-12.12 and rituximab significantly prevented tumor development in the unstaged Daudi tumor model (14/15 resistance to tumor challenge) (data not shown).

When these anti-CD40 monoclonal antibodies were further compared in a staged xenograft Daudi model, in which treatment started when the subcutaneous tumor was palpable, anti-CD40 mAb CHIR-12.12 at 1 mg/kg caused significant tumor reduction (p=0.003) with 60% complete regression (6/10), while rituximab at the same dose did not significantly inhibit the tumor growth nor did it cause complete regression (0/10) (data not shown).

In summary, the anti-CD40 mAb CHIR-12.12 significantly inhibited tumor growth in experimental lymphoma models. At the same dose and regimen, mAb CHIR-12.12 showed better anti-cancer activity than did Rituxan® (rituximab). Further, no clinical sign of toxicity was observed at this dose and regimen. These data suggest that the anti-CD40 mAb CHIR-12.12 has potent anti-human lymphoma activity in vitro and in xenograft models and could be clinically effective for the treatment of lymphoma.

Xenograft Human Colon Carcinoma Model

These candidate mAbs were further evaluated for their therapeutic anti-tumor activity in a solid tumor model. Similar to many human solid tumors, human colon carcinoma cell line HCT 116 expresses CD40 and was selected for a xenograft colon cancer model. Tumor cells were inoculated subcutaneously in the right flank of T-cell deficient nude mice (this tumor can grow in nude mice without prior irradiation) at $5 \times 10^6$ cells per mouse. One day after tumor inoculation, mice received intraperitoneal (i.p.) injection of anti-CD40 mAbs once a week for a total of 5 doses.

Figure 20:
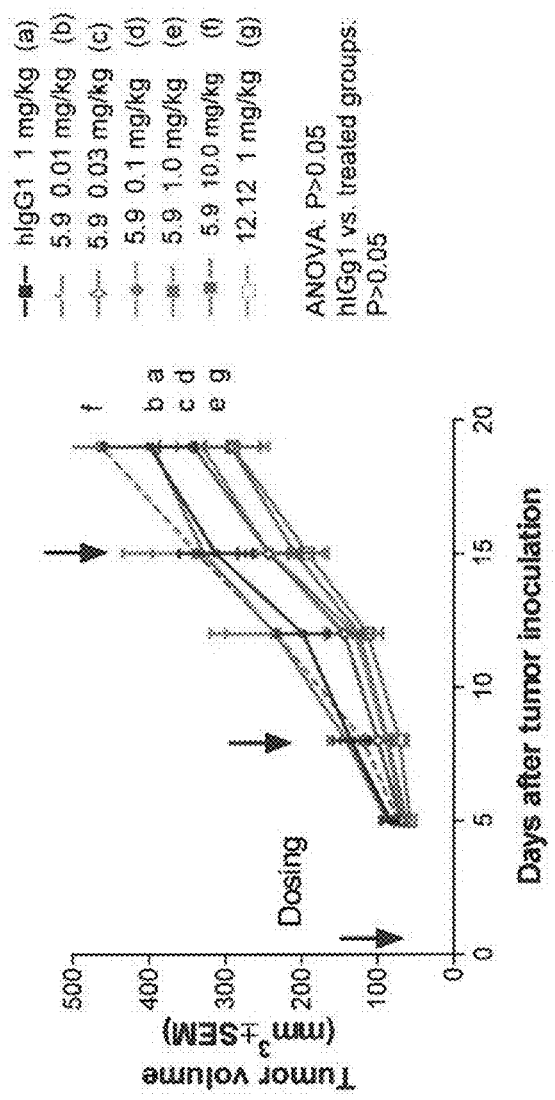
FIG. 20 demonstrates in vivo anti-tumor activity of monoclonal antibodies CHIR-5.9 (denoted 5.9 in figure) and CHIR-12.12 (denoted 12.12 in figure) using a xenograft colon cancer model based on the human colon carcinoma cell line HCT116.

Treatment with anti-CD40 mAbs showed a reproducible trend toward tumor growth inhibition in two repeated studies. The data from one of these two studies is shown in FIG. 20. Interestingly, a reversal of anti-tumor activity was observed at the highest dose (10 mg/kg) in this model suggesting an optimal dose/regimen may be needed to achieve best tumor growth inhibition. Monoclonal antibody CHIR-12.12, which showed higher ADCC activity in vitro and higher anti-tumor efficacy in a lymphoma model, was tested only at a single dose of 1 mg/kg in the colon carcinoma model. A dose titration of CHIR-12.12 is performed to determine the full potential of its anti-tumor efficacy in this xenograft human colon cancer model.

Unstaged (Prophylactic) Orthotopic Ovarian Cancer Model

The CHIR-12.12 mAb was also evaluated for its therapeutic anti-tumor activity in an unstaged (prophylactic) orthotopic murine model of ovarian cancer using the ovarian cancer cell line SKOV3i/p.1. Tumor cells were inoculated intraperitoneally (i.p.) into T-cell deficient nude mice at $2 \times 10^6$ cells per mouse. Beginning the first day after tumor inoculation, mice received i.p. injections of various doses of the CHIR-12.12 mAbs or Herceptin® (Genentech, Inc., San Francisco, Calif.), which is under clinical investigation for treatment of ovarian cancer. Antibody was dosed once a week for a total of 6 doses. Percent survival was calculated over time.

Figure 21:
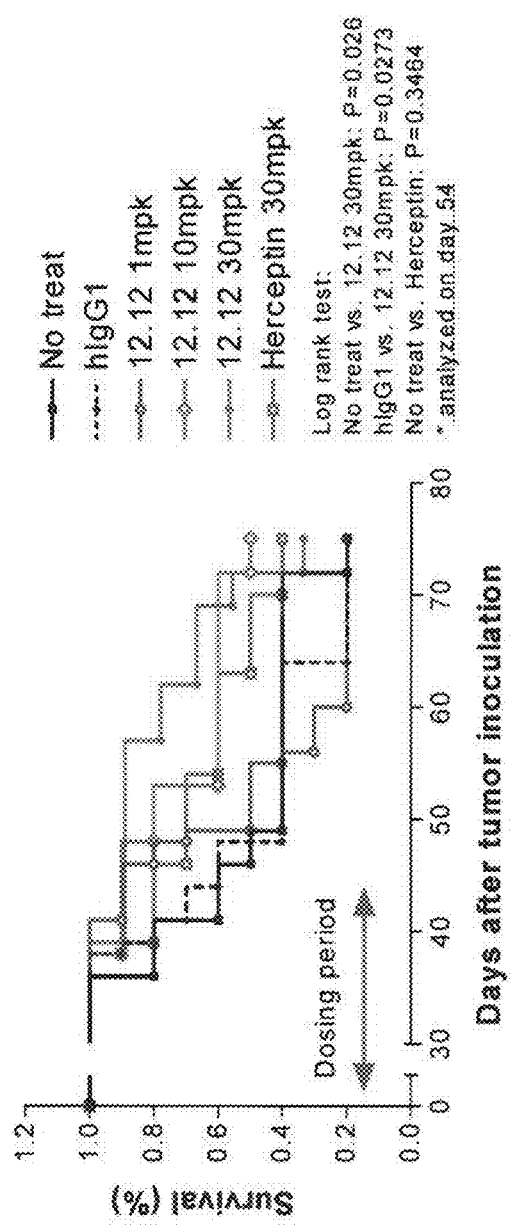
FIG. 21 shows the effects of intraperitoneally administered anti-CD40 monoclonal antibody CHIR-12.12 (denoted 12.12 in figure) or anti-HER2 monoclonal antibody Herceptin® on percent survival in an unstaged orthotopic murine model of ovarian cancer using the human ovarian cancer cell line SKOV3i.p. 1.

Treatment with the CHIR-12.12 mAb prolonged survival time in a dose-dependent manner (FIG. 21). Fifty-four days after tumor inoculation, percent survival was significantly higher for the group receiving 30 mg/kg of the CHIR-12.12 mAb than for the untreated control group. Though a similar dose of Herceptin® showed a trend toward prolonging survival, percent survival at 54 days post-inoculation was not significantly greater than that observed for the untreated control group.

Figure 22:
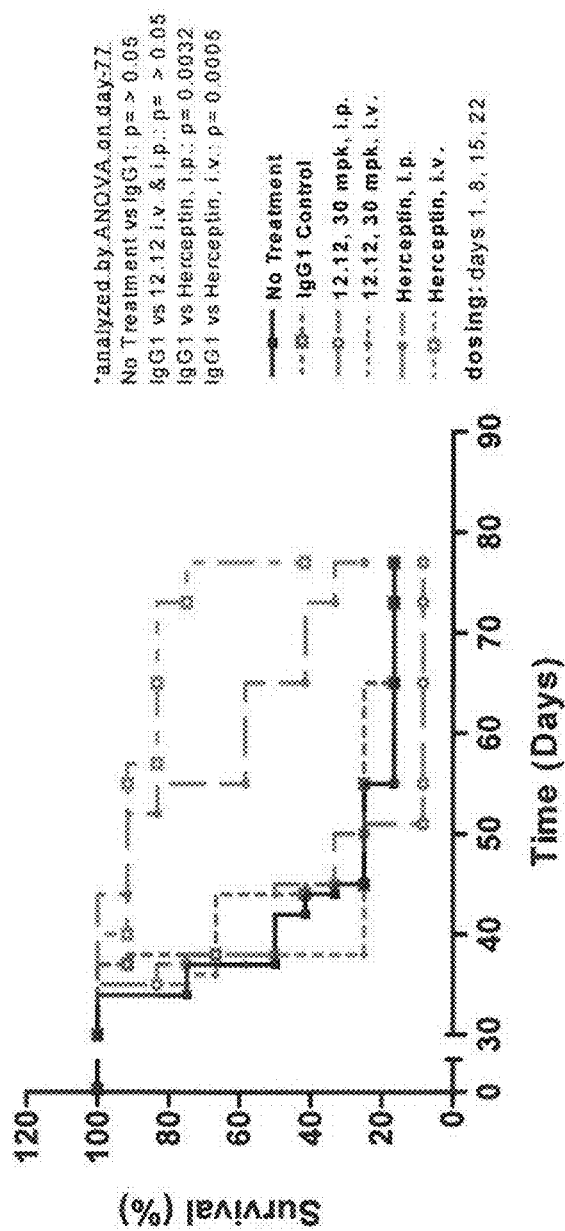
FIG. 22 compares the effects of intraperitoneally versus intravenously administered monoclonal antibody CHIR-12.12 (denoted 12.12 in figure) or Herceptin® on percent survival in an unstaged orthotopic murine model of ovarian cancer using the human ovarian cancer cell line SKOV3i.p.1.

FIG. 22 shows a comparison of the effects of the CHIR-12.12 mAb on percent survival in this unstaged orthotopic murine model of ovarian cancer when the antibody is administered intraperitoneally (i.p.) versus intravenously (i.v.). Treatment protocol was as described above. As can be seen in this figure, i.p. injection of the CHIR-12.12 mAb yielded improved percent survival relative to that observed with i.v. administration of this antibody.

Staged (Therapeutic) Murine Model of Ovarian Cancer

The CHIR-5.9 and CHIR-12.12 mAbs were further evaluated for their therapeutic anti-tumor activity in a staged (therapeutic) murine model of ovarian cancer using the ovarian cancer cell line SKOV3i.p. 1. For this study, tumor cells were inoculated subcutaneously into the right flank of T-cell deficient nude mice at $5 \times 10^6$ cells per mouse with 10% matrigel. Beginning 6 days after tumor inoculation (when the tumor volume reached 100-200 $mm^3$), mice received injections of these mAbs intraperitoneally once a week for a total of 4 doses. Tumor volume was measured twice a week following the first day of antibody dosing.

Figure 23:
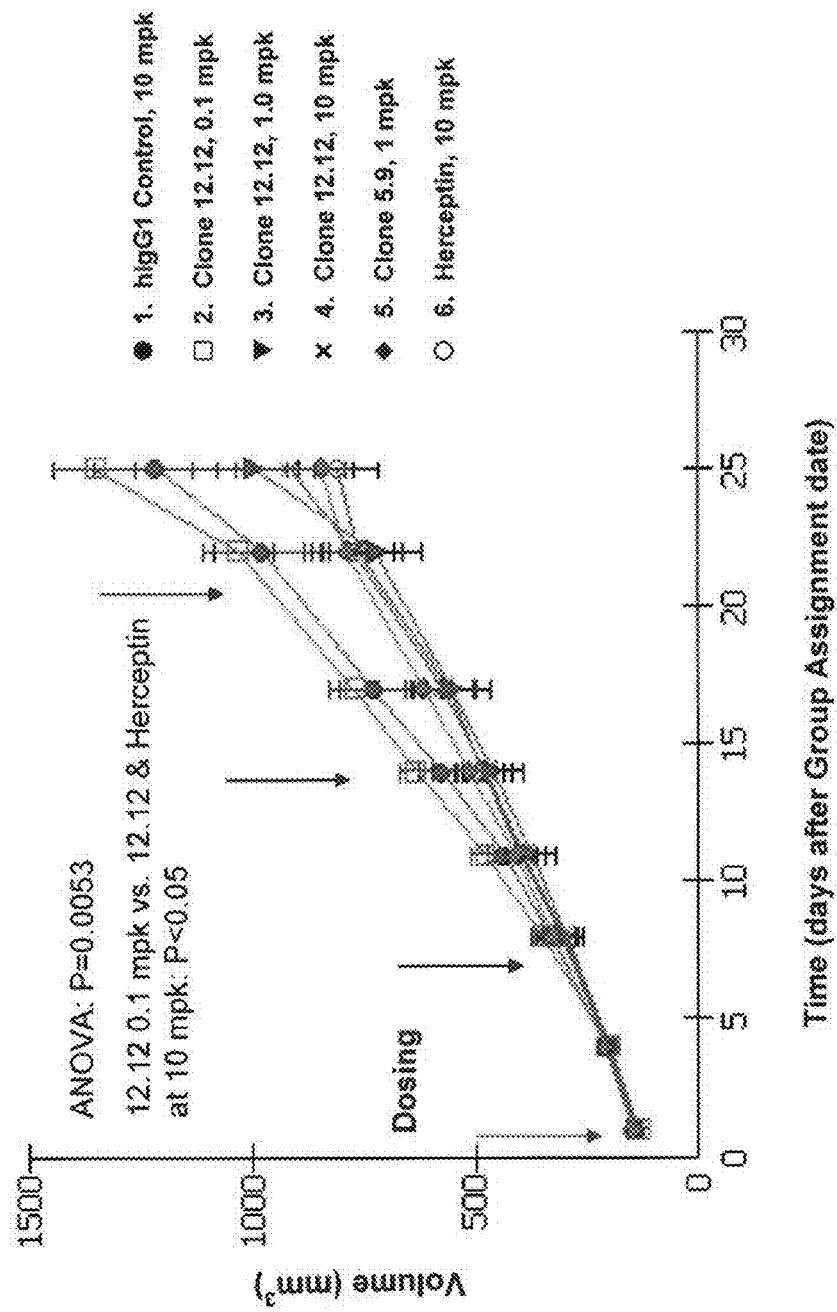
FIG. 23 demonstrates in vivo anti-tumor activity of monoclonal antibodies CHIR-12.12 (denoted 12.12 in figure) and CHIR-5.9 (denoted 5.9 in figure) versus that observed for Herceptin® using a staged murine model of ovarian cancer based on the human ovarian cancer cell line SKOV3i.p1.

The two candidate mAbs significantly inhibited tumor growth relative to that observed for the untreated control group (FIG. 23) at the higher antibody concentrations tested (1 mg/kg for the CHIR-5.9 mAb, and 10 mg/kg for the CHIR-12.12 mAb). For the CHIR-12.12 mAb (the only antibody for which dose was varied), inhibition of tumor growth occurred in a dose-dependent manner, with the greatest tumor reduction occurring at the highest dose (i.e., 10 mg/kg). At this highest dose, the CHIR-12.12 mAb was just as efficacious as an equivalent dose of Herceptin®.

Example 6

Clinical Studies with CHIR-5.9 and CHIR-12.12

Clinical Objectives

The overall objective is to provide an effective therapy for solid tumors comprising CD40-expressing carcinoma cells by targeting them with an anti-CD40 IgG1. These tumors include lung, breast, colon, ovarian, and skin carcinomas. The signal for these diseases is determined in phase II although some measure of activity may be obtained in phase I. Initially the agent is studied as a single agent, but will be combined with other agents, chemotherapeutics, and other antibodies, as development proceeds.

Phase I

Evaluate safety and pharmacokinetics—dose escalation in subjects with above-mentioned solid tumors.

Choose dose based on safety, tolerability, and change in serum markers of CD40. In general an MTD is sought but other indications of efficacy (depletion of CD40+ tumor cells, etc.) may be adequate for dose finding.

Consideration of more than one dose especially for different indications, e.g., the breast cancer dose may be different than the ovarian cancer dose. Thus, some dose finding may be necessary in phase II.

Patients are dosed weekly with real-time pharmacokinetic (Pk) sampling. Initially a 4-week cycle is the maximum dosing allowed. The Pk may be highly variable depending on the disease studied, density of CD40 etc.

This trial(s) is open to subjects with CD40-expressing solid tumors, including lung, breast, colon, ovarian, and skin carcinomas.

Decision to discontinue or continue studies is based on safety, dose, and preliminary evidence of anti-tumor activity.

Activity of drug as determined by response rate is determined in Phase II.

Identify dose(s) for Phase II.

Phase II

Several trials will be initiated in the above-mentioned tumor types with concentration on lung, ovarian, and breast cancer. More than one dose, and more than one schedule may be tested in a randomized phase II setting.

In each disease, target a population that has failed current standard of care:
   Lung: surgery, radiation therapy, chemotherapy
   Ovarian: surgery, radiation therapy, chemotherapy
   Breast: surgery, radiation therapy, chemotherapy, hormone therapy
      Decision to discontinue or continue with study is based on proof of therapeutic concept in Phase II
      Determine whether surrogate marker can be used as early indication of clinical efficacy
      Identify doses for Phase III
Phase III
   Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.
Chapter V: Methods of Therapy for B Cell-Related Cancers V. A. Overview This invention is directed to combination therapy with anti-CD40 antibodies and anti-CD20 antibodies as described herein below in sections V.B-V.F and in commonly owned U.S. Provisional Application No. 60/613,885, filed Sep. 28, 2004 and International Application No. PCT/US2004/037159, filed Nov. 4, 2004 and published as WO 2005/044307, which corresponds to copending U.S. National-Phase application Ser. No. 10/578,401, which published as U.S. Application Publication No. 20070098718, all of which are entitled "Methods of Therapy for B Cell-Related Cancers"; the contents of each of which are herein incorporated by reference in their entirety.

In this manner, this invention is directed to methods of combination antibody therapy for B cell-related cancers, particularly cancers comprising neoplastic cells expressing the CD40 and CD20 cell surface antigens. CD40 is a 55 kDa cell-surface antigen present on the surface of both normal and neoplastic human B cells, dendritic cells, other antigen presenting cells (APCs), endothelial cells, monocytic cells, and epithelial cells. Binding of the CD40 ligand to CD40 on the B cell membrane provides a positive costimulatory signal that stimulates B cell activation and proliferation, resulting in B cell maturation into a plasma cell that secretes high levels of soluble immunoglobulin. Transformed cells from patients with low- and high-grade B cell lymphomas, B cell acute lymphoblastic leukemia, multiple myeloma, chronic lymphocytic leukemia, and Hodgkin's disease express CD40. CD40 expression is also detected in two-thirds of acute myeloblastic leukemia cases and 50% of AIDS-related lymphomas. Malignant B cells from several tumors of B-cell lineage express a high level of CD40 and appear to depend on CD40 signaling for survival and proliferation. This renders the CD40 antigen a potential target for anti-cancer therapy.

Leukemia, lymphoma, and myeloma strike over 100,000 individuals every year in the U.S. alone. A large percentage of these cases are characterized by an outgrowth of neoplastic B cells expressing the CD40 and CD20 antigens. CD40 is a 55 kDa cell-surface antigen present on the surface of both normal and neoplastic human B cells, dendritic cells, other antigen presenting cells (APCs), endothelial cells, monocytic cells, and epithelial cells. Binding of the CD40 ligand to CD40 on the B cell membrane provides a positive costimulatory signal that stimulates B cell activation and proliferation, resulting in B cell maturation into a plasma cell that secretes high levels of soluble immunoglobulin. Transformed cells from patients with low- and high-grade B cell lymphomas, B cell acute lymphoblastic leukemia, multiple myeloma, chronic lymphocytic leukemia, and Hodgkin's disease express CD40. CD40 expression is also detected in two-thirds of acute myeloblastic leukemia cases and 50% of AIDS-related lymphomas. Malignant B cells from several tumors of B-cell lineage express a high level of CD40 and appear to depend on CD40 signaling for survival and proliferation. This renders the CD40 antigen a potential target for anti-cancer therapy.

CD20 is expressed early in B cell differentiation and remains on the cell surface throughout B cell development. CD20 is involved in B cell activation, is expressed at very high levels on neoplastic B cells, and is a clinically recognized therapeutic target (see, for example, Hooijberg et al. (1995) *Cancer Research* 55:2627). Antibodies targeting CD20, such as Rituxan®, have been approved by the U.S. Food and Drug Administration for the treatment of non-Hodgkin's lymphoma (see, for example, Boye et al. (2003) *Ann. Oncol.* 14:520). Rituxan® has been shown to be an effective treatment for low-, intermediate-, and high-grade non-Hodgkin's lymphoma (NHL) (see, for example, Maloney et al. (1994) *Blood* 84:2457-2466); McLaughlin et al. (1998) *J. Clin. Oncol.* 16:2825-2833; Maloney et al. (1997) *Blood* 90:2188-2195; Hainsworth et. al. (2000) *Blood* 95:3052-3056; Colombat et al. (2001) *Blood* 97:101-106; Coiffier et al. (1998) *Blood* 92:1927-1932); Foran et al. (2000) *J. Clin. Oncol.* 18:317-324; Anderson et al. (1997) *Biochem. Soc. Trans.* 25:705-708; Vose et al. (1999) *Ann. Oncol.* 10:58a).

Though the exact mechanism of action is not known, evidence indicates that the anti-lymphoma effects of Rituxan® are in part due to complement-mediated cytotoxicity (CMC), antibody-dependent cell-mediated cytotoxicity (ADCC), inhibition of cell proliferation, and finally direct induction of apoptosis. Some patients, however, become resistant to treatment with Rituxan® (Witzig et al. (2002) *J. Clin. Oncol.* 20:3262; Grillo-Lopez et al. (1998) *J. Clin. Oncol.* 16:2825; Jazirehi et al. (2003) *Mol. Cancer Ther.* 2:1183-1193). For example, some patients lose CD20 expression on malignant B cells after anti-CD20 antibody therapy (Davis et al. (1999) *Clin. Cancer Res.* 5:611). Furthermore, 30% to 50% of patients with low-grade NHL exhibit no clinical response to this monoclonal antibody (Hainsworth et. al. (2000) *Blood* 95:3052-3056; Colombat et al. (2001) *Blood* 97:101-106). For patients developing resistance to this monoclonal antibody, or having a B cell lymphoma that is resistant to initial therapy with this antibody, alternative forms of therapeutic intervention are needed.

Thus, there is a need for treatment regimens for B cell-related cancers that do not create antibody resistance and which can provide effective therapy in the event antibody resistance occurs. Consequently, the discovery of a combination antibody therapy with superior anti-tumor activity compared to single-agent Rituxan® could drastically improve methods of cancer therapy for individuals with myelomas, leukemias, and lymphomas, particularly B cell lymphomas.

V. B. Combination Therapy for Treatment of B Cell-Related Cancers

As used in this invention, "anti-CD40 antibody" encompasses any antibody that specifically recognizes the CD40 cell surface antigen, including polyclonal antibodies, monoclonal antibodies, single-chain antibodies, and fragments thereof such as Fab, F(ab')$_2$, F$_v$, and other fragments that retain the antigen-binding function of the parent anti-CD40 antibody. Of particular interest for practicing the methods of the present invention are anti-CD40 antibodies or antigen-binding fragments thereof that have the binding properties exhibited by the CHIR-5.9 and CHIR-12.12 human anti-CD40 monoclonal antibodies described herein above in Chapter I.

As used herein, "anti-CD20 antibody" encompasses any antibody that specifically recognizes the CD20 cell surface antigen, including polyclonal antibodies, monoclonal antibodies, single-chain antibodies, and fragments thereof such as Fab, F(ab')$_2$, F$_v$, and other fragments that retain the antigen-binding function of the parent anti-CD20 antibody. Of particular interest to the methods of the present invention are anti-CD20 antibodies or antigen-binding fragments thereof that have the binding properties exhibited by the IDEC-C2B8 monoclonal antibody described herein below.

For purposes of this invention, the term "synergy" is used to describe a combined effect of two or more active agents that is greater than the sum of the individual effects of each respective active agent. Thus, where the combined effect of two or more agents results in "synergistic inhibition" of an activity or process, for example, tumor growth, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

The terms "therapeutically effective dose," "therapeutically effective amount," or "effective amount" are intended to mean an amount of the antagonist anti-CD40 antibody (or antigen-binding fragment thereof) that, when administered in combination with an amount of the anti-CD20 antibody (or antigen-binding fragment thereof), brings about a positive therapeutic response with respect to treatment of a subject for a cancer comprising neoplastic B cells.

The present invention is directed to methods for treating a subject having a cancer characterized by neoplastic B cell growth. Such neoplastic B cells include, but are not limited to, neoplastic B cells derived from lymphomas including low-, intermediate-, and high-grade B cell lymphomas, immunoblastic lymphomas, non-Hodgkin's lymphomas, Hodgkin's disease, Epstein-Barr Virus (EBV) induced lymphomas, and AIDS-related lymphomas, as well as B cell acute lymphoblastic leukemias, myelomas, chronic lymphocytic leukemias, acute myeloblastic leukemias, and the like.

The methods of the invention encompass combination antibody therapy with an antagonist anti-CD40 antibody, or antigen-binding fragment thereof, and an anti-CD20 antibody, or antigen-binding fragment thereof. The methods of the invention are especially useful for the treatment of cancers comprising neoplastic B cells expressing both the CD40 and CD20 cell surface antigens, such as B cell lymphomas. Examples of lymphomas that may express the CD40 and CD20 antigen(s) include, but are not limited to, B cell acute lympohoblastic leukemia, Hodgkin's disease, diffuse small lymphocytic lymphoma, prolymphocytic leukemia, mucosal associated lymphoid tissue lymphoma, monocytoid B cell lymphoma, splenic lymphoma, lymphomatoid granulomatosis, intravascular lymphomatosis, immunoblastic lymphoma, AIDS-related lymphoma, and the like.

Thus, the methods of the invention find use in the treatment of non-Hodgkin's lymphomas related to abnormal, uncontrollable B cell proliferation or accumulation. For purposes of the present invention, such lymphomas will be referred to according to the Working Formulation classification scheme, that is those B cell lymphomas categorized as low grade, intermediate grade, and high grade (see "The Non-Hodgkin's Lymphoma Pathologic Classification Project," *Cancer* 49(1982):2112-2135). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the methods of the invention are useful in the therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), hairy cell leukemia, plasmacytoma/myeloma, diffuse large cell B cell lymphoma of the subtype primary mediastinal (thymic), Burkitt's lymphoma, and Burkitt's like high-grade B cell lymphoma; acute leukemias; acute lymphocytic leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); chronic lymphocytic leukemia; polycythemia vera; multiple myeloma; Waldenstrom's macroglobulinemia; heavy chain disease; and unclassifiable low-grade or high-grade B cell lymphomas.

In particular, the methods of the invention are useful for treating B cell lymphomas, including those listed above, that are refractory to (i.e., resistant to, or have become resistant to) first-line oncotherapeutic treatments. The term "oncotherapeutic" is intended to mean a treatment for cancer such as chemotherapy, surgery, radiation therapy, single anti-cancer antibody therapy, and combinations thereof.

"Treatment" is herein defined as the application or administration of an antagonist anti-CD40 antibody or antigen-binding fragment thereof to a subject, or application or administration of an antagonist anti-CD40 antibody or fragment thereof to an isolated tissue or cell line from a subject, in combination with the application or administration of an anti-CD20 antibody or antigen-binding fragment thereof to the subject, or to an isolated tissue or cell line from the subject, where the subject has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the combination of these antibodies or antigen-binding fragments thereof can be applied or administered to the subject, or to the isolated tissue or cell line from the subject, as part of a single pharmaceutical composition, or alternatively as part of individual pharmaceutical compositions, each comprising either the anti-CD40 antibody (or antigen binding fragment thereof) or anti-CD20 antibody (or antigen-binding fragment thereof), where the subject has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

Combination therapy with anti-CD20 antibodies (or antigen-binding fragments thereof) and antagonist anti-CD40 antibodies (or antigen-binding fragments thereof) provides a therapeutic benefit that is greater than that provided by the use of either of these anti-cancer agents alone. In addition, these two types of antibodies can be used in combination to treat tumors that are refractory to treatment with single antibody therapy, particularly anti-CD20 antibody therapy, either as a result of initial resistance to the single antibody therapy or as a result of resistance that develops during one or more time courses of therapy with the single antibody. In yet other embodiments, combination therapy with these two antibodies has a synergistic therapeutic effect against tumors that are refractory or non-refractory (i.e., responsive) to single antibody therapy. In some embodiments, the methods of the invention comprise combination therapy with the anti-CD20 monoclonal antibody IDEC-C2B8 and the anti-CD40 monoclonal antibody CHIR-12.12. In other embodiments, the methods of the invention comprise combination therapy with the anti-CD20 monoclonal antibody IDEC-C2B8 and the anti-CD40 monoclonal antibody CHIR-5.9. In yet other embodiments, the methods of the invention comprise combination therapy with an antigen-binding fragment of the anti-CD20 monoclonal antibody IDEC-C2B8 and an antigen-binding fragment of the anti-CD40 monoclonal antibody CHIR-12.12. or CHIR-5.9. In alternative embodiments, the methods of the invention comprise combination therapy with the anti-CD20 monoclonal antibody IDEC-C2B8 and an antigen-binding fragment of the anti-CD40 monoclonal antibody CHIR-12.12 or CHIR-5.9. In other embodiments, the methods of the invention comprise combination therapy with an antigen-binding fragment of the anti-CD20 monoclonal antibody IDEC-C2B8 and the anti-CD40 monoclonal antibody CHIR-12.12 or CHIR-5.9. The combination therapy described herein may comprise other variations, as long as both the CD20 and CD40 antigen are targeted in the treatment process.

Multiple parameters can be indicative of treatment efficacy. These include, but are not limited to, a reduction in the size of the tumor mass; a reduction in metastatic invasiveness of the tumor; a reduction in the rate of tumor growth; a decrease in severity or incidence of tumor-related sequelae such as cachexia and ascites production; a decrease and/or prevention of tumor-related complications such as pathologic bone fractures, autoimmune hemolytic anemia, prolymphocytic transformation, Richter's syndrome, and the like; sensitization of the tumor to chemotherapy and other treatments; an increased patient survival rate; an increase in observed clinical correlates of improved prognosis such as increased tumor infiltrating lymphocytes and decreased tumor vascularization; and the like. Thus, in some embodiments, administration of the combination of these two types of antibodies will result in an improvement of one or more of these parameters in a patient (i.e., subject) undergoing treatment. In other embodiments, the improvements in the patient will be synergistic with regard to some parameters, but additive with regard to others.

By "positive therapeutic response" with respect to cancer treatment is intended an improvement in the disease in association with the anti-tumor activity of these antibodies or fragments thereof, and/or an improvement in the symptoms associated with the disease. That is, an anti-proliferative effect, the prevention of further tumor outgrowths, a reduction in tumor size, a reduction in the number of cancer cells, and/or a decrease in one or more symptoms mediated by neoplastic B cells can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, flow cytometry or fluorescence-activated cell sorter (FACS) analysis, bioluminescent imaging, for example, luciferase imaging, bone scan imaging, and tumor biopsy sampling including bond marrow aspiration (BMA). In addition to these positive therapeutic responses, the subject undergoing therapy may experience the beneficial effect of an improvement in the symptoms associated with the disease. Thus, for B cell tumors, the subject may experience a decrease in the so-called B symptoms, i.e., night sweats, fever, weight loss, and/or urticaria.

By "therapeutically effective dose," "therapeutically effective amount," or "effective amount" is intended an amount of the antagonist anti-CD40 antibody (or antigen-binding fragment thereof) that, when administered in combination with an amount of the anti-CD20 antibody (or antigen-binding fragment thereof), brings about a positive therapeutic response with respect to treatment of a subject for a cancer comprising neoplastic B cells. In some embodiments of the invention, a therapeutically effective dose of either the anti-CD20 antibody (or antigen-binding fragment thereof) or antagonist anti-CD40 antibody (or antigen-binding fragment thereof) is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose of the antibody combination useful in the practice of the invention or multiple administrations of a therapeutically effective dose of the antibody combination.

One method of predicting clinical efficacy is to measure the effects of combination therapy with these antibodies in a suitable model; for example, the use of the combination of an anti-CD20 antibody and an antagonist anti-CD40 antibody in murine cancer models. These models include the nude mouse xenograft tumor models such as those using the human Burkitt's lymphoma cell lines known as Namalwa and Daudi. In some embodiments, anti-tumor activity is assayed in a staged nude mouse xenograft tumor model using the Daudi human lymphoma cell line as described in U.S. Patent Application Ser. No. 60/525,579, and International Application No. PCT/US2004/037152. A staged nude mouse xenograft tumor model cell line is generally more effective at distinguishing the therapeutic efficacy of a given antibody than is an unstaged model, as in the staged model antibody dosing is initiated only after the tumor has reached a measurable size.

In the unstaged model, antibody dosing is initiated generally within about 1 day of tumor inoculation and before a palpable tumor is present. The ability of an antibody to exhibit increased anti-tumor activity in a staged model is a strong indication that the antibody will be therapeutically effective.

The methods of the invention comprise using combination therapy. The term "combination" is used in its broadest sense and means that a subject is treated with at least two therapeutic regimens. Thus, "combination antibody therapy" is intended to mean a subject is treated with at least two antibody regimens, more particularly, with at least one anti-CD20 antibody (or antigen-binding fragment thereof) in combination with at least one anti-CD40 antibody (or antigen-binding fragment thereof), but the timing of administration of the different antibody regimens can be varied so long as the beneficial effects of the combination of these antibodies is achieved. Treatment with an anti-CD20 antibody (or antigen-binding fragment thereof) in combination with an antagonist anti-CD40 antibody (or antigen-binding fragment thereof) can be simultaneous (concurrent), consecutive (sequential), or a combination thereof. Therefore, a subject undergoing combination antibody therapy can receive both antibodies at the same time (i.e., simultaneously) or at different times (i.e., sequentially, in either order, on the same day, or on different days), so long as the therapeutic effect of the combination of both substances is caused in the subject undergoing therapy. In some embodiments, the combination of antibodies will be given simultaneously for one dosing, but other dosings will include sequential administration, in either order, on the same day, or on different days. Sequential administration may be performed regardless of whether the subject responds to the first monoclonal antibody administration. Where the two antibodies are administered simultaneously, they can be administered as separate pharmaceutical compositions, each comprising either the anti-CD20 antibody (or antigen-binding fragment thereof) or the antagonist anti-CD40 antibody (or antigen-binding fragment thereof), or can be administered as a single pharmaceutical composition comprising both of these anti-cancer agents.

Moreover, the treatment can be accomplished with varying doses as well as dosage regimens. In some embodiments, the dose of one monoclonal antibody will differ from the dose administered for the other monoclonal antibody, as long as the combination of these doses is effective at treating any one or more of a number of therapeutic parameters. These treatment regimens are based on doses and dosing schedules that maximize therapeutic effects, such as those described above. Those skilled in the art recognize that a dose of any one monoclonal antibody may not be therapeutically effective when administered individually, but will be therapeutically effective when administered in combination with the other antibody. See, for example, FIG. 24 in which anti-CD20 antibody administered alone was therapeutically ineffective, while the antagonist anti-CD40 antibody administered alone significantly inhibited the growth of the rituximab-resistant human lymphoma xenograft. When these two antibodies were administered in combination, synergistic anti-tumor activity was observed. Thus, in some embodiments, the therapeutically effective dose of a combination of anti-CD20 antibody and antagonistic anti-CD40 antibody may comprise doses of individual active agents that, when administered alone, would not be therapeutically effective or would be less therapeutically effective than when administered in combination with each other.

In some embodiments, the antibodies can be administered in equivalent amounts. Thus, where an equivalent dosing regimen is contemplated, the antagonist anti-CD40 antibody, for example, the anti-CD40 monoclonal antibody CHIR-12.12 or CHIR-5.9, is dosed at about 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, or 10 mg/kg, and the anti-CD20 antibody, for example, IDEC-C2B8 (Rituxan®) is also dosed at the equivalent dose of about 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, and 10 mg/kg, respectively. In other embodiments, these antibodies can be administered in non-equivalent amounts.

Those skilled in the art recognize that the methods of combination antibody therapy disclosed herein may be used before, after, or concurrently with other forms of oncotherapy. Such oncotherapy can include chemotherapy regimens such as treatment with CVP (cyclophosphamide, vincristine and prednisone), CHOP (cyclophosphamide, doxorubicin, vincristine and prednisone), ICE (ifosfamide, carboplatin, and etoposide), Mitozantrone, Cytarabine, DVP (daunorubicin, prednisone, and vincristine), ATRA (all-trans-retinoic acid), Idarubicin, hoelzer chemotherapy regime, La La chemotherapy regime, ABVD (adriamycin, bleomycin, vinblastine, and dacarbazine), CEOP (cyclophosphamide, epirubicin, vincristine, and prednisone), CEOP-BE (cyclophosphamide, epirubicin, vincristine, prednisone, bleomycin, and etoposide), 2-CdA (2-chlorodeoxyadenosine (2-CDA), FLAG & IDA (fludarabine, cytarabine, and idarubicin; with or without subsequent G-CSF treatment), VAD (vincristine, doxorubicin, and dexamethasone), M & P (melphalan and prednisone), C-Weekly (cyclophosphamide and prednisone), ABCM (adriamycin (doxorubicin), BCNU, cyclophosphamide, and melphalan), MOPP (nitrogen mustard, oncovin, procarbazine, and prednisone), and DHAP (dexamethasone, high-dose ara-C, and platinol). Alternatively, such oncotherapies can include radiation treatment, including myleoablative therapies. Thus, the methods of the invention find use as a concurrent treatment to kill residual tumor cells, either in vivo or ex vivo, after such oncotherapies.

V. C. Anti-CD40 and Anti-CD20 Antibodies for Use in Combination Therapy for Treating B Cell-Related Cancers Anti-CD40 and Anti-CD20 Antibodies.

Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674,492; 5,874,082; 5,677,165; 6,056,959; WO 00/63395; International Publication Nos. WO 02/28905 and WO 02/28904; Gordon et al. (1988) *J. Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J. Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference.

Of particular interest to the present invention are anti-CD40 antibodies that specifically bind a human CD40 antigen expressed on the surface of a human cell and are free of significant agonist activity but exhibit antagonist activity when bound to the CD40 antigen on a human CD40-expressing cell, including normal and neoplastic (whether malignant or benign) human B cells. In some embodiments, their binding to CD40 displayed on the surface of human cells results in inhibition of proliferation and differentiation of these human cells. Thus, the antagonist anti-CD40 antibodies suitable for use in the methods of the invention include those monoclonal antibodies that can exhibit antagonist activity toward normal and neoplastic human cells expressing the cell-surface CD40 antigen. These anti-CD40 antibodies and antigen-binding fragments thereof are referred to herein as "antagonist anti-CD40 antibodies." Such antibodies include, but are not limited to, the fully human monoclonal antibodies CHIR-5.9 and CHIR-12.12, and monoclonal antibodies having the binding characteristics of monoclonal antibodies CHIR-5.9 and CHIR-12.12. These monoclonal antibodies, which can be recombinantly produced, are described herein above in Chapter I. These monoclonal antibodies are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety.

In addition to the monoclonal antibodies CHIR-5.9 and CHIR-12.12, other anti-CD40 antibodies that would be useful in practicing the methods of the invention described herein include, but are not limited to: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen. Those skilled in the art recognize that the antibodies and antigen-binding fragments of these antibodies suitable for use in the methods disclosed herein include antibodies and antigen-binding fragments thereof that are produced recombinantly using methods well known in the art and described herein below, and include, for example, monoclonal antibodies CHIR-5.9 and CHIR-12.12 that have been recombinantly produced.

Anti-CD20 antibodies suitable for use in the methods of the invention specifically bind a human CD20 antigen expressed on the surface of a human cell. By "CD20 antigen" is intended a 33-37 kDa non-glycosylated transmembrane protein that is expressed on lineage-committed B cells from the pre-B cell stage to the B cell lymphoblast stage (GenBank Accession No. X12530; Barclay et al. (1997) *The Leucocyte Antigen Facts Book* (2d ed.; Academic Press, San Diego). The CD20 receptor is displayed on the surface of B cell types, as described elsewhere herein. By "displayed on the surface" and "expressed on the surface" is intended that all or a portion of the CD20 antigen is exposed to the exterior of the cell.

Anti-CD20 antibodies are known in the art. See, for example, U.S. Pat. Nos. 5,595,721, 6,399,061, and 6,455,043. Human and chimeric anti-CD20 antibodies are particularly useful in the practice of the methods of the invention. Examples of chimeric anti-CD20 antibodies include, but are not limited to, IDEC-C2B8, available commercially under the name Rituxan® (IDEC Pharmaceuticals Corp., San Diego, Calif.) and described in U.S. Pat. Nos. 5,736,137, 5,776,456, and 5,843,439; the chimeric antibodies described in U.S. Pat. No. 5,750,105; and those antibodies described in U.S. Pat. Nos. 5,500,362; 5,677,180; 5,721,108; and 5,843,685; the contents of each of which are herein incorporated by reference in their entirety. Anti-CD20 antibodies of murine origin are also suitable for use in the methods of the present invention. Examples of such murine anti-CD20 antibodies include, but are not limited to, the B1 antibody (described in U.S. Pat. No. 6,015,542); the IF5 antibody (see Press et al. (1989) *J. Clin. Oncol.* 7:1027); NKI-B20 and BCA-B20 anti-CD20 antibodies (described in Hooijberg et al. (1995) *Cancer Research* 55:840-846); and IDEC-2B8 (available commercially from IDEC Pharmaceuticals Corp., San Diego, Calif.); the 2H7 antibody (described in Clark et al. (1985) *Proc. Natl. Acad. Sci. USA* 82:1766-1770; and others described in Clark et al. (1985) supra and Stashenko et al. (1980) *J. Immunol.* 125:1678-1685.

The anti-CD20 antibodies useful in the practice of the invention can have one or many mechanisms of action. Although the methods of the invention are not bound by any particular mechanism of action, anti-CD20 antibodies have been shown to induce at least antibody-dependent cell-mediated cytotoxicity (ADCC), complement-dependent cytotoxicity (CDC), down-regulation of proliferation, and apoptosis in target cells. Such antibodies include, but are not limited to, the antibody IDEC-C2B8 (Biogen Idec Pharmaceuticals Corp., Cambridge, Mass.; commercially available under the tradename Rituxan®, also referred to as rituximab), which is a chimeric anti-CD20 monoclonal antibody containing human IgG1 and kappa constant regions with murine variable regions isolated from a murine anti-CD20 monoclonal antibody, IDEC-2B8 (Reff et al. (1994) *Blood* 83:435-445; see also U.S. Pat. No. 5,736,137); radiolabeled anti-CD20 antibody Zevalin® (Ibritumomab tiuxetan), manufactured by Biogen IDEC Pharmaceuticals Corp. (Cambridge, Mass.); Bexxar® (Tositumomab, which is the murine version of rituximab, combined with Iodine (I-131)-labeled Tositumomab), manufactured by Corixa Corp. (Seattle Wash.); the fully human antibody HuMax-CD20; R-1594; IMMU-106; TRU-015; AME-133; and monoclonal antibodies having the binding characteristics of IDEC-C2B8, that is the binding specificity of IDEC-C2B8 and capability of inducing one or more of the following activities when bound to CD20 antigen on CD20-expressing B cells: (1) antibody-dependent cell-mediated cytotoxicity (ADCC); (2) complement-dependent cytotoxicity (CDC), (3) down-regulation of B cell proliferation; and (4) apoptosis in target cells. In vitro and in vivo assays for measuring the ability of anti-CD20 antibodies to induce these activities are well known in the art. See, for example, the assays disclosed in U.S. Pat. No. 5,736,137, herein incorporated by reference in its entirety. Other antibodies useful in practicing the methods of the invention are murine and human anti-CD20 antibodies conjugated to radiolabels such as In-111 and Y-90 and other therapeutic agents such as toxins.

In addition to using the antagonist anti-CD40 antibodies and the anti-CD20 antibodies mentioned above, the methods of the present invention can be practiced using antibodies that have the binding characteristics of monoclonal antibodies CHIR-5.9, CHIR-12.12, or IDEC-C2B8 and competitively interfere with binding of these antibodies to their respective antigens or bind the same epitopes. One of skill in the art could determine whether an antibody competitively interferes with CHIR-5.9, CHIR-12.12, or IDEC-C2B8 binding using standard methods.

Production of Anti-CD40 and Anti-CD20 Antibodies.

The anti-CD40 antibodies and anti-CD20 antibodies for use in the methods of the present invention can be produced using any of the methods well known to those of skill in the art. Polyclonal sera may be prepared by conventional methods. In general, a solution containing the CD40 or the CD20 antigen is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 cells expressing CD40 or CD20 are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf9 (*Spodoptera frugiperda*) cells is disclosed in U.S. Pat. No. 6,004,552, incorporated herein by reference. Briefly, sequences encoding human CD40 were recombined into a baculovirus using transfer vectors. The plasmids were co-transfected with wild-type baculovirus DNA into Sf9 cells. Recombinant baculovirus-infected Sf9 cells were identified and clonally purified.

Preferably the antibody is monoclonal in nature. Monoclonal antibodies are highly specific, being directed against a single antigenic site, i.e., the CD40 or CD20 cell surface antigen. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, such as those produced by a clonal population of B cells, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Where the antagonist anti-CD40 antibodies of the invention are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. (1993) *Curr. Opinion in Immunol.* 5:256 and Phickthun (1992) *Immunol. Revs.* 130:151. As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

In some embodiments, the antagonist anti-CD40 antibody, for example, the CHIR-12.12 or CHIR-5.9 antibody, or antigen-binding fragment thereof is produced in CHO cells using the GS gene expression system (Lonza Biologics, Portsmouth, N.H.), which uses glutamine synthetase as a marker. See, also U.S. Pat. Nos. 5,122,464; 5,591,639; 5,658,759; 5,770,359; 5,827,739; 5,879,936; 5,891,693; and 5,981,216; the contents of which are herein incorporated by reference in their entirety.

The term "antigen epitope" as used herein refers to a three dimensional molecular structure (either linear or conformational) that is capable of immunoreactivity with an anti-CD40 monoclonal antibody or an anti-CD20 monoclonal antibody. Antigen epitopes may comprise proteins, protein fragments, peptides, carbohydrates, lipids, and other molecules, but for the purposes of the present invention are most commonly proteins, short oligopeptides, oligopeptide mimics (i e, organic compounds that mimic the antibody binding properties of the CD40 or CD20 antigen), or combinations thereof. Suitable oligopeptide mimics are described, inter alia, in PCT application US 91/04282.

Additionally, the term "antibody" as used herein encompasses chimeric anti-CD40 or anti-CD20 antibodies. Chimeric anti-CD40 antibodies for use in the methods of the invention have the binding characteristics of the anti-CD40 monoclonal antibody CHIR-12.12 or CHIR-5.9, while chimeric anti-CD20 antibodies for use in the methods of the invention have the binding characteristics of the anti-CD20 monoclonal antibody IDEC-C2B8. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the CD40 or CD20 cell-surface antigen. The non-human source can be any vertebrate source that can be used to generate antibodies to a human CD40 or CD20 cell-surface antigen or material comprising a human CD40 or CD20 cell-surface antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). As used herein, the phrase "immunologically active" when used in reference to chimeric anti-CD40 antibodies means a chimeric antibody that binds human CD40, or, when used in reference to chimeric anti-CD20 antibodies means a chimeric antibody that binds human CD20.

Humanized anti-CD40 and anti-CD20 antibodies represent additional anti-CD40 antibodies and anti-CD20 antibodies suitable for use in the methods of the present invention. By "humanized" is intended forms of anti-CD40 antibodies or anti-CD20 antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, e.g., Chothia et al (1987) *J. Mol. Biol.* 196:901-917; Kabat et al (1991) U.S. Dept. of Health and Human Services, NIH Publication No. 91-3242). The phrase "constant region" refers to the portion of the antibody molecule that confers effector functions. In previous work directed towards producing non-immunogenic antibodies for use in therapy of human disease, mouse constant regions were substituted by human constant regions. The constant regions of the subject humanized antibodies were derived from human immunoglobulins. However, these humanized antibodies still elicited an unwanted and potentially dangerous immune response in humans and there was a loss of affinity. Humanized anti-CD40 antibodies for use in the methods of the present invention have binding characteristics similar to those exhibited by the CHIR-5.9 and CHIR-12.12 monoclonal antibodies described herein. Humanized anti-CD20 antibodies for use in the methods of the present invention have binding characteristics similar to those exhibited by IDEC-C2B8 monoclonal antibodies described herein.

Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

Also encompassed by the term anti-CD40 antibodies or anti-CD20 antibodies are xenogeneic or modified anti-CD40 antibodies or anti-CD20 antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

Preferably, fully human antibodies to CD40 or CD20 are obtained by immunizing transgenic mice. One such mouse is obtained using XenoMouse® technology (Abgenix; Fremont, Calif.), and is disclosed in U.S. Pat. Nos. 6,075,181, 6,091,001, and 6,114,598, all of which are incorporated herein by reference. To produce the antibodies disclosed herein, mice transgenic for the human $IgG_1$ heavy chain locus and the human κ light chain locus can be immunized with Sf9 cells expressing human CD40 or human CD20. Mice can also be transgenic for other isotypes. Fully human antibodies useful in the methods of the present invention are characterized by binding properties similar to those exhibited by the CHIR-5.9, CHIR-12.12, and IDEC-C2B8 monoclonal antibodies.

Fragments of the anti-CD40 antibodies or anti-CD20 antibodies are suitable for use in the methods of the invention so long as they retain the desired affinity of the full-length antibody. Thus, a fragment of an anti-CD40 antibody will retain the ability to bind to the CD40 B cell surface antigen, and a fragment of an anti-CD20 antibody will retain the ability to bind the CD20 B cell surface antigen, respectively. Such fragments are characterized by properties similar to the corresponding full-length antibody. For example, antagonist anti-CD40 antibody fragments will specifically bind a human CD40 antigen expressed on the surface of a human cell, and are free of significant agonist activity but exhibit antagonist activity when bound to a CD40 antigen on a human CD40-expressing cell; whereas anti-CD20 antibody fragments will specifically bind CD20. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, $F(ab')_2$, and Fv fragments and single-chain antibody molecules. By "Fab" is intended a monovalent antigen-binding fragment of an immunoglobulin that is composed of the light chain and part of the heavy chain. By $F(ab')_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen-binding. For a review of sFv see Pluckthun (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al. (1992) *Bio/Technology* 10:163-167). According to another approach, $F(ab')_2$ fragments can be isolated directly from recombinant host cell culture. Other techniques for the production of antibody fragments will be apparent to the skilled practitioner.

Combinations of antibodies useful in the methods of the present invention include antagonist anti-CD40 antibodies such as the CHIR-5.9 and CHIR-12.12 monoclonal antibodies disclosed herein as well as anti-CD20 antibodies such as IDEC-C2B8 that differ in non-CDR regions; and antibodies with one or more amino acid addition(s), deletion(s), or substitution(s). The invention also encompasses de-immunized (humanized) anti-CD20 antibodies and antagonist anti-CD40 antibodies, which can be produced as described in, for example, International Publication Nos. WO 98/52976 and WO 0034317; herein incorporated by reference. In this manner, residues within the antibodies useful for the practicing the methods of the invention are modified so as to render the antibodies non- or less immunogenic to humans while retaining their binding specificity and biological activity, wherein such activity is measured by assays noted elsewhere herein. Also included within the scope of the claims are fusion proteins comprising anti CD20 antibodies or antagonist anti-CD40 antibodies, or a fragment thereof, which fusion proteins can be synthesized or expressed from corresponding polynucleotide vectors, as is known in the art. Such fusion proteins are described with reference to conjugation of antibodies as noted below.

The antibodies useful in practicing the methods of the invention can have sequence variations produced using methods described in, for example, Patent Publication Nos. EP 0 983 303 A1, WO 00/34317, and WO 98/52976, incorporated herein by reference. For example, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Any such conservative or non-conservative substitutions can be made using art-recognized methods, such as those noted elsewhere herein, and the resulting antibodies will fall within the scope of the invention. The variant antibodies can be routinely tested for antagonist activity, affinity, and specificity using methods described herein.

An antagonistic anti-CD40 antibody produced by any of the methods described above, or any other method not disclosed herein, will fall within the scope of the invention if it possesses at least one of the following biological activities in vitro or in vivo: inhibition of immunoglobulin secretion by normal human peripheral B cells stimulated by T cells; inhibition of proliferation of normal human peripheral B cells stimulated by Jurkat T cells; inhibition of proliferation of normal human peripheral B cells stimulated by CD40L-expressing cells or soluble CD40; and inhibition of proliferation of human malignant B cells as noted below. These assays can be performed as described in copending provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, the contents of each of which are herein incorporated by reference in their entirety. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

A representative assay to detect antagonistic anti-CD40 antibodies specific to the CD40-antigen epitopes identified herein or is a "competitive binding assay". Competitive binding assays are serological assays in which unknowns are detected and quantitated by their ability to inhibit the binding of a labeled known ligand to its specific antibody. This is also referred to as a competitive inhibition assay. In a representative competitive binding assay, labeled CD40 polypeptide is precipitated by candidate antibodies in a sample, for example, in combination with monoclonal antibodies raised against one or more epitopes of the monoclonal antibodies of the invention. Anti-CD40 antibodies that specifically react with an epitope of interest can be identified by screening a series of antibodies prepared against a CD40 protein or fragment of the protein comprising the particular epitope of the CD40 protein of interest. For example, for human CD40, epitopes of interest include epitopes comprising linear and/or nonlinear amino acid residues of the short isoform of human CD40 (see GenBank Accession No. NP_690593) set forth in FIG. 5B (SEQ ID NO:10), encoded by the sequence set forth in FIG. 5A (SEQ ID NO:9; see also GenBank Accession No. NM_152854), or of the long isoform of human CD40 (see GenBank Accession Nos. CAA43045 and NP_001241) set forth in FIG. 5D (SEQ ID NO:12), encoded by the sequence set forth in FIG. 5C (SEQ ID NO:11; see GenBank Accession Nos. X60592 and NM_001250). Alternatively, competitive binding assays with previously identified suitable antagonist anti-CD40 antibodies could be used to select monoclonal antibodies comparable to the previously identified antibodies.

An anti-CD20 antibody produced by any of the methods described above, or any other method not disclosed herein, will fall within the scope of the invention if it possesses at least one of the following biological activities: initiation of antibody-dependent cell-mediated cytotoxicity against a CD20 expressing cell; initiation of complement-mediated cytotoxicity against a CD20 expressing cell; delivery of a cytotoxin or radionuclide to a CD20 expressing cell; inhibition of immunoglobulin secretion by normal human peripheral B cells stimulated by T cells; inhibition of proliferation of normal human peripheral B cells stimulated by Jurkat T cells; inhibition of proliferation of normal human peripheral B cells stimulated by CD40L-expressing cells or soluble CD40; and inhibition of proliferation of human malignant B cells as noted below. Assays for detecting these activities are well known in the art, including those disclosed in U.S. Pat. No. 5,736,137, herein incorporated by reference in its entirety.

Any of the previously described antagonist anti-CD40 antibodies (or antigen-binding fragments thereof) or anti-CD20 antibodies (or antigen-binding fragments thereof) may be conjugated (e.g., labeled or conjugated to a therapeutic moiety or to a second antibody), as described herein above in Chapter I, prior to use in the methods for treating B cell-related cancers. In some embodiments, the anti-CD20 antibody is conjugated to the anti-CD40 antibody. In yet other embodiments, a single antibody comprises dual specificity toward both CD20 and CD40. Such bispecific antibodies are known in the art. See, for example, U.S. Pat. No. 5,959,084.

Variants of Antagonist Anti-CD40 Antibodies and Anti-CD20 Antibodies.

Suitable biologically active variants of the antagonist anti-CD40 antibodies or anti-CD20 antibodies can be used in the methods of the present invention. Such variants will retain the desired binding properties of the parent antibody, i.e., the parent antagonist anti-CD40 antibody or parent anti-CD20 antibody. Methods for making antibody variants are generally available in the art.

For example, amino acid sequence variants of an anti-CD20 antibody, for example IDEC-C2B8 described herein, or an antagonist anti-CD40 antibody, for example, the CHIR-5.9 or CHIR-12.12 monoclonal antibody described herein, can be prepared by mutations in the cloned DNA sequence encoding the antibody of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the anti-CD-20 antibody or antagonist anti-CD40 antibody polypeptide of interest, modifications are made such that variants continue to possess the desired activity, i.e., similar binding affinity and are capable of specifically binding to a human CD20 or CD40 antigen expressed on the surface of a human cell, respectively, and in the case of anti-CD40 being free of significant agonist activity but exhibiting antagonist activity when bound to a CD40 antigen on a human CD40-expressing cell. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an antagonist anti-CD40 antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference anti-CD20 antibody or antagonist anti-CD40 antibody have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference anti-CD20 antibody, for example IDEC-C2B8 as described herein, or reference antagonist anti-CD40 antibody molecule, for example, the CHIR-5.9 or CHIR-12.12 monoclonal antibody described herein, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antagonist anti-CD40 antibody or reference anti-CD20 antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The precise chemical structure of a polypeptide capable of specifically binding CD40 and retaining antagonist activity or a polypeptide specifically binding CD20, particularly when bound to antigen on malignant B cells, depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of antagonist anti-CD40 antibodies or anti-CD20 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CD40 antibody or an anti-CD20 antibody used herein so long as the binding properties of the anti-CD40 antibody (including antagonist activity) or anti-CD20 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desirable activity of the unmodified antibody do not remove the polypeptide sequence from the definition of the anti-CD40 and anti-CD20 antibodies of interest as used herein.

The art provides substantial guidance regarding the preparation and use of polypeptide variants. In preparing the antibody variants, one of skill in the art can readily determine which modifications to the native protein nucleotide or amino acid sequence will result in a variant that is suitable for use as a therapeutically active component of a pharmaceutical composition used in the methods of the present invention.

V. D. Pharmaceutical Formulations and Modes of Administration

The combination of the anti-CD20 antibody (or antigen-binding fragment thereof) and the antagonist anti-CD40 antibody (or antigen-binding fragment thereof) is administered at a concentration that is therapeutically effective to prevent or treat a cancer characterized by neoplastic B cell growth, particularly cancers comprising neoplastic B cells expressing both the CD40 and CD20 antigens. To accomplish this goal, the antibodies may be formulated, alone or in combination, using a variety of acceptable excipients known in the art, as noted herein above in Chapter I. Typically, the antibodies are administered by injection, either intravenously, intraperitoneally, or subcutaneously. Methods to accomplish this administration are known to those of ordinary skill in the art, and include those methods described hereinabove in Chapter I. It may also be possible to obtain compositions that may be topically or orally administered, or which may be capable of transmission across mucous membranes. Intravenous administration occurs preferably by infusion over a period of time, as described herein above in Chapter I. Possible routes of administration, preparation of suitable formulations, therapeutically effective amounts to be administered, and suitable dosing regimens are as described herein above in Chapter I, and summarized herein below. See also commonly owned U.S. Provisional Application No. 60/613,885.

Intravenous administration occurs preferably by infusion over a period of about 1 to about 10 hours, more preferably over about 1 to about 8 hours, even more preferably over about 2 to about 7 hours, still more preferably over about 4 to about 6 hours, depending upon the antibody being administered. The initial infusion with the pharmaceutical composition may be given over a period of about 4 to about 6 hours with subsequent infusions delivered more quickly. Subsequent infusions may be administered over a period of about 1 to about 6 hours, including, for example, about 1 to about 4 hours, about 1 to about 3 hours, or about 1 to about 2 hours.

A pharmaceutical composition of the invention is formulated to be compatible with its intended route of administration. Examples of possible routes of administration include parenteral, (e.g., intravenous (IV), intramuscular (IM), intradermal, subcutaneous (SC), or infusion), oral and pulmonary (e.g., inhalation), nasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The antibodies are typically provided by standard technique within a pharmaceutically acceptable buffer; for example, sterile saline, sterile buffered water, propylene glycol, combinations of the foregoing, etc. The antagonist anti-CD40 antibody (or antigen-binding fragment thereof) and the anti-CD20 antibody (or antigen-binding fragment thereof) can be formulated in separate pharmaceutical compositions, or can be formulated within a single pharmaceutical composition for simultaneous administration. Methods for preparing parenterally administrable agents are described in *Remington's Pharmaceutical Sciences* (18$^{th}$ ed.; Mack Publishing Company, Eaton, Pa., 1990), herein incorporated by reference. See, also, for example, WO 98/56418, which describes stabilized antibody pharmaceutical formulations suitable for use in the methods of the present invention.

The amount of a combination of at least one anti-CD40 antibody or antigen-binding fragment thereof and at least one anti-CD20 antibody or antigen-binding fragment thereof to be administered is readily determined by one of ordinary skill in the art without undue experimentation. Factors influencing the mode of administration and the respective amount of the combination of antibodies disclosed herein include, but are not limited to, the particular disease undergoing therapy, the severity of the disease, the history of the disease, and the age, height, weight, health, and physical condition of the individual undergoing therapy. Similarly, the amount of the combination of antibodies disclosed herein to be administered will be dependent upon the mode of administration and whether the subject will undergo a single dose or multiple doses of these anti-tumor agents. Generally, a higher dosage of the combination of antibodies disclosed herein is preferred with increasing weight of the patient undergoing therapy. The dose of either the anti-CD20 antibody (or antigen-binding fragment thereof) or the antagonistic anti-CD40 antibody (or antigen-binding fragment thereof) to be administered is in the range from about 0.003 mg/kg to about 50 mg/kg, preferably in the range of 0.01 mg/kg to about 40 mg/kg. Thus, for example, the dose of any one antibody of the combination can be 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg.

In another embodiment of the invention, the method comprises administration of multiple doses of anti-CD20 antibody (or antigen-binding fragment thereof) in combination with multiple doses of antagonistic anti-CD40 antibody (or antigen-binding fragment thereof). The method may comprise administration of 1, 2, 3, 4, 5, 6, 7, 8, 9, 10, 15, 20, 25, 30, 35, 40, or more therapeutically effective doses of a pharmaceutical composition comprising either anti-CD20 antibody (or antigen-binding fragment thereof) or antagonistic anti-CD40 antibody (or antigen-binding fragment thereof), or both. The frequency and duration of administration of multiple doses of the pharmaceutical compositions can be readily determined by one of skill in the art without undue experimentation. Moreover, treatment of a subject with a therapeutically effective amount of a combination of antibodies can include a single treatment or, preferably, can include a series of treatments. In a preferred example, a subject is treated with the combination of an anti-CD20 antibody (or antigen-binding fragment thereof) and an antagonistic anti-CD40 antibody (or antigen-binding fragment thereof), where both are administered at a dose in the range of between about 0.1 to about 20 mg/kg body weight, once per week for between about 1 to about 10 weeks, preferably between about 2 to about 8 weeks, more preferably between about 3 to about 7 weeks, and even more preferably for about 4, 5, or 6 weeks. Treatment may occur annually to prevent relapse or upon indication of relapse.

It will also be appreciated that the effective dosage of antibodies or antigen-binding fragments thereof used for treatment may increase or decrease over the course of a particular treatment. Changes in dosage may result and become apparent from the results of diagnostic assays as described herein. Thus, in one embodiment, the dosing regimen includes administration of a therapeutically effective dose of the anti-CD20 antibody (or antigen-binding fragment thereof) in combination with a therapeutically effective dose of the antagonistic anti-CD40 antibody (or antigen-binding fragment thereof), where the combination is administered on days 1, 8, 15, and 22 of a treatment period. In another embodiment, the dosing regimen includes administration of a therapeutically effective dose of the anti-CD20 antibody (or antigen-binding fragment thereof) in combination with a therapeutically effective dose of the antagonist anti-CD40 antibody (or antigen-binding fragment thereof), where the combination is administered on days 1, 2, 3, 4, 5, 6, and 7 of a week in a treatment period. Further embodiments include a dosing regimen where a therapeutically effective dose of the anti-CD20 antibody (or antigen-binding fragment thereof) is administered in combination with a therapeutically effective dose of the antagonist anti-CD40 antibody (or antigen-binding fragments thereof), where the combination is administered on days 1, 3, 5, and 7 of a week in a treatment period; a dosing regimen that includes administration of a therapeutically effective dose of the anti-CD20 antibody (or antigen-binding fragment thereof) in combination with a therapeutically effective dose of the antagonist anti-CD40 antibody (or antigen-binding fragment thereof), where the combination of antibodies is administered on days 1 and 3 of a week in a treatment period; and a preferred dosing regimen that includes administration of a therapeutically effective dose of the anti-CD20 antibody (or antigen-binding fragment thereof) in combination with the antagonist anti-CD40 antibody (or antigen-binding fragments thereof) on day 1 of any given week in a treatment period. The treatment period may comprise 1 week, 2 weeks, 3 weeks, a month, 3 months, 6 months, or a year. Treatment periods may be subsequent or separated from each other by a day, a week, 2 weeks, a month, 3 months, 6 months, or a year. Treatment using a combination of antagonist anti-CD40 antibody (or antigen-binding fragment thereof) and anti-CD20 antibody (or antigen-binding fragment thereof) may comprise administration of one or both antibodies simultaneously or concurrently, as long as the treatment includes the combination of anti-CD20 antibody (or antigen-binding fragment thereof) and antagonist anti-CD40 antibody (or antigen-binding fragment thereof) at some point during treatment. The effect of the combination therapy can also be optimized by varying the timing of administration of either the anti-CD20 antibody and/or the antagonist anti-CD40 antibody treatment. Treatment with an anti-CD20 antibody or antigen-binding fragment thereof in combination with an antagonist anti-CD40 antibody or antigen-binding fragment thereof can be simultaneous (concurrent), consecutive (sequential), or a combination thereof. Therefore, a subject undergoing combination antibody therapy can receive both the anti-CD20 antibody (or antigen-binding fragment thereof) and antagonist anti-CD40 (or antigen-binding fragment thereof) at the same time (i.e., simultaneously) or at different times (i.e., sequentially, in either order, on the same day, or on different days). Thus, in some embodiments, the anti-CD20 antibody, such as Rituxan® (or antigen-binding fragment thereof) is administered simultaneously with the antagonist anti-CD40 antibody, such as the monoclonal antibody CHIR-12.12. or CHIR-5.9 (or antigen-binding fragment thereof). In other embodiments, the anti-CD20 antibody, such as Rituxan® (or antigen-binding fragment thereof) is administered first and then the antagonist anti-CD40 antibody, such as the monoclonal antibody CHIR-12.12. or CHIR-5.9 (or antigen-binding fragment thereof) is administered next. In yet other embodiments, the antagonist anti-CD40 antibody, such as the monoclonal antibody CHIR-12.12 or CHIR-5.9 (or antigen-binding fragment thereof) is administered first, and the anti-CD20 antibody, such as Rituxan® (or antigen-binding fragment thereof) is administered next. In some embodiments, the combination of anti-CD20 antibodies and antagonist anti-CD40 antibodies, such as Rituxan® and monoclonal antibodies CHIR-12.12 or CHIR-5.9, is given concurrently for one dosing, but other dosings include sequential administration, in either order, on the same day, or on different days. Where the anti-CD20 antibody such as Rituxan® and the antagonist anti-CD40 antibody such as the monoclonal antibody CHIR-12.12 or CHIR-5.9 are administered simultaneously, they can be administered as separate pharmaceutical compositions, each comprising either the anti-CD20 antibody (or antigen-binding fragment thereof) or the antagonist anti-CD40 antibody (or antigen-binding fragment thereof), or can be administered as a single pharmaceutical composition comprising both of these anti-cancer agents.

In some embodiments, the therapeutically effective doses of antagonist anti-CD40 antibody or antigen-binding fragment thereof ranges from about 0.003 mg/kg to about 50 mg/kg, from about 0.01 mg/kg to about 40 mg/kg, from about 0.01 mg/kg to about 30 mg/kg, from about 0.1 mg/kg to about 30 mg/kg, from about 0.5 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. Thus, for example, the dose of any one antagonist anti-CD40 antibody or antigen-binding fragment thereof, for example the anti-CD40 monoclonal antibody CHIR-12.12 or CHIR-5.9 or antigen-binding fragment thereof, can be 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.003 mg/kg to about 50 mg/kg. The same therapeutically effective dose of an antagonist anti-CD40 antibody or antigen-binding fragment thereof can be administered throughout each week of antibody dosing. Alternatively, different therapeutically effective doses of an antagonist anti-CD40 antibody or antigen-binding fragment thereof can be used over the course of a treatment period.

In other embodiments, the initial therapeutically effective dose of an antagonist anti-CD40 antibody or antigen-binding fragment thereof as defined elsewhere herein can be in the lower dosing range (i.e., about 0.003 mg/kg to about 20 mg/kg) with subsequent doses falling within the higher dosing range (i.e., from about 20 mg/kg to about 50 mg/kg).

In alternative embodiments, the initial therapeutically effective dose of an antagonist anti-CD40 antibody or antigen-binding fragment thereof as defined elsewhere herein can be in the upper dosing range (i.e., about 20 mg/kg to about 50 mg/kg) with subsequent doses falling within the lower dosing range (i.e., 0.003 mg/kg to about 20 mg/kg). Thus, in one embodiment, the initial therapeutically effective dose of the antagonist anti-CD40 antibody or antigen-binding fragment thereof is about 20 mg/kg to about 35 mg/kg, including about 20 mg/kg, about 25 mg/kg, about 30 mg/kg, and about 35 mg/kg, and subsequent therapeutically effective doses of the antagonist anti-CD40 antibody or antigen binding fragment thereof are about 5 mg/kg to about 15 mg/kg, including about 5 mg/kg, 8 mg/kg, 10 mg/kg, 12 mg/kg, and about 15 mg/kg.

In some embodiments of the invention, antagonist anti-CD40 antibody therapy is initiated by administering a "loading dose" of the antibody or antigen-binding fragment thereof to the subject in need of antagonist anti-CD40 antibody therapy. By "loading dose" is intended an initial dose of the antagonist anti-CD40 antibody or antigen-binding fragment thereof that is administered to the subject, where the dose of the antibody or antigen-binding fragment thereof administered falls within the higher dosing range (i.e., from about 20 mg/kg to about 50 mg/kg). The "loading dose" can be administered as a single administration, for example, a single infusion where the antibody or antigen-binding fragment thereof is administered IV, or as multiple administrations, for example, multiple infusions where the antibody or antigen-binding fragment thereof is administered IV, so long as the complete "loading dose" is administered within about a 24-hour period. Following administration of the "loading dose," the subject is then administered one or more additional therapeutically effective doses of the antagonist anti-CD40 antibody or antigen-binding fragment thereof. Subsequent therapeutically effective doses can be administered, for example, according to a weekly dosing schedule, or once every two weeks, once every three weeks, or once every four weeks. In such embodiments, the subsequent therapeutically effective doses generally fall within the lower dosing range (i.e., 0.003 mg/kg to about 20 mg/kg).

Alternatively, in some embodiments, following the "loading dose," the subsequent therapeutically effective doses of the antagonist anti-CD40 antibody or antigen-binding fragment thereof are administered according to a "maintenance schedule," wherein the therapeutically effective dose of the antibody or antigen-binding fragment thereof is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the antagonist anti-CD40 antibody or antigen-binding fragment thereof fall within the lower dosing range (i.e., 0.003 mg/kg to about 20 mg/kg), particularly when the subsequent doses are administered at more frequent intervals, for example, once every two weeks to once every month, or within the higher dosing range (i.e., from about 20 mg/kg to about 50 mg/kg), particularly when the subsequent doses are administered at less frequent intervals, for example, where subsequent doses are administered about one month to about 12 months apart.

The pharmaceutical compositions useful in the methods of the invention may comprise biologically active variants of either anti-CD20 antibody (or antigen-binding fragments thereof) or antagonistic anti-CD40 antibody (or antigen-binding fragments thereof), or both. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant antibody will serve as a therapeutically active component in the pharmaceutical composition in a manner similar to that observed for the native antagonist antibody; for example, monoclonal antibody CHIR-5.9 or CHIR-12.12 as expressed by the hybridoma cell line 5.9 or 12.12, and IDEC-C2B8, respectively. Methods are available in the art for determining whether a variant antibody retains the desired biological activity, and hence, serves as a therapeutically active component in the pharmaceutical composition. Biological activity of antibody variants can be measured using assays specifically designed for measuring activity of the native antagonist antibody, including assays described in the present invention.

Any pharmaceutical composition comprising an anti-CD20 antibody having the binding properties described herein, or an antagonist anti-CD40 antibody having the binding properties described herein, as the therapeutically active component can be used in the methods of the invention. Thus, liquid, lyophilized, or spray-dried compositions comprising one or more of the antibodies useful in the practice of the invention may be prepared as an aqueous or nonaqueous solution or suspension for subsequent administration to a subject in accordance with the methods of the invention. Each of these compositions will comprise at least one of the anti-CD20 antibodies (or antigen-binding fragment thereof) or antagonist anti-CD40 antibodies (or antigen-binding fragment thereof) as a therapeutically or prophylactically active component. By "therapeutically or prophylactically active component" is intended the antibody or antigen-binding fragment thereof is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

Formulants may be added to pharmaceutical compositions comprising antibodies useful in the practice of the invention. These formulants may include, but are not limited to, oils, polymers, vitamins, carbohydrates, amine acids, salts, buffers, albumin, surfactants, or bulking agents. Preferably carbohydrates include sugar or sugar alcohols such as mono-, di-, or polysaccharides, or water soluble glucans. The saccharides or glucans can include fructose, glucose, mannose, sorbose, xylose, maltose, sucrose, dextran, pullulan, dextrin, $\alpha$ and $\beta$ cyclodextrin, soluble starch, hydroxyethyl starch, and carboxymethylcellulose, or mixtures thereof. "Sugar alcohol" is defined as a $C_4$ to $C_8$ hydrocarbon having a hydroxyl group and includes galactitol, inositol, mannitol, xylitol, sorbitol, glycerol, and arabitol. These sugars or sugar alcohols may be used individually or in combination. The sugar or sugar alcohol concentration is between 1.0% and 7% w/v, more preferably between 2.0% and 6.0% w/v. Preferably, amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. Surfactants that can be added to the formulation are shown in EP Nos. 270,799 and 268,110.

Additionally, antibodies can be chemically modified by covalent conjugation to a polymer to increase their circulating half-life, for example. Preferred polymers and methods to attach them to peptides, are shown in U.S. Pat. Nos. 4,766, 106; 4,179,337; 4,495,285; and 4,609,546, which are all hereby incorporated by reference in their entireties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al. (1988) *J. Bio. Chem.* 263:15064-15070, and a discussion of POG/IL-2 conjugates is found in U.S. Pat. No. 4,766, 106, both of which are hereby incorporated by reference in their entireties.

Another drug delivery system for increasing circulatory half-life is the liposome. Methods of preparing liposome delivery systems are discussed in Gabizon et al. (1982) *Cancer Research* 42:4734; Cafiso (1981) *Biochem Biophys Acta* 649:129; and Szoka (1980) *Ann. Rev. Biophys. Eng.* 9:467. Other drug delivery systems are known in the art and are described in, e.g., Poznansky et al. (1980) *Drug Delivery Systems* (R. L. Juliano, ed., Oxford, N.Y.) pp. 253-315; Poznansky (1984) *Pharm Revs* 36:277.

Suitable pharmaceutical formulations for the anti-CD40 antibody or antigen-binding fragment thereof include those formulations described herein above in Chapter I, and disclosed in U.S. Provisional Application No. 60/613,885, filed Sep. 28, 2004 and International Application No. PCT/US2004/037159, filed Nov. 4, 2004 and published as WO 2005/044307, which corresponds to copending U.S. National-Phase application Ser. No. 10/578,401, which published as U.S. Application Publication No. 20070098718; the contents of each of which are herein incorporated by reference in their entirety.

V. E. Use of Antagonist Anti-CD40 Antibodies and Anti-CD20 Antibodies in the Manufacture of Medicaments for Treating B Cell-Related Cancers The present invention also provides for the use of an antagonist anti-CD40 antibody or antigen-binding fragment thereof in the manufacture of a medicament for treating a subject for a cancer characterized by neoplastic B cell growth, wherein the medicament is coordinated with treatment using an anti-CD20 antibody or antigen-binding fragment thereof. Such cancers include, but are not limited to, the B cell-related cancers discussed herein above, for example, non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lymphoblastic leukemia, myeloblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, and mantle cell lymphoma.

By "coordinated" is intended the medicament comprising the antagonist anti-CD40 antibody or antigen-binding fragment thereof is to be used either prior to, during, or after treatment of the subject using an anti-CD20 antibody or antigen-binding fragment thereof. In one such embodiment, the present invention provides for the use of the monoclonal antibody CHIR-12.12 or CHIR-5.9 in the manufacture of a medicament for treating a B cell-related cancer in a subject, wherein the medicament is coordinated with treatment using an anti-CD20 antibody, for example, rituximab (Rituxan®), or antigen-binding fragment thereof, wherein the medicament is to be used either prior to, during, or after treatment of the subject using the anti-CD20 antibody or antigen-binding fragment thereof.

In some embodiments, the medicament comprising the antagonist anti-CD40 antibody, for example, the monoclonal antibody CHIR-12.12 or CHIR-5.9 disclosed herein, or antigen-binding fragment thereof is coordinated with treatment using an anti-CD20 antibody or antigen-binding fragment thereof and at least one other type of cancer therapy. Examples of other cancer therapies include, but are not limited to, those described herein above, i.e., surgery; radiation therapy; chemotherapy, optionally in combination with autologous bone marrow transplant, where suitable chemotherapeutic agents include, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, and IL-21 therapy; steroid therapy; or other cancer therapy; where treatment with the anti-CD20 antibody or antigen-binding fragment thereof and the additional cancer therapy, or additional cancer therapies, occurs prior to, during, or subsequent to treatment of the subject with the medicament comprising the antagonist anti-CD40 antibody or antigen-binding fragment thereof, as noted herein above. Where the medicament comprising the antagonist anti-CD40 antibody or antigen-binding fragment thereof is coordinated with treatment using an anti-CD20 antibody or antigen-binding fragment thereof and at least one other cancer therapy, use of the medicament can be prior to, during, or after treatment of the subject with either or both of the other cancer therapies.

The present invention also provides for the use of a synergistic combination of an antagonist anti-CD40 antibody or antigen-binding fragment thereof in the manufacture of a medicament for treating a subject for a cancer characterized by neoplastic B cell growth, including the B cell-related cancers described herein above, wherein the medicament is coordinated with treatment using an anti-CD20 antibody or antigen-binding fragment thereof. By "synergistic combination" is intended the medicament comprises an amount of the antagonist anti-CD40 antibody or antigen-binding fragment thereof that provides for a synergistic therapeutic effect when the medicament is coordinated with treatment using an anti-CD20 antibody or antigen-binding fragment thereof in the manner set forth herein above. "Synergistic therapeutic effect" refers to a therapeutic effect observed with a combination of two or more therapies (in this case, the antagonist anti-CD40 antibody therapy and anti-CD20 antibody therapy) wherein the therapeutic effect (as measured by any of a number of parameters, including the measures of efficacy described herein above) is greater than the sum of the respective individual therapeutic effects observed with the respective individual therapies.

In one such embodiment, the present invention provides for the use of a synergistic combination of the monoclonal antibody CHIR-12.12 or CHIR-5.9 in the manufacture of a medicament for treating a B cell-related cancer in a subject, wherein the medicament is coordinated with treatment using an anti-CD20 antibody, for example, rituximab (Rituxan®), or antigen-binding fragment thereof, wherein the medicament is to be used either prior to, during, or after treatment of the subject using the anti-CD20 antibody or antigen-binding fragment thereof. In some embodiments, the medicament comprising the synergistic combination of the antagonist anti-CD40 antibody, for example, the monoclonal antibody CHIR-12.12 or CHIR-5.9 disclosed herein, or antigen-binding fragment thereof is coordinated with treatment using an anti-CD20 antibody, for example, rituximab (Rituxan®), or antigen binding fragment thereof and at least one other type of cancer therapy as noted herein above.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating a subject for a cancer characterized by neoplastic B cell growth, including the B cell-related cancers described herein above, wherein the medicament is used in a subject that has been pretreated with an anti-CD20 antibody, for example, rituximab (Rituxan®), or antigen-binding fragment thereof. By "pretreated" or "pretreatment" is intended the subject has received anti-CD20 antibody therapy (i.e., been treated using an anti-CD20 antibody or antigen-binding fragment thereof) prior to receiving the medicament comprising the antagonist anti-CD40 antibody or antigen-binding fragment thereof. "Pretreated" or "pretreatment" includes subjects that have been treated using an anti-CD20 antibody or antigen-binding fragment thereof variant thereof, alone or in combination with other cancer therapies, within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior anti-CD20 antibody therapy, or prior anti-CD20 antibody therapy and other cancer therapies. Thus, the subject that receives the medicament comprising the antagonist anti-CD40 antibody or antigen-binding fragment thereof could have responded, or could have failed to respond (i.e. the cancer was refractory), to pretreatment with the prior anti-CD20 antibody therapy, or to one or more of the prior cancer therapies where pretreatment comprised multiple cancer therapies one of which was anti-CD20 antibody therapy, for example, anti-CD20 antibody therapy and surgery; anti-CD20 antibody therapy and chemotherapy; anti-CD20 antibody therapy and IL-2 therapy; or anti-CD20 antibody therapy, chemotherapy, and IL-2 therapy.

Thus, in some embodiments, the invention provides for the use of an antagonist anti-CD40 antibody, for example the monoclonal antibody CHIR-12.12 or CHIR-5.9 disclosed herein, or antigen-binding fragment thereof in the manufacture of a medicament that is to be used in a subject in need of treatment for a cancer characterized by neoplastic B cell growth, for example, a B cell-related cancer such as that described herein above, where the subject has been pretreated with anti-CD20 antibody therapy, or has been pretreated with anti-CD20 antibody therapy and one or more of the following other cancer therapies: surgery; radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, and IL-21 therapy; steroid therapy; or other cancer therapy.

The present invention also provides for the use of an anti-CD20 antibody or antigen-binding fragment thereof in the manufacture of a medicament for treating a subject for a cancer characterized by neoplastic B cell growth, including a B cell-related cancer, wherein the medicament is coordinated with treatment using an antagonist anti-CD40 antibody or antigen binding fragment thereof. In these embodiments, "coordinated" is intended to mean the medicament comprising the anti-CD20 antibody or antigen-binding fragment thereof is to be used either prior to, during, or after treatment of the subject using the antagonist anti-CD40 antibody or antigen-binding fragment thereof. In one such embodiment, the present invention provides for the use of an anti-CD20 antibody, for example, rituximab (Rituxan®), or antigen-binding fragment thereof in the manufacture of a medicament for treating a subject for a cancer characterized by neoplastic B cell growth, such as a B cell-related cancer, wherein the medicament is coordinated with treatment using the monoclonal antibody CHIR-12.12 or CHIR-5.9, wherein the medicament is to be used either prior to, during, or after treatment of the subject with the monoclonal antibody CHIR-12.12 or CHIR-5.9.

In some embodiments, the medicament comprising the anti-CD20 antibody, for example, rituximab (Rituxan®), or antigen-binding fragment thereof is coordinated with treatment using an antagonist anti-CD40 antibody, for example, the monoclonal antibody CHIR-12.12 or CHIR-5.9, or antigen-binding fragment thereof, and at least one other type of cancer therapy. Examples of other cancer therapies include, but are not limited to, those described herein above, i.e., surgery; radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anticancer monoclonal antibody therapy (for example, alemtuzumab (Campath®) or other anti-CD52 antibody targeting the CD52 cell-surface glycoprotein on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, and IL-21 therapy; steroid therapy; or other cancer therapy; where treatment with the antagonist anti-CD40 antibody or antigen-binding fragment thereof and the additional cancer therapy, or additional cancer therapies, occurs prior to, during, or subsequent to treatment of the subject with the medicament comprising the anti-CD20 antibody or antigen-binding fragment thereof. Where the medicament comprising the anti-CD20 antibody or antigen-binding fragment thereof is coordinated with treatment using the antagonist anti-CD40 antibody or antigen-binding fragment thereof and at least one other cancer therapy, use of the medicament can be prior to, during, or after treatment of the subject with either or both of the other cancer therapies.

"Treatment" in the context of coordinated use of a medicament described herein with one or more other cancer therapies is herein defined as the application or administration of the medicament or of the other cancer therapy to a subject, or application or administration of the medicament or other cancer therapy to an isolated tissue or cell line from a subject, where the subject has a cancer characterized by neoplastic B cell growth, a symptom associated with such a cancer, or a predisposition toward development of such a cancer, where the purpose is to cure, heal, alleviate, relieve, alter, remedy, ameliorate, improve, or affect the cancer, any associated symptoms of the cancer, or the predisposition toward the development of the cancer.

The following examples for this invention are offered by way of illustration and not by way of limitation.

V. F. EXPERIMENTAL

The antagonist anti-CD40 antibodies used in the examples below are 5.9 and CHIR-12.12, described in Chapter I above, and in commonly owned U.S. Provisional Application No. 60/613,885, filed Sep. 28, 2004 and International Application No. PCT/US2004/037159, filed Nov. 4, 2004 and published as WO 2005/044307, which corresponds to copending U.S. National-Phase application Ser. No. 10/578,401, which published as U.S. Application Publication No. 20070098718; the contents of each of which are herein incorporated by reference in their entirety.

Example 1

The Combination of mAb CHIR-12.12 and Rituxan® Show Anti-Tumor Activity Against Aggressive, Rituxan®-Resistant Burkitt's Lymphoma in a Xenograft Model Combinations of the chimeric anti-CD20 monoclonal antibody rituximab (Rituxan®; IDEC-C2B8; IDEC Pharmaceuticals Corp., San Diego, Calif.)) and antagonistic anti-CD40 monoclonal antibody CHIR-12.12 were tested in a murine model. Specifically, 120 nu/nu, 5-week-old female mice (Charles River Laboratories, Wilmington, Mass.) underwent an acclimation period of at least 7 days. One day prior to tumor cell inoculation, mice received 3 Gy irradiation using Gammacell 40 Cesium 137 irradiation unit manufactured by Atomic Energy of Canada. Namalwa cells (ATCC, Manassas, Va.), a human Rituxan®-resistant, aggressive Burkitt's lymphoma cell line, were cultured in RPMI 1640 media with 15% fetal bovine serum. On the day of inoculation, the cells were harvested, counted, and resuspended in 50% HBSS+50% matrigel at the density of $5 \times 10^7$ cells/mL. Tumor cells were inoculated subcutaneously at the right flank at $5 \times 10^6$ cells/100 µl/mouse.

One day after tumor inoculation, mice were randomized and injected intraperitoneally (i.p.) once every 7 days (q7d) with anti-CD40 mAb CHIR-12.12 and Rituxan® as indicated below:

a. IgG1, 10 mg/kg, i.p., q7d, ×up to 5 doses.
b. Rituxan®, 10 mg/kg, i.p., q7d, ×up to 5 doses.
c. Rituxan®, 20 mg/kg, i.p., q7d, ×up to 5 doses.
d. CHIR-12.12, 5 mg/kg, i.p., q7d, ×up to 5 doses.
e. CHIR-12.12, 10 mg/kg, i.p., q7d, ×up to 5 doses.
f. Rituxan®, 10 mg/kg+IgG1, 5 mg/kg, i.p., q7d, ×up to 5 doses.
g. Rituxan®, 10 mg/kg+CHIR-12.12, 5 mg/kg, i.p., q7d, ×up to 5 doses.
h. Rituxan®, 10 mg/kg+IgG1, 10 mg/kg, i.p., q7d, ×up to 5 doses.
i. Rituxan®, 10 mg/kg+CHIR-12.12, 10 mg/kg, i.p., q7d, ×up to 5 doses.

Tumor volume was measured twice a week using an electronic caliper. When the mean of tumor volume in one group reached 2000 mm³, mice in that group were sacrificed. If tumor in treatment group responded, mice were kept until the mean tumor volume reached 2000 mm³.

ANOVA was used to analyze the difference of mean tumor volume among all the groups. Tuckey multi-comparison on the Least Squares Means was used to compare the difference of mean tumor volume between two specific groups.

Figure 24:
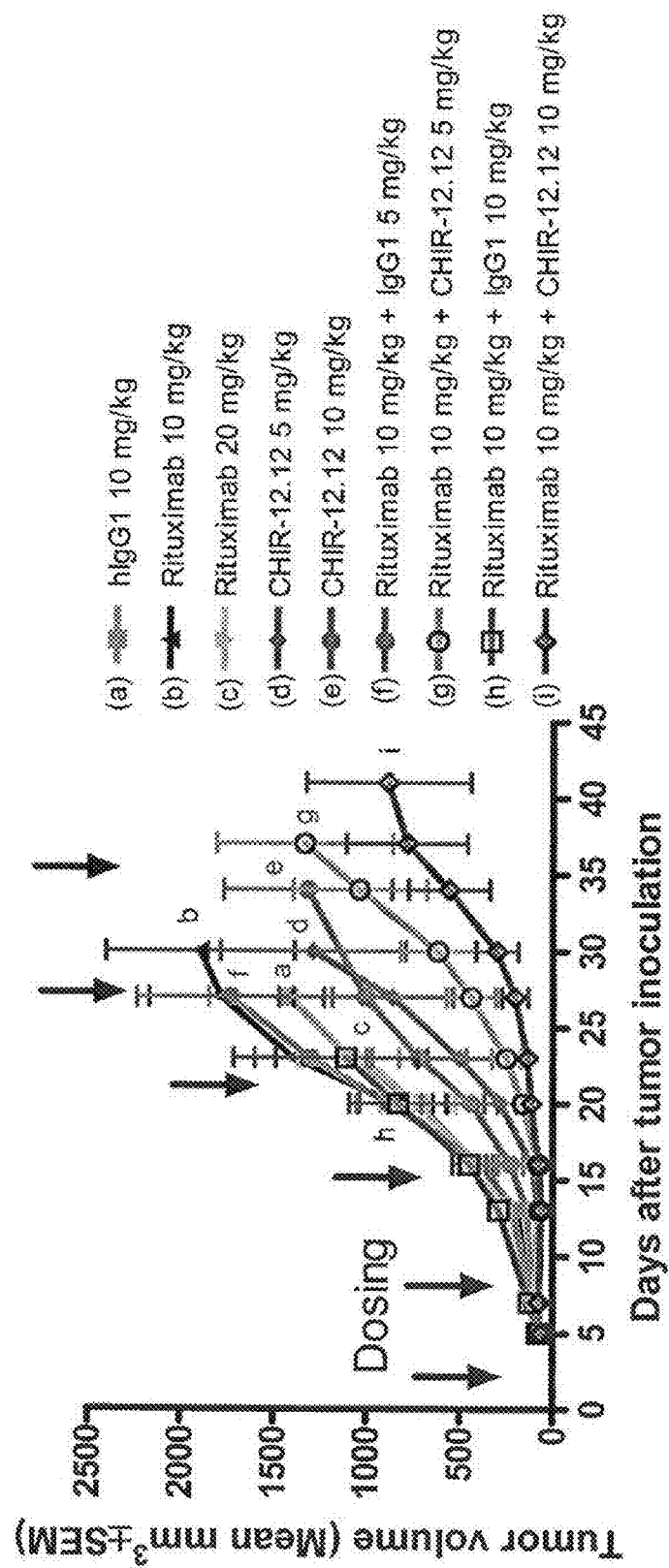
FIG. 24 shows the effect of combined administration of mAb CHIR-12.12 and mAb IDEC-C2B8 on tumor volume in a murine Rituxan®-resistant tumor model over time.

As shown in FIG. 24, primary tumor growth was significantly inhibited by i.p. administration of CHIR-12.12 alone at 5 mg/kg once a week for up to 5 weeks (60%, P=0.02). CHIR-12.12 administered alone at 10 mg/kg showed a trend toward significant tumor volume inhibition (39%, P=0.22). Rituxan® alone at 10 mg/kg and 20 mg/kg did not inhibit the tumor growth at all. The combination of CHIR-2.12 and Rituxan® resulted in synergistic and CHIR-12.12 dose-dependent tumor growth inhibition with 77% (P=0.001) and 83% (P=0.003) tumor volume inhibition for CHIR-12.12 at 5 mg/kg plus Rituxan® at 10 mg/kg and CHIR-12.12 at 10 mg/kg and Rituxan® at 10 mg/kg, respectively. No clinical sign of toxicity was observed among all the treated animals under the current doses and regimens. These data suggest that mAb CHIR-12.12 alone is a therapeutic agent for aggressive and Rituxan®-resistant lymphoma. However, mAb CHIR-12.12 when used in combination with Rituxan® was more efficacious than mAb CHIR-12.12 alone, Rituxan® alone, or the sum of the efficacies of these two mAbs used alone.

Example 2

Clinical Studies with CHIR-5.9 and CHIR-12.12

Clinical Objectives

The overall objective is to provide an effective therapy for B cell tumors by targeting them with a combination of an antagonist anti-CD40 antibody and an anti-CD20 antibody. These tumors include B-cell lymphoma, Chronic Lymphocytic Lymphoma (CLL), Acute Lymphoblastic Leukemia (ALL), Multiple Myeloma (MM), Waldenstrom's Macroglobulinemia, and Systemic Castleman's Disease. The signal for these diseases is determined in phase II although some measure of activity may be obtained in phase I. The initial antagonist anti-CD40 antibody is the mAb CHIR-12.12, and the initial anti-CD20 antibody is rituximab (Rituxan®). Later investigations study the combined effects of the mAb CHIR-12.12 or CHIR-5.9 with other anti-CD20 antibodies having the binding characteristics of rituximab.

Phase I

Evaluate safety and pharmacokinetics—dose escalation of these two antibodies in subjects with B cell malignancies.

Choose dose of each antibody based on safety, tolerability, and change in serum markers of respective targets, i.e., CD40 or CD20. In general an MTD for each of these antibodies when used in combination is sought but other indications of efficacy (depletion of CD40+ and/or CD20+ B cells, etc.) may be adequate for dose finding.

Consideration of more than one combination of doses especially for different indications, e.g., the CLL combination dose may be different than that for NHL. Thus, some dose finding may be necessary in phase II.

Patients are dosed weekly with real-time pharmacokinetic (Pk) sampling. Initially a 4-week cycle is the maximum dosing allowed. The Pk may be highly variable depending on the disease studied, density of CD40 and/or CD20, etc.

This trial(s) is open to subjects with B-cell lymphoma, CLL, and potentially other B cell malignancies.

Decision to discontinue or continue studies is based on safety, dose, and preliminary evidence of anti-tumor activity, particularly synergistic in nature.

Activity of combination antibody therapy as determined by response rate is determined in Phase II.

Identify combination dose(s) for Phase II.

Phase II

Several trials will be initiated in the above-mentioned tumor types with concentration on B-cell lymphoma, CLL, and Multiple Myeloma (MM). Separate trials may be required in low grade and intermediate/high grade NHL as CD40 and/or CD20 may have a different function depending on the grade of lymphoma. More than one combination of antibody doses and more than one schedule may be tested in a randomized phase II setting.

In each disease, target a population that has failed current standard of care:

CLL: patients who were resistant to Campath® and chemotherapy.

Low grade NHL: Rituxan® or CHOP-R failures

Intermediate NHL: CHOP-R failures

Multiple Myeloma: Chemotherapy failures

Decision to discontinue or continue with study is based on proof of therapeutic concept in Phase II Determine whether surrogate marker can be used as early indication of clinical efficacy Identify doses for Phase III Phase III Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.

Chapter VI: Methods of Therapy for Cancers Expressing the CD40 Antigen

VI. A. Overview

This invention is directed to combination therapy with anti-CD40 antibodies and IL-2 or biologically active variant thereof, as described herein below in sections VI. B-VI. J., and in commonly owned International Application No. PCT/US2004/036958, filed Nov. 4, 2004 and published as WO 2005/044294, which corresponds to copending U.S. National-Phase application Ser. No. 10/578,590, each entitled "Methods of Therapy for Cancers Expressing the CD40 Antigen"; the contents of each of which are herein incorporated by reference in their entirety.

The present invention relates to methods of combination therapy for cancers comprising neoplastic cells expressing the CD40 antigen, including B cell-related cancers and solid tumors. Over one million Americans are diagnosed with cancer every year. Leukemia, lymphoma, and myeloma strike over 100,000 individuals in the U.S. alone. Solid tumors such as breast cancer, ovarian cancer, and lung cancer, affect an even greater number of individuals. To combat these diseases, immunotherapy has been developed. Generally, immunotherapy boosts the patient's anti-tumor response against target tumor cells. Cytokine therapy is one method of immunotherapy that activates immunosurveillance, especially against tumors and tumor antigens. Alternatively, cancer cells can be directly targeted using antibody therapy. These antibodies are specific to individual cell-surface antigens that are expressed on cancer cells, and the clinical trial results are promising. Successful therapeutic results have been obtained using antibodies that target such antigens as CD20 (expressed on normal B cells and many B cell lymphomas) and HER2 (expressed in many breast carcinomas).

A large percentage of cancer cases are characterized by an outgrowth of neoplastic cells expressing the CD40 antigen. CD40 is a 55 kDa cell-surface antigen present on the surface of both normal and neoplastic human B cells, dendritic cells, other antigen presenting cells (APCs), endothelial cells, monocytic cells, and epithelial cells. Binding of the CD40 ligand to CD40 on the B cell membrane provides a positive costimulatory signal that stimulates B cell activation and proliferation, resulting in B cell maturation into a plasma cell that secretes high levels of soluble immunoglobulin. Transformed cells from patients with low- and high-grade B cell lymphomas, B cell acute lymphoblastic leukemia, multiple myeloma, chronic lymphocytic leukemia, and Hodgkin's disease express CD40. CD40 expression is detected in two-thirds of acute myeloblastic leukemia cases and 50% of AIDS-related lymphomas. Malignant B cells from several tumors of B-cell lineage express a high level of CD40 and appear to depend on CD40 signaling for survival and proliferation.

CD40 expression has also been detected in many non-B cell cancers. CD40-expressing carcinomas include urinary bladder carcinoma (Paulie et al. (1989) *J. Immunol.* 142:590-595; Braesch-Andersen et al. (1989) *J. Immunol.* 142:562-567), breast carcinoma (Hirano et al. (1999) *Blood* 93:2999-3007; Wingett et al. (1998) *Breast Cancer Res. Treat.* 50:27-36); prostate cancer (Rokhlin et al. (1997) *Cancer Res.* 57:1758-1768), renal cell carcinoma (Kluth et al. (1997) *Cancer Res.* 57:891-899), undifferentiated nasopharyngeal carcinoma (UNPC) (Agathanggelou et al. (1995) *Am. J. Pathol.* 147:1152-1160), squamous cell carcinoma (SCC) (Amo et al. (2000) *Eur. J. Dermatol.* 10:438-442; Posner et al. (1999) *Clin. Cancer Res.* 5:2261-2270), thyroid papillary carcinoma (Smith et al. (1999) *Thyroid* 9:749-755), cutaneous malignant melanoma (van den Oord et al. (1996) *Am. J. Pathol.* 149: 1953-1961), ovarian cancer (Ciaravino et al. (2004) *Eur. J. Gynaecol. Oncol.* 25:27-32), lung cancer (Sabel et al. (2000) *Cancer Immunol. Immunother.* 49:101-8), cervical cancer (Altenberg et al. (1999) *J. Immunol.* 162:4140-4147), gastric carcinoma (Yamaguchi et al. (2003) *Int. J. Oncol.* 23(6): 1697-702), sarcomas (see, for example, Lollini et al. (1998) *Clin. Cancer Res.* 4(8):1843-849, discussing human osteosarcoma and Ewing's sarcoma), and liver carcinoma (see, for example, Sugimoto et al. (1999) *Hepatology* 30(4):920-26, discussing human hepatocellular carcinoma). The role of CD40 in these non-B cell cancers is not well understood. Some studies have shown that ligation of CD40 in transformed cells can result in cell death by apoptosis. However, in some cancers such as malignant melanoma and lung cancer, expression of CD40 can be a negative prognostic indicator (see, for example, Sabel et al. (2000) *Cancer Immuno. Immunother.* 49(2):101-108; Ottaiano et al. (2004) *Clin. Cancer Res.* 10(8):2824-2831).

Interleukin-2 (IL-2) is a cytokine that is a potent stimulator of natural killer (NK) and T-cell proliferation and function (see, for example, Morgan et al. (1976) *Science* 193:1007-1011; Weil-Hillman et al. (1989) *Cancer Res.* 49(13):3680-3688). IL-2 has anti-tumor activity against a variety of malignancies either alone or when combined with lymphokine-activated killer (LAK) cells or tumor-infiltrating lymphocytes (TIL) (see, for example, Rosenberg et al. (1987) *N. Engl. J. Med.* 316:889-897; Rosenberg (1988) *Ann. Surg.* 208:121-135; Topalian et al. (1988) *J. Clin. Oncol.* 6:839-853; Rosenberg et al. (1988) *N. Engl. J. Med.* 319:1676-1680; and Weber et al. (1992) *J. Clin. Oncol.* 10:33-40). Although the anti-tumor activity of IL-2 has best been described in patients with metastatic melanoma and renal cell carcinoma, other diseases, including lymphoma, also appear to respond to treatment with IL-2 (see, for example, Dutcher and Wiernik (1993) *Sem. Oncol.* 20(6 Suppl. 9):33-40). However, high doses of IL-2 used to achieve positive therapeutic results with respect to tumor growth frequently cause severe side effects, including capillary leakage, hypotension, and neurological changes (see, for example, Duggan et al. (1992) *J. Immunotherapy* 12:115-122; Gisselbrecht et al. (1994) *Blood* 83:2081-2085; and Sznol and Parkinson 1994) *Blood* 83:2020-2022). Moreover, clinical responses to IL-2 are variable. For example, the median survival rate for renal cell carcinoma patient subgroups treated with IL-2 can be between 28 and 5 months depending on risk factors (Palmer et al. (1992) *Ann. Oncol.* 3:475-80).

Although any one immunotherapeutic agent may provide a benefit to the patient, further methods are needed to reduce toxicity, improve efficacy, and improve treatment outcomes. In addition, cancer can often become refractory to treatment with single-agent oncotherapy, either as a result of initial resistance to a single antibody therapy or single cytokine therapy, or as a result of resistance that develops during one or more time courses of therapy with the single antibody or the single cytokine.

Consequently, the discovery of a combination immunotherapy that can simultaneously improve the treatment outcomes relative to single-agent oncotherapy and reduce the toxicity of any one immunotherapeutic can greatly reduce the mortality and morbidity of cancer patients especially those suffering from solid tumors, myelomas, leukemias, and lymphomas.

VI. B. Combination Therapy with Anti-CD40 Antibodies and Interleukin-2

1. Introduction.

The present invention relates to methods for treating a human subject for a cancer comprising neoplastic cells expressing CD40 antigen, including, but not limited to, solid tumors, lymphomas, such as B-cell lymphoma, leukemias, and myelomas. The methods comprise combination therapy with interleukin-2 (IL-2) or biologically active variant thereof and at least one antagonist anti-CD40 antibody or antigen-binding fragment thereof, each of which is administered according to a particular dosing regimen disclosed herein. In some embodiments of the invention, these dosing regimens are followed until the subject is taken off anti-CD40 antibody therapy, for example, when the subject exhibits a complete response or exhibits one or more symptoms of anti-CD40 antibody toxicity, or until the subject is taken off IL-2 therapy due to development of IL-2 toxicity symptoms noted herein below. Where the subject is taken off IL-2 therapy due to toxicity, the anti-CD40 antibody therapy can be continued, following the recommended antibody dosing regimen, or discontinued; and once IL-2 toxicity symptoms have subsided or been resolved, the IL-2 therapy, or the IL-2 therapy and the anti-CD40 antibody therapy where the antibody therapy was discontinued, can be reinstated using the same IL-2 dosing regimen and dose of IL-2 or biologically active variant thereof, the same IL-2 dosing regimen with a lower dose of this therapeutic agent, or a different IL-2 dosing regimen disclosed herein.

In other embodiments of the invention, the dosing regimen for the anti-CD20 antibody therapy is followed for a fixed time period, for example, 2 weeks to 16 weeks, and administered in combination an IL-2 dosing regimen disclosed herein, wherein a given treatment period comprises an overlapping time period in which the subject is receiving both anti-CD40 antibody therapy and IL-2 therapy in accordance with the dosing regimens and doses disclosed herein. In such embodiments, generally the duration of anti-CD20 antibody administration is about 4 weeks to about 12 weeks, including 4, 5, 6, 7, 8, 9, 10, 11, or 12 weeks. The duration of IL-2 administration is a function of the IL-2 dosing regimen used.

Combination therapy with these two therapeutic agents provides for anti-tumor activity. By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Subjects undergoing therapy with a combination of IL-2 (or variant thereof) and at least one antagonist anti-CD40 antibody (or antigen-binding fragment thereof) experience a physiological response that is beneficial with respect to treatment of a cancer comprising neoplastic cells expressing CD40 antigen, including, but not limited to, B cell-related cancers and solid tumors as noted herein below.

While the methods of the invention are directed to treatment of an existing cancer, it is recognized that the methods may be useful in preventing further tumor outgrowths arising during therapy. Combination therapy with IL-2 (or biologically active variant thereof) and an antagonist anti-CD40 antibody (or antigen-binding fragment thereof) provides a therapeutic benefit that is greater than that provided by the use of either of these therapeutic agents alone. In addition, these two therapeutic agents can be used in combination to treat tumors that are refractory to treatment with either of these agents alone (i.e., single-agent therapy), either as a result of initial resistance to the single antibody therapy or single cytokine therapy, or as a result of resistance that develops during one or more time courses of therapy with the single antibody or the single cytokine. In yet other embodiments, combination therapy with these two therapeutic agents has a synergistic therapeutic effect against tumors that are refractory or non-refractory (i.e., responsive) to single-agent therapy.

The term "oncotherapy" is intended to mean any cancer treatment, including chemotherapy, radiation therapy, immunotherapy, combinations thereof, and the like. Agents used in oncotherapy are referred to herein as "oncotherapeutic agents." The term "immunotherapy" is applicable to any cancer therapy where the immune system is modulated, and includes cytokine administration, antibody administration, antigen administration/vaccination, immune cell administration, immune cell priming, combinations thereof, and the like.

As used in this aspect of the invention, "anti-CD40 antibody" encompasses any antibody that specifically recognizes the CD40 cell surface antigen, including polyclonal antibodies, monoclonal antibodies, single-chain antibodies, and fragments thereof such as Fab, F(ab')$_2$, F$_v$, and other fragments that retain the antigen-binding function of the parent anti-CD40 antibody. Of particular interest for practicing the methods of the present invention are anti-CD40 antibodies or antigen-binding fragments thereof that have the binding properties exhibited by the CHIR-5.9 and CHIR-12.12 human anti-CD40 monoclonal antibodies described herein above in Chapter I, and also herein below.

The term "interleukin-2" (IL-2) as used herein refers to a cytokine with a reported molecular weight in the range of 13,000 to 17,000 daltons (Gillis and Watson (1980) *J. Exp. Med.* 159:1709) and with an isoelectric point in the range of 6-8.5. IL-2 is naturally produced by normal T cells and is present in the body at low concentrations. IL-2 was first described by Morgan et al. (1976) *Science* 193:1007-1008 and originally called T cell growth factor because of its ability to induce proliferation of stimulated T lymphocytes. The methods encompassing combination therapy with an anti-CD40 antibody and IL-2 can be practiced with biologically active variants of IL-2, as noted herein below.

The term "synergy" is used to describe a combined effect of two or more active agents that is greater than the sum of the individual effects of each respective active agent. Thus, where the combined effect of two or more agents results in "synergistic inhibition" of an activity or process, for example, tumor growth, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

The terms "therapeutically effective dose," "therapeutically effective amount," or "effective amount" are intended to mean an amount of the antagonist anti-CD40 antibody (or antigen-binding fragment thereof) or interleukin-2 (or variant thereof) that, when administered as a part of a combination therapy comprising at least these two agents, brings about a positive therapeutic response with respect to treatment of a subject for a cancer comprising neoplastic cells.

In this manner, the present invention is directed to methods for treating a subject having a cancer characterized by neoplastic cell growth. The methods of the invention encompass combination therapy with an antagonist anti-CD40 antibody or antigen-binding fragment thereof and IL-2 or biologically active variant thereof. The methods of the invention are especially useful for the treatment of cancers comprising neoplastic cells expressing the CD40 cell surface antigen, such as many solid tumors and B cell lymphomas.

Solid tumors that can be treated using the methods of the present invention include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas). B cell-related cancers such as lymphomas include low-, intermediate-, and high-grade B cell lymphomas, immunoblastic lymphomas, non-Hodgkin's lymphomas, Hodgkin's disease, Epstein-Barr Virus (EBV) induced lymphomas, and AIDS-related lymphomas, as well as B cell acute lymphoblastic leukemias, myelomas, chronic lymphocytic leukemias, acute myeloblastic leukemias, and the like, as noted herein below.

Thus, the methods of the invention find use in the treatment of non-Hodgkin's lymphomas related to abnormal, uncontrollable B cell proliferation or accumulation. For purposes of the present invention, such lymphomas will be referred to according to the Working Formulation classification scheme, that is those B cell lymphomas categorized as low grade, intermediate grade, and high grade (see "The Non-Hodgkin's Lymphoma Pathologic Classification Project," *Cancer* 49(1982):2112-2135). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the methods of the invention are useful in the therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), hairy cell leukemia, plasmacytoma/myeloma, diffuse large cell B cell lymphoma of the subtype primary mediastinal (thymic), Burkitt's lymphoma, and Burkitt's like high-grade B cell lymphoma; acute leukemias; acute lymphocytic leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); chronic lymphocytic leukemia; polycythemia vera; multiple myeloma; Waldenstrom's macroglobulinemia; heavy chain disease; and unclassifiable low-grade or high-grade B cell lymphomas.

In particular, the methods of the invention are useful for treating solid tumors comprising neoplastic cells expressing the CD40 antigen and B cell lymphomas, including those listed above.

"Treatment" is herein defined as the application or administration of an antagonist anti-CD40 antibody or antigen-binding fragment thereof to a subject, or application or administration of an antagonist anti-CD40 antibody or anti-gen-binding fragment thereof to an isolated tissue or cell line from a subject, in combination with the application or administration of IL-2 (or biologically active variant thereof) to the subject, or to an isolated tissue or cell line from the subject, where the subject has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the combination of the antagonist anti-CD40 antibody (or antigen-binding fragment thereof) and IL-2 (or biologically active variant thereof) can be applied or administered to the subject, or to the isolated tissue or cell line from the subject, as part of a single pharmaceutical composition, or alternatively as part of individual pharmaceutical compositions, each comprising either the antagonist anti-CD40 antibody (or antigen-binding fragment thereof) or IL-2 (or biologically active variant thereof), where the subject has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

2. Brief Description of the Oncotherapeutic Agents.

Antagonist anti-CD40 antibodies suitable for use in the methods of the invention specifically bind a human CD40 antigen expressed on the surface of a human cell and are free of significant agonist activity but exhibit antagonist activity when bound to the CD40 antigen on a human CD40-expressing cell, including normal and neoplastic (whether malignant or benign) human cells. In some embodiments, their binding to CD40 displayed on the surface of human cells results in inhibition of proliferation and differentiation of these human cells. Thus, the antagonist anti-CD40 antibodies suitable for use in the methods of the invention include those monoclonal antibodies that can exhibit antagonist activity toward normal and neoplastic human cells expressing the cell-surface CD40 antigen. These anti-CD40 antibodies and antigen-binding fragments thereof are referred to herein as "antagonist anti-CD40 antibodies." Such antibodies include, but are not limited to, the fully human monoclonal antibodies CHIR-5.9 and CHIR-12.12 described elsewhere herein and monoclonal antibodies having the binding characteristics of monoclonal antibodies CHIR-5.9 and CHIR-12.12. These monoclonal antibodies, which can be recombinantly produced, are described herein above in Chapter I. These monoclonal antibodies are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety.

In addition to the monoclonal antibodies CHIR-5.9 and CHIR-12.12, other anti-CD40 antibodies that would be useful in practicing the methods of the invention described herein include, but are not limited to: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen. Those skilled in the art recognize that the antibodies and antigen-binding fragments of these antibodies suitable for use in the methods disclosed herein include antibodies and antigen-binding fragments thereof that are produced recombinantly using methods well known in the art and described herein below, and include, for example, monoclonal antibodies CHIR-5.9 and CHIR-12.12 that have been recombinantly produced.

Fragments of the anti-CD40 antibodies disclosed herein are suitable for use in the methods of the invention so long as they retain the desired affinity of the full-length antibody. Thus, a fragment of an anti-CD40 antibody will retain the ability to bind to the CD40 B-cell surface antigen. Such fragments are characterized by properties similar to the corresponding full-length antibody. For example, antagonist anti-CD40 antibody fragments will specifically bind a human CD40 antigen expressed on the surface of a human cell, and are free of significant agonist activity but exhibit antagonist activity when bound to a CD40 antigen on a human CD40-expressing cell. Such fragments are referred to herein as "antigen-binding" fragments.

In addition to using the antagonist anti-CD40 antibodies mentioned above, and described more fully herein below, the methods of the present invention can be practiced using antibodies that have the binding characteristics of monoclonal antibodies CHIR-5.9 or CHIR-12.12 and which competitively interfere with binding of these antibodies to their respective antigens or bind the same epitopes. One of skill in the art could determine whether an antibody competitively interferes with CHIR-5.9 or CHIR-12.12 binding using standard methods.

The IL-2, or biologically active variant thereof, for use in the methods of the present invention may be from any source, but preferably is recombinant IL-2, more particularly recombinant human IL-2. By "recombinant IL-2" is intended IL-2 that has comparable biological activity to native-sequence IL-2 and that has been prepared by recombinant DNA techniques as described, for example, by Taniguchi et al. (1983) *Nature* 302:305-310 and Devos (1983) *Nucleic Acids Res.* 11:4307-4323 or mutationally altered IL-2 as described by Wang et al. (1984) *Science* 224:1431-1433. In general, the gene coding for IL-2 is cloned and then expressed in transformed organisms, preferably a microorganism, for example *E. coli*, as described herein. The host organism expresses the foreign gene to produce IL-2 under expression conditions. Synthetic recombinant IL-2 can also be made in eukaryotes, such as yeast or human cells. Processes for growing, harvesting, disrupting, or extracting the IL-2 from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

For examples of variant IL-2 proteins, see European Patent Application No. 136,489; European Patent Application No.

83101035.0 filed Feb. 3, 1983 (published Oct. 19, 1983 under Publication No. 91539); European Patent Application No. 82307036.2, filed Dec. 22, 1982 (published Sep. 14, 1983 under No. 88195); the recombinant IL-2 muteins described in European Patent Application No. 83306221.9, filed Oct. 13, 1983 (published May 30, 1984 under No. 109748), which is the equivalent to Belgian Patent No. 893,016, commonly owned U.S. Pat. No. 4,518,584; the muteins described in U.S. Pat. No. 4,752,585 and WO 99/60128; and the IL-2 mutein des-alanyl-1, serine-125 human IL-2 (also referred to as "aldesleukin") used in the examples herein and described in U.S. Pat. No. 4,931,543, as well as the other IL-2 muteins described in this U.S. patent; all of which are herein incorporated by reference. Also see the IL-2 muteins described in the copending provisional application entitled "Improved Interleukin-2 Muteins," filed Mar. 5, 2004, and assigned U.S. Patent Application No. 60/550,868; and copending provisional application entitled "Combinatorial Interleukin-2 Muteins," filed Jul. 7, 2004, assigned U.S. Patent Application No. 60/585,980; the contents of which are herein incorporated by reference in their entirety. Additionally, IL-2 can be modified with polyethylene glycol to provide enhanced solubility and an altered pharmokinetic profile (see U.S. Pat. No. 4,766,106, hereby incorporated by reference in its entirety). See also below where suitable variants of IL-2 are more fully discussed.

In some embodiments, the methods of the invention comprise combination therapy with IL-2, for example, human IL-2, and the anti-CD40 monoclonal antibody CHIR-12.12. In other embodiments, the methods of the invention comprise combination therapy with IL-2, for example, human IL-2, and the anti-CD40 monoclonal antibody CHIR-5.9. In yet other embodiments, the methods of the invention comprise combination therapy with IL-2, for example, human IL-2, and an antigen-binding fragment of the anti-CD40 monoclonal antibody CHIR-12.12 or CHIR-5.9.

In alternative embodiments, the methods of the invention comprise combination therapy with a biologically active variant of IL-2, for example, the IL-2 mutein des-alanyl-1, serine-125 human IL-2 (also referred to as "aldesleukin," which is available commercially as a formulation that is marketed under the tradename Proleukin® (Chiron Corporation, Emeryville, Calif.)), and the anti-CD40 monoclonal antibody CHIR-12.12 or CHIR-5.9. In other embodiments, the methods of the invention comprise combination therapy with a biologically active variant of IL-2, for example, the IL-2 mutein des-alanyl-1, serine-125 human IL-2, and an antigen-binding fragment of the anti-CD40 monoclonal antibody CHIR-12.12 or CHIR-5.9. The combination therapy described herein may comprise other variations, as long the CD40 antigen is targeted in the treatment process.

3. Measurements of Clinical Efficacy.

In accordance with the methods of the present invention, IL-2 or biologically active variant thereof and at least one antagonist anti-CD40 antibody or antigen-binding fragment thereof as defined elsewhere herein are used in combination to promote a positive therapeutic response with respect to a cancer comprising neoplastic cells expressing the CD40 antigen. By "positive therapeutic response" is intended an improvement in the disease in association with the combined anti-tumor activity of these administered therapeutic agents, and/or an improvement in the symptoms associated with the disease. Thus, for example, a positive therapeutic response would refer to one or more of the following improvements in the disease: (1) a reduction in tumor size; (2) a reduction in the number of cancer (i.e., neoplastic) cells; (3) an increase in neoplastic cell death; (4) inhibition of neoplastic cell survival; (4) inhibition (i.e., slowing to some extent, preferably halting) of tumor growth; (5) inhibition (i.e., slowing to some extent, preferably halting) of cancer cell infiltration into peripheral organs; (6) inhibition (i.e., slowing to some extent, preferably halting) of tumor metastasis; (7) the prevention of further tumor outgrowths; (8) an increased patient survival rate; and (9) some extent of relief from one or more symptoms associated with the cancer. Such therapeutic responses may be further characterized as to degree of improvement. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. A complete response can be unconfirmed if no repeat evaluation of tumor status is done at least one month after the initial response is evaluated. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Multiple parameters can be indicative of treatment efficacy. These include, but are not limited to, a reduction in the size of the tumor mass; a reduction in metastatic invasiveness of the tumor; a reduction in the rate of tumor growth; a decrease in severity or incidence of tumor related sequelae such as cachexia and ascites production; a decrease and/or prevention of tumor related complications such as pathologic bone fractures, autoimmune hemolytic anemia, prolymphocytic transformation and Richter's syndrome, etc.; sensitization of the tumor to chemotherapy and other treatments; an increased patient survival rate; an increase in observed clinical correlates of improved prognosis such as increased tumor infiltrating lymphocytes and decreased tumor vascularization; and the like. Thus, in some embodiments, administration of the therapeutic combination will result in an improvement of one or more of these parameters in a patient (i.e., subject) undergoing treatment. In other embodiments, the improvements in the patient will be synergistic with regard to some parameters, but additive with regard to others.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, flow cytometry or fluorescence-activated cell sorter (FACS) analysis, bioluminescent imaging, for example, luciferase imaging, bone scan imaging, and tumor biopsy sampling including bone marrow aspiration (BMA). In addition to these positive therapeutic responses, the subject undergoing therapy may experience the beneficial effect of an improvement in the symptoms associated with the disease. Thus, for B cell tumors, the subject may experience a decrease in the so-called B symptoms, i.e., night sweats, fever, weight loss, and/or urticaria.

One method of predicting clinical efficacy is to measure the effects of combination therapy with these two therapeutic agents in a suitable model, for example, the use of the combination of IL-2 or biologically active variant thereof and an antagonist anti-CD40 antibody or antigen-binding fragment thereof in one or more murine cancer models. For lymphomas, these models include, for example, the nude mouse xenograft tumor models such as those using the human Burkitt's lymphoma cell lines known as Namalwa and Daudi. Thus, in some embodiments, anti-tumor activity of the combination of these two therapeutic agents is assayed in a human NHL Namalwa xenograft model as described in the examples herein below. The Namalwa cell line gives rise to aggressive rituximab-resistant tumors when implanted in nude mice.

In other embodiments, anti-tumor activity of the combination of these two therapeutic agents is assayed in a staged nude mouse xenograft tumor model using the Daudi human lymphoma cell line as described in the commonly owned application entitled "Antagonist Anti-CD40 Monoclonal Antibodies and Methods for Their Use," filed Apr. 27, 2004 and assigned U.S. Patent Application No. 60/565,710 and in related International Application No. PCT/US2004/037152; herein incorporated by reference in its entirety. A staged nude mouse xenograft tumor model is generally more effective at distinguishing the therapeutic efficacy of a given therapeutic protocol than is an unstaged model, as in the staged model therapeutic dosing is initiated only after the tumor has reached a measurable size. In the unstaged model, therapeutic dosing is initiated generally within about 1 day of tumor inoculation and before a palpable tumor is present. The ability of a combination therapeutic regimen to exhibit increased anti-tumor activity in a staged model is a strong indication that the combination therapeutic regimen will be therapeutically effective.

Other tumor models are well known in the art. For example, for multiple myeloma (MM), tumor models include, but are not limited to, those in which cell lines are grown in immunodeficient mice and the mice are then treated with the therapeutics of interest, and those in which patient myeloma cells are implanted along with fetal bone in immunodeficient mice and the mice are then treated with the therapeutics of interest. Thus, for example, anti-tumor activity of the combination of these two therapeutic agents can be assayed in vivo in a human MM IM-9 xenograft model, which uses the human MM cell line IM-9. In this manner, efficacy of combination therapy with IL-2 or biologically active variant thereof and an antagonist anti-CD40 antibody or antigen-binding fragment thereof can be evaluated using an unstaged conditional survival model, where treatment with these therapeutic agents begins one day after intravenous inoculation of the IM-9 tumor cells. Alternatively, efficacy of this combination therapy can be evaluated using a staged subcutaneous model, where the IM-9 cells are injected SC into SCID nice, and then combination treatment with these therapeutic agents begins once the tumor reaches a measurable size.

Anti-tumor activity of combination therapy with IL-2 or biologically active variant thereof and an antagonist anti-CD40 antibody or antigen-binding fragment thereof can be evaluated in a murine solid tumor model. Examples include, but are not limited to, a xenograft colon cancer model using the human colon carcinoma cell line HCT 116, which expresses CD40; an unstaged (prophylactic) orthotopic murine model of ovarian cancer using the ovarian cancer cell line SKOV3i.p.1; and a staged (therapeutic) murine model of ovarian cancer using the ovarian cancer cell line SKOV3i.p.1. See, for example, the use of these models disclosed in the application entitled "Methods of Therapy for Solid Tumors Expressing the CD40 Cell-Surface Antigen," filed Apr. 27, 2004, and assigned U.S. Patent Application No. 60/565,634 and in related International Application No. PCT/US2004/036955; herein incorporated by reference in its entirety.

4. Modes of Administration.

For purposes of carrying out the combination therapy described herein, pharmaceutical compositions comprising these two classes of therapeutic agents (i.e., the cytokine and the anti-CD40 antibody or antigen-binding fragment thereof) as therapeutically active components may be administered using any acceptable method known in the art. Thus, for example, a pharmaceutical composition comprising IL-2 (or biologically active variant thereof), a pharmaceutical composition comprising antagonist anti-CD40 antibody (or antigen-binding fragment thereof), or a pharmaceutical composition comprising IL-2 (or variant thereof) and antagonist anti-CD40 antibody (or antigen-binding fragment thereof) can be administered by any form of injection, including intravenous (IV), intratumoral (IT), intraperitoneal (IP), intramuscular (IM), or subcutaneous (SC) injection. In some embodiments, a pharmaceutical composition comprising IL-2 (or biologically active variant thereof) is administered by IV, IM, IP, or SC injection, and a pharmaceutical composition comprising antagonist anti-CD40 antibody (or antigen-binding fragment thereof) is administered by IV, IP, or SC injection. In other embodiments, a pharmaceutical composition comprising IL-2 (or biologically active variant thereof) is administered by IV, IT, or SC injection, and a pharmaceutical composition comprising antagonist anti-CD40 antibody (or antigen-binding fragment thereof) is administered by IV or SC injection.

In some embodiments of the invention, a pharmaceutical composition comprising IL-2 or variant thereof is administered by SC injection and a pharmaceutical composition comprising the anti-CD40 antibody or antigen-binding fragment thereof is administered intravenously. When administered intravenously, the pharmaceutical composition comprising the anti-CD40 antibody or antigen-binding fragment thereof can be administered by infusion over a period of about 1 to about 10 hours. In some embodiments, infusion occurs over a period of about 2 to about 8 hours, over a period of about 3 to about 7 hours, over a period of about 4 to about 6 hours, or over a period of about 6 hours, depending upon the antagonist anti-CD40 antibody being administered.

5. Combination Therapy.

The methods of the invention comprise using combination therapy. The term "combination" is used in its broadest sense and means that a subject is treated with at least two therapeutic regimens. Thus, "combination therapy" is intended to mean a subject is treated with at least two oncotherapeutic regimens, more particularly, with at least IL-2 or biologically active variant thereof in combination with at least one antagonist anti-CD40 antibody or antigen-binding fragment thereof, but the timing of administration of the different oncotherapeutic regimens can be varied so long as the beneficial effects of the combination of these two therapeutic agents is achieved.

Treatment with IL-2 or biologically active variant thereof in combination with an antagonist anti-CD40 antibody or antigen-binding fragment thereof can be simultaneous (concurrent), consecutive (sequential, in either order), or a combination thereof. Therefore, a subject undergoing combination therapy can receive treatment with both of these therapeutic agents at the same time (i.e., simultaneously) or at different times (i.e., sequentially, in either order, on the same day, or on different days), so long as the therapeutic effect of the combination of both substances is caused in the subject undergoing therapy. In some embodiments, the combination of IL-2 or biologically active variant thereof and anti-CD40 antibody or antigen-binding fragment thereof will be given simultaneously for one dosing, but other dosings will include sequential administration, in either order, on the same day, or on different days. Sequential administration may be performed regardless of whether the subject responds to the first therapeutic agent administered. Where these two therapeutic agents are administered simultaneously, they can be administered as separate pharmaceutical compositions, each comprising either the IL-2 (or biologically active variant thereof)

or the antagonist anti-CD40 antibody (or antigen-binding fragment thereof), or they can be administered as a single pharmaceutical composition comprising both of these therapeutic agents.

The effect of the combination therapy can also be optimized by varying the timing of administration of either IL-2 (or biologically active variant thereof) and/or the antagonist anti-CD40 antibody (or antigen-binding fragment thereof). Thus, in some embodiments, the IL-2 (or biologically active variant thereof, such as des-alanyl C125S human IL-2 mutein) will be administered simultaneously with the antagonist anti-CD40 antibody, such as the monoclonal antibody CHIR-12.12. or CHIR-5.9 (or antigen-binding fragment thereof). In other embodiments, the IL-2 (or biologically active variant thereof, such as des-alanyl C125S human IL-2 mutein) will be administered first and then the antagonist anti-CD40 antibody, such as the monoclonal antibody CHIR-12.12 or CHIR-5.9 (or antigen-binding fragment thereof), will be administered next. In yet other embodiments, the antagonist anti-CD40 antibody, such as the monoclonal antibody CHIR-12.12 or CHIR-5.9 (or antigen-binding fragment thereof), will be administered first, and the IL-2 (or biologically active variant thereof, such as des-alanyl C125S human IL-2 mutein) will be administered next. In some embodiments, the combination of the IL-2 (or biologically active variant thereof, such as des-alanyl C125S human IL-2 mutein) and antagonist anti-CD40 antibody, such as monoclonal antibody CHIR-12.12 or CHIR-5.9 (or antigen-binding fragment thereof), will be given concurrently for one dosing, but other dosings will include sequential administration, in either order, on the same day, or on different days. As previously noted, where the IL-2 (or biologically active variant thereof, such as des-alanyl C125S human IL-2 mutein) and the antagonist anti-CD40 antibody, such as the monoclonal antibody CHIR-12.12 or CHIR-5.9 (or antigen-binding fragment thereof), are administered simultaneously, they can be administered as separate pharmaceutical compositions, each comprising either the IL-2 (or biologically active variant thereof) or the antagonist anti-CD40 antibody (or antigen-binding fragment thereof), or can be administered as a single pharmaceutical composition comprising both of these therapeutic agents.

Therapy with an effective amount of the combination of IL-2 (or biologically active variant thereof) and at least one antagonist anti-CD40 antibody (or antigen-binding fragment thereof) promotes a positive therapeutic response for a cancer comprising neoplastic cells expressing the CD40 antigen, including B-cell related lymphomas and solid tumors as defined elsewhere herein. Concurrent therapy with both of these anti-tumor agents potentiates the anti-tumor activity of each of these agents, thereby providing a positive therapeutic response that is improved with respect to that observed with administration of IL-2 (or biologically active variant thereof) alone or administration of antagonist anti-CD40 antibody (or antigen-binding fragment thereof) alone. Improvement of the positive therapeutic response may be additive in nature or synergistic in nature. Where synergistic, concurrent therapy with IL-2 (or biologically active variant thereof) and at least one antagonist anti-CD40 antibody (or antigen-binding fragment thereof) results in a positive therapeutic response that is greater than the sum of the positive therapeutic responses achieved with the separate IL-2 (or biologically active variant thereof) and antagonist anti-CD40 antibody (or antigen-binding fragment thereof) components.

Moreover, the treatment can be accomplished with varying doses as well as dosing regimens, as long as the combination of these doses is effective at treating any one or more of a number of therapeutic parameters. These treatment regimens are based on doses and dosing schedules that maximize therapeutic effects, such as those described below. Those skilled in the art recognize that a dose of any one monoclonal antibody or any one cytokine such as IL-2 may not be therapeutically effective when administered individually, but will be therapeutically effective when administered in combination with the other agent. Thus, in some embodiments, the therapeutically effective dose of a combination of IL-2 and antagonist anti-CD40 antibody may comprise doses of individual active agents that, when administered alone, would not be therapeutically effective or would be less therapeutically effective than when administered in combination with each other.

Because the combined administration of these two therapeutic agents potentiates the effectiveness of both of these agents, a positive therapeutic response that is similar to that achieved with a particular dose of IL-2 alone can be achieved with lower doses of this agent. The significance of this is two-fold. First, the potential therapeutic benefits of treatment of B cell malignancies or solid tumors with IL-2 or variant thereof can be realized at IL-2 doses that minimize toxicity responses normally associated with high-dose IL-2 administration. Such toxicity responses include, but are not limited to, chronic fatigue, nausea, hypotension, fever, chills, weight gain, pruritis or rash, dysprea, azotemia, confusion, thrombocytopenia, myocardial infarction, gastrointestinal toxicity, and vascular leak syndrome (see, for example, Allison et al. (1989) *J. Clin. Oncol.* 7(1):75-80). Secondly, targeting of specific molecules on a tumor cell surface by monoclonal antibodies can select for clones that are not recognized by the antibody or are not affected by its binding, resulting in tumor escape, and loss of effective therapeutic treatment. Improved anti-tumor activity of antagonist anti-CD40 antibody (or a fragment thereof) administered in combination with IL-2 (or variant thereof) may translate into increased potency of monoclonal antibodies, less frequent administration of monoclonal antibodies, and/or lower dose of monoclonal antibodies, thereby lessening the potential for tumor escape. Further, monoclonal antibody ADCC activity may also arise from activity from the neutrophils and monocytes/macrophage polulation. See, for example, Hernandez-Ilizaliturri et al. (2003) *Clin. Cancer Res.* 9(16, Pt 1):5866-5873; and Uchida et al. (2004) *J. Exp. Med.* 199(12):1659-1669). As IL-2 is known to activate these cell populations, combination therapy of the antagonist anti-CD40 antibody with IL-2 or biologically active variant thereof may improve ADCC-mediated anti-tumor activity of the antibody.

The amount of at least one antagonist anti-CD40 antibody (or antigen-binding fragment thereof) to be administered in combination with an amount of IL-2 (or variant thereof) and the amount of either of these therapeutic agents needed to potentiate the effectiveness of the other therapeutic agent are readily determined by one of ordinary skill in the art without undue experimentation given the disclosure set forth herein. Factors influencing the mode of administration and the respective amount of IL-2 (or variant thereof) and antagonist anti-CD40 antibody (or antigen-binding fragment thereof) administered in combination include, but are not limited to, the particular lymphoma or solid tumor undergoing therapy, the severity of the disease, the history of the disease, and the age, height, weight, health, and physical condition of the individual undergoing therapy. Similarly, the amount of these therapeutic agents to be administered in combination therapy will be dependent upon the mode of administration and whether the subject will undergo a single dose or multiple doses of each of these therapeutic agents. Generally, a higher dosage of the antibody agent is preferred with increasing weight of the subject undergoing therapy.

VI. C. Exemplary Protocols for Combination IL-2/Antagonist Anti-CD40 Antibody Therapy 1. Introduction.

In some embodiments of the invention, combination therapy is achieved by administering recommended total weekly doses of a pharmaceutical composition comprising IL-2 (or biologically active variant thereof) in combination with recommended therapeutically effective doses of a pharmaceutical composition comprising the antagonist anti-CD40 antibody (or antigen-binding fragment thereof), each being administered according to a particular dosing regimen. By "therapeutically effective dose or amount" is intended an amount of one of these two therapeutic agents that, when administered with a therapeutically effective dose or amount of the other of these two therapeutic agents, brings about a positive therapeutic response with respect to treatment of cancers comprising neoplastic cells expressing the CD40 cell surface antigen. As previously noted above, administration of the separate pharmaceutical compositions can be at the same time or at different times, so long as the therapeutic effect of the combination of both substances is caused in the subject undergoing therapy.

In accordance with some embodiments of the invention, the human subject undergoing treatment with one or more weekly doses of antagonist anti-CD40 antibody or antigen-binding fragment thereof as defined herein below is also administered IL-2 or biologically active variant thereof as defined herein below according to a constant IL-2 dosing regimen or according to a two-level IL-2 dosing regimen. An important aspect of this combination therapy is an overlapping period of time during which both of these therapeutic agents are being administered to the subject, each according to the particular dosing regimen disclosed herein. Accordingly, where combination therapy comprises this overlapping time period of dosing with these two therapeutic agents, the combination therapy is also referred to as "concurrent therapy." The first therapeutically effective dose administered to the subject can be the antagonist anti-CD40 antibody (or antigen-binding fragment thereof) or can be the IL-2 (or biologically active variant thereof). On those days where both an antagonist anti-CD40 antibody (or antigen-binding fragment thereof) and IL-2 (or biologically active variant thereof) are scheduled to be administered to the subject, these therapeutic agents can be administered either at the same time (i.e., simultaneous administration) or at different times (i.e., sequential administration, in either order). Although the following discussion of preferred dosing regimens refers to dosing of an antagonist anti-CD40 antibody as defined herein in combination with IL-2 as defined herein, it is recognized that the protocols (i.e., initiation of treatment, duration of antibody and IL-2 treatment, antibody and IL-2 dosing regimens, interruption of IL-2 dosing, subsequent courses of combination IL-2/antagonist antiCD40 antibody therapy, IL-2 dosing schedule, and the like) are equally applicable to dosing with an antigen-binding fragment of an antagonist anti-CD40 antibody as defined herein in combination with IL-2 as defined herein, dosing with an antigen-binding fragment of an antagonist anti-CD40 antibody as defined herein in combination with a biologically active variant of IL-2 as defined herein, or dosing with an antagonist anti-CD40 antibody as defined herein in combination with a biologically active variant of IL-2 as defined herein.

2. Concurrent Therapy: Initiation of Treatment.

Where concurrent therapy with IL-2 and antagonist anti-CD40 antibody comprises one or more cycles of a constant IL-2 dosing regimen, the initial therapeutic agent to be administered to the subject at the start of a treatment period can be either the IL-2 or the antagonist anti-CD40 antibody, so long as the subject has an overlapping period of time during which both therapeutic agents are being administered to the subject, each according to the particular dosing regimen disclosed herein.

Thus, in one embodiment, concurrent therapy with these two therapeutic agents comprises intitating the constant IL-2 dosing regimen prior to initiating administration of therapeutically effective doses of antagonist anti-CD40 antibody, which are administered weekly, or, alternatively, once every two, three, or four weeks. In this manner, a first dose of IL-2 is administered up to one month before the first dose of antagonist anti-CD40 antibody is administered. By "up to one month" is intended the first dose of IL-2 is administered at least one day before initiating antagonist anti-CD40 antibody administration, but not more than one month (i.e., 30 days) before initiating antagonist anti-CD40 antibody administration. Thus, IL-2 administration can begin, for example, 1 day, 2 days, 3 days, 4 days, 5 days, 6 days, 7 days (i.e., 1 week), 10 days, 14 days (i.e., two weeks), 17 days, 21 days (i.e., 3 weeks), 24 days, 28 days (4 weeks), or up to one month (i.e., 30 or 31 days) before administering the first therapeutically effective dose of the antagonist anti-CD40 antibody.

In other embodiments, the constant IL-2 dosing regimen and antagonist anti-CD40 antibody administration begin concurrently on the same day, either at the same time (i.e., simultaneous administration) or at different times (i.e., sequential administration, in either order). Thus, for example, in one embodiment where concurrent therapy with these two therapeutic agents begins on day 1 of a treatment period, a first therapeutically effective dose of antagonist anti-CD40 antibody and a first dose of IL-2 would both be administered on day 1 of this treatment period. In one such embodiment, the dose of antagonist anti-CD40 antibody is administered first, followed by administration of the dose of IL-2 within about 10 minutes to about 4 hours of the completion of administering the dose of antagonist anti-CD40 antibody, such as within about 10, 15, 20, 25, 30, 45, 60, 90, 120, 150, 180, 210, or 240 minutes.

In alternative embodiments, the initial therapeutic agent to be administered to the subject at the start of a treatment period is the antagonist anti-CD40 antibody, while the first cycle of constant IL-2 dosing is initiated by administering a first dose of IL-2 subsequently, for example, within 10 days following administration of the first therapeutically effective dose of the antagonist anti-CD40 antibody, for example, within 1, 2, 3, 4, 5, 6, 7, 8, 9, or 10 days. In some embodiments, the first cycle of constant IL-2 dosing is initiated by administering a first dose of IL-2 within 7 days of administering the first therapeutically effective dose of antagonist anti-CD40 antibody, such as within 1, 2, 3, 4, 5, 6, or 7 days. Thus, for example, in one embodiment, a therapeutically effective dose of the antagonist anti-CD40 antibody is administered on day 1 of a treatment period, and the first cycle of constant IL-2 dosing is initiated 7 days later, i.e., by administering the initial dose of IL-2 on day 8 of the treatment period.

Following completion of the first cycle of constant IL-2 dosing, a human subject that is receiving therapeutically effective doses of the antagonist anti-CD40 antibody accordingly to a weekly dosing schedule, or, alternatively, once every two, three, or four weeks, can be administered one or more subsequent cycles of constant IL-2 dosing. During the second and all subsequent cycles of constant IL-2 dosing, generally the first therapeutic agent to be administered to the subject is the antagonist anti-CD40 antibody, with the second or subsequent cycle of constant IL-2 dosing being initiated by administering a first dose of IL-2 within 24 hours, such as within 0.5, 1, 2, 4, 8, 12, 16, 20, or 24 hours of administering the dose of antagonist anti-CD40 antibody. On those days where both antagonist anti-CD40 antibody and IL-2 are scheduled to be administered to the subject, these therapeutic agents can be administered either at the same time (i.e., simultaneous administration) or at different times (i.e., sequential administration, in either order). In one such embodiment, the dose of antagonist anti-CD40 antibody is administered first, followed by administration of the dose of IL-2 within about 10 minutes to about 4 hours of the completion of administering the dose of antagonist anti-CD40 antibody, such as within about 10, 15, 20, 25, 30, 45, 60, 90, 120, 150, 180, 210, or 240 minutes.

Where concurrent therapy with IL-2 and antagonist anti-CD40 antibody comprises one or more cycles of a two-level IL-2 dosing regimen, the initial therapeutic agent to be administered to the subject at the start of a treatment period can be either the IL-2 or the antagonist antiCD40 antibody, so long as the subject has an overlapping period of time during which both therapeutic agents are being administered to the subject, each according to the particular dosing regimen disclosed herein.

Thus, in one embodiment, concurrent therapy with these two therapeutic agents comprises initiating the two-level IL-2 dosing regimen prior to initiating administration of therapeutically effective doses of antagonist anti-CD40 antibody, where a therapeutically effective dose of the antibody is administered according to a weekly dosing schedule, or, alternatively, once every two, three, or four weeks. In this manner, a first dose of IL-2 is administered up to one month before the first dose of antagonist anti-CD40 antibody is administered. By "up to one month" is intended the first dose of IL-2 is administered at least one day before initiating antagonist anti-CD40 antibody administration, but not more than one month (i.e., 30 days) before initiating antagonist anti-CD40 antibody administration. Thus, IL-2 administration can begin, for example, 1 day, 2 days, 3 days, 4 days, 5 days, 6 days, 7 days (i.e., 1 week), 10 days, 14 days (i.e., two weeks), 17 days, 21 days (i.e., 3 weeks), 24 days, 28 days (4 weeks), or up to one month (i.e., 30 or 31 days) before administering the first therapeutically effective dose of the antagonist anti-CD40 antibody.

In other embodiments, the two-level IL-2 dosing regimen and antagonist anti-CD40 antibody administration begin concurrently on the same day, either at the same time (i.e., simultaneous administration) or at different times (i.e., sequential administration, in either order). Thus, for example, in one embodiment where concurrent therapy with these two therapeutic agents begins on day 1 of a treatment period, a first therapeutically effective dose of antagonist anti-CD40 antibody and a first dose of IL-2 would both be administered on day 1 of this treatment period. In one such embodiment, the dose of antagonist anti-CD40 antibody is administered first, followed by administration of the dose of IL-2 within about 10 minutes to about 4 hours of the completion of administering the dose of antagonist anti-CD40 antibody, such as within about 10, 15, 20, 25, 30, 45, 60, 90, 120, 150, 180, 210, or 240 minutes.

In alternative embodiments, a first therapeutically effective dose of antagonist anti-CD40 antibody is administered to the subject, for example, on day 1 of a treatment period, and the two-level IL-2 dosing regimen is initiated by administering a first dose of IL-2 within 10 days of administering the first therapeutically effective dose of antagonist anti-CD40 antibody. In such embodiments, preferably the two-level IL-2 dosing regimen is initiated by administering a first dose of IL-2 within 7 days of administering the first therapeutically effective dose of antagonist anti-CD40 antibody, such as within 1, 2, 3, 4, 5, 6, or 7 days.

Depending upon the severity of the disease, the patient's health, and prior history of the patient's disease, one or more cycles of a two-level IL-2 dosing regimen can be administered concurrently with antagonist anti-CD40 antibody therapy, where therapeutically effective doses of the antibody are administered weekly, or, alternatively, once every two, three, or four weeks.

3. Duration of Antibody and IL-2 Treatment.

In accordance with the methods of the present invention, a therapeutically effective dose of antagonist anti-CD40 antibody is administered weekly, or is administered once every two, three, or four weeks, in combination with one or more cycles of a constant IL-2 dosing regimen or in combination with one or more cycles of a two-level IL-2 dosing regimen. When a subject is undergoing concurrent therapy with these two therapeutic agents in the manner set forth herein, the duration of antagonist anti-CD40 antibody administration and the duration of any given cycle of either of the IL-2 dosing regimens will depend upon the subject's overall health, history of disease progression, and tolerance of the particular antagonist anti-CD40 antibody/IL-2 administration protocol.

Thus, in some embodiments, therapeutically effective doses of antagonist anti-CD40 antibody are administered weekly (i.e., once a week), or once every two to four weeks, for example, once every two weeks, once every three weeks, or once every four weeks, throughout a treatment period, where the treatment period includes one or more cycles of a constant IL-2 dosing regimen or one or more cycles of a two-level IL-2 dosing regimen.

Alternatively, the anti-CD40 antibody therapy can have a fixed duration within a treatment period. In this manner, a therapeutically effective dose of antagonist anti-CD40 antibody is administered weekly, or is administered once every two, three, or four weeks, for a fixed period of about 4 weeks to about 16 weeks, including 4, 5, 6, 7, 8, 9, 10, 11, 12, 13, 14, 15, or 16 weeks, in combination with one or more cycles of a constant IL-2 dosing regimen or in combination with one or more cycles of a two level-IL-2 dosing regimen. Thus, for example, where the antibody is administered weekly for a duration of 4 weeks or 8 weeks, the subject would receive four or eight therapeutically effective doses of the anti-CD40 antibody, respectively, during concurrent therapy with IL-2. Similarly, where the antibody is administered once every two weeks for a duration of 4 weeks or 8 weeks, for example, the subject would receive two or four therapeutically effective doses of the antagonist anti-CD40 antibody, respectively, during concurrent therapy with IL-2. Where the antibody is administered once every three weeks for a duration of 6 weeks, 9 weeks, 12 weeks, or 15 weeks, for example, the subject would receive two, three, four, or five therapeutically effective doses of the antagonist anti-CD40 antibody, respectively, during concurrent therapy with IL-2. Similarly, where the antibody is administered once every four weeks for a duration of 8 weeks, 12 weeks, or 16 weeks, the subject would receive two, three, or four therapeutically effective doses of the antagonist anti-CD40 antibody, respectively, during concurrent therapy with IL-2.

The duration of IL-2 administration during concurrent therapy with these two therapeutic agents is a function of the IL-2 dosing regimen used. Generally, IL-2 is administered according to the disclosed protocols, and a subject can repeat one or more cycles of a constant or two-level IL-2 dosing regimen as needed, unless IL-2 toxicity symptoms develop. Should such toxicity symptoms develop, the subject can be taken off of IL-2 dosing until complete resolution of any observed toxicity symptoms. Such IL-2 toxicity responses include but are not limited to, chronic fatigue, nausea, hypotension, fever, chills, weight gain, pruritis or rash, dysprea, azotemia, confusion, thrombocytopenia, myocardial infarction, gastrointestinal toxicity, and vascular leak syndrome (see, for example, Allison et al. (1989) *J. Clin. Oncol.* 7(1):75-80). The subject may resume concurrent therapy with these two therapeutic agents as needed following resolution of signs and symptoms of these IL-2 toxicity symptoms. Resumption of concurrent therapy with these two therapeutic agents can entail either of the antagonist anti-CD40 antibody/IL-2 administration protocols disclosed herein (i.e., antagonist anti-CD40 antibody with the constant IL-2 dosing regimen or antagonist anti-CD40 antibody with the two-level IL-2 dosing regimen) depending upon the overall health of the subject, relevant disease state, and tolerance for the particular antagonist anti-CD40 antibody/IL-2 administration protocol.

4. Constant IL-2 Dosing Regimen.

In some embodiments of the invention, the subject undergoing concurrent therapy with these two therapeutic agents is administered one or more cycles of a constant IL-2 dosing regimen in combination with the antagonist anti-CD40 antibody dosing schedule disclosed herein (i.e., therapeutically effective doses of antagonist anti-CD40 antibody administered weekly, or administered once every two, three, or four weeks, throughout a treatment period or for a fixed duration within the treatment period as noted herein above). By "constant IL-2 dosing regimen" is intended the subject undergoing concurrent therapy with IL-2 and antagonist anti-CD40 antibody is administered a constant total weekly dose of IL-2 over the course of any given cycle of IL-2 administration. One complete cycle of a constant IL-2 dosing regimen comprises administering a constant total weekly dose of IL-2 for a period of about 2 weeks to about 12 weeks, such as about 2, 3, 4, 5, 6, 7, 8, 9, 10, 11, or 12 weeks, followed by a time period off of IL-2 dosing, which has a duration of about 1 week to about 4 weeks, including 1, 2, 3, or 4 weeks. Thus, each cycle of a constant IL-2 dosing regimen comprises a first time period during which the subject is administered a constant total weekly dose of IL-2, and a second time period during which IL-2 dosing is withheld (i.e., a "rest" period or "holiday" from IL-2 administration). Preferably the subject is administered the constant total weekly dose of IL-2 for at least 4 weeks up to about 12 weeks, at which time IL-2 dosing is withheld for a period of about 1 week to about 4 weeks. As noted herein above, either of these therapeutic agents can be administered first in order to intitiate this concurrent therapy protocol.

Where the subject is to receive antagonist anti-CD40 antibody therapy throughout a treatment period (i.e., a time period during which the subject in undergoing concurrent therapy with these two therapeutic agents), during each cycle of the constant IL-2 dosing regimen, the subject remains on the recommended dosing regimen for the antagonist anti-CD40 antibody, and thus receives a therapeutically effective dose of antagonist anti-CD40 antibody according to a weekly dosing schedule, or according to a once every two weeks, once every three weeks, or once every four weeks dosing schedule.

Alternatively, where the subject is to receive antagonist anti-CD40 antibody therapy for a fixed duration throughout a treatment period, the treatment period comprises administering a therapeutically effective dose of the anti-CD40 antibody for a fixed duration of about 4 weeks to about 16 weeks, where the antibody is administered once every week, once every two weeks, once every three weeks, or once every four weeks, and administering one or more cycles of the constant IL-2 dosing regimen. Thus, for example, in some embodiments, the subject is administered a therapeutically effective dose of the antagonist anti-CD40 antibody once per week for a fixed duration of 4 weeks or 8 weeks, in combination with at least one cycle of a constant IL-2 dosing regimen. In such embodiments, each complete cycle of the constant IL-2 dosing regimen comprises administering a constant total weekly dose of IL-2 for a period of about 2 weeks to about 12 weeks, such as about 2, 3, 4, 5, 6, 7, 8, 9, 10, 11, or 12 weeks, followed by a time period off of IL-2 dosing, which has a duration of about 1 week to about 4 weeks, including 1, 2, 3, or 4 weeks.

At the discretion of the managing physician, the subject undergoing weekly antagonist anti-CD40 antibody administration, or antagonist anti-CD40 antibody administration once every two, three, or four weeks, can continue receiving the constant total weekly dose of IL-2 for an extended period of time beyond 12 weeks, for example, for an additional 1-8 weeks, providing the antagonist anti-CD40 antibody/constant IL-2 dosing protocol is well tolerated and the subject is exhibiting minimal signs of either antagonist anti-CD40 antibody and/or IL-2 toxicity symptoms. In such an embodiment, conclusion of IL-2 dosing would be followed by a period of about 1 week to about 4 weeks during which IL-2 dosing would be withheld to allow the subject time off of this therapeutic agent before starting a subsequent cycle of the constant IL-2 dosing regimen.

In one embodiment, a subject in need of concurrent therapy with antagonist anti-CD40 antibody and IL-2 is administered a therapeutically effective dose of antagonist anti-CD40 antibody once per week throughout a treatment period, or is administered a therapeutically effective dose of antagonist anti-CD40 antibody once every three weeks throughout this treatment period, beginning on day 1 of this treatment period, and the first cycle of a constant IL-2 dosing regimen is initiated beginning on day 3, 4, 5, 6, 7, 8, 9, or of the same treatment period. In one such embodiment, the first cycle of the constant IL-2 dosing regimen begins on day 8 (i.e., at the start of week 2) of the treatment period, and has a duration of IL-2 administration of about 4 weeks to about 12 weeks, followed by a time period off of IL-2 administration that has a duration of about 1 week to about 4 weeks. At the conclusion of this first cycle of the constant IL-2 dosing regimen, the subject receives one or more subsequent cycles of the constant IL-2 dosing regimen as noted herein above.

In another embodiment, the subject is administered a therapeutically effective dose of antagonist anti-CD40 antibody once per week throughout a treatment period, or is administered a therapeutically effective dose of antagonist anti-CD40 antibody once every three weeks throughout this treatment period, beginning on day 1 of this treatment period, and a first cycle of the constant IL-2 dosing regimen begins on day 8 (i.e., at the start of week 2) of the treatment period, and has a duration of IL-2 administration of 4 weeks, followed by a time period off of IL-2 administration having a duration of 1 week. At the discretion of the managing physician, the subject is then administered one or more subsequent cycles of this constant IL-2 dosing regimen, i.e., administration of the constant total weekly dose of IL-2 for 4 weeks, followed by 1 week off of IL-2 administration. During the entire treatment period, the subject continues to receive the therapeutically effective dose of antagonist anti-CD40 antibody according to the once-a-week dosing schedule, or the once-every-three-weeks dosing schedule, with the proviso that the subject does not exhibit symptoms of antagonist anti-CD40 antibody toxicity. Thus, for example, if the subject undergoes three cycles of the constant IL-2 dosing regimen in combination with weekly (i.e., once-per-week) administration of antagonist anti-CD40 antibody, with the first cycle of IL-2 administration beginning on day 8 of a treatment period (i.e., day 1 of week 2), therapeutically effective doses of the antagonist anti-CD40 antibody would be administered to this subject on day 1 of each week of treatment (i.e., day 1 of weeks 1-16), and a constant total weekly dose of IL-2 would be administered during weeks 2-5, weeks 7-10, and weeks 12-15, with time off from IL-2 dosing occurring during weeks 6, 11, and 16.

In alternative embodiments, a subject in need of concurrent therapy with antagonist anti-CD40 antibody and IL-2 is administered a therapeutically effective dose of antagonist anti-CD40 antibody once per week, or is administered a therapeutically effective dose of antagonist anti-CD40 antibody once every two weeks, for a fixed duration of 4 weeks or 8 weeks beginning on day 1 of a treatment period, and the first cycle of a constant IL-2 dosing regimen is initiated beginning on day 3, 4, 5, 6, 7, 8, 9, or 10 of the same treatment period. In one such embodiment, the first cycle of the constant IL-2 dosing regimen begins on day 8 (i.e., at the start of week 2) of the treatment period, and has a duration of IL-2 administration of about 4 weeks to about 12 weeks, followed by a time period off of IL-2 administration that has a duration of about 1 week to about 4 weeks. At the conclusion of this first cycle of the constant IL-2 ced dosing regimen, the subject receives one or more subsequent cycles of the constant IL-2 dosing regimen as noted herein above.

In another embodiment, the subject is administered a therapeutically effective dose of antagonist anti-CD40 antibody once per week, or once every two weeks, for a fixed duration of 4 weeks or 8 weeks beginning on day 1 of a treatment period, and a first cycle of the constant IL-2 dosing regimen begins on day 8 (i.e., at the start of week 2) of the treatment period, and has a duration of IL-2 administration of 4 weeks, followed by a time period off of IL-2 administration having a duration of 1 week. At the discretion of the managing physician, the subject is then administered one or more subsequent cycles of this constant IL-2 dosing regimen, i.e., administration of the constant total weekly dose of IL-2 for 4 weeks, followed by 1 week off of IL-2 administration. Thus, for example, if the subject undergoes three cycles of the constant IL-2 dosing regimen in combination with weekly (i.e., once-per-week) administration of antagonist anti-CD40 antibody for a fixed duration of 4 weeks, with the first cycle of IL-2 administration beginning on day 8 of a treatment period (i.e., day 1 of week 2), therapeutically effective doses of the antagonist anti-CD40 antibody would be administered to this subject on day 1 of weeks 1-4 of the treatment period, and a constant total weekly dose of IL-2 would be administered during weeks 2-5, weeks 7-10, and weeks 12-15, with time off from IL-2 dosing occurring during weeks 6, 11, and 16. Alternatively, if the subject undergoes three cycles of the constant IL-2 dosing regimen in combination with weekly (i.e., once-per-week) administration of antagonist anti-CD40 antibody for a fixed duration of 8 weeks, with the first cycle of IL-2 administration beginning on day 8 of a treatment period (i.e., day 1 of week 2), therapeutically effective doses of the antagonist anti-CD40 antibody would be administered to this subject on day 1 of weeks 1-8 of the treatment period, and a constant total weekly dose of IL-2 would be administered during weeks 2-5, weeks 7-10, and weeks 12-15, with time off from IL-2 dosing occurring during weeks 6, 11, and 16.

5. Two-Level IL-2 Dosing Regimen.

In other embodiments of the invention, concurrent therapy with antagonist anti-CD40 antibody and IL-2 comprises administering a therapeutically effective dose of antagonist anti-CD40 antibody once per week, or once every two, three, or four weeks, throughout a treatment period or for a fixed duration within the treatment period, in combination with one or more cycles of a "two-level IL-2 dosing regimen" during the course of this treatment period. By "two-level IL-2 dosing regimen" is intended the subject undergoing concurrent therapy with IL-2 and antagonist anti-CD40 antibody is administered IL-2 during two time periods of IL-2 dosing, which have a combined duration of about 2 weeks to about 16 weeks, including, 2, 3, 4, 5, 6, 7, 8, 9, 10, 11, 12, 13, 14, 15, or 16 weeks. In one embodiment, the two-level IL-2 dosing regimen has a combined duration of about 4 weeks to about 12 weeks; in other embodiments, the two-level IL-2 dosing regimen has a combined duration of about 4 weeks to about 8 weeks, including about 4, 5, 6, 7, or 8 weeks. The total weekly dose of IL-2 that is to be administered during the first and second time periods of the two-level IL-2 dosing regimen is chosen such that a higher total weekly dose of IL-2 is given during the first time period and a lower total weekly dose of IL-2 is given during the second time period.

The duration of the individual first and second time periods of any given cycle of the two-level IL-2 dosing regimen can vary, depending upon the health of the individual and history of disease progression. Generally, the subject is administered higher total weekly doses of IL-2 for at least 1 week out of the 4-week to 16-week two-level IL-2 dosing regimen. In one embodiment, higher total weekly doses of IL-2 are administered during the first half of the two-level IL-2 dosing regimen, with lower total weekly doses being administered during the second half of the two-level IL-2 dosing regimen. Thus, for example, where one complete cycle of the two-level IL-2 dosing regimen has a combined duration of 8 weeks, the higher total weekly doses of IL-2 would be administered for the first 4 weeks of IL-2 dosing, and the lower total weekly doses of IL-2 would be administered for the second 4 weeks of IL-2 dosing.

Where the subject is to receive antagonist anti-CD40 antibody therapy throughout a treatment period (i.e., a time period during which the subject in undergoing concurrent therapy with these two therapeutic agents), during each cycle of the two-level IL-2 dosing regimen, the subject remains on the recommended dosing regimen for the antagonist anti-CD40 antibody, and thus receives a therapeutically effective dose of antagonist anti-CD40 antibody according to a weekly dosing schedule, or according to a once every two weeks, once every three weeks, or once every four weeks dosing schedule.

Alternatively, where the subject is to receive antagonist anti-CD40 antibody therapy for a fixed duration throughout a treatment period, the treatment period comprises administering a therapeutically effective dose of the anti-CD40 antibody for a fixed duration of about 4 weeks to about 16 weeks, where the antibody is administered once every week, once every two weeks, once every three weeks, or once every four weeks, and administering one or more cycles of the two-level IL-2 dosing regimen. Thus, for example, in some embodiments, the subject is administered a therapeutically effective dose of the antagonist anti-CD40 antibody once per week for a fixed duration of 4 weeks or 8 weeks, in combination with at least one cycle of a two-level IL-2 dosing regimen as defined herein above.

Though specific dosing regimens are disclosed herein below, it is recognized that the invention encompasses any administration protocol that provides for concurrent therapy with an antagonist anti-CD40 antibody and one or more cycles of a two-level IL-2 dosing regimen that provides for initial exposure to higher total weekly doses of IL-2, and subsequent exposure to lower total weekly doses of IL-2. While not being bound by theory, it is believed that administering a higher dose of IL-2 during the initial stages of IL-2 dosing provides for an initial stimulation of NK cell activity that can be maintained by a lower dose during the subsequent weeks of IL-2 dosing. As IL-2 side effects are dose-related, the lowered dose of IL-2 will increase tolerability of this therapeutic agent during the extended treatment period.

Thus, the methods of the invention contemplate treatment regimens where a therapeutically effective dose of at least one antagonist anti-CD40 antibody is administered once a week throughout a treatment period, or is administered once every two, three, or four weeks throughout this treatment period, in combination with a two-level IL-2 dosing having a combined duration of about 2 weeks to about 16 weeks, including 2, 3, 4, 5, 6, 7, 8, 9, 10, 11, 12, 13, 14, 15, or 16 weeks. Either agent could be administered first, as explained above for this two-level IL-2 dosing regimen. For example, in one embodiment, a therapeutically effective dose of antagonist anti-CD40 antibody is administered first, for example, on day 1 of a treatment period, followed by initiation of the two-level IL-2 dosing regimen within 10 days, preferably within 7 days of the first administration of the antagonist anti-CD40 antibody, for example, within 1, 2, 3, 4, 5, 6, or 7 days. During the two-level IL-2 dosing regimen, a higher total weekly dose of IL-2 is administered in the first time period of the two-level IL-2 dosing regimen, for example, over the first 1-4 weeks of IL-2 administration, and lower total weekly doses of IL-2 are administered during the second time period of the two-level IL-2 dosing regimen (i.e., over the remaining course of the two-level IL-2 dosing regimen).

In one embodiment, the methods of the invention provide for administering a therapeutically effective dose of a pharmaceutical composition comprising at least one antagonist anti-CD40 antibody weekly (i.e., once per week) throughout a treatment period, or administering this therapeutically effective dose of antagonist anti-CD40 antibody once every three weeks throughout this treatment period, in combination with one or more cycles of a two-level IL-2 dosing regimen during the course of this treatment period, where each cycle of the two-level IL-2 dosing regimen has a combined duration of 4 weeks to 8 weeks, including 4, 5, 6, 7, or 8 weeks. Thus, for example, where the antagonist anti-CD40 antibody is to be dosed once per week, a therapeutically effective dose of at least one antagonist anti-CD40 antibody is administered on day 1 of each week of the treatment period, and the first cycle of a 4-week to 8-week two-level IL-2 dosing regimen is initiated beginning on day 3, 4, 5, 6, 7, 8, 9, or 10 of the same treatment period.

In one such embodiment, therapeutically effective doses of the pharmaceutical composition comprising the antagonist anti-CD40 antibody are administered weekly beginning on day 1 of a treatment period and continuing throughout the treatment period, and a first cycle of the two-level IL-2 dosing regimen begins on day 8 of the same treatment period and continues for 8 weeks (i.e., during weeks 2-9 of the treatment period).

Alternatively, the methods of the invention contemplate treatment regimens for a subject in need thereof where a therapeutically effective dose of at least one antagonist anti-CD40 antibody is administered once per week, or is administered once every two weeks, for a fixed duration of 4 weeks or 8 weeks, in combination with a two-level IL-2 dosing regimen having a combined duration of about 2 weeks to about 16 weeks, including 2, 3, 4, 5, 6, 7, 8, 9, 10, 11, 12, 13, 14, 15, or 16 weeks. Either agent could be administered first, as explained above for this two-level IL-2 dosing regimen. For example, in one embodiment, a therapeutically effective dose of antagonist anti-CD40 antibody is administered first, for example, on day 1 of a treatment period, followed by initiation of the two-level IL-2 dosing regimen within 10 days, preferably within 7 days of the first administration of the antagonist anti-CD40 antibody, for example, within 1, 2, 3, 4, 5, 6, or 7 days. During the two-level IL-2 dosing regimen, a higher total weekly dose of IL-2 is administered in the first time period of the two-level IL-2 dosing regimen, for example, over the first 1-4 weeks of IL-2 administration, and lower total weekly doses of IL-2 are administered during the second time period of the two-level IL-2 dosing regimen (i.e., over the remaining course of the two-level IL-2 dosing regimen).

In one embodiment, the methods of the invention provide for administering a therapeutically effective dose of a pharmaceutical composition comprising at least one antagonist anti-CD40 antibody weekly (i.e., once per week) or once every two weeks for a fixed duration of 4 weeks or 8 weeks, in combination with one or more cycles of a two-level IL-2 dosing regimen during the course of this treatment period, where each cycle of the two-level IL-2 dosing regimen has a combined duration of 4 weeks to 8 weeks, including 4, 5, 6, 7, or 8 weeks. Thus, for example, where the antagonist anti-CD40 antibody is to be dosed once per week for a duration of 4 weeks, a therapeutically effective dose of at least one antagonist anti-CD40 antibody is administered on day 1 of weeks 1-4 of the treatment period, and the first cycle of a 4-week to 8-week two-level IL-2 dosing regimen is initiated beginning on day 3, 4, 5, 6, 7, 8, 9, or 10 of the same treatment period.

In one such embodiment, therapeutically effective doses of the pharmaceutical composition comprising the antagonist anti-CD40 antibody are administered weekly for a fixed duration of 4 weeks beginning on day 1 of a treatment period, and a first cycle of the two-level IL-2 dosing regimen begins on day 8 of the same treatment period and continues for 8 weeks (i.e., during weeks 2-9 of the treatment period).

6. Interruption of IL-2 Dosing.

The methods of the present invention also contemplate embodiments where a subject undergoing antagonist anti-CD40 antibody administration according to the dosing schedule recommended herein in combination with administration of one or more cycles of a two-level IL-2 dosing regimen is given a "drug holiday" or a time period off from IL-2 dosing, or from the IL-2 dosing and the antagonist anti-CD40 antibody dosing, between the conclusion of the first time period of any given cycle of the two-level IL-2 dosing regimen and the initiation of the second time period of that particular cycle of the two-level IL-2 dosing regimen. In these embodiments, the two-level IL-2 dosing regimen is interrupted such that IL-2 dosing is withheld for a period of about 1 week to about 4 weeks following conclusion of the first time period of a given cycle of the two-level IL-2 dosing regimen during which the higher total weekly dose has been administered. During this time period off of IL-2 dosing, the subject may continue to receive a therapeutically effective dose of antagonist anti-CD40 antibody according to the dosing schedule recommended herein (i.e., once per week, or once every two, three, or four weeks) or, alternatively, antagonist anti-CD40 antibody dosing can also be stopped. The length of this interruption in IL-2 dosing will depend upon the health of the subject, history of disease progression, and responsiveness of the subject to the initial IL-2/antibody therapy received during the first time period of any given cycle of the two-level IL-2 dosing regimen. Generally, IL-2 dosing is interrupted for a period of about 1 week to about 4 weeks, at which time the subject is administered the second time period of the two-level IL-2 dosing regimen, where lower total weekly doses of IL-2 are administered in combination with the weekly administration of therapeutically effective doses of the antagonist anti-CD40 antibody. In order to complete any given cycle of a two-level IL-2 dosing regimen, a subject must be administered both the first period of higher total weekly dosing and the second period of lower total weekly dosing.

During this drug holiday (i.e., time period off of IL-2 administration, or time period off of IL-2 and antagonist anti-CD40 antibody administration), natural-killer (NK) cell counts are monitored to determine when the two-level IL-2 dosing regimen, or the two-level IL-2 dosing regimen and weekly administration of antagonist anti-CD40 antibody, are to be resumed. NK cell levels above 200 cells/µl may be an important factor influencing positive clinical response to antagonist anti-CD40 antibody therapy. Therefore, monitoring of NK cell count during, at the conclusion, and following any given cycle of IL-2 dosing provides a means for determining when and if IL-2 therapy should be reinstated following a time off of IL-2 dosing, which may or may not include a time off of antagonist anti-CD40 antibody administration.

In this manner, NK cell counts are measured bi-weekly or monthly during the two-level IL-2 dosing regimen, and at the conclusion of the first time period of the two-level IL-2 dosing regimen before the drug holiday is initiated. Where NK cell count exceeds an acceptable threshold level, the two-level IL-2 dosing regimen can be interrupted. By "acceptable threshold level" is intended the subject undergoing treatment has an NK cell count that is about 150 cells/µl or greater, preferably 200 cells/µl or greater. Following discontinuance of the IL-2 dosing, which may or may not include discontinuance of antagonist anti-CD40 antibody administration, NK cell counts are then measured once per week or twice per week thereafter, or can be monitored less frequently, for example, once every two weeks or once every three weeks. An NK cell count falling below the acceptable threshold level of about 150 cells/µl, for example, an NK cell count of less than 150 cells/µl, is indicative of the necessity to resume the two-level IL-2 dosing regimen, or the two-level IL-2 dosing regimen and the antagonist anti-CD40 antibody dosing regimen where the drug holiday also includes time off of antagonist anti-CD40 antibody administration. Preferably the two-level IL-2 dosing regimen is resumed when NK cell count falls below a threshold level of about 200 cells/µl, i.e., an NK cell count of less than 200 cells/µl. At this time, the subject is administered the second time period of the two-level IL-2 dosing regimen, where lower total weekly doses of IL-2 are administered in combination with the antagonist anti-CD40 antibody, wherein a therapeutically effective dose of the antibody is administered once per week or is administered once every two, three, or four weeks.

Depending upon the overall health of the subject, clinical response, and tolerability of concurrent therapy with these two therapeutic agents, following completion of a first cycle of a two-level IL-2 dosing regimen, the subject can be administered one or more subsequent cycles of a two-level IL-2 dosing regimen in combination with administration of therapeutically effective doses of antagonist anti-CD40 antibody, where a therapeutically effective dose of the antibody is administered once per week or is administered once every two, three, or four weeks. In such embodiments, the managing physician can allow for a drug holiday or time period off of IL-2 administration between successive cycles. Thus, upon completion of any given cycle of a two-level IL-2 dosing regimen, which itself may or may not include a time period off of IL-2 administration between the first and second periods of IL-2 dosing, the subject can be given a break in IL-2 administration before initiating a subsequent cycle of the two-level IL-2 dosing regimen. Generally, the time period off of IL-2 administration between any given cycle of two-level IL-2 dosing is about 1 week to about 4 weeks, including about 1, 2, 3, or 4 weeks. During IL-2 drug holidays, the subject may continue to receive therapeutically effective doses of antagonist anti-CD40 antibody, which can be administered once per week, or once every two, three, or four weeks, or, alternatively, the antagonist anti-CD40 antibody dosing can also be stopped.

7. Subsequent Courses of Combination IL-2/Antagonist Anti-CD40 Antibody Therapy.

Where a subject undergoing therapy in accordance with the previously mentioned dosing regimens exhibits a partial response, or a relapse following a prolonged period of remission, subsequent courses of concurrent therapy may be needed to achieve complete remission of the disease. Thus, subsequent to a period of time off from a first treatment period, which may have comprised a constant IL-2 dosing regimen or a two-level IL-2 dosing regimen in combination with anti-CD40 antibody therapy throughout the treatment period or for a fixed duration within the treatment period, a subject may receive one or more additional treatment periods comprising either constant or two-level IL-2 dosing regimens in combination with antagonist anti-CD40 antibody administration, where the antibody can be administered throughout the additional treatment period(s) or administered for a fixed duration within the treatment period. Such a period of time off between treatment periods is referred to herein as a time period of discontinuance. It is recognized that the length of the time period of discontinuance is dependent upon the degree of tumor response (i.e., complete versus partial) achieved with any prior treatment periods of concurrent therapy with these two therapeutic agents.

Thus, for example, where a subject is undergoing concurrent therapy with weekly doses of antagonist anti-CD40 antibody and a two-level IL-2 dosing regimen, which may or may not include a drug holiday between the first and second time periods of the two-level IL-2 dosing regimen, their treatment regimen may include multiple treatment sessions, each of which comprises concurrent therapy with weekly doses of antagonist anti-CD40 antibody and a two-level IL-2 dosing regimen. These multiple treatment sessions are referred to herein as maintenance cycles, where each maintenance cycle comprises antagonist anti-CD40 antibody administration in combination with a completed two-level IL-2 dosing regimen. By "completed two-level IL-2 dosing regimen" is intended the subject has been administered both the first period of higher total weekly dosing and the second period of lower total weekly dosing. The necessity for multiple maintenance cycles can be assessed by monitoring NK cell count in a manner similar to that used to determine when a drug holiday is warranted, and when such a drug holiday must be concluded. Thus, upon completion of the two-level IL-2 dosing regimen in any given maintenance cycle, the treating physician obtains a measurement of NK cell count. This indicator is then measured at monthly intervals (i.e., once a month) following completion of any given two-level IL-2 dosing regimen. As with drug holidays, an NK cell count falling below an acceptable threshold level (i.e., below about 150 cells/μl, preferably below about 200 cells/μl) is indicative of the need for administering another maintenance cycle to the subject. The duration between maintenance cycles can be about 1 month to about 6 months, including 1 month, 1.5 months, 2 months, 2.5 months, 3 months, 3.5 months, 4 months, 4.5 months, 5 months, 5.5 months, 6 months, or other such time periods falling within the range of about 1 month to about 6 months.

Thus, the administration methods of the present invention provide an improved means for managing cancers that comprise CD40-expressing cells, for example, B-cell related cancers such as lymphomas, myelomas, and leukemia, and solid cancers, such as kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas). Without being bound by theory, the constant IL-2 dosing schedule with interruptions between provides an intermittent dosing schedule that allows for less frequent administration of the IL-2 during antagonist anti-CD40 antibody therapy, and better tolerability of long-term IL-2 therapy. The two-level IL-2 dosing regimen offers the opportunity to provide a patient with higher total weekly doses of IL-2, which provide for expansion of NK cell numbers that can be maintained by a lower dose during the subsequent weeks of IL-2 dosing. This administration protocol has the additional attraction of providing IL-2 drug holidays between the higher and lower total weekly IL-2 dosing schedules, as well as IL-2 drug holidays between completed cycles of the two-level IL-2 dosing regimen, again contributing to increased tolerability of concurrent therapy with antagonist anti-CD40 antibody and IL-2.

It is recognized that where a subject undergoing therapy in accordance with the previously mentioned dosing regimens exhibits a partial response, or a relapse following a prolonged period of remission, the subject could receive the antagonist anti-CD40 antibody as a single therapeutic agent, or in combination with another oncotherapy. Thus, a subject that has undergone previous concurrent therapy with IL-2 and antagonist anti-CD40 antibody for treatment of a cancer comprising CD40-expressing neoplastic cells and who is need of further treatment for the cancer can undergo therapy with an antagonist anti-CD40 antibody alone, or an antagonist anti-CD40 antibody and at least one other oncotherapy prior to, or as an alternative to, further concurrent therapy with antagonist anti-CD40 antibody and IL-2. Other types of oncotherapy include, but are not limited to, those described herein below.

8. IL-2 Dosing Schedule.

For human subjects undergoing concurrent therapy with antagonist anti-CD40 antibody according to the administration schedule recommended herein in combination with one or more cycles of a constant IL-2 dosing regimen or one or more cycles of a two-level IL-2 dosing regimen, the total weekly dose of IL-2 to be administered during periods of IL-2 dosing can be administered as a single dose, or can be partitioned into a series of equivalent doses that are administered according to a two- three-, four-, five-, six-, or seven-times-a-week dosing schedule. Where higher total weekly doses are to be administered during a first time period, and lower total weekly doses are to be administered during a second time period, it is not necessary that the total weekly dose be administered in the same manner over the course of both dosing periods. Thus, for example, the higher total weekly dose during the first time period of a two-level IL-2 dosing regimen can be administered as a single dose, or can be partitioned into a series of equivalent doses that are administered according to a two- three-, four-, five-, six-, or seven-times-a-week dosing schedule. Similarly, the lower total weekly dose during the second time period of a two-level IL-2 dosing regimen can be administered as a single dose, or can be partitioned into a series of equivalent doses that are administered according to a two-, three-, four-, five-, six-, or seven-times-a-week dosing schedule.

For purposes of the present invention, a "two-, three-, four-, five-, six-, or seven-times-a-week dosing schedule" is intended to mean that the total weekly dose is partitioned into two, three, four, five, six, or seven equivalent doses, respectively, which are administered to the subject over the course of a 7-day period, with no more than one equivalent dose being administered per 24-hour period. The series of equivalent doses can be administered on sequential days, or can be administered such that one or more days occur between any two consecutive doses, depending upon the total number of equivalent doses administered per week.

Thus, for example, where a series of two equivalent doses of IL-2 are administered per week (i.e., over a 7-day period) and the first equivalent dose of that week is administered on day 1, the second equivalent dose of IL-2 can be administered on day 2, 3, 4, 5, 6, or 7 of that week. In one embodiment, the total weekly dose of IL-2 is partitioned into two equivalent doses that are administered to the subject within a 7-day period, allowing for a minimum of 72 hours between doses and a maximum of 96 hours between doses.

Similarly, where a series of three equivalent doses of IL-2 are administered per week and the first equivalent dose of that week is administered on day 1, the second equivalent dose can be administered on day 2, 3, 4, 5, or 6 of that week, and the third equivalent dose can be administered on day 3, 4, 5, 6, or 7 of that week, so long as about 24 hours occur between administration of the second and third equivalent doses. In one embodiment, the total weekly dose of IL-2 is partitioned into three equivalent doses that are administered to the subject within a 7-day period, allowing for a minimum of 25 hours between doses and a maximum of 72 hours between doses.

Where a series of four equivalent doses of IL-2 are administered per week and the first equivalent dose of that week is administered on day 1, the second equivalent dose can be administered on day 2, 3, 4, or 5 of that week, the third equivalent dose can be administered on day 3, 4, 5, or 6 of that week, and the fourth equivalent dose can be administered on day 4, 5, 6, or 7 of that week, so long as about 24 hours occur between administration of any two consecutive doses (i.e., between the first and second equivalent doses, between the second and third equivalent doses, and between the third and fourth equivalent doses).

Where a series of five equivalent doses are administered per week and the first equivalent dose of that week is administered on day 1, the second equivalent dose can be administered on day 2, 3, or 4 of that week, the third equivalent dose can be administered on day 3, 4, or 5 of that week, the fourth equivalent dose can be administered on day 4, 5, or 6 of that week, and the fifth equivalent dose can be administered on day 5, 6, or 7 of that week, so long as about 24 hours occur between administration of any two consecutive doses (i.e., between the first and second equivalent doses, between the second and third equivalent doses, between the third and fourth equivalent doses, and between the fourth and fifth equivalent doses).

Where a series of six equivalent doses of IL-2 are administered per week and the first equivalent dose of that week is administered on day 1, the second equivalent dose can be administered on day 2 or 3 of that week, the third equivalent dose can be administered on day 3 or 4 of that week, the fourth equivalent dose can be administered on day 4 or 5 of that week, the fifth equivalent dose can be administered on day 5 or 6 of that week, and the sixth equivalent dose can be administered on day 6 or 7 of that week, so long as about 24 hours occur between administration of any two consecutive doses (i.e., between the first and second equivalent doses, between the second and third equivalent doses, between the third and fourth equivalent doses, between the fourth and fifth equivalent doses, and between the fifth and sixth equivalent doses).

In one embodiment, the total weekly dose of IL-2 is partitioned into seven equivalent doses, which are administered daily over the 7-day period, with about 24 hours occurring between each consecutive dose.

It is not necessary that the same dosing schedule be followed throughout a constant IL-2 dosing regimen, or that the same dosing schedule be followed for both the first and second periods of the two-level IL-2 dosing regimen. Thus, the dosing schedule can be adjusted to accommodate an individual's tolerance of prolonged IL-2 therapy in combination with antagonist anti-CD40 antibody therapy, and to reflect the individual's responsiveness to concurrent therapy with these two therapeutic agents. The preferred dosing schedule during the constant IL-2 dosing regimen and the two time periods of the two-level IL-2 dosing regimen is readily determined by the managing physician given the patient's medical history and the guidance provided herein.

VI. D. Antagonist Anti-CD40 Antibody Dose Ranges for Use in Combination IL-2/Antagonist Anti-CD40 Antibody Therapy For purposes of the present invention, the therapeutically effective dose of an antagonist anti-CD40 antibody or antigen-binding fragment thereof as defined elsewhere herein to be administered in combination with IL-2 therapy as disclosed herein ranges from about 0.003 mg/kg to about 50 mg/kg, from about 0.01 mg/kg to about 40 mg/kg, from about 0.01 mg/kg to about 30 mg/kg, from about 0.1 mg/kg to about 30 mg/kg, from about 0.5 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. Thus, for example, the dose of any one antagonist anti-CD40 antibody or antigen-binding fragment thereof, for example the anti-CD40 monoclonal antibody CHIR-12.12 or CHIR-5.9 or antigen-binding fragment thereof, can be 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.003 mg/kg to about 50 mg/kg. The same therapeutically effective dose of an antagonist anti-CD40 antibody or antigen-binding fragment thereof can be administered throughout each week of antibody dosing. Alternatively, different therapeutically effective doses of an antagonist anti-CD40 antibody or antigen-binding fragment thereof can be used over the course of a treatment period.

Thus, in some embodiments, the initial therapeutically effective dose of an antagonist anti-CD40 antibody or antigen-binding fragment thereof as defined elsewhere herein can be in the lower dosing range (i.e., about 0.003 mg/kg to about 20 mg/kg) with subsequent doses falling within the higher dosing range (i.e., from about 20 mg/kg to about 50 mg/kg). In alternative embodiments, the initial therapeutically effective dose of an antagonist anti-CD40 antibody or antigen-binding fragment thereof as defined elsewhere herein can be in the upper dosing range (i.e., about 20 mg/kg to about 50 mg/kg) with subsequent doses falling within the lower dosing range (i.e., 0.003 mg/kg to about 20 mg/kg). Thus, in one embodiment, the initial therapeutically effective dose of the antagonist anti-CD40 antibody or antigen-binding fragment thereof is about 20 mg/kg to about 35 mg/kg, including about 20 mg/kg, about 25 mg/kg, about 30 mg/kg, and about 35 mg/kg, and subsequent therapeutically effective doses of the antagonist anti-CD40 antibody or antigen binding fragment thereof are about 5 mg/kg to about 15 mg/kg, including about 5 mg/kg, 8 mg/kg, 10 mg/kg, 12 mg/kg, and about 15 mg/kg.

In some embodiments of the invention, antagonist anti-CD40 antibody therapy is initiated by administering a "loading dose" of the antibody or antigen-binding fragment thereof to the subject in need of IL-2/antagonist anti-CD40 antibody combination therapy. By "loading dose" is intended an initial dose of the antagonist anti-CD40 antibody or antigen-binding fragment thereof that is administered to the subject, where the dose of the antibody or antigen-binding fragment thereof administered falls within the higher dosing range (i.e., from about 20 mg/kg to about 50 mg/kg). The "loading dose" can be administered as a single administration, for example, a single infusion where the antibody or antigen-binding fragment thereof is administered IV, or as multiple administrations, for example, multiple infusions where the antibody or antigen-binding fragment thereof is administered IV, so long as the complete "loading dose" is administered within about a 24-hour period. Following administration of the "loading dose," the subject is then administered one or more additional therapeutically effective doses of the antagonist anti-CD40 antibody or antigen-binding fragment thereof. Subsequent therapeutically effective doses can be administered according to a weekly dosing schedule, or once every two weeks, once every three weeks, or once every four weeks as noted herein above. In such embodiments, the subsequent therapeutically effective doses generally fall within the lower dosing range (i.e., 0.003 mg/kg to about 20 mg/kg).

Alternatively, in some embodiments, following the "loading dose," the subsequent therapeutically effective doses of the antagonist anti-CD40 antibody or antigen-binding fragment thereof are administered according to a "maintenance schedule," wherein the therapeutically effective dose of the antibody or antigen-binding fragment thereof is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the antagonist anti-CD40 antibody or antigen-binding fragment thereof fall within the lower dosing range (i.e., 0.003 mg/kg to about 20 mg/kg), particularly when the subsequent doses are administered at more frequent intervals, for example, once every two weeks to once every month, or within the higher dosing range (i.e., from about 20 mg/kg to about 50 mg/kg), particularly when the subsequent doses are administered at less frequent intervals, for example, where subsequent doses are administered about one month to about 12 months apart.

VI. E. IL-2 Dose Ranges for Use in Combination IL-2/Antagonist Anti-CD40 Antibody Therapy For purposes of the following discussion of therapeutically effective doses of IL-2 or biologically active variant thereof to be administered in combination with antagonist-antiCD40 antibody therapy, the IL-2 pharmaceutical composition commercially available under the tradename Proleukin® (Chiron Corporation, Emeryville, Calif.) is used as the reference IL-2 standard. By "reference IL-2 standard" is intended the formulation of IL-2 that serves as the basis for determination of the therapeutically effective doses of IL-2 or biologically active variant thereof to be administered to a human subject with a cancer comprising CD40-expressing cells in combination with antagonist anti-CD40 antibody therapy. The active moiety used in this IL-2 product is the recombinant human IL-2 mutein aldesleukin (referred to as des-alanyl-1, serine-125 human interleukin-2; see U.S. Pat. No. 4,931,543, herein incorporated by reference).

Thus, for example, where the source of the IL-2 is Proleukin®, the total weekly dose of Proleukin® IL-2 to be administered in combination with antagonist-antiCD40 antibody therapy is in the range from about 18 million international units (MIU) to about 54 MIU, depending upon the medical history of the patient undergoing therapy and the recommended IL-2 dosing regimen (for example, constant versus two-level IL-2 dosing regimen). Where higher doses of IL-2 are to be administered, the total weekly dose of Proleukin® IL-2 can be in the range from about 42.0 MIU to about 54.0 MIU, including about 42.0 MIU, 43.5 MIU, 45.0 MIU, 46.5 MIU, 48.0 MIU, 49.5 MIU, 51.0 MIU, 52.5 MIU, and 54.0 MIU, and other such values falling within this range. Where intermediate doses of IL-2 are to be administered, the total weekly dose of Proleukin® IL-2 can be in the range from about 30.0 MIU to about 42.0 MIU, including about 30.0 MIU, 31.5 MIU, 33.0 MIU, 34.5 MIU, 36.0 MIU, 37.5 MIU, 39.0 MIU, 40.5 MIU, and 42.0 MIU, and other such values falling within this range. Where lower doses of IL-2 are to be administered, the total weekly dose of Proleukin® IL-2 can be in the range from about 18.0 MIU to about 30.0 MIU, including about 18.0 MIU, 19.5 MIU, 21.0 MIU, 22.5 MIU, 24.0 MIU, 25.5 MIU, 27.0 MIU, 28.5 MIU, and 30.0 MIU, and other such values falling within this range.

1. Recommended Doses for Constant IL-2 Dosing Regimen.

Where Proleukin® IL-2 is to be administered according to a constant IL-2 dosing regimen in combination with antagonist-antiCD40 antibody therapy, the total weekly dose of this reference IL-2 standard is about 18.0 MIU to about 54.0 MIU. Thus, for example, in some embodiments, the total amount of Proleukin® IL-2 that is to be administered per week as part of a constant IL-2 dosing regimen is about 18.0 MIU, 20 MIU, 22.0 MIU, 24.0 MIU, 26.0 MIU, 28.0 MIU, 30.0 MIU, 32.0 MIU, 34.0 MIU, 36.0 MIU, 38.0 MIU, 40.0 MIU, 42.0 MIU, 44.0 MIU, 46.0 MIU, 48.0 MIU, 50.0 MIU, 52.0 MIU, or 54.0 MIU, and other such doses falling within the range of about 18.0 MIU to about 54.0 MIU. In some embodiment, the total weekly dose of Proleukin® IL-2 falls within the range of about 42.0 MIU to about 54.0 MIU, for example, 42.0 MIU, 44.0 MIU, 46.0 MIU, 48.0 MIU, 50.0 MIU, 52.0 MIU, or 54.0 MIU. In other embodiments, the total weekly dose of Proleukin® IL-2 falls within the range of about 30.0 MIU to about 42.0 MIU, for example, about 30.0 MIU, 32.0 MIU, 34.0 MIU, 36.0 MIU, 38.0 MIU, 40.0 MIU, or 42.0 MIU. In alternative embodiments, the total weekly dose of Proleukin® IL-2 is about 18.0 MIU to about 30.0 MIU, for example, 18.0 MIU, 20 MIU, 22.0 MIU, 24.0 MIU, 26.0 MIU, 28.0 MIU, or 30.0 MIU.

As previously noted, the total weekly dose of IL-2 during a constant IL-2 dosing regimen can be administered as a single dose, or can be partitioned into a series of equivalent doses that are administered according to a two-, three-, four-, five-, six- or seven-times-a-week dosing schedule. Thus, for example, where the total weekly dose of Proleukin® IL-2 is 54.0 MIU, the three equivalent doses of this IL-2 source to be administered during each week would be 18.0 MIU, and the two equivalent doses of this IL-2 source to be administered during each week would be 27.0 MIU. Similarly, where the total weekly dose of Proleukin® IL-2 is 42.0 MIU, the three equivalent doses of this IL-2 source to be administered during each week would be 14.0 MIU, and the two equivalent doses of this IL-2 source to be administered during each week would be 21.0 MIU. Where the total weekly dose of Proleukin® IL-2 is 30.0 MIU, the three equivalent doses of this IL-2 source to be administered during each week of IL-2 dosing would be 10.0 MIU, and the two equivalent doses of this IL-2 source to be administered during each week of IL-2 dosing would be 15 MIU. Similarly, where the total weekly dose of Proleukin®IL-2 is 18.0 MIU, the three equivalent doses of this IL-2 source to be administered during each week would be 6.0 MIU, and the two equivalent doses of this IL-2 source to be administered during each week would be 9.0 MIU.

In accordance with the methods of the present invention, the subject is administered this constant IL-2 dosing regimen in combination with therapeutically effective doses of the antagonist anti-CD40 antibody or antigen-binding fragment thereof, where the therapeutically effective dose of the antibody or antigen-binding fragment thereof is administered according to a dosing regimen disclosed herein (i.e., once per week, once every two weeks, once every three weeks, or once every four weeks throughout a treatment period or for a fixed duration within a treatment period). The therapeutically effective dose of anti-CD40 antibody or antigen-binding fragment thereof to be administered is in the range from about 0.003 mg/kg to about 50 mg/kg, including about 0.5 mg/kg to about 30 mg/kg. Thus, for example, in some embodiments, the total amount of antagonist anti-CD40 antibody or antigen-binding fragment thereof is about 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.003 mg/kg to about 50 mg/kg.

Thus, for example, in some embodiments, the total amount of Proleukin® IL-2 that is to be administered per week as part of a constant IL-2 dosing regimen is about 42.0 MIU, 44.0 MIU, 46.0 MIU, 48.0 MIU, 50.0 MIU, 52.0 MIU, or 54.0 MIU, and the therapeutically effective dose of antagonist anti-CD40 antibody or antigen-binding fragment thereof that is to be administered in combination with the constant IL-2 dosing regimen is about 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg, where this dose of the antagonist anti-CD40 antibody or antigen-binding fragment thereof is administered once per week, once every two weeks, once every three weeks, or once every four weeks, throughout a treatment period or for a fixed duration within a treatment period. In one such embodiment, the total amount of Proleukin® IL-2 that is to be administered per week as part of a constant IL-2 dosing regimen is about 42.0 MIU, and the therapeutically effective dose of antagonist anti-CD40 antibody or antigen-binding fragment thereof that is to be administered in combination with the constant IL-2 dosing regimen is about 0.5 mg/kg, 1 mg/kg, 5 mg/kg, 7 mg/kg, 10 mg/kg, 15 mg/kg, 20 mg/kg, 25 mg/kg, 30 mg/kg, or 35 mg/kg, where this dose of the antagonist anti-CD40 antibody or antigen-binding fragment thereof is administered once per week, once every two weeks, once every three weeks, or once every four weeks, throughout a treatment period or for a fixed duration within a treatment period. In preferred embodiments, this total weekly dose of 42.0 MIU Proleukin® IL-2 is partitioned into two or three equivalent doses that are administered according to a two- or three-times-a-week dosing schedule, respectively. In this manner, the two equivalent doses of this IL-2 source to be administered during each week of the constant IL-2 dosing regimen would be 21.0 MIU, and the three equivalent doses of this IL-2 source to be administered during each week of the constant IL-2 dosing regimen would be 14.0 MIU.

In other embodiments, the total amount of Proleukin® IL-2 that is to be administered per week as part of a constant IL-2 dosing regimen is about 30.0 MIU, 32.0 MIU, 34.0 MIU, 36.0 MIU, 38.0 MIU, 40.0 MIU, or 42.0 MIU, and the therapeutically effective dose of antagonist anti-CD40 antibody or antigen-binding fragment thereof that is to be administered in combination with the constant IL-2 dosing regimen is about 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg, where this dose of the antagonist anti-CD40 antibody or antigen-binding fragment thereof is administered once per week, once every two weeks, once every three weeks, or once every four weeks, throughout a treatment period or for a fixed duration within a treatment period. In one such embodiment, the total amount of Proleukin® IL-2 that is to be administered per week as part of a constant IL-2 dosing regimen is about 30.0 MIU, and the therapeutically effective dose of antagonist anti-CD40 antibody or antigen-binding fragment thereof that is to be administered in combination with the constant IL-2 dosing regimen is about 0.5 mg/kg, 1 mg/kg, 5 mg/kg, 7 mg/kg, 10 mg/kg, 15 mg/kg, 20 mg/kg, 25 mg/kg, 30 mg/kg, or 35 mg/kg, where this dose of the antagonist anti-CD40 antibody or antigen-binding fragment thereof is administered once per week, once every two weeks, once every three weeks, or once every four weeks, throughout a treatment period or for a fixed duration within a treatment period. In preferred embodiments, this total weekly dose of 30.0 MIU Proleukin® IL-2 is partitioned into two or three equivalent doses that are administered according to a two- or three-times-a-week dosing schedule, respectively. In this manner, the two equivalent doses of this IL-2 source to be administered during each week of the constant IL-2 dosing regimen would be 15.0 MIU, and the three equivalent doses of this IL-2 source to be administered during each week of the constant IL-2 dosing regimen would be 10.0 MIU.

In yet other embodiments, the total amount of Proleukin®IL-2 that is to be administered per week as part of a constant IL-2 dosing regimen is about 18.0 MIU, 20 MIU, 22.0 MIU, 24.0 MIU, 26.0 MIU, 28.0 MIU, or 30.0 MIU, and the therapeutically effective dose of antagonist anti-CD40 antibody or antigen-binding fragment thereof that is to be administered in combination with the constant IL-2 dosing regimen is about 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, or 50 mg/kg, where this dose of the antagonist anti-CD40 antibody or antigen-binding fragment thereof is administered once per week, once every two weeks, once every three weeks, or once every four weeks, throughout a treatment period or for a fixed duration within a treatment period. In one such embodiment, the total amount of Proleukin® IL-2 that is to be administered per week as part of a constant IL-2 dosing regimen is about 18.0 MIU, and the therapeutically effective dose of antagonist anti-CD40 antibody or antigen-binding fragment thereof that is to be administered in combination with the constant IL-2 dosing regimen is about 0.5 mg/kg, 1 mg/kg, 5 mg/kg, 7 mg/kg, 10 mg/kg, 15 mg/kg, 20 mg/kg, 25 mg/kg, 30 mg/kg, or 35 mg/kg, where this dose of the antagonist anti-CD40 antibody or antigen-binding fragment thereof is administered once per week, once every two weeks, once every three weeks, or once every four weeks, throughout a treatment period or for a fixed duration within a treatment period. In preferred embodiments, this total weekly dose of 18.0 MIU Proleukin®IL-2 is partitioned into two or three equivalent doses that are administered according to a two- or three-times-a-week dosing schedule, respectively. In this manner, the two equivalent doses of this IL-2 source to be administered during each week of the constant IL-2 dosing regimen would be 9.0 MIU, and the three equivalent doses of this IL-2 source to be administered during each week of the constant IL-2 dosing regimen would be 6.0 MIU.

2. Recommended Doses for Two-Level IL-2 Dosing Regimen.

Where Proleukin® IL-2 is to be administered according to a two-level IL-2 dosing regimen in combination with antagonist anti-CD40 antibody therapy, the higher total weekly dose of this reference IL-2 standard that is administered during the first time period of this IL-2 dosing regimen is about 30.0 MIU to about 54.0 MIU, and the lower total weekly dose that is administered during the second time period of this IL-2 dosing regimen is about 18.0 MIU to about 39.0 MIU. As previously noted, the total weekly dose administered during the first time period of the two-level IL-2 dosing regimen, for example, during the first half of this dosing regimen, is always higher than the total weekly dose administered during the second time period of the two-level IL-2 dosing regimen, for example, during the second half of this dosing regimen.

Thus, in some embodiments, the higher total weekly dose of Proleukin® IL-2 that is administered during the first time period of the two-level IL-2 dosing regimen is about 30.0 MIU to about 54.0 MIU, including about 30.0 MIU, 32.0 MIU, 35.0 MIU, 37.0 MIU, 40.0 MIU, 42.0 MIU, 45.0 MIU, 47.0 MIU, 50.0 MIU, 52.0 MIU, or 54.0 MIU, and other such values falling within this higher dosing range; and the lower total weekly dose of Proleukin® IL-2 is about 18.0 MIU to about 39.0 MIU, including 18.0 MIU, 20.0 MIU, 23.0 MIU, 25.0 MIU, 27.0 MIU, 30.0 MIU, 32 MIU, 35.0 MIU, 37.0 MIU, or 39.0 MIU, and other such values falling within this lower dosing range.

As previously noted, the total weekly dose of IL-2 during the first and second time periods of a two-level IL-2 dosing regimen is administered as a single dose, or is partitioned into a series of equivalent doses that are administered according to a two-, three-, four-, five-, six-, or seven-times-a-week dosing schedule. Thus, for example, where the total weekly dose of Proleukin® IL-2 during the first period of the two-level IL-2 dosing regimen is 42.0 MIU, the three equivalent doses of this reference IL-2 standard to be administered during each week would be 14.0 MIU, and the two equivalent doses of this reference IL-2 standard to be administered during each week would be 21.0 MIU. Similarly, where the total weekly dose of Proleukin® IL-2 during the second period of the two-level IL-2 dosing regimen is 30.0 MIU, the three equivalent doses of this reference IL-2 standard to be administered during each week would be 10.0 MIU, and the two equivalent doses of this reference IL-2 standard to be administered during each week would be 15.0 MIU.

In accordance with the methods of the present invention, the subject is administered this two-level IL-2 dosing regimen in combination with therapeutically effective doses of the antagonist anti-CD40 antibody or antigen-binding fragment thereof, where the therapeutically effective dose of the antibody or antigen-binding fragment thereof is administered once per week, once every two weeks, once every three weeks, or once every four weeks throughout a treatment period or for a fixed duration within a treatment period. The therapeutically effective dose of anti-CD40 antibody or antigen-binding fragment thereof to be administered is in the range from about 0.003 mg/kg to about 50 mg/kg, including about 0.1 mg/kg to about 30 mg/kg. Thus, for example, in some embodiments, the therapeutically effective dose of antagonist anti-CD40 antibody or antigen-binding fragment thereof is about 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.003 mg/kg to about 50 mg/kg.

In one embodiment, therapeutically effective doses of the antagonist anti-CD40 antibody or antigen-binding fragment thereof as noted above are administered once per week, once every two weeks, once every three weeks, or once every four weeks throughout a treatment period or for a fixed duration within a treatment period, and the two-level IL-2 dosing regimen that is to be administered in combination with this antagonist anti-CD40 antibody dosing regimen has a combined duration of 4 weeks to 8 weeks, where the higher total weekly dose of Proleukin® IL-2 that is administered during the first time period of the two-level IL-2 dosing regimen is about 30.0 MIU to about 54.0 MIU, such as 30.0 MIU, 32.0 MIU, 34.0 MIU, 36.0 MIU, 38.0 MIU, 40.0 MIU, 42.0 MIU, 45.0 MIU, 47.0 MIU, 50.0 MIU, 52.0 MIU, or 54.0 MIU, and the lower total weekly dose of Proleukin® IL-2 that is administered during the second time period of the two-level IL-2 dosing regimen is about 18.0 MIU to about 39.0 MIU, such as 18.0, 20.0, 22.0, 24.0, 26.0, 28.0, 30.0 MIU, 32.0 MIU, 35.0 MIU, 37.0 MIU, or 39.0 MIU. In one such embodiment, the higher total weekly dose of Proleukin® IL-2 that is administered during the first time period of the two-level IL-2 dosing regimen is 42.0 MIU and the lower total weekly dose of Proleukin® IL-2 that is administered during the second time period of the two-level IL-2 dosing regimen is 30.0 MIU.

Thus, for example, in some embodiments, the subject undergoes concurrent therapy with weekly administration of antagonist anti-CD40 antibody or antigen-binding fragment thereof, and a two level-IL-2 dosing regimen having a combined duration of 8 weeks. For this particular embodiment, the IL-2 dosing begins on day 1 of week 2 (i.e., on day 8 following the first dosing with antagonist anti-CD40 antibody or antigen-binding fragment thereof on day 1 of this treatment period). In this manner, the total weekly dose of Proleukin® IL-2 to be administered during weeks 2-5 of the treatment period is in the range of about 30.0 MIU to about 54.0 MIU, such as 30.0 MIU, 32.0 MIU, 35.0 MIU, 37.0 MIU, 40.0 MIU, 42.0 MIU, 45.0 MIU, 47.0 MIU, 50.0 MIU, 52.0 MIU, or 54.0 MIU, or other such values falling within this higher dosing range. In this embodiment, the total weekly dose of Proleukin® IL-2 to be administered during weeks 6-9 of the treatment period is in the range of about 18.0 MIU to about 39.0 MIU, such as 18.0, 20.0, 22.0, 24.0, 26.0, 28.0, 30.0 MIU, 32.0 MIU, 35.0 MIU, 37.0 MIU, or 39.0 MIU, and other such values falling within this range. As previously noted, the total weekly dose to be administered during the first and second periods of the two-level IL-2 dosing regimen are chosen from within these ranges such that a higher total weekly dose is administered during the first period of the two-level IL-2 dosing regimen (for example, weeks 2-5 of a 9-week treatment period), and a lower total weekly dose is administered during the second period of the two-level IL-2 dosing regimen (for example, weeks 6-9 of the same 9-week treatment period). Thus, for example, where the total weekly dose of IL-2 during the first period of the two-level IL-2 dosing regimen is about 42.0 MIU to about 54.0 MIU, the total weekly dose of Proleukin® IL-2 during the second period of IL-2 dosing preferably falls within the range of about 18.0 MIU to about 39.0 MIU.

Thus, where the duration of a treatment period with concurrent therapy with weekly antagonist anti-CD40 antibody dosing and a two-level IL-2 dosing regimen is about 9 weeks, in one embodiment the total weekly dose of Proleukin® IL-2 during weeks 2-5 of the treatment period is about 30.0 MIU to about 54.0 MIU or about 30.0 MIU to about 42.0 MIU, and the total weekly dose of Proleukin® IL-2 during weeks 6-9 of this treatment period is about 18.0 MIU to about 30.0 MIU.

In one embodiment, the total weekly dose of Proleukin® IL-2 during weeks 2-5 is about 42.0 MIU, and the total weekly dose of Proleukin® IL-2 during weeks 6-9 is about 30.0 MIU. In this embodiment, each of the higher and lower total weekly doses of Proleukin® IL-2 are partitioned into two equivalent doses that are administered according to a two-times-a-week dosing schedule, where the two equivalent doses are administered to the subject within a 7-day period, allowing for a minimum of 72 hours between doses and a maximum of 96 hours between doses. In an alternative embodiment, each of the higher and lower total weekly doses of Proleukin® IL-2 are partitioned into three equivalent doses that are administered according to a three-times-a-week dosing schedule, where the three equivalent doses are administered to the subject within a 7-day period, allowing for a minimum of 25 hours between doses and a maximum of 72 hours between doses. As noted above, the therapeutically effective dose of antagonist anti-CD40 antibody or antigen-binding fragment thereof that is to be administered in combination with the two-level IL-2 dosing regimen is about 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.003 mg/kg to about 50 mg/kg, where this dose of the antagonist anti-CD40 antibody or antigen-binding fragment thereof is administered weekly, either throughout the treatment period or for a fixed duration of 4 weeks to 8 weeks within the treatment period. In an alternative embodiment, this therapeutically effective dose of the antibody or antigen-binding fragment thereof is administered once every two weeks, once every three weeks, or once every four weeks, throughout a treatment period, or is administered once every two weeks for a fixed duration of 4 weeks to 8 weeks within the treatment period, wherein the subject is also administered the two-level IL-2 dosing regimen described above.

3. Relative Versus Absolute Doses for IL-2 Dosing.

The foregoing total weekly doses of Proleukin® IL-2 are expressed in terms of MIU, which represent total amounts or absolute doses that are to be administered to a human subject on a weekly basis. The corresponding relative total weekly dose of Proleukin® IL-2 to be administered to a person to can readily be calculated. The average person has a body surface area of approximately 1.7 $m^2$. Thus, where the absolute total weekly dose of Proleukin® IL-2 to be administered is about 42.0 MIU to about 54.0 MIU, the corresponding relative total weekly dose of Proleukin® IL-2 is about 24.7 MIU/$m^2$ to about 31.8 MIU/$m^2$. Similarly, when the absolute total weekly dose is about 30.0 MIU to 42.0 MIU, the corresponding relative total weekly dose is about 17.6 MIU/$m^2$ to about 24.7 MIU/$m^2$. When the absolute total weekly dose is about 18.0 MIU to about 30.0 MIU, the corresponding relative total weekly dose is about 10.6 MIU/m$^2$ to about 17.6 MIU/m$^2$.

The international unit (IU) for IL-2 biological activity was established in 1988 by the World Health Organization (WHO) International Laboratory for Biological Standards. The IL-2 biological reference materials provided by the National Institute for Biological Standards and Control (NIBSC), which belongs to WHO, has 100 international units per ampoule of native human, Jurkat-derived IL-2. Activity of an IL-2 product can be measured against this international standard in an in vitro potency assay by HT-2 cell proliferation. Thus, for example, Proleukin® IL-2 has a biological activity of about 16.36 MIU per mg of this IL-2 product as determined by an HT-2 cell proliferation assay (see, for example, Gearing and Thorpe (1988) *J. Immunological Methods* 114:3-9; Nakanishi et al. (1984) *J. Exp. Med.* 160(6): 1605-1621). The active moiety used in this product is the recombinant human IL-2 mutein aldesleukin (referred to as des-alanyl-1, serine-125 human interleukin-2; see U.S. Pat. No. 4,931,543, herein incorporated by reference). Using this information, one can calculate the recommended therapeutically effective absolute dose of Proleukin® IL-2 in micrograms.

Hence, where the absolute total weekly dose of Proleukin® IL-2 is about 18.0 MIU to about 54.0 MIU, the corresponding absolute total weekly dose of Proleukin® IL-2 in micrograms is about 1100 μg to about 3300 μg of this product. Similarly, where the absolute total weekly dose in MIU is about 18.0 MIU to about 30.0 MIU, the corresponding absolute total weekly dose of Proleukin® IL-2 in μg is about 1100 μg to about 1834 μg. Where the absolute total weekly dose of Proleukin® IL-2 in MIU is about 30.0 MIU to about 42.0 MIU, the corresponding absolute total weekly dose in μg is about 1833 μg to about 2567 μg. Thus, given an absolute total weekly dose of Proleukin® IL-2 expressed in MIU, one of skill in the art can readily compute the corresponding absolute total weekly dose expressed in μg of this particular IL-2 product.

4. Calculation of IL-2 Doses for Different Aldesleukin Formulations.

For purposes of describing this invention, the doses of IL-2 have been presented using Proleukin® IL-2 as the reference IL-2 standard. One of skill in the art can readily determine what the corresponding doses would be for different aldesleukin formulations and routes of administration using a conversion factor based on comparative pharmacokinetic (PK) data and the serum concentration-time curve (AUC) for PK data collected during a 24-hour period for Proleukin® IL-2. Using PK data, the IL-2 exposure in human subjects that were administered a single dose of the reference IL-2 standard was determined. These subjects were selected such that they had not previously received exogenous IL-2 therapy (i.e., these subjects were naïve to IL-2 therapy). By "exogenous IL-2 therapy" is intended any intervention whereby a subject has been exposed to an exogenous source of IL-2, as opposed to exposure that occurs with the body's production of naturally occurring IL-2. Some of these subjects had received a single dose of 4.5 MIU of the reference IL-2 standard, while others had received a single dose of 7.5 or 18.0 MIU of the reference IL-2 standard.

Following administration of the single dose of the reference IL-2 standard, the IL-2 exposure in the blood serum was monitored over the first 10 to 12 hours post-injection, then extrapolated to 24 hours, and the resulting area under the serum concentration-time curve (AUC) for data collected during that 24-hour period was calculated. This area under the serum concentration-time curve is referred to herein as the $AUC_{0-24}$. Methods for measuring IL-2 exposure in this manner are well known in the art. See, for example, Gustavson (1998) *J. Biol. Response Modifiers* 1998:440-449; Thompson et al. (1987) *Cancer Research* 47:4202-4207; Kirchner et al. (1998) *Br. J. Clin. Pharmacol.* 46:5-10; Piscitelli et al. (1996) *Pharmacotherapy* 16(5):754-759; and Example 8 below. Thus, for those subjects receiving a dose of 4.5 MIU (275 μg) of Proleukin® IL-2, the $AUC_{0-24}$ value was 51 IU*hr/ml (SD=14); for those subjects receiving a dose of 7.5 MIU (458 μg) of Proleukin® IL-2, the $AUC_{0-24}$ value was 79 IU*hr/ml (SD=29); and for those subjects receiving the 18.0 MIU (1100 μg) dose of Proleukin® IL-2, the $AUC_{0-24}$ value was 344 IU*hr/ml (SD=127). When such $AUC_{0-24}$ data is determined for the reference IL-2 standard, Proleukin® IL-2, the therapeutically effective doses described herein result in an IL-2 exposure within a range from about 23 IU*hour/ml serum to about 598 IU*hour/ml serum (see Example 8 below).

The sum of individual $AUC_{0-24}$ from individual doses will comprise the total weekly $AUC_{0-24}$ in partitioned individual doses. For example, if a dose of 18 MIU is administered three-times-a-week, the individual $AUC_{0-24}$ is estimated at 344 IU*hr/ml, and the total weekly $AUC_{0-24}$ will be 1032 IU*hr/ml based on linear assumption of increased $AUC_{0-24}$ with dose as shown in the Table 1 below.

TABLE 1

$AUC_{0-24}$ values obtained after administration of Proleukin ® IL-2.

| Proleukin ® IL-2 Dose (MIU/μg) | $AUC_{0-24}$ (IU * hr/ml) |
|---|---|
| 18/1100 | 344 |
| 30/1834 | 574 |
| 42/2567 | 803 |
| 54/3300 | 1032 |

The same total weekly $AUC_{0-24}$ of 1032 IU*hr/ml could also be obtained by dosing two-times-a-week at 27 MIU or dosing five-times-a-week at about 11 MIU.

For any other aldesleukin formulation, a comparable recommended dose for use in the methods of the invention can be determined based on this $AUC_{0-24}$ data for Proleukin® IL-2. In this manner, a single dose of the aldesleukin formulation of interest is administered to a human subject, and the level of IL-2 in the serum following this initial IL-2 exposure is determined by collecting PK data and generating an $AUC_{0-24}$ for the aldesleukin formulation of interest. By "initial IL-2 exposure" is intended the subject used to measure IL-2 exposure has not previously undergone therapy with an exogenous source of IL-2 as noted above. This $AUC_{0-24}$ is then compared to the $AUC_{0-24}$ for Proleukin® IL-2 to determine a conversion factor that can be used to calculate a dose of the aldesleukin formulation of interest that is comparable to the recommended dose for Proleukin® IL-2. See, for example, the calculations for a representative monomeric IL-2 formulation, L2-7001, that are shown in Example 8 below. Thus, for any other aldesleukin formulation used in the methods of the present invention, the total weekly dose of IL-2 to be administered during a constant IL-2 dosing regimen, or during a two-level IL-2 dosing regimen, is in an amount equivalent to the recommended total weekly dose of the reference IL-2 standard, i.e., Proleukin® IL-2, as determined by the area under the serum concentration-time curve from human PK data.

5. Calculation of IL-2 Doses for Different IL-2 Molecules.

Biologically active variants of IL-2 may have altered intrinsic biological activity. See, for example, the IL-2 muteins described in the copending provisional application entitled "Improved Interleukin-2 Muteins," filed Mar. 5, 2004, and assigned U.S. Patent Application No. 60/550,868; and copending provisional application entitled "Combinatorial Interleukin-2 Muteins," filed Jul. 7, 2004, assigned U.S. Patent Application No. 60/585,980; the contents of which are herein incorporated by reference in their entirety. To estimate the dose of an IL-2 variant other than aldesleukin or the dose of native-sequence IL-2 that will be comparable to the doses of aldesleukin disclosed herein, the relative biological activity of the IL-2 variant or native-sequence IL-2 should be determined by testing its biological effect.

The relevant biological activity of an IL-2 or variant thereof according to the present invention is the ability to activate and/or achieve expansion of human NK cells to mediate lymphokine activated killer (LAK) activity and antibody-dependent cellular cytotoxicity (ADCC). Such activity is measured using a standard assay such as that disclosed in Nagler et al. (1989) *J. Immunol.* 143:3183-3191. To determine suitable doses of IL-2 variants that are not aldesleukin or suitable doses of native-sequence IL-2, a series of doses of the IL-2 molecule of interest (i.e., an IL-2 variant other than aldesleukin or native-sequence IL-2) are administered to human subjects by the same route of administration and freshly isolated PBMC (peripheral blood mononuclear cells) from the subjects are tested for NK cytoxicity against K562 cells as described, for example, by Nagler et al. (1989) supra. The NK stimulatory effect of the IL-2 molecule being tested is compared with that of the reference IL-2 standard (i.e., aldesleukin as formulated in Proleukin®) when administered in the same µg amounts by the same route of administration using the same procedure described for the IL-2 molecule being tested. Alternatively, suitable doses could be determined in vitro, using untreated human PBMC, subjected to a series of doses of the IL-2 molecule of interest. The IL-2 molecule of interest (i.e., an IL-2 variant other than aldesleukin or native-sequence IL-2) will have an NK cell stimulatory potency (i.e., activity) that is preferably at least 100% that of the same amount of the reference IL-2 standard (i.e., aldesleukin as formulated in Proleukin®), or 95%, 90%, 80%, 70%, or 60% that of the same amount of the reference IL-2 standard. The IL-2 variant should be substantially biologically active, as defined as having at least 50% of the NK stimulatory activity of the same dose of the reference IL-2 standard, administered by the same route.

Thus, where a subject is to receive combination therapy with antagonist anti-CD40 antibody and a constant IL-2 dosing regimen, the total weekly dose of any IL-2 or biologically active variant thereof is an amount equivalent to a total weekly dose of the reference IL-2 standard (i.e., aldesleukin as formulated in Proleukin®) in the range of about 1100 µg (i.e., 18.0 MIU) to about 3300 µg (i.e., about 54.0 MIU), preferably in the range of about 1100 µg to about 2567 µg (i.e., about 42.0 MIU), wherein the total weekly dose of the IL-2 or biologically active variant thereof is an amount that provides at least 50% of the NK stimulatory activity of the total weekly dose of the reference IL-2 standard (i.e., aldesleukin as formulated in Proleukin®).

In some embodiments, the total weekly dose of the IL-2 or biologically active variant thereof to be administered in the constant IL-2 dosing regimen is an amount that provides at least 60% of the NK stimulatory activity of a total weekly dose of the reference IL-2 standard administered in the range of about 1100 µg to about 3300 µg, for example, at least 60% of the NK stimulatory activity of a total weekly dose of the reference IL-2 standard administered at about 1100 µg (18.0 MIU), 1222 µg (20.0 MIU), 1345 µg (22.0 MIU), 1467 µg (24.0 MIU), 1589 µg (26.0 MIU), 1711 µg (28.0 MIU), 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU). In other embodiments, the total weekly dose of the IL-2 or biologically active variant thereof to be administered in the constant IL-2 dosing regimen is an amount that provides at least 70% of the NK stimulatory activity of a total weekly dose of the reference IL-2 standard administered in the range of about 1100 µg to about 3300 µg, for example, at least 70% of the NK stimulatory activity of a total weekly dose of the reference IL-2 standard administered at about 1100 µg (18.0 MIU), 1222 µg (20.0 MIU), 1345 µg (22.0 MIU), 1467 µg (24.0 MIU), 1589 µg (26.0 MIU), 1711 µg (28.0 MIU), 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU).

In some embodiments, the total weekly dose of the IL-2 or biologically active variant thereof to be administered in the constant IL-2 dosing regimen is an amount that provides at least 80% of the NK stimulatory activity of a total weekly dose of the reference IL-2 standard administered in the range of about 1100 µg to about 3300 µg, for example, at least 80% of the NK stimulatory activity of a total weekly dose of the reference IL-2 standard administered at about 1100 µg (18.0 MIU), 1222 µg (20.0 MIU), 1345 µg (22.0 MIU), 1467 µg (24.0 MIU), 1589 µg (26.0 MIU), 1711 µg (28.0 MIU), 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU). In alternative embodiments, the total weekly dose of the IL-2 or biologically active variant thereof to be administered in the constant IL-2 dosing regimen is an amount that provides at least 90% of the NK stimulatory activity of a total weekly dose of the reference IL-2 standard administered in the range of about 1100 µg to about 3300 µg, for example, at least 90% of the NK stimulatory activity of a total weekly dose of the reference IL-2 standard administered at about 1100 µg (18.0 MIU), 1222 µg (20.0 MIU), 1345 µg (22.0 MIU), 1467 µg (24.0 MIU), 1589 µg (26.0 MIU), 1711 µg (28.0 MIU), 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU).

In yet other embodiments, the total weekly dose of the IL-2 or biologically active variant thereof to be administered in the constant IL-2 dosing regimen is an amount that provides at least 95% of the NK stimulatory activity of a total weekly dose of the reference IL-2 standard administered in the range of about 1100 µg to about 3300 µg, for example, at least 95% of the NK stimulatory activity of a total weekly dose of the reference IL-2 standard administered at about 1100 µg (18.0 MIU), 1222 µg (20.0 MIU), 1345 µg (22.0 MIU), 1467 µg (24.0 MIU), 1589 µg (26.0 MIU), 1711 µg (28.0 MIU), 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU).

In some embodiments, the total weekly dose of the IL-2 or biologically active variant thereof to be administered in the constant IL-2 dosing regimen is an amount that provides 100% of the NK stimulatory activity of a total weekly dose of the reference IL-2 standard administered in the range of about 1100 µg to about 3300 µg, for example, 100% of the NK stimulatory activity of a total weekly dose of the reference IL-2 standard administered at about 1100 µg (18.0 MIU), 1222 µg (20.0 MIU), 1345 µg (22.0 MIU), 1467 µg (24.0 MIU), 1589 µg (26.0 MIU), 1711 µg (28.0 MIU), 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU).

In a similar manner, where a subject is to receive combination therapy with antagonist anti-CD40 antibody and a two-level IL-2 dosing regimen, the total weekly dose of any IL-2 or biologically active variant thereof to be administered during the first period or during the second period of the two-level IL-2 dosing regimen can be expressed as an amount equivalent to the total weekly dose of the IL-2 reference standard that is administered during the two-level IL-2 dosing regimen. Thus, the total weekly dose of any IL-2 or biologically active variant thereof to be administered during the first period of the two-level IL-2 dosing regimen is an amount equivalent to a total weekly dose of the reference IL-2 standard (i.e., aldesleukin as formulated in Proleukin®) in the range of about 1834 µg (i.e., 30.0 MIU) to about 3300 µg (i.e., about 54.0 MIU), wherein the total weekly dose of the IL-2 or biologically active variant thereof is an amount that provides at least 50% of the NK stimulatory activity of the total weekly dose of the reference IL-2 standard (i.e., aldesleukin as formulated in Proleukin®). Similarly, the total weekly dose of any IL-2 or biologically active variant thereof to be administered during the second period of the two-level IL-2 dosing regimen is an amount equivalent to a total weekly dose of the reference IL-2 standard (i.e., aldesleukin as formulated in Proleukin®) in the range of about 1100 µg (i.e., 18.0 MIU) to about 2384 µg (i.e., about 39.0 MIU), wherein the total weekly dose of the IL-2 or biologically active variant thereof is an amount that provides at least 50% of the NK stimulatory activity of the total weekly dose of the reference IL-2 standard (i.e., aldesleukin as formulated in Proleukin As previously noted, the total weekly dose administered during the first time period of the two-level IL-2 dosing regimen, for example, during the first half of this dosing regimen, is always higher than the total weekly dose administered during the second time period of the two-level IL-2 dosing regimen, for example, during the second half of this dosing regimen.

Thus, in some embodiments, the total weekly dose of the IL-2 or biologically active variant thereof to be administered in the first period of the two-level IL-2 dosing regimen is an amount that provides at least 60% of the NK stimulatory activity of a total weekly dose of the reference IL-2 standard administered in the range of about 1834 µg (i.e., 30.0 MIU) to about 3300 µg (i.e., about 54.0 MIU), for example, at least 60% of the NK stimulatory activity of a total weekly dose of the reference IL-2 standard administered at about 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU). For these embodiments, the total weekly dose of the IL-2 or biologically active variant thereof to be administered in the second period of the two-level IL-2 dosing regimen is an amount that provides at least 60% of the NK stimulatory activity of a total weekly dose of the reference IL-2 standard administered in the range of about 1100 µg (i.e., 18.0 MIU) to about 2384 µg (i.e., about 39.0 MIU), for example, at least 60% of the NK stimulatory activity of a total weekly dose of the reference IL-2 standard administered at about 1100 µg (18.0 MIU), 1222 µg (20.0 MIU), 1406 µg (23.0 MIU), 1528 µg (25.0 MIU), 1650 µg (27.0 MIU), 1834 µg (30.0 MIU), 1956 µg (32 MIU), 2139 µg (35.0 MIU), 2262 µg (37.0 MIU), or 2384 µg (39.0 MIU). Alternatively, the total weekly dose of the IL-2 or biologically active variant thereof to be administered in the second period of the two-level IL-2 dosing regimen is an amount that provides at least 70%, at least 80%, at least 90%, at least 95%, or even 100% of the NK stimulatory activity of a total weekly dose of the reference IL-2 standard administered in the range of about 1100 µg (i.e., 18.0 MIU) to about 2384 µg (i.e., about 39.0 MIU), for example, at least 70%, at least 80%, at least 90%, at least 95%, or even 100% of the NK stimulatory activity of a total weekly dose of the reference IL-2 standard administered at about 1100 µg (18.0 MIU), 1222 µg (20.0 MIU), 1406 µg (23.0 MIU), 1528 µg (25.0 MIU), 1650 µg (27.0 MIU), 1834 µg (30.0 MIU), 1956 µg (32 MIU), 2139 µg (35.0 MIU), 2262 µg (37.0 MIU), or 2384 µg (39.0 MIU).

In other embodiments, the total weekly dose of the IL-2 or biologically active variant thereof to be administered in the first period of the two-level IL-2 dosing regimen is an amount that provides at least 70% of the NK stimulatory activity of a total weekly dose of the reference IL-2 standard administered in the range of about 1834 µg (i.e., 30.0 MIU) to about 3300 µg (i.e., about 54.0 MIU), for example, at least 70% of the NK stimulatory activity of a total weekly dose of the reference IL-2 standard administered at about 1834 µg (30.0 MIU), 1956 µg (32.0 MIU), 2078 µg (34.0 MIU), 2200 µg (36.0 MIU), 2323 µg (38.0 MIU), 2445 µg (40.0 MIU), 2567 µg (42.0 MIU), 2689 µg (44.0 MIU), 2812 µg (46.0 MIU), 2934 µg (48.0 MIU), 3056 µg (50.0 MIU), 3178 µg (52.0 MIU), or 3300 µg (54.0 MIU). For these embodiments, the total weekly dose of the IL-2 or biologically active variant thereof to be administered in the second period of the two-level IL-2 dosing regimen is an amount that provides at least 60% of the NK stimulatory activity of a total weekly dose of the reference IL-2 standard administered in the range of about 1100 µg (i.e., 18.0 MIU) to about 2384 µg (i.e., about 39.0 MIU), for example, at least 60% of the NK stimulatory activity of a total weekly dose of the reference IL-2 standard administered at about 1100 µg (18.0 MIU), 1222 µg (20.0 MIU), 1406 µg (23.0 MIU), 1528 µg (25.0 MIU), 1650 µg (27.0 MIU), 1834 µg (30.0 MIU), 1956 µg (32 MIU), 2139 µg (35.0 MIU), 2262 µg (37.0 MIU), or 2384 µg (39.0 MIU). Alternatively, the total weekly dose of the IL-2 or biologically active variant thereof to be administered in the second period of the two-level IL-2 dosing regimen is an amount that provides at least 70%, at least 80%, at least 90%, at least 95%, or even 100% of the NK stimulatory activity of a total weekly dose of the reference IL-2 standard administered in the range of about 1100 µg (i.e., 18.0 MIU) to about 2384 µg (i.e., about 39.0 MIU), for example, at least 70%, at least 80%, at least 90%, at least 95%, or even 100% of the NK stimulatory activity of a total weekly dose of the reference IL-2 standard administered at about 1100 µg (18.0 MIU), 1222 µg (20.0 MIU), 1406 µg (23.0 MIU), 1528 µg (25.0 MIU), 1650 µg (27.0 MIU), 1834 µg (30.0 MIU), 1956 µg (32 MIU), 2139 µg (35.0 MIU), 2262 µg (37.0 MIU), or 2384 µg (39.0 MIU).

In yet other embodiments, the total weekly dose of the IL-2 or biologically active variant thereof to be administered in the first period of the two-level IL-2 dosing regimen is an amount that provides at least 80% of the NK stimulatory activity of a total weekly dose of the reference IL-2 standard administered in the range of about 1834 μg (i.e., 30.0 MIU) to about 3300 μg (i.e., about 54.0 MIU), for example, at least 80% of the NK stimulatory activity of a total weekly dose of the reference IL-2 standard administered at about 1834 μg (30.0 MIU), 1956 μg (32.0 MIU), 2078 μg (34.0 MIU), 2200 μg (36.0 MIU), 2323 μg (38.0 MIU), 2445 μg (40.0 MIU), 2567 μg (42.0 MIU), 2689 μg (44.0 MIU), 2812 μg (46.0 MIU), 2934 μg (48.0 MIU), 3056 μg (50.0 MIU), 3178 μg (52.0 MIU), or 3300 μg (54.0 MIU). For these embodiments, the total weekly dose of the IL-2 or biologically active variant thereof to be administered in the second period of the two-level IL-2 dosing regimen is an amount that provides at least 60% of the NK stimulatory activity of a total weekly dose of the reference IL-2 standard administered in the range of about 1100 μg (i.e., 18.0 MIU) to about 2384 μg (i.e., about 39.0 MIU), for example, at least 60% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU). Alternatively, the total weekly dose of the IL-2 or biologically active variant thereof to be administered in the second period of the two-level IL-2 dosing regimen is an amount that provides at least 70%, at least 80%, at least 90%, at least 95%, or even 100% of the NK stimulatory activity of a total weekly dose of the reference IL-2 standard administered in the range of about 1100 μg (i.e., 18.0 MIU) to about 2384 μg (i.e., about 39.0 MIU), for example, at least 70%, at least 80%, at least 90%, at least 95%, or even 100% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU).

In alternative embodiments, the total weekly dose of the IL-2 or biologically active variant thereof to be administered in the first period of the two-level IL-2 dosing regimen is an amount that provides at least 90% of the NK stimulatory activity of a total weekly dose of the reference IL-2 standard administered in the range of about 1834 μg (i.e., 30.0 MIU) to about 3300 μg (i.e., about 54.0 MIU), for example, at least 90% of the NK stimulatory activity of a total weekly dose of the reference IL-2 standard administered at about 1834 μg (30.0 MIU), 1956 μg (32.0 MIU), 2078 μg (34.0 MIU), 2200 μg (36.0 MIU), 2323 μg (38.0 MIU), 2445 μg (40.0 MIU), 2567 μg (42.0 MIU), 2689 μg (44.0 MIU), 2812 μg (46.0 MIU), 2934 μg (48.0 MIU), 3056 μg (50.0 MIU), 3178 μg (52.0 MIU), or 3300 μg (54.0 MIU). For these embodiments, the total weekly dose of the IL-2 or biologically active variant thereof to be administered in the second period of the two-level IL-2 dosing regimen is an amount that provides at least 60% of the NK stimulatory activity of a total weekly dose of the reference IL-2 standard administered in the range of about 1100 μg (i.e., 18.0 MIU) to about 2384 μg (i.e., about 39.0 MIU), for example, at least 60% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU). Alternatively, the total weekly dose of the IL-2 or biologically active variant thereof to be administered in the second period of the two-level IL-2 dosing regimen is an amount that provides at least 70%, at least 80%, at least 90%, at least 95%, or even 100% of the NK stimulatory activity of a total weekly dose of the reference IL-2 standard administered in the range of about 1100 μg (i.e., 18.0 MIU) to about 2384 μg (i.e., about 39.0 MIU), for example, at least 70%, at least 80%, at least 90%, at least 95%, or even 100% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU).

In still other embodiments, the total weekly dose of the IL-2 or biologically active variant thereof to be administered in the first period of the two-level IL-2 dosing regimen is an amount that provides at least 95% of the NK stimulatory activity of a total weekly dose of the reference IL-2 standard administered in the range of about 1834 μg (i.e., 30.0 MIU) to about 3300 μg (i.e., about 54.0 MIU), for example, at least 95% of the NK stimulatory activity of a total weekly dose of the reference IL-2 standard administered at about 1834 μg (30.0 MIU), 1956 μg (32.0 MIU), 2078 μg (34.0 MIU), 2200 μg (36.0 MIU), 2323 μg (38.0 MIU), 2445 μg (40.0 MIU), 2567 μg (42.0 MIU), 2689 μg (44.0 MIU), 2812 μg (46.0 MIU), 2934 μg (48.0 MIU), 3056 μg (50.0 MIU), 3178 μg (52.0 MIU), or 3300 μg (54.0 MIU). For these embodiments, the total weekly dose of the IL-2 or biologically active variant thereof to be administered in the second period of the two-level IL-2 dosing regimen is an amount that provides at least 60% of the NK stimulatory activity of a total weekly dose of the reference IL-2 standard administered in the range of about 1100 μg (i.e., 18.0 MIU) to about 2384 μg (i.e., about 39.0 MIU), for example, at least 60% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU). Alternatively, the total weekly dose of the IL-2 or biologically active variant thereof to be administered in the second period of the two-level IL-2 dosing regimen is an amount that provides at least 70%, at least 80%, at least 90%, at least 95%, or even 100% of the NK stimulatory activity of a total weekly dose of the reference IL-2 standard administered in the range of about 1100 μg (i.e., 18.0 MIU) to about 2384 μg (i.e., about 39.0 MIU), for example, at least 70%, at least 80%, at least 90%, at least 95%, or even 100% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU).

In some embodiments, the total weekly dose of the IL-2 or biologically active variant thereof to be administered in the first period of the two-level IL-2 dosing regimen is an amount that provides 100% of the NK stimulatory activity of a total weekly dose of the reference IL-2 standard administered in the range of about 1834 μg (i.e., 30.0 MIU) to about 3300 μg (i.e., about 54.0 MIU), for example, 100% of the NK stimulatory activity of a total weekly dose of the reference IL-2 standard administered at about 1834 μg (30.0 MIU), 1956 μg (32.0 MIU), 2078 μg (34.0 MIU), 2200 μg (36.0 MIU), 2323 μg (38.0 MIU), 2445 μg (40.0 MIU), 2567 μg (42.0 MIU), 2689 μg (44.0 MIU), 2812 μg (46.0 MIU), 2934 μg (48.0 MIU), 3056 μg (50.0 MIU), 3178 μg (52.0 MIU), or 3300 μg (54.0 MIU). For these embodiments, the total weekly dose of the IL-2 or biologically active variant thereof to be administered in the second period of the two-level IL-2 dosing regimen is an amount that provides at least 60% of the NK stimulatory activity of a total weekly dose of the reference IL-2 standard administered in the range of about 1100 μg (i.e., 18.0 MIU) to about 2384 μg (i.e., about 39.0 MIU), for example, at least 60% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU). Alternatively, the total weekly dose of the IL-2 or biologically active variant thereof to be administered in the second period of the two-level IL-2 dosing regimen is an amount that provides at least 70%, at least 80%, at least 90%, at least 95%, or even 100% of the NK stimulatory activity of a total weekly dose of the reference IL-2 standard administered in the range of about 1100 μg (i.e., 18.0 MIU) to about 2384 μg (i.e., about 39.0 MIU), for example, at least 70%, at least 80%, at least 90%, at least 95%, or even 100% of the NK stimulatory activity of a total weekly dose of the reference IL-2 standard administered at about 1100 μg (18.0 MIU), 1222 μg (20.0 MIU), 1406 μg (23.0 MIU), 1528 μg (25.0 MIU), 1650 μg (27.0 MIU), 1834 μg (30.0 MIU), 1956 μg (32 MIU), 2139 μg (35.0 MIU), 2262 μg (37.0 MIU), or 2384 μg (39.0 MIU).

VI. F. Additional Oncotherapy for Use with Combination IL-2/Anti-CD40 Antibody Therapy Those skilled in the art recognize that the methods of combination therapy disclosed herein may be used before, after, or concurrently with other forms of oncotherapy. Such oncotherapy can include chemotherapy regimens such as treatment with CVP (cyclophosphamide, vincristine and prednisone), CHOP (cyclophosphamide, doxorubicin, vincristine and prednisone), ICE (ifosfamide, carboplatin, and etoposide), Mitozantrone, Cytarabine, DVP (daunorubicin, prednisone, and vincristine), ATRA (all-trans-retinoic acid), Idarubicin, hoelzer chemotherapy regime, La La chemotherapy regime, ABVD (adriamycin, bleomycin, vinblastine, and dacarbazine), CEOP (cyclophosphamide, epirubicin, vincristine, and prednisone), CEOP-BE (cyclophosphamide, epirubicin, vincristine, prednisone, bleomycin, and etoposide), 2-CdA (2-chlorodeoxyadenosine (2-CDA), FLAG & IDA (fludarabine, cytarabine, and idarubicin; with or without subsequent G-CSF treatment), VAD (vincristine, doxorubicin, and dexamethasone), M & P (melphalan and prednisone), C-Weekly (cyclophosphamide and prednisone), ABCM (adriamycin (doxorubicin), BCNU, cyclophosphamide, and melphalan), MOPP (nitrogen mustard, oncovin, procarbazine, and prednisone), DHAP (dexamethasone, high-dose ara-C, and platinol), fludarabine and cyclophosphamide. Alternatively, such oncotherapies can include surgery or surgical procedures, radiation treatment, including myeloablative therapies, or other anti-cancer monoclonal antibody therapy. Thus, the methods of the invention find use as a concurrent treatment to kill residual tumor cells, either in vivo or ex vivo after such oncotherapies.

In this manner, combination therapy with IL-2 (or biologically active variant thereof) and the antagonist anti-CD40 antibodies described herein, or antigen-binding fragments thereof, can be used in combination with at least one other cancer therapy, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/1-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, and IL-12 therapy; steroid therapy; or other cancer therapy; where the additional cancer therapy is administered prior to, during, or subsequent to the IL-2/antagonist anti-CD40 antibody combination therapy. Thus, where the combined therapies comprise IL-2/antagonist anti-CD40 antibody combination therapy in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass coadministration, using separate formulations or a single pharmaceutical formulation, or and consecutive administration in either order. Where the methods of the present invention comprise combined therapeutic regimens, these therapies can be given simultaneously, i.e., the IL-2/antagonist anti-CD40 antibody combination therapy is administered concurrently or within the same time frame as the other cancer therapy (i.e., the therapies are going on concurrently, but the IL-2/antagonist anti-CD40 antibody combination therapy is not administered precisely at the same time as the other cancer therapy). Alternatively, the IL-2/antagonist anti-CD40 antibody combination therapy may also be administered prior to or subsequent to the other cancer therapy. Sequential administration of the different cancer therapies may be performed regardless of whether the treated subject responds to the first course of therapy to decrease the possibility of remission or relapse.

Thus, for example, in some embodiments, a subject undergoing the IL-2/antagonist anti-CD40 antibody combination therapy disclosed herein is also undergoing therapy with FCR (fludarabine, cyclophosphamide, and rituximab). In other embodiments, a subject undergoing the IL-2/antagonist anti-CD40 antibody combination therapy disclosed herein is also undergoing therapy with CHOP-R(CHOP plus rituximab), or CFAR (fludarabine, cyclophosphamide, rituximab, and alemtuzumab). In alternative embodiments, a subject undergoing the IL-2/antagonist anti-CD40 antibody combination therapy disclosed herein is also undergoing therapy with FC (fludarabine, cyclophosphamide) and any other anti-CD20 antibody targeting the CD20 antigen on malignant B cells, including, but not limited to, the fully human antibody HuMax-CD20, R-1594, IMMU-106, TRU-015, AME-133, tositumomab/1-131 tositumomab (Bexxar®), and ibritumomab tiuxetan (Zevalin®). In yet other embodiments, a subject undergoing the IL-2/antagonist anti-CD40 antibody combination therapy disclosed herein is also undergoing therapy with CHOP plus other anti-CD20 antibody or CFA (fludarabine, cyclophosphamide, and alemtuzumab) plus other anti-CD20 antibody, where the other anti-CD20 antibody targets the CD20 antigen on malignant B cells, including, but not limited to, the fully human antibody HuMax-CD20, R-1594, IMMU-106, TRU-015, AME-133, tositumomab/I-131 tositumomab (Bexxar®), and ibritumomab tiuxetan (Zevalin®).

VI. G. Interleukin-2 and Biologically Active Variants Thereof

1. Introduction.

The IL-2 described in the pharmaceutical formulations set forth herein and which is to be used in the methods of the invention may be native or obtained by recombinant techniques, and may be from any source, including mammalian sources such as, e.g., rat, rabbit, primate, pig, and human. When the subject undergoing treatment is a human subject, preferably the IL-2 is derived from a human source, and includes human IL-2 that is recombinantly produced, such as recombinant IL-2 polypeptides produced by microbial hosts.

Human IL-2 is initially translated as a precursor polypeptide, shown in SEQ ID NO:14, which is encoded by a nucleotide sequence such as that set forth in SEQ ID NO:13. The precursor polypeptide includes a signal sequence at residues 1-20 of SEQ ID NO:14. The term "mature human IL-2" refers to the amino acid sequence set forth as SEQ ID NO:16, which is encoded by a nucleotide sequence such as that set forth as SEQ ID NO:15. The terms "des-alanyl-1, C125S human IL-2" and "des-alanyl-1, serine-125 human IL-2" refer to a mutein of mature human IL-2 that has a substitution of serine for cysteine at amino acid position 125 of the mature human IL-2 sequence and which lacks the N-terminal alanine that resides at position 1 of the mature human IL-2 sequence (i.e., at position 1 of SEQ ID NO:16). Des-alanyl-1, C125S human IL-2 has the amino acid sequence set forth in SEQ ID NO:18, which is encoded by a nucleotide sequence such as that set forth in SEQ ID NO:17. The *E. coli* recombinantly produced des-alanyl-1, C125S human IL-2 mutein, which is referred to as "aldesleukin," is available commercially as a formulation that is marketed under the tradename Proleukin® (Chiron Corporation, Emeryville, Calif.). Proleukin® IL-2 serves as the reference IL-2 standard for determining suitable IL-2 dosing ranges for the combination IL-2/antagonist anti-CD40 antibody therapy protocols described herein.

2. Biologically Active Variants of IL-2.

The pharmaceutical compositions useful in the methods of the invention may comprise biologically active variants of IL-2. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant polypeptide will serve as a therapeutically active component in the pharmaceutical composition in a manner similar to that observed for the native polypeptide. Methods are available in the art for determining whether a variant polypeptide retains the desired biological activity, and hence serves as a therapeutically active component in the pharmaceutical composition. Biological activity can be measured using assays specifically designed for measuring activity of the native polypeptide or protein, including assays described in the present invention. Additionally, antibodies raised against a biologically active native polypeptide can be tested for their ability to bind to the variant polypeptide, where effective binding is indicative of a polypeptide having a conformation similar to that of the native polypeptide. For purposes of the present invention, the IL-2 biological activity of interest is the ability of IL-2 to activate and/or expand natural killer (NK) cells to mediate lymphokine activated killer (LAK) activity and antibody-dependent cellular cytotoxicity (ADCC). Thus, an IL-2 variant (for example, a mutein of human IL-2) for use in the methods of the present invention will activate and/or expand natural killer (NK) cells to mediate lymphokine activated killer (LAK) activity and antibody-dependent cellular cytotoxicity (ADCC). NK cells mediate spontaneous or natural cytotoxicity against certain cell targets in vitro referred to as "NK-cell sensitive" targets, such as the human erythroleukemia K562 cell line. Following activation by IL-2, NK cells acquire LAK activity. Such LAK activity can be assayed by the ability of IL-2 activated NK cells to kill a broad variety of tumor cells and other "NK-insensitive" targets, such as the Daudi B-cell lymphoma line, that are normally resistant to lysis by resting (nonactivated) NK cells. Similarly, ADCC activity can be assayed by the ability of IL-2 activated NK cells to lyse "NK-insensitive" target cells, such as Daudi B-cell lymphoma line, or other target cells not readily lysed by resting NK cells in the presence of optimal concentrations of relevant tumor cell specific antibodies. Methods for generating and measuring cytotoxic activity of NK/LAK cells and ADCC are known in the art. See for example, *Current Protocols in Immunology: Immunologic Studies in Humans*, Supplement 17, Unit 7.7, 7.18, and 7.27 (John Wiley & Sons, Inc., 1996), herein incorporated by reference. For purposes of the present invention, NK cells activated by an IL-2 variant for use in the methods of the present invention demonstrate a specific lysing activity of NK-insensitive cells in the presence (ADCC activity) or absence (LAK activity) of antibody, more particularly NK-insensitive Daudi cells in the presence of B-cell specific antibodies including rituximab, that is at least about 20% greater, or at least about 25%, or 30%, or 35%, or 40% greater than baseline lysing activity of resting NK cells (i.e., nonactivated) as measured using effector to target ratios between 12.5 to 50:1 in a standard 4-hr $^{51}$Cr-release cytotoxicity assay (see *Current Protocols in Immunology: Immunologic Studies in Humans*, Unit 7.7, Supplement 17, Section 17.18.1 (John Wiley & Sons, Inc., 1996), herein incorporated by reference. In some embodiments, the specific lysing activity of these IL-2 variant-activated NK cells is at least about 45% greater, at least about 50% greater, at least about 55% greater, at least about 60% greater, at least about 65% greater, at least about 70% greater, at least about 75% greater, or at least about 80% greater than baseline lysing activity of resting NK cells when measured as noted above.

Suitable biologically active variants of native or naturally occurring IL-2 can be fragments, analogues, and derivatives of that polypeptide. By "fragment" is intended a polypeptide consisting of only a part of the intact polypeptide sequence and structure, and can be a C-terminal deletion or N-terminal deletion of the native polypeptide. By "analogue" is intended an analogue of either the native polypeptide or of a fragment of the native polypeptide, where the analogue comprises a native polypeptide sequence and structure having one or more amino acid substitutions, insertions, or deletions. "Muteins", such as those described herein, and peptides having one or more peptoids (peptide mimics) are also encompassed by the term analogue (see International Publication No. WO 91/04282). By "derivative" is intended any suitable modification of the native polypeptide of interest, of a fragment of the native polypeptide, or of their respective analogues, such as glycosylation, phosphorylation, polymer conjugation (such as with polyethylene glycol), or other addition of foreign moieties, so long as the desired biological activity of the native polypeptide is retained. Methods for making polypeptide fragments, analogues, and derivatives are generally available in the art.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly ⇔ Ala, Val ⇔ Ile ⇔ Leu, Asp ⇔ Glu, Lys ⇔ Arg, Asn ⇔ Gln, and Phe ⇔ Trp ⇔ Tyr In constructing variants of the IL-2 polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an antagonist anti-CD40 antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Biologically active variants of IL-2 will generally have at least 70%, preferably at least 80%, more preferably about 90% to 95% or more, and most preferably at least 96%, 97%, 98% or 99% sequence identity to the amino acid sequence of the reference polypeptide molecule, which serves as the basis for comparison. Thus, where the IL-2 reference molecule is human IL-2, a biologically active variant thereof will have at least 70%, preferably at least 80%, more preferably about 90% to 95% or more, and most preferably at least 96%, 97%, 98% or 99% sequence identity to the amino acid sequence for human IL-2.

For purposes of the present invention, percent sequence identity between amino acid sequences is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference IL-2 sequence by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, 100 or more amino acid residues. Corrections for sequence identity associated with conservative residue substitutions or gaps can be made (see Smith-Waterman homology search algorithm).

The precise chemical structure of a polypeptide having IL-2 activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides having IL-2 activity as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an IL-2 polypeptide used herein so long as the IL-2 activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of IL-2 polypeptides of interest as used herein.

The art provides substantial guidance regarding the preparation and use of polypeptide variants. In preparing the IL-2 variants, one of skill in the art can readily determine which modifications to the native protein nucleotide or amino acid sequence will result in a variant that is suitable for use as a therapeutically active component of a pharmaceutical composition used in the methods of the present invention.

For examples of variant IL-2 proteins, see European Patent (EP) Publication No. EP 136,489 (which discloses one or more of the following alterations in the amino acid sequence of naturally occurring IL-2: Asn26 to Gln26; Trp121 to Phe121; Cys58 to Ser58 or Ala58, Cys105 to Ser105 or Ala105; Cys125 to Ser125 or Ala125; deletion of all residues following Arg 120; and the Met-1 forms thereof); and the recombinant IL-2 muteins described in European Patent Application No. 83306221.9, filed Oct. 13, 1983 (published May 30, 1984 under Publication No. EP 109,748), which is the equivalent to Belgian Patent No. 893,016, and commonly owned U.S. Pat. No. 4,518,584 (which disclose recombinant human IL-2 mutein wherein the cysteine at position 125, numbered in accordance with native human IL-2, is deleted or replaced by a neutral amino acid; alanyl-ser125-IL-2; and des-alanayl-ser125-IL-2). See also U.S. Pat. No. 4,752,585 (which discloses the following variant IL-2 proteins: ala104 ser125 IL-2, ala104 IL-2, ala104 ala125 IL-2, val104 ser125 IL-2, val104 IL-2, val104 ala125 IL-2, des-ala1 ala104 ser125 IL-2, des-ala1 ala104 IL-2, des-ala1 ala104 ala125 IL-2, des-ala1 val104 ser125 IL-2, des-ala1 val104 IL-2, des-ala1 val104 ala125 IL-2, des-ala1 des-pro2 ala104 ser125 IL-2, des-ala1 des-pro2 ala104 IL-2, des-ala1 des-pro2 ala104 ala125 IL-2, des-ala1 des-pro2 val104 ser125 IL-2, des-ala1 des-pro2 val104 IL-2, des-ala1 des-pro2 val104 ala125 IL-2, des-ala1 des-pro2 des-thr3 ala104 ser125 IL-2, des-ala1 des-pro2 des-thr3 ala104 IL-2, des-ala1 des-pro2 des-thr3 ala104 ala125 IL-2, des-ala1 des-pro2 des-thr3 val104 ser125 IL-2, des-ala1 des-pro2 des-thr3 val104 IL-2, des-ala1 des-pro2 des-thr3 val104 ala125 IL-2, des-ala1 des-pro2 des-thr3 des-ser4 ala104 ser125 IL-2, des-ala1 des-pro2 des-thr3 des-ser4 ala104 IL-2, des-ala1 des-pro2 des-thr3 des-ser4 ala104 ala125 IL-2, des-ala1 des-pro2 des-thr3 des-ser4 val104 ser125 IL-2, des-ala1 des-pro2 des-thr3 des-ser4 val104 IL-2, des-ala1 des-pro2 des-thr3 des-ser4 val104 ala125 IL-2, des-ala1 des-pro2 des-thr3 des-ser4 des-ser5 ala104 ser125 IL-2, des-ala1 des-pro2 des-thr3 des-ser4 des-ser5 ala104 IL-2, des-ala1 des-pro2 des-thr3 des-ser4 des-ser5 ala104 ala125 IL-2, des-ala1 des-pro2 des-thr3 des-ser4 des-ser5 val104 ser125 IL-2, des-ala1 des-pro2 des-thr3 des-ser4 des-ser5 val 104 IL-2, des-ala1 des-pro2 des-thr3 des-ser4 des-ser5 val104 ala125 IL-2, des-ala1 des-pro2 des-thr3 des-ser4 des-ser5 des-ser6 ala104 ala125 IL-2, des-ala1 des-pro2 des-thr3 des-ser4 des-ser5 des-ser6 ala104 IL-2, des-ala1 des-pro2 des-thr3 des-ser4 des-ser5 des-ser6 ala104 ser125 IL-2, des-ala1 des-pro2 des-thr3 des-ser4 des-ser5 des-ser6 val104 ser125 IL-2, des-ala1 des-pro2 des-thr3 des-ser4 des-ser5 des-ser6 val104 IL-2, and des-ala1 des-pro2 des-thr3 des-ser4 des-ser5 des-ser6 val104 ala125 IL-2) and U.S. Pat. No. 4,931,543 (which discloses the IL-2 mutein des-alanyl-1, serine-125 human IL-2 used in the examples herein, as well as the other IL-2 muteins).

Also see European Patent Publication No. EP 200,280 (published Dec. 10, 1986), which discloses recombinant IL-2 muteins wherein the methionine at position 104 has been replaced by a conservative amino acid. Examples include the following muteins: ser4 des-ser5 ala104 IL-2; des-ala1 des-pro2 des-thr3 des-ser4 des-ser5 ala104 ala125 IL-2; des-ala1 des-pro2 des-thr3 des-ser4 des-ser5 glu104 ser125 IL-2; des-ala1 des-pro2 des-thr3 des-ser4 des-ser5 glu104 IL-2; des-ala1 des-pro2 des-thr3 des-ser4 des-ser5 glu104 ala125 IL-2; des-ala1 des-pro2 des-thr3 des-ser4 des-ser5 des-ser6 ala104 ala125 IL-2; des-ala1 des-pro2 des-thr3 des-ser4 des-ser5 des-ser6 ala104 IL-2; des-ala1 des-pro2 des-thr3 des-ser4 des-ser5 des-ser6 ala104 ser125 IL-2; des-ala1 des-pro2 des-thr3 des-ser4 des-ser5 des-ser6 glu104 ser125 IL-2; des-ala1 des-pro2 des-thr3 des-ser4 des-ser5 des-ser6 glu104 IL-2; and des-ala1 des-pro2 des-thr3 des-ser4 des-ser5 des-ser6 glu104 ala125 IL-2. See also European Patent Publication No. EP 118,617 and U.S. Pat. No. 5,700,913, which disclose unglycosylated human IL-2 variants bearing alanine instead of native IL-2's methionine as the N-terminal amino acid; an unglycosylated human IL-2 with the initial methionine deleted such that proline is the N-terminal amino acid; and an unglycosylated human IL-2 with an alanine inserted between the N-terminal methionine and proline amino acids.

Other IL-2 muteins include the those disclosed in WO 99/60128 (substitutions of the aspartate at position 20 with histidine or isoleucine, the asparagine at position 88 with arginine, glycine, or isoleucine, or the glutamine at position 126 with leucine or gulatamic acid), which reportedly have selective activity for high affinity IL-2 receptors expressed by cells expressing T cell receptors in preference to NK cells and reduced IL-2 toxicity; the muteins disclosed in U.S. Pat. No. 5,229,109 (substitutions of arginine at position 38 with alanine, or substitutions of phenylalanine at position 42 with lysine), which exhibit reduced binding to the high affinity IL-2 receptor when compared to native IL-2 while maintaining the ability to stimulate LAK cells; the muteins disclosed in International Publication No. WO 00/58456 (altering or deleting a naturally occurring (x)D(y) sequence in native IL-2 where D is aspartic acid, (x) is leucine, isoleucine, glycine, or valine, and (y) is valine, leucine or serine), which are claimed to reduce vascular leak syndrome; the IL-2 p 1-30 peptide disclosed in International Publication No. WO 00/04048 (corresponding to the first 30 amino acids of IL-2, which contains the entire a-helix A of IL-2 and interacts with the b chain of the IL-2 receptor), which reportedly stimulates NK cells and induction of LAK cells; and a mutant form of the IL-2 p1-30 peptide also disclosed in WO 00/04048 (substitution of aspartic acid at position 20 with lysine), which reportedly is unable to induce vascular bleeds but remains capable of generating LAK cells. Additionally, IL-2 can be modified with polyethylene glycol to provide enhanced solubility and an altered pharmokinetic profile (see U.S. Pat. No. 4,766,106).

Also see the IL-2 muteins described in the copending provisional application entitled "Improved Interleukin-2 Muteins," filed Mar. 5, 2004, and assigned U.S. Patent Application No. 60/550,868; and copending provisional application entitled "Combinatorial Interleukin-2 Muteins," filed Jul. 7, 2004, assigned U.S. Patent Application No. 60/585,980; the contents of which are herein incorporated by reference in their entirety. These applications disclose muteins of IL-2 that have improved functional profiles predictive of reduced toxicities. The muteins induce a lower level of pro-inflammatory cytokine production by NK cells while maintaining or increasing NK cell proliferation, maintaining NK-cell-mediated NK, LAK, and ADCC cytolytic functions, and maintaining T cell proliferative function as compared to the desalanyl-1, C125S human IL-2 or C125S human IL-2 muteins. Examples of these improved IL-2 muteins include, but are not limited to, T7A, L36G, P65E, R81L, T7D, L36H, P65F, R81M, T7R, L36I, P65G, R81N, K8L, L36K, P65H, R81P, K9A, L36M, P65I, R81T, K9D, L36N, P65K, D84R, K9R, L36P, P65L, S87T, K9S, L36R, P65N, N88D, K9V, L36S, P65Q, N88H, K9W, L36W, P65R, N88T, T10K, L36Y, P65S, V91A, T10N, R38D, P65T, V91D, Q11A, R38G, P65V, V91E, Q11R, R38N, P65W, V91F, Q11T, R38P, P65Y, V91G, E15A, R38S, L66A, V91Q, H16D, L40D, L66F, V91W, H16E, L40G, E67A, V91N, L19D, L40N, L72G, L94A, L19E, L40S, L72N, L94I, D20E, T41E, L72T, L94T, 124L, T41G, F78S, L94V, K32A, F42A, F78W, L94Y, K32W, F42E, H79F, E95D, N33E, F42R, H79M, E95G, P34E, F42T, H79N, E95M, P34R, F42V, H79P, T102S, P34S, K43H, H79Q, T102V, P34T, F44K, H79S, M104G, P34V, M46I, H79V, E106K, K35D, E61K, L80E, Y107H, K35I, E61M, L80F, Y107K, K35L, E61R, L80G, Y107L, K35M, E62T, L80K, Y107Q, K35N, E62Y, L80N, Y107R, K35P, K64D, L80R, Y107T, K35Q, K64E, L80T, E116G, K35T, K64G, L80V, N119Q, L36A, K64L, L80W, T123S, L36D, K64Q, L80Y, T123C, L36E, K64R, R81E, Q126I, L36F, P65D, R81K, and Q126V, where residue position is relative to the position within the mature human IL-2 sequence set forth in SEQ ID NO:16. Examples of these combinatorial IL-2 muteins include, but are not limited to, 19D40D, 19D81K, 36D42R, 36D61R, 36D65L, 40D36D, 40D61R, 40D65Y, 40D72N, 40D80K, 40G36D, 40G65Y, 80K36D, 80K65Y, 81K36D, 81K42E, 81K61R, 81K65Y, 81K72N, 81K88D, 81K91D, 81K107H, 81L107H, 91N95G, 107H36D, 107H42E, 107H65Y, 107R36D, 107R72N, 40D81K107H, 40G81K107H, and 91N94Y95G, where residue position is relative to the position within the mature human IL-2 sequence set forth in SEQ ID NO:16.

The term IL-2 as used herein is also intended to include IL-2 fusions or conjugates comprising IL-2 fused to a second protein or covalently conjugated to polyproline or a water-soluble polymer to reduce dosing frequencies or to improve IL-2 tolerability. For example, the IL-2 (or a variant thereof as defined herein) can be fused to human albumin or an albumin fragment using methods known in the art (see WO 01/79258). Alternatively, the IL-2 can be covalently conjugated to polyproline or polyethylene glycol homopolymers and polyoxyethylated polyols, wherein the homopolymer is unsubstituted or substituted at one end with an alkyl group and the poplyol is unsubstituted, using methods known in the art (see, for example, U.S. Pat. Nos. 4,766,106, 5,206,344, and 4,894,226).

3. Pharmaceutical Formulations of IL-2 or Variant Thereof.

Any pharmaceutical composition comprising IL-2 or suitable biologically active variant thereof as the therapeutically active component can be used in the methods of the invention. Such pharmaceutical compositions are known in the art and include, but are not limited to, those disclosed in U.S. Pat. Nos. 4,604,377; 4,745,180; 4,766,106; 4,816,440; 4,894,226; 4,931,544; 4,992,271; 5,078,997; and 6,525,102; herein incorporated by reference. Thus liquid, lyophilized, or spray-dried compositions comprising IL-2 or variants thereof that are known in the art may be prepared as an aqueous or non-aqueous solution or suspension for subsequent administration to a subject in accordance with the methods of the invention. Each of these compositions will comprise IL-2 or variants thereof as a therapeutically or prophylactically active component. By "therapeutically or prophylactically active component" is intended the IL-2 or variants thereof is specifically incorporated into the composition to bring about a desired therapeutic or prophylactic response with regard to treatment, prevention, or diagnosis of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

For example, U.S. Pat. No. 4,604,377 shows an IL-2 formulation that has a therapeutic amount of IL-2, which is substantially free from non-IL-2 protein and endotoxin, a physiologically acceptable water-soluble carrier, and a sufficient amount of a surface active agent to solubilize the IL-2, such as sodium dodecyl sulfate. Other ingredients can be included, such as sugars. U.S. Pat. No. 4,766,106 shows formulations including polyethylene glycol (PEG) modified IL-2. European patent application, Publication No. 268,110, shows IL-2 formulated with various non-ionic surfactants selected from the group consisting of polyoxyethylene sorbitan fatty acid esters (Tween-80), polyethylene glycol monostearate, and octylphenoxy polyethoxy ethanol compounds (Triton X405). U.S. Pat. No. 4,992,271 discloses IL-2 formulations comprising human serum albumin and U.S. Pat. No. 5,078,997 discloses IL-2 formulations comprising human serum albumin and amino acids. U.S. Pat. No. 6,525,102 discloses IL-2 formulations comprising an amino acid base, which serves as the primary stabilizing agent of the polypeptide, and an acid and/or its salt form to buffer the solution within an acceptable pH range for stability of the polypeptide. Copending U.S. patent application Ser. No. 10/408,648 discloses IL-2 formulations suitable for pulmonary delivery. All of the above patents and patent applications are hereby incorporated by reference in their entireties.

VI. H. Anti-CD40 Antibodies for Use in Combination IL-2/Antagonist Anti-CD40 Antibody Therapy Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674,492; 5,874,082; 5,677,165; 6,056,959; WO 00/63395; International Publication Nos. WO 02/28905 and WO 02/28904; Gordon et al. (1988) *J. Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J. Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference. Of particular interest to the present invention are the antagonist anti-CD40 antibodies disclosed herein that share the binding characteristics of the monoclonal antibodies CHIR-5.9 and CHIR-12.12, as described above and elsewhere herein in Chapter I. These monoclonal antibodies, which can be recombinantly produced, are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety.

Any of these antagonist anti-CD40 antibodies or antibody fragments thereof may be conjugated (e.g., labeled or conjugated to a therapeutic moiety or to a second antibody), as described herein above in Chapter I, prior to use in these methods for treating a cancer in a human patient, where the cancer expresses the CD40 antigen. Furthermore, suitable biologically variants of the antagonist anti-CD40 antibodies described elsewhere herein can be used in the methods of the present invention. Such variants, including those described herein above in Chapter I, will retain the desired binding properties of the parent antagonist anti-CD40 antibody. Methods for making antibody variants are generally available in the art; see, for example, the methods described herein above in Chapter I.

The antagonist anti-CD40 antibodies of this invention are administered at a concentration that is therapeutically effective to prevent or treat the B cell-related cancer of interest. To accomplish this goal, the antibodies may be formulated using a variety of acceptable excipients known in the art, as noted herein above in Chapter I. Typically, the antibodies are administered by injection, either intravenously, intraperitoneally, or subcutaneously. Methods to accomplish this administration are known to those of ordinary skill in the art, and include those methods described hereinabove in Chapter I. It may also be possible to obtain compositions that may be topically or orally administered, or which may be capable of transmission across mucous membranes. Intravenous administration occurs preferably by infusion over a period of time, as described herein above in Chapter I. Possible routes of administration, preparation of suitable formulations, therapeutically effective amounts to be administered, and suitable dosing regimens are as described herein above in Chapter I. See also commonly owned International Application No. PCT/US2004/036958, filed Nov. 4, 2004 and published as WO 2005/044294, which corresponds to copending U.S. National-Phase application Ser. No. 10/578,590, each entitled "Methods of Therapy for Cancers Expressing the CD40 Antigen"; the contents of each of which are herein incorporated by reference in their entirety.

VI. I. Use of Antagonist Anti-CD40 Antibodies and IL-2 in the Manufacture of Medicaments for Combination Therapy for Cancers Expression the CD40 Antigen The present invention also provides for the use of an antagonist anti-CD40 antibody or antigen-binding fragment thereof in the manufacture of a medicament for treating a CD40-expressing cancer in a subject, wherein the medicament is coordinated with treatment with IL-2 or biologically active variant thereof. By "CD40-expressing cancer" is intended any cancer that comprises neoplastic cells expressing the CD40 cell surface antigen. As noted herein above, such cancers include, but are not limited to, B cell-related cancers, for example, non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, myeloblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, and mantle cell lymphoma; and solid tumors expressing the CD40 antigen, including, but not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), and skin cancers such as melanoma, and sarcomas (including, for example, osteosarcomas and Ewing's sarcomas).

By "coordinated" is intended the medicament comprising the antagonist anti-CD40 antibody or antigen-binding fragment thereof is to be used either prior to, during, or after treatment of the subject with IL-2 or biologically active variant thereof. In one such embodiment, the present invention provides for the use of the monoclonal antibody CHIR-12.12 or CHIR-5.9 in the manufacture of a medicament for treating a CD40-expressing cancer in a subject, wherein the medicament is coordinated with treatment with IL-2 or biologically active variant thereof, for example, human IL-2 or the desalanyl-1, serine-125 human IL-2 mutein, wherein the medicament is to be used either prior to, during, or after treatment of the subject with IL-2 or biologically active variant thereof.

In some embodiments, the medicament comprising the antagonist anti-CD40 antibody, for example, the monoclonal antibody CHIR-12.12 or CHIR-5.9 disclosed herein, or antigen-binding fragment thereof is coordinated with treatment with IL-2 or biologically active variant thereof and at least one other type of cancer therapy. Examples of other cancer therapies include, but are not limited to, those described herein above, i.e., surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/1-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, IL-12 therapy, IL-15 therapy, and IL-21 therapy; steroid therapy; or other cancer therapy; where treatment with the IL-2 or biologically active variant thereof and the additional cancer therapy, or additional cancer therapies, occurs prior to, during, or subsequent to treatment of the subject with the medicament comprising the antagonist anti-CD40 antibody or antigen-binding fragment thereof, as noted herein above. Where the medicament comprising the antagonist anti-CD40 antibody or antigen-binding fragment thereof is coordinated with IL-2 or biologically active variant thereof and at least one other cancer therapy, use of the medicament can be prior to, during, or after treatment of the subject with either or both of the other cancer therapies.

The present invention also provides for the use of a synergistic combination of an antagonist anti-CD40 antibody or antigen-binding fragment thereof in the manufacture of a medicament for treating a CD40-expressing cancer in a subject, as defined herein above, wherein the medicament is coordinated with treatment with IL-2 or biologically active variant thereof. By "synergistic combination" is intended the medicament comprises an amount of the antagonist anti-CD40 antibody or antigen-binding fragment thereof that provides for a synergistic therapeutic effect when the medicament is coordinated with treatment with IL-2 or biologically active variant thereof in the manner set forth herein above. "Synergistic therapeutic effect" refers to a therapeutic effect observed with a combination of two or more therapies (in this case, the antagonist anti-CD40 antibody therapy and IL-2 therapy) wherein the therapeutic effect (as measured by any of a number of parameters, including the measures of efficacy described herein above) is greater than the sum of the respective individual therapeutic effects observed with the respective individual therapies.

In one such embodiment, the present invention provides for the use of a synergistic combination of the monoclonal antibody CHIR-12.12 or CHIR-5.9 in the manufacture of a medicament for treating a CD40-expressing cancer in a subject, wherein the medicament is coordinated with treatment with IL-2 or biologically active variant thereof, for example, human IL-2 or the des-alanyl-1, serine-125 human IL-2 mutein, wherein the medicament is to be used either prior to, during, or after treatment of the subject with IL-2 or biologically active variant thereof. In some embodiments, the medicament comprising the synergistic combination of the antagonist anti-CD40 antibody, for example, the monoclonal antibody CHIR-12.12 or CHIR-5.9 disclosed herein, or antigen-binding fragment thereof is coordinated with treatment with IL-2 or biologically active variant thereof and at least one other type of cancer therapy as noted herein above.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating a CD40-expressing cancer in a subject, as defined herein above, wherein the medicament is used in a subject that has been pretreated with IL-2 or biologically active variant thereof. By "pretreated" or "pretreatment" is intended the subject has received IL-2 therapy (i.e., been treated with IL-2 or biologically active variant thereof) prior to receiving the medicament comprising the antagonist anti-CD40 antibody or antigen-binding fragment thereof. "Pretreated" or "pretreatment" includes subjects that have been treated with IL-2 or biologically active variant thereof, alone or in combination with other cancer therapies, within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior IL-2 therapy, or prior IL-2 and other cancer therapies. Thus, the subject that receives the medicament comprising the antagonist anti-CD40 antibody or antigen-binding fragment thereof could have responded, or could have failed to respond, to pretreatment with the prior IL-2 therapy, or to one or more of the prior cancer therapies where pretreatment comprised multiple cancer therapies one of which was IL-2 therapy, for example, IL-2 therapy and other anti-cancer antibody therapy, for example, rituximab or other anti-CD20 antibody therapy; IL-2 therapy and surgery; IL-2 therapy and chemotherapy; or IL-2 therapy, chemotherapy, and other anticancer antibody therapy.

Thus, in some embodiments, the invention provides for the use of an antagonist anti-CD40 antibody, for example the monoclonal antibody CHIR-12.12 or CHIR-5.9 disclosed herein, or antigen-binding fragment thereof in the manufacture of a medicament that is used in a subject in need of treatment for a CD40-expressing cancer defined herein above, where the subject has been pretreated with IL-2 therapy, or has been pretreated with IL-2 therapy and one or more of the following other cancer therapies: surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anticancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/1-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, IL-12 therapy, IL-15 therapy, and IL-21 therapy; steroid therapy; or other cancer therapy.

The present invention also provides for the use of IL-2 or biologically active variant thereof in the manufacture of a medicament for treating a CD40-expressing cancer in a subject, as defined herein above, wherein the medicament is coordinated with treatment with an antagonist anti-CD40 antibody or antigen binding fragment thereof. In these embodiments, "coordinated" is intended the medicament comprising the IL-2 or biologically active variant thereof is to be used either prior to, during, or after treatment of the subject with the antagonist anti-CD40 antibody or antigen-binding fragment thereof. In one such embodiment, the present invention provides for the use of IL-2 or biologically active variant thereof, for example, human IL-2 or the des-alanyl-1, serine-125 human IL-2 mutein, in the manufacture of a medicament for treating a CD40-expressing cancer in a subject, wherein the medicament is coordinated with treatment with the monoclonal antibody CHIR-12.12 or CHIR-5.9, wherein the medicament is to be used either prior to, during, or after treatment of the subject with the monoclonal antibody CHIR-12.12 or CHIR-5.9.

In some embodiments, the medicament comprising the IL-2 or biologically active variant thereof is coordinated with treatment with an antagonist anti-CD40 antibody, for example, the monoclonal antibody CHIR-12.12 or CHIR-5.9 or antigen-binding fragment thereof, and at least one other type of cancer therapy. Examples of other cancer therapies include, but are not limited to, those described herein above, i.e., surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/1-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; other anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, IL-12 therapy, IL-15 therapy, and IL-21 therapy; steroid therapy; or other cancer therapy; where treatment with the antagonist anti-CD40 antibody or antigen-binding fragment thereof and the additional cancer therapy, or additional cancer therapies, occurs prior to, during, or subsequent to treatment of the subject with the medicament comprising the IL-2 or variant thereof, as noted herein above. Where the medicament comprising the IL-2 or biologically active variant thereof is coordinated with treatment with the antagonist anti-CD40 antibody or antigen-binding fragment thereof and at least one other cancer therapy, use of the medicament can be prior to, during, or after treatment of the subject with either or both of the other cancer therapies.

The following examples for this invention are offered by way of illustration and not by way of limitation.

VI. J. EXPERIMENTAL

The antagonist anti-CD40 antibodies used in the examples below are 5.9 and CHIR-12.12, described in Chapter I above, and in commonly owned International Application No. PCT/US2004/036958, filed Nov. 4, 2004 and published as WO 2005/044294, which corresponds to copending U.S. National-Phase application Ser. No. 10/578,590; the contents of each of which are herein incorporated by reference in their entirety.

Example 1

Combination Treatment with CHIR-12.12 and IL-2 Shows Additive Anti-Tumor Activity in Animal Models The CHIR-12.12 mAb is expected to produce desired pharmacological effects to reduce tumor burden by either/both of two anti-tumor mechanisms, blockade of proliferation/survival signal and induction of ADCC. The currently available human lymphoma xenograft models use long-term lymphoma cell lines that, in contrast to primary cancer cells, do not depend on CD40 stimulation for their growth and survival. Therefore, the component of these mAbs' anti-tumor activity based on blocking the tumor proliferation/survival signal is not expected to contribute to anti-tumor efficacy in these models. The efficacy in these models is dependent on the ADCC, the second anti-tumor mechanism associated with the CHIR-12.12 mAb.

Combination treatment with CHIR-12.12 mAb and IL-2 were evaluated in a staged human NHL Namalwa xenograft model. To ensure consistent tumor growth, T cell-deficient nude mice were whole-body irradiated at 3 Gy to further suppress the immune system one day before tumor inoculation. Tumor cells were inoculated subcutaneously in the right flank at $5 \times 10^6$ cells per mouse. Treatment was initiated when tumor volume reached about 100-200 mm$^3$ (about 7 days after tumor inoculation). Tumor-bearing mice were treated as follows: (1) IgG1 at 10 mg/kg, intraperitoneally, once a week for 4 weeks; (2) CHIR-12.12 mAb at 1 mg/kg, intraperitoneally, once a week for 4 weeks; (3) IL-2 at 0.5 mg/kg, subcutaneously, daily for 8 days; (4) IL-2 at 0.5 mg/kg, subcutaneously, daily for 8 days+CHIR-12.12 mAb at 1 mg/kg, intraperitoneally, once a week for 4 weeks, and (5) IL-2 at 0.5 mg/kg, subcutaneously, daily for 8 days+CHIR-12.12 mAb at 10 mg/kg, intraperitoneally, once a week for 4 weeks. Tumor volumes were recorded twice a week. Data were analyzed using ANOVA.

Figure 25:
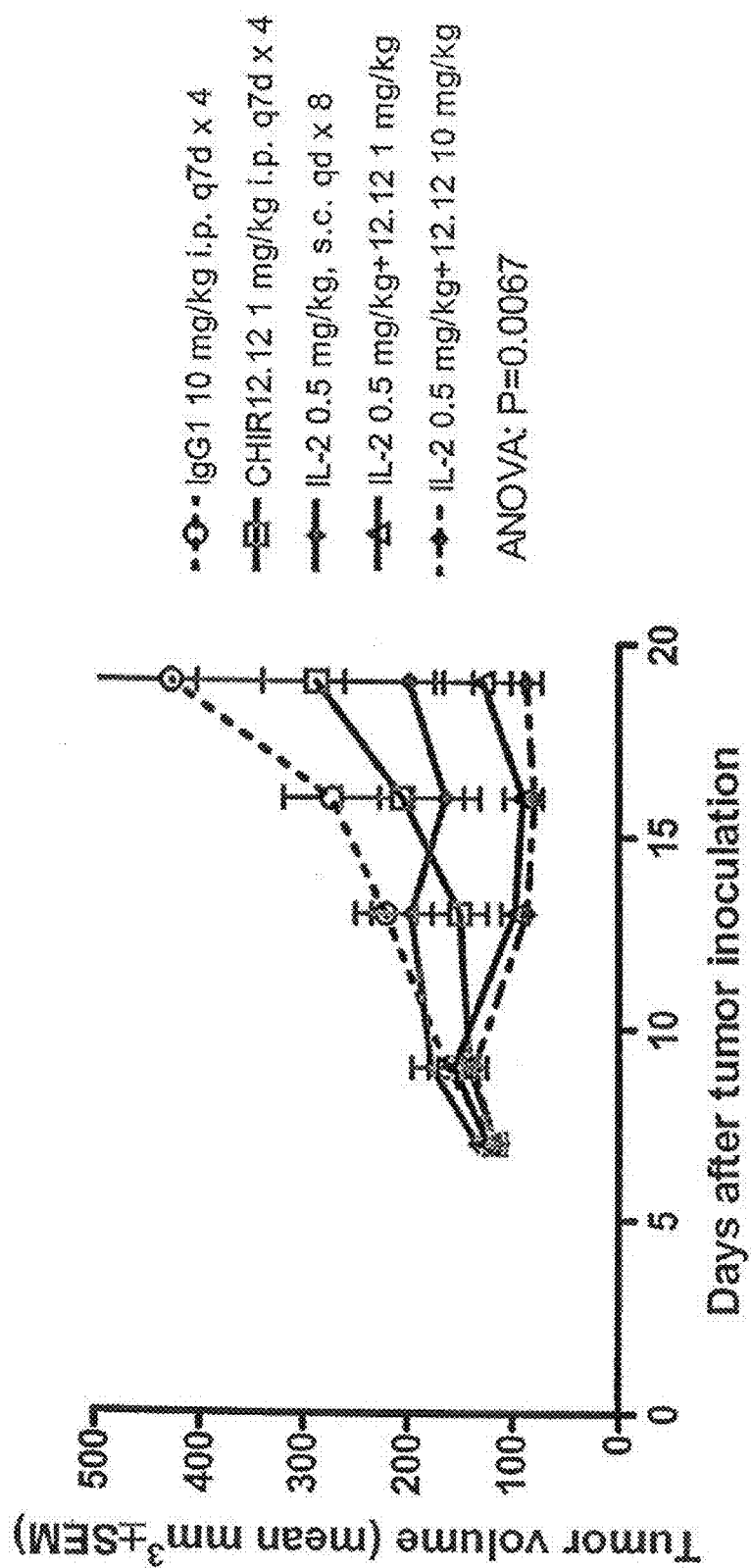
FIG. 25 demonstrates enhanced in vivo anti-tumor activity of combination treatment with the monoclonal antibody CHIR-12.12 and IL-2 using a human non-Hodgkin's lymphoma (NHL) Namalwa xenograft model.

CHIR-12.12 and IL-2 alone both inhibited the growth of Namalwa tumors (N=10 mice/group). The combination of CHIR-12.12 and IL-2 resulted in additive anti-tumor activity (FIG. 25).

Example 2

Clinical Studies with IL-2 and Antagonisitic Anti-CD40 Antibodies

Clinical Objectives

The overall objective is to provide an effective therapy for CD40-expressing solid tumors and B-cell related cancers by targeting them with a combination of an antagonist anti-CD40 antibody and IL-2 or biologically active variant thereof. These tumors include solid tumors such as urinary bladder carcinoma, breast carcinoma, prostate cancer, renal cell carcinoma, nasopharyngeal carcinoma, squamous cell carcinoma, thyroid papillary carcinoma, melanoma, ovarian carcinoma, lung carcinoma, cervical carcinoma, gastric carcinoma, liver carcinoma, and sarcomas. B-cell related cancers include, but are not limited to, B cell lymphoma, chronic lymphocytic lyphoma (CLL), acute lymphoblastic leukemia (ALL), multiple myeloma (MM), Waldenstrom's Macroglobulinemia, and Systemic Castleman's Disease. The signal for these diseases is determined in phase II although some measure of activity may be obtained in phase I. The initial antagonist anti-CD40 antibody is the mAb CHIR-12.12, and the initial IL-2 product Proleukin®, which contains the recombinantly produced IL-2 mutein des-alanyl-1, serine-125 human IL-2.

Phase I
Evaluate safety and pharmacokinetics—dose escalation of these two oncotherapies in malignancies.
Choose dose of each oncotherapy based on safety, tolerability, and change in serum markers of respective targets, i.e., CD40. In general an MTD for each of these antibodies when used in combination is sought but other indications of efficacy (depletion of CD40$^+$, etc.) may be adequate for dose finding.
Consideration of more than one combination of doses especially for different indications, e.g., the CLL combination dose may be different than that for NHL. Thus, some dose finding may be necessary in phase II.
Patients are dosed weekly with real-time pharmacokinetic (Pk) sampling. Initially a 4-week cycle is the maximum dosing allowed. The Pk may be highly variable depending on the disease studied, density of CD40, etc.
This trial(s) is open to subjects with CD40$^+$ solid tumors and B-cell lymphoma, CLL, and potentially other malignancies.
Decision to discontinue or continue studies is based on safety, dose, and preliminary evidence of anti-tumor activity, particularly synergistic in nature.
Activity of combination therapy as determined by response rate is determined in Phase II.
Identify combination dose(s) for Phase II.

Phase II
Several trials will be initiated in the above-mentioned tumor types with concentration on solid tumors and B-cell lymphoma, CLL, and Multiple Myeloma (MM). Separate trials may be required in low grade and intermediate/high grade NHL as CD40 may have a different function depending on the grade of lymphoma. More than one combination of doses, and more than one schedule may be tested in a randomized phase II setting.
In each disease, target a population that has failed current standard of care:
CLL: patients who were resistant to Campath® and chemotherapy.
Low grade NHL: Rituxan® or CHOP-R failures
Intermediate NHL: CHOP-R failures
Multiple Myeloma: Chemotherapy failures, dexamethazone plus thalidomide failures, or high-dose chemotherapy plus stem cell transplant failures
Decision to discontinue or continue with study is based on proof of therapeutic concept in Phase II
Determine whether surrogate marker can be used as early indication of clinical efficacy
Identify doses for Phase III Phase III
Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.

Example 3

Calculation IL-2 Serum Concentration-Time Curves for Pharmaceutical Formulations of IL-2

The area under the serum concentration-time curve (AUC) of Proleukin® IL-2 administered subcutaneously (SC) at 4.5 million international units (MIU) (equivalent to approximately 275 µg protein) was determined using data from an unpublished HIV study. Serum concentration time profiles were measured in 8 IL-2 naïve, HIV patients following an initial exposure to IL-2 dosing in this study. For each patient, the AUC was calculated using the linear trapezoidal rule up to the last measurable concentrations and extrapolated to 24 hours (Winnonlin software version 3.1, Pharsight Corporation, California). The average $AUC_{0-24}$, SD, and the lower and upper 95% confidence limits at 4.5 MIU dose are presented in Table 11.

The $AUC_{0-24}$ value of Proleukin® IL-2 administered SC at doses equivalent to 18 MIU (1100 µg) was estimated using data from three different studies where this IL-2 product was administered SC. Two are published studies, one in HIV patients (N=3) (Piscitelli et al. (1996) *Pharmacotherapy* 16(5):754-759) and one in cancer patients (N=7) (Kirchner et al. (1998) *Br. J. Clin. Pharmacol.* 46:5-10). The third is an unpublished study in which serum concentration time data were available from 6 cancer patients after SC doses of IL-2. The similarity of the AUC in cancer and HIV patients was previously established (unpublished data). The actual doses administered in these three studies ranged between 18 and 34 MIU. For the two published trials, the AUC up to 24 hours ($AUC_{0-24}$) values were normalized to 18 MIU dose by multiplying the AUC with the quotient of 18 and actual dose in MIU. For example, if the $AUC_{0-24}$ for a 20 MIU dose was calculated to be 400, the normalized $AUC_{0-24}$ would be 400*18/20=360. For the unpublished cancer-patient study, individual AUC values were calculated from the serum concentration time data using the linear trapezoidal rule up to the last measurable concentrations and extrapolated to 24 hours (Winnonlin software version 3.1, Pharsight Corporation, California) then were normalized to 18 MIU dose as noted above. The overall mean and SD for all three studies was calculated as the weighted average of the means and variances, respectively, using equations 1 and 2.

$$\bar{X}_P = \frac{(n_1 \bar{X}_1 + n_2 \bar{X}_2 + n_3 \bar{X}_3)}{(n_1 + n_2 + n_3)}. \quad 1$$

$$SD_P = \sqrt{\frac{(n_1 - 1)s_1^2 + (n_2 - 1)s_2^2 + (n_3 - 1)s_3^2}{(n_1 + n_2 + n_3 - 3)}}. \quad 2$$

Where $n_1, n_2, n_3, \bar{X}_1, \bar{X}_2, \bar{X}_3$ and $s_1^2, s_2^2, s_3^2$ are the number of subjects, means, and variances for each of the three studies, respectively. $\bar{X}_P$ and $SD_P$ are estimates of the overall mean and standard deviation. The overall average AUC, SD, and the lower and upper 95% confidence limits at 18 MIU are also presented in Table 1.

TABLE 1

Average (±SD) $AUC_{0-24}$ obtained after initial exposure to a single dose administration of Proleukin ® IL-2 administered subcutaneously.

| Proleukin ® IL-2 Dose (MIU/µg) | $AUC_{0-24}$ (IU * hr/ml) | SD | LL of 95% CI[1] | UL of 95% CI[1] |
|---|---|---|---|---|
| 4.5/275 | 51 | 14 | 23 | 78 |
| 6.0/367[2] | 65 | | 22 | 107 |
| 7.5/458 | 79 | 29 | 21 | 137 |
| 18/1100 | 344 | 127 | 90 | 598 |

[1]Upper (UL) and lower (LL) limits of the 95% confidence intervals (CI). 95% CI were calculated as the mean ±2 SD.
[2]Values for 6.0 MIU are estimated based on actual values for 4.5 MIU and 7.5 MIU.

Similar to Proleukin®IL-2, L2-7001, a liquid formulation of monomeric IL-2, was administered to HIV patients at doses ranging from 50 to 180 µg (unpublished data). The exposures obtained from this study as measured by AUC are shown in Table 2. These exposure values were within the range of the exposure values generated using Proleukin® IL-2 (Table 1).

TABLE 2

Average (±SD) $AUC_{0-24}$ obtained after an initial exposure to a single dose administration of the monomeric IL-2 formulation L2-7001.

| L2-7001 Dose (MIU/µg) | $AUC_{0-24}$ (IU * hr/ml) | SD |
|---|---|---|
| 0.82/50 | 60 | 11 |
| 1.5/90 | 110 | 36 |
| 2.2/135 | 143 | 41 |
| 2.9/180 | 275 | 99 |

The IL-2 exposure data (AUC) was obtained from the published literature where recombinant human native IL-2 was administered SC to 8 cancer patients at doses ranging from 0.1 MU to 3.0 MU. The reported average (% CV) AUCs for the 0.3, 1, and 3 MU dose levels were 120 (38), 177 (36), and 359 (46) U*hr/ml (Gustavson (1998) *J. Biol. Response Modifiers* 1998:440-449). As indicated in Thompson et al. (1987) *Cancer Research* 47:4202-4207, the units measured in this study were normalized to BRMP units (Rossio et al. (1986) *Lymphokine Research* 5 (suppl 1):S13-S18), which was adopted later as international units (IU) by WHO (Gearing and Thorpe (1988) *J. Immunological Methods* 114:3-9). The AUC values generated under the study conditions also agree well with the established Proleukin® IL-2 exposure.

Chapter VII: Use of Antagonist Anti-CD40 Antibodies for Treatment of Autoimmune and Inflammatory Diseases and Organ Transplant Rejection VII. A. Overview This invention is directed to methods for treating human subjects having autoimmune diseases and/or inflammatory diseases, as described herein below in sections II.B-II.F and in commonly owned International Application No. PCT/US2004/036957, filed Nov. 4, 2004 and published as WO 2005/044306, which corresponds to copending U.S. National-Phase application Ser. No. 10/576,943, all of which are entitled "Use of Antagonist Anti-CD40 Monocolonal Antibodies for Treatment of Autoimmune and Inflammatory Diseases and Organ Transplant Rejection"; the contents of each of which are herein incorporated by reference in their entirety. The methods involve treatment with an anti-CD40 antibody described herein, or an antigen-binding fragment thereof, where administration of the antibody or antigen-binding fragment thereof promotes a positive therapeutic response within the subject undergoing this method of therapy for an autoimmune disease and/or an inflammatory disease.

These methods are especially useful in treating diseases that include, but are not limited to, autoimmune diseases such as systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hashimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, and the like. Additionally, these antagonist anti-CD40 antibodies and antigen-binding fragments thereof are especially useful in treating diseases associated with inflammation, including, but not limited to, type 1, 2, 3, and 4 delayed-type hypersensitivity, allergy or allergic disorders, unwanted/unintended immune responses to therapeutic proteins (see for example, U.S. Patent Application No. US 2002/0119151 and Koren, et al. (2002) *Curr. Pharm. Biotechnol.* 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like.

VII. B. Anti-CD40 Antibodies for Use in Treating Autoimmune Diseases and/or Inflammatory Diseases Anti-CD40 antibodies suitable for use in the methods of the invention specifically bind a human CD40 antigen expressed on the surface of a human cell and are free of significant agonist activity, but exhibit antagonist activity when bound to the CD40 antigen on a human CD40-expressing cell. These anti-CD40 antibodies and antigen-binding fragments thereof are referred to herein as "antagonist anti-CD40 antibodies." Such antibodies include, but are not limited to, the fully human monoclonal antibodies 5.9 and CHIR-12.12, and monoclonal antibodies having the binding characteristics of monoclonal antibodies 5.9 and CHIR-12.12, as described herein above in Chapter I. These monoclonal antibodies, which can be recombinantly produced, are also disclosed in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety.

Antibodies that have the binding characteristics of monoclonal antibodies CHIR-5.9 and CHIR-12.12 include antibodies that competitively interfere with binding CD40 and/or bind the same epitopes as CHIR-5.9 and CHIR-12.12. One of skill in the art could determine whether an antibody competitively interferes with CHIR-5.9 or CHIR-12.12 using standard methods known in the art.

When these antibodies bind CD40 displayed on the surface of human cells, such as, for example, human B cells, T cells, dendritic cells, endothelial cells, activated platelets, inflamed vascular smooth muscle cells, eosinophils, synovial membranes, dermal fibroblasts, and the like, the antibodies are free of significant agonist activity. In some embodiments, their binding to CD40 displayed on the surface of human cells results in inhibition of activation and differentiation of these human cells. Thus, the antagonist anti-CD40 antibodies suitable for use in the methods of the invention include those monoclonal antibodies that can exhibit antagonist activity toward normal and abnormal human cells expressing the cell-surface CD40 antigen.

By "agonist activity" is intended that the substance functions as an agonist. An agonist combines with a receptor on a cell and initiates a reaction or activity that is similar to or the same as that initiated by the receptor's natural ligand. For example, an agonist of CD40 induces any or all of, but not limited to, the following responses: cell proliferation and/or differentiation; upregulation of intercellular adhesion via such molecules as ICAM-1, E-selectin, VCAM, and the like; secretion of pro-inflammatory cytokines such as IL-1, IL-6, IL-8, IL-12, TNF, and the like; signal transduction through the CD40 receptor by such pathways as TRAF (e.g., TRAF2 and/or TRAF3), MAP kinases such as NIK (NF-κB inducing kinase), 1-kappa B kinases (IKK α/β), transcription factor NF-κB, Ras and the MEK/ERK pathway, the PI3K/Akt pathway, the P38 MAPK pathway, and the like; transduction of an anti-apoptotic signal by such molecules as XIAP, Mcl-1, BCLx, and the like; B and/or T cell memory generation; B cell antibody production; B cell isotype switching, up-regulation of cell-surface expression of MHC Class II and CD80/86, and the like. By "antagonist activity" is intended that the substance functions as an antagonist. For example, an antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring anti-CD40 antibody and CD40-ligand binding specificity and antagonist activity are known to one of skill in the art and include, but are not limited to, standard competitive binding assays, assays for monitoring immunoglobulin secretion by B cells, B cell proliferation assays, Banchereau-Like-B cell proliferation assays, T cell helper assays for antibody production, co-stimulation of B cell proliferation assays, and assays for up-regulation of B cell activation markers. See, for example, such assays disclosed in WO 00/75348, U.S. Pat. No. 6,087,329, and copending provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, the contents of each of which are herein incorporated by reference in their entirety.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in a bioassay such as a B cell response assay. Preferably, "significant" agonist activity is an agonist activity that is at least 2-fold greater or at least 3-fold greater than the agonist activity induced by a neutral substance or negative control as measured in a bioassay such as a B cell response assay. Thus, for example, where a B cell response is of interest a B cell proliferation assay is used, and "significant" agonist activity would be induction of a level of B cell proliferation that is at least 2-fold greater or at least 3-fold greater than the level of B cell proliferation induced by a neutral substance or negative control. In one embodiment, a non-specific immunoglobulin, for example IgG1, that does not bind to CD40 serves as the negative control. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in a bioassay such as a B cell response assay. The antagonist anti-CD40 antibodies useful in the methods of the present invention are free of significant agonist activity as noted above when bound to a CD40 antigen on a human cell. In one embodiment of the invention, the antagonist anti-CD40 antibody is free of significant agonist activity in one cellular response. In another embodiment of the invention, the antagonist anti-CD40 antibody is free of significant agonist activity in assays of more than one cellular response (e.g., proliferation and differentiation, or proliferation, differentiation, and, for B cells, antibody production).

As used herein "anti-CD40 antibody" encompasses any antibody that specifically recognizes the CD40 antigen, including polyclonal antibodies, monoclonal antibodies, single-chain antibodies, and fragments thereof such as Fab, F(ab')$_2$, F$_v$, and other fragments which retain the antigen binding function of the parent anti-CD40 antibody. Of particular interest to the methods of the present invention are antagonist anti-CD40 antibodies that share the binding characteristics of the monoclonal antibodies CHIR-5.9 and CHIR-12.12 described above.

Thus, in addition to the monoclonal antibodies CHIR-5.9 and CHIR-12.12, other antibodies that would be useful in practicing the methods of the invention described herein in Chapter VII include, but are not limited to, the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen. Those skilled in the art recognize that the antagonist anti-CD40 antibodies and antigen-binding fragments of these antibodies suitable for use in the methods disclosed herein include antagonist anti-CD40 antibodies and antigen-binding fragments thereof that are produced recombinantly using methods well known in the art and described herein below, and include, for example, monoclonal antibodies CHIR-5.9 and CHIR-12.12 that have been recombinantly produced.

Any of these antagonist anti-CD40 antibodies or antibody fragments thereof may be conjugated (e.g., labeled or conjugated to a therapeutic moiety or to a second antibody), as described herein above in Chapter I, prior to use in these methods for treating an autoimmune disease and/or inflammatory disease in a human patient. Furthermore, suitable biologically variants of the antagonist anti-CD40 antibodies described elsewhere herein can be used in the methods of the present invention. Such variants, including those described herein above in Chapter I, will retain the desired binding properties of the parent antagonist anti-CD40 antibody. Methods for making antibody variants are generally available in the art; see, for example, the methods described herein above in Chapter I.

The anti-CD40 antibodies useful in the practice of this invention can have one or many mechanisms of action. An antibody produced by any of the methods described above, or any other method not disclosed herein, will fall within the scope of the invention if it possesses at least one of the following biological activities in vitro and/or in vivo: inhibition of immunoglobulin secretion by normal human peripheral B cells stimulated by T cells; inhibition of survival and/or proliferation of normal human peripheral B cells stimulated by CD40L-expressing cells or soluble CD40 ligand (sCD40L); inhibition of survival and/or proliferation of normal human peripheral B cells stimulated by Jurkat T cells; inhibition of "survival" anti-apoptotic intracellular signals in any cell stimulated by sCD40L or solid-phase CD40L; and, inhibition of CD40 signal transduction in any cell upon ligation with sCD40L or solid-phase CD40L, deletion, anergy and/or tolerance induction of CD40-bearing target cells or cells bearing cognate ligands to CD40 including, but not limited to, T cells and B cells, induction of expansion or activation of CD4$^+$ CD25$^+$ regulatory T cells (see for example, donor alloantigen-specific tissue rejection via CD40-CD40L interference, van Maurik et al. (2002) *J. Immunol.* 169:5401-5404), cytotoxicity via any mechanism (including, but not limited to, antibody-dependent cell-mediated cytotoxicity (ADCC), complement-dependent cytotoxicity (CDC), down-regulation of proliferation, and/or apoptosis in target cells), modulation of target cell cytokine secretion and/or cell surface molecule expression, and combinations thereof. Assays for such biological activities can be performed as described herein above in Chapter I, and in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565, 710, respectively, and in International Application No. PCT/US2004/037152, filed Nov. 4, 2004 and published as WO 2005/044854, which corresponds to copending U.S. National-Phase patent application Ser. No. 10/577,390; the contents of each of which are herein incorporated by reference in their entirety. See also commonly owned International Application No. PCT/US2004/036957, filed Nov. 4, 2004 and published as WO 2005/044306, which corresponds to copending U.S. National-Phase application Ser. No. 10/576, 943, all of which are entitled "Use of Antagonist Anti-CD40 Monocolonal Antibodies for Treatment of Autoimmune and Inflammatory Diseases and Organ Transplant Rejection"; the contents of each of which are herein incorporated by reference in their entirety.

See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12;

Kwekkeboom et al. (1993) *Immunology* 79:439-444; and U.S. Pat. Nos. 5,674,492 and 5,847,082; herein incorporated by reference.

VII. C. Methods of Therapy for Treating Autoimmune Diseases and/or Inflammatory Diseases The methods of this invention are directed to the use of antagonist anti-CD40 antibodies to treat subjects (i.e., patients) having an autoimmune disease and/or inflammatory disease, or a predisposition to developing an autoimmune disease and/or inflammatory disease, wherein the disease and/or inflammation is mediated by CD40 ligand-mediated CD40 signaling on cells expressing the CD40 antigen. By the term "CD40-expressing cell," it is intended cells that express the CD40 antigen. Methods for detecting CD40 expression in cells are well known in the art and include, but are not limited to, PCR techniques, immunohistochemistry, flow cytometry, Western blot, ELISA, and the like.

The methods of the invention are especially useful for treating inflammatory and/or autoimmune diseases wherein CD40L-mediated CD40 stimulation is involved. The compositions of the invention may be administered prophylactically or therapeutically or a combination thereof.

Inflammatory diseases are characterized by inflammation and tissue destruction, or a combination thereof. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens.

Further, for purposes of the present invention, the term "inflammatory disease(s)" includes "autoimmune disease(s) ." As used herein, the term "autoimmunity" is generally understood to encompass inflammatory immune-mediated processes involving "self" antigens. In autoimmune diseases, self antigen(s) trigger host immune responses.

Also, the present invention includes treatment of inflammation associated with tissue transplant rejection. "Transplant rejection" or "graft rejection" refers to any host-mounted immune response against a graft including but not limited to HLA antigens, blood group antigens, and the like.

The invention can also be used to treat graft versus host disease, such as that associated with bone marrow transplantation, for example. In such graft versus host disease, the donor bone marrow includes lymphocytes and cells that mature into lymphocytes. The donor's lymphocytes recognize the recipient's antigens as non-self and mount an inflammatory immune response. Hence, as used herein, "graft versus host disease" or "graft versus host reaction" refers to any T cell mediated immune response in which donor lymphocytes react to the host's antigens.

The antagonist anti-CD40 antibodies and antigen-binding fragments thereof described herein can be used in accordance with the methods of the invention to treat autoimmune and/or inflammatory disorders including, but not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example, U.S. Patent Application No. US 2002/0119151 and Koren, et al. (2002) *Curr. Pharm. Biotechnol.* 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like. In some other embodiments, the antagonistic anti-CD40 antibodies of the invention are useful in treating pulmonary inflammation including but not limited to lung graft rejection, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow and/or lung transplantation or other causes, graft atherosclerosis/graft phlebosclerosis, as well as pulmonary fibrosis resulting from collagen, vascular, and autoimmune diseases such as rheumatoid arthritis and lupus erythematosus.

"Treatment" is herein defined as the application or administration of an antagonist anti-CD40 antibody or antigen-binding fragment thereof to a subject, or application or administration of an antagonist anti-CD40 antibody or antigen-binding fragment thereof to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease. By "treatment" is also intended the application or administration of a pharmaceutical composition comprising an antagonist anti-CD40 antibodies or antigen-binding fragment thereof to a subject, or application or administration of a pharmaceutical composition comprising an antagonist anti-CD40 antibody or antigen-binding fragment thereof to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease.

By "anti-inflammatory activity" is intended a reduction or prevention of inflammation. Therapy with at least one antagonist anti-CD40 antibody (or antigen-binding fragment thereof) as defined elsewhere herein causes a physiological response that is beneficial with respect to treatment of an autoimmune disease and/or inflammatory disease, where the disease involves cells expressing the CD40 antigen. It is recognized that the methods of the invention may be useful in preventing phenotypic change in cells such as proliferation, activation, and the like.

In accordance with the methods of the present invention, at least one antagonist anti-CD40 antibody (or antigen-binding fragment thereof) as defined elsewhere herein is used to promote a positive therapeutic response with respect to treatment or prevention of an autoimmune disease and/or inflammatory disease. By "positive therapeutic response" with respect to an autoimmune disease and/or inflammatory disease is intended an improvement in the disease in association with the anti-inflammatory activity of these antibodies or antigen-binding fragments thereof, and/or an improvement in the symptoms associated with the disease. That is, an anti-proliferative effect, the prevention of further proliferation of the CD40-expressing cell, a reduction in the inflammatory response including but not limited to reduced secretion of inflammatory cytokines, adhesion molecules, proteases, immunoglobulins (in instances where the CD40 bearing cell is a B cell), combinations thereof, and the like, increased production of anti-inflammatory proteins, a reduction in the number of autoreactive cells, an increase in immune tolerance, inhibition of autoreactive cell survival, and/or a decrease in one or more symptoms mediated by stimulation of CD40-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomography (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the antagonist anti-CD40 antibody or antigen-binding fragment thereof may experience the beneficial effect of an improvement in the symptoms associated with the disease.

By "therapeutically effective dose or amount" or "effective amount" is intended an amount of antagonist anti-CD40 antibody or antigen-binding fragment thereof that, when administered brings about a positive therapeutic response with respect to treatment of a subject with an autoimmune disease and/or inflammatory disease. In some embodiments of the invention, a therapeutically effective dose of the anti-CD40 antibody or fragment thereof is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody or antigen-binding fragment thereof.

A further embodiment of the invention is the use of antagonist anti-CD40 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

The antagonist anti-CD40 antibodies and suitable antigen-binding fragments thereof can be used in combination with any known therapies for autoimmune and inflammatory diseases, including any agent or combination of agents that are known to be useful, or which have been used or are currently in use, for treatment of autoimmune and inflammatory diseases. Such therapies and therapeutic agents include, but are not limited to, surgery or surgical procedures (e.g. splenectomy, lymphadenectomy, thyroidectomy, plasmaphoresis, leukophoresis, cell, tissue, or organ transplantation, intestinal procedures, organ perfusion, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy, and the like. In this manner, the antagonist anti-CD40 antibodies described herein, or antigen-binding fragments thereof, are administered in combination with at least one other therapy, including, but not limited to, surgery, organ perfusion, radiation therapy, steroid therapy, non-steroidal therapy, antibiotic therapy, antifungal therapy, hormone therapy, cytokine therapy, therapy with dermatological agents (for example, topical agents used to treat skin conditions such as allergies, contact dermatitis, and psoriasis), immunosuppressive therapy, other anti-inflammatory monoclonal antibody therapy, combinations thereof, and the like. Thus, where the combined therapies comprise administration of an antagonist anti-CD40 antibody or antigen-binding fragment thereof in combination with administration of another therapeutic agent, as with steroids as one example, the methods of the invention encompass coadministration, using separate formulations or a single pharmaceutical formulation, and consecutive administration in either order.

Where the methods of the present invention comprise combined therapeutic regimens, these therapies can be given simultaneously, i.e., the antagonist anti-CD40 antibody or antigen-binding fragment thereof is administered concurrently or within the same time frame as the other therapy (i.e., the therapies are going on concurrently, but the anti-CD40 antibody or antigen-binding fragment thereof is not administered precisely at the same time as the other therapy). Alternatively, the antagonist anti-CD40 antibody of the present invention or antigen-binding fragment thereof may also be administered prior to or subsequent to the other therapy. Sequential administration of the different therapies may be performed regardless of whether the treated subject responds to the first course of therapy to decrease the possibility of remission or relapse.

In some embodiments of the invention, the antagonist anti-CD40 antibodies described herein, or antigen-binding fragments thereof, are administered in combination with immunosuppressive drugs or anti-inflammatory drugs, wherein the antibody and the therapeutic agent(s) may be administered sequentially, in either order, or simultaneously (i.e., concurrently or within the same time frame). Examples of suitable immunosuppressive drugs that can be administered in combination with the antagonistic anti-CD40 antibodies of the invention include, but are not limited to, methotrexate, cyclophosphamide, mizoribine, chlorambucil, cyclosporine, such as, for example, aerosolized cyclosporine (see, U.S. Patent Application Publication No. US20020006901, herein incorporated by reference in its entirety), tacrolimus (FK506; Pro-Graf™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA4 antibodies and Ig fusions, anti-B lymphocyte stimulator antibodies (e.g., LYMPHOSTAT-B™) and Ig fusions (BLyS-Ig), anti-CD80 antibodies and etanercept (Enbrel®), as well as anti-T cell antibodies such as anti-CD3 (OKT3), anti-CD4, and the like. Examples of suitable anti-inflammatory agents include, but are not limited to, corticosteroids such as, for example, clobetasol, halobetasol, hydrocortisone, triamcinolone, betamethasone, fluocinole, fluocinonide, prednisone, prednisolone, methylprednisolone; non-steroidal anti-inflammatory drugs (NSAIDs) such as, for example, sulfasalazine, medications containing mesalamine (known as 5-ASA agents), celecoxib, diclofenac, etodolac, fenprofen, flurbiprofen, ibuprofen, ketoprofen, meclofamate, meloxicam, nabumetone, naproxen, oxaprozin, piroxicam, rofecoxib, salicylates, sulindac, and tolmetin; anti-inflammatory antibodies such as adalimumab (HUMIRA®, a TNF-α antagonist) and infliximab (Remicade®, a TNF-α antagonist), and the like.

Transplant rejection and graft versus host disease can be hyperacute (humoral), acute (T cell mediated), or chronic (unknown etiology), or a combination thereof. Thus, the antagonistic anti-CD40 antibodies of the invention are used in some embodiments to prevent and/or ameliorate rejection and/or symptoms associated with hyperacute, acute, and/or chronic transplant rejection of any tissue, including, but not limited to, liver, kidney, pancreas, pancreatic islet cells, small intestine, lung, heart, corneas, skin, blood vessels, bone, heterologous or autologous bone marrow, and the like. Graft tissues may be obtained from any donor and transplanted into any recipient host, and thus the transplant procedure may comprise transplanting animal tissue to humans (e.g., xenografts), transplanting tissue from one human to another human (e.g., allografts), and/or transplanting tissue from one part of a human's body to another (e.g., autografts). Treatment with the antibodies of the invention may also reduce transplantation sequelae such as fever, anorexia, hemodynamic abnormalities, leukopenia, white cell infiltration of the transplanted organ/tissue, as well as opportunistic infections.

In some embodiments, the antagonistic anti-CD40 antibodies of the invention may be used alone or in combination with immunosuppressive drugs to treat and/or prevent transplant rejection such as hyperacute, acute, and/or chronic rejection and/or graft versus host disease. Thus, in some embodiments where the antagonistic anti-CD40 antibodies of the invention are used to treat graft rejection, the antibodies may used in combination with suitable immunosuppressive drugs, including, but not limited, to methotrexate; cyclophosphamide; mizoribine; chlorambucil; cyclosporine, such as, for example, aerosolized cyclosporine (see, U.S. Patent Application Publication No. US20020006901, herein incorporated by reference in its entirety), tacrolimus (FK506; Pro-Graf™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD80 antibodies and etanercept (Enbrel®), as well as anti-T cell antibodies such as anti-CD3 (OKT3), anti-CD4, and the like.

As such, it is specifically contemplated that the compositions and methods of the invention are used in combination with other drugs to further improve symptoms and outcomes in transplant recipients, such as those receiving lung grafts, for example. Thus, in some embodiments, the antagonistic anti-CD40 antibodies of the invention are used to treat transplant rejection (such as, for example hyperacute, acute, and/or chronic rejection or graft versus host disease in lung transplant recipients) alone or in combination with parenterally and/or non-parenterally administered cyclosporine, including for example oral cyclosporine, injectable cyclosporine, aerosolized (e.g., inhaled) cyclosporine, and combinations thereof. In some embodiments where at least a component of the therapy is aerosolized cyclosporine, the cyclosporine is delivered to the lung of the recipient by inhalation of cyclosporine in aerosol spray form using, for example, a pressurized delivery device or nebulizer. The cyclosporine may be administered in either dry powder or wet form.

In some other embodiments, the antagonistic anti-CD40 antibodies of the invention may be used alone or in combination with immunosuppressive drugs to treat and/or prevent rheumatoid arthritis. Thus in some embodiments where the antagonistic anti-CD40 antibodies of the invention are used to treat rheumatoid arthritis, the antibodies may used in combination with suitable immunosuppressive drugs, including, but not limited to, methotrexate, cyclophosphamide, mizoribine, chlorambucil, cyclosporine, tacrolimus (FK506; PROGRAF™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD20 antibodies (e.g. RITUXAN®); the fully human antibody HuMax-CD20, R-1594, IMMU-106, TRU-015, AME-133, tositumomab/I-131, tositumomab (Bexxar®), ibritumomab tituxetan (Zevalin®); anti-CD80 antibodies, and etanercept (ENBREL®), as well as anti-T cell antibodies such as anti-CD3 (OKT3), anti-CD4, and the like. As discussed above, treatment effectiveness may be assessed using any means and includes, but is not limited to, effectiveness as measured by clinical responses defined by the American College of Rheumatology criteria, the European League of Rheumatism criteria, or any other criteria. See for example, Felson et al. (1995) *Arthritis. Rheum.* 38:727-35 and van Gestel et al. (1996) *Arthritis Rheum.* 39:34-40.

In yet other embodiments, the antagonistic anti-CD40 antibodies of the invention may be used alone or in combination with immunosuppressive drugs to treat and/or prevent multiple sclerosis. Thus in some embodiments where the antagonistic anti-CD40 antibodies of the invention are used to treat multiple sclerosis, the antibodies may used in combination with suitable immunosuppressive drugs, including, but not limited to, methotrexate, cyclophosphamide, mizoribine, chlorambucil, cyclosporine, tacrolimus (FK506; PROGRAF™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD20 antibodies (e.g., RITUXAN®); the fully human antibody HuMax-CD20, R-1594, IMMU-106, TRU-015, AME-133, tositumomab/1-131, tositumomab (Bexxar®), ibritumomab tituxetan (Zevalin®); anti-CD80 antibodies, and etanercept (ENBREL®), as well as anti-T cell antibodies such as anti-CD3 (OKT3), anti-CD4, and the like.

VII. D. Pharmaceutical Formulations and Modes of Administration

The antagonist anti-CD40 antibodies of this invention are administered at a concentration that is therapeutically effective to prevent or treat autoimmune diseases and/or inflammatory diseases. To accomplish this goal, the antibodies may be formulated using a variety of acceptable excipients known in the art, as noted herein above in Chapter I. Typically, the antibodies are administered by injection, for example, either intravenously, intraperitoneally, or subcutaneously. Methods to accomplish this administration are known to those of ordinary skill in the art, and include those methods described hereinabove in Chapter I. It may also be possible to obtain compositions that may be topically or orally administered, or which may be capable of transmission across mucous membranes. Intravenous administration occurs preferably by infusion over a period of time, as described herein above in Chapter I. Possible routes of administration, preparation of suitable formulations, therapeutically effective amounts to be administered, and suitable dosing regimens are as described herein above in Chapter I. See also commonly owned International Application No. PCT/US2004/036957, filed Nov. 4, 2004 and published as WO 2005/044306, which corresponds to copending U.S. National-Phase application Ser. No. 10/576,943, all of which are entitled "Use of Antagonist Anti-CD40 Monocolonal Antibodies for Treatment of Autoimmune and Inflammatory Diseases and Organ Transplant Rejection"; the contents of each of which are herein incorporated by reference in their entirety.

VII. E. Use of Antagonist Anti-CD40 Antibodies in the Manufacture of Medicaments for Treating Autoimmune Diseases and/or Inflammatory Diseases The present invention also provides for the use of an antagonist anti-CD40 antibody or antigen-binding fragment thereof in the manufacture of a medicament for treating an autoimmune disease and/or inflammatory disease in a subject, wherein the medicament is coordinated with treatment with at least one other therapy. By "coordinated" is intended the medicament is to be used either prior to, during, or after treatment of the subject with at least one other therapy. Examples of other therapies include, but are not limited to, those described herein above, i.e., surgery or surgical procedures (e.g. splenectomy, lymphadenectomy, thyroidectomy, plasmaphoresis, leukophoresis, cell, tissue, or organ transplantation, organ perfusion, intestinal procedures, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy, and the like, where treatment with the additional therapy, or additional therapies, occurs prior to, during, or subsequent to treatment of the subject with the medicament comprising the antagonist anti-CD40 antibody or antigen-binding fragment thereof, as noted herein above. In one such embodiment, the present invention provides for the use of the monoclonal antibody CHIR-12.12 or CHIR-5.9 in the manufacture of a medicament for treating an autoimmune disease and/or inflammatory disease in a subject, wherein the medicament is coordinated with treatment with at least one other therapy as noted herein above.

In some embodiments, the medicament comprising the antagonist anti-CD40 antibody, for example, the monoclonal antibody CHIR-12.12 or CHIR-5.9 disclosed herein, or antigen-binding fragment thereof is coordinated with treatment with two other therapies. Where the medicament comprising the antagonist anti-CD40 antibody is coordinated with two other therapies, use of the medicament can be prior to, during, or after treatment of the subject with either or both of the other therapies.

The invention also provides for the use of an antagonist anti-CD40 antibody, for example, the monoclonal antibody CHIR-12.12 or CHIR-5.9 disclosed herein, or antigen-binding fragment thereof in the manufacture of a medicament for treating an autoimmune disease and/or inflammatory disease in a subject, wherein the medicament is used in a subject that has been pretreated with at least one other therapy. By "pretreated" or "pretreatment" is intended the subject has been treated with one or more other therapies prior to receiving the medicament comprising the antagonist anti-CD40 antibody or antigen-binding fragment thereof. "Pretreated" or "pretreatment" includes subjects that have been treated with the other therapy, or other therapies, within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the antagonist anti-CD40 antibody, for example, the monoclonal antibody CHIR-12.12 or CHIR-5.9 disclosed herein, or antigen-binding fragment thereof. It is not necessary that the subject was a responder to pretreatment with the prior therapy, or prior therapies. Thus, the subject that receives the medicament comprising the antagonist anti-CD40 antibody or antigen-binding fragment thereof could have responded, or could have failed to respond, to pretreatment with the prior therapy, or to one or more of the prior therapies where pretreatment comprised multiple therapies.

The following examples for this invention are offered by way of illustration and not by way of limitation.

VII. F. EXPERIMENTAL

The antagonist anti-CD40 antibodies used in the examples below are 5.9 and CHIR-12.12, described in Chapter I above, and in commonly owned International Application No. PCT/US2004/036957, filed Nov. 4, 2004 and published as WO 2005/044306, which corresponds to copending U.S. National-Phase application Ser. No. 10/576,943; the contents of each of which are herein incorporated by reference in their entirety.

Example 1

Testing in Autoimmune and Inflammatory Disease Models

Systemic Lupus Erythematosus (SLE) Model.

CHIR-12.12 is tested in a model of human systemic lupus erythematosus (SLE) in which peripheral blood mononuclear cells (PMBCs) from SLE patients are engrafted into SCID mice. See, for example, the model described in Duchosal et al. (1990) *J. Exp. Med.* 172:985-8.

After transfer of PBMCs from SLE patients into SCID mice, it is determined whether or not CHIR-12.12 treatment influences the T lymphocyte response to auto-antigen and auto-antibody production and disease manifestations such as glomerulonephritis. The first set of studies tests CHIR-12.12 as a single agent followed by testing the effect in a combination with other agents such as CTLA4-Ig.

Multiple Sclerosis Model.

Marmoset monkey experimental autoimmune encephalitis (EAE) is a model for human multiple sclerosis. See, for example, the model described in Raine et al. (1999) *Ann. Neurol.* 46:144-60 and Hart et al. (2004) *Lancet Neurol.* 3:588-97. CHIR-12.12 binds to marmoset CD40 and is tested for efficacy in this model.

Inflammation and Atherosclerosis.

CHIR-12.12 is tested in vitro for its ability to inhibit CD40L-induced production of matrix-degrading enzymes, tissue factor expression, proinflammatory cytokines, and upregulation of adhesion molecules. Subsequent studies test the ability of CHIR-12.12 to show anti-inflammatory activities in vivo using transgenic mice expressing the human CD40 molecule. See, for example, the model described in Yasui (2002) *Int. Immunol.* 14:319-29.

Transplantation.

CHIR-12.12 is tested for its ability to prevent transplant rejection in non-human primate models. Cynomolgus monkey renal allograft recipients are treated with CHIR-12.12 antibody to demonstrate the effect on graft acceptance with or without additional immunosuppressive drugs such as cyclosporine, FK506, rapamycin, corticosteroids, CTLA4-Ig, and anti-B Lymphocyte Stimulator antibody, and the like. See, the model described in Wee et al. (1992) *Transplantation* 53:501-7.

Alzheimer's Disease.

CHIR-12.12 is tested first in vitro for its ability to block microglial activation. In vivo efficacy studies with CHIR-12.12 are conducted in double-transgenic mice expressing human CD40 and overproducing amyloid-beta peptide. See, for example, the model described in Tan et al. (2002) *Nat. Neurosci.* 5:1288-93.

Example 2

Clinical Studies with CHIR-5.9 and CHIR-12.12

Clinical Objectives

The overall objective is to provide an effective therapy for rheumatoid arthritis (RA) by targeting cells with an antagonistic anti-CD40 IgG$_1$. The signal for this disease is determined in phase I although some measure of activity may be obtained in phase I. Initially the agent is studied as a single agent, but will be combined with other therapeutic agents as development proceeds.

Phase I

Evaluate safety and pharmacokinetics—dose escalation in subjects with RA.

Choose dose based on safety, tolerability, and change in serum markers of CD40. In general an MTD is sought but other indications of efficacy (depletion of CD40$^+$ bearing cells, etc.) may be adequate for dose finding.

Consideration of more than one dose, as some dose finding may be necessary in phase II.

Patients are dosed weekly with real-time pharmacokinetic (Pk) sampling. Initially a 4-week cycle is the maximum dosing allowed. The Pk may be highly variable depending on the disease state, density of CD40 etc.

This trial(s) is open to subjects with RA.

Decision to discontinue or continue studies is based on safety, dose, and preliminary evidence of therapeutic activity.

Activity of drug as determined by response rate is determined in Phase II.

Identify dose(s) for Phase II.

Phase II

Several trials will be initiated in subjects with RA. More than one dose, and more than one schedule may be tested in a randomized phase II setting.

Target a RA population that has failed current standard of care (nonsteroidal antiinflammatory drugs (NSAIDs) and disease-modifying antirheumatic drugs (DMARDs; e.g. gold and penicillamine) therapy failures)

Decision to discontinue or continue with study is based on proof of therapeutic concept in Phase II Determine whether surrogate marker can be used as early indication of clinical efficacy Identify doses for Phase III Phase III Phase III will depend on where the signal is detected in phase II, and what competing therapies are considered to be the standard. If the signal is in a stage of disease where there is no standard of therapy, then a single arm, well-controlled study could serve as a pivotal trial. If there are competing agents that are considered standard, then head-to-head studies are conducted.

Many modifications and other embodiments of the inventions set forth herein in chapters I-VII will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed is:

1. A method for inhibiting growth or differentiation of a normal human B cell, or for inhibiting proliferation of a normal human B cell wherein said proliferation is augmented by the interaction of CD40 ligand with CD40 expressed on the surface of said B cell, comprising contacting said B cell with an effective amount of a human anti-CD40 monoclonal antibody that is capable of specifically binding to human CD40 expressed on the surface of said B cell, wherein said monoclonal antibody is selected from the group consisting of:
   a) the monoclonal antibody CHIR-12.12 produced by the hybridoma cell line deposited with the ATCC as Patent Deposit No. PTA-5543;
   b) a monoclonal antibody comprising a light chain variable domain comprising residues 21-132 of SEQ ID NO:2;
   c) a monoclonal antibody comprising a heavy chain variable domain comprising residues 20-139 of SEQ ID NO:4;
   d) a monoclonal antibody comprising an amino acid sequence selected from the group consisting of:
      (i) residues 21-239 of SEQ ID NO:2;
      (ii) SEQ ID NO:2;
      (iii) residues 20-469 of SEQ ID NO:4;
      (iv) SEQ ID NO:4;
      (v) residues 20-469 of SEQ ID NO:5;
      (vi) SEQ ID NO:5;
      (vii) residues 21-132 of SEQ ID NO:2 and residues 20-139 of SEQ ID NO:4;
      (viii) residues 21-239 of SEQ ID NO:2 and residues 20-469 of SEQ ID NO:4;
      (ix) residues 21-239 of SEQ ID NO:2 and residues 20-469 of SEQ ID NO:5;
      (x) SEQ ID NO:2 and SEQ ID NO:4; and
      (xi) SEQ ID NO:2 and SEQ ID NO:5;
   e) a monoclonal antibody comprising the complementarity determining regions (CDRs) of the monoclonal antibody CHIR-12.12 produced by the hybridoma cell line deposited with the ATCC as Patent Deposit No. PTA-5543;
   f) a monoclonal antibody comprising a light chain variable domain containing the complementarity determining region (CDR) residues of SEQ ID NO:2, and a heavy chain variable domain containing the complementarity determining region (CDR) residues of SEQ ID NO:4;
   g) a monoclonal antibody that is an antigen-binding fragment of a monoclonal antibody of any one of preceding items a)-f), wherein said fragment retains the capability of specifically binding to said human CD40; and
   h) a conjugated form of the monoclonal antibody of any one of preceding items a)-g);
   said monoclonal antibody being free of significant agonist activity, and whereby when said antibody binds to said CD40 antigen on said B cell, the growth or differentiation of said B cell is inhibited.

2. A method for inhibiting antibody production by B cells in a human patient, comprising administering to a human patient an effective amount of a human anti-CD40 monoclonal antibody that is capable of specifically binding to human CD40 expressed on the surface of CD40-expressing B cells, where said monoclonal antibody is selected from the group consisting of:
   a) the monoclonal antibody CHIR-12.12 produced by the hybridoma cell line deposited with the ATCC as Patent Deposit No. PTA-5543;
   b) a monoclonal antibody comprising a light chain variable domain comprising residues 21-132 of SEQ ID NO:2;
   c) a monoclonal antibody comprising a heavy chain variable domain comprising residues 20-139 of SEQ ID NO:4;

d) a monoclonal antibody comprising an amino acid sequence selected from the group consisting of:
  (i) residues 21-239 of SEQ ID NO:2;
  (ii) SEQ ID NO:2;
  (iii) residues 20-469 of SEQ ID NO:4;
  (iv) SEQ ID NO:4;
  (v) residues 20-469 of SEQ ID NO:5;
  (vi) SEQ ID NO:5;
  (vii) residues 21-132 of SEQ ID NO:2 and residues 20-139 of SEQ ID NO:4;
  (viii) residues 21-239 of SEQ ID NO:2 and residues 20-469 of SEQ ID NO:4;
  (ix) residues 21-239 of SEQ ID NO:2 and residues 20-469 of SEQ ID NO:5;
  (x) SEQ ID NO:2 and SEQ ID NO:4; and
  (xi) SEQ ID NO:2 and SEQ ID NO:5;
e) a monoclonal antibody comprising the complementarity determining regions (CDRs) of the monoclonal antibody CHIR-12.12 produced by the hybridoma cell line deposited with the ATCC as Patent Deposit No. PTA-5543;
f) a monoclonal antibody comprising a light chain variable domain containing the complementarity determining region (CDR) residues of SEQ ID NO:2, and a heavy chain variable domain containing the complementarity determining region (CDR) residues of SEQ ID NO:4;
g) a monoclonal antibody that is an antigen-binding fragment of a monoclonal antibody of any one of preceding items a)-f), wherein said fragment retains the capability of specifically binding to said human CD40; and
h) a conjugated form of the monoclonal antibody of any one of preceding items a)-g);
said monoclonal antibody being free of significant agonist activity, and whereby when said antibody binds to said CD40 antigen on said B cell, the growth or differentiation of said B cell is inhibited.

3. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:
  a) the monoclonal antibody CHIR-12.12 produced by the hybridoma cell line deposited with the ATCC as Patent Deposit No. PTA-5543;
  b) a monoclonal antibody comprising a light chain variable domain comprising residues 21-132 of SEQ ID NO:2;
  c) a monoclonal antibody comprising a heavy chain variable domain comprising residues 20-139 of SEQ ID NO:4;
  d) a monoclonal antibody comprising an amino acid sequence selected from the group consisting of:
    (i) residues 21-239 of SEQ ID NO:2;
    (ii) SEQ ID NO:2;
    (iii) residues 20-469 of SEQ ID NO:4;
    (iv) SEQ ID NO:4;
    (v) residues 20-469 of SEQ ID NO:5;
    (vi) SEQ ID NO:5;
    (vii) residues 21-132 of SEQ ID NO:2 and residues 20-139 of SEQ ID NO:4;
    (viii) residues 21-239 of SEQ ID NO:2 and residues 20-469 of SEQ ID NO:4;
    (ix) residues 21-239 of SEQ ID NO:2 and residues 20-469 of SEQ ID NO:5;
    (x) SEQ ID NO:2 and SEQ ID NO:4; and
    (xi) SEQ ID NO:2 and SEQ ID NO:5;
  e) a monoclonal antibody that is an antigen-binding fragment of a monoclonal antibody of any one of preceding items a)-d), wherein said fragment retains the capability of specifically binding to said human CD40; and
  f) a conjugated form of the monoclonal antibody of any one of preceding items a)-e).

4. The method of claim 3, wherein said fragment is selected from the group consisting of a Fab fragment, an F(ab')$_2$ fragment, an Fv fragment, and a single-chain Fv fragment.

5. The method of claim 3, wherein said monoclonal antibody is recombinantly produced in a Chinese Hamster Ovary (CHO) cell line.

6. The method of claim 3, wherein said inflammatory disease or autoimmune disease is selected from the group consisting of systemic lupus erythematosus (SLE), discoid lupus, lupus nephritis, sarcoidosis, juvenile arthritis, rheumatoid arthritis, psoriatic arthritis, Reiter's syndrome, ankylosing spondylitis, gouty arthritis, rejection of an organ or tissue transplant, graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hashimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, and chronic inflammatory demyelinating polyneuropathy.

7. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) the monoclonal antibody CHIR-12.12 produced by the hybridoma cell line deposited with the ATCC as Patent Deposit No. PTA-5543;
  b) a monoclonal antibody comprising a light chain variable domain comprising residues 21-132 of SEQ ID NO:2;
  c) a monoclonal antibody comprising a heavy chain variable domain comprising residues 20-139 of SEQ ID NO:4;
  d) a monoclonal antibody comprising an amino acid sequence selected from the group consisting of:
    (i) residues 21-239 of SEQ ID NO:2;
    (ii) SEQ ID NO:2;
    (iii) residues 20-469 of SEQ ID NO:4;
    (iv) SEQ ID NO:4;
    (v) residues 20-469 of SEQ ID NO:5;

(vi) SEQ ID NO:5;
(vii) residues 21-132 of SEQ ID NO:2 and residues 20-139 of SEQ ID NO:4;
(viii) residues 21-239 of SEQ ID NO:2 and residues 20-469 of SEQ ID NO:4;
(ix) residues 21-239 of SEQ ID NO:2 and residues 20-469 of SEQ ID NO:5;
(x) SEQ ID NO:2 and SEQ ID NO:4; and
(xi) SEQ ID NO:2 and SEQ ID NO:5;
e) a monoclonal antibody that is an antigen-binding fragment of a monoclonal antibody of any one of preceding items a)-d), wherein said fragment retains the capability of specifically binding to said human CD40; and
f) a conjugated form of the monoclonal antibody of any one of preceding items a)-e).

8. The method of claim 7, wherein said fragment is selected from the group consisting of a Fab fragment, an F(ab')₂ fragment, an Fv fragment, and a single-chain Fv fragment.

9. The method of claim 7, wherein said monoclonal antibody is recombinantly produced in a Chinese Hamster Ovary (CHO) cell line.

10. The method of claim 7, wherein said treatment further comprises administering an immunosuppressive agent in a pharmaceutically acceptable excipient.

11. The method of claim 10, wherein the immunosuppressive agent is selected from the group consisting of cyclosporine, FK506, rapamycin, corticosteroids, CTLA4-Ig, and anti-B Lymphocyte Stimulator antibody.

12. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
a) the monoclonal antibody CHIR-12.12 produced by the hybridoma cell line deposited with the ATCC as Patent Deposit No. PTA-5543;
b) a monoclonal antibody comprising a light chain variable domain comprising residues 21-132 of SEQ ID NO:2;
c) a monoclonal antibody comprising a heavy chain variable domain comprising residues 20-139 of SEQ ID NO:4;
d) a monoclonal antibody comprising an amino acid sequence selected from the group consisting of:
(i) residues 21-239 of SEQ ID NO:2;
(ii) SEQ ID NO:2;
(iii) residues 20-469 of SEQ ID NO:4;
(iv) SEQ ID NO:4;
(v) residues 20-469 of SEQ ID NO:5;
(vi) SEQ ID NO:5;
(vii) residues 21-132 of SEQ ID NO:2 and residues 20-139 of SEQ ID NO:4;
(viii) residues 21-239 of SEQ ID NO:2 and residues 20-469 of SEQ ID NO:4;
(ix) residues 21-239 of SEQ ID NO:2 and residues 20-469 of SEQ ID NO:5;
(x) SEQ ID NO:2 and SEQ ID NO:4; and
(xi) SEQ ID NO:2 and SEQ ID NO:5;
e) a monoclonal antibody that is an antigen-binding fragment of a monoclonal antibody of any one of preceding items a)-d), wherein said fragment retains the capability of specifically binding to said human CD40; and
f) a conjugated form of the monoclonal antibody of any one of preceding items a)-e).

13. The method of claim 12, wherein said fragment is selected from the group consisting of a Fab fragment, an F(ab')₂ fragment, an Fv fragment, and a single-chain Fv fragment.

14. The method of claim 12, wherein said monoclonal antibody is recombinantly produced in a Chinese Hamster Ovary (CHO) cell line.

15. The method of claim 12, wherein said treatment further comprises administering an immunosuppressive agent in a pharmaceutically acceptable excipient.

16. The method of claim 15, wherein the immunosuppressive agent is selected from the group consisting of cyclosporine, FK506, rapamycin, corticosteroids, CTLA4-Ig, an anti-CD20 antibody, and anti-B Lymphocyte Stimulator antibody.

17. The method of claim 3, further comprising combination therapy with at least one other therapy for said inflammatory disease or autoimmune disease, wherein said at least one other therapy is administered to said human subject prior to, during, or subsequent to administration of said antagonist anti-CD40 monoclonal antibody.

18. The method of claim 17, wherein said at least one other therapy is selected from the group consisting of: surgery, organ perfusion, radiation therapy, steroid therapy, non-steroidal therapy, antibiotic therapy, antifungal therapy, hormone therapy, cytokine therapy, therapy with dermatological agents, immunosuppressive therapy, and other anti-inflammatory monoclonal antibody therapy.

19. A method for inhibiting a CD40 ligand-mediated CD40 signaling pathway in a normal human CD40-expressing cell, said method comprising contacting said cell with an effective amount of an antagonist human anti-CD40 monoclonal antibody that is capable of specifically binding to human CD40 expressed on the surface of said cell, wherein said monoclonal antibody is selected from the group consisting of:
a) the monoclonal antibody CHIR-12.12 produced by the hybridoma cell line deposited with the ATCC as Patent Deposit No. PTA-5543;
b) a monoclonal antibody comprising a light chain variable domain comprising residues 21-132 of SEQ ID NO:2;
c) a monoclonal antibody comprising a heavy chain variable domain comprising residues 20-139 of SEQ ID NO:4;
d) a monoclonal antibody comprising an amino acid sequence selected from the group consisting of:
(i) residues 21-239 of SEQ ID NO:2;
(ii) SEQ ID NO:2;
(iii) residues 20-469 of SEQ ID NO:4;
(iv) SEQ ID NO:4;
(v) residues 20-469 of SEQ ID NO:5;
(vi) SEQ ID NO:5;
(vii) residues 21-132 of SEQ ID NO:2 and residues 20-139 of SEQ ID NO:4;
(viii) residues 21-239 of SEQ ID NO:2 and residues 20-469 of SEQ ID NO:4;
(ix) residues 21-239 of SEQ ID NO:2 and residues 20-469 of SEQ ID NO:5;
(x) SEQ ID NO:2 and SEQ ID NO:4; and
(xi) SEQ ID NO:2 and SEQ ID NO:5;
e) a monoclonal antibody comprising the complementarity determining regions (CDRs) of the monoclonal antibody CHIR-12.12 produced by the hybridoma cell line deposited with the ATCC as Patent Deposit No. PTA-5543;
f) a monoclonal antibody comprising a light chain variable domain containing the complementarity determining region (CDR) residues of SEQ ID NO:2, and a heavy chain variable domain containing the complementarity determining region (CDR) residues of SEQ ID NO:4;

g) a monoclonal antibody that is an antigen-binding fragment of a monoclonal antibody of any one of preceding items a)-f), wherein said fragment retains the capability of specifically binding to said human CD40; and h) a conjugated form of the monoclonal antibody of any one of preceding items a)-g).

20. The method of claim 19, wherein said normal human CD40-expressing cell is a normal human B cell and said CD40 signaling pathway is B cell survival.

21. The method of claim 1, wherein said fragment is selected from the group consisting of a Fab fragment, an F(ab')$_2$ fragment, an Fv fragment, and a single-chain Fv fragment.

22. The method of claim 2, wherein said fragment is selected from the group consisting of a Fab fragment, an F(ab')$_2$ fragment, an Fv fragment, and a single-chain Fv fragment.

23. The method of claim 19, wherein said fragment is selected from the group consisting of a Fab fragment, an F(ab')$_2$ fragment, an Fv fragment, and a single-chain Fv fragment.

24. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:

a) a monoclonal antibody comprising a light chain variable domain containing the complementarity determining region (CDR) residues of SEQ ID NO:2, and a heavy chain variable domain containing the complementarity determining region (CDR) residues of SEQ ID NO:4;

b) a monoclonal antibody comprising the complementarity determining regions (CDRs) of the monoclonal antibody CHIR-12.12 produced by the hybridoma cell line deposited with the ATCC as Patent Deposit No. PTA-5543;

c) a monoclonal antibody that is an antigen-binding fragment of a monoclonal antibody of preceding item a) or b), wherein said fragment retains the capability of specifically binding to said human CD40; and d) a conjugated form of the monoclonal antibody of any one of preceding items a)-c).

25. The method of claim 24, wherein said fragment is selected from the group consisting of a Fab fragment, an F(ab')$_2$ fragment, an Fv fragment, and a single-chain Fv fragment.

26. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:

a) the monoclonal antibody CHIR-12.12 produced by the hybridoma cell line deposited with the ATCC as Patent Deposit No. PTA-5543 or an antigen-binding fragment thereof, wherein said fragment retains the capability of specifically binding to said human CD40; and b) a conjugated form of the monoclonal antibody or antigen-binding fragment of preceding item a).

27. The method of claim 26, wherein said antigen-binding fragment is selected from the group consisting of a Fab fragment, an F(ab')$_2$ fragment, an Fv fragment, and a single-chain Fv fragment.

28. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:

a) a monoclonal antibody comprising residues 21-132 of SEQ ID NO:2 and residues 20-139 of SEQ ID NO:4;

b) a monoclonal antibody comprising residues 21-239 of SEQ ID NO:2 and residues 20-469 of SEQ ID NO:4;

c) a monoclonal antibody comprising residues 21-239 of SEQ ID NO:2 and residues 20-469 of SEQ ID NO:5; and d) a conjugated form of the monoclonal antibody of any one of preceding items a)-c).

29. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:

a) a monoclonal antibody comprising a light chain variable domain containing the complementarity determining region (CDR) residues of SEQ ID NO:2, and a heavy chain variable domain containing the complementarity determining region (CDR) residues of SEQ ID NO:4;

b) a monoclonal antibody comprising the complementarity determining regions (CDRs) of the monoclonal antibody CHIR-12.12 produced by the hybridoma cell line deposited with the ATCC as Patent Deposit No. PTA-5543;

c) a monoclonal antibody that is an antigen-binding fragment of a monoclonal antibody of preceding item a) or b), wherein said fragment retains the capability of specifically binding to said human CD40; and d) a conjugated form of the monoclonal antibody of any one of preceding items a)-c).

30. The method of claim 29, wherein said fragment is selected from the group consisting of a Fab fragment, an F(ab')$_2$ fragment, an Fv fragment, and a single-chain Fv fragment.

31. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) the monoclonal antibody CHIR-12.12 produced by the hybridoma cell line deposited with the ATCC as Patent Deposit No. PTA-5543 or an antigen-binding fragment thereof, wherein said fragment retains the capability of specifically binding to said human CD40; and
  b) a conjugated form of the monoclonal antibody or antigen-binding fragment of preceding item a).

32. The method of claim 31, wherein said antigen-binding fragment is selected from the group consisting of a Fab fragment, an F(ab')$_2$ fragment, an Fv fragment, and a single-chain Fv fragment.

33. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) a monoclonal antibody comprising residues 21-132 of SEQ ID NO:2 and residues 20-139 of SEQ ID NO:4;
  b) a monoclonal antibody comprising residues 21-239 of SEQ ID NO:2 and residues 20-469 of SEQ ID NO:4;
  c) a monoclonal antibody comprising residues 21-239 of SEQ ID NO:2 and residues 20-469 of SEQ ID NO:5; and
  d) a conjugated form of the monoclonal antibody of any one of preceding items a)-c).

34. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) a monoclonal antibody comprising a light chain variable domain containing the complementarity determining region (CDR) residues of SEQ ID NO:2, and a heavy chain variable domain containing the complementarity determining region (CDR) residues of SEQ ID NO:4;
  b) a monoclonal antibody comprising the complementarity determining regions (CDRs) of the monoclonal antibody CHIR-12.12 produced by the hybridoma cell line deposited with the ATCC as Patent Deposit No. PTA-5543;
  c) a monoclonal antibody that is an antigen-binding fragment of a monoclonal antibody of preceding item a) or b), wherein said fragment retains the capability of specifically binding to said human CD40; and
  d) a conjugated form of the monoclonal antibody of any one of preceding items a)-c).

35. The method of claim 34, wherein said fragment is selected from the group consisting of a Fab fragment, an F(ab')$_2$ fragment, an Fv fragment, and a single-chain Fv fragment.

36. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) the monoclonal antibody CHIR-12.12 produced by the hybridoma cell line deposited with the ATCC as Patent Deposit No. PTA-5543 or an antigen-binding fragment thereof, wherein said fragment retains the capability of specifically binding to said human CD40; and
  b) a conjugated form of the monoclonal antibody or antigen-binding fragment of preceding item a).

37. The method of claim 36, wherein said antigen-binding fragment is selected from the group consisting of a Fab fragment, an F(ab')$_2$ fragment, an Fv fragment, and a single-chain Fv fragment.

38. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) a monoclonal antibody comprising residues 21-132 of SEQ ID NO:2 and residues 20-139 of SEQ ID NO:4;
  b) a monoclonal antibody comprising residues 21-239 of SEQ ID NO:2 and residues 20-469 of SEQ ID NO:4;
  c) a monoclonal antibody comprising residues 21-239 of SEQ ID NO:2 and residues 20-469 of SEQ ID NO:5; and
  d) a conjugated form of the monoclonal antibody of any one of preceding items a)-c).

39. A method for inhibiting growth or differentiation of a normal human B cell, or for inhibiting proliferation of a normal human B cell wherein said proliferation is augmented by the interaction of a CD40 ligand with a CD40 expressed on the surface of said B cell, comprising contacting said B cell with an effective amount of a human anti-CD40 monoclonal antibody that is capable of specifically binding to human CD40 expressed on the surface of said B cell, wherein said monoclonal antibody is selected from the group consisting of:
  a) the monoclonal antibody CHIR-5.9 produced by the hybridoma cell line deposited with the ATCC as Patent Deposit No. PTA-5542;
  b) a monoclonal antibody comprising a light chain variable domain comprising residues 21-132 of SEQ ID NO:6;
  c) a monoclonal antibody comprising a heavy chain variable domain comprising residues 20-144 of SEQ ID NO:7;
  d) a monoclonal antibody comprising an amino acid sequence selected from the group consisting of:
    (i) residues 21-239 of SEQ ID NO:6;
    (ii) SEQ ID NO:6;
    (iii) residues 20-474 of SEQ ID NO:7;
    (iv) SEQ ID NO:7;
    (v) residues 20-474 of SEQ ID NO:8;
    (vi) SEQ ID NO:8;
    (vii) residues 21-132 of SEQ ID NO:6 and residues 20-144 of SEQ ID NO:7;
    (viii) residues 21-239 of SEQ ID NO:6 and residues 20-474 of SEQ ID NO:7;
    (ix) residues 21-239 of SEQ ID NO:6 and residues 20-474 of SEQ ID NO:8;
    (x) SEQ ID NO:6 and SEQ ID NO:7; and
    (xi) SEQ ID NO:6 and SEQ ID NO:8;
  e) a monoclonal antibody comprising the complementarity determining regions (CDRs) of the monoclonal antibody CHIR-5.9 produced by the hybridoma cell line deposited with the ATCC as Patent Deposit No. PTA-5542;
f) a monoclonal antibody comprising a light chain variable domain containing the complementarity determining region (CDR) residues of SEQ ID NO:6, and a heavy chain variable domain containing the complementarity determining region (CDR) residues of SEQ ID NO:7;
g) a monoclonal antibody that is an antigen-binding fragment of a monoclonal antibody of any one of preceding items a)-f), wherein said fragment retains the capability of specifically binding to said human CD40; and
h) a conjugated form of the monoclonal antibody of any one of preceding items a)-g);
said monoclonal antibody being free of significant agonist activity, and whereby when said antibody binds to said CD40 antigen on said B cell, the growth or differentiation of said B cell is inhibited.

40. The method of claim 39, wherein said fragment is selected from the group consisting of a Fab fragment, an F(ab')$_2$ fragment, an Fv fragment, and a single-chain Fv fragment.

41. A method for inhibiting antibody production by B cells in a human patient, comprising administering to a human patient an effective amount of a human anti-CD40 monoclonal antibody that is capable of specifically binding to human CD40 expressed on the surface of CD40-expressing B cells, where said monoclonal antibody is selected from the group consisting of:
   a) the monoclonal antibody CHIR-5.9 produced by the hybridoma cell line deposited with the ATCC as Patent Deposit No. PTA-5542;
   b) a monoclonal antibody comprising a light chain variable domain comprising residues 21-132 of SEQ ID NO:6;
   c) a monoclonal antibody comprising a heavy chain variable domain comprising residues 20-144 of SEQ ID NO:7;
   d) a monoclonal antibody comprising an amino acid sequence selected from the group consisting of:
      (i) residues 21-239 of SEQ ID NO:6;
      (ii) SEQ ID NO:6;
      (iii) residues 20-474 of SEQ ID NO:7;
      (iv) SEQ ID NO:7;
      (v) residues 20-474 of SEQ ID NO:8;
      (vi) SEQ ID NO:8;
      (vii) residues 21-132 of SEQ ID NO:6 and residues 20-144 of SEQ ID NO:7;
      (viii) residues 21-239 of SEQ ID NO:6 and residues 20-474 of SEQ ID NO:7;
      (ix) residues 21-239 of SEQ ID NO:6 and residues 20-474 of SEQ ID NO:8;
      (x) SEQ ID NO:6 and SEQ ID NO:7; and
      (xi) SEQ ID NO:6 and SEQ ID NO:8;
   e) a monoclonal antibody comprising the complementarity determining regions (CDRs) of the monoclonal antibody CHIR-5.9 produced by the hybridoma cell line deposited with the ATCC as Patent Deposit No. PTA-5542;
   f) a monoclonal antibody comprising a light chain variable domain containing the complementarity determining region (CDR) residues of SEQ ID NO:6, and a heavy chain variable domain containing the complementarity determining region (CDR) residues of SEQ ID NO:7;
   g) a monoclonal antibody that is an antigen-binding fragment of a monoclonal antibody of any one of preceding items a)-f), wherein said fragment retains the capability of specifically binding to said human CD40; and
   h) a conjugated form of the monoclonal antibody of any one of preceding items a)-g);
   said monoclonal antibody being free of significant agonist activity, and whereby when said antibody binds to said CD40 antigen on said B cell, the growth or differentiation of said B cell is inhibited.

42. The method of claim 41, wherein said fragment is selected from the group consisting of a Fab fragment, an F(ab')$_2$ fragment, an Fv fragment, and a single-chain Fv fragment.

43. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:
   a) the monoclonal antibody CHIR-5.9 produced by the hybridoma cell line deposited with the ATCC as Patent Deposit No. PTA-5542;
   b) a monoclonal antibody comprising a light chain variable domain comprising residues 21-132 of SEQ ID NO:6;
   c) a monoclonal antibody comprising a heavy chain variable domain comprising residues 20-144 of SEQ ID NO:7;
   d) a monoclonal antibody comprising an amino acid sequence selected from the group consisting of:
      (i) residues 21-239 of SEQ ID NO:6;
      (ii) SEQ ID NO:6;
      (iii) residues 20-474 of SEQ ID NO:7;
      (iv) SEQ ID NO:7;
      (v) residues 20-474 of SEQ ID NO:8;
      (vi) SEQ ID NO:8;
      (vii) residues 21-132 of SEQ ID NO:6 and residues 20-144 of SEQ ID NO:7;
      (viii) residues 21-239 of SEQ ID NO:6 and residues 20-474 of SEQ ID NO:7;
      (ix) residues 21-239 of SEQ ID NO:6 and residues 20-474 of SEQ ID NO:8;
      (x) SEQ ID NO:6 and SEQ ID NO:7; and
      (xi) SEQ ID NO:6 and SEQ ID NO:8;
   e) a monoclonal antibody that is an antigen-binding fragment of a monoclonal antibody of any one of preceding items a)-d), wherein said fragment retains the capability of specifically binding to said human CD40; and
   f) a conjugated form of the monoclonal antibody of any one of preceding items a)-e).

44. The method of claim 43, wherein said fragment is selected from the group consisting of a Fab fragment, an F(ab')$_2$ fragment, an Fv fragment, and a single-chain Fv fragment.

45. The method of claim 43, wherein said antibody is produced in a Chinese Hamster Ovary (CHO) cell line.

46. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:
  a) a monoclonal antibody comprising a light chain variable domain containing the complementarity determining region (CDR) residues of SEQ ID NO:6, and a heavy chain variable domain containing the complementarity determining region (CDR) residues of SEQ ID NO:7;
  b) a monoclonal antibody comprising the complementarity determining regions (CDRs) of the monoclonal antibody CHIR-5.9 produced by the hybridoma cell line deposited with the ATCC as Patent Deposit No. PTA-5542;
  c) a monoclonal antibody that is an antigen-binding fragment of a monoclonal antibody of preceding item a) or b), wherein said fragment retains the capability of specifically binding to said human CD40; and
  d) a conjugated form of the monoclonal antibody of any one of preceding items a)-c).

47. The method of claim 46, wherein said fragment is selected from the group consisting of a Fab fragment, an F(ab')$_2$ fragment, an Fv fragment, and a single-chain Fv fragment.

48. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:
  a) the monoclonal antibody CHIR-5.9 produced by the hybridoma cell line deposited with the ATCC as Patent Deposit No. PTA-5542 or an antigen-binding fragment thereof, wherein said fragment retains the capability of specifically binding to said human CD40; and
  b) a conjugated form of the monoclonal antibody or antigen-binding fragment of preceding item a) or b).

49. The method of claim 48, wherein said antigen-binding fragment is selected from the group consisting of a Fab fragment, an F(ab')$_2$ fragment, an Fv fragment, and a single-chain Fv fragment.

50. A method for reducing one or more symptoms of an inflammatory disease or autoimmune disease in a human subject in need thereof, wherein said one or more symptoms are mediated by stimulation of CD40-expressing cells by CD40 ligand binding to CD40 on said cells in said human subject, said method comprising administering to said subject an effective amount of an antagonist human anti-CD40 monoclonal antibody that is capable of specifically binding to human CD40 expressed on the surface of CD40-expressing cells, said monoclonal antibody being free of significant agonist activity when bound to human CD40 expressed on the surface of said CD40-expressing cells, wherein said monoclonal antibody is selected from the group consisting of:
  a) a monoclonal antibody comprising residues 21-132 of SEQ ID NO:6 and residues 20-144 of SEQ ID NO:7;
  b) a monoclonal antibody comprising residues 21-239 of SEQ ID NO:6 and residues 20-474 of SEQ ID NO:7;
  c) a monoclonal antibody comprising residues 21-239 of SEQ ID NO:6 and residues 20-474 of SEQ ID NO:8; and
  d) a conjugated form of the monoclonal antibody of any one of preceding items a)-c).

51. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) the monoclonal antibody CHIR-5.9 produced by the hybridoma cell line deposited with the ATCC as Patent Deposit No. PTA-5542;
  b) a monoclonal antibody comprising a light chain variable domain comprising residues 21-132 of SEQ ID NO:6;
  c) a monoclonal antibody comprising a heavy chain variable domain comprising residues 20-144 of SEQ ID NO:7;
  d) a monoclonal antibody comprising an amino acid sequence selected from the group consisting of:
    (i) residues 21-239 of SEQ ID NO:6;
    (ii) SEQ ID NO:6;
    (iii) residues 20-474 of SEQ ID NO:7;
    (iv) SEQ ID NO:7;
    (v) residues 20-474 of SEQ ID NO:8;
    (vi) SEQ ID NO:8;
    (vii) residues 21-132 of SEQ ID NO:6 and residues 20-144 of SEQ ID NO:7;
    (viii) residues 21-239 of SEQ ID NO:6 and residues 20-474 of SEQ ID NO:7;
    (ix) residues 21-239 of SEQ ID NO:6 and residues 20-474 of SEQ ID NO:8;
    (x) SEQ ID NO:6 and SEQ ID NO:7; and
    (xi) SEQ ID NO:6 and SEQ ID NO:8;
  e) a monoclonal antibody that is an antigen-binding fragment of a monoclonal antibody of any one of preceding items a)-d), wherein said fragment retains the capability of specifically binding to said human CD40; and
  f) a conjugated form of the monoclonal antibody of any one of preceding items a)-e).

52. The method of claim 51, wherein said fragment is selected from the group consisting of a Fab fragment, an F(ab')$_2$ fragment, an Fv fragment, and a single-chain Fv fragment.

53. The method of claim 51, wherein said antibody is produced in a Chinese Hamster Ovary (CHO) cell line.

54. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:
  a) a monoclonal antibody comprising a light chain variable domain containing the complementarity determining region (CDR) residues of SEQ ID NO:6, and a heavy chain variable domain containing the complementarity determining region (CDR) residues of SEQ ID NO:7;
  b) a monoclonal antibody comprising the complementarity determining regions (CDRs) of the monoclonal antibody CHIR-5.9 produced by the hybridoma cell line deposited with the ATCC as Patent Deposit No. PTA-5542;

c) a monoclonal antibody that is an antigen-binding fragment of a monoclonal antibody of preceding item a) or b), wherein said fragment retains the capability of specifically binding to said human CD40; and d) a conjugated form of the monoclonal antibody of any one of preceding items a)-c).

55. The method of claim 54, wherein said fragment is selected from the group consisting of a Fab fragment, an F(ab')$_2$ fragment, an Fv fragment, and a single-chain Fv fragment.

56. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:

a) the monoclonal antibody CHIR-5.9 produced by the hybridoma cell line deposited with the ATCC as Patent Deposit No. PTA-5542 or an antigen-binding fragment thereof, wherein said fragment retains the capability of specifically binding to said human CD40; and b) a conjugated form of the monoclonal antibody or antigen-binding fragment of preceding item a).

57. The method of claim 56, wherein said antigen-binding fragment is selected from the group consisting of a Fab fragment, an F(ab')$_2$ fragment, an Fv fragment, and a single-chain Fv fragment.

58. A method for treating a human subject for transplant rejection, said method comprising administering to said subject an effective amount of an antagonist human anti-CD40 monoclonal antibody that is capable of specifically binding to human CD40 expressed on the surface of human CD40-expressing cells, said monoclonal antibody being free of significant agonist activity when bound to human CD40 expressed on the surface of said cells, wherein said monoclonal antibody is selected from the group consisting of:

a) a monoclonal antibody comprising residues 21-132 of SEQ ID NO:6 and residues 20-144 of SEQ ID NO:7;

b) a monoclonal antibody comprising residues 21-239 of SEQ ID NO:6 and residues 20-474 of SEQ ID NO:7;

c) a monoclonal antibody comprising residues 21-239 of SEQ ID NO:6 and residues 20-474 of SEQ ID NO:8; and d) a conjugated form of the monoclonal antibody of any one of preceding items a)-c).

59. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said antibody being free of significant agonist activity when bound to human CD40 expressed on the surface of said cells, wherein said monoclonal antibody is selected from the group consisting of:

a) the monoclonal antibody CHIR-5.9 produced by the hybridoma cell line deposited with the ATCC as Patent Deposit No. PTA-5542;

b) a monoclonal antibody comprising a light chain variable domain comprising residues 21-132 of SEQ ID NO:6;

c) a monoclonal antibody comprising a heavy chain variable domain comprising residues 20-144 of SEQ ID NO:7;

d) a monoclonal antibody comprising an amino acid sequence selected from the group consisting of:
  (i) residues 21-239 of SEQ ID NO:6;
  (ii) SEQ ID NO:6;
  (iii) residues 20-474 of SEQ ID NO:7;
  (iv) SEQ ID NO:7;
  (v) residues 20-474 of SEQ ID NO:8;
  (vi) SEQ ID NO:8;
  (vii) residues 21-132 of SEQ ID NO:6 and residues 20-144 of SEQ ID NO:7;
  (viii) residues 21-239 of SEQ ID NO:6 and residues 20-474 of SEQ ID NO:7;
  (ix) residues 21-239 of SEQ ID NO:6 and residues 20-474 of SEQ ID NO:8;
  (x) SEQ ID NO:6 and SEQ ID NO:7; and
  (xi) SEQ ID NO:6 and SEQ ID NO:8;

e) a monoclonal antibody that is an antigen-binding fragment of a monoclonal antibody of any one of preceding items a)-d), wherein said fragment retains the capability of specifically binding to said human CD40; and f) a conjugated form of the monoclonal antibody of any one of preceding items a)-e).

60. The method of claim 59, wherein said fragment is selected from the group consisting of a Fab fragment, an F(ab')$_2$ fragment, an Fv fragment, and a single-chain Fv fragment.

61. The method of claim 59, wherein said antibody is produced in a Chinese Hamster Ovary (CHO) cell line.

62. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said antibody being free of significant agonist activity when bound to human CD40 expressed on the surface of said cells, wherein said mooclonal antibody is selected from the group consisting of:

a) a monoclonal antibody comprising a light chain variable domain containing the complementarity determining region (CDR) residues of SEQ ID NO:6, and a heavy chain variable domain containing the complementarity determining region (CDR) residues of SEQ ID NO:7;

b) a monoclonal antibody comprising the complementarity determining regions (CDRs) of the monoclonal antibody CHIR-5.9 produced by the hybridoma cell line deposited with the ATCC as Patent Deposit No. PTA-5542;

c) a monoclonal antibody that is an antigen-binding fragment of a monoclonal antibody of preceding item a) or b), wherein said fragment retains the capability of specifically binding to said human CD40; and d) a conjugated form of the monoclonal antibody of any one of preceding items a)-c).

63. The method of claim 62, wherein said fragment is selected from the group consisting of a Fab fragment, an F(ab')$_2$ fragment, an Fv fragment, and a single-chain Fv fragment.

64. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said antibody being free of significant agonist activity when bound to human CD40 expressed on the surface of said cells, wherein said monoclonal antibody is selected from the group consisting of:

a) the monoclonal antibody CHIR-5.9 produced by the hybridoma cell line deposited with the ATCC as Patent Deposit No. PTA-5542 or an antigen-binding fragment thereof, wherein said fragment retains the capability of specifically binding to said human CD40; and
b) a conjugated form of the monoclonal antibody or antigen-binding fragment of preceding item a).

65. The method of claim 64, wherein said antigen-binding fragment is selected from the group consisting of a Fab fragment, an F(ab')₂ fragment, an Fv fragment, and a single-chain Fv fragment.

66. A method for treating a human subject for rheumatoid arthritis, comprising administering an effective amount of an antagonist human anti-CD40 monoclonal antibody that is capable of specifically binding to human CD40 expressed on the surface of human CD40-expressing cells, said antibody being free of significant agonist activity when bound to human CD40 expressed on the surface of said cells, wherein said monoclonal antibody is selected from the group consisting of:
 a) a monoclonal antibody comprising residues 21-132 of SEQ ID NO:6 and residues 20-144 of SEQ ID NO:7;
 b) a monoclonal antibody comprising residues 21-239 of SEQ ID NO:6 and residues 20-474 of SEQ ID NO:7;
 c) a monoclonal antibody comprising residues 21-239 of SEQ ID NO:6 and residues 20-474 of SEQ ID NO:8; and
 d) a conjugated form of the monoclonal antibody of any one of preceding items a)-c).

67. A method for inhibiting a CD40 ligand-mediated CD40 signaling pathway in a normal human CD40-expressing cell, said method comprising contacting said cell with an effective amount of an antagonist human anti-CD40 monoclonal antibody that is capable of specifically binding to human CD40 expressed on the surface of said cell, wherein said monoclonal antibody is selected from the group consisting of:
 a) the monoclonal antibody CHIR-5.9 produced by the hybridoma cell line deposited with the ATCC as Patent Deposit No. PTA-5542;
 b) a monoclonal antibody comprising a light chain variable domain comprising residues 21-132 of SEQ ID NO:6;
 c) a monoclonal antibody comprising a heavy chain variable domain comprising residues 20-144 of SEQ ID NO:7;
 d) a monoclonal antibody comprising an amino acid sequence selected from the group consisting of:
  (i) residues 21-239 of SEQ ID NO:6;
  (ii) SEQ ID NO:6;
  (iii) residues 20-474 of SEQ ID NO:7;
  (iv) SEQ ID NO:7;
  (v) residues 20-474 of SEQ ID NO:8;
  (vi) SEQ ID NO:8;
  (vii) residues 21-132 of SEQ ID NO:6 and residues 20-144 of SEQ ID NO:7;
  (viii) residues 21-239 of SEQ ID NO:6 and residues 20-474 of SEQ ID NO:7;
  (ix) residues 21-239 of SEQ ID NO:6 and residues 20-474 of SEQ ID NO:8;
  (x) SEQ ID NO:6 and SEQ ID NO:7; and
  (xi) SEQ ID NO:6 and SEQ ID NO:8;
 e) a monoclonal antibody comprising the complementarity determining regions (CDRs) of the monoclonal antibody CHIR-5.9 produced by the hybridoma cell line deposited with the ATCC as Patent Deposit No. PTA-5542;
 f) a monoclonal antibody comprising a light chain variable domain containing the complementarity determining region (CDR) residues of SEQ ID NO:6, and a heavy chain variable domain containing the complementarity determining region (CDR) residues of SEQ ID NO:7;
 g) a monoclonal antibody that is an antigen-binding fragment of a monoclonal antibody of any one of preceding items a)-f), wherein said fragment retains the capability of specifically binding to said human CD40; and
 h) a conjugated form of the monoclonal antibody of any one of preceding items a)-g).

68. The method of claim 67, wherein said normal human CD40-expressing cell is a normal human B cell and said CD40 signaling pathway is B cell survival.

69. The method of claim 67, wherein said fragment is selected from the group consisting of a Fab fragment, an F(ab')₂ fragment, an Fv fragment, and a single-chain Fv fragment.

* * * * *

SEQUENCE LISTING

<160> NUMBER OF SEQ ID NOS: 18

<210> SEQ ID NO 1
<211> LENGTH: 720
<212> TYPE: DNA
<213> ORGANISM: Artificial Sequence -continued

```
<220> FEATURE:
<223> OTHER INFORMATION: Coding sequence for light chain of 12.12 human
      anti-CD40 antibody
<221> NAME/KEY: CDS
<222> LOCATION: (1)...(720)

<400> SEQUENCE: 1 atg gcg ctc cct gct cag ctc ctg ggg ctg cta atg ctc tgg gtc tct      48
Met Ala Leu Pro Ala Gln Leu Leu Gly Leu Leu Met Leu Trp Val Ser
1               5                   10                  15 gga tcc agt ggg gat att gtg atg act cag tct cca ctc tcc ctg acc      96
Gly Ser Ser Gly Asp Ile Val Met Thr Gln Ser Pro Leu Ser Leu Thr
            20                  25                  30 gtc acc cct gga gag ccg gcc tcc atc tcc tgc agg tcc agt cag agc     144
Val Thr Pro Gly Glu Pro Ala Ser Ile Ser Cys Arg Ser Ser Gln Ser
        35                  40                  45 ctc ctg tat agt aat gga tac aac tat ttg gat tgg tac ctg cag aag     192
Leu Leu Tyr Ser Asn Gly Tyr Asn Tyr Leu Asp Trp Tyr Leu Gln Lys
    50                  55                  60 cca ggg cag tct cca cag gtc ctg atc tct ttg ggt tct aat cgg gcc     240
Pro Gly Gln Ser Pro Gln Val Leu Ile Ser Leu Gly Ser Asn Arg Ala
65                  70                  75                  80 tcc ggg gtc cct gac agg ttc agt ggc agt gga tca ggc aca gat ttt     288
Ser Gly Val Pro Asp Arg Phe Ser Gly Ser Gly Ser Gly Thr Asp Phe
                85                  90                  95 aca ctg aaa atc agc aga gtg gag gct gag gat gtt ggg gtt tat tac     336
Thr Leu Lys Ile Ser Arg Val Glu Ala Glu Asp Val Gly Val Tyr Tyr
            100                 105                 110 tgc atg caa gct cga caa act cca ttc act ttc ggc cct ggg acc aaa     384
Cys Met Gln Ala Arg Gln Thr Pro Phe Thr Phe Gly Pro Gly Thr Lys
        115                 120                 125 gtg gat atc aga cga act gtg gct gca cca tct gtc ttc atc ttc ccg     432
Val Asp Ile Arg Arg Thr Val Ala Ala Pro Ser Val Phe Ile Phe Pro
    130                 135                 140 cca tct gat gag cag ttg aaa tct gga act gcc tct gtt gtg tgc ctg     480
Pro Ser Asp Glu Gln Leu Lys Ser Gly Thr Ala Ser Val Val Cys Leu
145                 150                 155                 160 ctg aat aac ttc tat ccc aga gag gcc aaa gta cag tgg aag gtg gat     528
Leu Asn Asn Phe Tyr Pro Arg Glu Ala Lys Val Gln Trp Lys Val Asp
                165                 170                 175 aac gcc ctc caa tcg ggt aac tcc cag gag agt gtc aca gag cag gac     576
Asn Ala Leu Gln Ser Gly Asn Ser Gln Glu Ser Val Thr Glu Gln Asp
            180                 185                 190 agc aag gac agc acc tac agc ctc agc agc acc ctg acg ctg agc aaa     624
Ser Lys Asp Ser Thr Tyr Ser Leu Ser Ser Thr Leu Thr Leu Ser Lys
        195                 200                 205 gca gac tac gag aaa cac aaa gtc tac gcc tgc gaa gtc acc cat cag     672
Ala Asp Tyr Glu Lys His Lys Val Tyr Ala Cys Glu Val Thr His Gln
    210                 215                 220 ggc ctg agc tcg ccc gtc aca aag agc ttc aac agg gga gag tgt tag     720
Gly Leu Ser Ser Pro Val Thr Lys Ser Phe Asn Arg Gly Glu Cys *
225                 230                 235

<210> SEQ ID NO 2
<211> LENGTH: 239
<212> TYPE: PRT
<213> ORGANISM: Artificial Sequence
<220> FEATURE:
<223> OTHER INFORMATION: Light chain of 12.12 human anti-CD40 antibody

<400> SEQUENCE: 2

Met Ala Leu Pro Ala Gln Leu Leu Gly Leu Leu Met Leu Trp Val Ser
1               5                   10                  15
```

```
Gly Ser Ser Gly Asp Ile Val Met Thr Gln Ser Pro Leu Ser Leu Thr
            20                  25                  30

Val Thr Pro Gly Glu Pro Ala Ser Ile Ser Cys Arg Ser Gln Ser
        35                  40                  45

Leu Leu Tyr Ser Asn Gly Tyr Asn Tyr Leu Asp Trp Tyr Leu Gln Lys
    50                  55                  60

Pro Gly Gln Ser Pro Gln Val Leu Ile Ser Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Arg Gln Thr Pro Phe Thr Phe Gly Pro Gly Thr Lys
        115                 120                 125

Val Asp Ile Arg Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 3
<211> LENGTH: 2016
<212> TYPE: DNA
<213> ORGANISM: Artificial Sequence
<220> FEATURE:
<223> OTHER INFORMATION: Coding sequence for heavy chain of 12.12 human
      anti-CD40 antibody (with introns)

<400> SEQUENCE: 3 atg gag ttt ggg ctg agc tgg gtt ttc ctt gtt gct att tta aga ggt      48
gtc cag tgt cag gtg cag ttg gtg gag tct ggg gga ggc gtg gtc cag      96
cct ggg agg tcc ctg aga ctc tcc tgt gca gcc tct gga ttc acc ttc     144
agt agc tat ggc atg cac tgg gtc cgc cag gct cca ggc aag ggg ctg     192
gag tgg gtg gca gtt ata tca tat gag gaa agt aat aga tac cat gca     240
gac tcc gtg aag ggc cga ttc acc atc tcc aga gac aat tcc aag atc     288
acg ctg tat ctg caa atg aac agc ctc aga act gag gac acg gct gtg     336
tat tac tgt gcg aga gat ggg ggt ata gca gca cct ggg cct gac tac     384
tgg ggc cag gga acc ctg gtc acc gtc tcc tca gct agc acc aag ggc     432
cca tcc gtc ttc ccc ctg gcg ccc gct agc aag agc acc tct ggg ggc     480
aca gcg gcc ctg ggc tgc ctg gtc aag gac tac ttc ccc gaa ccg gtg     528
acg gtg tcg tgg aac tca ggc gcc ctg acc agc ggc gtg cac acc ttc     576
ccg gct gtc cta cag tcc tca gga ctc tac tcc ctc agc agc gtg gtg     624
acc gtg ccc tcc agc agc ttg ggc acc cag acc tac atc tgc aac gtg     672
aat cac aag ccc agc aac acc aag gtg gac aag aga gtt ggt gag agg     720
cca gca cag gga ggg agg gtg tct gct gga agc cag gct cag cgc tcc     768
tgc ctg gac gca tcc cgg cta tgc agt ccc agt cca gga cag caa ggc     816
agg ccc cgt ctg cct ctt cac cgg agg cct ctg ccc gcc cca ctc at      864
gct cag gga gag gtc ttc tgc ttt ccc cca ggc tct ggg cag gca         912
cag gct agg tgc ccc taa ccc agg ccc tgc aca caa agg ggc agg tgc     960
tgg gct cag acc tgc caa gag cca tat ccg gga ggg ccc tgc tga        1008
cct aag ccc acc cca aag gcc aaa ctc tcc act ccc tca gct cgg aca    1056
cct tct ctc ctc cca gat tcc agt aac tcc caa tct tct ctc tgc aga    1104
gcc caa atc ttg tga caa aac tca cac atg ccc acc gtg ccc agg taa    1152
gcc agc cca ggc ctc gcc ctc cag ctc aag gcg gga cag tgc cct ag     1200
agt agc ctg cat cca ggg aca ggc ccc agc cgg gtg ctg aca cgt cca   1248
```

```
cct cca tct ctt cct cag cac ctg aac tcc tgg ggg gac cgt cag tct    1296
tcc tct tcc ccc caa aac cca agg aca ccc tca tga tct ccc gga ccc    1344
ctg agg tca cat gcg tgg tgg tgg acg tga gcc acg aag acc ctg agg    1392
tca agt tca act ggt acg tgg acg gcg tgg agg tgc ata atg cca aga    1440
caa agc cgc ggg agg agc agt aca aca gca cgt acc gtg tgg tca gcg    1488
tcc tca ccg tcc tgc acc agg act ggc tga atg gca agg agt aca agt    1536
gca agg tct cca aca aag ccc tcc cag ccc cca tcg aga aaa cca tct    1584
cca aag cca aag gtg gga ccc gtg ggg tgc gag ggc cac atg gac aga    1632
ggc cgg ctc ggc cca ccc tct gcc ctg aga gct gct gta cca acc       1680
tct gtc cct aca ggg cag ccc cga gaa cca cag gtg tac acc ctg ccc    1728
cca tcc cgg gag gag atg acc aag aac cag gtc agc ctg acc tgc ctg    1776
gtc aaa ggc ttc tat ccc agc gac atc gcc gtg gag tgg gag agc aat    1824
ggg cag ccg gag aac aac tac aag acc acg cct ccc gtg ctg gac tcc    1872
gac ggc tcc ttc ttc ctc tat agc aag ctc acc gtg gac aag agc agg    1920
tgg cag cag ggg aac gtc ttc tca tgc tcc gtg atg cat gag gct ctg    1968
cac aac cac tac acg cag aag agc ctc tcc ctg tct ccg ggt aaa tga    2016

<210> SEQ ID NO 4
<211> LENGTH: 469
<212> TYPE: PRT
<213> ORGANISM: Artificial Sequence
<220> FEATURE:
<223> OTHER INFORMATION: Heavy chain of 12.12 human anti-CD40 antibody

<400> SEQUENCE: 4

Met Glu Phe Gly Leu Ser Trp Val Phe Leu Val Ala Ile Leu Arg Gly
 1               5                  10                  15

Val Gln Cys Gln Val Gln Leu Val Glu Ser Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Ser Tyr Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ala Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 5
<211> LENGTH: 469
<212> TYPE: PRT
<213> ORGANISM: Artificial Sequence
<220> FEATURE:
<223> OTHER INFORMATION: Heavy chain of variant of 12.12 human anti-CD40
      antibody

<400> SEQUENCE: 5

Met Glu Phe Gly Leu Ser Trp Val Phe Leu Val Ala Ile Leu Arg Gly
  1                 5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175
```

```
Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 6
<211> LENGTH: 239
<212> TYPE: PRT
<213> ORGANISM: Artificial Sequence
<220> FEATURE:
<223> OTHER INFORMATION: Light chain of 5.9 human anti-CD40 antibody

<400> SEQUENCE: 6

Met Ala Leu Leu Ala Gln Leu Leu Gly Leu Leu Met Leu Trp Val Pro
1               5                   10                  15

Gly Ser Ser Gly Ala Ile Val Met Thr Gln Pro Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60
```

```
Pro Gly Gln Pro Pro Arg Leu Leu Ile Tyr Lys Phe Phe Arg Arg Leu
 65                  70                  75                  80

Ser Gly Val Pro Asp Arg Phe Ser Gly Ser Gly Ala Gly Thr Asp Phe
                 85                  90                  95

Thr Leu Lys Ile Ser Arg Val Glu Ala Glu Asp Val Gly Val Tyr Tyr
            100                 105                 110

Cys Met Gln Val Thr Gln Phe Pro His Thr Phe Gly Gln Gly Thr Arg
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 7
<211> LENGTH: 474
<212> TYPE: PRT
<213> ORGANISM: Artificial Sequence
<220> FEATURE:
<223> OTHER INFORMATION: Heavy chain of 5.9 human anti-CD40 antibody

<400> SEQUENCE: 7

Met Gly Ser Thr Ala Ile Leu Ala Leu Leu Leu Ala Val Leu Gln Gly
  1               5                  10                  15

Val Cys Ala Glu Val Gln Leu Val Gln Ser Gly Ala Glu Val Lys Lys
             20                  25                  30

Pro Gly Glu Ser Leu Lys Ile Ser Cys Lys Gly Ser Gly Tyr Ser Phe
         35                  40                  45

Thr Ser Tyr Trp Ile Gly Trp Val Arg Gln Met Pro Gly Lys Gly Leu
     50                  55                  60

Glu Trp Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
                 85                  90                  95

Thr Ala Tyr Leu Gln Trp Ser Ser Leu Lys Ala Ser Asp Thr Ala Met
            100                 105                 110

Tyr Tyr Cys Ala Arg Gly Thr Ala Ala Gly Arg Asp Tyr Tyr Tyr Tyr
        115                 120                 125

Tyr Gly Met Asp Val Trp Gly Gln Gly Thr Thr Val Thr Val Ser Ser
130                 135                 140

Ala Ser Thr Lys Gly Pro Ser Val Phe Pro Leu Ala Pro Ala Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
```

```
                195                 200                 205
Leu Ser Ser Val Val Thr Val Pro Ser Ser Leu Gly Thr Gln Thr
210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Glu Glu
                370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 8
<211> LENGTH: 474
<212> TYPE: PRT
<213> ORGANISM: Artificial Sequence
<220> FEATURE:
<223> OTHER INFORMATION: Heavy chain of variant of 5.9 human anti-CD40
      antibody

<400> SEQUENCE: 8

Met Gly Ser Thr Ala Ile Leu Ala Leu Leu Ala Val Leu Gln Gly
 1               5                  10                  15

Val Cys Ala Glu Val Gln Leu Val Gln Ser Gly Ala Glu Val Lys Lys
                20                  25                  30

Pro Gly Glu Ser Leu Lys Ile Ser Cys Lys Gly Ser Gly Tyr Ser Phe
                35                  40                  45

Thr Ser Tyr Trp Ile Gly Trp Val Arg Gln Met Pro Gly Lys Gly Leu
                50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
```

```
                    85                  90                  95
Thr Ala Tyr Leu Gln Trp Ser Ser Leu Lys Ala Ser Asp Thr Ala Met
                100                 105                 110
Tyr Tyr Cys Ala Arg Gly Thr Ala Ala Gly Arg Asp Tyr Tyr Tyr Tyr
                115                 120                 125
Tyr Gly Met Asp Val Trp Gly Gln Gly Thr Thr Val Thr Val Ser Ser
                130                 135                 140
Ala Ser Thr Lys Gly Pro Ser Val Phe Pro Leu Ala Pro Ser Ser Lys
145                 150                 155                 160
Ser Thr Ser Gly Gly Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
                180                 185                 190
Gly Val His Thr Phe Pro Ala Val Leu Gln Ser Ser Gly Leu Tyr Ser
                195                 200                 205
Leu Ser Ser Val Val Thr Val Pro Ser Ser Ser Leu Gly Thr Gln Thr
                210                 215                 220
Tyr Ile Cys Asn Val Asn His Lys Pro Ser Asn Thr Lys Val Asp Lys
225                 230                 235                 240
Arg Val Glu Pro Lys Ser Cys Asp Lys Thr His Thr Cys Pro Pro Cys
                245                 250                 255
Pro Ala Pro Glu Leu Leu Gly Gly Pro Ser Val Phe Leu Phe Pro Pro
                260                 265                 270
Lys Pro Lys Asp Thr Leu Met Ile Ser Arg Thr Pro Glu Val Thr Cys
                275                 280                 285
Val Val Val Asp Val Ser His Glu Asp Pro Glu Val Lys Phe Asn Trp
                290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
                340                 345                 350
Lys Ala Leu Pro Ala Pro Ile Glu Lys Thr Ile Ser Lys Ala Lys Gly
                355                 360                 365
Gln Pro Arg Glu Pro Gln Val Tyr Thr Leu Pro Pro Ser Arg Glu Glu
                370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
                420                 425                 430
Leu Tyr Ser Lys Leu Thr Val Asp Lys Ser Arg Trp Gln Gln Gly Asn
                435                 440                 445
Val Phe Ser Cys Ser Val Met His Glu Ala Leu His Asn His Tyr Thr
450                 455                 460
Gln Lys Ser Leu Ser Leu Ser Pro Gly Lys
465                 470

<210> SEQ ID NO 9
<211> LENGTH: 612
<212> TYPE: DNA
<213> ORGANISM: Homo sapiens
<220> FEATURE:
```

```
<221> NAME/KEY: CDS
<222> LOCATION: (1)...(612)
<221> NAME/KEY: misc_feature
<222> LOCATION: (0)...(0)
<223> OTHER INFORMATION: Coding sequence for short isoform of human CD40

<400> SEQUENCE: 9 atg gtt cgt ctg cct ctg cag tgc gtc ctc tgg ggc tgc ttg ctg acc       48
Met Val Arg Leu Pro Leu Gln Cys Val Leu Trp Gly Cys Leu Leu Thr
1               5                   10                  15 gct gtc cat cca gaa cca ccc act gca tgc aga gaa aaa cag tac cta       96
Ala Val His Pro Glu Pro Pro Thr Ala Cys Arg Glu Lys Gln Tyr Leu
            20                  25                  30 ata aac agt cag tgc tgt tct ttg tgc cag cca gga cag aaa ctg gtg      144
Ile Asn Ser Gln Cys Cys Ser Leu Cys Gln Pro Gly Gln Lys Leu Val
        35                  40                  45 agt gac tgc aca gag ttc act gaa acg gaa tgc ctt cct tgc ggt gaa      192
Ser Asp Cys Thr Glu Phe Thr Glu Thr Glu Cys Leu Pro Cys Gly Glu
    50                  55                  60 agc gaa ttc cta gac acc tgg aac aga gag aca cac tgc cac cag cac      240
Ser Glu Phe Leu Asp Thr Trp Asn Arg Glu Thr His Cys His Gln His
65                  70                  75                  80 aaa tac tgc gac ccc aac cta ggg ctt cgg gtc cag cag aag ggc acc      288
Lys Tyr Cys Asp Pro Asn Leu Gly Leu Arg Val Gln Gln Lys Gly Thr
                85                  90                  95 tca gaa aca gac acc atc tgc acc tgt gaa gaa ggc tgg cac tgt acg      336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc      384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag      432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa      480
Pro Cys Pro Val Gly Phe Phe Ser Asn Val Ser Ser Ala Phe Glu Lys
145                 150                 155                 160 tgt cac cct tgg aca agg tcc cca gga tcg gct gag agc cct ggt ggt      528
Cys His Pro Trp Thr Arg Ser Pro Gly Ser Ala Glu Ser Pro Gly Gly
                165                 170                 175 gat ccc cat cat ctt cgg gat cct gtt tgc cat cct ctt ggt gct ggt      576
Asp Pro His His Leu Arg Asp Pro Val Cys His Pro Leu Gly Ala Gly
            180                 185                 190 ctt tat caa aaa ggt ggc caa gaa gcc aac caa taa                      612
Leu Tyr Gln Lys Gly Gly Gln Glu Ala Asn Gln *
        195                 200

<210> SEQ ID NO 10
<211> LENGTH: 203
<212> TYPE: PRT
<213> ORGANISM: Homo sapiens

<400> SEQUENCE: 10

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60
```

```
Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
        195                 200
```

```
<210> SEQ ID NO 11
<211> LENGTH: 834
<212> TYPE: DNA
<213> ORGANISM: Homo sapiens
<220> FEATURE:
<221> NAME/KEY: CDS
<222> LOCATION: (1)...(834)
<221> NAME/KEY: misc_feature
<222> LOCATION: (0)...(0)
<223> OTHER INFORMATION: Coding sequence for long isoform of human CD40

<400> SEQUENCE: 11 atg gtt cgt ctg cct ctg cag tgc gtc ctc tgg ggc tgc ttg ctg acc      48
Met Val Arg Leu Pro Leu Gln Cys Val Leu Trp Gly Cys Leu Leu Thr
  1               5                  10                  15 gct gtc cat cca gaa cca ccc act gca tgc aga gaa aaa cag tac cta      96
Ala Val His Pro Glu Pro Pro Thr Ala Cys Arg Glu Lys Gln Tyr Leu
             20                  25                  30 ata aac agt cag tgc tgt tct ttg tgc cag cca gga cag aaa ctg gtg     144
Ile Asn Ser Gln Cys Cys Ser Leu Cys Gln Pro Gly Gln Lys Leu Val
         35                  40                  45 agt gac tgc aca gag ttc act gaa acg gaa tgc ctt cct tgc ggt gaa     192
Ser Asp Cys Thr Glu Phe Thr Glu Thr Glu Cys Leu Pro Cys Gly Glu
     50                  55                  60 agc gaa ttc cta gac acc tgg aac aga gag aca cac tgc cac cag cac     240
Ser Glu Phe Leu Asp Thr Trp Asn Arg Glu Thr His Cys His Gln His
 65                  70                  75                  80 aaa tac tgc gac ccc aac cta ggg ctt cgg gtc cag cag aag ggc acc     288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc tgg cac tgt acg     336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc     384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag     432
Phe Gly Val Lys Gln Ile Ala Thr Gly Val Ser Asp Thr Ile Cys Glu
130                 135                 140 ccc tgc cca gtc ggc ttc ttc tcc aat gtg tca tct gct ttc gaa aaa     480
Pro Cys Pro Val Gly Phe Phe Ser Asn Val Ser Ser Ala Phe Glu Lys
145                 150                 155                 160
```

| | | |
|---|---|---|
| tgt cac cct tgg aca agc tgt gag acc aaa gac ctg gtt gtg caa cag<br>Cys His Pro Trp Thr Ser Cys Glu Thr Lys Asp Leu Val Val Gln Gln<br>165                      170                    175 | | 528 |
| gca ggc aca aac aag act gat gtt gtc tgt ggt ccc cag gat cgg ctg<br>Ala Gly Thr Asn Lys Thr Asp Val Val Cys Gly Pro Gln Asp Arg Leu<br>        180                    185                    190 | | 576 |
| aga gcc ctg gtg gtg atc ccc atc atc ttc ggg atc ctg ttt gcc atc<br>Arg Ala Leu Val Val Ile Pro Ile Ile Phe Gly Ile Leu Phe Ala Ile<br>195                      200                    205 | | 624 |
| ctc ttg gtg ctg gtc ttt atc aaa aag gtg gcc aag aag cca acc aat<br>Leu Leu Val Leu Val Phe Ile Lys Lys Val Ala Lys Lys Pro Thr Asn<br>        210                    215                    220 | | 672 |
| aag gcc ccc cac ccc aag cag gaa ccc cag gag atc aat ttt ccc gac<br>Lys Ala Pro His Pro Lys Gln Glu Pro Gln Glu Ile Asn Phe Pro Asp<br>225                      230                    235                    240 | | 720 |
| gat ctt cct ggc tcc aac act gct gct cca gtg cag gag act tta cat<br>Asp Leu Pro Gly Ser Asn Thr Ala Ala Pro Val Gln Glu Thr Leu His<br>                245                    250                    255 | | 768 |
| gga tgc caa ccg gtc acc cag gag gat ggc aaa gag agt cgc atc tca<br>Gly Cys Gln Pro Val Thr Gln Glu Asp Gly Lys Glu Ser Arg Ile Ser<br>        260                    265                    270 | | 816 |
| gtg cag gag aga cag tga<br>Val Gln Glu Arg Gln *<br>275 | | 834 |

<210> SEQ ID NO 12
<211> LENGTH: 277
<212> TYPE: PRT
<213> ORGANISM: Homo sapiens

<400> SEQUENCE: 12

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

```
Leu Leu Val Leu Val Phe Ile Lys Lys Val Ala Lys Lys Pro Thr Asn
        210             215                 220
Lys Ala Pro His Pro Lys Gln Glu Pro Gln Glu Ile Asn Phe Pro Asp
225                 230                 235                 240
Asp Leu Pro Gly Ser Asn Thr Ala Ala Pro Val Gln Glu Thr Leu His
                245                 250                 255
Gly Cys Gln Pro Val Thr Gln Glu Asp Gly Lys Glu Ser Arg Ile Ser
            260                 265                 270
Val Gln Glu Arg Gln
        275

<210> SEQ ID NO 13
<211> LENGTH: 459
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Human IL-2 precursor
<221> NAME/KEY: CDS
<222> LOCATION: (1)...(459)

<400> SEQUENCE: 13 atg tac agg atg caa ctc ctg tct tgc att gca cta agt ctt gca ctt        48
Met Tyr Arg Met Gln Leu Leu Ser Cys Ile Ala Leu Ser Leu Ala Leu
1               5                   10                  15 gtc gca aac agt gca cct act tca agt tct aca aag aaa aca cag cta        96
Val Ala Asn Ser Ala Pro Thr Ser Ser Ser Thr Lys Lys Thr Gln Leu
                20                  25                  30 caa ctg gag cat tta ctg ctg gat tta cag atg att ttg aat gga att       144
Gln Leu Glu His Leu Leu Leu Asp Leu Gln Met Ile Leu Asn Gly Ile
            35                  40                  45 aat aat tac aag aat ccc aaa ctc acc agg atg ctc aca ttt aag ttt       192
Asn Asn Tyr Lys Asn Pro Lys Leu Thr Arg Met Leu Thr Phe Lys Phe
        50                  55                  60 tac atg ccc aag aag gcc aca gaa ctg aaa cat ctt cag tgt cta gaa       240
Tyr Met Pro Lys Lys Ala Thr Glu Leu Lys His Leu Gln Cys Leu Glu
65                  70                  75                  80 gaa gaa ctc aaa cct ctg gag gaa gtg cta aat tta gct caa agc aaa       288
Glu Glu Leu Lys Pro Leu Glu Glu Val Leu Asn Leu Ala Gln Ser Lys
                85                  90                  95 aac ttt cac tta aga ccc agg gac tta atc agc aat atc aac gta ata       336
Asn Phe His Leu Arg Pro Arg Asp Leu Ile Ser Asn Ile Asn Val Ile
            100                 105                 110 gtt ctg gaa cta aag gga tct gaa aca aca ttc atg tgt gaa tat gct       384
Val Leu Glu Leu Lys Gly Ser Glu Thr Thr Phe Met Cys Glu Tyr Ala
        115                 120                 125 gat gag aca gca acc att gta gaa ttt ctg aac aga tgg att acc ttt       432
Asp Glu Thr Ala Thr Ile Val Glu Phe Leu Asn Arg Trp Ile Thr Phe
130                 135                 140 tgt cag agc atc atc tca aca ctg act                                   459
Cys Gln Ser Ile Ile Ser Thr Leu Thr
145                 150

<210> SEQ ID NO 14
<211> LENGTH: 153
<212> TYPE: PRT
<213> ORGANISM: Homo sapiens

<400> SEQUENCE: 14

Met Tyr Arg Met Gln Leu Leu Ser Cys Ile Ala Leu Ser Leu Ala Leu
1               5                   10                  15
```

```
Val Ala Asn Ser Ala Pro Thr Ser Ser Ser Thr Lys Lys Thr Gln Leu
             20                  25                  30

Gln Leu Glu His Leu Leu Leu Asp Leu Gln Met Ile Leu Asn Gly Ile
         35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
             100                 105                 110

Val Leu Glu Leu Lys Gly Ser Glu Thr Thr Phe Met Cys Glu Tyr Ala
         115                 120                 125

Asp Glu Thr Ala Thr Ile Val Glu Phe Leu Asn Arg Trp Ile Thr Phe
     130                 135                 140

Cys Gln Ser Ile Ile Ser Thr Leu Thr
145                 150

<210> SEQ ID NO 15
<211> LENGTH: 399
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Mature human IL-2
<221> NAME/KEY: CDS
<222> LOCATION: (1)...(399)

<400> SEQUENCE: 15 gca cct act tca agt tct aca aag aaa aca cag cta caa ctg gag cat     48
Ala Pro Thr Ser Ser Ser Thr Lys Lys Thr Gln Leu Gln Leu Glu His
 1               5                  10                  15 tta ctg ctg gat tta cag atg att ttg aat gga att aat aat tac aag     96
Leu Leu Leu Asp Leu Gln Met Ile Leu Asn Gly Ile Asn Asn Tyr Lys
             20                  25                  30 aat ccc aaa ctc acc agg atg ctc aca ttt aag ttt tac atg ccc aag    144
Asn Pro Lys Leu Thr Arg Met Leu Thr Phe Lys Phe Tyr Met Pro Lys
         35                  40                  45 aag gcc aca gaa ctg aaa cat ctt cag tgt cta gaa gaa gaa ctc aaa    192
Lys Ala Thr Glu Leu Lys His Leu Gln Cys Leu Glu Glu Glu Leu Lys
     50                  55                  60 cct ctg gag gaa gtg cta aat tta gct caa agc aaa aac ttt cac tta    240
Pro Leu Glu Glu Val Leu Asn Leu Ala Gln Ser Lys Asn Phe His Leu
 65                  70                  75                  80 aga ccc agg gac tta atc agc aat atc aac gta ata gtt ctg gaa cta    288
Arg Pro Arg Asp Leu Ile Ser Asn Ile Asn Val Ile Val Leu Glu Leu
                 85                  90                  95 aag gga tct gaa aca aca ttc atg tgt gaa tat gct gat gag aca gca    336
Lys Gly Ser Glu Thr Thr Phe Met Cys Glu Tyr Ala Asp Glu Thr Ala
            100                 105                 110 acc att gta gaa ttt ctg aac aga tgg att acc ttt tgt cag agc atc    384
Thr Ile Val Glu Phe Leu Asn Arg Trp Ile Thr Phe Cys Gln Ser Ile
        115                 120                 125 atc tca aca ctg act                                                 399
Ile Ser Thr Leu Thr
        130

<210> SEQ ID NO 16
<211> LENGTH: 133
```

```
<212> TYPE: PRT
<213> ORGANISM: Homo sapiens

<400> SEQUENCE: 16

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Cys Gln Ser Ile
         115                 120                 125

Ile Ser Thr Leu Thr
        130

<210> SEQ ID NO 17
<211> LENGTH: 396
<212> TYPE: DNA
<213> ORGANISM: Artificial Sequence
<220> FEATURE:
<223> OTHER INFORMATION: des-alanyl 1, C125S human IL-2 mutein
<221> NAME/KEY: CDS
<222> LOCATION: (1)...(396)

<400> SEQUENCE: 17 cct act tca agt tct aca aag aaa aca cag cta caa ctg gag cat tta      48
Pro Thr Ser Ser Ser Thr Lys Lys Thr Gln Leu Gln Leu Glu His Leu
 1               5                  10                  15 ctg ctg gat tta cag atg att ttg aat gga att aat aat tac aag aat      96
Leu Leu Asp Leu Gln Met Ile Leu Asn Gly Ile Asn Asn Tyr Lys Asn
             20                  25                  30 ccc aaa ctc acc agg atg ctc aca ttt aag ttt tac atg ccc aag aag     144
Pro Lys Leu Thr Arg Met Leu Thr Phe Lys Phe Tyr Met Pro Lys Lys
         35                  40                  45 gcc aca gaa ctg aaa cat ctt cag tgt cta gaa gaa gaa ctc aaa cct     192
Ala Thr Glu Leu Lys His Leu Gln Cys Leu Glu Glu Glu Leu Lys Pro
 50                  55                  60 ctg gag gaa gtg cta aat tta gct caa agc aaa aac ttt cac tta aga     240
Leu Glu Glu Val Leu Asn Leu Ala Gln Ser Lys Asn Phe His Leu Arg
 65                  70                  75                  80 ccc agg gac tta atc agc aat atc aac gta ata gtt ctg gaa cta aag     288
Pro Arg Asp Leu Ile Ser Asn Ile Asn Val Ile Val Leu Glu Leu Lys
                 85                  90                  95 gga tct gaa aca aca ttc atg tgt gaa tat gct gat gag aca gca acc     336
Gly Ser Glu Thr Thr Phe Met Cys Glu Tyr Ala Asp Glu Thr Ala Thr
             100                 105                 110 att gta gaa ttt ctg aac aga tgg att acc ttt tct cag agc atc atc     384
Ile Val Glu Phe Leu Asn Arg Trp Ile Thr Phe Ser Gln Ser Ile Ile
         115                 120                 125 tca aca ctg act                                                     396
Ser Thr Leu Thr
        130
```

```
<210> SEQ ID NO 18
<211> LENGTH: 132
<212> TYPE: PRT
<213> ORGANISM: Artificial Sequence
<220> FEATURE:
<223> OTHER INFORMATION: des-alanyl 1, C125S human IL-2 mutein

<400> SEQUENCE: 18

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```